(12) United States Patent
Levin et al.

(10) Patent No.: US 12,344,897 B2
(45) Date of Patent: Jul. 1, 2025

(54) URINARY MICROBIOMIC PROFILING

(71) Applicant: Convergent Genomics, Inc., South San Francisco, CA (US)

(72) Inventors: Trevor Levin, South San Francisco, CA (US); Kevin Phillips, South San Francisco, CA (US); Christian Rees, South San Francisco, CA (US)

(73) Assignee: Convergent Genomics, Inc., South San Francisco, CA (US)

( * ) Notice: Subject to any disclaimer, the term of this patent is extended or adjusted under 35 U.S.C. 154(b) by 0 days.

(21) Appl. No.: 18/603,943

(22) Filed: Mar. 13, 2024

(65) Prior Publication Data
US 2024/0254558 A1 Aug. 1, 2024

Related U.S. Application Data

(63) Continuation of application No. 17/262,670, filed as application No. PCT/US2019/043231 on Jul. 24, 2019.

(Continued)

(51) Int. Cl.
*C12Q 1/6883* (2018.01)
*C12Q 1/6806* (2018.01)
(Continued)

(52) U.S. Cl.
CPC ......... *C12Q 1/6883* (2013.01); *C12Q 1/6806* (2013.01); *C12Q 1/6869* (2013.01);
(Continued)

(58) Field of Classification Search
CPC .. C12Q 1/6883; C12Q 1/6806; C12Q 1/6869; C12Q 1/689; G16B 50/30; G16B 40/30
See application file for complete search history.

(56) References Cited

U.S. PATENT DOCUMENTS 6,326,040 B1 * 12/2001 Kearney ............... A23L 2/68
426/271
2006/0014214 A1 1/2006 Baker
(Continued)

FOREIGN PATENT DOCUMENTS

EP 1513952 A2 3/2005
WO WO 2014/059417 A1 4/2014

OTHER PUBLICATIONS

EP European Search Report in European Application No. 19841042.5 dated Mar. 22, 2022, 14 pages.
(Continued)

*Primary Examiner* — Brian R Gordon
*Assistant Examiner* — Dwan A Gerido
(74) *Attorney, Agent, or Firm* — DLA Piper LLP (US)

(57) ABSTRACT

Methods and systems for identifying and/or treating urinary disorders are provided. The methods and systems generally operate by obtaining a urine sample from a subject, identifying (such as by using nucleic acid sequencing) an abundance of a first set of one or more microbes (such as one or more bacteria or viruses) in the urine sample, and determining whether the subject suffers from a urinary disorder based on the abundance of the first set of one or more microbes. In some cases, the methods and systems further operate by identifying a second set of microbes to supplement a microbiome in the urinary tract of the subject. In some instances, the methods and systems further operate by treating the urinary disorder using the second set of microbes. In some instances a preservation solution is utilized.

24 Claims, 55 Drawing Sheets

Related U.S. Application Data

(60) Provisional application No. 62/793,693, filed on Jan. 17, 2019, provisional application No. 62/703,352, filed on Jul. 25, 2018.

(51) Int. Cl.
| | |
|---|---|
| *C12Q 1/6869* | (2018.01) |
| *C12Q 1/689* | (2018.01) |
| *G16B 40/30* | (2019.01) |
| *G16B 50/30* | (2019.01) |

(52) U.S. Cl.
CPC ............ *C12Q 1/689* (2013.01); *G16B 40/30* (2019.02); *G16B 50/30* (2019.02)

(56) References Cited

U.S. PATENT DOCUMENTS

| | | |
|---|---|---|
| 2008/0064108 A1 | 3/2008 | Baker |
| 2011/0300550 A1 | 12/2011 | Tanigami |
| 2012/0064535 A1 | 3/2012 | Tanigami et al. |
| 2012/0101260 A1* | 4/2012 | Farinas ............... A61K 47/61 530/391.1 |
| 2013/0056211 A1* | 3/2013 | Berkland ............. A61K 47/58 166/305.1 |
| 2014/0154189 A1 | 6/2014 | Polson et al. |
| 2016/0122804 A1 | 5/2016 | Smith et al. |
| 2017/0318801 A1* | 11/2017 | Yokoyama ............ G01N 33/48 |

OTHER PUBLICATIONS

EP Office Action in European Application No. 19841042.5 dated Sep. 5, 2023, 9 pages.

Finnegan and Percival, "EDTA: An Antimicrobial and Antibiofilm Agent for Use in Wound Care," *Adv. Wound Care* (2015), 4(7):415-421, Mary Ann Liebert, Inc.

Geisenhof et al., "Enterobactin—Structure and Function," (2016), 5 pages.

* cited by examiner

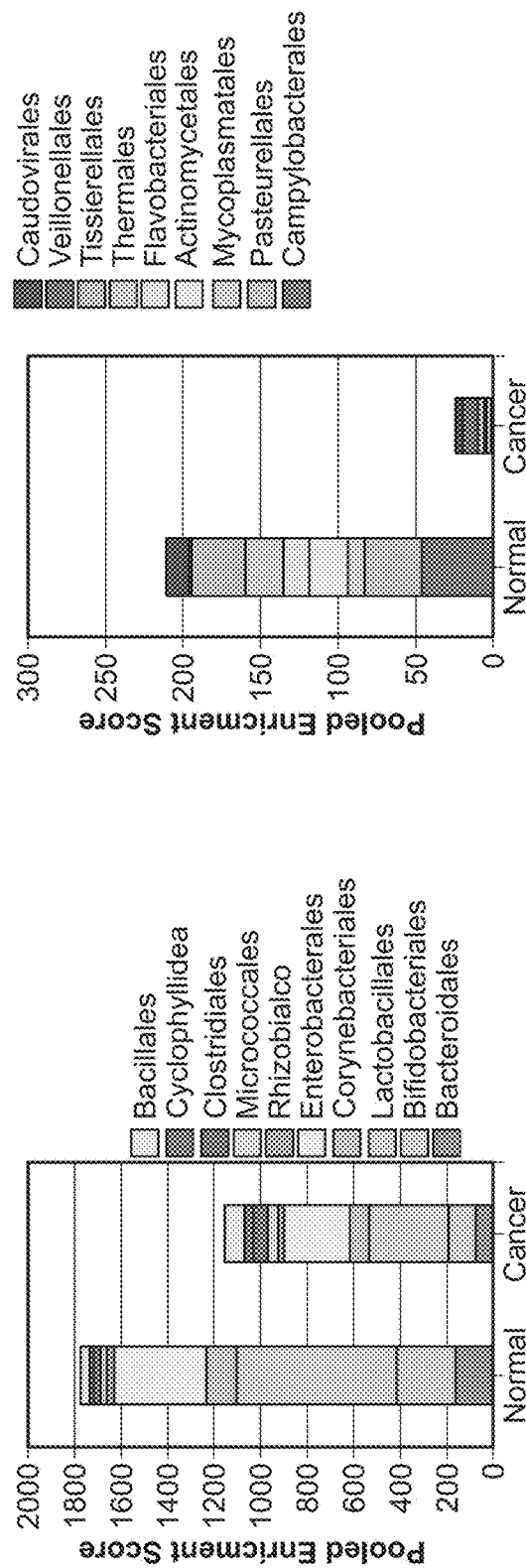
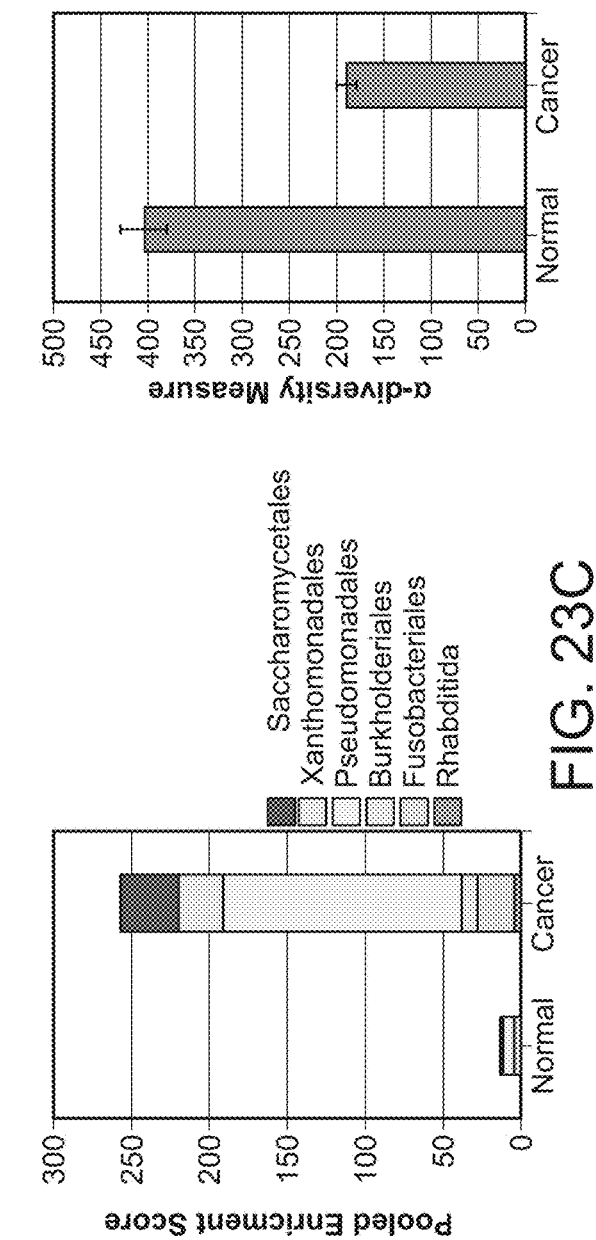
FIG. 23A, FIG. 23B, FIG. 23C, FIG. 23D

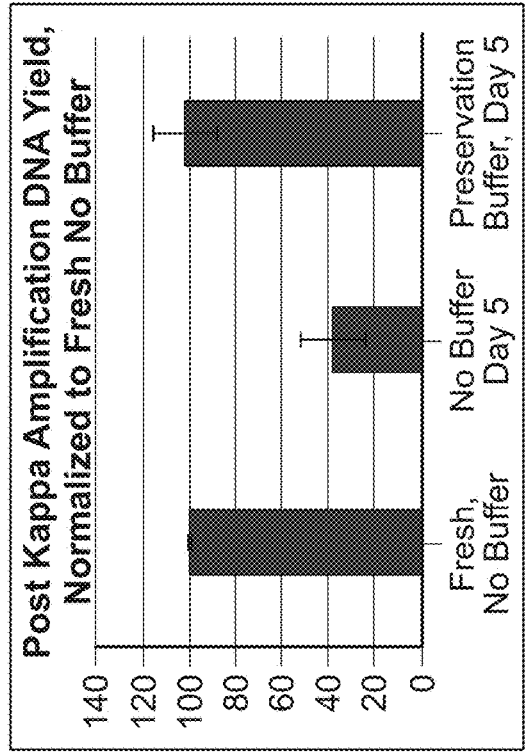
FIG. 41A
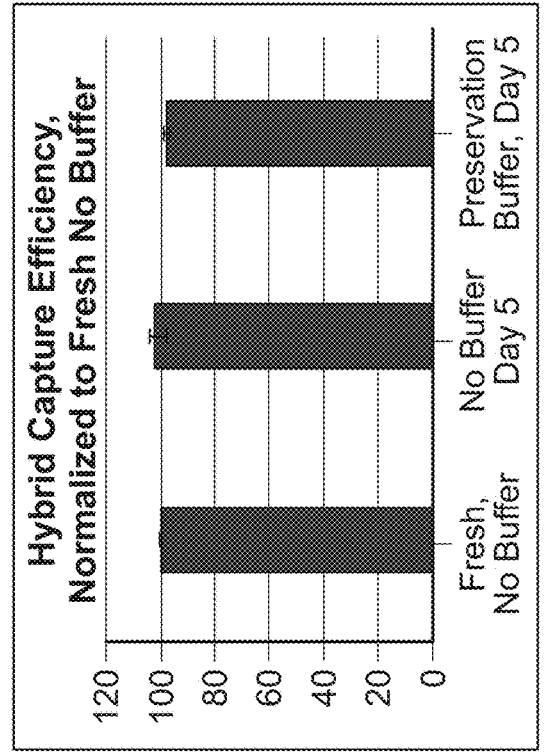
FIG. 41B
FIG. 41C
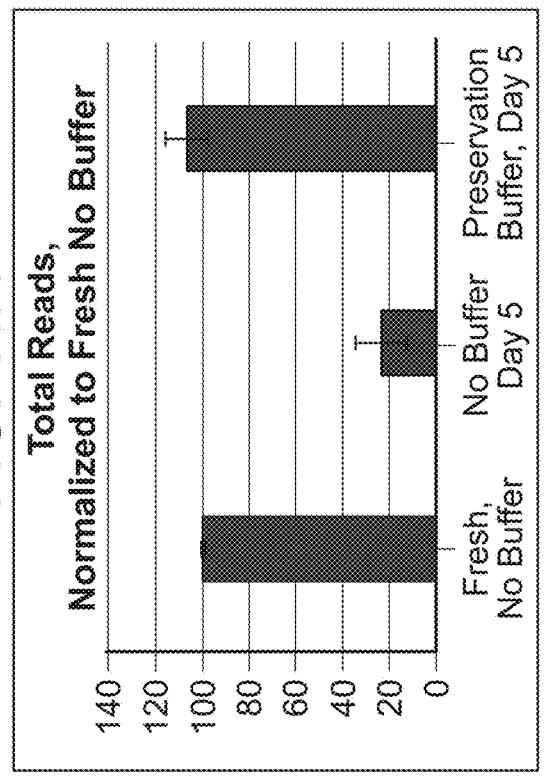
FIG. 41D

URINARY MICROBIOMIC PROFILING

CROSS-REFERENCE TO RELATED APPLICATIONS

This application is a continuation application of U.S. application Ser. No. 17/262,670 filed Jan. 22, 2021, now; which is a 35 USC § 371 National Stage application of International Application No. PCT/US2019/043231 filed Jul. 24, 2019; which claims the benefit under 35 USC § 119(e) to U.S. Application Ser. No. 62/793,693 filed Jan. 17, 2019 and to U.S. Application Ser. No. 62/703,352 filed Jul. 25, 2018. The disclosure of each of the prior applications is considered part of and is incorporated by reference in the disclosure of this application.

SUMMARY OF THE INVENTION

Provided herein are methods and systems for identifying and/or treating urinary disorders. The methods and systems generally operate by obtaining a urine sample from a subject, identifying (such as by using nucleic acid sequencing) an abundance of a first set of one or more microbes (such as one or more bacteria or viruses) in the urine sample, and determining whether the subject suffers from a urinary disorder based on the abundance of the first set of one or more microbes. In some cases, the methods and systems further operate by identifying a second set of microbes to supplement a microbiome in the urinary tract of the subject. In some instances, the methods and systems further operate by treating the urinary disorder using the second set of microbes.

In an aspect, the present disclosure provides a preservation mixture comprising an iron chelator, wherein said preservation mixture is configured to preserve nucleic acid molecules in a urine sample and prevent growth of microbes in said sample.

In some embodiments, said iron chelator is configured to preserve nucleic acid molecules in a urine sample and prevent growth of microbes in said sample. In some embodiments, said iron chelator is selected from the group consisting of enterobactin and Deferoxamine Mesylate. In some embodiments, the preservation mixture further comprises EDTA. In some embodiments, the preservation mixture further comprises poly-L-lysine hydrobromide. In some embodiments, the preservation mixture further comprises D-alpha-tocopherol polyethylene glycol 1000 succinate. In some embodiments, the preservation mixture further comprises an antimicrobial selected from the group consisting of penicillin, streptomycin, Amphotericin B, and urine Stabilur tablet. In some embodiments, the preservation mixture further comprises penicillin, streptomycin, Amphotericin B, and urine Stabilur tablet.

In another aspect, the present disclosure provides a method for processing a urine sample, comprising: (a) receiving a solution comprising nucleic acid molecules in a urine of a subject, which solution comprises a preservation mixture; and sequencing a plurality of nucleic acid molecules derived from said nucleic acid molecules to generate a plurality of sequencing reads, wherein said preservation mixture provides for sequencing said plurality of nucleic acid molecules to generate said plurality of sequencing reads at a greater coverage as compared to other nucleic acid molecules in said urine preserved in a composition comprising: a volume-excluding polymer that is present in an amount from about 10% to about 50% by weight of said composition, an osmotic agent present in an amount of about 1% to about 20% by weight of said composition, and an enzyme inhibitor present in an amount from about 1% to about 30% by weight of said composition.

In some embodiments, said preservation mixture comprises a first chelator and one or more member(s) selected from the group consisting of: a pH buffer, a second chelator that is different from said first chelator, a cell membrane stabilizer, a nucleic acid compactor, and an antimicrobial agent. In some embodiments, said preservation mixture comprises said first chelator and said second chelator. In some embodiments, said pH buffer maintains said preservation mixture at a pH that is between 7 and 9. In some embodiments, said first chelator has a first binding affinity for a first metal and said second chelator has a second binding affinity for said first metal, said first binding affinity being greater than said second binding affinity. In some embodiments, said first metal comprises one or more member(s) selected from the group consisting of: vanadium (V), chromium (Cr), manganese (Mn), iron (Fe), cobalt (Co), copper (Cu), zinc (Zn), and molybdenum (Mo). In some embodiments, said first chelator has a third binding affinity for a second metal and said second chelator has a fourth binding affinity for said second metal, said second metal being different from said first metal, and said third binding affinity being less than said fourth binding affinity. In some embodiments, said first chelator comprises one or more member(s) selected from the group consisting of: a siderophore, a nucleoside monophosphate, a nucleoside diphosphate, a nucleoside triphosphate, and a functional variant thereof. In some embodiments, said siderophore comprises one or more member(s) selected from the group consisting of: Achromobactina, Acinetobactin, Acinetoferrin, Aerobactin, Aeruginic acid, Agrobactin, Agrobactin A, Albomycin, Alcaligin, Alterobactin A, Alterobactin A, Aminochelin, Amonabactin P693, Amonabactin P750, Amonabactin T732, Amonabactin T789, Amphibactin B, Amphibactin C, Amphibactin D, Amphibactin E, Amphibactin F, Amphibactin G, Amphibactin H, Amphibactin I, Amphibactin S, Amphibactin T, Amphi-enterobactin, Amphi-enterobactin C12-OH, Amycolachrome, Anachelin 1, Anachelin 2, Anguibactin, Aquachelin A, Aquachelin B, Aquachelin C, Aquachelin D, Aquachelin I, Aquachelin J, Arthrobactin, Asperchrome A, Asperchrome B1, Asperchrome B2, Asperchrome B3, Asperchrome C, Asperchrome D1, Asperchrome D2, Asperchrome D3, Asperchrome E, Asperchrome F1, Asperchrome F2, Asperchrome F3, Aspergillic acid, Avenic acid, Azotobactin, Azotobactin 87, Azotobactin D, Azotochelin, Azoverdin, Bacillibactin, Basidiochrome, Bisucaberin, Carboxymycobactin, Carboxymycobactin 1, Carboxymycobactin 2, Carboxymycobactin 3, Carboxymycobactin 4, Cepabactin, Chrysobactin, Citrate, Coelichelin, Coprogen, Coprogen B, Corynebactin, Deoxydistichonic acid, 2'-Deoxymugineic acud, Deoxyschizokinen, Des(diserylglycyl)-ferrirhodin, Desacetylcoprogen, Deferoxamine Mesylate, Desferrioxamine A1A, Desferrioxamine A1B, Desferrioxamine A2, Desferrioxamine B, Desferrioxamine D1, Desferrioxamine D2, Desferrioxamine E, Desferrioxamine Et1, Desferrioxamine Et2, Desferrioxamine Et3, Desferrioxamine G1, Desferrioxamine G2A, Desferrioxamine G2B, Desferrioxamine G2C, Desferrioxamine H, Desferrioxamine N, Desferrioxamine P1, Desferrioxamine T1, Desferrioxamine T2, Desferrioxamine T3, Desferrioxamine T7, Desferrioxamine T8, Desferrioxamine Te1, Desferrioxamine Te2, Desferrioxamine Te3, Desferrioxamine X1, Desferrioxamine X2, Desferrioxamine X3, Desferrioxamine X4, Desferrithiocin, 2,3-Dihydroxybenzoylserine, Dimerum acid, Dimethylcoprogen, Dimethylneocoprogen I, Dimethyltriornicin, Distichonic acid, E,E-putrebactene, Enantio Rhizoferrin, Enantio-Pyochelin, Enterobactin, Enterochelin, E-putrebactene, Exochelin MN, Exochelin MS, Ferrichrome, Ferrichrome A, Ferrichrome C, Ferrichrysin, Ferricrocin, Ferrimycin A, Ferrirhodin, Ferrirubin, Ferrocin A, Fimsbactin A, Fimsbactin B, Fimsbactin C, Fimsbactin D, Fimsbactin E, Fimsbactin F, Fluvibactin, Formobactin, Fusarinine, Fusarinine A, Fusarinine B, Fusarinine C, Heterobactin A, Heterobactin B, Hydroxycopren, Hydroxyisoneocoprogen I, 3-Hydroxymugineic acid, Hydroxy-neocoprogen I, Isoneocoprogen I, Isopyoverdin 10.7, Isopyoverdin 6.7, Isopyoverdin 7.13, Isopyoverdin 90-33, Isopyoverdin 90-44, Isopyoverdin BTP1, Isotriornicin, Itoic acid, Loihichelin A, Loihichelin B, Loihichelin C, Loihichelin D, Loihichelin E, Loihichelin F, Maduraferrin, Malonichrome, Marinobactin, Marinobactin, Marinobactin, Marinobactin, Marinobactin, Marinobactin, Micacocidin, Moanachelins, Moanachelins, Moanachelins, Moanachelins, Moanachelins, Monoglucosylated, Mugineic, Mycobactin A, Mycobactin Av, Mycobactin F, Mycobactin H, Mycobactin J, Mycobactin M, Mycobactin N, Mycobactin NA, Mycobactin P, Mycobactin R, Mycobactin S, Mycobactin T, Myxochelin, Nannochelin A, Nannochelin B, Nannochelin C, Neocoprogen I, Neocoprogen II, Neurosporin, Nocobactin, Ochrobactin A, Ochrobactin B, Ochrobactin C, Ornibactin-C4, Ornibactin-C6, Ornibactin-C8, Ornicorrugatin, Palmitoylcoprogen, Parabactin, Parabactin A, Petrobactin, Petrobactin disulphonate, Petrobactin sulphonate, Pistillarin, Protochelin, Pseudoalterobactin A, Pseudoalterobactin B, Pseudobactin, Pseudobactin 589A, Putrebactin, Pyochelin, Pyoverdin 1, Pyoverdin 10.1, Pyoverdin 10.10, Pyoverdin 10.2, Pyoverdin 10.3, Pyoverdin 10.4, Pyoverdin 10.5, Pyoverdin 10.6, Pyoverdin 10.8, Pyoverdin 10.9, Pyoverdin 11.1, Pyoverdin 11.2, Pyoverdin 11370, Pyoverdin 12, Pyoverdin 12.1, Pyoverdin 12.2, Pyoverdin 13525, Pyoverdin 1547, Pyoverdin 17400, Pyoverdin 18-1, Pyoverdin 19310, Pyoverdin 2192, Pyoverdin 2392, Pyoverdin 2461, Pyoverdin 2798, Pyoverdin 51 W, Pyoverdin 6.1, Pyoverdin 6.2, Pyoverdin 6.3, Pyoverdin 6.4, Pyoverdin 6.5, Pyoverdin 6.6, Pyoverdin 6.8, Pyoverdin 7.1, Pyoverdin 7.10, Pyoverdin 7.11, Pyoverdin 7.12, Pyoverdin 7.14, Pyoverdin 7.15, Pyoverdin 7.16, Pyoverdin 7.17, Pyoverdin 7.18, Pyoverdin 7.19, Pyoverdin 7.2, Pyoverdin 7.3, Pyoverdin 7.4, Pyoverdin 7.5, Pyoverdin 7.6, Pyoverdin 7.7, Pyoverdin 7.8, Pyoverdin 7.9, Pyoverdin 8.1, Pyoverdin 8.2, Pyoverdin 8.3, Pyoverdin 8.4, Pyoverdin 8.5, Pyoverdin 8.6, Pyoverdin 8.7, Pyoverdin 8.8, Pyoverdin 8.9, Pyoverdin 9.1, Pyoverdin 9.10, Pyoverdin 9.11, Pyoverdin 9.12, Pyoverdin 9.2, Pyoverdin 9.3, Pyoverdin 9.4, Pyoverdin 9.5, Pyoverdin 9.6, Pyoverdin 9.7, Pyoverdin 9.8, Pyoverdin 9.9, Pyoverdin 90-51, Pyoverdin 95-275, Pyoverdin 96-312, Pyoverdin 96-318, Pyoverdin 9AW, Pyoverdin A214, Pyoverdin BTP2, Pyoverdin C, Pyoverdin CHAO, Pyoverdin D-TR133, Pyoverdin E, Pyoverdin G, Pyoverdin GM, Pyoverdin I-III, Pyoverdin P19, Pyoverdin Pau, Pyoverdin PL8, Pyoverdin PVD, Pyoverdin R', Pyoverdin Thai, Pyoverdin TII, Pyridoxatin, Quinolobactin, Rhizobactin, Rhizobactin 1021, Rhizoferrin, Rhizoferrin analogues, Rhodotrulic acid, Sake Colorant A, Salmochelin S1, Salmochelin S2, Salmochelin S4, Salmochelin SX, Salmycin A, Schizokinen, Serratiochelin, Siderochelin A, Snychobactin A, Snychobactin B, Snychobactin C, Staphyloferrin A, Staphyloferrin B, Taiwachelin, Tetraglycine ferrichrome, Thiazostatin, Triacetylfusarine, Triornicin, Vibriobactin, Vibrioferrin, Vicibactin, Vulnibactin, and Yersiniabactin. In some embodiments, said second chelator comprises one or more member(s) selected from the group consisting of: ethylenediamintetraacetic acid (EDTA), nitrilotriacetic acid (NTA), trans-1,2-cyclohexanediaminetetraacetic acid (CyDTA), diethylenetriaminepentaacetic acid (DTPA), glycoletherdiaminetetraacetic acid (GEDTA), triethylenetetramine-N,N,N',N'',N''',N''''-hexaacetic acid (TTHA), dihydroxyethylglycine (DHEG), iminodiacetic acid (IDA), nitrilotrimethylphosphonic acid (NTP), N-(2-hydroxyethyl) iminodiacetic acid (HIDA), ethylenediamine-N,N'-dipropionic acid (EDDP), ethylenediaminetetra(methylenephosphonic) acid (EDTPO), nitrilotrimethylphosphonic acid (NTP) and 1,2-bis(o-aminophenoxy)ethane-N,N,N',N'-tetraacetic acid (BAPTA). In some embodiments, said cell membrane stabilizer comprises one or more member(s) selected from the group consisting of: a vitamin E conjugate, poly-L-lysine, diazolidinyl urea, imidazolidinyl urea, dimethoylol-5,5dimethylhydantoin, dimethylol urea, 2-bromo-2-nitropropane-1,3-diol, oxazolidines, sodium hydroxymethyl glycinate, 5-hydroxymethoxymethyl-1-1-aza-3,7-dioxabicyclo [3,3.0]octane, 5-hydroxymethyl-1-1-aza-3,7-dioxabicyclo[3,3.0]octane, 5-hydroxypoly[methyleneoxy]methyl-1-1-aza-3, 7-dioxabicyclo[3,3.0]octane, and quaternary adamantine. In some embodiments, said nucleic acid compactor comprises one or more member(s) selected from the group consisting of: a cationic polymer, a polyamine, poly-L-lysine, spermine, and spermidine. In some embodiments, said antimicrobial agent comprises one or more member(s) selected from the group consisting of: penicillin, streptomycin, and amphotericin B. In some embodiments, the method further comprises, prior to (b), extracting said plurality of nucleic acid molecules from said solution. In some embodiments, in presence of said preservation mixture for a time period of at least 3 days, said nucleic acid molecules have an average length greater than about 30 nucleic acid bases. In some embodiments, in presence of said preservation mixture at a temperature that is within a range from about −40 degrees Celsius (° C.) to about 20° C., said nucleic acid molecules have an average length greater than about 30 nucleic acid bases. In some embodiments, in presence of said preservation mixture at a temperature that is within a range from about 20° C. to about 40° C., said nucleic acid molecules have an average length greater than about 30 nucleic acid bases. In some embodiments, in presence of said preservation mixture for a period of at least about 3 days at a temperature that is within a range from about 40° C. to about 80° C., said nucleic acid molecules have an average length greater than about 30 nucleic acid bases. In some embodiments, subsequent to storage of said preservation mixture for at least 6 months, when in presence of said preservation mixture, said nucleic acid molecules have an average length greater than about 30 nucleic acid bases. In some embodiments, the method further comprises identifying a presence or absence of a urinary disorder based at least in part on said sequencing reads. In some embodiments, said identifying comprises one or more of a sensitivity of at least about 90%, a specificity of at least about 90%, and an accuracy of at least about 90%. In some embodiments, said identifying comprises one or more of a sensitivity of at least about 90%, a specificity of at least about 90%, and an accuracy of at least about 90%. In some embodiments, said identifying comprises applying a machine learning procedure to said sequencing reads. In some embodiments, said machine learning procedure comprises one or more member(s) selected from the group consisting of: support vector machines, random forest, artificial neural networks, convolutional neural networks, deep learning, ultra-deep learning, gradient boosting, AdaBoosting, decision trees, linear regression, and logistic regression. In some embodiments, said greater molecular complexity comprises a greater unique molecule coverage. In some embodiments, said greater molecular complexity comprises a greater diversity of unique molecules. In some embodiments, said greater molecular complexity comprises a greater number of unique sequencing reads.

In another aspect, the present disclosure provides a method for processing a urine sample, comprising: (a) receiving a solution comprising nucleic acid molecules from a urine of a subject, which solution comprises a preservation mixture, wherein, in presence of said preservation mixture for a time period of at least 3 days, said nucleic acid molecules have an average length greater about 30 nucleic acid bases; (b) sequencing a plurality of nucleic acid molecules derived from said nucleic acid molecules to generate a plurality of sequencing reads; and (c) generating an output with said plurality of sequencing reads.

In some embodiments, said time period is at least 5 days. In some embodiments, said time period is at least 1 week.

In another aspect, the present disclosure provides a preservation mixture comprising an iron chelator, wherein said preservation mixture is configured to preserve nucleic acid molecules in a urine sample.

In some embodiments, said iron chelator is selected from the group consisting of Enterobactin and Desferrioxamine.

In another aspect, the present disclosure provides a preservation mixture that is configured to preserve a first set of nucleic acid molecules in a urine sample to yield at least about a 5% greater sequencing molecular complexity upon sequencing said nucleic acid molecules or derivatives thereof, which at least about 5% greater sequencing molecular complexity is as compared to a second set of said nucleic acid molecules being preserved in a reference composition comprising: a volume-excluding polymer present in an amount from about 10% to about 50% by weight of said reference composition, an osmotic agent present in an amount of about 1% to about 20% by weight of said reference composition, and an enzyme inhibitor present in an amount from about 1% to about 30% by weight of said reference composition.

In some embodiments, said preservation mixture comprises a first chelator and one or more member(s) selected from the group consisting of: a pH buffer, a second chelator that is different from said first chelator, a cell membrane stabilizer, a nucleic acid compactor, and an antimicrobial agent. In some embodiments, said preservation mixture comprises said first chelator and said second chelator. In some embodiments, said pH buffer maintains said preservation mixture at a pH that is between 7 and 9. In some embodiments, said first chelator has a first binding affinity for a first metal and said second chelator has a second binding affinity for said first metal, said first binding affinity being greater than said second binding affinity. In some embodiments, said first metal comprises one or more member(s) selected from the group consisting of: vanadium (V), chromium (Cr), manganese (Mn), iron (Fe), cobalt (Co), copper (Cu), zinc (Zn), and molybdenum (Mo). In some embodiments, said first chelator has a third binding affinity for a second metal and said second chelator has a fourth binding affinity for said second metal, said second metal being different from said first metal, and said third binding affinity being less than said fourth binding affinity. In some embodiments, said first chelator comprises one or more member(s) selected from the group consisting of: a siderophore, a nucleoside monophosphate, a nucleoside diphosphate, a nucleoside triphosphate, and a functional variant thereof. In some embodiments, said siderophore comprises one or more member(s) selected from the group consisting of: Achromobactina, Acinetobactin, Acinetoferrin, Aerobactin, Aeruginic acid, Agrobactin, Agrobactin A, Albomycin, Alcaligin, Alterobactin A, Alterobactin A, Aminochelin, Amonabactin P693, Amonabactin P750, Amonabactin T732, Amonabactin T789, Amphibactin B, Amphibactin C, Amphibactin D, Amphibactin E, Amphibactin F, Amphibactin G, Amphibactin H, Amphibactin I, Amphibactin S, Amphibactin T, Amphi-enterobactin, Amphi-enterobactin C12-OH, Amycolachrome, Anachelin 1, Anachelin 2, Anguibactin, Aquachelin A, Aquachelin B, Aquachelin C, Aquachelin D, Aquachelin I, Aquachelin J, Arthrobactin, Asperchrome A, Asperchrome B1, Asperchrome B2, Asperchrome B3, Asperchrome C, Asperchrome D1, Asperchrome D2, Asperchrome D3, Asperchrome E, Asperchrome F1, Asperchrome F2, Asperchrome F3, Aspergillic acid, Avenic acid, Azotobactin, Azotobactin 87, Azotobactin D, Azotochelin, Azoverdin, Bacillibactin, Basidiochrome, Bisucaberin, Carboxymycobactin, Carboxymycobactin 1, Carboxymycobactin 2, Carboxymycobactin 3, Carboxymycobactin 4, Cepabactin, Chrysobactin, Citrate, Coelichelin, Coprogen, Coprogen B, Corynebactin, Deoxydistichonic acid, 2'-Deoxymugineic acud, Deoxyschizokinen, Des(diserylglycyl)-ferrirhodin, Desacetylcoprogen, Desferrioxamine A1A, Desferrioxamine A1B, Desferrioxamine A2, Desferrioxamine B, Desferrioxamine D1, Desferrioxamine D2, Desferrioxamine E, Desferrioxamine Et1, Desferrioxamine Et2, Desferrioxamine Et3, Desferrioxamine G1, Desferrioxamine G2A, Desferrioxamine G2B, Desferrioxamine G2C, Desferrioxamine H, Desferrioxamine N, Desferrioxamine P1, Desferrioxamine T1, Desferrioxamine T2, Desferrioxamine T3, Desferrioxamine T7, Desferrioxamine T8, Desferrioxamine Te1, Desferrioxamine Te2, Desferrioxamine Te3, Desferrioxamine X1, Desferrioxamine X2, Desferrioxamine X3, Desferrioxamine X4, Desferrithiocin, 2,3-Dihydroxybenzoylserine, Dimerum acid, Dimethylcoprogen, Dimethylneocoprogen I, Dimethyltriornicin, Distichonic acid, E,E-putrebactene, Enantio Rhizoferrin, Enantio-Pyochelin, Enterobactin, Enterochelin, E-putrebactene, Exochelin MN, Exochelin MS, Ferrichrome, Ferrichrome A, Ferrichrome C, Ferrichrysin, Ferricrocin, Ferrimycin A, Ferrirhodin, Ferrirubin, Ferrocin A, Fimsbactin A, Fimsbactin B, Fimsbactin C, Fimsbactin D, Fimsbactin E, Fimsbactin F, Fluvibactin, Formobactin, Fusarinine, Fusarinine A, Fusarinine B, Fusarinine C, Heterobactin A, Heterobactin B, Hydroxycopren, Hydroxyisoneocoprogen I, 3-Hydroxymugineic acid, Hydroxy-neocoprogen I, Isoneocoprogen I, Isopyoverdin 10.7, Isopyoverdin 6.7, Isopyoverdin 7.13, Isopyoverdin 90-33, Isopyoverdin 90-44, Isopyoverdin BTP1, Isotriornicin, Itoic acid, Loihichelin A, Loihichelin B, Loihichelin C, Loihichelin D, Loihichelin E, Loihichelin F, Maduraferrin, Malonichrome, Marinobactin, Marinobactin, Marinobactin, Marinobactin, Marinobactin, Marinobactin, Micacocidin, Moanachelins, Moanachelins, Moanachelins, Moanachelins, Moanachelins, Monoglucosylated, Mugineic, Mycobactin A, Mycobactin Av, Mycobactin F, Mycobactin H, Mycobactin J, Mycobactin M, Mycobactin N, Mycobactin NA, Mycobactin P, Mycobactin R, Mycobactin S, Mycobactin T, Myxochelin, Nannochelin A, Nannochelin B, Nannochelin C, Neocoprogen I, Neocoprogen II, Neurosporin, Nocobactin, Ochrobactin A, Ochrobactin B, Ochrobactin C, Ornibactin-C4, Ornibactin-C6, Ornibactin-C8, Ornicorrugatin, Palmitoylcoprogen, Parabactin, Parabactin A, Petrobactin, Petrobactin disulphonate, Petrobactin sulphonate, Pistillarin, Protochelin, Pseudoalterobactin A, Pseudoalterobactin B, Pseudobactin, Pseudobactin 589A, Putrebactin, Pyochelin, Pyoverdin 1, Pyoverdin 10.1, Pyoverdin 10.10, Pyoverdin 10.2, Pyoverdin 10.3, Pyoverdin 10.4, Pyoverdin 10.5, Pyoverdin 10.6, Pyoverdin 10.8, Pyoverdin 10.9, Pyoverdin 11.1, Pyoverdin 11.2, Pyoverdin 11370, Pyoverdin 12, Pyoverdin 12.1, Pyoverdin 12.2, Pyoverdin 13525, Pyoverdin 1547, Pyoverdin 17400, Pyoverdin 18-1, Pyoverdin 19310, Pyoverdin 2192, Pyoverdin 2392, Pyoverdin 2461, Pyoverdin 2798, Pyoverdin 51 W, Pyoverdin 6.1, Pyoverdin 6.2, Pyoverdin 6.3, Pyoverdin 6.4, Pyoverdin 6.5, Pyoverdin 6.6, Pyoverdin 6.8, Pyoverdin 7.1, Pyoverdin 7.10, Pyoverdin 7.11, Pyoverdin 7.12, Pyoverdin 7.14, Pyoverdin 7.15, Pyoverdin 7.16, Pyoverdin 7.17, Pyoverdin 7.18, Pyoverdin 7.19, Pyoverdin 7.2, Pyoverdin 7.3, Pyoverdin 7.4, Pyoverdin 7.5, Pyoverdin 7.6, Pyoverdin 7.7, Pyoverdin 7.8, Pyoverdin 7.9, Pyoverdin 8.1, Pyoverdin 8.2, Pyoverdin 8.3, Pyoverdin 8.4, Pyoverdin 8.5, Pyoverdin 8.6, Pyoverdin 8.7, Pyoverdin 8.8, Pyoverdin 8.9, Pyoverdin 9.1, Pyoverdin 9.10, Pyoverdin 9.11, Pyoverdin 9.12, Pyoverdin 9.2, Pyoverdin 9.3, Pyoverdin 9.4, Pyoverdin 9.5, Pyoverdin 9.6, Pyoverdin 9.7, Pyoverdin 9.8, Pyoverdin 9.9, Pyoverdin 90-51, Pyoverdin 95-275, Pyoverdin 96-312, Pyoverdin 96-318, Pyoverdin 9AW, Pyoverdin A214, Pyoverdin BTP2, Pyoverdin C, Pyoverdin CHAO, Pyoverdin D-TR133, Pyoverdin E, Pyoverdin G, Pyoverdin GM, Pyoverdin I-III, Pyoverdin P19, Pyoverdin Pau, Pyoverdin PL8, Pyoverdin PVD, Pyoverdin R', Pyoverdin Thai, Pyoverdin TII, Pyridoxatin, Quinolobactin, Rhizobactin, Rhizobactin 1021, Rhizoferrin, Rhizoferrin analogues, Rhodotrulic acid, Sake Colorant A, Salmochelin S1, Salmochelin S2, Salmochelin S4, Salmochelin SX, Salmycin A, Schizokinen, Serratiochelin, Siderochelin A, Snychobactin A, Snychobactin B, Snychobactin C, Staphyloferrin A, Staphyloferrin B, Taiwachelin, Tetraglycine ferrichrome, Thiazostatin, Triacetylfusarine, Triornicin, Vibriobactin, Vibrioferrin, Vicibactin, Vulnibactin, and Yersiniabactin. In some embodiments, said second chelator comprises one or more member(s) selected from the group consisting of: ethylenediamintetraacetic acid (EDTA), nitrilotriacetic acid (NTA), trans-1,2-cyclohexanediaminetetraacetic acid (CyDTA), diethylenetriaminepentaacetic acid (DTPA), glycoletherdiaminetetraacetic acid (GEDTA), triethylenetetramine-N,N,N',N'',N''',N''''-hexaacetic acid (TTHA), dihydroxyethylglycine (DHEG), iminodiacetic acid (IDA), nitrilotrimethylphosphonic acid (NTP), N-(2-hydroxyethyl) iminodiacetic acid (HIDA), ethylenediamine-N,N'-dipropionic acid (EDDP), ethylenediaminetetra(methylenephosphonic) acid (EDTPO), nitrilotrimethylphosphonic acid (NTP) and 1,2-bis(o-aminophenoxy)ethane-N,N,N',N'-tetraacetic acid (BAPTA). In some embodiments, said cell membrane stabilizer comprises one or more member(s) selected from the group consisting of: a vitamin E conjugate, poly-L-lysine, diazolidinyl urea, imidazolidinyl urea, dimethoylol-5,5dimethylhydantoin, dimethylol urea, 2-bromo-2-nitropropane-1,3-diol, oxazolidines, sodium hydroxymethyl glycinate, 5-hydroxymethoxymethyl-1-1-aza-3,7-dioxabicyclo [3,3.0]octane, 5-hydroxymethyl-1-1-aza-3,7-dioxabicyclo[3,3.0]octane, 5-hydroxypoly[methyleneoxy]methyl-1-1-aza-3, 7-dioxabicyclo[3,3.0]octane, and quaternary adamantine. In some embodiments, said nucleic acid compactor comprises one or more member(s) selected from the group consisting of: a cationic polymer, a polyamine, poly-L-lysine, spermine, and spermidine. In some embodiments, said antimicrobial agent comprises one or more member(s) selected from the group consisting of: penicillin, streptomycin, and amphotericin B. In some embodiments, in presence of said preservation mixture for a time period of at least 3 days, said nucleic acid molecules have an average length greater than about 30 nucleic acid bases. In some embodiments, in presence of said preservation mixture at a temperature that is within a range from about −40 degrees Celsius (° C.) to about 20° C., said nucleic acid molecules have an average length greater than about 30 nucleic acid bases. In some embodiments, in presence of said preservation mixture at a temperature that is within a range from about 20° C. to about 40° C., said nucleic acid molecules have an average length greater than about 30 nucleic acid bases. In some embodiments, in presence of said preservation mixture for a period of at least about 3 days at a temperature that is within a range from about 40° C. to about 80° C., said nucleic acid molecules have an average length greater than about 30 nucleic acid bases. In some embodiments, subsequent to storage of said preservation mixture for at least 6 months, when in presence of said preservation mixture, said nucleic acid molecules have an average length greater than about 30 nucleic acid bases. In some embodiments, said greater molecular complexity comprises a greater unique molecule coverage. In some embodiments, said greater molecular complexity comprises a greater diversity of unique molecules. In some embodiments, said greater molecular complexity comprises a greater number of unique sequencing reads. In some embodiments, said preservation mixture demonstrates at least about a 5% greater shelf life when compared to said reference composition. In some embodiments, said nucleic acid molecules have an average length greater than about 30 nucleic acid bases when in presence of said preservation mixture for a time period at least about 5% greater than when in presence of said reference composition.

In another aspect, the present disclosure provides a preservation mixture comprising: a pH buffer, a first chelator, a second chelator, a cell membrane stabilizer, a nucleic acid compactor, and an antimicrobial agent.

In another aspect, the present disclosure provides a preservation mixture comprising 100 mM Tris-HCl buffer, 50 mM EDTA, 110 μg poly-L-lysine hydrobormide at a mixed molecular weight of 1,000 Da to 5,000 Da, 1 mg D-alpha-tocopherol polyethylene glycol 1000 succinate (water soluble vitamin E conjugate), 5 μM Enterobactin, 100 units of penicillin, 100 units of streptomycin, and 0.25 μg/mL Amphotericin B.

In some embodiments, the present disclosure provides a kit for performing a method disclosed herein for preserving a urine sample in a preservation mixture, the kit comprising: a preservation mixture comprising: (a) a pH buffer, a first chelator, a second chelator, a cell membrane stabilizer, a nucleic acid compactor, and an antimicrobial agent; and (b) instructions for using said preservation mixture to preserve said urine sample.

In another aspect, the present disclosure provides a preservation mixture comprising at least two different chelators and one or more member(s) selected from the group consisting of: an antimicrobial agent, a cell membrane stabilizer, and a nucleic acid compactor.

In some embodiments, said at least two different chelators comprise a first chelator, which first chelator is selected from the group consisting of: a siderophore, a nucleoside monophosphate, a nucleoside diphosphate, and a nucleoside triphosphate.

In another aspect, the present disclosure provides a kit for preserving a urine sample in a preservation mixture, comprising: (a) a preservation mixture comprising at least two different chelators and one or more member(s) selected from the group consisting of: an antimicrobial agent, a cell membrane stabilizer, and a nucleic acid compactor; and (b) instructions for using said preservation mixture to preserve said urine sample.

In another aspect, the present disclosure provides a preservation mixture comprising: (a) a first chelator, said first chelator having a stability constant of at least 25.2 for formation of a complex with a metal; and (b) a second chelator that is different from said first chelator, wherein said second chelator has a stability constant that is less than 25.2 for formation of a complex with said metal. In some embodiments, said metal is iron.

In another aspect, the present disclosure provides a kit for preserving a urine sample in a preservation mixture, comprising: (a) a preservation mixture comprising: (i) a first chelator, said first chelator having a stability constant of at least 25.2 for formation of a complex with a metal and (ii) a second chelator that is different from said first chelator, wherein said second chelator has a stability constant that is less than 25.2 for formation of a complex with said metal; and (b) instructions for using said preservation mixture to preserve said urine sample.

In another aspect, the present disclosure provides a method for identifying a urinary tract disorder, comprising: (a) processing a urine sample of a subject to generate a data set comprising a set of microbes in a urinary tract of said subject; (b) processing said set of microbes to generate a classification of said urine sample as being positive or negative for said urinary tract disorder at sensitivity and specificity of at least 90%; and (c) outputting a report identifying said subject as having or not having said urinary tract disorder based on said classification.

In some embodiments, generating said classification comprises determining the presence of one or more cancer-associated microbes selected from the group consisting of *Finegoldia magna[s]*, *Bacteroides dorei[s]*, *Bacteroides vulgatus[ec]*, *Pseudomonas* sp. 1217[ec], *Enterococcus* sp. 7L76[ec], *Staphylococcus[ec]*, *Bacteroides* sp. 148[ec], *Stenotrophomonas maltophilia[ec]*, *Ralstonia insidiosa[ec]*, *Streptococcus pasteurianus[ec]*, *Bifidobacterium longum[ec]*, *Bacteroides ovatus[ec]*, *Enterococcus faecalis[ec]*, *Staphylococcus epidermidis[ec]*, *Staphylococcus aureus[ec]*, *Bacteroides fragilis[ec]*, Betapolyomavirus Human polyomavirus[ec], *Alistipes shahii[c]*, *Bacteroides salanitronis[c]*, *Clostridioides difficile[c]*, *Erysipelothrix rhusiopathiae[c]*, Lambdavirus uncultured virus[c], *Pseudomonas frederiksbergensis[c]*, *Ralstonia mannitolilytica[c]*, *Rhodococcus erythropolis[c]*, *Rhodoccus* species 008[c], *Sphingomonas echinoides[c]*, *Staphylococcus agnetis[c]*, *Staphylococcus lugdunensis[c]*, *Staphyloccus saprophyticus[c]*, *Streptococcus gallolyticus[c]*, *Streptococcus infantarius[c]*, *Streptococcus lutetiensis[c]*, *Streptococcus macedonicus[c]*, *Streptomyces* uncultured bacteria 37b14[c], *Streptomyces* uncultured bacterium 39k17[c], *Triavirus staphylococcus* phage 3A[c], *Triavirus staphylococcus* phage tp310-2[c], and *Triavirus staphylococcus* phage StB20[c].

In some embodiments, generating said classification comprises determining the presence of one or more LUTS-associated microbes selected from the group consisting of Bacteria_Firmicutes_Clostridia_Clostridiales_Peptococcaceae_Desulfitobacterium_hafnien se, Bacteria_Proteobacteria_Gammaproteobacteria_Pseudomonadales_Pseudomonadaceae_Pseudomonas_aeruginosa group, Bacteria_Proteobacteria_Gammaproteobacteria_Pseudomonadales_Pseudomonadaceae_Pseudomonas_aeruginosa, Bacteria_Firmicutes_Bacilli_Bacillales_Staphylococcaceae_Staphylococcus_epidermidis, Bacteria_Firmicutes_Bacilli_Lactobacillales_Streptococcaceae_Streptococcus_anginosus, Bacteria_Bacteroidetes_Bacteroidia_Bacteroidales_Bacteroidaceae_Bacteroides_dorei, Bacteria_Actinobacteria_Actinobacteria_Propionibacteriales_Propionibacteriaceae_Cutibacterium_avidum, Bacteria_Bacteroidetes_Bacteroidia_Bacteroidales_Prevotellaceae_Prevotella_melaninogenica, Bacteria_Actinobacteria_Actinobacteria_Corynebacteriales_Corynebacteriaceae_Corynebacterium_sp. NML98-0116, Bacteria_Firmicutes_Bacilli_Lactobacillales_Aerococcaceae_Aerococcus_urinae, Bacteria_Firmicutes_Tissierellia_Tissierellales_Peptoniphilaceae_Anaerococcus_prevotii, Bacteria_Bacteroidetes_Bacteroidia_Bacteroidales_Porphyromonadaceae_Porphyromonas_asaccharolytica, Bacteria_Firmicutes_Bacilli_Lactobacillales_Streptococcaceae_Streptococcus_anginosus group, Bacteria_Bacteroidetes_Bacteroidia_Bacteroidales_Bacteroidaceae_Bacteroides_fragilis, Bacteria_Actinobacteria_Actinobacteria_Corynebacteriales_Corynebacteriaceae_Corynebacterium_diphtheriae, Viruses_Polyomaviridae_Betapolyomavirus_Human polyomavirus 2, Bacteria_Firmicutes_Bacilli_Bacillales_Staphylococcaceae_Staphylococcus_haemolyticus, Bacteria_Proteobacteria_Gammaproteobacteria_Enterobacterales_Enterobacteriaceae_Escherichia_coli, Bacteria_Firmicutes_Tissierellia_Ezakiella_massiliensis Viruses_Caudovirales_Myoviridae_Hp1virus_Haemophilus virus HP1, Viruses_Caudovirales_Siphoviridae_, Viruses_Caudovirales_Siphoviridae_Lambdavirus_Phage 21, Viruses_Caudovirales_Siphoviridae_Lambdavirus_Enterobacteria phage mEp043 c-1, Bacteria_Firmicutes_Bacilli_Lactobacillales_Streptococcaceae_Streptococcus_dysgalactiae group, Viruses_Caudovirales_Siphoviridae_Lambdavirus_Stx2-converting phage Stx2a_F451, Bacteria_Firmicutes_Tissierellia_Tissierellales_Peptoniphilaceae_Finegoldia_magna, Bacteria_Proteobacteria_Betaproteobacteria_Burkholderiales_Comamonadaceae_Comamonas_bacterium 36B, Bacteria_Firmicutes_Bacilli_Lactobacillales_Streptococcaceae_Streptococcus_suis, Bacteria_Actinobacteria_Actinobacteria_Actinomycetales_Actinomycetaceae_Actinomyces_radingae, Bacteria_Firmicutes_Bacilli_Lactobacillales_Streptococcaceae_Streptococcus_pyogenes, Bacteria_Firmicutes_Bacilli_Lactobacillales_Streptococcaceae_Streptococcus_dysgalactiae, Bacteria_Firmicutes_Bacilli_Lactobacillales_Streptococcaceae_Streptococcus_intermedius, Bacteria_Proteobacteria_Gammaproteobacteria_Enterobacterales_Enterobacteriaceae_Citrobacter_freundii complex, Bacteria_Proteobacteria_Gammaproteobacteria_Pseudomonadales_Pseudomonadaceae_Pseudomonas_putida group, Viruses_Caudovirales_Podoviridae_P22virus_Escherichia phage MSU52-L1, Bacteria_Proteobacteria_Alphaproteobacteria_Sphingomonadales_Erythrobacteraceae_Porphyrobacter_uncultured bacterium Contig1644, Bacteria_Firmicutes_Clostridia_Clostridiales_Peptostreptococcaceae_Filifactor_alocis, Bacteria_Firmicutes_Tissierellia_Ezakiella_peruensis, Bacteria_Actinobacteria_Actinobacteria_Corynebacteriales_Corynebacteriaceae_Corynebacterium_sp. ATCC 6931, Bacteria_Firmicutes_Clostridia_Clostridiales_Peptostreptococcaceae_Clostridioides_difficile, Bacteria_Proteobacteria_Gammaproteobacteria_Enterobacterales_Enterobacteriaceae_Escherichia_marmotae, Viruses_Caudovirales_Podoviridae_Escherichia coli O157 typing phage 10, Viruses_Caudovirales_Podoviridae_Escherichia coli O157 typing phage 9, Viruses_Caudovirales_Podoviridae_Enterobacteria phage Sf101, Bacteria_Actinobacteria_Actinobacteria_Corynebacteriales_Corynebacteriaceae_Lawsonella_clevelandensis, Bacteria_Proteobacteria_Alphaproteobacteria_Sphingomonadales_Sphingomonadaceae_Sphingomonas_panacis, Viruses_Caudovirales_Myoviridae_Enterobacteria phage P88, Bacteria_Actinobacteria_Actinobacteria_Corynebacteriales_Corynebacteriaceae_Corynebacterium_imitans, Bacteria_Proteobacteria_Gammaproteobacteria_Enterobacterales_Enterobacteriaceae_Enterobacter_hormaechei, Bacteria_Firmicutes_Bacilli_Lactobacillales_Lactobacillaceae_Lactobacillus_gasseri, Bacteria_Actinobacteria_Actinobacteria_Propionibacteriales_Propionibacteriaceae_Tessaracoccus_flavus, Bacteria_Firmicutes_Erysipelotrichia_Erysipelotrichales_Erysipelotrichaceae_Erysipelothrix_rhusiopathiae, Bacteria_Proteobacteria_Gammaproteobacteria_Enterobacterales_Yersiniaceae_Yersinia_pseudotuberculosis complex, Bacteria_Actinobacteria_Actinobacteria_Corynebacteriales_Corynebacteriaceae_Corynebacterium_aurimucosum, Bacteria_Firmicutes_Negativicutes_Veillonellales_Veillonellaceae_Negativicoccus_ massiliensis, Bacteria_Bacteroidetes_Bacteroidia_Bacteroidales, Bacteria_Firmicutes_Clostridia_Clostridiales_Peptostreptococcaceae_ Clostridioides_uncultured Clostridiales bacterium, Bacteria_Proteobacteria_Gammaproteobacteria_Pseudomonadales_Pseudomonadaceae_Pseudomonas_versuta, Bacteria_Bacteroidetes_Bacteroidia_Bacteroidales_Bacteroidaceae_Bacteroides_caecimuris, Bacteria_Proteobacteria_Gammaproteobacteria_Enterobacterales_Enterobacteriaceae_Shigella_sp. PAMC 28760, Bacteria_Firmicutes_Tissierellia_Tissierellales_Tissierellaceae_uncultured Tissierellaceae bacterium, Bacteria_Firmicutes_Tissierellia_Tissierellales_Peptoniphilaceae_Anaerococcus_mediterraneensis, Bacteria_Firmicutes_Tissierellia_Tissierellales_Peptoniphilaceae_Ndongobacter_massiliensis, Bacteria_Actinobacteria_Actinobacteria_Propionibacteriales_Propionibacteriaceae_Propionimicrobium_sp. Marseille-P3275, Bacteria_Firmicutes_Tissierellia_Tissierellales_Peptoniphilaceae_Peptoniphilus_sp. ING2-D1G, Bacteria_ Firmicutes_Bacilli_Lactobacillales_Streptococcaceae_Streptococcus_pasteurianus, Viruses_Caudovirales_Podoviridae_Nona33virus, Viruses_Caudovirales_Podoviridae_Nona33virus_ Escherichia virus Min27, Viruses_Caudovirales_Podoviridae_ Epsilon15virus_Escherichia virus phiV10, Bacteria_ Bacteroidetes_Bacteroidia_Bacteroidales_Tannerellaceae_ Parabacteroides_sp. CT06, Viruses_Caudovirales_Myoviridae_Escherichia phage APC_JM3.2, Bacteria_Actinobacteria_Actinobacteria_Actinomycetales_Actinomycetaceae_ Mobiluncus_curtisii, Viruses_Caudovirales_Myoviridae_Escherichia phage YDC107_2, Bacteria_Proteobacteria_Gammaproteobacteria_Enterobacterales_Enterobacteriaceae_Kosakonia_cowanii, Bacteria_Proteobacteria_Gammaproteobacteria_Enterobacterales_Enterobacteriaceae_Escherichia_albertii, Bacteria_Proteobacteria_Gammaproteobacteria_Enterobacterales_Enterobacteriaceae_Escherichia_uncultured *Escherichia* sp., Bacteria_Firmicutes_Clostridia_Clostridiales_Oscillospiraceae_Oscillibacter_uncultured Clostridia bacterium, Bacteria_Bacteroidetes_Bacteroidia_Bacteroidales_Bacteroidaceae_Bacteroides_cellulosilyticus, Bacteria_Proteobacteria_Gammaproteobacteria_Pasteurellales_Pasteurellaceae_Haemophilus_pittmaniae, Bacteria_Actinobacteria_Actinobacteria_ Bifidobacteriales_Bifidobacteriaceae_Gardnerella_vaginalis, Bacteria_Firmicutes_Bacilli_Bacillales_Staphylococcaceae_Staphylococcus_lugdunensis, Bacteria_Bacteroidetes_ Bacteroidia_Bacteroidales_Tannerellaceae_ Tannerella_forsythia, Bacteria_Bacteroidetes_Bacteroidia_Bacteroidales_Prevotellaceae_Prevotella_buccalis, Bacteria_Bacteroidetes_Bacteroidia_Bacteroidales_Prevotellaceae_Prevotella_denticola, Bacteria_Proteobacteria_Gammaproteobacteria_Pseudomonadales_Pseudomonadaceae_Pseudomonas_, Bacteria_Proteobacteria_Gammaproteobacteria_Enterobacterales_Enterobacteriaceae_Salmonella_enterica, Viruses_Caudovirales_Siphoviridae_Lambdavirus_Enterobacteria phage CP-1639, Bacteria_Firmicutes_ Clostridia_Clostridiales_Lachnospiraceae_Flavonifractor_ plautii, Bacteria_Proteobacteria_Gammaproteobacteria_Pseudomonadales_Pseudomonadaceae_Pseudomonas_putida, Bacteria_Actinobacteria_Actinobacteria_Propionibacteriales_Propionibacteriaceae_Propionimicrobium_ lymphophilum, Bacteria_Firmicutes_Bacilli_Lactobacillales_Lactobacillaceae_Lactobacillus_johnsonii, Bacteria_Actinobacteria_Actinobacteria_Corynebacteriales_Corynebacteriaceae_Corynebacterium_marinum, Bacteria_Firmicutes_Clostridia_Clostridiales_Oscillospiraceae_Oscillibacter_valericigenes, Bacteria_Proteobacteria_Gammaproteobacteria_Enterobacterales_Enterobacteriaceae_Enterobacter_cloacae complex, Bacteria_Proteobacteria_Alphaproteobacteria_Rhizobiales, Bacteria_Proteobacteria_Gammaproteobacteria_Enterobacterales_Enterobacteriaceae_Citrobacter_amalonaticus, Bacteria_Proteobacteria_Alphaproteobacteria_Rhizobiales_Rhizobiaceae_Rhizobium, Bacteria_Actinobacteria_Actinobacteria_Corynebacteriales_Corynebacteriaceae_Corynebacterium_jeikeium, Bacteria_Bacteroidetes_Bacteroidia_Bacteroidales_Prevotellaceae_Prevotella_timonensis, Bacteria_Firmicutes_ Clostridia_Clostridiales_Lachnospiraceae_Eubacterium rectale, Bacteria_Firmicutes_Clostridia_Clostridiales_Ruminococcaceae_Ruminiclostridium_[Eubacterium] siraeum, Bacteria_Firmicutes_Tissierellia_Tissierellales_Peptoniphilaceae_Helcococcus_kunzii, Bacteria_Actinobacteria_Actinobacteria_Corynebacteriales_Corynebacteriaceae_Corynebacterium_ureicelerivorans, Bacteria_Proteobacteria_Gammaproteobacteria_Enterobacterales_Morganellaceae_Xenorhabdus_bovienii, Bacteria_Proteobacteria_Alphaproteobacteria_Sphingomonadales_Sphingomonadaceae_Sphingobium_sp. MI1205, Viruses_Caudovirales_Siphoviridae_Lambdavirus_Enterobacteria phage HK106, Bacteria_Proteobacteria_Betaproteobacteria_Burkholderiales_Comamonadaceae_Variovorax_boronicumulans, Bacteria_Actinobacteria_Actinobacteria_Corynebacteriales_Corynebacteriaceae_Corynebacterium_striatum, Bacteria_Proteobacteria_Alphaproteobacteria_Sphingomonadales_Sphingomonadaceae_Sphingobium_chlorophenolicum, Bacteria_Proteobacteria_Gammaproteobacteria_Pseudomonadales_Moraxellaceae_Acinetobacter_baumannii, Bacteria_Proteobacteria_Gammaproteobacteria_Pseudomonadales_Pseudomonadaceae_Pseudomonas_ azotoformans, Bacteria_Proteobacteria_Alphaproteobacteria_Sphingomonadales_Sphingomonadaceae_Sphingobium_sp. YBL2, Bacteria_Proteobacteria_Betaproteobacteria_Neisseriales_Neisseriaceae_Neisseria_gonorrhoeae, Bacteria_Proteobacteria_Betaproteobacteria_Neisseriales_ Neisseriaceae_Neisseria_meningitidis, Bacteria_Proteobacteria_Betaproteobacteria_Neisseriales_Neisseriaceae_ Neisseria_sicca, Bacteria_Proteobacteria_Betaproteobacteria_Neisseriales_Neisseriaceae_Neisseria_elonga ta, Bacteria_Bacteroidetes_Flavobacteriia_Flavobacteriales_Flavobacteriaceae, Bacteria_Bacteroidetes_Bacteroidia_Bacteroidales_Porphyromonadaceae_Porphyromonas_bennonis, Bacteria_Proteobacteria_Gammaproteobacteria_Pasteurellales_Pasteurellaceae_Haemophilus_sp. 1595, Bacteria_Proteobacteria_Gammaproteobacteria_Enterobacterales_Erwiniaceae_Pantoea_, Bacteria_Proteobacteria_Betaproteobacteria_Neisseriales_Neisseriaceae_Eikenella_corrodens, Viruses_Caudovirales_Podoviridae_P22virus_Enterobacteria phage CUS-3, Viruses_Caudovirales_Podoviridae_Epsilon15virus, Bacteria_Proteobacteria_Gammaproteobacteria_Enterobacterales_Enterobacteriaceae, Bacteria_Proteobacteria_Gammaproteobacteria_Enterobacterales_Enterobacteriaceae_Citrobacter_koseri, Bacteria_Proteobacteria_Gammaproteobacteria_Enterobacterales_Enterobacteriaceae_Citrobacter_freundii, Bacteria_Proteobacteria_Gammaproteobacteria_Enterobacterales_Enterobacteriaceae_Klebsiella_aerogenes, Bacteria_Proteobacteria_Gammaproteobacteria_Enterobacterales_Enterobacteriaceae_Enterobacter_cloacae, Bacteria_Proteobacteria_Gammaproteobacteria_Pasteurellales_Pasteurellaceae_Haemophilus_sp. CCUG 30218, Bacteria_Proteobacteria_Gammaproteobacteria_Enterobacterales_Enterobacteriaceae_Escherichia, Bacteria_Proteobacteria_Gammaproteobacteria_Enterobacterales_Enterobacteriaceae_Escherichia_fergusonii, Bacteria_Proteobacteria_Gammaproteobacteria_Enterobacterales_Enterobacteriaceae_Klebsiella, Bacteria_Proteobacteria_Gammaproteobacteria_Enterobacterales_Enterobacteriaceae_Klebsiella_pneumoniae, Bacteria_Proteobacteria_Gammaproteobacteria_Enterobacterales_Enterobacteriaceae_Klebsiella_sp., Bacteria_Proteobacteria_Gammaproteobacteria_Enterobacteales_Morganellaceae_Morganella_morganii, Bacteria_Proteobacteria_Gammaproteobacteria_Enterobacterales_Morganellaceae_Proteus_mirabilis, Bacteria_Proteobacteria_Gammaproteobacteria_Enterobacterales_Enterobacteriaceae_Klebsiella_sp. 2N3, Bacteria_Bacteroidetes_Bacteroidia_Bacteroidales_Prevotellaceae_Prevotella_fusca, Bacteria_Bacteroidetes_Bacteroidia_Bacteroidales_Prevotellaceae_Prevotella_scopos, Bacteria_Actinobacteria_Actinobacteria_Actinomycetales_Actinomycetaceae_Actinotignum_schaalii, Bacteria_Proteobacteria_Gammaproteobacteria_Enterobacterales_Yersiniaceae_Serratia, Bacteria_Proteobacteria_Gammaproteobacteria_Enterobacterales_Enterobacteriaceae_Shigella, Bacteria_Proteobacteria_Gammaproteobacteria_Enterobacterales_Enterobacteriaceae_Shigella_boydii, Bacteria_Proteobacteria_Gammaproteobacteria_Enterobacterales_Enterobacteriaceae_Shigella_dysenteriae, Bacteria_Proteobacteria_Gammaproteobacteria_Enterobacterales_Enterobacteriaceae_Shigella_flexneri, Bacteria_Proteobacteria_Gammaproteobacteria_Enterobacterales_Enterobacteriaceae_Shigella_sonnei, Bacteria_Proteobacteria_Gammaproteobacteria_Enterobacterales_Yersiniaceae_Yersinia, Bacteria_Proteobacteria_Gammaproteobacteria_Enterobacterales_Yersiniaceae_Yersinia_enterocolitica, Bacteria_Proteobacteria_Gammaproteobacteria_Enterobacterales_Yersiniaceae_Yersinia_pestis, Bacteria_Proteobacteria_Gammaproteobacteria_Enterobacterales_Yersiniaceae_Yersinia_pseudotuberculosis, Bacteria_Proteobacteria_Gammaproteobacteria_Aeromonadales_Aeromonadaceae_Aeromonas_veronii, Bacteria_Proteobacteria_Betaproteobacteria_Neisseriales_Neisseriaceae_Neisseria_sp. KEM232, Bacteria_Proteobacteria_Alphaproteobacteria_Sphingomonadales_Erythrobacteraceae_Porphyrobacter_mixed culture bacterium CY_gF1DD01_14, Bacteria_Proteobacteria_Gammaproteobacteria_Enterobacterales_Hafniaceae_Edwardsiella_ictaluri, Bacteria_Proteobacteria_Gammaproteobacteria_Enterobacterales_Enterobacteriaceae_Citrobacter_rodentium, Bacteria_Proteobacteria_Gammaproteobacteria_Enterobacterales_Enterobacteriaceae_Citrobacter_werkmanii, Viruses_Caudovirales_Siphoviridae_Lambdavirus_Enterobacteria phage H-19B, Bacteria_Proteobacteria_Gammaproteobacteria_Pseudomonadales_Pseudomonadaceae_Pseudomonas_plecoglossicida, Bacteria_Fusobacteria_Fusobacteriia_Fusobacteriales_leptotrichiaceae_Leptotrichia_sp. oral taxon 212, Bacteria_Proteobacteria_Gammaproteobacteria_Pasteurellales_Pasteurellaceae_Aggregatibacter_actinomycetemcomitans, Bacteria_Proteobacteria_Gammaproteobacteria_Pasteurellales_Pasteurellaceae_Haemophilus_haemolyticus, Bacteria_Proteobacteria_Gammaproteobacteria_Pasteurellales_Pasteurellaceae_Haemophilus_influenzae, Bacteria_Proteobacteria_Gammaproteobacteria_Pasteurellales_Pasteurellaceae_Haemophilus_parainfluenzae, Bacteria_Proteobacteria_Gammaproteobacteria_Pasteurellales_Pasteurellaceae_Histophilus_somni, Bacteria_Proteobacteria_Gammaproteobacteria_Pasteurellales_Pasteurellaceae_Aggregatibacter_aphrophilus, Bacteria_Proteobacteria_Epsilonproteobacteria_Campylobacterales_Campylobacteraceae_Campylobacter_hominis, Bacteria_Proteobacteria_Gammaproteobacteria_Pseudomonadales_Pseudomonadaceae_Pseudomonas_monteilii, Bacteria_Proteobacteria_Betaproteobacteria_Burkholderiales_Comamonadaceae_Comamonas_uncultured bacterium, Bacteria_Proteobacteria_Epsilonproteobacteria_Campylobacterales_Campylobacteraceae_Campylobacter_ureolyticus, Bacteria_Bacteroidetes_Bacteroidia_Bacteroidales_Porphyromonadaceae_Porphyromonas_gingivalis, Bacteria_Proteobacteria_Gammaproteobacteria_Pseudomonadales_Moraxellaceae_Acinetobacter_calcoaceticus/baumannii complex, and Bacteria_Proteobacteria_Alphaproteobacteria_Rhizobiales_Bradyrhizobiaceae_Tardiphaga_robinia.

In some embodiments, generating said classification comprises determining the presence of one or more normal condition-associated microbes selected from the group consisting of *Klebsiella pneumoniae*$^{en}$, *Shigella sonnei*$^{en}$, *Klebsiella variicola*$^{en}$, *Prevotella* sp. oral taxon 299$^{en}$, *Shigella dysenteriae*$^{en}$, *Shigella*$^{en}$, *Pseudomonas aeruginosa*$^{en}$, *Pseudomonas aeruginosa* group$^{en}$, *Salmonella enterica*$^{en}$, *Escherichia coli*$^{en}$, *Shigella boydii*$^{en}$, *Shigella* sp. PAMC 28760$^{en}$, *Shigella flexneri*$^{en}$, Betapolyomavirus Human polyomavirus 2$^{en}$, *Escherichia fergusonii*$^{en}$, *Prevotella scopos*$^{en}$, *Prevotella melaninogenica*$^{en}$, *Escherichia albertii*$^{en}$, *Klebsiella* [Enterobacter] *aerogenes*$^{en}$, *Barnesiella viscericola*$^{en}$, *Bacteroides*$^{en}$, *Devosias* sp. H5989$^{en}$, *Streptococcus pneumoniae*$^{en}$, *Citrobacter freundii*$^{en}$, *Prevotella enoeca*$^{en}$, *Bacteroides thetaiotaomicron*$^{en}$, *Escherichia* uncultured *Escherichia* sp.$^{en}$, *Helcococcus kunzii*$^{en}$, *Parabacteroides distasonis*$^{en}$, *Pseudomonas oleovorans/pseudoalcaligenes* group$^{en}$, *Pseudomonas pseudoalcaligenes*$^{en}$, *Mobiluncus curtisii*$^{en}$, *Streptococcus dysgalactiae*$^{en}$, *Streptococcus dysgalactiae* group$^{en}$, *Gardnerella vaginalis*$^{en}$, and *Streptococcus pyogenes*$^{en}$.

In some embodiments, said urine is preserved in a preservation solution. In some embodiments, said urine is processed immediately after collection. In some embodiments, generating said classification comprises applying a machine learning classification to said set of microbes. In some embodiments, said classification is at a sensitivity of at least 90%. In some embodiments, said classification is at a specificity of at least 90%. In some embodiments, said data set further comprises a plurality of nucleic acid molecules originating from a tissue of said subject. In some embodiments, the method further comprises processing said plurality of nucleic acid molecules from said data set to identify (i) one or more genetic aberrations, and/or (ii) an increase or a decrease in a level of expression of at least a subset of said plurality of nucleic acid molecules relative to a reference. In some embodiments, the method further comprises using said machine learning classifier to identify said one or more genetic aberrations and/or said increase or decrease in said level of expression. In some embodiments, (a) comprises processing said urine sample to identify a relative abundance of said set of microbes in said urinary tract of said subject. In some embodiments, (a) comprises subjecting said urine sample to nucleic acid sequencing. In some embodiments, (b) comprises generating said classification based on (i) one or more genetic aberrations identified from said nucleic acid sequencing and (ii) a set of one or more of said set of microbes. In some embodiments, (b) comprises generating data indicative of a level of said set of microbes and processing said data against a reference to identify said relative abundance. In some embodiments, said relative abundance is an excess or deficiency of said set of microbes. In some embodiments, said excess or deficiency of said set of microbes is associated with a urinary tract disorder. In some embodiments, said urinary tract disorder is a lower urinary tract disorder. In some embodiments, said urinary tract disorder is a bladder disorder. In some embodiments, said bladder disorder comprises one or more member(s) selected from the group consisting of: bladder cancer, bladder exstrophy, bladder outlet obstruction, bladder sphincter dyssynergia, catheter-associated urinary tract infection, choluria, cystitis, cystitis glandularis, glomerulation, Gouverneur's syndrome, hemorrhagic cystitis, Hunner's ulcer, insterstitial cystitis, megacystitis, neurogenic bladder dysfunction, overactive bladder, spermaturia, trigonitis, underactive bladder, urinary bladder neck obstruction, urge incontinence, vesicointestinal fistula, and vesicoureteral reflux. In some embodiments, said urinary tract disorder is a kidney disorder. In some embodiments, said kidney disorder comprises one or more member(s) selected from the group consisting of: Abderhalden-Kaufmann-Lignac syndrome, acute proliferative glomerulonephritis, adenine phosphoribosyltransferase deficiency, Alport syndrome, analgesic nephropathy, autosomal dominant polycystic kidney disease, autosomal recessive polycystic kidney disease, Balkan endemic nephropathy, benign nephrosclerosis, Bright's disease, cardiorenal syndrome, chronic kidney disease, congenital nephrotic syndrome, conorenal syndrome, contrast-induced nephropathy, cystic kidney disease, Dent's disease, diabetic nephropathy, diffuse proliferative nephritis, distal renal tubular acidosis, diuresis, EAST syndrome, Fanconi syndrome, Fechtner syndrome, focal proliferative nephritis, focal segmental glomerulosclerosis, Fraley syndrome, Galloway Mowat syndrome, Gitelman syndrome, glomerulocystic kidney disease, glomerulopathy, Goldblatt kidney, Goodpasture syndrome, high anion gap metabolic acidosis, HIV-associated nephropathy, horseshoe kidney, hydronephrosis, hypertensive kidney disease, IgA nephropathy, interstitial nephritis, juvenile nephronopthisis, kidney cancer, kidney stone disease, Lightwood-Albright syndrome, lupus nephritis, malarial nephropathy, medullary cystic kidney disease, medullary sponge kidney, membranous glomerulonephritis, Mesoamerican nephropathy, milk-alkali syndrome, minimal mesangial glomerulonephritis, multicystic dysplastic kidney, nephritis, nephrocalcinosis, nephrogenic diabetes insipidus, nephromegaly, nephrotosis, nephrosis, nephrotic syndrome, Nutcracker syndrome, papillorenal syndrome, phosphate neuropathy, polycystic kidney disease, primary hyperoxaluria, proximal renal tubular acidosis, pyelonephritis, pyonephrosis, rapidly progressive glomerulonephritis, renal agenesis, renal angina, renal artery stenosis, renal cyst, renal ischemia, renal osteodystrophy, renal papillary necrosis, renal tubular acidosis, renal vein thrombosis, reninoma, secondary hypertension, serpentine fibula-polycystic kidney syndrome, shunt nephritis, sickle cell nephropathy, thin basement membrane disease, transplant glomerulopathy, tubulointerstitital nephritis and uveitis, tubulopathy, uremia, uremic frost, and Wunderlich syndrome. In some embodiments, said urinary tract disorder is a urethra disorder. In some embodiments, said urethra disorder comprises one or more member(s) selected from the group consisting of: urethral meatal stenosis, urethral caruncle, urethral foreign body, urethral stricture, urethral syndrome, urethritis, and urethrorrhagia. In some embodiments, said urinary tract disorder is a ureter disorder. In some embodiments, said ureter disorder comprises one or more member(s) selected from the group consisting of: duplicated ureter, megaureter, ureteritis, and ureterocele. In some embodiments, said urinary tract disorder is a prostate disorder. In some embodiments, said prostate disorder comprises one or more member(s) selected from the group consisting of: prostatitis, acute prostatitis, asymptomatic inflammatory prostatitis, chronic bacterial prostatitis, chronic prostatitis, granulomatous prostatitis, IgG4-related prostatitis, male accessory gland infection, benign prostatic hyperplasia, and prostate cancer. In some embodiments, said urinary tract disorder is a testicular disorder. In some embodiments, said testicular disorder comprises one or more member(s) selected from the group consisting of: ectopic testis, epididymitis, gonadal torsion, orchitis, orchialgia, macroorchidism, testicular cancer, genital tuberculosis, hydrocele, hydrocele testis, rete tubular ectasia, Sertoli cell nodule, testicular atrophy, testicular dysgenesis syndrome, testicular microlithiasis, testicular pain, testicular rupture, testicular sarcoidosis, testicular torsion, and testicular trauma. In some embodiments, said urinary tract disorder is a penile disorder. In some embodiments, said penile disorder comprises one or more member(s) selected from the group consisting of: penile cancer, erectile dysfunction, priapism, induratio penis plastic, Peyronie's disease, aposthia, balanitis, penile fracture, penile injury, penile pain, and penile artery shunt syndrome. In some embodiments, said urinary tract disorder comprises one or more member(s) selected from the group consisting of: reactive arthritis, Reiter's syndrome, and urosepsis. In some embodiments, the method further comprises repeating (a)-(c) for each of a plurality of subjects, identifying a subset of subjects from said plurality of subjects, wherein each subject of said subset of subjects is associated with a urine sample classified as being positive for said urinary tract disorder, and wherein each subject of said subset of subjects does not display symptoms of said urinary tract disorder. In some embodiments, said first set of microbes comprises one or more microbes from a taxonomic kingdom selected from the group consisting of: Bacteria, Viruses, Bacteriophages, and Archaea. In some embodiments, said set of microbes comprises one or more microbes from a taxonomic phylum selected from the group consisting of: Proteobacteria, Firmicutes, Actinobacteria, Bacteroidetes, Aquificae, Deinococcus-Thermus, Fusobacteria, and Tenericutes. In some embodiments, said set of microbes comprises one or more microbes from a taxonomic class selected from the group consisting of: Gammaproteobacteria, Betaproteobacteria, Clostridia, Alphaproteobacteria, Bacilli, Actinobacteria, Tissierellia, Bacteroidia, Erysipelotrichia, Aquificiae, Deinococci, Epsilonproteobacteria, Flavobacteria, Fusobacteria, Mollicutes, Negativicutes, and Coriobacteria. In some embodiments, said set of microbes comprises one or more microbes from a taxonomic order selected from the group consisting of: Pseudomonadales, Enterobacterales, Caudovirales, Actinomycetales, Corynebacteriales, Burkholderiales, Clostridiales, Rhizobiales, Streptomycetales, Sphingomonadales, Lactobacillales, Bifidobacteriales, Pseudonocardiales, Bacteroidales, Xanthomonadales, Bacillales, Erysipelotrichales, Acidaminococcales, Campylobacterales, Desulfurobacteriales, Fusobacteriales, Herpesvirales, Micrococcales, Mycoplasmatales, Neisseriales, Pasteurellales, Picornavirales, Propionibacteriales, Thermales, Veillonellales, Vibrionales, Flavobacteriales, Tissierellales, Aeromonadales, Coriobacteriales, and Eggerthellales. In some embodiments, said set of microbes comprises one or more microbes from a taxonomic family selected from the group consisting of: Myoviridae, Porphyromonadaceae, Pseudomonoadaceae, Enterobacteriaceae, Actinomycetaceae, Prevotellaceae, Burkholderiaceae, Siphoviridae, Hyphoicrobiaceae, Streptomycetaceae, Sphingomonadaceae, Peptoniphilaceae, Bifidobacteriaceae, Peptostreptococcaceae, Polyomaviridae, Xanthomonadaceae, Staphylococcaceae, Bacteroidaceae, Erysipelotrichaceae, Nocardiaceae, Rikenellaceae, Acidaminococcaceae, Aerococcaceae, Bradyrhizobiaceae, Campylobacteraceae, Comamonadaceae, Corynebacteriaceae, Desulfurobacteriaceae, Erwiniaceae, Flavobacteriaceae, Hafniaceae, Helicobacteraceae, Herpesviridae, Lachnospiraceae, Lactobacillaceae, Leptotrichiaceae, Microbacteriaceae, Micrococcaceae, Morganellaceae, Mycoplasmataceae, Neisseriaceae, Oxalobacteraceae, Paenibacillaceae, Pasteurellaceae, Peptococcaceae, Picornaviridae, Podoviridae, Propionibacteriaceae, Rhizobiaceae, Ruminococcaceae, Thermaceae, Veillonellaceae, Vibrionaceae, Yersiniaceae, Arenaviridae, Streptococcaceae, Tissierellaceae, Tannerellaceae, Oscillospiraceae, Aeromonadaceae, Erythrobacteraceae, Moraxellaceae, Barnesiellaceae, Intrasporangiaceae, Coriobacteriaceae, and Eggerthellaceae. In some embodiments, said set of microbes comprises one or more microbes from a taxonomic genus selected from the group consisting of: *Klebsiella, Lambdavirus, Shigella, Pseudomonas, Citrobacter, Salmonella, Escherichia, Prevoltella, Barnesiella, Devosia, Streptomyces, Bifidobacterium, Sphingomonas, Helcococcus, Parabacteroides, Mobilunus, Gardnerella, Finegoldia, Streptococcus,* Betapolyomavirus, *Stenotrophomonas, Enterococcus, Ralstonia, Staphylococcus, Bacteroides, Alistipes, Clostridioides, Erysipelothrix, Rhodococcus, Triavirus, Acidaminococcus, Actinomyces, Actinotignum, Aerococcus, Aggregatibacter, Anaerococcus, Blautia, Bradyrhizobium, Burkholderia, Campylobacter, Cornyebacterium, Cutibacterium, Desulfitobacterium, Enterobacter,* Epsilon15virus, *Ezakiella,* F116virus, *Faecalibacterium, Filifactor, Fusobacterium, Haemophilus, Hafnia, Helicobacter, Histophilus, Janthinobacterium, Kluyvera, Lacnoclostridium, Lactobacillus, Lawsonella, Limnohabitans, Lymphocryptovirus, Mageeibacillus, Microbacterium, Micrococcus, Morganella, Neisseria, Ornithobacterium,* P22virus, P2virus, *Paenibacillus, Pantoea, Parvimonas, Peptoniphilus, Porphyromonas, Propionibacterium, Propionmicrobium, Proteus, Pseudarthrobacter, Raoultella, Rhizobium, Rhodopseudomonas, Roseolovirus, Rothia, Ruminiclostridium, Ruminococcus, Salivirus, Serratia, Sneathia, Sphingobium, Thermovibrio, Thermus, Ureaplasma, Varibaculum, Veillonella, Vibrio, Xenorhabdus, Yersinia, Mammarenavirus, Variovorax, Prevotella, Methylibium, Polynucleobacter,* P68virus, *Thiomonas, Phycicoccus, Acidovorax, Anaerostipes, Collinsella, Hydrogenophaga, Lachnoclostridium, Eggerthella, Negativicoccus, Ndongobacter, Mobiluncus, Kosakonia, Oscillibacter, Tannerella, Flavonifractor, Tessaracoccus, Eikenella, Aeromonas, Porphyrobacter, Edwardsiella, Leptotrichia, Comamonas, Acinetobacter,* and *Tardiphaga.* In some embodiments, said set of microbes comprises one or more microbes from a taxonomic species selected from the group consisting of: *Klebsiellas pneumoniae, Shigellas sonnei, Klebsiellas varicola, Prevotellas* species oral taxon 299, *Shigellas dysenteriae, Pseudomonas aeruginosa, Salmonellas enterica, Escherichias coli, Shigellas boydii, Shigellas* species PAMC 28760, *Shigellas fexneri,* Betapolyomavirus human, *Excherichias fergusonii, Prevotellas scopos, Prevotellas melaninogenica, Escherichias albertii barnesiellas viscericola, Devosias* species H5989, *Streptococcus pneumoniae, Citrobacters freundii, Prevotellas enoeca, Bacteroides thetaiotaomicron, Helcococcus kunzii, Parabacteroidess distasonis, Pseudomonas oleovorans, Mobiluncus curtisii, Streptococcus dysgalactiae, Streptococcus pyogenes, Gardnerellas vaginalis, Finegoldias magna, Bacteroides dorei, Bacteroides vulgatus, Pseudomonas* species 1217, *Enterococcus* species 7L76, *Bacteroides* species L48, *Ralstonias insidiosa, Streptococcus pasteurianus, Bifidobacterium longum, Bacteroides ovatus, Enterococcus faecalis, Staphylococcus epidermis, Staphylococcus aureus, Bacteroides fragilis, Alistipes shahii, Bacteroides salanitronis, Clostridioides difficile, Erysipelothrix rhusiopathiae,* Lambdavirus uncultured virus, *Pseudomonas frederiksbergensis, Ralstonia mannitolilytica, Rhodococcus erythropolis, Rhodoccus* species 008, *Sphingomonas echinoides, Staphylococcus agnetis, Staphylococcus lugdunensis, Staphyloccus saprophyticus, Streptococcus gallolyticus, Streptococcus infantarius, Streptococcus lutetiensis, Streptococcus macedonicus, Streptomyces* uncultured bacteria 37b14, *Streptomyces* uncultured bacterium 39k17, *Triavirus staphylococcus* phage 3A, *Triavirus staphylococcus* phage tp310-2, *Triavirus staphylococcus* phage StB20, Human herpesvirus 6, Human gammaherpesvirus 4, *Bordetella hinzii, Methylibium petroleiphilum, Shigella* species LN126, Podoviridae, *Lactobacillus jensenii, Burkholderia pseudomallei* group, *Pseudomonas* phage phi297, *Klebsiella michiganensis, Lactobacillus* species B164, *Streptococcus* species I-G2, *Kosakonia sacchari, Ruminococcus bicirculans, Prevotella jejuni, Bradyrhizobium* species llw1, *Agrobacterium tumefaciens* complex, *Pseudomonas* phage YMC/0/01/P52_PAE BP, *Aerococcus sanguinicola, Prevotella* species S4-10, *Corynebacterium frankenforstense, Prevotella* species Sc00026, *Streptococcus* phage EJ-1, Comamonas bacterium 36B, *Micrococcus luteus, Pseudomonas sihuiensis, Staphylococcus haemolyticus, Streptococcus* phage phiD12, *Staphylococcus hominis, Pseudomonas* species ATCC 13867, *Streptococcus oralis, Streptococcus salivarius, Streptococcus suis, Acinetobacter chlamydia*-associated clinical sample 198-T, *Sphingobium* species TKS, *Streptococcus parasanguinis, Tessaracoccus aquimaris, Pluralibacter lignolyticus, Streptococcus intermedius, Ureaplasma parvum, Pseudomonas fluorescens* group, *Pseudomonas putida* group, *Sphingobium yanoikuyae*, *Aerococcus urinae*, *Burkholderia* species BDU6, *Sphingomonas* species LK11, *Bacillus cereus*, *Paenibacillus polymyxa*, *Streptococcus* species VT 162, Comamonadaceae bacterium B1, *Klebsiella quasipneumoniae*, *Corynebacterium simulans*, *Lactobacillus iners*, *Corynebacterium* species ATCC 6931, *Klebsiella* species NCTC 8172, *Lawsonella clevelandensis*, *Lactobacillus* species wkB8, *Sphingomonas taxi*, *Bradyrhizobium* species lamp2, *Streptococcus* phage SpSL1, Enterobacteria phage P88, *Corynebacterium riegelii*, *Corynebacterium imitans*, *Lactobacillus acidophilus*, *Lactobacillus buchneri*, *Lactobacillus delbrueckii*, *Lactobacillus helveticus*, *Cedecea neteri*, *Enterobacter hormaechei*, *Lactobacillus plantarum*, *Lactobacillus gasseri*, *Lactobacillus acetotolerans*, *Lactobacillus amylophilus*, *Lactobacillus amylovorus*, *Tessaracoccus flavus*, *Lactobacillus farciminis*, *Corynebacterium singulare*, *Erwinia gerundensis*, *Hoeflea* species IMCC20628, *Lactobacillus ruminis*, *Pseudomonas lini*, Propionibacterium phage PHLD30, Propionibacterium phage PHL064, Propionibacterium phage PHL082, *Yersinia pseudotuberculosis* complex, *Actinomyces naeslundii*, *Acidovorax* species NA2, *Acidovorax* species P3, *Acidovorax* species P4, *Bifidobacterium adolescentis*, *Bifidobacterium breve*, *Corynebacterium aurimucosum*, *Negativicoccus massiliensis*, *Massilia* species WG5, *Turicibacter* species H121, *Corynebacterium diphtheriae*, *Corynebacterium glutamicum*, *Rothia aeria*, *Propionibacterium freudenreichii*, *Cutibacterium acnes*, *Pseudomonas* phage phi1, *Streptococcus* species A12, *Pseudomonas* species bs2935, *Pseudomonas* phage JBD44, *Pseudomonas* phage YMC11/07/P54_PAE_BP, *Gemella* species oral taxon 928, *Sinorhizobium* species RAC02, *Hydrogenophaga* species RAC07, *Acidovorax* species T1, Lambdavirus, *Sneathia amnii*, *Ndongobacter massiliensis*, *Acidaminococcus intestini*, *Varibaculum* species, *Streptococcus* species NPS 308, *Tessaracoccus* species 72.5-30, *Corynebacterium sphenisci*, *Corynebacterium atypicum*, *Streptococcus* phage IPPS, *Delftia* species HK171, *Klebsiella* species M5a1, *Staphylococcus* phage St 134, Propionibacterium virus Lauchelly, Propionibacterium virus PHL082M03, Propionibacterium virus PHLJ17M01, Propionibacterium virus Stormborn, *Microbacterium paraoxydans*, *Thauera* species K11, Escherichia phage Ayreon, *Dickeya zeae*, *Pseudomonas* species HLS-6, *Paracoccus* species CBA4604, *Citrobacter freundii* complex species CFNIH2, *Citrobacter freundii* complex species CFNIH3, *Alkaliphilus metalliredigens*, *Lachnoclostridium bolteae*, *Ureaplasma urealyticum*, Yersinia virus L413C, *Pseudomonas* species M18, Lachnoclostridium butyrate-producing bacterium SM4/1, Lachnoclostridium butyrate-producing bacterium SS3/4, Plasmid ColV-K30, *Bacteroides cellulosilyticus*, Plasmid R1-19, *Haemophilus pittmaniae*, *Bradyrhizobium canariense*, *Streptococcus pseudopneumoniae*, *Corynebacterium resistens*, *Lactobacillus kefiranofaciens*, *Sphaerochaeta coccoides*, *Thermus thermophilus*, *Bifidobacterium animalis*, *Streptococcus mitis*, *Acinetobacter lwoffli*, *Porphyromonas asaccharolytica*, *Prevotella denticola*, *Prevotella disiens*, *Ornithobacterium rhinotracheale*, Enterobacteria phage CP-1639, *Burkholderia cepacia*, *Brevundimonas diminuta*, *Staphylococcus capitis*, *Pseudomonas fluorescens*, *Pseudomonas tolaasii*, *Veillonella parvula*, *Shigella* species AR-21793, *Turneriella parva*, *Roseburia hominis*, *Pseudomonas putida*, Human betaherpesvirus 6B, *Cutibacterium avidum*, *Cutibacterium granulosum*, *Parvimonas micra*, *Anaerococcus prevotii*, *Sphingobium indicum*, *Sphingobium japonicum*, *Variovorax paradoxus*, *Pseudomonas* phage PA11, *Enterobacter cloacae* complex, *Citrobacter amalonaticus*, *Agrobacterium tumefaciens*, *Verminephrobacter eiseniae*, *Bacteroides xylanisolvens*, *Corynebacterium* species L2-79-05, Enterobacteria phage 933 W sensu lato, *Lactobacillus backii*, *Thermus scotoductus*, *Sinorhizobium fredii*, *Rhizobium leguminosarum*, *Prevotella timonensis*, *Mesorhizobium ciceri*, *Veillonella atypica*, *Tessaracoccus favescens*, *Enterobacter* species 638, *Streptococcus merionis*, *Micrococcus* species A), *Blautia obeum*, *Polyangium brachysporum*, *Azoarcus olearius*, *Thiomonas arsenitoxydans*, *Ralstonia* species Is-C065, *Variovorax boronicumulans*, *Rothia mucilaginosa*, *Enterococcus cecorum*, *Bradyrhizobium oligotrophicum*, *Phycicoccus dokdonensis*, Enterobacteria phage VT1-Sakai, *Lactobacillus crispatus*, *Pseudomonas azotoformans*, *Pseudomonas fulva*, *Neisseria gonorrhoeae*, *Neisseria lactamica*, *Neisseria meningitidis*, *Burkholderia contaminans*, *Neisseria sicca*, *Prevotella dentalis*, *Lactobacillus gallinarum*, *Ochrobactrum anthropi*, *Peptoniphilus harei*, *Raoultella ornithinolytica*, *Enterobacter cloacae*, *Pantoea cypripedii*, *Acidovorax* species NA3, *Thiomonas* species CB2, Enterobacteria phage YYZ-2008, *Thermus brockianus*, *Afipia* genospecies 3, *Citrobacter braakii*, *Lactobacillus* phage Lv-1, *Burkholderia thailandensis*, *Proteus mirabilis*, *Klebsiella* species 2N3, *Prevotella fusca*, *Actinotignum schaalii*, *Serratia liquefaciens*, *Serratia marcescens*, *Kluyvera intermedia*, *Yersinia pestis*, *Yersinia pseudotuberculosis*, *Edwardsiella tarda*, *Aeromonas salmonicida*, *Anaerostipes hadrus*, *Prevotella* species oral taxon 299, *Myxococcus* mixed culture bacterium AM_gF3SD01_05, *Desulfitobacterium* mixed culture bacterium AX_gF3SD01_48, *Comamonas* mixed culture bacterium PE_gF1DD01_04, *Streptococcus anginosus* group, *Rhodoplanes* species Z2-YC6860, *Citrobacter rodentium*, *Citrobacter gillenii*, *Altererythrobacter dongtanensis*, *Corynebacterium* species NML98-0116, *Actinomyces* species oral taxon 414, *Streptococcus* species oral taxon 064, *Streptococcus* species oral taxon 431, *Kocuria palustris*, *Haemophilus influenzae*, *Haemophilus parainfluenzae*, *Aggregatibacter aphrophilus*, *Collinsella aerofaciens*, *Campylobacter hominis*, *Streptococcus constellatus*, *Campylobacter hominis*, *Hydrogenophaga* species PBC, *Delftia acidovorans*, *Campylobacter ureolyticus*, *Leclercia adecarboxylata*, *Lactobacillus amylolyticus*, *Porphyromonas gingivalis*, *Lachnoclostridium saccharolyticum*, *Eggerthella lenta*, *Fusobacterium nucleatum*, *Faecalibacterium prausnitzii*, *Streptococcus* phage phi-SsUD.1, *Bacillus cereus* group, *Aerococcus christensenii*, *Burkholderia cepacia* complex, *Corynebacterium flavum*, *Micrococcus* species MG-2010-D12, *Actinomyces succiniciruminis*, *Streptococcus agalactiae*, *Guanarito mammarenavirus*, *Prevotella intermedia*, *Prevotella enoeca*, *Desulfitobacterium hafniense*, *Pseudomonas aeruginosa* group, *Staphylococcus epidermidis*, *Bacteroides dorei*, *Prevotella melaninogenica*, and Human polyomavirus 2.

In another aspect, the present disclosure provides a method for staging a cancer of a subject, comprising identifying a presence and an amount of one or more microbes indicative of a stage of said cancer.

In some embodiments, the method comprises determining the presence of one or more microbes selected from the group consisting of *Enterobacter aerogenes*, *Erysipelothrix rhusiopathiae*, *Bifidobacterium longum*, *Stenotrophomonas maltophilia*, *Staphylococcus saprophyticus*, *Ruminococcus bromii*, *Sneathia amnii*, *Bradyrhizobium* sp., *Streptococcus salivarius*, *Clostridioides difficile*, *Ralstonia insidiosa*, *Pseudomonas aeruginosa* group, *Staphylococcus epidermidis*, *Streptococcus agalactiae*, *Streptococcus pyogenes*, *Pseudomonas aeruginosa*, *Burkholderia cepacia*, *Faecali-*

*bacterium prausnitzii, Streptococcus lutetiensis, Anaerococcus prevotii, Barnesiella viscericola, Protopolystoma xenopodis, Eubacterium rectale,* Firmicutes bacterium, *Prevotella enoeca,* and Human Polyomavirus 1. In some embodiments, said cancer has a stage Ta, and the method comprises determining the presence of one or more microbes selected from the group consisting of *Streptococcus gallolyticus, Streptococcus pasteurianus, Pseudomonas* sp. 1217, *Enterobacter aerogenes, Erysipelothrix rhusiopathiae, Bifidobacterium longum, Stenotrophomonas maltophilia, Staphylococcus saprophyticus, Ruminococcus bromii, Sneathia amnii, Bradyrhizobium* sp., *Streptococcus salivarius, Clostridioides difficile, Ralstonia insidiosa, Pseudomonas aeruginosa* group, *Staphylococcus epidermidis, Streptococcus agalactiae, Streptococcus pyogenes, Pseudomonas aeruginosa, Burkholderia cepacia, Faecalibacterium prausnitzii, Streptococcus lutetiensis, Anaerococcus prevotii, Barnesiella viscericola, Protopolystoma xenopodis, Eubacterium rectale,* Firmicutes bacterium, *Prevotella enoeca, Morganella morganii, Staphylococcus aureus, Pseudomonas oleovorans, Pseudomonas pseudoalcaligenes, Enterococcus* sp. 7L76, *Bacteroides fragilis,* uncultured *Escherichia* sp., *Bacteroides ovatus, Alistipes shahii, Gardnerella vaginalis, Escherichia coli, Escherichia albertii, Salmonella enterica, Rhodopseudomonas palustris, Shigella flexneri, Bacteroides* sp. 148, *Brugia timori, Bacteroides dorei, Escherichia fergusonii, Shigella dysenteriae, Parabacteroides distasonis, Bacteroides thetaiotaomicron,* and *Shigella boydii.* In some embodiments, said cancer has a stage T1, and the method comprises determining the presence of Human Polyomavirus 1 microbes. In some embodiments, said cancer has a stage T2, and the method comprises determining the presence of one or more microbes selected from the group consisting of *Morganella morganii, Staphylococcus aureus, Pseudomonas oleovorans, Pseudomonas pseudoalcaligenes,* and *Enterococcus* sp. 7L76. In some embodiments, said cancer has a stage T3, and the method comprises determining the presence of one or more microbes selected from the group consisting of *Bacteroides fragilis,* uncultured *Escherichia* sp., *Bacteroides ovatus, Alistipes shahii, Gardnerella vaginalis, Escherichia coli, Escherichia albertii, Salmonella enterica, Rhodopseudomonas palustris, Shigella flexneri, Bacteroides* sp. 148, *Brugia timori, Bacteroides dorei, Escherichia fergusonii, Shigella dysenteriae, Parabacteroides distasonis, Bacteroides thetaiotaomicron,* and *Shigella boydii.*

In another aspect, the present disclosure provides a method for grading a cancer of a subject, comprising identifying a presence and an amount of one or more microbes indicative of a grade of said cancer.

In some embodiments, said cancer has a low grade, and the method comprises determining the presence of one or more microbes selected from the group consisting of *Streptococcus gallolyticus, Streptococcus pasteurianus, Pseudomonas aeruginosa* group, *Bifidobacterium longum, Pseudomonas aeruginosa, Streptococcus salivarius, Clostridioides difficile, Ruminococcus bromii,* and *Streptococcus lutetiensis.* In some embodiments, said cancer has a high grade, and the method comprises determining the presence of one or more microbes selected from the group consisting of *Bacteroides fragilis,* Human polyomavirus 1, *Staphylococcus aureus, Gardnerella vaginalis, Alistipes shahii, Bacteroides ovatus, Staphylococcus epidermidis, Brugia timori, Bacteroides dorei, Bacteroides* sp. 148, *Ralstonia insidiosa, Enterococcus faecalis, Stenotrophomonas maltophilia,* and *Morganella morganii.*

In another aspect, the present disclosure provides a method for measuring cancer recurrence in a subject, comprising identifying a presence and an amount of one or more microbes indicative of recurrence of said cancer.

In some embodiments, said subject has recurrence positivity of said cancer, and the method comprises determining the presence of one or more microbes selected from the group consisting of *Corynebacterium* sp. NML98-0116, *Corynebacterium resistens, Aerococcus urinae, Anaerococcus prevotii, Bacteroides fragilis, Clostridioides difficile, Erysipelothrix rhusiopathiae, Fusobacterium nucleatum, Helcococcus kunzii, Lawsonella clevelandensis, Ruminiclostridium* sp. KB18, *Ruminococcus bromii, Streptococcus agalactiae, Streptococcus anginosus, Streptococcus anginosus* group, *Streptococcus gallolyticus, Streptococcus infantarius, Streptococcus lutetiensis, Streptococcus macedonicus, Streptococcus mitis, Streptococcus parasanguinis, Streptococcus pasteurianus, Streptococcus pseudopneumoniae, Streptococcus pyogenes, Streptococcus* sp. VT 162, *Streptococcus* sp. oral taxon 064, *Streptococcus* sp. oral taxon 431, and *Eubacterium rectale.* In some embodiments, said subject has recurrence negativity, and the method comprises determining the presence of one or more microbes selected from the group consisting of *Corynebacterium jeikeium, Kocuria palustris, Lactobacillus crispatus, Amycolatopsis lurida, Finegoldia magna, Streptococcus thermophilus,* Human polyomavirus 2, *Shigella boydii, Spirometra erinaceieuropaei, Streptococcus pneumoniae, Schistosoma curassoni, Desulfitobacterium hafniense, Klebsiella pneumoniae,* and *Shigella sonnei.* In some embodiments, (a) comprises preserving said urine sample in a preservation solution comprising: a pH buffer, a chelator, a cell membrane stabilizer, a DNA compactor, and an antimicrobial. In some embodiments, said pH buffer maintains said preservation solution at a pH that is between 7 and 9. In some embodiments, said chelator comprises one or more member(s) selected from the group consisting of: a magnesium (Mg) chelator, a calcium (Ca chelator), and an iron (Fe) chelator. In some embodiments, said chelator is Enterobactin. In some embodiments, said cell membrane stabilizer comprises one or more member(s) selected from the group consisting of: vitamin E conjugate and poly-L-lysine. In some embodiments, said DNA compactor comprises poly-L-lysine. In some embodiments, said antimicrobial comprises one or more member(s) selected from the group consisting of: penicillin, streptomycin, and amphotericin B.

In another aspect, the present disclosure provides a system for identifying a urinary tract disorder, comprising: a database configured to contain a data set comprising a set of microbes in a urinary tract of said subject; and one or more computer processors operatively coupled to said database, wherein said one or more computer processors are individually or collectively programmed to: (i) process said set of microbes to generate a classification of said urine sample as being positive or negative for said urinary tract disorder at a sensitivity and specificity of at least 90%, and (ii) output a report identifying said subject as having or not having said urinary tract disorder based on said classification.

In some embodiments, the system further comprises a communications interface operatively coupled to said one or more computer processors, wherein said communications interface is configured to transmit said report to said subject or a healthcare provider of said subject.

In another aspect, the present disclosure provides a method for supplementing a microbiome in a urinary tract of a subject, comprising: (a) identifying a relative abundance of a first set of microbes in said urinary tract of said subject; (b)

identifying a second set of microbes for said urinary tract of said subject, which second set of microbes is different than said first set of microbes, wherein said second set of microbes is configured to supplement said microbiome in said urinary tract of said subject; and (c) contacting said second set of microbes with said urinary tract of said subject.

In another aspect, the present disclosure provides a method for treating a condition in a subject, comprising: (a) identifying a relative abundance of a first set of microbes in a urinary tract of said subject; (b) selecting one or more active microbes based on (i) said relative abundance of a first set of microbes in a urinary tract of said subject and (ii) having a high prevalence in individuals with no detected urinary symptoms or diseases; and (c) supplementing a microbiome of said urinary tract of said subject with said selected one or more active microbes to reduce a severity or presence of said condition, wherein supplementing comprises introducing one or more microbes to said urinary tract of said subject.

In some embodiments, the method further comprises administering an antimicrobial agent to said subject prior to (c). In some embodiments, the method further comprises obtaining a urine sample from said subject, and processing said urine sample in a preservation solution to extract a plurality of nucleic acids. In some embodiments, the method further comprises subjecting said nucleic acid to sequencing. In some embodiments, (a) comprises generating data indicative of a level of said first set of microbes and processing said data against a reference to identify said relative abundance. In some embodiments, said relative abundance is an excess or deficiency of said first set of microbes. In some embodiments, said excess or deficiency of said first set of microbes is associated with a urinary tract disorder. In some embodiments, said urinary tract disorder is a lower urinary tract disorder. In some embodiments, said urinary tract disorder is a bladder disorder. In some embodiments, said bladder disorder comprises one or more member(s) selected from the group consisting of: bladder cancer, bladder exstrophy, bladder outlet obstruction, bladder sphincter dyssynergia, catheter-associated urinary tract infection, choluria, cystitis, cystitis glandularis, glomerulation, Gouverneur's syndrome, hemorrhagic cystitis, Hunner's ulcer, insterstitial cystitis, megacystitis, neurogenic bladder dysfunction, overactive bladder, spermaturia, trigonitis, underactive bladder, urinary bladder neck obstruction, urge incontinence, vesicointestinal fistula, and vesicoureteral reflux. In some embodiments, said urinary tract disorder is a kidney disorder. In some embodiments, said kidney disorder comprises one or more member(s) selected from the group consisting of: Abderhalden-Kaufmann-Lignac syndrome, acute proliferative glomerulonephritis, adenine phosphoribosyltransferase deficiency, Alport syndrome, analgesic nephropathy, autosomal dominant polycystic kidney disease, autosomal recessive polycystic kidney disease, Balkan endemic nephropathy, benign nephrosclerosis, Bright's disease, cardiorenal syndrome, chronic kidney disease, congenital nephrotic syndrome, conorenal syndrome, contrast-induced nephropathy, cystic kidney disease, Dent's disease, diabetic nephropathy, diffuse proliferative nephritis, distal renal tubular acidosis, diuresis, EAST syndrome, Fanconi syndrome, Fechtner syndrome, focal proliferative nephritis, focal segmental glomerulosclerosis, Fraley syndrome, Galloway Mowat syndrome, Gitelman syndrome, glomerulocystic kidney disease, glomerulopathy, Goldblatt kidney, Goodpasture syndrome, high anion gap metabolic acidosis, HIV-associated nephropathy, horseshoe kidney, hydronephrosis, hypertensive kidney disease, IgA nephropathy, interstitial nephritis, juvenile nephronopthisis, kidney cancer, kidney stone disease, Lightwood-Albright syndrome, lupus nephritis, malarial nephropathy, medullary cystic kidney disease, medullary sponge kidney, membranous glomerulonephritis, Mesoamerican nephropathy, milk-alkali syndrome, minimal mesangial glomerulonephritis, multicystic dysplastic kidney, nephritis, nephrocalcinosis, nephrogenic diabetes insipidus, nephromegaly, nephrotosis, nephrosis, nephrotic syndrome, Nutcracker syndrome, papillorenal syndrome, phosphate neuropathy, polycystic kidney disease, primary hyperoxaluria, proximal renal tubular acidosis, pyelonephritis, pyonephrosis, rapidly progressive glomerulonephritis, renal agenesis, renal angina, renal artery stenosis, renal cyst, renal ischemia, renal osteodystrophy, renal papillary necrosis, renal tubular acidosis, renal vein thrombosis, reninoma, secondary hypertension, serpentine fibula-polycystic kidney syndrome, shunt nephritis, sickle cell nephropathy, thin basement membrane disease, transplant glomerulopathy, tubulointerstitital nephritis and uveitis, tubulopathy, uremia, uremic frost, and Wunderlich syndrome. In some embodiments, said urinary tract disorder is a urethra disorder. In some embodiments, said urethra disorder comprises one or more member(s) selected from the group consisting of: urethral meatal stenosis, urethral caruncle, urethral foreign body, urethral stricture, urethral syndrome, urethritis, and urethrorrhagia. In some embodiments, said urinary tract disorder is a ureter disorder. In some embodiments, said ureter disorder comprises one or more member(s) selected from the group consisting of: duplicated ureter, megaureter, ureteritis, and ureterocele. In some embodiments, said urinary tract disorder is a prostate disorder. In some embodiments, said prostate disorder comprises one or more member(s) selected from the group consisting of: prostatitis, acute prostatitis, asymptomatic inflammatory prostatitis, chronic bacterial prostatitis, chronic prostatitis, granulomatous prostatitis, IgG4-related prostatitis, male accessory gland infection, benign prostatic hyperplasia, and prostate cancer. In some embodiments, said urinary tract disorder is a testicular disorder. In some embodiments, said testicular disorder comprises one or more member(s) selected from the group consisting of: ectopic testis, epididymitis, gonadal torsion, orchitis, orchialgia, macroorchidism, testicular cancer, genital tuberculosis, hydrocele, hydrocele testis, rete tubular ectasia, Sertoli cell nodule, testicular atrophy, testicular dysgenesis syndrome, testicular microlithiasis, testicular pain, testicular rupture, testicular sarcoidosis, testicular torsion, and testicular trauma. In some embodiments, said urinary tract disorder is a penile disorder. In some embodiments, said penile disorder comprises one or more member(s) selected from the group consisting of: penile cancer, erectile dysfunction, priapism, induratio penis plastic, Peyronie's disease, aposthia, balanitis, penile fracture, penile injury, penile pain, and penile artery shunt syndrome. In some embodiments, said urinary tract disorder comprises one or more member(s) selected from the group consisting of: reactive arthritis, Reiter's syndrome, and urosepsis. In some embodiments, said first set of microbes comprises one or more microbes from a taxonomic kingdom selected from the group consisting of: Bacteria, Viruses, Bacteriophages, and Archaea. In some embodiments, said first set of microbes comprises one or more microbes from a taxonomic phylum selected from the group consisting of: Proteobacteria, Firmicutes, Actinobacteria, Bacteroidetes, Aquificae, Deinococcus-Thermus, Fusobacteria, and Tenericutes. In some embodiments, said first set of microbes comprises one or more microbes from a taxonomic class selected from the group consisting of: Gammaproteobacteria, Betaproteobacteria, Clostridia, Alphaproteobacteria, Bacilli, Actinobacteria, Tissierellia, Bacteroidia, Erysipelotrichia, Aquificiae, Deinococci, Epsilonproteobacteria, Flavobacteria, Fusobacteria, Mollicutes, Negativicutes, and Coriobacteria. In some embodiments, said first set of microbes comprises one or more microbes from a taxonomic order selected from the group consisting of: Pseudomonadales, Enterobacterales, Caudovirales, Actinomycetales, Corynebacteriales, Burkholderiales, Clostridiales, Rhizobiales, Streptomycetales, Sphingomonadales, Lactobacillales, Bifidobacteriales, Pseudonocardiales, Bacteroidales, Xanthomonadales, Bacillales, Erysipelotrichales, Acidaminococcales, Campylobacterales, Desulfurobacteriales, Fusobacteriales, Herpesvirales, Micrococcales, Mycoplasmatales, Neisseriales, Pasteurellales, Picornavirales, Propionibacteriales, Thermales, Veillonellales, Vibrionales, Flavobacteriales, Tissierellales, Aeromonadales, Coriobacteriales, and Eggerthellales. In some embodiments, said first set of microbes comprises one or more microbes from a taxonomic family selected from the group consisting of: Myoviridae, Porphyromonadaceae, Pseudomonoadaceae, Enterobacteriaceae, Actinomycetaceae, Prevotellaceae, Burkholderiaceae, Siphoviridae, Hyphoicrobiaceae, Streptomycetaceae, Sphingomonadaceae, Peptoniphilaceae, Bifidobacteriaceae, Peptostreptococcaceae, Polyomaviridae, Xanthomonadaceae, Staphylococcaceae, Bacteroidaceae, Erysipelotrichaceae, Nocardiaceae, Rikenellaceae, Acidaminococcaceae, Aerococcaceae, Bradyrhizobiaceae, Campylobacteraceae, Comamonadaceae, Corynebacteriaceae, Desulfurobacteriaceae, Erwiniaceae, Flavobacteriaceae, Hafniaceae, Helicobacteraceae, Herpesviridae, Lachnospiraceae, Lactobacillaceae, Leptotrichiaceae, Microbacteriaceae, Micrococcaceae, Morganellaceae, Mycoplasmataceae, Neisseriaceae, Oxalobacteraceae, Paenibacillaceae, Pasteurellaceae, Peptococcaceae, Picornaviridae, Podoviridae, Propionibacteriaceae, Rhizobiaceae, Ruminococcaceae, Thermaceae, Veillonellaceae, Vibrionaceae, Yersiniaceae, Arenaviridae, Streptococcaceae, Tissierellaceae, Tannerellaceae, Oscillospiraceae, Aeromonadaceae, Erythrobacteraceae, Moraxellaceae, Barnesiellaceae, Intrasporangiaceae, Coriobacteriaceae, and Eggerthellaceae. In some embodiments, said first set of microbes comprises one or more microbes from a taxonomic genus selected from the group consisting of: *Klebsiella, Lambdavirus, Shigella, Pseudomonas, Citrobacter, Salmonella, Escherichia, Prevoltella, Barnesiella, Devosia, Streptomyces, Bifidobacterium, Sphingomonas, Helcococcus, Parabacteroides, Mobilunus, Gardnerella, Finegoldia, Streptococcus,* Betapolyomavirus, *Stenotrophomonas, Enterococcus, Ralstonia, Staphylococcus, Bacteroides, Alistipes, Clostridioides, Erysipelothrix, Rhodococcus, Triavirus, Acidaminococcus, Actinomyces, Actinotignum, Aerococcus, Aggregatibacter, Anaerococcus, Blautia, Bradyrhizobium, Burkholderia, Campylobacter, Cornyebacterium, Cutibacterium, Desulfitobacterium, Enterobacter,* Epsilon15virus, *Ezakiella,* F116virus, *Faecalibacterium, Filifactor, Fusobacterium, Haemophilus, Hafnia, Helicobacter, Histophilus, Janthinobacterium, Kluyvera, Lacnoclostridium, Lactobacillus, Lawsonella, Limnohabitans, Lymphocryptovirus, Mageeibacillus, Microbacterium, Micrococcus, Morganella, Neisseria, Ornithobacterium,* P22virus, P2virus, *Paenibacillus, Pantoea, Parvimonas, Peptoniphilus, Porphyromonas, Propionibacterium, Propionmicrobium, Proteus, Pseudarthrobacter, Raoultella, Rhizobium, Rhodopseudomonas, Roseolovirus, Rothia, Ruminiclostridium, Ruminococcus, Salivirus, Serratia, Sneathia, Sphingobium, Thermovibrio, Thermus, Ureaplasma, Varibaculum, Veillonella, Vibrio, Xenorhabdus, Yersinia, Mammarenavirus, Variovorax, Prevotella, Methylibium, Polynucleobacter,* P68virus, *Thiomonas, Phycicoccus, Acidovorax, Anaerostipes, Collinsella, Hydrogenophaga, Lachnoclostridium, Eggerthella, Negativicoccus, Ndongobacter, Mobiluncus, Kosakonia, Oscillibacter, Tannerella, Flavonifractor, Tessaracoccus, Eikenella, Aeromonas, Porphyrobacter, Edwardsiella, Leptotrichia, Comamonas, Acinetobacter,* and *Tardiphaga*. In some embodiments, said first set of microbes comprises one or more microbes from a taxonomic species selected from the group consisting of: *Klebsiellas pneumoniae, Shigellas sonnei, Klebsiellas varicola, Prevotellas* species oral taxon 299, *Shigellas dysenteriae, Pseudomonas aeruginosa, Salmonellas enterica, Escherichias coli, Shigellas boydii, Shigellas* species PAMC 28760, *Shigellas flexneri,* Betapolyomavirus human, *Excherichias fergusonii, Prevotellas scopos, Prevotellas melaninogenica, Escherichias albertii barnesiellas viscericola, Devosias* species H5989, *Streptococcus pneumoniae, Citrobacters freundii, Prevotellas enoeca, Bacteroides thetaiotaomicron, Helcococcus kunzii, Parabacteroidess distasonis, Pseudomonas oleovorans, Mobiluncus curtisii, Streptococcus dysgalactiae, Streptococcus pyogenes, Gardnerellas vaginalis, Finegoldias magna, Bacteroides dorei, Bacteroides vulgatus, Pseudomonas* species 1217, *Enterococcus* species 7L76, *Bacteroides* species L48, *Ralstonias insidiosa, Streptococcus pasteurianus, Bifidobacterium longum, Bacteroides ovatus, Enterococcus faecalis, Staphylococcus epidermis, Staphylococcus aureus, Bacteroides fragilis, Alistipes shahii, Bacteroides salanitronis, Clostridioides difficile, Erysipelothrix rhusiopathiae,* Lambdavirus uncultured virus, *Pseudomonas frederiksbergensis, Ralstonia mannitolilytica, Rhodococcus erythropolis, Rhodoccus* species 008, *Sphingomonas echinoides, Staphylococcus agnetis, Staphylococcus lugdunensis, Staphyloccus saprophyticus, Streptococcus gallolyticus, Streptococcus infantarius, Streptococcus lutetiensis, Streptococcus macedonicus, Streptomyces* uncultured bacteria 37b14, *Streptomyces* uncultured bacterium 39k17, *Triavirus staphylococcus* phage 3A, *Triavirus staphylococcus* phage tp310-2, *Triavirus staphylococcus* phage StB20, Human herpesvirus 6, Human gammaherpesvirus 4, *Bordetella hinzii, Methylibium petroleiphilum, Shigella* species LN126, Podoviridae, *Lactobacillus jensenii, Burkholderia pseudomallei* group, *Pseudomonas* phage phi297, *Klebsiella michiganensis, Lactobacillus* species B164, *Streptococcus* species I-G2, *Kosakonia sacchari, Ruminococcus bicirculans, Prevotella jejuni, Bradyrhizobium* species llw1, *Agrobacterium tumefaciens* complex, *Pseudomonas* phage YMC/01/01/P52_PAE BP, *Aerococcus sanguinicola, Prevotella* species S4-10, *Corynebacterium frankenforstense, Prevotella* species Sc00026, *Streptococcus* phage EJ-1, Comamonas bacterium 36B, *Micrococcus luteus, Pseudomonas sihuiensis, Staphylococcus haemolyticus, Streptococcus* phage phiD12, *Staphylococcus hominis, Pseudomonas* species ATCC 13867, *Streptococcus oralis, Streptococcus salivarius, Streptococcus suis, Acinetobacter chlamydia*-associated clinical sample 198-T, *Sphingobium* species TKS, *Streptococcus parasanguinis, Tessaracoccus aquimaris, Pluralibacter lignolyticus, Streptococcus intermedius, Ureaplasma parvum, Pseudomonas fluorescens* group, *Pseudomonas putida* group, *Sphingobium yanoikuyae, Aerococcus urinae, Burkholderia* species BDU6, *Sphingomonas* species LK11, *Bacillus cereus, Paenibacillus polymyxa, Streptococcus* species VT 162, Comamonadaceae bacterium B1, *Klebsiella quasipneumoniae, Corynebacterium simulans, Lactobacillus iners, Corynebacterium* species ATCC 6931, *Klebsiella* species NCTC 8172, *Lawsonella clevelandensis, Lactoba-* cillus species wkB8, *Sphingomonas taxi*, *Bradyrhizobium* species lamp2, *Streptococcus* phage SpSL1, *Enterobacteria* phage P88, *Corynebacterium riegelii*, *Corynebacterium imitans*, *Lactobacillus acidophilus*, *Lactobacillus buchneri*, *Lactobacillus delbrueckii*, *Lactobacillus helveticus*, *Cedecea neteri*, *Enterobacter hormaechei*, *Lactobacillus plantarum*, *Lactobacillus gasseri*, *Lactobacillus acetotolerans*, *Lactobacillus amylophilus*, *Lactobacillus amylovorus*, *Tessaracoccus flavus*, *Lactobacillus farciminis*, *Corynebacterium singulare*, *Erwinia gerundensis*, *Hoeflea* species IMCC20628, *Lactobacillus ruminis*, *Pseudomonas lini*, *Propionibacterium* phage PHLD30, *Propionibacterium* phage PHLD64, *Propionibacterium* phage PHL082, *Yersinia pseudotuberculosis* complex, *Actinomyces naeslundii*, *Acidovorax* species NA2, *Acidovorax* species P3, *Acidovorax* species P4, *Bifidobacterium adolescentis*, *Bifidobacterium breve*, *Corynebacterium aurimucosum*, *Negativicoccus massiliensis*, *Massilia* species WG5, *Turicibacter* species H121, *Corynebacterium diphtheriae*, *Corynebacterium glutamicum*, *Rothia aeria*, *Propionibacterium freudenreichii*, *Cutibacterium acnes*, *Pseudomonas* phage phi1, *Streptococcus* species A12, *Pseudomonas* species bs2935, *Pseudomonas* phage JBD44, *Pseudomonas* phage YMC11/07/P54_PAE_BP, *Gemella* species oral taxon 928, *Sinorhizobium* species RAC02, *Hydrogenophaga* species RAC07, *Acidovorax* species T1, Lambdavirus, *Sneathia amnii*, *Ndongobacter massiliensis*, *Acidaminococcus intestini*, *Varibaculum* species, *Streptococcus* species NPS 308, *Tessaracoccus* species 72.5-30, *Corynebacterium sphenisci*, *Corynebacterium atypicum*, *Streptococcus* phage IPPS, *Delftia* species HK171, *Klebsiella* species M5a1, *Staphylococcus* phage St 134, *Propionibacterium* virus Lauchelly, *Propionibacterium* virus PHLD82M03, *Propionibacterium* virus PHLJ17M01, *Propionibacterium* virus Stormborn, *Microbacterium paraoxydans*, *Thauera* species K11, *Escherichia* phage Ayreon, *Dickeya zeae*, *Pseudomonas* species HLS-6, *Paracoccus* species CBA4604, *Citrobacter freundii* complex species CFNIH2, *Citrobacter freundii* complex species CFNIH3, *Alkaliphilus metalliredigens*, *Lachnoclostridium bolteae*, *Ureaplasma urealyticum*, *Yersinia* virus L413C, *Pseudomonas* species M18, Lachnoclostridium butyrate-producing bacterium SM4/1, Lachnoclostridium butyrate-producing bacterium SS3/4, Plasmid ColV-K30, *Bacteroides cellulosilyticus*, Plasmid R1-19, *Haemophilus pittmaniae*, *Bradyrhizobium canariense*, *Streptococcus pseudopneumoniae*, *Corynebacterium resistens*, *Lactobacillus kefiranofaciens*, *Sphaerochaeta coccoides*, *Thermus thermophilus*, *Bifidobacterium animalis*, *Streptococcus mitis*, *Acinetobacter lwoffli*, *Porphyromonas asaccharolytica*, *Prevotella denticola*, *Prevotella disiens*, *Ornithobacterium rhinotracheale*, *Enterobacteria* phage CP-1639, *Burkholderia cepacia*, *Brevundimonas diminuta*, *Staphylococcus capitis*, *Pseudomonas fluorescens*, *Pseudomonas tolaasii*, *Veillonella parvula*, *Shigella* species AR-21793, *Turneriella parva*, *Roseburia hominis*, *Pseudomonas putida*, Human betaherpesvirus 6B, *Cutibacterium avidum*, *Cutibacterium granulosum*, *Parvimonas micra*, *Anaerococcus prevotii*, *Sphingobium indicum*, *Sphingobium japonicum*, *Variovorax paradoxus*, *Pseudomonas* phage PA11, *Enterobacter cloacae* complex, *Citrobacter amalonaticus*, *Agrobacterium tumefaciens*, *Verminephrobacter eiseniae*, *Bacteroides xylanisolvens*, *Corynebacterium* species L2-79-05, *Enterobacteria* phage 933 W sensu lato, *Lactobacillus backii*, *Thermus scotoductus*, *Sinorhizobium fredii*, *Rhizobium leguminosarum*, *Prevotella timonensis*, *Mesorhizobium ciceri*, *Veillonella atypica*, *Tessaracoccus flavescens*, *Enterobacter* species 638, *Streptococcus merionis*, *Micrococcus* species A1, *Blautia obeum*, *Polyangium brachysporum*, *Azoarcus olearius*, *Thiomonas arsenitoxydans*, *Ralstonia* species Is-C065, *Variovorax boronicumulans*, *Rothia mucilaginosa*, *Enterococcus cecorum*, *Bradyrhizobium oligotrophicum*, *Phycicoccus dokdonensis*, *Enterobacteria* phage VT1-Sakai, *Lactobacillus crispatus*, *Pseudomonas azotoformans*, *Pseudomonas fulva*, *Neisseria gonorrhoeae*, *Neisseria lactamica*, *Neisseria meningitidis*, *Burkholderia contaminans*, *Neisseria sicca*, *Prevotella dentalis*, *Lactobacillus gallinarum*, *Ochrobactrum anthropi*, *Peptoniphilus harei*, *Raoultella ornithinolytica*, *Enterobacter cloacae*, *Pantoea cypripedii*, *Acidovorax* species NA3, *Thiomonas* species CB2, *Enterobacteria* phage YYZ-2008, *Thermus brockianus*, *Afipia* genospecies 3, *Citrobacter braakii*, *Lactobacillus* phage Lv-1, *Burkholderia thailandensis*, *Proteus mirabilis*, *Klebsiella* species 2N3, *Prevotella fusca*, *Actinotignum schaalii*, *Serratia liquefaciens*, *Serratia marcescens*, *Kluyvera intermedia*, *Yersinia pestis*, *Yersinia pseudotuberculosis*, *Edwardsiella tarda*, *Aeromonas salmonicida*, *Anaerostipes hadrus*, *Prevotella* species oral taxon 299, *Myxococcus* mixed culture bacterium AM_gF3SD01_05, *Desulfitobacterium* mixed culture bacterium AX_gF3SD01_48, Comamonas mixed culture bacterium PE_gF1DD01_04, *Streptococcus anginosus* group, *Rhodoplanes* species Z2-YC6860, *Citrobacter rodentium*, *Citrobacter gillenii*, *Altererythrobacter dongtanensis*, *Corynebacterium* species NML98-0116, *Actinomyces* species oral taxon 414, *Streptococcus* species oral taxon 064, *Streptococcus* species oral taxon 431, *Kocuria palustris*, *Haemophilus influenzae*, *Haemophilus parainfluenzae*, *Aggregatibacter aphrophilus*, *Collinsella aerofaciens*, *Campylobacter hominis*, *Streptococcus constellatus*, *Campylobacter hominis*, *Hydrogenophaga* species PBC, *Delftia acidovorans*, *Campylobacter ureolyticus*, *Leclercia adecarboxylata*, *Lactobacillus amylolyticus*, *Porphyromonas gingivalis*, *Lachnoclostridium saccharolyticum*, *Eggerthella lenta*, *Fusobacterium nucleatum*, *Faecalibacterium prausnitzii*, *Streptococcus* phage phi-SsUD.1, *Bacillus cereus* group, *Aerococcus christensenii*, *Burkholderia cepacia* complex, *Corynebacterium flavum*, *Micrococcus* species MG-2010-D12, *Actinomyces succiniciruminis*, *Streptococcus agalactiae*, Guanarito mammarenavirus, *Prevotella intermedia*, *Prevotella enoeca*, *Desulfitobacterium hafniense*, *Pseudomonas aeruginosa* group, *Staphylococcus epidermidis*, *Bacteroides dorei*, *Prevotella melaninogenica*, and Human polyomavirus 2. In some embodiments, said second set of microbes comprises one or more microbes selected from a taxonomic kingdom selected from the group consisting of: Bacteria, Viruses, Bacteriophages, and Archaea. In some embodiments, said second set of microbes comprises one or more microbes selected from a taxonomic phylum selected from the group consisting of: Bacteroidetes, Firmicutes, Actinobacteria, Proteobacteria, Deinococcus-Thermus, and Polyomaviridae. In some embodiments, said second set of microbes comprises one or more microbes selected from a taxonomic class selected from the group consisting of: Bacteroidia, Bacilli, Actinobacteria, Gammaproteobacteria, Deinococci, Tissierellia, Epsilonproteobacteria, Flavobacteriia, Negativicutes, Clostridia, Alphaproteobacteria, and Betapolyomavirus. In some embodiments, said second set of microbes comprises one or more microbes selected from a taxonomic order selected from the group consisting of: Bacteroidales, Lactobacillales, Corynebacteriales, Propionibacteriales, Pseudomonadales, Thermales, Micrococcales, Tissierellales, Pasteurellales, Campylobacterales, Bifidobacteriales, Actinomycetales, Flavobacteriales, Veillonellales, Clostridiales, and Rhizobiales. In some embodiments, said second set of microbes comprises one or more microbes selected from a taxonomic family selected from the group consisting of: Prevotellaceae, Lactobacillaceae, Corynebacteriaceae, Propionibacteriaceae, Pseudomonadaceae, Thermaceae, Streptococcaceae, Porphyromonadaceae, Micrococcaceae, Aerococcaceae, Peptoniphilaceae, Pasteurellaceae, Campylobacteraceae, Bifidobacteriaceae, Actinomycetaceae, Flavobacteriaceae, Veillonellaceae, Ruminococcaceae, Bradyrhizobiaceae, Hyphomicrobiaceae, and Bacteroidaceae. In some embodiments, said second set of microbes comprises one or more microbes selected from a taxonomic genus selected from the group consisting of: *Prevotella, Lactobacillus, Corynebacterium, Cutibacterium, Pseudomonas, Thermus, Streptococcus, Porphyromonas, Micrococcus, Aerococcus, Lawsonella, Anaerococcus, Haemophilus, Campylobacter, Bifidobacterium, Mobiluncus, Ornithobacterium, Veillonella, Aggregatibacter, Faecalibacterium, Bradyrhizobium, Rhodopseudomonas, Devosia, Bacteroides*, and *Mageeibacillus*. In some embodiments, said second set of microbes comprises one or more microbes selected from a taxonomic species selected from the group consisting of: *Prevotella jejuni, Lactobacillus gasseri, Corynebacterium* species NML98-0116, *Cutibacterium acnes, Lactobacillus amylovorus, Lactobacillus johnsonii, Lactobacillus jensenii, Pseudomonas fluorescens* group, *Thermus scotoductus, Streptococcus anginosus* group, *Streptococcus anginosus, Streptococcus mitis, Porphyromonas asaccharolytica, Lactobacillus crispatus, Micrococcus luteus, Lactobacillus helveticus, Pseudomonas tolaasii, Prevotella fusca, Aerococcus christensenii, Streptococcus parasanguinis, Lawsonella clevelandensis, Lactobacillus delbrueckii, Streptococcus pseudopneumoniae, Thermus thermophilus, Anaerococcus prevotii, Prevotella* species oral taxon 299, *Haemophilus influenzae, Campylobacter ureolyticus, Porphyromonas gingivalis, Streptococcus oralis, Lactobacillus, Lactobacillus acidophilus, Bifidobacterium breve, Corynebacterium aurimucosum, Mobiluncus curtisii, Lactobacillus kefiranofaciens, Ornithobacterium rhinotracheale, Cutibacterium avidum, Veillonella atypica, Lactobacillus gallinarum, Aggregatibacter aphrophilus, Faecalibacterium prausnitzii, Bradyrhizobium diazoefficiens, Rhodopseudomonas palustris, Devosia* species H5989, *Bradyrhizobium* species SK17, *Pseudomonas* species AK6U, *Bifidobacterium longum, Bradyrhizobium* species S23321, *Bacteroides thetaiotaomicron*, and *Mageeibacillus indolicus*. In some embodiments, the method further comprises supplying said second set of microbes to said urinary tract of said subject. In some embodiments, the method further comprises outputting a report that identifies said second set of microbes. In some embodiments, (a) comprises preserving said urine sample in a preservation solution comprising: a pH buffer, a chelator, a cell membrane stabilizer, a DNA compactor, and an antimicrobial. In some embodiments, said pH buffer maintains said preservation solution at a pH that is between 7 and 9. In some embodiments, said chelator comprises one or more member(s) selected from the group consisting of: a magnesium (Mg) chelator, a calcium (Ca chelator), and an iron (Fe) chelator. In some embodiments, said chelator is selected from the group consisting of enterobactin and Deferoxamine Mesylate. In some embodiments, said cell membrane stabilizer comprises one or more member(s) selected from the group consisting of: vitamin E conjugate and poly-L-lysine. In some embodiments, said DNA compactor comprises poly-L-lysine. In some embodiments, said antimicrobial comprises one or more member(s) selected from the group consisting of: penicillin, streptomycin, amphotericin B, and urine Stabilur tablet.

In another aspect, the present disclosure provides a method of treating a urinary tract disorder, comprising supplementing a urinary tract of a subject having a first set of microbes with a second set of microbes, wherein said second set of microbes is different than said first set of microbes, and wherein said second set of microbes is selected to treat a urinary tract disorder.

In some embodiments, said urinary tract is contacted with a liquid formulation comprising said second set of microbes. In some embodiments, said microbiome is supplemented using a liquid or tablet or capsule comprising said second set of microbes. In some embodiments, said first set of microbes comprises said second set of microbes. In some embodiments, said first set of microbes comprises at most a subset of said second set of microbes.

In another aspect, the present disclosure provides a system for supplementing a microbiome in a urinary tract of a subject, comprising: a database; and one or more computer processors operatively coupled to said database, wherein said one or more computer processors are individually or collectively programmed to: (i) identify a relative abundance of a first set of microbes in a urinary tract of said subject, (ii) identify a second set of microbes for said urinary tract of said subject, which second set of microbes is different than said first set of microbes, wherein said second set of microbes is configured to supplement said microbiome in said urinary tract of said subject, and (iii) store said second set of microbes in said database.

Additional aspects and advantages of the present disclosure will become readily apparent to those skilled in this art from the following detailed description, wherein only illustrative embodiments of the present disclosure are shown and described. As will be realized, the present disclosure is capable of other and different embodiments, and its several details are capable of modifications in various obvious respects, all without departing from the disclosure. Accordingly, the drawings and description are to be regarded as illustrative in nature, and not as restrictive.

INCORPORATION BY REFERENCE

All publications, patents, and patent applications mentioned in this specification are herein incorporated by reference to the same extent as if each individual publication, patent, or patent application was specifically and individually indicated to be incorporated by reference. To the extent publications and patents or patent applications incorporated by reference contradict the disclosure contained in the specification, the specification is intended to supersede and/or take precedence over any such contradictory material.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings (also "Figure" and "FIG." herein), of which:

FIG. 23A shows pooled enrichment scores for microbes shared between the urinary microbiomes of cancerous and normal individuals.

FIG. 23B shows pooled enrichment scores for microbes enriched in the urinary microbiomes of normal individuals.

FIG. 23C shows pooled enrichment scores for microbes enriched in the urinary microbiomes of cancerous individuals.

FIG. 23D shows alpha-diversity scores for the urinary microbiomes of cancerous and non-cancerous individuals.

FIG. 41A shows the total DNA yield from urine samples containing no preservation solution (no buffer) and urine samples containing the preservation solution (preservation buffer) described herein.

FIG. 41B shows the total DNA post Kappa amplification from urine samples containing no preservation solution (no buffer) and urine samples containing the preservation solution (preservation buffer) described herein.

FIG. 41C shows the total number of nucleic acid sequencing reads from urine samples containing no preservation solution (no buffer) and urine samples containing the preservation solution (preservation buffer) described herein.

FIG. 41D shows the hybrid capture efficiency from urine sample containing no preservation solution (no buffer) and urine samples containing the preservation solution (preservation buffer) described herein.

DETAILED DESCRIPTION OF THE INVENTION

Figure 1:
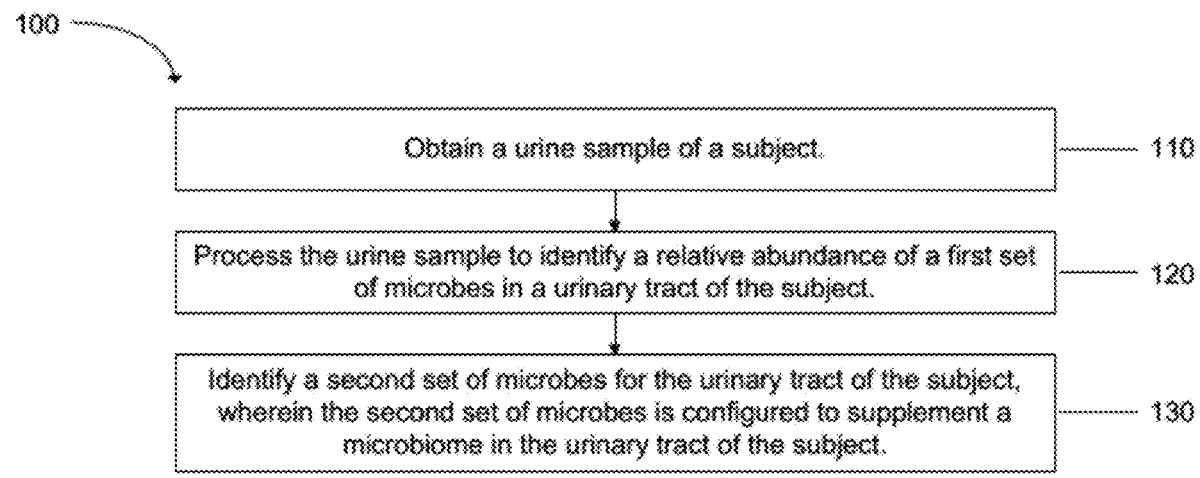
FIG. 1 shows a flowchart for a first method for supplementing a microbiome in a urinary tract of a subject.

While various embodiments of the invention have been shown and described herein, it will be obvious to those skilled in the art that such embodiments are provided by way of example only. Numerous variations, changes, and substitutions may occur to those skilled in the art without departing from the invention. It should be understood that various alternatives to the embodiments of the invention described herein may be employed.

Unless otherwise defined, all technical terms used herein have the same meaning as commonly understood by one of ordinary skill in the art to which this invention belongs. As used in this specification and the appended claims, the singular forms "a," "an," and "the" include plural references unless the context clearly dictates otherwise. Any reference to "or" herein is intended to encompass "and/or" unless otherwise stated.

The term "about" or "approximately", as used herein, when applied to one or more values or elements of interest, refers to a value or element that is similar to a stated reference value or element. In certain embodiments, the term "about" or "approximately" refers to a range of values or elements that falls within 25%, 20%, 19%, 18%, 17%, 16%, 15%, 14%, 13%, 12%, 11%, 10%, 9%, 8%, 7%, 6%, 5%, 4%, 3%, 2%, 1%, or less in either direction (greater than or less than) of the stated reference value or element unless otherwise stated or otherwise evident from the context (except where such number would exceed 100% of a possible value or element).

Whenever the term "at least," "greater than," or "greater than or equal to" precedes the first numerical value in a series of two or more numerical values, the term "at least," "greater than" or "greater than or equal to" applies to each of the numerical values in that series of numerical values. For example, greater than or equal to 1, 2, or 3 is equivalent to greater than or equal to 1, greater than or equal to 2, or greater than or equal to 3.

Whenever the term "no more than," "less than," "less than or equal to," or "at most" precedes the first numerical value in a series of two or more numerical values, the term "no more than," "less than," "less than or equal to," or "at most" applies to each of the numerical values in that series of numerical values. For example, less than or equal to 3, 2, or 1 is equivalent to less than or equal to 3, less than or equal to 2, or less than or equal to 1.

Where values are described as ranges, it will be understood that such disclosure includes the disclosure of all possible sub-ranges within such ranges, as well as specific numerical values that fall within such ranges irrespective of whether a specific numerical value or specific sub-range is expressly stated.

As used herein, like characters refer to like elements.

The term "subject," as used herein, generally refers to an animal, such as a mammalian species (such as a human) or avian (such as a bird) species, or other organism, such as a plant. The subject can be a vertebrate, a mammal, a mouse, a primate, a simian, or a human. Animals may include, but are not limited to, farm animals, sport animals, and pets. A subject can be a healthy or asymptomatic individual, an individual that has or is suspected of having a disease (such as a cancer) or a pre-disposition to the disease, or an individual that is in need of therapy or suspected of needing therapy. A subject can be a patient.

The term "sample" or "urine sample," as used herein, generally refers to a sample obtained from the urinary tract of a subject. The sample may be obtained from any part of the urinary tract of the subject, such as a bladder, kidney, urethra, ureter, prostate, testicle, or penis of the subject. The sample may be passively obtained, such as by collecting urine excreted by the subject. The sample may be actively obtained, such as by extracting urine from the urinary tract of the subject. For instance, the sample may be obtained by inserting a needle into the urinary tract of the subject and withdrawing a urinary sample. The sample may be a cell-free or cell free sample or a prepared sample (such as nucleic acid fragments). A cell-free sample may include extracellular polynucleotides. Extracellular polynucleotides may be isolated from the sample.

The term "urinary tract", as used herein, generally refers to the group of internal or external organs which may be involved in the processing or excretion of urine by a subject as described herein. For instance, the term "urinary tract" may include any or all of a subject's lower urinary tract, bladder, kidney(s), urethra, ureter(s), prostate, testicle(s), or penis.

The term "sequencing", as used herein, generally refers to methods and technologies for determining the sequence of molecular constituents of a macromolecule. The term "sequencing" may refer to nucleic acid sequencing, as defined herein. The term "sequencing" may refer to protein sequencing, polypeptide sequencing, or peptide sequencing, as defined herein.

The term "nucleic acid sequencing," as used herein, generally refers to methods and technologies for determining the sequence of nucleotide bases in one or more polynucleotides. The polynucleotides can be, for example, deoxyribonucleic acid (DNA) or ribonucleic acid (RNA), including variants or derivatives thereof (such as single stranded DNA or double stranded DNA). Such methods and technologies may provide a plurality of raw genetic data corresponding to the genetic information of a subject (such as a human), as generated from a sample provided by the subject using the systems and methods described herein. In some cases, nucleic acid sequencing may be used to sequence a nucleic acid that has been partially or fully methylated. In some cases, nucleic acid sequencing may be used to determine a degree of methylation of a nucleic acid molecule.

Various nucleic acid sequencing techniques may be used to read the encoded information from the nucleic acid sample. A variety of sequencing approaches may be used including, but not limited to, polymerase chain reaction (PCR), digital PCR, real-time PCR, quantitative PCR (qPCR), Sanger sequencing, high-throughput sequencing, sequencing-by-synthesis, single-molecule sequencing, sequencing-by-ligation, RNA-Seq (Illumina), Next generation sequencing, Digital Gene Expression (Helicos), array hybridization, Clonal Single MicroArray (Solexa), shotgun sequencing, Maxim-Gilbert sequencing, or massively-parallel sequencing.

The term "machine learning", as used herein, generally refers to methods and technologies for using statistical techniques to infer one or more traits from one or more sets of data. Such methods and technologies may comprise supervised, supervised, semi-supervised, or unsupervised machine learning techniques. Machine learning techniques may comprise regression analysis, regularization, classification, dimensionality reduction, ensemble learning, meta learning, reinforcement learning, association rule learning, cluster analysis, anomaly detection, or deep learning. Machine learning techniques may comprise, but are not limited to: k-means, k-means clustering, k-nearest neighbors, learning vector quantization, linear regression, non-linear regression, least squares regression, partial least squares regression, logistic regression, stepwise regression, multivariate adaptive regression splines, ridge regression, principle component regression, least absolute shrinkage and selection operation, least angle regression, canonical correlation analysis, factor analysis, independent component analysis, linear discriminant analysis, multidimensional scaling, non-negative matrix factorization, principal components analysis, principal coordinates analysis, projection pursuit, Sammon mapping, t-distributed stochastic neighbor embedding, AdaBoost, boosting, bootstrap aggregation, ensemble averaging, decision trees, conditional decision trees, boosted decision trees, gradient boosted decision trees, random forests, stacked generalization, Bayesian networks, Bayesian belief networks, naïve Bayes, Gaussian naïve Bayes, multinomial naïve Bayes, hidden Markov models, hierarchical hidden Markov models, support vector machines, encoders, decoders, auto-encoders, stacked auto-encoders, perceptrons, multi-layer perceptrons, artificial neural networks, feedforward neural networks, convolutional neural networks, recurrent neural networks, long short-term memory, deep belief networks, deep Boltzmann machines, deep convolutional neural networks, deep recurrent neural networks, or generative adversarial networks.

The term "preserve nucleic acid molecules", as used herein, generally refers to less than about 0.5% degradation, less than about 1% degradation, less than about 2% degradation, less than about 3% degradation, less than about 4% degradation, less than about 5% degradation, less than about 6% degradation, less than about 7% degradation, less than about 8% degradation, less than about 9% degradation, less than about 10% degradation, or less than about 20% degradation of the nucleic acid molecules.

The term "prevent growth of microbes", as used herein, generally refers to less than about 0.5% growth, less than about 1% growth, less than about 2% growth, less than about 3% growth, less than about 4% growth, less than about 5% growth, less than about 6% growth, less than about 7% growth, less than about 8% growth, less than about 9% growth, less than about 10% growth, or less than about 20% growth of the nucleic acid molecules.

The term "genetic aberration", as used herein, generally refers to single nucleotide somatic mutations, amplification or deletion of genes, amplification or deletion of chromosomes or portions of chromosomes, translocations, or changes in nucleic acid methylation.

The term "expression", as used herein, generally relates to genetic aberrations and refers to the number of copies of a gene or abundance of a sequencing read, counts of a methylated base, counts of an alternate single base allele, or counts of sequencing reads that pass through a site of genetic translocation. In some embodiments, increases or decreases in expression are compared to a reference dataset or reference locations within the same dataset.

In an aspect, the present disclosure provides a method for supplementing a microbiome in a urinary tract of a subject. The method may comprise obtaining a urine sample of the subject. Next, the urine sample may be processed to identify a relative abundance of a first set of microbes in the urinary tract of the subject. Then, a second set of microbes for the urinary tract of the subject may be identified. The second set of microbes may be different than the first set of microbes. The second set of microbes may be configured to supplement the microbiome in the urinary tract of the subject.

A preservation mixture comprising at least two different chelators and one or more member(s) selected from the group consisting of: an antimicrobial agent, a cell membrane stabilizer, and a nucleic acid compactor.

FIG. 1 shows a flowchart for a first method 100 for supplementing a microbiome in a urinary tract of a subject. In a first operation 110, the method may comprise obtaining a urine sample of the subject. The first operation may further comprise preserving the urine sample in a preservation solution comprising: a pH buffer, a chelator, a cell membrane stabilizer, a DNA compactor, and an antimicrobial. The pH buffer may maintain the preservation solution at or near a particular pH value. For instance, the pH buffer may maintain the preservation solution at a pH of at least about 7, 7.1, 7.2, 7.3, 7.4, 7.5, 7.6, 7.7, 7.8, 7.9, 8.0, 8.1, 8.2, 8.3, 8.4, 8.5, 8.6, 8.7, 8.8, 8.9, or 9.0, or more. The pH buffer may maintain the preservation solution at a pH of at most about 9.0, 8.9, 8.8, 8.7, 8.6, 8.5, 8.4, 8.3, 8.2, 8.1, 8.0, 7.9, 7.8, 7.7, 7.6, 7.5, 7.4, 7.3, 7.2, 7.1, or 7.0, or less. The pH buffer may maintain the preservation solution at a pH that is within a range defined by any two of the preceding values. For instance, the pH buffer may maintain the preservation solution at a pH that is between 7 and 9. The pH buffer may maintain the preservation solution at a pH of about 8. The pH buffer may be a Tris buffer. The pH buffer may mitigate degradation or fragmentation of nucleic acids contained in the urine sample when the sample is subjected to freezing or defrosting. The pH buffer may prevent nucleic acid base damage, such as de-purination or deamination.

The chelator may chelate one or more metals. The chelator may comprise one or more member(s) selected from the group consisting of: a magnesium (Mg) chelator, a calcium (Ca chelator), and an iron (Fe) chelator. The chelator may comprise Enterobactin. The chelator may chelate Mg or Ca salts to inhibit nuclease activity or protease activity. The urine sample may be subject to high Fe concentrations, which may damage nucleic acids in the urine sample, such as by promoting oxidation reactions. Enterobactin may bind well to Fe. Use of Enterobactin as a Fe chelator may allow for a decreased concentration of ethylenediaminetetraacetic acid (EDTA), which may otherwise be required at a high concentration that may inhibit downstream processing, such as downstream molecular biology or sequencing library preparation. Enterobactin may further act as a ligation or polymerase chain reaction (PCR) enzyme reaction enhancer.

The cell membrane stabilizer may stabilize cell membranes. The cell membrane stabilizer may comprise one or more member(s) selected from the group consisting of: vitamin E conjugate and poly-L-lysine. The cell membrane stabilizer may prevent microbes or human cells from spilling associated nucleases into the preservation buffer. The cell membrane stabilizer may further prevent cell-associated nucleic acids from contaminating a cell-free nucleic acid compartment. The cell membrane stabilizer may thus keep cell-associated nucleic acids sequencing signals separated from cell-free nucleic acids sequencing signals, enhancing the sensitivity of nucleic acid sequencing. In a preferred embodiment, the cell membrane stabilizer may use poly-L-lysine trimers with a molecular weight of 1,000-5,000 Da.

The DNA compactor may compact cell-associated DNA. The DNA compactor may comprise poly-L-lysine. Urine samples may be susceptible to variable salt concentrations due to person-to-person or sample-to-sample variations. High salt or urea concentrations may cause cell-free nucleic acids to dissociate from endogenous proteins that otherwise protect the nucleic acid from nuclease fragmentation or hydrolysis damage reactions. The DNA compactor may protect the nucleic acids in urine samples having high salt or urea concentrations. Poly-L-Lysine may protect the nucleic acids by compacting free nucleic acids, such as by engaging in transient electrostatic or other charge-based associations with the nucleic acids. The poly-L-lysine may have a molecular weight of at least about 100 Daltons (Da), 200 Da, 300 Da, 400 Da, 500 Da, 600 Da, 700 Da, 800 Da, 900 Da, 1,000 Da, 2,000 Da, 3,000 Da, 4,000 Da, 5,000 Da, 6,000 Da, 7,000 Da, 8,000 Da, 9,000 Da, or 10,000 Da, or more. The poly-L-lysine may have a molecular weight of at most about 10,000 Da, 9,000 Da, 8,000 Da, 7,000 Da, 6,000 Da, 5,000 Da, 4,000 Da, 3,000 Da, 2,000 Da, 1,000 Da, 900 Da, 800 Da, 700 Da, 600 Da, 500 Da, 400 Da, 300 Da, 200 Da, or 100 Da, or less. The poly-L-lysine may have molecular weight that is within a range defined by any two of the preceding values, and multiple species of different size ranges may be included together in various ratios. For instance, the poly-L-lysine may have a molecular weight that is within a range from 1,000 Da to 5,000 Da. A preferred embodiment may include poly-L-lysine trimers with a molecular weight of 402.53 Da. A combination of molecular weights may be used together to facilitate both cell membrane stabilization and optimal DNA compaction. For example, various ratios of poly-L-lysine species may be used, such as about 10%, 20%, 30% 40% 50%, or 60% of species being in the range of 1,000-5,000 Da and the other about 90%, 80%, 70%, 60%, 50%, or 40% of species being in the range of around 400 Da.

The antimicrobial may comprise one or more member(s) selected from the group consisting of: penicillin, streptomycin, amphotericin B, and Stabilur tablet. The antimicrobial may prevent or reduce the excessive reproduction of microbes in the urine sample. An antimicrobial may be particularly important in a preservation solution that contains a reduced EDTA concentration or a preservation solution that contains Enterobactin or Deferoxamine Mesylate.

In a second operation 120, the method may comprise processing the urine sample to identify a relative abundance of a first set of microbes, or any subset thereof, in the urinary tract of the subject. The method may comprise subjecting the urine sample to nucleic acid sequencing. For instance, the method may comprise subjecting the urine sample to any nucleic acid sequencing described herein. The method may comprise subjecting the urine sample to nucleic acid sequencing to obtain one or more nucleic acid sequencing reads. The method may comprise assigning nucleic acid sequencing reads that do not match a genome of the subject to the genomes of the first set of microbes, or any subset thereof, thereby identifying the first set of microbes, or any subset thereof. The method may comprise assigning nucleic acid sequencing reads to the first set of microbes, or any subset thereof, at any level of taxonomic classification, such as a taxonomic kingdom, phylum, class order, family, genus, species, or strain of microbe. The method may comprise generating data (such as nucleic acid reads) indicative of a level of the first set of microbes, or any subset thereof, and processing the data against a reference to identify the relative abundance of the first set of microbes, or any subset thereof. The relative abundance may be an excess or a deficiency of the first set of microbes, or any subset thereof. An excess may comprise a greater number, level, or concentration of microbes as compared to a reference, such as a healthy subject or a population of healthy subjects. A deficiency may comprise a lesser number, level, or concentration of microbes as compared to the reference.

The excess or deficiency of the first set of microbes, or any subset thereof, may be associated with a urinary tract disorder. The urinary tract disorder may be a lower urinary tract disorder.

The urinary tract disorder may be a bladder disorder. The bladder disorder may comprise one or more member(s) selected from the group consisting of: bladder cancer, bladder exstrophy, bladder outlet obstruction, bladder sphincter dyssynergia, catheter-associated urinary tract infection, choluria, cystitis, cystitis glandularis, glomerulation, Gouverneur's syndrome, hemorrhagic cystitis, Hunner's ulcer, interstitial cystitis, megacystitis, neurogenic bladder dysfunction, overactive bladder, spermaturia, trigonitis, underactive bladder, urinary bladder neck obstruction, urge incontinence, vesicointestinal fistula, and vesicoureteral reflux.

The urinary tract disorder may be a kidney disorder. The kidney disorder may comprise one or more member(s) selected from the group consisting of: Abderhalden-Kaufmann-Lignac syndrome, acute proliferative glomerulonephritis, adenine phosphoribosyltransferase deficiency, Alport syndrome, analgesic nephropathy, autosomal dominant polycystic kidney disease, autosomal recessive polycystic kidney disease, Balkan endemic nephropathy, benign nephrosclerosis, Bright's disease, cardiorenal syndrome, chronic kidney disease, congenital nephrotic syndrome, conorenal syndrome, contrast-induced nephropathy, cystic kidney disease, Dent's disease, diabetic nephropathy, diffuse proliferative nephritis, distal renal tubular acidosis, diuresis, EAST syndrome, Fanconi syndrome, Fechtner syndrome, focal proliferative nephritis, focal segmental glomerulosclerosis, Fraley syndrome, Galloway Mowat syndrome, Gitelman syndrome, glomerulocystic kidney disease, glomerulopathy, Goldblatt kidney, Goodpasture syndrome, high anion gap metabolic acidosis, HIV-associated nephropathy, horseshoe kidney, hydronephrosis, hypertensive kidney disease, IgA nephropathy, interstitial nephritis, juvenile nephronopthisis, kidney cancer, kidney stone disease, Lightwood-Albright syndrome, lupus nephritis, malarial nephropathy, medullary cystic kidney disease, medullary sponge kidney, membranous glomerulonephritis, Mesoamerican nephropathy, milk-alkali syndrome, minimal mesangial glomerulonephritis, multicystic dysplastic kidney, nephritis, nephrocalcinosis, nephrogenic diabetes insipidus, nephromegaly, nephrotosis, nephrosis, nephrotic syndrome, Nutcracker syndrome, papillorenal syndrome, phosphate neuropathy, polycystic kidney disease, primary hyperoxaluria, proximal renal tubular acidosis, pyelonephritis, pyonephrosis, rapidly progressive glomerulonephritis, renal agenesis, renal angina, renal artery stenosis, renal cyst, renal ischemia, renal osteodystrophy, renal papillary necrosis, renal tubular acidosis, renal vein thrombosis, reninoma, secondary hypertension, serpentine fibula-polycystic kidney syndrome, shunt nephritis, sickle cell nephropathy, thin basement membrane disease, transplant glomerulopathy, tubulointerstitital nephritis and uveitis, tubulopathy, uremia, uremic frost, and Wunderlich syndrome.

The urinary disorder may be a urethra disorder. The urethra disorder may comprise one or more member(s) selected from the group consisting of: urethral meatal stenosis, urethral caruncle, urethral foreign body, urethral stricture, urethral syndrome, urethritis, and urethrorrhagia.

The urinary disorder may be a ureter disorder. The ureter disorder may comprise one or more member(s) selected from the group consisting of: duplicated ureter, megaureter, ureteritis, and ureterocele.

The urinary tract disorder may be a prostate disorder. The prostate disorder may comprise one or more member(s) selected from the group consisting of: prostatitis, acute prostatitis, asymptomatic inflammatory prostatitis, chronic bacterial prostatitis, chronic prostatitis, granulomatous prostatitis, IgG4-related prostatitis, male accessory gland infection, benign prostatic hyperplasia, and prostate cancer.

The urinary tract disorder may be a testicular disorder. The testicular disorder may comprise one or more member (s) selected from the group consisting of: ectopic testis, epididymitis, gonadal torsion, orchitis, orchialgia, macroorchidism, testicular cancer, genital tuberculosis, hydrocele, hydrocele testis, rete tubular ectasia, Sertoli cell nodule, testicular atrophy, testicular dysgenesis syndrome, testicular microlithiasis, testicular pain, testicular rupture, testicular sarcoidosis, testicular torsion, and testicular trauma.

The urinary tract disorder may be a penile disorder. The penile disorder may comprise one or more member(s) selected from the group consisting of: penile cancer, erectile dysfunction, priapism, induratio penis plastic, Peyronie's disease, aposthia, balanitis, penile fracture, penile injury, penile pain, and penile artery shunt syndrome.

The urinary tract disorder may be a system disorder. The urinary tract disorder may comprise one or more member(s) selected from the group consisting of: reactive arthritis, Reiter's syndrome, and urosepsis.

The first set of microbes may comprise at least about 1, 2, 3, 4, 5, 6, 7, 8, 9, 10, 20, 30, 40, 50, 60, 70, 80, 90, 100, 200, 300, 400, 500, 600, 700, 800, 900, 1,000, 2,000, 3,000, 4,000, 5,000, 6,000, 7,000, 8,000, 9,000, 10,000, 20,000, 30,000, 40,000, 50,000, 60,000, 70,000, 80,000, 90,000, 100,000, 200,000, 300,000, 400,000, 500,000, 600,000, 700,000, 800,000, 900,000, 1,000,000, or more different types of microbes. The first set of microbes may comprise at most about 1,000,000, 900,000, 800,000, 700,000, 600,000, 500,000, 400,000, 300,000, 200,000, 100,000, 90,000, 80,000, 70,000, 60,000, 50,000, 40,000, 30,000, 20,000, 10,000, 9,000, 8,000, 7,000, 6,000, 5,000, 4,000, 3,000, 2,000, 1,000, 900, 800, 700, 600, 500, 400, 300, 200, 100, 90, 80, 70, 60, 50, 40, 30, 20, 10, 9, 8, 7, 6, 5, 4, 3, 2, or 1 different types of microbes. The first set of microbes may comprise a number of types of microbes that is within a range defined by any two of the preceding values. The first set of microbes, or any subset thereof, may comprise microbes from any number of taxonomic kingdoms, phyla, classes, orders, families, genera, species, or strains of microbes.

The first set of microbes, or any subset thereof, may comprise one or more microbes from a taxonomic kingdom selected from the group consisting of: Bacteria, Viruses, Bacteriophages, and Archaea. The first set of microbes, or any subset thereof, may comprise one or more microbes selected from any 1, 2, 3, or 4 of the preceding taxonomic kingdoms.

The first set of microbes, or any subset thereof, may comprise one or more microbes from a taxonomic phylum selected from the group consisting of: Proteobacteria, Firmicutes, Actinobacteria, Bacteroidetes, Aquificae, Deinococcus-Thermus, Fusobacteria, and Tenericutes. The first set of microbes, or any subset thereof, may comprise one or more microbes selected from any 1, 2, 3, 4, 5, 6, 7, or 8 of the preceding taxonomic phyla.

The first set of microbes, or any subset thereof, may comprise one or more microbes from a taxonomic class selected from the group consisting of: Gammaproteobacteria, Betaproteobacteria, Clostridia, Alphaproteobacteria, Bacilli, Actinobacteria, Tissierellia, Bacteroidia, Erysipelotrichia, Aquificiae, Deinococci, Epsilonproteobacteria, Flavobacteria, Fusobacteria, Mollicutes, Negativicutes, and Coriobacteria. The first set of microbes, or any subset thereof, may comprise one or more microbes selected from any 1, 2, 3, 4, 5, 6, 7, 8, 9, 10, 11, 12, 13, 14, 15, 16, or 17 of the preceding taxonomic classes.

The first set of microbes, or any subset thereof, may comprise one or more microbes from a taxonomic order selected from the group consisting of: Pseudomonadales, Enterobacterales, Caudovirales, Actinomycetales, Corynebacteriales, Burkholderiales, Clostridiales, Rhizobiales, Streptomycetales, Sphingomonadales, Lactobacillales, Bifidobacteriales, Pseudonocardiales, Bacteroidales, Xanthomonadales, Bacillales, Erysipelotrichales, Acidaminococcales, Campylobacterales, Desulfurobacteriales, Fusobacteriales, Herpesvirales, Micrococcales, Mycoplasmatales, Neisseriales, Pasteurellales, Picornavirales, Propionibacteriales, Thermales, Veillonellales, Vibrionales, Flavobacteriales, Tissierellales, Aeromonadales, Coriobacteriales, and Eggerthellales. The first set of microbes, or any subset thereof, may comprise one or more microbes selected from any 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, or 36 of the preceding taxonomic orders.

The first set of microbes, or any subset thereof, may comprise one or more microbes from a taxonomic family selected from the group consisting of: Myoviridae, Porphyromonadaceae, Pseudomonoadaceae, Enterobacteriaceae, Actinomycetaceae, Prevotellaceae, Burkholderiaceae, Siphoviridae, Hyphoicrobiaceae, Streptomycetaceae, Sphingomonadaceae, Peptoniphilaceae, Bifidobacteriaceae, Peptostreptococcaceae, Polyomaviridae, Xanthomonadaceae, Staphylococcaceae, Bacteroidaceae, Erysipelotrichaceae, Nocardiaceae, Rikenellaceae, Acidaminococcaceae, Aerococcaceae, Bradyrhizobiaceae, Campylobacteraceae, Comamonadaceae, Corynebacteriaceae, Desulfurobacteriaceae, Erwiniaceae, Flavobacteriaceae, Hafniaceae, Helicobacteraceae, Herpesviridae, Lachnospiraceae, Lactobacillaceae, Leptotrichiaceae, Microbacteriaceae, Micrococcaceae, Morganellaceae, Mycoplasmataceae, Neisseriaceae, Oxalobacteraceae, Paenibacillaceae, Pasteurellaceae, Peptococcaceae, Picornaviridae, Podoviridae, Propionibacteriaceae, Rhizobiaceae, Ruminococcaceae, Thermaceae, Veillonellaceae, Vibrionaceae, Yersiniaceae, Arenaviridae, Streptococcaceae, Tissierellaceae, Tannerellaceae, Oscillospiraceae, Aeromonadaceae, Erythrobacteraceae, Moraxellaceae, Barnesiellaceae, Intrasporangiaceae, Coriobacteriaceae, and Eggerthellaceae. The first set of microbes, or any subset thereof, may comprise one or more microbes selected from any 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, or 66 of the preceding taxonomic families.

The first set of microbes, or any subset thereof, may comprise one or more microbes from a taxonomic genus selected from the group consisting of: *Klebsiella, Lambdavirus, Shigella, Pseudomonas, Citrobacter, Salmonella, Escherichia, Prevoltella, Barnesiella, Devosia, Streptomyces, Bifidobacterium, Sphingomonas, Helcococcus, Parabacteroides, Mobilunus, Gardnerella, Finegoldia, Streptococcus, Betapolyomavirus, Stenotrophomonas, Enterococcus, Ralstonia, Staphylococcus, Bacteroides, Alistipes, Clostridioides, Erysipelothrix, Rhodococcus, Triavirus, Acidaminococcus, Actinomyces, Actinotignum, Aerococcus, Aggregatibacter, Anaerococcus, Blautia, Bradyrhizobium, Burkholderia, Campylobacter, Cornyebacterium, Cutibacterium, Desulfitobacterium, Enterobacter,* Epsilon15virus, *Ezakiella,* F116virus, *Faecalibacterium, Filifactor, Fusobacterium, Haemophilus, Hafnia, Helicobacter, Histophilus, Janthinobacterium, Kluyvera, Lacnoclostridium, Lactobacillus, Lawsonella, Limnohabitans, Lymphocryptovirus, Mageeibacillus, Microbacterium, Micrococcus, Morganella, Neisseria, Ornithobacterium,* P22virus, P2virus, *Paenibacillus, Pantoea, Parvimonas, Peptoniphilus, Porphyromonas, Propionibacterium, Propionmicrobium, Proteus, Pseudarthrobacter, Raoultella, Rhizobium, Rhodopseudomonas, Roseolovirus, Rothia, Ruminiclostridium, Ruminococcus,* Salivirus, *Serratia, Sneathia, Sphingobium, Thermovibrio, Thermus, Ureaplasma, Varibaculum, Veillonella, Vibrio, Xenorhabdus, Yersinia,* Mammarenavirus, *Variovorax, Prevotella, Methylibium, Polynucleobacter,* P68virus, *Thiomonas, Phycicoccus, Acidovorax, Anaerostipes, Collinsella, Hydrogenophaga, Lachnoclostridium, Eggerthella, Negativicoccus, Ndongobacter, Mobiluncus, Kosakonia, Oscillibacter, Tannerella, Flavonifractor, Tessaracoccus, Eikenella, Aeromonas, Porphyrobacter, Edwardsiella, Leptotrichia, Comamonas, Acinetobacter,* and *Tardiphaga.* The first set of microbes, or any subset thereof, may comprise one or more microbes selected from any 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, or 97 of the preceding taxonomic genera.

The first set of microbes, or any subset thereof, may comprise one or more microbes from a taxonomic species selected from the group consisting of: *Klebsiellas pneumoniae, Shigellas sonnei, Klebsiellas varicola, Prevotellas* species oral taxon 299, *Shigellas dysenteriae, Pseudomonas aeruginosa, Salmonellas enterica, Escherichias coli, Shigellas boydii, Shigellas* species PAMC 28760, *Shigellas flexneri,* Betapolyomavirus human, *Exscherichias fergusonii, Prevotellas scopos, Prevotellas melaninogenica, Escherichias albertii barnesiellas viscericola, Devosias* species H5989, *Streptococcus pneumoniae, Citrobacters freundii, Prevotellas enoeca, Bacteroides thetaiotaomicron, Helcococcus kunzii, Parabacteroidess distasonis, Pseudomonas oleovorans, Mobiluncus curtisii, Streptococcus dysgalactiae, Streptococcus pyogenes, Gardnerellas vaginalis, Finegoldias magna, Bacteroides dorei, Bacteroides vulgatus, Pseudomonas* species 1217, *Enterococcus* species 7L76, *Bacteroides* species L48, *Ralstonias insidiosa, Streptococcus pasteurianus, Bifidobacterium longum, Bacteroides ovatus, Enterococcus faecalis, Staphylococcus epidermis, Staphylococcus aureus, Bacteroides fragilis, Alistipes shahii, Bacteroides salanitronis, Clostridioides difficile, Erysipelothrix rhusiopathiae,* Lambdavirus uncultured virus, *Pseudomonas frederiksbergensis, Ralstonia mannitolilytica, Rhodococcus erythropolis, Rhodoccus* species 008, *Sphingomonas echinoides, Staphylococcus agnetis, Staphyloccuccus lugdunensis, Staphyloccus saprophyticus, Streptococcus gallolyticus, Streptococcus infantarius, Streptococcus lutetiensis, Streptococcus macedonicus, Streptomyces* uncultured bacteria 37b14, *Streptomyces* uncultured bacterium 39k17, *Triavirus staphylococcus* phage 3A, *Triavirus staphylococcus* phage tp310-2, *Triavirus staphylococcus* phage StB20, Human herpesvirus 6, Human gammaherpesvirus 4, *Bordetella hinzii, Methylibium petroleiphilum, Shigella* species LN126, Podoviridae, *Lactobacillus jensenii, Burkholderia pseudomallei* group, *Pseudomonas* phage phi297, *Klebsiella michiganensis, Lactobacillus* species B164, *Streptococcus* species I-G2, *Kosakonia sacchari, Ruminococcus bicirculans, Prevotella jejuni, Bradyrhizobium* species llw1, *Agrobacterium tumefaciens* complex, *Pseudomonas* phage YMC/01/01/P52_PAE BP, *Aerococcus sanguinicola, Prevotella* species S4-10, *Corynebacterium frankenforstense, Prevotella* species Sc00026, *Streptococcus* phage EJ-1, Comamonas bacterium 36B, *Micrococcus luteus, Pseudomonas sihuiensis, Staphylococcus haemolyticus, Streptococcus* phage phiD12, *Staphylococcus hominis, Pseudomonas* species ATCC 13867, *Streptococcus oralis, Streptococcus salivarius, Streptococcus suis, Acinetobacter chlamydia*-associated clinical sample 198-T, *Sphingobium* species TKS, *Streptococcus parasanguinis, Tessaracoccus*

*aquimaris, Pluralibacter lignolyticus, Streptococcus intermedius, Ureaplasma parvum, Pseudomonas fluorescens* group, *Pseudomonas putida* group, *Sphingobium yanoikuyae, Aerococcus urinae, Burkholderia* species BDU6, *Sphingomonas* species LK11, *Bacillus cereus, Paenibacillus polymyxa, Streptococcus* species VT 162, Comamonadaceae bacterium B1, *Klebsiella quasipneumoniae, Corynebacterium simulans, Lactobacillus iners, Corynebacterium* species ATCC 6931, *Klebsiella* species NCTC 8172, *Lawsonella clevelandensis, Lactobacillus* species wkB8, *Sphingomonas taxi, Bradyrhizobium* species lamp2, *Streptococcus* phage SpSL1, *Enterobacteria* phage P88, *Corynebacterium riegelii, Corynebacterium imitans, Lactobacillus acidophilus, Lactobacillus buchneri, Lactobacillus delbrueckii, Lactobacillus helveticus, Cedecea neteri, Enterobacter hormaechei, Lactobacillus plantarum, Lactobacillus gasseri, Lactobacillus acetotolerans, Lactobacillus amylophilus, Lactobacillus* amylovorus, *Tessaracoccus flavus, Lactobacillus farciminis, Corynebacterium singulare, Erwinia gerundensis, Hoeflea* species IMCC20628, *Lactobacillus ruminis, Pseudomonas lini, Propionibacterium* phage PHLD30, *Propionibacterium* phage PHLD64, *Propionibacterium* phage PHL082, *Yersinia pseudotuberculosis* complex, *Actinomyces naeslundii, Acidovorax* species NA2, *Acidovorax* species P3, *Acidovorax* species P4, *Bifidobacterium adolescentis, Bifdobacterium breve, Corynebacterium aurimucosum, Negativicoccus massiliensis, Massilia* species WG5, *Turicibacter* species H121, *Corynebacterium diphtheriae, Corynebacterium glutamicum, Rothia aeria, Propionibacterium freudenreichii, Cutibacterium acnes, Pseudomonas* phage phi1, *Streptococcus* species A12, *Pseudomonas* species bs2935, *Pseudomonas* phage JBD44, *Pseudomonas* phage YMC11/07/P54_PAE_BP, *Gemella* species oral taxon 928, *Sinorhizobium* species RAC02, *Hydrogenophaga* species RAC07, *Acidovorax* species T1, Lambdavirus, *Sneathia amnii, Ndongobacter massiliensis, Acidaminococcus intestini, Varibaculum* species, *Streptococcus* species NPS 308, *Tessaracoccus* species 72.5-30, *Corynebacterium sphenisci, Corynebacterium atypicum, Streptococcus* phage IPPS, *Delftia* species HK171, *Klebsiella* species M5a1, *Staphylococcus* phage St 134, *Propionibacterium* virus Lauchelly, *Propionibacterium* virus PHLD82M03, *Propionibacterium* virus PHLJ17M01, *Propionibacterium* virus Stormborn, *Microbacterium paraoxydans, Thauera* species K11, *Escherichia* phage Ayreon, *Dickeya zeae, Pseudomonas* species HLS-6, *Paracoccus* species CBA4604, *Citrobacter freundii* complex species CFNIH2, *Citrobacter freundii* complex species CFNIH3, *Alkaliphilus metalliredigens, Lachnoclostridium bolteae, Ureaplasma urealyticum, Yersinia* virus L413C, *Pseudomonas* species M18, *Lachnoclostridium* butyrate-producing bacterium SM4/1, *Lachnoclostridium* butyrate-producing bacterium SS3/4, Plasmid ColV-K30, *Bacteroides cellulosilyticus,* Plasmid R1-19, *Haemophilus pittmaniae, Bradyrhizobium canariense, Streptococcus pseudopneumoniae, Corynebacterium resistens, Lactobacillus kefiranofaciens, Sphaerochaeta coccoides, Thermus thermophilus, Bifidobacterium animalis, Streptococcus mitis, Acinetobacter lwoffli, Porphyromonas asaccharolytica, Prevotella denticola, Prevotella disiens, Ornithobacterium rhinotracheale, Enterobacteria* phage CP-1639, *Burkholderia cepacia, Brevundimonas diminuta, Staphylococcus capitis, Pseudomonas fluorescens, Pseudomonas tolaasii, Veillonella parvula, Shigella* species AR-21793, *Turneriella parva, Roseburia hominis, Pseudomonas putida,* Human betaherpesvirus 6B, *Cutibacterium avidum, Cutibacterium granulosum, Parvimonas micra, Anaerococcus prevotii, Sphingobium indicum, Sphingobium japonicum, Variovorax paradoxus, Pseudomonas* phage PA11, *Enterobacter cloacae* complex, *Citrobacter amalonaticus, Agrobacterium tumefaciens, Verminephrobacter eiseniae, Bacteroides xylanisolvens, Corynebacterium* species L2-79-05, *Enterobacteria* phage 933 W sensu lato, *Lactobacillus backii, Thermus scotoductus, Sinorhizobium fredii, Rhizobium leguminosarum, Prevotella timonensis, Mesorhizobium ciceri, Veillonella atypica, Tessaracoccus fiavescens, Enterobacter* species 638, *Streptococcus merionis, Micrococcus* species A1, *Blautia obeum, Polyangium brachysporum, Azoarcus olearius, Thiomonas arsenitoxydans, Ralstonia* species Is-C065, *Variovorax boronicumulans, Rothia mucilaginosa, Enterococcus cecorum, Bradyrhizobium oligotrophicum, Phycicoccus dokdonensis, Enterobacteria* phage VT1-Sakai, *Lactobacillus crispatus, Pseudomonas azotoformans, Pseudomonas fulva, Neisseria gonorrhoeae, Neisseria lactamica, Neisseria meningitidis, Burkholderia contaminans, Neisseria sicca, Prevotella dentalis, Lactobacillus gallinarum, Ochrobactrum anthropi, Peptoniphilus harei, Raoultella ornithinolytica, Enterobacter cloacae, Pantoea cypripedii, Acidovorax* species NA3, *Thiomonas* species CB2, *Enterobacteria* phage YYZ-2008, *Thermus brockianus, Afipia* genospecies 3, *Citrobacter braakii, Lactobacillus* phage Lv-1, *Burkholderia thailandensis, Proteus mirabilis, Klebsiella* species 2N3, *Prevotella fusca, Actinotignum schaalii, Serratia liquefaciens, Serratia marcescens, Kluyvera intermedia, Yersinia pestis, Yersinia pseudotuberculosis, Edwardsiella tarda, Aeromonas salmonicida, Anaerostipes hadrus, Prevotella* species oral taxon 299, *Myxococcus* mixed culture bacterium AM_gF3SD01_05, *Desulfitobacterium* mixed culture bacterium AX_gF3SD01_48, *Comamonas* mixed culture bacterium PE_gF1DD01_04, *Streptococcus anginosus* group, *Rhodoplanes* species Z2-YC6860, *Citrobacter rodentium, Citrobacter gillenii, Altererythrobacter dongtanensis, Corynebacterium* species NML98-0116, *Actinomyces* species oral taxon 414, *Streptococcus* species oral taxon 064, *Streptococcus* species oral taxon 431, *Kocuria palustris, Haemophilus influenzae, Haemophilus parainfluenzae, Aggregatibacter aphrophilus, Collinsella aerofaciens, Campylobacter hominis, Streptococcus constellatus, Campylobacter hominis, Hydrogenophaga* species PBC, *Delftia acidovorans, Campylobacter ureolyticus, Leclercia adecarboxylata, Lactobacillus amylolyticus, Porphyromonas gingivalis, Lachnoclostridium saccharolyticum, Eggerthella lenta, Fusobacterium nucleatum, Faecalibacterium prausnitzii, Streptococcus* phage phi-SsUD.1, *Bacillus cereus* group, *Aerococcus christensenii, Burkholderia cepacia* complex, *Corynebacterium flavum, Micrococcus* species MG-2010-D12, *Actinomyces succiniciruminis, Streptococcus agalactiae,* Guanarito mammarenavirus, *Prevotella intermedia, Prevotella enoeca, Desulfitobacterium hafniense, Pseudomonas aeruginosa* group, *Staphylococcus epidermidis, Bacteroides dorei, Prevotella melaninogenica,* and Human polyomavirus 2. The first set of microbes, or any subset thereof, may comprise one or more microbes selected from any 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317, 318, 319, 320, 321, 322, 323, 324, 325, 326, 327, 328, 329, 330, 331, 332, 333, 334, 335, 336, 337, 338, 339, 340, 341, 342, 343, 344, 345, or 346 of the preceding taxonomic species.

In a third operation 130, the method may comprise identifying a second set of microbes for the urinary tract of the subject, wherein the second set of microbes is configured to supplement the microbiome in the urinary tract of the subject. The second set of microbes may be selected to have a beneficial impact on the microbiome of the urinary tract of the patient. The second set of microbes may be selected to increase a concentration of one or more microbes from the first set of microbes that has been identified as deficient. For instance, the second set of microbes may comprise one or more microbes from the first set of microbes. When administered to the subject, the second set of microbes may thus increase a concentration of one or more of the microbes identified as deficient. Alternatively or in combination, the second set of microbes may comprise one or more microbes that have a symbiotic relationship with one or more of the microbes identified as deficient. When administered to the subject, the second set of microbes may thus increase a concentration of one or more of the microbes identified as deficient through the symbiotic relationship. The second set of microbes may be selected to decrease a concentration of one or more microbes from the first set of microbes that has been identified as excessive. For instance, the second set of microbes may comprise one or more microbes that have a completive or parasitic relationship with one or more of the microbes identified as excessive. When administered to the subject, the second set of microbes may thus decrease a concentration of one or more of the microbes identified as excessive or enhance the concentration of one or more of the microbes identified as deficient.

The second set of microbes may be different than the first set of microbes. The second set of microbes may comprise the first set of microbes. The second set of microbes may comprise any subset of the first set of microbes. The second set of microbes may comprise at least any subset of the first set of microbes. The second set of microbes may comprise at most any subset of the first set of microbes. The first set of microbes may comprise the second set of microbes. The first set of microbes may comprise any subset of the second set of microbes. The first set of microbes may comprise at least any subset of the second set of microbes. The first set of microbes may comprise at most any subset of the second set of microbes.

The second set of microbes may comprise at least about 1, 2, 3, 4, 5, 6, 7, 8, 9, 10, 20, 30, 40, 50, 60, 70, 80, 90, 100, 200, 300, 400, 500, 600, 700, 800, 900, 1,000, 2,000, 3,000, 4,000, 5,000, 6,000, 7,000, 8,000, 9,000, 10,000, 20,000, 30,000, 40,000, 50,000, 60,000, 70,000, 80,000, 90,000, 100,000, 200,000, 300,000, 400,000, 500,000, 600,000, 700, 000, 800,000, 900,000, 1,000,000, or more different types of microbes. The second set of microbes may comprise at most about 1,000,000, 900,000, 800,000, 700,000, 600,000, 500, 000, 400,000, 300,000, 200,000, 100,000, 90,000, 80,000, 70,000, 60,000, 50,000, 40,000, 30,000, 20,000, 10,000, 9,000, 8,000, 7,000, 6,000, 5,000, 4,000, 3,000, 2,000, 1,000, 900, 800, 700, 600, 500, 400, 300, 200, 100, 90, 80, 70, 60, 50, 40, 30, 20, 10, 9, 8, 7, 6, 5, 4, 3, 2, or 1 different types of microbes. The second set of microbes may comprise a number of types of microbes that is within a range defined by any two of the preceding values. The second set of microbes, or any subset thereof, may comprise microbes from any number of taxonomic kingdoms, phyla, classes, orders, families, genera, species, or strains of microbes.

The second set of microbes, or any subset thereof, may comprise one or more microbes from a taxonomic kingdom selected from the group consisting of: Bacteria, Viruses, Bacteriophages, and Archaea. The second set of microbes, or any subset thereof, may comprise one or more microbes selected from any 1, 2, 3, or 4 of the preceding taxonomic kingdoms.

The second set of microbes, or any subset thereof, may comprise one or more microbes selected from a taxonomic phylum selected from the group consisting of: Bacteroidetes, Firmicutes, Actinobacteria, Proteobacteria, Deinococcus-Thermus, and Polyomaviridae. The second set of microbes, or any subset thereof, may comprise one or more microbes selected from any 1, 2, 3, 4, 5, or 6 of the preceding taxonomic phyla.

The second set of microbes, or any subset thereof, may comprise one or more microbes selected from a taxonomic class selected from the group consisting of: Bacteroidia, Bacilli, Actinobacteria, Gammaproteobacteria, Deinococci, Tissierellia, Epsilonproteobacteria, Flavobacteriia, Negativicutes, Clostridia, Alphaproteobacteria, and Betapolyomavirus. The second set of microbes, or any subset thereof, may comprise one or more microbes selected from any 1, 2, 3, 4, 5, 6, 7, 8, 9, 10, 11, or 12 of the preceding taxonomic classes.

The second set of microbes, or any subset thereof, may comprise one or more microbes selected from a taxonomic order selected from the group consisting of: Bacteroidales, Lactobacillales, Corynebacteriales, Propionibacteriales, Pseudomonadales, Thermales, Micrococcales, Tissierellales, Pasteurellales, Campylobacterales, Bifidobacteriales, Actinomycetales, Flavobacteriales, Veillonellales, Clostridiales, and Rhizobiales. The second set of microbes, or any subset thereof, may comprise one or more microbes selected from any 1, 2, 3, 4, 5, 6, 7, 8, 9, 10, 11, 12, 13, 14, 15, or 16 of the preceding taxonomic orders.

The second set of microbes, or any subset thereof, may comprise one or more microbes selected from a taxonomic family selected from the group consisting of: Prevotellaceae, Lactobacillaceae, Corynebacteriaceae, Propionibacteriaceae, Pseudomonadaceae, Thermaceae, Streptococcaceae, Porphyromonadaceae, Micrococcaceae, Aerococcaceae, Peptoniphilaceae, Pasteurellaceae, Campylobacteraceae, Bifidobacteriaceae, Actinomycetaceae, Flavobacteriaceae, Veillonellaceae, Ruminococcaceae, Bradyrhizobiaceae, Hyphomicrobiaceae, and Bacteroidaceae. The second set of microbes, or any subset thereof, may comprise one or more microbes selected from any 1, 2, 3, 4, 5, 6, 7, 8, 9, 10, 11, 12, 13, 14, 15, 16, 17, 18, 19, 20, or 21 of the preceding taxonomic families.

The second set of microbes, or any subset thereof, may comprise one or more microbes selected from a taxonomic genus selected from the group consisting of: *Prevotella, Lactobacillus, Corynebacterium, Cutibacterium,*

*Pseudomonas, Thermus, Streptococcus, Porphyromonas, Micrococcus, Aerococcus, Lawsonella, Anaerococcus, Haemophilus, Campylobacter, Bifidobacterium, Mobiluncus, Ornithobacterium, Veillonella, Aggregatibacter, Faecalibacterium, Bradyrhizobium, Rhodopseudomonas, Devosia, Bacteroides,* and Mageeibacillus. The second set of microbes, or any subset thereof, may comprise one or more microbes selected from any 1, 2, 3, 4, 5, 6, 7, 8, 9, 10, 11, 12, 13, 14, 15, 16, 17, 18, 19, 20, 21, 22, 23, 24, or 25 of the preceding taxonomic genera.

The second set of microbes, or any subset thereof, may comprise one or more microbes selected from a taxonomic species selected from the group consisting of: *Prevotella jejuni, Lactobacillus gasseri, Corynebacterium* species NML98-0116, *Cutibacterium acnes, Lactobacillus amylovorus, Lactobacillus johnsonii, Lactobacillus jensenii, Pseudomonas fluorescens* group, *Thermus scotoductus, Streptococcus anginosus* group, *Streptococcus anginosus, Streptococcus mitis, Porphyromonas asaccharolytica, Lactobacillus crispatus, Micrococcus luteus, Lactobacillus helveticus, Pseudomonas tolaasii, Prevotella fusca, Aerococcus christensenii, Streptococcus parasanguinis, Lawsonella clevelandensis, Lactobacillus delbrueckii, Streptococcus pseudopneumoniae, Thermus thermophilus, Anaerococcus prevotii, Prevotella* species oral taxon 299, *Haemophilus influenzae, Campylobacter ureolyticus, Porphyromonas gingivalis, Streptococcus oralis, Lactobacillus acidophilus, Bifidobacterium breve, Corynebacterium aurimucosum, Mobiluncus curtisii, Lactobacillus kefiranofaciens, Ornithobacterium rhinotracheale, Cutibacterium avidum, Veillonella atypica, Lactobacillus gallinarum, Aggregatibacter aphrophilus, Faecalibacterium prausnitzii, Bradyrhizobium diazoefficiens, Rhodopseudomonas palustris, Devosia* species H5989, *Bradyrhizobium* species SK17, *Pseudomonas* species AK6U, *Bifidobacterium longum, Bradyrhizobium* species S23321, *Bacteroides thetaiotaomicron,* and *Mageeibacillus indolicus*. The second set of microbes, or any subset thereof, may comprise one or more microbes selected from any 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 of the preceding taxonomic species.

The method may further comprise supplying the second set of microbes to the urinary tract of the subject.

The method may further comprise outputting a report that identifies the second set of microbes.

In another aspect, the present disclosure provides a system for supplementing a microbiome in a urinary tract of a subject. The system may comprise a database and one or more computer processors operatively coupled to the database. The one or more computer processors may be individually or collectively programmed to implement the method of FIG. 1. The one or more computer processors may be individually or collectively programmed to identify a relative abundance of a first set of microbes in the urinary tract of the subject. The one or more computer processors may be individually or collectively programmed to identify a second set of microbes for the urinary tract of the subject. The second set of microbes may be different than the first set of microbes. The second set of microbes may be configured to supplement the microbiome in the urinary tract of the subject. The one or more computer processors may be individually or collectively programmed to store the second set of microbes in the database.

In another aspect, the present disclosure provides a method comprising supplementing a microbiome of a urinary tract of a subject having a first set of microbes with a second set of microbes. The second set of microbes may be different than the first set of microbes. The second set of microbes may be selected to treat a urinary tract disorder.

Figure 2:
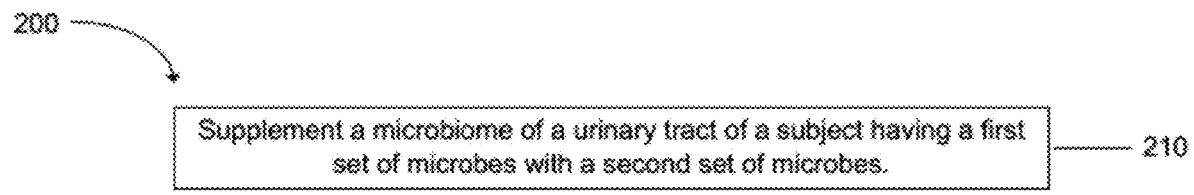
FIG. 2 shows a flowchart for a second method for supplementing a microbiome in a urinary tract of a subject.

FIG. 2 shows a flowchart for a second method 200 for supplementing a microbiome in a urinary tract of a subject. In a first operation 210, the method may comprise supplementing a microbiome of a urinary tract of a subject having a first set of microbes with a second set of microbes. The first set of microbes may comprise any first set of microbes described herein with respect to method 100. The second set of microbes may comprise any second set of microbes described herein with respect to method 100. The second set of microbes may be different than the first set of microbes, as described herein. The first set of microbes may comprise the second set of microbes. The first set of microbes may comprise a subset of the second set of microbes. The second of microbes may be selected to treat a urinary tract disorder, as described herein. For instance, the second set of microbes may be used to treat any urinary tract disorder described herein. The microbiome may be supplemented using a liquid formulation comprising the second set of microbes. The liquid formulation may be a liquid formulation that is intended to be administered orally, by catheter into the bladder, by catheter into the urethra, by subcutaneous injection, by intramuscular injection, by intravenous injection, or by injection into any part of the urinary tract of the subject, such as by injection into a bladder, kidney, urethra, ureter, prostate, testicle, or penis of the subject. Alternatively or in combination, the microbiome may be supplemented using a tablet or capsule comprising the second set of microbes. The tablet or capsule may be intended to be administered orally.

In various aspects, the present disclosure provides compositions of beneficial microbes that are formulated for application to a catheter prior to insertion into the urethra. In particular, in certain aspects, the present disclosure provides compositions comprising beneficial microbes that are configured to be used, e.g., by a clinician, without a need to culture the beneficial organism prior to administration.

In some embodiments, the beneficial microbe(s) are administered through a catheter to the bladder of an individual, thereby supplementing the microbial constituency of the bladder.

In some embodiments, the beneficial microbe is a bacterium, and, in certain embodiments, the bacterium is selected from the group consisting of *Prevotella jejuni, Lactobacillus gasseri, Corynebacterium* species NML98-0116, *Cutibacterium acnes, Lactobacillus amylovorus, Lactobacillus johnsonii, Lactobacillus jensenii, Pseudomonas fluorescens* group, *Thermus scotoductus, Streptococcus anginosus* group, *Streptococcus anginosus, Streptococcus mitis, Porphyromonas asaccharolytica, Lactobacillus crispatus, Micrococcus luteus, Lactobacillus helveticus, Pseudomonas tolaasii, Prevotella fusca, Aerococcus christensenii, Streptococcus parasanguinis, Lawsonella clevelandensis, Lactobacillus delbrueckii, Streptococcus pseudopneumoniae, Thermus thermophilus, Anaerococcus prevotii, Prevotella* species oral taxon 299, *Haemophilus influenzae, Campylobacter ureolyticus, Porphyromonas gingivalis, Streptococcus oralis, Lactobacillus acidophilus, Bifidobacterium breve, Corynebacterium aurimucosum, Mobiluncus curtisii, Lactobacillus kefiranofaciens, Ornithobacterium rhinotracheale, Cutibacterium avidum, Veillonella atypica, Lactobacillus gallinarum, Aggregatibacter aphrophilus, Faecalibacterium prausnitzii, Bradyrhizobium diazoefficiens, Rhodopseudomonas palustris, Devosia* species H5989, *Bradyrhizobium* species SK17, *Pseudomonas* species AK6U, *Bifidobacterium longum, Bradyrhizobium* species S23321,

*Bacteroides thetaiotaomicron*, and *Mageeibacillus indolicus*. The second set of microbes, or any subset thereof, may comprise one or more microbes selected from any 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 of the preceding taxonomic species.

The compositions of the present disclosure are not limited to those containing a single species or type of microbe. It is contemplated that combinations of beneficial organisms may be used in the methods and compositions disclosed herein.

In various aspects, the present disclosure provides a preparation of a beneficial microbe configured for stable storage, e.g., a freeze-dried preparation. Without limiting the embodiments of the present disclosure to any particular mechanism, freeze-drying, or "lyophilization" generally stabilizes a formulation by removing the solvent component or components to levels that no longer support chemical reactions. This removal may be accomplished by first freezing the formulation, thereby separating the solutes from the solvent. The solvent may then be removed by drying, or sublimation, while the sample remains frozen. In some embodiments, the procedure comprises removal of solvent(s) by primary drying, followed by a secondary drying or desorption.

Formulations for freeze-drying may generally comprise at least the active ingredient, e.g., a beneficial microbe, and a solvent system (e.g., water, in the case of an aqueous liquid). Formulations of the present disclosure generally further comprise a protective agent.

In the freezing of formulations containing biological organisms, the formation of ice within a cell may lead to cell membrane rupture, thereby destroying the organism. In preferred embodiments, a protective protects the beneficial microbe during the freezing process (e.g., it acts as a "cryoprotectant"). Examples of cryoprotectants that may be used with the methods and compositions of the present disclosure include, e.g., non-fat milk solids, trehalose, glycerol, betaine, sucrose, glucose, lactose, polymers such as dextran and polyethylene glycol, sorbitol, mannitol, poly vinyl propylene (PVP), potassium glutamate, monosodium glutamate, Tween 20 detergent, Tween 80 detergent, Nonidet-P40, and amino acids, such as proline, histidine, arginine hydrochloride, glycine, lysine, glutanuc acid, aspartic acid, etc. In some preferred embodiments, the protective agent is included in the formulation prior to freezing in a concentration of about 0.1% to 20% w/v.

Generally, the compositions of the present disclosure are not limited to those containing a single protective agent. It is contemplated that combinations of protective agents may be used in the methods and compositions of the present disclosure.

In a preferred embodiment, the present disclosure provides a composition comprising a beneficial microbe, a pharmaceutically acceptable gelling agent, and a pharmaceutically acceptable first protective agent, in freeze-dried form. In some embodiments, the composition further comprises a pharmaceutically acceptable second protective agent. In some preferred embodiments, the second protective agent is included in the formulation prior to freezing in a concentration of about 0.1% to 20% w/v.

In various aspects, the present disclosure provides methods of making the compositions described above. In some embodiments, the methods comprise providing a fluid mixture comprising a beneficial microbe, a protective agent, and a gelling agent, and freeze-drying the mixture to produce a dried preparation.

In some embodiments, the solvent system is a completely aqueous solution. In other embodiments, the solvent system contains other solvents, such as an alcohol. In some embodiments, the solvent system comprises a buffer that provides dried buffer components to the freeze-dried composition.

In certain embodiments, the solvent is first removed by sublimation while the temperature of the frozen matrix is maintained below the eutectic temperature (e.g., a point on a phase diagram where the temperature of the system or the concentration of the solution at the point cannot be altered without changing the number of phases present) or collapse temperature of the formulation. This may be the primary drying process. The chamber pressure and product and shelf temperatures during primary drying may be generally based on the formulation's eutectic temperature or collapse temperature.

In a preferred embodiment, after primary drying, residual moisture on the resulting cake surface is reduced to levels that no longer support biological growth and chemical reactions. This process may be referred to as secondary drying. The reduction of moisture in the cake during secondary drying may be generally accomplished by increasing the shelf temperature and reducing the partial pressure of water vapor in the container. The required partial pressure of water vapor and shelf temperature may be generally ascertained from stability studies of lyophilized or vacuum-dried products having varied amounts of residual moisture.

In some embodiments, the methods of the present disclosure further comprise dissolving or resuspending the dried beneficial composition in a fluid, e.g., sterile water. In a preferred embodiment, the dried composition comprises a gelling agent, and resuspension of the cake in fluid produces a gel.

In various aspects, the present disclosure provides a method of administering a beneficial microbe to a subject, comprising providing a freeze-dried preparation comprising a beneficial microbe, a gelling agent, and a protective agent; exposing the freeze-dried preparation to an aqueous fluid to form a gel comprising an effective amount of said beneficial microbe; and contacting the subject with the gel. In a preferred embodiment, contacting the subject with the gel comprises contacting a device (e.g., a medical device) with the gel, then contacting the medical device with the subject. In a preferred embodiment, the device is a urinary catheter.

Another aspect present disclosure provides a method for coating a medical device, comprising applying to at least a portion of the surface of the device a gel composition, comprising a beneficial microbe present in an effective amount to inhibit the growth of bacterial and fungal organisms relative to an uncoated medical device.

In a preferred embodiment, the gel comprising the beneficial microbe is used in conjunction with a conventional catheter lubricant (e.g., SteriLub lubricant, SurgiLube, lubricant, KY Jelly) prior to catheter insertion. In particular preferred embodiments, the gel comprising the beneficial microbe is used in place of a conventional catheter lubricant prior to catheter insertion.

An aspect of the present disclosure provides kits or trays comprising one or more components for e.g., treating a subject. In a preferred embodiment, a kit is configured for easy delivery to and use by medical personnel, e.g., in a hospital, clinic, or medical office. In some embodiments, a kit according to the present disclosure is configured to be used in conjunction with a standard catherization kit or tray.

In other embodiments, a kit according to the present disclosure is configured to replace a standard catheterization kit or tray. In a preferred embodiment, the kit comprises all necessary components for catheterization according to the methods of the present disclosure.

In some embodiments, the kit provides, e.g., in a container, a freeze-dried composition comprising a beneficial microbe, a pharmaceutically acceptable gelling agent, and a pharmaceutically acceptable first protective agent. In some embodiments of the kit, the composition further comprises a pharmaceutically acceptable second protective agent.

In some embodiments, the kit further comprises a container of sterile fluid, e.g., an aqueous fluid such as water or a buffer solution, for suspending dried composition to form a lubricant gel, e.g., for use in inserting a catheter. In a preferred embodiment, a kit of the present disclosure further comprises a catheter.

Method 200 may further comprise any or all of operations 110, 120, or 130 of method 100 described herein.

In another aspect, the present disclosure provides a method for identifying a urinary tract disorder. The method may comprise obtaining a urine sample from the subject. Next, the method may comprise processing the urine sample to generate a data set comprising a set of microbes in a urinary tract of the subject. Then, the method may comprise using a machine learning classifier to process the set of microbes, to generate a classification of the urine sample as being positive or negative for the urinary tract disorder at a sensitivity, specificity, or accuracy of at least 90%. Finally, the method may comprise outputting a report identifying the classification.

Figure 3:
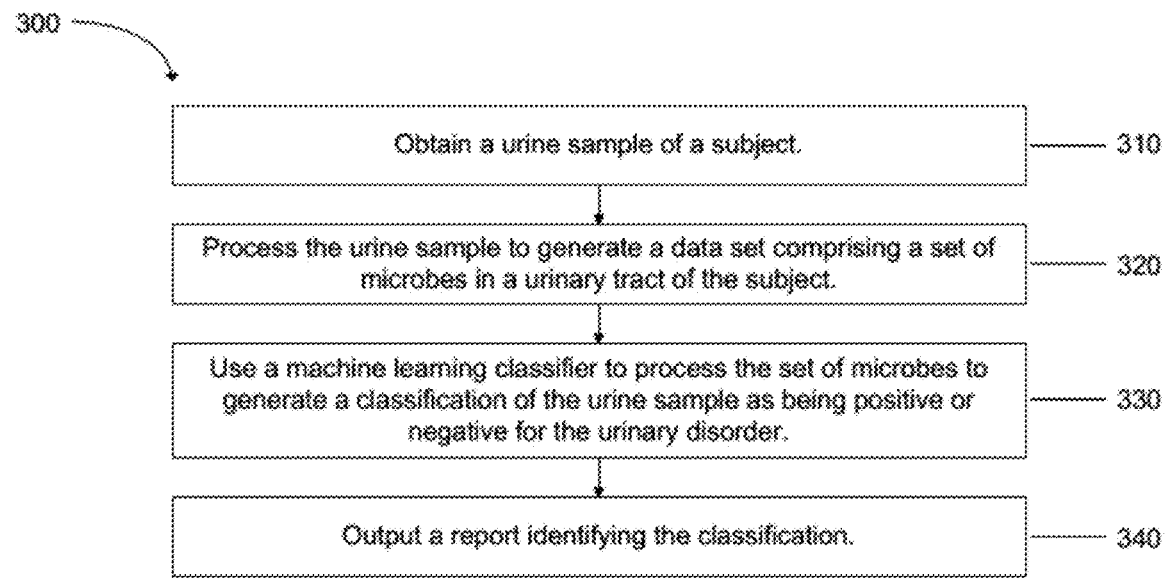
FIG. 3 shows a flowchart for a method for identifying a urinary tract disorder.

FIG. 3 shows a flowchart for a method 300 for identifying a urinary tract disorder. In a first operation 310, the method may comprise obtaining a urine sample from the subject. The first operation may further comprise preserving the urine sample in a preservation solution comprising: a pH buffer, a chelator, a cell membrane stabilizer, a DNA compactor, and an antimicrobial, as described herein. The pH buffer may maintain the preservation solution at any pH described herein. The chelator may comprise one or more member(s) selected from the group consisting of: a magnesium (Mg) chelator, a calcium (Ca chelator), and an iron (Fe) chelator, as described herein. The chelator may comprise Enterobactin, as described herein. The cell membrane stabilizer may comprise one or more member(s) selected from the group consisting of: vitamin E conjugate and poly-L-lysine, as described herein. The DNA compactor may comprise poly-L-lysine, as described herein. The antimicrobial may comprise one or more member(s) selected from the group consisting of: penicillin, streptomycin, and amphotericin B, as described herein.

In a second operation 320, the method may comprise processing the urinary sample to generate a data set comprising a set of microbes in a urinary tract of the subject. The method may comprise processing the urine sample to identify a relative abundance of the set of microbes, or any subset thereof, in the urinary tract of the subject. The method may comprise subjecting the urine sample to nucleic acid sequencing. For instance, the method may comprise subjecting the urine sample to any nucleic acid sequencing described herein. The method may comprise subjecting the urine sample to nucleic acid sequencing to obtain one or more nucleic acid sequencing reads. The method may comprise assigning nucleic acid sequencing reads that do not match a genome of the subject to the genomes of the set of microbes, or any subset thereof, thereby identifying the set of microbes, or any subset thereof. The method may comprise assigning nucleic acid sequencing reads to the set of microbes, or any subset thereof, at any level of taxonomic classification, such as a taxonomic kingdom, phylum, class order, family, genus, species, or strain of microbe. The method may comprise generating data (such as nucleic acid reads) indicative of a level of the set of microbes, or any subset thereof, and processing the data against a reference to identify the relative abundance of the set of microbes, or any subset thereof. The relative abundance may be an excess or a deficiency of the set of microbes, or any subset thereof.

The excess or deficiency of the set of microbes, or any subset thereof, may be associated with a urinary tract disorder. The urinary tract disorder may be a lower urinary tract disorder.

The urinary tract disorder may be a bladder disorder. The bladder disorder may comprise one or more member(s) selected from the group consisting of: bladder cancer, bladder exstrophy, bladder outlet obstruction, bladder sphincter dyssynergia, catheter-associated urinary tract infection, choluria, cystitis, cystitis glandularis, glomerulation, Gouverneur's syndrome, hemorrhagic cystitis, Hunner's ulcer, interstitial cystitis, megacystitis, neurogenic bladder dysfunction, overactive bladder, spermaturia, trigonitis, underactive bladder, urinary bladder neck obstruction, urge incontinence, vesicointestinal fistula, and vesicoureteral reflux.

The urinary tract disorder may be a kidney disorder. The kidney disorder may comprise one or more member(s) selected from the group consisting of: Abderhalden-Kaufmann-Lignac syndrome, acute proliferative glomerulonephritis, adenine phosphoribosyltransferase deficiency, Alport syndrome, analgesic nephropathy, autosomal dominant polycystic kidney disease, autosomal recessive polycystic kidney disease, Balkan endemic nephropathy, benign nephrosclerosis, Bright's disease, cardiorenal syndrome, chronic kidney disease, congenital nephrotic syndrome, conorenal syndrome, contrast-induced nephropathy, cystic kidney disease, Dent's disease, diabetic nephropathy, diffuse proliferative nephritis, distal renal tubular acidosis, diuresis, EAST syndrome, Fanconi syndrome, Fechtner syndrome, focal proliferative nephritis, focal segmental glomerulosclerosis, Fraley syndrome, Galloway Mowat syndrome, Gitelman syndrome, glomerulocystic kidney disease, glomerulopathy, Goldblatt kidney, Goodpasture syndrome, high anion gap metabolic acidosis, HIV-associated nephropathy, horseshoe kidney, hydronephrosis, hypertensive kidney disease, IgA nephropathy, interstitial nephritis, juvenile nephronopthisis, kidney cancer, kidney stone disease, Lightwood-Albright syndrome, lupus nephritis, malarial nephropathy, medullary cystic kidney disease, medullary sponge kidney, membranous glomerulonephritis, Mesoamerican nephropathy, milk-alkali syndrome, minimal mesangial glomerulonephritis, multicystic dysplastic kidney, nephritis, nephrocalcinosis, nephrogenic diabetes insipidus, nephromegaly, nephrotosis, nephrosis, nephrotic syndrome, Nutcracker syndrome, papillorenal syndrome, phosphate neuropathy, polycystic kidney disease, primary hyperoxaluria, proximal renal tubular acidosis, pyelonephritis, pyonephrosis, rapidly progressive glomerulonephritis, renal agenesis, renal angina, renal artery stenosis, renal cyst, renal ischemia, renal osteodystrophy, renal papillary necrosis, renal tubular acidosis, renal vein thrombosis, reninoma, secondary hypertension, serpentine fibula-polycystic kidney syndrome, shunt nephritis, sickle cell nephropathy, thin basement membrane disease, transplant glomerulopathy, tubulointerstitital nephritis and uveitis, tubulopathy, uremia, uremic frost, and Wunderlich syndrome.

The urinary disorder may be a urethra disorder. The urethra disorder may comprise one or more member(s) selected from the group consisting of: urethral meatal stenosis, urethral caruncle, urethral foreign body, urethral stricture, urethral syndrome, urethritis, and urethrorrhagia.

The urinary disorder may be a ureter disorder. The ureter disorder may comprise one or more member(s) selected from the group consisting of: duplicated ureter, megaureter, ureteritis, and ureterocele.

The urinary tract disorder may be a prostate disorder. The prostate disorder may comprise one or more member(s) selected from the group consisting of: prostatitis, acute prostatitis, asymptomatic inflammatory prostatitis, chronic bacterial prostatitis, chronic prostatitis, granulomatous prostatitis, IgG4-related prostatitis, male accessory gland infection, benign prostatic hyperplasia, and prostate cancer.

The urinary tract disorder may be a testicular disorder. The testicular disorder may comprise one or more member (s) selected from the group consisting of: ectopic testis, epididymitis, gonadal torsion, orchitis, orchialgia, macroorchidism, testicular cancer, genital tuberculosis, hydrocele, hydrocele testis, rete tubular ectasia, Sertoli cell nodule, testicular atrophy, testicular dysgenesis syndrome, testicular microlithiasis, testicular pain, testicular rupture, testicular sarcoidosis, testicular torsion, and testicular trauma.

The urinary tract disorder may be a penile disorder. The penile disorder may comprise one or more member(s) selected from the group consisting of: penile cancer, erectile dysfunction, priapism, induratio penis plastic, Peyronie's disease, aposthia, balanitis, penile fracture, penile injury, penile pain, and penile artery shunt syndrome.

The urinary tract disorder may be a system disorder. The urinary tract disorder may comprise one or more member(s) selected from the group consisting of: reactive arthritis, Reiter's syndrome, and urosepsis.

The set of microbes may comprise at least about 1, 2, 3, 4, 5, 6, 7, 8, 9, 10, 20, 30, 40, 50, 60, 70, 80, 90, 100, 200, 300, 400, 500, 600, 700, 800, 900, 1,000, 2,000, 3,000, 4,000, 5,000, 6,000, 7,000, 8,000, 9,000, 10,000, 20,000, 30,000, 40,000, 50,000, 60,000, 70,000, 80,000, 90,000, 100,000, 200,000, 300,000, 400,000, 500,000, 600,000, 700,000, 800,000, 900,000, 1,000,000, or more different types of microbes. The set of microbes may comprise at most about 1,000,000, 900,000, 800,000, 700,000, 600,000, 500,000, 400,000, 300,000, 200,000, 100,000, 90,000, 80,000, 70,000, 60,000, 50,000, 40,000, 30,000, 20,000, 10,000, 9,000, 8,000, 7,000, 6,000, 5,000, 4,000, 3,000, 2,000, 1,000, 900, 800, 700, 600, 500, 400, 300, 200, 100, 90, 80, 70, 60, 50, 40, 30, 20, 10, 9, 8, 7, 6, 5, 4, 3, 2, or 1 different types of microbes. The set of microbes may comprise a number of types of microbes that is within a range defined by any two of the preceding values. The set of microbes, or any subset thereof, may comprise microbes from any number of taxonomic kingdoms, phyla, classes, orders, families, genera, species, or strains of microbes.

The set of microbes, or any subset thereof, may comprise one or more microbes from a taxonomic kingdom selected from the group consisting of: Bacteria, Viruses, Bacteriophages, and Archaea. The set of microbes, or any subset thereof, may comprise one or more microbes selected from any 1, 2, 3, or 4 of the preceding taxonomic kingdoms.

The set of microbes, or any subset thereof, may comprise one or more microbes from a taxonomic phylum selected from the group consisting of: Proteobacteria, Firmicutes, Actinobacteria, Bacteroidetes, Aquificae, Deinococcus-Thermus, Fusobacteria, and Tenericutes. The set of microbes, or any subset thereof, may comprise one or more microbes selected from any 1, 2, 3, 4, 5, 6, 7, or 8 of the preceding taxonomic phyla.

The set of microbes, or any subset thereof, may comprise one or more microbes from a taxonomic class selected from the group consisting of: Gammaproteobacteria, Betaproteobacteria, Clostridia, Alphaproteobacteria, Bacilli, Actinobacteria, Tissierellia, Bacteroidia, Erysipelotrichia, Aquificiae, Deinococci, Epsilonproteobacteria, Flavobacteria, Fusobacteria, Mollicutes, Negativicutes, and Coriobacteria. The set of microbes, or any subset thereof, may comprise one or more microbes selected from any 1, 2, 3, 4, 5, 6, 7, 8, 9, 10, 11, 12, 13, 14, 15, 16, or 17 of the preceding taxonomic classes.

The set of microbes, or any subset thereof, may comprise one or more microbes from a taxonomic order selected from the group consisting of: Pseudomonadales, Enterobacterales, Caudovirales, Actinomycetales, Corynebacteriales, Burkholderiales, Clostridiales, Rhizobiales, Streptomycetales, Sphingomonadales, Lactobacillales, Bifidobacteriales, Pseudonocardiales, Bacteroidales, Xanthomonadales, Bacillales, Erysipelotrichales, Acidaminococcales, Campylobacterales, Desulfurobacteriales, Fusobacteriales, Herpesvirales, Micrococcales, Mycoplasmatales, Neisseriales, Pasteurellales, Picornavirales, Propionibacteriales, Thermales, Veillonellales, Vibrionales, Flavobacteriales, Tissierellales, Aeromonadales, Coriobacteriales, and Eggerthellales. The set of microbes, or any subset thereof, may comprise one or more microbes selected from any 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, or 36 of the preceding taxonomic orders.

The set of microbes, or any subset thereof, may comprise one or more microbes from a taxonomic family selected from the group consisting of: Myoviridae, Porphyromonadaceae, Pseudomonoadaceae, Enterobacteriaceae, Actinomycetaceae, Prevotellaceae, Burkholderiaceae, Siphoviridae, Hyphoicrobiaceae, Streptomycetaceae, Sphingomonadaceae, Peptoniphilaceae, Bifidobacteriaceae, Peptostreptococcaceae, Polyomaviridae, Xanthomonadaceae, Staphylococcaceae, Bacteroidaceae, Erysipelotrichaceae, Nocardiaceae, Rikenellaceae, Acidaminococcaceae, Aerococcaceae, Bradyrhizobiaceae, Campylobacteraceae, Comamonadaceae, Corynebacteriaceae, Desulfurobacteriaceae, Erwiniaceae, Flavobacteriaceae, Hafniaceae, Helicobacteraceae, Herpesviridae, Lachnospiraceae, Lactobacillaceae, Leptotrichiaceae, Microbacteriaceae, Micrococcaceae, Morganellaceae, Mycoplasmataceae, Neisseriaceae, Oxalobacteraceae, Paenibacillaceae, Pasteurellaceae, Peptococcaceae, Picornaviridae, Podoviridae, Propionibacteriaceae, Rhizobiaceae, Ruminococcaceae, Thermaceae, Veillonellaceae, Vibrionaceae, Yersiniaceae, Arenaviridae, Streptococcaceae, Tissierellaceae, Tannerellaceae, Oscillospiraceae, Aeromonadaceae, Erythrobacteraceae, Moraxellaceae, Barnesiellaceae, Intrasporangiaceae, Coriobacteriaceae, and Eggerthellaceae. The set of microbes, or any subset thereof, may comprise one or more microbes selected from any 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, or 66 of the preceding taxonomic families.

The set of microbes, or any subset thereof, may comprise one or more microbes from a taxonomic genus selected from the group consisting of: *Klebsiella, Lambdavirus, Shigella, Pseudomonas, Citrobacter, Salmonella, Escherichia, Pre-* voltella, Barnesiella, Devosia, Streptomyces, Bifidobacterium, Sphingomonas, Helcococcus, Parabacteroides, Mobiluncus, Gardnerella, Finegoldia, Streptococcus, Betapolyomavirus, Stenotrophomonas, Enterococcus, Ralstonia, Staphylococcus, Bacteroides, Alistipes, Clostridioides, Erysipelothrix, Rhodococcus, Triavirus, Acidaminococcus, Actinomyces, Actinotignum, Aerococcus, Aggregatibacter, Anaerococcus, Blautia, Bradyrhizobium, Burkholderia, Campylobacter, Cornyebacterium, Cutibacterium, Desulfitobacterium, Enterobacter, Epsilon15virus, Ezakiella, F116virus, Faecalibacterium, Filifactor, Fusobacterium, Haemophilus, Hafnia, Helicobacter, Histophilus, Janthinobacterium, Kluyvera, Lacnoclostridium, Lactobacillus, Lawsonella, Limnohabitans, Lymphocryptovirus, Mageeibacillus, Microbacterium, Micrococcus, Morganella, Neisseria, Ornithobacterium, P22virus, P2virus, Paenibacillus, Pantoea, Parvimonas, Peptoniphilus, Porphyromonas, Propionibacterium, Propionmicrobium, Proteus, Pseudarthrobacter, Raoultella, Rhizobium, Rhodopseudomonas, Roseolovirus, Rothia, Ruminiclostridium, Ruminococcus, Salivirus, Serratia, Sneathia, Sphingobium, Thermovibrio, Thermus, Ureaplasma, Varibaculum, Veillonella, Vibrio, Xenorhabdus, Yersinia, Mammarenavirus, Variovorax, Prevotella, Methylibium, Polynucleobacter, P68virus, Thiomonas, Phycicoccus, Acidovorax, Anaerostipes, Collinsella, Hydrogenophaga, Lachnoclostridium, Eggerthella, Negativicoccus, Ndongobacter, Mobiluncus, Kosakonia, Oscillibacter, Tannerella, Flavonifractor, Tessaracoccus, Eikenella, Aeromonas, Porphyrobacter, Edwardsiella, Leptotrichia, Comamonas, Acinetobacter, and Tardiphaga. The set of microbes, or any subset thereof, may comprise one or more microbes selected from any 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 68, 69, 70, 71, 72, 73, 74, 75, 76, 77, 78, 79, 80, 81, 82, 83, 84, 85, 86, 87, 88, 89, 90, 91, 92, 93, 94, 95, 96, or 97 of the preceding taxonomic genera.

The set of microbes, or any subset thereof, may comprise one or more microbes from a taxonomic species selected from the group consisting of: Klebsiellas pneumoniae, Shigellas sonnei, Klebsiellas varicola, Prevotellas species oral taxon 299, Shigellas dysenteriae, Pseudomonas aeruginosa, Salmonellas enterica, Escherichias coli, Shigellas boydii, Shigellas species PAMC 28760, Shigellas flexneri, Betapolyomavirus human, Excherichias fergusonii, Prevotellas scopos, Prevotellas melaninogenica, Escherichias albertii barnesiellas viscericola, Devosias species H5989, Streptococcus pneumoniae, Citrobacters freundii, Prevotellas enoeca, Bacteroides thetaiotaomicron, Helcococcus kunzii, Parabacteroidess distasonis, Pseudomonas oleovorans, Mobiluncus curtisii, Streptococcus dysgalactiae, Streptococcus pyogenes, Gardnerellas vaginalis, Finegoldias magna, Bacteroides dorei, Bacteroides vulgatus, Pseudomonas species 1217, Enterococcus species 7L76, Bacteroides species L48, Ralstonias insidiosa, Streptococcus pasteurianus, Bifidobacterium longum, Bacteroides ovatus, Enterococcus faecalis, Staphylococcus epidermis, Staphylococcus aureus, Bacteroides fragilis, Alistipes shahii, Bacteroides salanitronis, Clostridioides difficile, Erysipelothrix rhusiopathiae, Lambdavirus uncultured virus, Pseudomonas frederiksbergensis, Ralstonia mannitolilytica, Rhodococcus erythropolis, Rhodoccus species 008, Sphingomonas echinoides, Staphylococcus agnetis, Staphylococcus lugdunensis, Staphyloccus saprophyticus, Streptococcus gallolyticus, Streptococcus infantarius, Streptococcus lutetiensis, Streptococcus macedonicus, Streptomyces uncultured bacteria 37b14, Streptomyces uncultured bacterium 39k17, Triavirus staphylococcus phage 3A, Triavirus staphylococcus phage tp310-2, Triavirus staphylococcus phage StB20, Human herpesvirus 6, Human gammaherpesvirus 4, Bordetella hinzii, Methylibium petroleiphilum, Shigella species LN126, Podoviridae, Lactobacillus jensenii, Burkholderia pseudomallei group, Pseudomonas phage phi297, Klebsiella michiganensis, Lactobacillus species B164, Streptococcus species I-G2, Kosakonia sacchari, Ruminococcus bicirculans, Prevotella jejuni, Bradyrhizobium species llw1, Agrobacterium tumefaciens complex, Pseudomonas phage YMC/01/01/P52_PAE BP, Aerococcus sanguinicola, Prevotella species S4-10, Corynebacterium frankenforstense, Prevotella species Sc00026, Streptococcus phage EJ-1, Comamonas bacterium 36B, Micrococcus luteus, Pseudomonas sihuiensis, Staphylococcus haemolyticus, Streptococcus phage phiD12, Staphylococcus hominis, Pseudomonas species ATCC 13867, Streptococcus oralis, Streptococcus salivarius, Streptococcus suis, Acinetobacter chlamydia-associated clinical sample 198-T, Sphingobium species TKS, Streptococcus parasanguinis, Tessaracoccus aquimaris, Pluralibacter lignolyticus, Streptococcus intermedius, Ureaplasma parvum, Pseudomonas fluorescens group, Pseudomonas putida group, Sphingobium yanoikuyae, Aerococcus urinae, Burkholderia species BDU6, Sphingomonas species LK11, Bacillus cereus, Paenibacillus polymyxa, Streptococcus species VT 162, Comamonadaceae bacterium B), Klebsiella quasipneumoniae, Corynebacterium simulans, Lactobacillus iners, Corynebacterium species ATCC 6931, Klebsiella species NCTC 8172, Lawsonella clevelandensis, Lactobacillus species wkB8, Sphingomonas taxi, Bradyrhizobium species lamp2, Streptococcus phage SpSL1, Enterobacteria phage P88, Corynebacterium riegelii, Corynebacterium imitans, Lactobacillus acidophilus, Lactobacillus buchneri, Lactobacillus delbrueckii, Lactobacillus helveticus, Cedecea neteri, Enterobacter hormaechei, Lactobacillus plantarum, Lactobacillus gasseri, Lactobacillus acetotolerans, Lactobacillus amylophilus, Lactobacillus amylovorus, Tessaracoccus flavus, Lactobacillus farciminis, Corynebacterium singulare, Erwinia gerundensis, Hoeflea species IMCC20628, Lactobacillus ruminis, Pseudomonas lini, Propionibacterium phage PHL030, Propionibacterium phage PHL064, Propionibacterium phage PHL82, Yersinia pseudotuberculosis complex, Actinomyces naeslundii, Acidovorax species NA2, Acidovorax species P3, Acidovorax species P4, Bifidobacterium adolescentis, Bifidobacterium breve, Corynebacterium aurimucosum, Negativicoccus massiliensis, Massilia species WG5, Turicibacter species H121, Corynebacterium diphtheriae, Corynebacterium glutamicum, Rothia aeria, Propionibacterium freudenreichii, Cutibacterium acnes, Pseudomonas phage phi1, Streptococcus species A12, Pseudomonas species bs2935, Pseudomonas phage JBD44, Pseudomonas phage YMC11/07/P54_PAE_BP, Gemella species oral taxon 928, Sinorhizobium species RAC02, Hydrogenophaga species RAC07, Acidovorax species T1, Lambdavirus, Sneathia amnii, Ndongobacter massiliensis, Acidaminococcus intestini, Varibaculum species, Streptococcus species NPS 308, Tessaracoccus species 72.5-30, Corynebacterium sphenisci, Corynebacterium atypicum, Streptococcus phage IPPS, Delftia species HK171, Klebsiella species M5a1, Staphylococcus phage St 134, Propionibacterium virus Lauchelly, Propionibacterium virus PHL082M03, Propionibacterium virus PHLJ17M01, Propionibacterium virus Stormborn, Microbacterium paraoxydans, Thauera species K11, Escherichia phage Ayreon, Dickeya zeae, Pseudomonas species HLS-6, *Paracoccus* species CBA4604, *Citrobacter freundii* complex species CFNIH2, *Citrobacter freundii* complex species CFNIH3, *Alkaliphilus metalliredigens*, *Lachnoclostridium bolteae*, *Ureaplasma urealyticum*, *Yersinia* virus L413C, *Pseudomonas* species M18, Lachnoclostridium butyrate-producing bacterium SM4/1, Lachnoclostridium butyrate-producing bacterium SS3/4, Plasmid ColV-K30, *Bacteroides cellulosilyticus*, Plasmid R1-19, *Haemophilus pittmaniae*, *Bradyrhizobium canariense*, *Streptococcus pseudopneumoniae*, *Corynebacterium resistens*, *Lactobacillus kefiranofaciens*, *Sphaerochaeta coccoides*, *Thermus thermophilus*, *Bifidobacterium animalis*, *Streptococcus mitis*, *Acinetobacter lwoffli*, *Porphyromonas asaccharolytica*, *Prevotella denticola*, *Prevotella disiens*, *Ornithobacterium rhinotracheale*, *Enterobacteria* phage CP-1639, *Burkholderia cepacia*, *Brevundimonas diminuta*, *Staphylococcus capitis*, *Pseudomonas fluorescens*, *Pseudomonas tolaasii*, *Veillonella parvula*, *Shigella* species AR-21793, *Turneriella parva*, *Roseburia hominis*, *Pseudomonas putida*, Human betaherpesvirus 6B, *Cutibacterium avidum*, *Cutibacterium granulosum*, *Parvimonas micra*, *Anaerococcus prevotii*, *Sphingobium indicum*, *Sphingobium japonicum*, *Variovorax paradoxus*, *Pseudomonas* phage PA11, *Enterobacter cloacae* complex, *Citrobacter amalonaticus*, *Agrobacterium tumefaciens*, *Verminephrobacter eiseniae*, *Bacteroides xylanisolvens*, *Corynebacterium* species L2-79-05, *Enterobacteria* phage 933 W sensu lato, *Lactobacillus backii*, *Thermus scotoductus*, *Sinorhizobium fredii*, *Rhizobium leguminosarum*, *Prevotella timonensis*, *Mesorhizobium ciceri*, *Veillonella atypica*, *Tessaracoccus favescens*, *Enterobacter* species 638, *Streptococcus merionis*, *Micrococcus* species A), *Blautia obeum*, *Polyangium brachysporum*, *Azoarcus olearius*, *Thiomonas arsenitoxydans*, *Ralstonia* species Is-C065, *Variovorax boronicumulans*, *Rothia mucilaginosa*, *Enterococcus cecorum*, *Bradyrhizobium oligotrophicum*, *Phycicoccus dokdonensis*, *Enterobacteria* phage VT1-Sakai, *Lactobacillus crispatus*, *Pseudomonas azotoformans*, *Pseudomonas fulva*, *Neisseria gonorrhoeae*, *Neisseria lactamica*, *Neisseria meningitidis*, *Burkholderia contaminans*, *Neisseria sicca*, *Prevotella dentalis*, *Lactobacillus gallinarum*, *Ochrobactrum anthropi*, *Peptoniphilus harei*, *Raoultella ornithinolytica*, *Enterobacter cloacae*, *Pantoea cypripedii*, *Acidovorax* species NA3, *Thiomonas* species CB2, *Enterobacteria* phage YYZ-2008, *Thermus brockianus*, *Afipia* genospecies 3, *Citrobacter braakii*, *Lactobacillus* phage Lv-1, *Burkholderia thailandensis*, *Proteus mirabilis*, *Klebsiella* species 2N3, *Prevotella fusca*, *Actinotignum schaalii*, *Serratia liquefaciens*, *Serratia marcescens*, *Kluyvera intermedia*, *Yersinia pestis*, *Yersinia pseudotuberculosis*, *Edwardsiella tarda*, *Aeromonas salmonicida*, *Anaerostipes hadrus*, *Prevotella* species oral taxon 299, *Myxococcus* mixed culture bacterium AM_gF3SD01_05, *Desulfitobacterium* mixed culture bacterium AX_gF3SD01_48, *Comamonas* mixed culture bacterium PE_gF1DD01_04, *Streptococcus anginosus* group, *Rhodoplanes* species Z2-YC6860, *Citrobacter rodentium*, *Citrobacter gillenii*, *Altererythrobacter dongtanensis*, *Corynebacterium* species NML98-0116, *Actinomyces* species oral taxon 414, *Streptococcus* species oral taxon 064, *Streptococcus* species oral taxon 431, *Kocuria palustris*, *Haemophilus influenzae*, *Haemophilus parainfluenzae*, *Aggregatibacter aphrophilus*, *Collinsella aerofaciens*, *Campylobacter hominis*, *Streptococcus constellatus*, *Campylobacter hominis*, *Hydrogenophaga* species PBC, *Delftia acidovorans*, *Campylobacter ureolyticus*, *Leclercia adecarboxylata*, *Lactobacillus amylolyticus*, *Porphyromonas gingivalis*, *Lachnoclostridium saccharolyticum*, *Eggerthella lenta*, *Fusobacterium nucleatum*, *Faecalibacterium prausnitzii*, *Streptococcus* phage phi-SsUD.1, *Bacillus cereus* group, *Aerococcus christensenii*, *Burkholderia cepacia* complex, *Corynebacterium flavum*, *Micrococcus* species MG-2010-D12, *Actinomyces succiniciruminis, Streptococcus agalactiae, Guanarito mammarenavirus, Prevotella intermedia, Prevotella enoeca, Desulfitobacterium hafniense, Pseudomonas aeruginosa* group, *Staphylococcus epidermidis, Bacteroides dorei, Prevotella melaninogenica*, and Human polyomavirus 2. The set of microbes, or any subset thereof, may comprise one or more microbes selected from any 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317, 318, 319, 320, 321, 322, 323, 324, 325, 326, 327, 328, 329, 330, 331, 332, 333, 334, 335, 336, 337, 338, 339, 340, 341, 342, 343, 344, 345, or 346 of the preceding taxonomic species.

In a third operation 330, the method may comprise using a machine learning classifier to process the set of microbes to generate a classification of the urine sample as being positive or negative for the urinary disorder. The method may comprise using a machine learning classifier comprising one or more member(s) selected from the group consisting of: supervised, semi-supervised, and unsupervised machine learning techniques. The method may comprise using a machine learning classifier comprising one or more member(s) selected from the group consisting of: k-means, k-means clustering, k-nearest neighbors, learning vector quantization, linear regression, non-linear regression, least squares regression, partial least squares regression, logistic regression, stepwise regression, multivariate adaptive regression splines, ridge regression, principle component regression, least absolute shrinkage and selection operation, least angle regression, canonical correlation analysis, factor analysis, independent component analysis, linear discriminant analysis, multidimensional scaling, non-negative matrix factorization, principal components analysis, principal coordinates analysis, projection pursuit, Sammon mapping, t-distributed stochastic neighbor embedding, AdaBoost, boosting, bootstrap aggregation, ensemble averaging, decision trees, conditional decision trees, boosted decision trees, gradient boosted decision trees, random forests, stacked generalization, Bayesian networks, Bayesian belief networks, naïve Bayes, Gaussian naïve Bayes, multinomial naïve Bayes, hidden Markov models, hierarchical hidden Markov models, support vector machines, encoders, decoders, auto-encoders, stacked auto-encoders, perceptrons, multi-layer perceptrons, artificial neural networks, feedforward neural networks, convolutional neural networks, recurrent neural networks, long short-term memory, deep belief networks, deep Boltzmann machines, deep convolutional neural networks, deep recurrent neural networks, and generative adversarial networks. In a preferred embodiment, the classifier is applied subsequent to non-linear dimensionality reduction of the underlying data, wherein a distance metric is selected from the group consisting of a Euclidean distance, an L1-norm distance, an L2-norm distance, and beta diversity metrics listed in Table 1 of [Koleff, Patricia, Kevin J. Gaston, and Jack J. Lennon. Measuring beta diversity for presence-absence data." *Journal of Animal Ecology* 72.3 (2003): 367-382], which is incorporated herein by reference in its entirety.

The machine learning classifier may generate the classification of the urine sample as being positive or negative for the urinary tract disorder at an accuracy of at least about 50%, 55%, 60%, 65%, 70%, 75%, 80%, 81%, 82%, 83%, 84%, 85%, 86%, 86%, 87%, 88%, 89%, 90%, 91%, 92%, 93%, 94%, 95%, 96%, 97%, 98%, 99%, 99.1%, 99.2%, 99.3%, 99.4%, 99.5% 99.6%, 99.7%, 99.8%, 99.9%, or more. The machine learning classifier may generate the classification of the urine sample as being positive or negative for the urinary tract disorder at an accuracy that is within a range defined by any two of the preceding values. The accuracy of identifying the urinary tract disorder by the machine learning classifier may be calculated as the percentage of independent test samples (e.g., subjects known to have the urinary tract disorder or subjects with negative clinical test results for the urinary tract disorder) that are correctly identified or classified as having or not having the urinary tract disorder.

The machine learning classifier may generate the classification of the urine sample as being positive or negative for the urinary tract disorder at a sensitivity of at least about 50%, 55%, 60%, 65%, 70%, 75%, 80%, 81%, 82%, 83%, 84%, 85%, 86%, 86%, 87%, 88%, 89%, 90%, 91%, 92%, 93%, 94%, 95%, 96%, 97%, 98%, 99%, 99.1%, 99.2%, 99.3%, 99.4%, 99.5% 99.6%, 99.7%, 99.8%, 99.9%, or more. The machine learning classifier may generate the classification of the urine sample as being positive or negative for the urinary tract disorder at a sensitivity that is within a range defined by any two of the preceding values. The sensitivity of identifying the urinary tract disorder using the machine learning classifier may be calculated as the percentage of independent test samples associated with presence of the urinary tract disorder (e.g., subjects known to have the urinary tract disorder) that are correctly identified or classified as having the urinary tract disorder.

The machine learning classifier may generate the classification of the urine sample as being positive or negative for the urinary tract disorder at a specificity of at least about 50%, 55%, 60%, 65%, 70%, 75%, 80%, 81%, 82%, 83%, 84%, 85%, 86%, 86%, 87%, 88%, 89%, 90%, 91%, 92%, 93%, 94%, 95%, 96%, 97%, 98%, 99%, 99.1%, 99.2%, 99.3%, 99.4%, 99.5%, 99.6%, 99.7%, 99.8%, 99.9%, or more. The machine learning classifier may generate the classification of the urine sample as being positive or negative for the urinary tract disorder at a specificity that is within a range defined by any two of the preceding values. The specificity of identifying the urinary tract disorder using the machine learning classifier may be calculated as the percentage of independent test samples associated with absence of the urinary tract disorder (e.g., subjects with negative clinical test results for the urinary tract disorder) that are correctly identified or classified as not having the urinary tract disorder.

The machine learning classifier may generate the classification of the urine sample as being positive or negative for the urinary tract disorder at a positive predictive value (PPV) of at least about 50%, 55%, 60%, 65%, 70%, 75%, 80%, 81%, 82%, 83%, 84%, 85%, 86%, 86%, 87%, 88%, 89%, 90%, 91%, 92%, 93%, 94%, 95%, 96%, 97%, 98%, 99%, 99.1%, 99.2%, 99.3%, 99.4%, 99.5% 99.6%, 99.7%, 99.8%, 99.9%, or more. The machine learning classifier may generate the classification of the urine sample as being positive or negative for the urinary tract disorder at a PPV that is within a range defined by any two of the preceding values. The PPV of identifying the urinary tract disorder using the machine learning classifier may be calculated as the percentage of individuals identified or classified as having the urinary tract disorder that truly have the urinary tract disorder.

The machine learning classifier may generate the classification of the urine sample as being positive or negative for the urinary tract disorder at a negative predictive value (NPV) of at least about 50%, 55%, 60%, 65%, 70%, 75%, 80%, 81%, 82%, 83%, 84%, 85%, 86%, 86%, 87%, 88%, 89%, 90%, 91%, 92%, 93%, 94%, 95%, 96%, 97%, 98%, 99%, 99.1%, 99.2%, 99.3%, 99.4%, 99.5% 99.6%, 99.7%, 99.8%, 99.9%, or more. The machine learning classifier may generate the classification of the urine sample as being positive or negative for the urinary tract disorder at an NPV that is within a range defined by any two of the preceding values. The NPV of identifying the urinary tract disorder using the machine learning classifier may be calculated as the percentage of individuals identified or classified as not having the urinary tract disorder that truly do not have the urinary tract disorder.

The machine learning classifier may generate the classification of the urine sample as being positive or negative for the urinary tract disorder with an Area-Under-Curve (AUC) of about 0.50, 0.55, 0.60, 0.65, 0.70, 0.75, 0.80, 0.81, 0.82, 0.83, 0.84, 0.85, 0.86, 0.87, 0.88, 0.89, 0.90, 0.91, 0.92, 0.93, 0.94, 0.95, 0.96, 0.97, 0.98, 0.99, or more. The machine learning classifier may generate the classification of the urine sample as being positive or negative for the urinary tract disorder with an AUC that is within a range defined by any two of the preceding values. The AUC may be calculated as an integral of the Receiver Operator Characteristic (ROC) curve (e.g., the area under the ROC curve) associated with the machine learning classifier in classifying individuals as having or not having the urinary tract disorder.

The machine learning classifier may be trained (e.g., adjusted or tuned) to improve one or more of the performance, accuracy, PPV, NPV, clinical sensitivity, clinical specificity, or AUC of identifying the urinary tract disorder. The machine learning classifier may be adjusted or tuned by adjusting parameters of the machine learning classifier (e.g., a set of cutoff values used to classify an individual, or weights of a neural network). The machine learning classifier may be adjusted or tuned continuously during a training process or after a training process has completed.

After the machine learning classifier is initially trained, a subset of the inputs may be identified as most influential or most important to be included for making high-quality classifications. For example, a subset of populations of microbes may be identified as most influential or most important to be included for making high-quality classifications or identifications of urinary tract disorders. The subset of populations of microbes may be ranked based on classification metrics indicative of each microbe's influence or importance toward making high-quality classifications or identifications of urinary tract disorders. Such metrics may be used to reduce, in some cases significantly, the number of input variables (e.g., predictor variables) that may be used to train the machine learning classifier to a desired performance level (e.g., based on a desired minimum accuracy, PPV, NPV, sensitivity, specificity, AUC, or a combination thereof). For example, if training the machine learning classifier with a plurality comprising several dozen or hundreds of input variables in the machine learning classifier results in an accuracy of classification of more than 99%, then training the machine learning classifier instead with only a selected subset of no more than about 5, no more than about 10, no more than about 15, no more than about 20, no more than about 25, no more than about 30, no more than about 35, no more than about 40, no more than about 45, no more than about 50, or no more than about 100 such most influential or most important input variables among the plurality can yield decreased but still acceptable accuracy of classification (e.g., at least about 50%, at least about 55%, at least about 60%, at least about 65%, at least about 70%, at least about 75%, at least about 80%, at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, or at least about 99%). The subset may be selected by rank-ordering the entire plurality of input variables and selecting a predetermined number (e.g., no more than about 5, no more than about 10, no more than about 15, no more than about 20, no more than about 25, no more than about 30, no more than about 35, no more than about 40, no more than about 45, no more than about 50, or no more than about 100) of input variables with the best classification metrics.

In a fourth operation 340, the method may further comprise outputting a report identifying the classification. The method may further comprise directing the report to another party, such as the subject or a health care provider (such as the subject's doctor).

The data set may further comprise a plurality of nucleic acid molecules originating from a tissue of the subject. For instance, the data set may comprise a plurality of nucleic acid molecules originating from a urinary tract, lower urinary tract, bladder, kidney, urethra, ureter, prostate, testicle, or penis of a subject. The plurality of nucleic acids may comprise a mixture of cell-free and cell-associated nucleic acid molecules, or also referred to as nucleic acid compartments. In some embodiments, these compartments have distinct molecular size ranges. In some embodiments, the cell-free compartment ranges from about 30 bp to about 500 bp. In some embodiments, the cell-associated complex is about 500 bp or higher. The method may provide for concurrent preservation of both nucleic acid compartments. Processing of the urine sample may separate these two compartments or may keep them together. In a preferred embodiment the nucleic acid compartments are extracted from urine together and the purified DNA is processed to selectively fragment the cell associated compartment to a size range generally exclusive from that of the cell-free compartment; wherein sequencing read insert size can then be used to subsequently deconvolve these two compartments. The method may further comprise process the plurality of nucleic acid molecules originating from the subject to identify one or more genetic aberrations and/or an increase or decrease in a level of expression of at least a subset of the plurality of nucleic acid molecules relative to a reference. In some cases, the genetic aberrations and/or increase or decrease in the level of expression may be indicative that a subject is positive or negative for a urinary tract, lower urinary tract, bladder, kidney, urethra, ureter, prostate, testicular, or penile disorder, such as any urinary tract, lower urinary tract, bladder, kidney, urethra, ureter, prostate, testicular, or penile disorder described herein. Such an indication may be correlated with information obtained from the set of microbes in order to strength a classification of the subject as being positive or negative for the urinary tract, lower urinary tract, bladder, kidney, urethra, ureter, prostate, testicular, or penile disorder. The method may further comprise using the machine learning classifier to identify the one or more genetic aberrations and/or increase or decrease in the level of expression.

The method may further comprise repeating any 1, 2, 3, or 4 of operations 310, 320, 330, and 340 for each of a plurality of subjects. For instance, the method may further comprise repeating any or all of the operations for at least about 2, 3, 4, 5, 6, 7, 8, 9, 10, 20, 30, 40, 50, 60, 70, 80, 90, 100, 200, 300, 400, 500, 600, 700, 800, 900, 1,000, 2,000, 3,000, 4,000, 5,000, 6,000, 7,000, 8,000, 9,000, 10,000, 20,000, 30,000, 40,000, 50,000, 60,000, 70,000, 80,000, 90,000, 100,000, 200,000, 300,000, 400,000, 500,000, 600,000, 700,000, 800,000, 900,000, 1,000,000, 2,000,000, 3,000,000, 4,000,000, 5,000,000, 6,000,000, 7,000,000, 8,000,000, 9,000,000, 10,000,000, 20,000,000, 30,000,000, 40,000,000, 50,000,000, 60,000,000, 70,000,000, 80,000,000, 90,000,000, 100,000,000, 200,000,000, 300,000,000, 400,000,000, 500,000,000, 600,000,000, 700,000,000, 800,000,000, 900,000,000, or 1,000,000,000, or more subjects. The method may comprise repeating any or all of the operations for a number of subjects that is within a range defined by any two of the preceding values.

The method may further comprise identifying a subset of subject from the plurality of subjects. Each subject of the subset of subjects may be associated with a urine sample classified as being positive for any urinary tract disorder described herein. Each subject of the subset of subjects may not display symptoms of the urinary tract disorder. This subset of subjects may be regarded as an exceptional group of subjects in that they may be classified as being positive for a urinary tract disorder but do not display symptoms of the urinary tract disorder. Such a subset of subjects may harbor microbiomes that allow them to host a set of microbes that may typically cause symptoms of a urinary tract disorder while failing to display symptoms of the urinary tract disorder. This subset of subjects may have biological traits, such as microbiomes or genetic traits, which allow them to remain free of symptoms of the urinary tract disorder. As such, such a subset of subjects may be worthy of further testing and analysis to determine the biological traits that allow them to remain free of symptoms of the urinary tract disorder.

In another aspect, the present disclosure provides a method for processing a urine sample. The method may comprise receiving a solution comprising nucleic acid molecules in a urine of a subject. The solution may comprise a preservation mixture. Next, the method may comprise sequencing a plurality of nucleic acid molecules derived from the nucleic acid molecules to generate a plurality of sequencing reads. The preservation mixture may provide for sequencing the plurality of nucleic acid molecules to generate the plurality of sequencing reads at a greater molecular complexity as compared to other nucleic acid molecules in the urine preserved in a composition. The composition may comprise a volume-excluding polymer that is present in an amount from about 10% to about 50% by weight of the composition, an osmotic agent present in an amount of about 1% to about 20% by weight of the composition, and an enzyme inhibitor present in an amount from about 1% to about 30% by weight of the composition.

Figure 42:
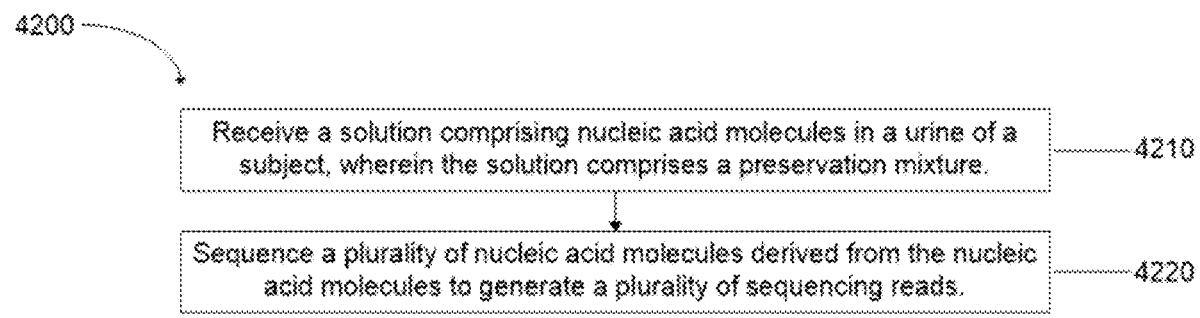
FIG. 42 shows a flowchart for a method for processing a urine sample.

FIG. 42 shows a flowchart for a method 4200 for processing a urine sample. In a first operation 4210, the method 4200 may comprise receiving a solution comprising nucleic acid molecules in a urine of a subject. The solution may comprise a preservation mixture. The preservation mixture may comprise any at least 1, 2, 3, 4, 5, or 6 member(s) selected from the group consisting of: a first chelator, a second chelator that is different from the first chelator, a pH buffer, a cell membrane stabilizer, nucleic acid compactor, and an antimicrobial agent. The preservation mixture may comprise any at most 6, 5, 4, 3, 2, or 1 member(s) selected from the group consisting of: a first chelator, a second chelator that is different from the first chelator, a pH buffer, a cell membrane stabilizer, nucleic acid compactor, and an antimicrobial agent. The preservation mixture may comprise a number of member(s) that is within a range defined by any two of the preceding values.

For instance, the preservation mixture may comprise a first chelator and one or more member(s) selected from the group consisting of: a pH buffer, a second chelator that is different from the first chelator, a cell membrane stabilizer, a nucleic acid compactor, and an antimicrobial agent. The preservation mixture may comprise the first chelator and the second chelator. The preservation mixture may comprise a pH buffer, a first chelator, a second chelator, a cell membrane stabilizer, a nucleic acid compactor, and an antimicrobial agent. The preservation mixture may comprise at least two different chelators and one or more member(s) selected from the group consisting of: an antimicrobial agent, a cell membrane stabilizer, and a nucleic acid compactor.

The preservation mixture may comprise a pH buffer. The pH buffer may maintain the preservation mixture at a pH that is between 7 and 9.

The first chelator may have a first binding affinity for a first metal and the second chelator may have a second binding affinity for the first metal. The first binding affinity may be greater than the second binding affinity. The first metal may comprise any at least 1, 2, 3, 4, 5, 6, 7, or 8 member(s) selected from the group consisting of: vanadium (V), chromium (Cr), manganese (Mn), iron (Fe), cobalt (Co), copper (Cu), zinc (Zn), and molybdenum (Mo). The first metal may comprise any at most 8, 7, 6, 5, 4, 3, 2, or 1 member(s) selected from the group consisting of: vanadium (V), chromium (Cr), manganese (Mn), iron (Fe), cobalt (Co), copper (Cu), zinc (Zn), and molybdenum (Mo). The first metal may comprise a number of member(s) that is within a range defined by any two of the preceding values.

The first chelator may have a third binding affinity for a second metal and the second chelator may have a fourth binding affinity for the second metal. The second metal may be different from the first metal. The third binding affinity may be less than the fourth binding affinity. The second metal may comprise any at least 1, 2, 3, 4, or 5 member(s) selected from the group consisting of: lithium (Li), sodium (Na), potassium (K), magnesium (Mg), and calcium (Ca). The second metal may comprise any at most 5, 4, 3, 2, or 1 member(s) selected from the group consisting of: lithium (Li), sodium (Na), potassium (K), magnesium (Mg), and calcium (Ca). The second metal may comprise a number of member(s) that is within a range defined by any two of the preceding values.

The first chelator may comprise at least 1, 2, 3, or 4 member(s) selected from the group consisting of: a siderophore, a nucleoside monophosphate, a nucleoside diphosphate, a nucleoside triphosphate, and functional variants thereof. The first chelator may comprise at most 4, 3, 2, or 1 member(s) selected from the group consisting of: a siderophore, a nucleoside monophosphate, a nucleoside diphosphate, a nucleoside triphosphate, and functional variants thereof. The first chelator may comprise a number of member(s) that is within a range defined by any two of the preceding values.

The siderophore may comprise one or more member(s) selected from the group consisting of: Achromobactina, Acinetobactin, Acinetoferrin, Aerobactin, Aeruginic acid, Agrobactin, Agrobactin A, Albomycin, Alcaligin, Alterobactin A, Alterobactin A, Aminochelin, Amonabactin P693, Amonabactin P750, Amonabactin T732, Amonabactin T789, Amphibactin B, Amphibactin C, Amphibactin D, Amphibactin E, Amphibactin F, Amphibactin G, Amphibactin H, Amphibactin I, Amphibactin S, Amphibactin T, Amphi-enterobactin, Amphi-enterobactin C12-OH, Amycolachrome, Anachelin 1, Anachelin 2, Anguibactin, Aquachelin A, Aquachelin B, Aquachelin C, Aquachelin D, Aquachelin I, Aquachelin J, Arthrobactin, Asperchrome A, Asperchrome B1, Asperchrome B2, Asperchrome B3, Asperchrome C, Asperchrome D1, Asperchrome D2, Asperchrome D3, Asperchrome E, Asperchrome F1, Asperchrome F2, Asperchrome F3, Aspergillic acid, Avenic acid, Azotobactin, Azotobactin 87, Azotobactin D, Azotochelin, Azoverdin, Bacillibactin, Basidiochrome, Bisucaberin, Carboxymycobactin, Carboxymycobactin 1, Carboxymycobactin 2, Carboxymycobactin 3, Carboxymycobactin 4, Cepabactin, Chrysobactin, Citrate, Coelichelin, Coprogen, Coprogen B, Corynebactin, Deoxydistichonic acid, 2'-Deoxymugineic acud, Deoxyschizokinen, Des(diserylglycyl)-ferrirhodin, Desacetylcoprogen, Desferrioxamine A1A, Desferrioxamine A1B, Desferrioxamine A2, Desferrioxamine B, Desferrioxamine D1, Desferrioxamine D2, Desferrioxamine E, Desferrioxamine Et1, Desferrioxamine Et2, Desferrioxamine Et3, Desferrioxamine G1, Desferrioxamine G2A, Desferrioxamine G2B, Desferrioxamine G2C, Desferrioxamine H, Desferrioxamine N, Desferrioxamine P1, Desferrioxamine T1, Desferrioxamine T2, Desferrioxamine T3, Desferrioxamine T7, Desferrioxamine T8, Desferrioxamine Te1, Desferrioxamine Te2, Desferrioxamine Te3, Desferrioxamine X1, Desferrioxamine X2, Desferrioxamine X3, Desferrioxamine X4, Desferrithiocin, 2,3-Dihydroxybenzoylserine, Dimerum acid, Dimethylcoprogen, Dimethylneocoprogen I, Dimethyltriornicin, Distichonic acid, E,E-putrebactene, Enantio Rhizoferrin, Enantio-Pyochelin, Enterobactin, Enterochelin, E-putrebactene, Exochelin MN, Exochelin MS, Ferrichrome, Ferrichrome A, Ferrichrome C, Ferrichrysin, Ferricrocin, Ferrimycin A, Ferrirhodin, Ferrirubin, Ferrocin A, Fimsbactin A, Fimsbactin B, Fimsbactin C, Fimsbactin D, Fimsbactin E, Fimsbactin F, Fluvibactin, Formobactin, Fusarinine, Fusarinine A, Fusarinine B, Fusarinine C, Heterobactin A, Heterobactin B, Hydroxycopropen, Hydroxyisoneocoprogen I, 3-Hydroxymugineic acid, Hydroxy-neocoprogen I, Isoneocoprogen I, Isopyoverdin 10.7, Isopyoverdin 6.7, Isopyoverdin 7.13, Isopyoverdin 90-33, Isopyoverdin 90-44, Isopyoverdin BTP1, Isotriornicin, Itoic acid, Loihichelin A, Loihichelin B, Loihichelin C, Loihichelin D, Loihichelin E, Loihichelin F, Maduraferrin, Malonichrome, Marinobactin, Marinobactin, Marinobactin, Marinobactin, Marinobactin, Marinobactin, Micacocidin, Moanachelins, Moanachelins, Moanachelins, Moanachelins, Moanachelins, Monoglucosylated, Mugineic, Mycobactin A, Mycobactin Av, Mycobactin F, Mycobactin H, Mycobactin J, Mycobactin M, Mycobactin N, Mycobactin NA, Mycobactin P, Mycobactin R, Mycobactin S, Mycobactin T, Myxochelin, Nannochelin A, Nannochelin B, Nannochelin C, Neocoprogen I, Neocoprogen II, Neurosporin, Nocobactin, Ochrobactin A, Ochrobactin B, Ochrobactin C, Ornibactin-C4, Ornibactin-C6, Ornibactin-C8, Ornicorrugatin, Palmitoylcoprogen, Parabactin, Parabactin A, Petrobactin, Petrobactin disulphonate, Petrobactin sulphonate, Pistillarin, Protochelin, Pseudoalterobactin A, Pseudoalterobactin B, Pseudobactin, Pseudobactin 589A, Putrebactin, Pyochelin, Pyoverdin 1, Pyoverdin 10.1, Pyoverdin 10.10, Pyoverdin 10.2, Pyoverdin 10.3, Pyoverdin 10.4, Pyoverdin 10.5, Pyoverdin 10.6, Pyoverdin 10.8, Pyoverdin 10.9, Pyoverdin 11.1, Pyoverdin 11.2, Pyoverdin 11370, Pyoverdin 12, Pyoverdin 12.1, Pyoverdin 12.2, Pyoverdin 13525, Pyoverdin 1547, Pyoverdin 17400, Pyoverdin 18-1, Pyoverdin 19310, Pyoverdin 2192, Pyoverdin 2392, Pyoverdin 2461, Pyoverdin 2798, Pyoverdin 51 W, Pyoverdin 6.1, Pyoverdin 6.2, Pyoverdin 6.3, Pyoverdin 6.4, Pyoverdin 6.5, Pyoverdin 6.6, Pyoverdin 6.8, Pyoverdin 7.1, Pyoverdin 7.10, Pyoverdin 7.11, Pyoverdin 7.12, Pyoverdin 7.14, Pyoverdin 7.15, Pyoverdin 7.16, Pyoverdin 7.17, Pyoverdin 7.18, Pyoverdin 7.19, Pyoverdin 7.2, Pyoverdin 7.3, Pyoverdin 7.4, Pyoverdin 7.5, Pyoverdin 7.6, Pyoverdin 7.7, Pyoverdin 7.8, Pyoverdin 7.9, Pyoverdin 8.1, Pyoverdin 8.2, Pyoverdin 8.3, Pyoverdin 8.4, Pyoverdin 8.5, Pyoverdin 8.6, Pyoverdin 8.7, Pyoverdin 8.8, Pyoverdin 8.9, Pyoverdin 9.1, Pyoverdin 9.10, Pyoverdin 9.11, Pyoverdin 9.12, Pyoverdin 9.2, Pyoverdin 9.3, Pyoverdin 9.4, Pyoverdin 9.5, Pyoverdin 9.6, Pyoverdin 9.7, Pyoverdin 9.8, Pyoverdin 9.9, Pyoverdin 90-51, Pyoverdin 95-275, Pyoverdin 96-312, Pyoverdin 96-318, Pyoverdin 9AW, Pyoverdin A214, Pyoverdin BTP2, Pyoverdin C, Pyoverdin CHAO, Pyoverdin D-TR133, Pyoverdin E, Pyoverdin G, Pyoverdin GM, Pyoverdin I-III, Pyoverdin P19, Pyoverdin Pau, Pyoverdin PL8, Pyoverdin PVD, Pyoverdin R', Pyoverdin Thai, Pyoverdin TII, Pyridoxatin, Quinolobactin, Rhizobactin, Rhizobactin 1021, Rhizoferrin, Rhizoferrin analogues, Rhodotrulic acid, Sake Colorant A, Salmochelin S1, Salmochelin S2, Salmochelin S4, Salmochelin SX, Salmycin A, Schizokinen, Serratiochelin, Siderochelin A, Snychobactin A, Snychobactin B, Snychobactin C, Staphyloferrin A, Staphyloferrin B, Taiwachelin, Tetraglycine ferrichrome, Thiazostatin, Triacetylfusarine, Triornicin, Vibriobactin, Vibrioferrin, Vicibactin, Vulnibactin, and Yersiniabactin.

The nucleoside monophosphate may comprise any at least 1, 2, 3, 4, or 5 member(s) selected from the group consisting of: adenosine monophosphate (AMP), cytidine monophosphate (CMP), guanosine monophosphate (GMP), thymidine monophosphate (TMP), and uridine monophosphate (UMP). The nucleoside monophosphate may comprise any at most 5, 4, 3, 2, or 1 member(s) selected from the group consisting of: AMP, CMP, GMP, TMP, and UMP. The nucleoside monophosphate may comprise a number of member(s) that is within a range defined by any two of the preceding values.

The nucleoside diphosphate may comprise any at least 1, 2, 3, 4, or 5 member(s) selected from the group consisting of: adenosine diphosphate (ADP), cytidine diphosphate (CDP), guanosine diphosphate (GDP), thymidine diphosphate (TDP), and uridine diphosphate (UDP). The nucleoside diphosphate may comprise any at most 5, 4, 3, 2, or 1 member(s) selected from the group consisting of: ADP, CDP, GDP, TDP, and UDP. The nucleoside diphosphate may comprise a number of member(s) that is within a range defined by any two of the preceding values.

The nucleoside triphosphate may comprise any at least 1, 2, 3, 4, or 5 member(s) selected from the group consisting of: adenosine triphosphate (ATP), cytidine triphosphate (CTP), guanosine triphosphate (GTP), thymidine triphosphate (TTP), and uridine triphosphate (UTP). The nucleoside triphosphate may comprise any at most 5, 4, 3, 2, or 1 member(s) selected from the group consisting of: ATP, CTP, GTP, TTP, and UTP. The nucleoside triphosphate may comprise a number of member(s) that is within a range defined by any two of the preceding values.

The first chelator may have a stability constant of at least about 25.2, 25.3, 25.4, 25.6, 25.7, 25.8, 25.9, 26, 27, 28, 28, 29, 30, or more for formation of a complex with a metal. The metal may comprise one or more member(s) selected from the group consisting of: vanadium (V), chromium (Cr), manganese (Mn), iron (Fe), cobalt (Co), copper (Cu), zinc (Zn), and molybdenum (Mo).

The second chelator may comprise one or more member(s) selected from the group consisting of: ethylenediaminetetraacetic acid (EDTA), nitrilotriacetic acid (NTA), trans-1,2-cyclohexanediaminetetraacetic acid (CyDTA), diethylenetriaminepentaacetic acid (DTPA), glycoletherdiaminetetraacetic acid (GEDTA), triethylenetetramine-N,N,N',N'',N''',N''''-hexaacetic acid (TTHA), dihydroxyethylglycine (DHEG), iminodiacetic acid (IDA), nitrilotrimethylphosphonic acid (NTP), N-(2-hydroxyethyl) iminodiacetic acid (HIDA), ethylenediamine-N,N'-dipropionic acid (EDDP), ethylenediaminetetra(methylenephosphonic) acid (EDTPO), nitrilotrimethylphosphonic acid (NTP) and 1,2-bis(o-aminophenoxy)ethane-N,N,N',N'-tetraacetic acid (BAPTA).

The second chelator may have a stability constant of at most about 25.2, 25.1, 25, 24, 23, 22, 21, 20, or less for formation of a complex with the metal. The metal may comprise one or more member(s) selected from the group consisting of: vanadium (V), chromium (Cr), manganese (Mn), iron (Fe), cobalt (Co), copper (Cu), zinc (Zn), and molybdenum (Mo).

The cell membrane stabilizer may comprise one or more member(s) selected from the group consisting of: a vitamin E conjugate, poly-L-lysine, diazolidinyl urea, imidazolidinyl urea, dimethoylol-5,5dimethylhydantoin, dimethylol urea, 2-bromo-2-nitropropane-1,3-diol, oxazolidines, sodium hydroxymethyl glycinate, 5-hydroxymethoxymethyl-1-1-aza-3,7-dioxabicyclo [3,3.0]octane, 5-hydroxymethyl-1-1-aza-3,7-dioxabicyclo[3,3.0]octane, 5-hydroxypoly[methyleneoxy]methyl-1-1-aza-3, 7-dioxabicyclo[3, 3.0]octane, and quaternary adamantine.

The nucleic acid compactor may comprise at least 1, 2, 3, 4, or 5 member(s) selected from the group consisting of: a cationic polymer, a polyamine, poly-L-lysine, spermine, and spermidine. The nucleic acid compactor may comprise at most 5, 4, 3, 2, or 1 member(s) selected from the group consisting of: a cationic polymer, a polyamine, poly-L-lysine, spermine, and spermidine. The nucleic acid compactor may comprise a number of member(s) that is within a range defined by any two of the preceding values.

The antimicrobial agent may comprise at least 1, 2, or 3 member(s) selected from the group consisting of: penicillin, streptomycin, and amphotericin B. The antimicrobial agent may comprise at most 3, 2, or 1 member(s) selected from the group consisting of: penicillin, streptomycin, and amphotericin B. The antimicrobial agent may comprise a number of member(s) that is within a range defined by any two of the preceding values.

In a second operation 4220, the method 4200 may comprise sequencing a plurality of nucleic acid molecules derived from the nucleic acid molecules to generate a plurality of sequencing reads. The sequencing may comprise any nucleic acid sequencing described herein. For instance, the sequencing may comprise PCR, digital PCR, real-time PCR, qPCR, Sanger sequencing, high-throughput sequencing, sequencing-by-synthesis, single-molecule sequencing, sequencing-by-ligation, RNA-Seq (Illumina), Next generation sequencing, Digital Gene Expression (Helicos), array hybridization, Clonal Single MicroArray (Solexa), shotgun sequencing, Maxim-Gilbert sequencing, or massively-parallel sequencing.

Prior to operation 4220, the method 4200 may comprise extracting the plurality of nucleic acids from the solution.

The method may further comprise identifying a presence or absence of a urinary disorder (such as any urinary disorder described herein) based at least in part on the sequencing reads. The identifying may at least 1, 2, or 3 of a sensitivity of at least about 80%, 85%, 90%, 95%, 99%, or more, a specificity of at least about 80%, 85%, 90%, 95%, 99%, or more, and an accuracy of at least about 80%, 85%, 90%, 95%, 99%, or more.

The identifying may comprise applying a machine learning procedure to the sequencing reads. The machine learning procedure may comprise any machine learning procedure described herein. For instance, the machine learning procedure may comprise regression analysis, regularization, classification, dimensionality reduction, ensemble learning, meta learning, reinforcement learning, association rule learning, cluster analysis, anomaly detection, or deep learning. The machine learning procedure may comprise k-means, k-means clustering, k-nearest neighbors, learning vector quantization, linear regression, non-linear regression, least squares regression, partial least squares regression, logistic regression, stepwise regression, multivariate adaptive regression splines, ridge regression, principle component regression, least absolute shrinkage and selection operation, least angle regression, canonical correlation analysis, factor analysis, independent component analysis, linear discriminant analysis, multidimensional scaling, non-negative matrix factorization, principal components analysis, principal coordinates analysis, projection pursuit, Sammon mapping, t-distributed stochastic neighbor embedding, AdaBoost, boosting, bootstrap aggregation, ensemble averaging, decision trees, conditional decision trees, boosted decision trees, gradient boosted decision trees, random forests, stacked generalization, Bayesian networks, Bayesian belief networks, naïve Bayes, Gaussian naïve Bayes, multinomial naïve Bayes, hidden Markov models, hierarchical hidden Markov models, support vector machines, encoders, decoders, auto-encoders, stacked auto-encoders, perceptrons, multi-layer perceptrons, artificial neural networks, feedforward neural networks, convolutional neural networks, recurrent neural networks, long short-term memory, deep belief networks, deep Boltzmann machines, deep convolutional neural networks, deep recurrent neural networks, or generative adversarial networks.

The method may further comprise generating an output with the plurality of sequencing reads.

The preservation mixture may provide greater sequencing molecular complexity than previous compositions. The preservation mixture may provide for sequencing the plurality of nucleic acid molecules to generate the plurality of sequencing reads at a greater molecular complexity as compared to other nucleic acid molecules in urine preserved in a reference composition. The reference composition may comprise a volume-excluding polymer that is present in an amount from about 10% to about 50% by weight of the reference composition, an osmotic agent present in an amount of about 1% to about 20% by weight of the reference composition, and an enzyme inhibitor present in an amount from about 1% to about 30% by weight of the reference composition. The volume-excluding polymer may comprise polyethylene glycol (PEG). The osmotic agent may comprise sodium chloride (NaCl). The enzyme may comprise ethylenediaminetetraacetic acid (EDTA) or a citrate. The reference composition may further comprise a metabolic inhibitor present in an amount from about 0.01% to about 10% by weight of the reference composition. The metabolic inhibitor may comprise sodium azide ($NaN_3$).

The preservation mixture may provide for sequencing the plurality of nucleic acid molecules to generate the plurality of sequencing reads at a molecular complexity at least about 1%, 2%, 3%, 4%, 5%, 6%, 7%, 8%, 9%, 10%, 20%, 30%, 40%, 50%, 60%, 70%, 80%, 90%, 100%, or more, greater as compared to other nucleic acid molecules in urine preserved in the reference composition. The preservation mixture may provide for sequencing the plurality of nucleic acid molecules to generate the plurality of sequencing reads at a molecular complexity at most about 100%, 90%, 80%, 70%, 60%, 50%, 40%, 30%, 20%, 10%, 9%, 8%, 7%, 6%, 5%, 4%, 3%, 2%, 1%, or less, greater as compared to other nucleic acid molecules in urine preserved in the reference composition. The preservation mixture may provide for sequencing the plurality of nucleic acid molecules to generate the plurality of sequencing reads at a molecular complexity greater by any amount that is within a range defined by any two of the preceding values as compared to other nucleic acid molecules in urine preserved in the reference composition. The greater molecular complexity may comprise a greater unique molecule molecular complexity. The greater molecular complexity may comprise a greater diversity of unique molecules. The greater molecular complexity may comprise a greater number of unique sequencing reads.

The preservation mixture may preserve nucleic acids in the urine for an extended period of time. For instance, the nucleic acid molecules may have an average length of at least about 10, 20, 30, 40, 50, 60, 70, 80, 90, 100, or more nucleic acids in the presence of the preservation mixture for a period of at least about 1, 2, 3, 4, 5, 6, 7, 8, 9, 10, or more days.

The preservation mixture may preserve nucleic acids in the urine for an extended period of time at a variety of different temperatures. For instance, the nucleic acid molecules may have an average length of at least about 10, 20, 30, 40, 50, 60, 70, 80, 90, 100, or more nucleic acids in the presence of the preservation mixture at a temperature that is within a range from about −40 degrees Celsius (° C.) to about 20° C., a temperature that is within a range from about 20° C. to about 40° C., or a temperature that is within a range from about 40° C. to about 80° C.

The preservation mixture may preserve nucleic acids in the urine for an extended period of time subsequent to storage of the preservation mixture. For instance, the nucleic acid molecules may have an average length of at least about 10, 20, 30, 40, 50, 60, 70, 80, 90, 100, or more nucleic acids in the presence of the preservation mixture subsequent to storage of the preservation mixture for at least about 1 day, 2 days, 3 days, 4 days, 5 days, 6 days, 1 week, 2 weeks, 3 weeks, 4 weeks, 1 month, 2 months, 3 months, 4 months, 5 months, 6 months, 7 months, 8 months, 9 months, 10 months, 11 months, 1 year, or more.

Many variations, alterations, and adaptations based on any one or more of the methods 100, 200, 300, or 4200 provided herein are possible. For example, the order of the operations of the methods 100, 200, 300, or 4200 may be changed, some of the operations removed, some of the operations duplicated, and additional operations added as appropriate. Some of the operations may be performed in succession. Some of the operations may be performed in parallel. Some of the operations may be performed once. Some of the operations may be performed more than once. Some of the operations may comprise sub-operations. Some of the operations may be automated and some of the operations may be manual.

In another aspect, the present disclosure provide a method for processing a urine sample. The method may comprise receiving a solution comprising nucleic acid molecules from a urine of a subject, which solution comprises a preservation mixture, wherein, in presence of the preservation mixture for a time period of at least 3 days, the nucleic acid molecules have an average length greater about 30 nucleic acid bases. Next, the method may comprise sequencing a plurality of nucleic acid molecules derived from the nucleic acid molecules to generate a plurality of sequencing reads. Then, the method may comprise generating an output with the plurality of sequencing reads.

In another aspect, the present disclosure provides a preservation mixture that is configured to preserve a first set of nucleic acid molecules in a urine sample to yield at least about a 5% greater sequencing molecular complexity upon sequencing the nucleic acid molecules or derivatives thereof, which at least about 5% greater sequencing molecular complexity is as compared to a second set of the nucleic the molecules being preserved in a reference composition. The reference composition may comprise: a volume-excluding polymer present in an amount from about 10% to about 50% by weight of the reference composition, an osmotic agent present in an amount of about 1% to about 20% by weight of the reference composition, and an enzyme inhibitor present in an amount from about 1% to about 30% by weight of the reference composition.

In another aspect, the present disclosure provide a preservation mixture that is configured to preserve a first set of nucleic acid molecules in a urine sample to yield at least about a 5% greater sequencing molecular complexity upon sequencing the nucleic acid molecules or derivatives thereof, which at least about 5% greater sequencing molecular complexity is as compared to a second set of said nucleic acid molecules being preserved in a reference composition. The reference composition may comprise: a volume-excluding polymer present in an amount from about 10% to about 50% by weight of the reference composition, an osmotic agent present in an amount of about 1% to about 20% by weight of the reference composition, and an enzyme inhibitor present in an amount from about 1% to about 30% by weight of the reference composition.

In another aspect, the present disclosure provides a preservation mixture comprising: a pH buffer, a first chelator, a second chelator, a cell membrane stabilizer, a nucleic acid compactor, and an antimicrobial agent.

In another aspect, the present disclosure provides a preservation mixture comprising at least two different chelators and one or more member(s) selected from the group consisting of: an antimicrobial agent, a cell membrane stabilizer, and a nucleic acid compactor.

In another aspect, the present disclosure provides a preservation mixture comprising: a first chelator, said first chelator having a stability constant of at least 25.2 for formation of a complex with a metal; and a second chelator that is different from the first chelator, wherein the second chelator has a stability constant that is less than 25.2 for formation of a complex with the metal.

In another aspect, the preservation mixture may include antimicrobials selected from the group consisting of Aminoglycosides, Amikacin, Gentamicin, Kanamycin, Neomycin, Netilmicin, Tobramycin, Paromomycin, Streptomycin, Spectinomycin(Bs), Ansamycins, Geldanamycin, Herbimycin, Rifaximin, Carbacephem, Loracarbef, Carbapenems, Ertapenem, Doripenem, Imipenem/Cilastatin, Meropenem, Cephalosporins (First generation), Cefadroxil, Cefazolin, Cephradine, Cephapirin, Cephalothin, Cefalexin, Cephalosporins (Second generation), CefaclorCefoxitin, Cefotetan, Cefamandole, Cefmetazole, Cefonicid, Loracarbef, Cefprozil, Cefuroxime, Cephalosporins (Third generation), Cefixime, Cefdinir, Cefditoren, Cefoperazone [Unlike most third-generation agents, cefoperazone is active against *Pseudomonas aeruginosa*], combination Cefoperazone with Sulbactam makes more effective antibiotic, because Sulbactam avoid degeneration of Cefoperazone, Cefotaxime, Cefpodoxime, Ceftazidime (Unlike most third-generation agents, ceftazidime is active against *Pseudomonas aeruginosa*, but less active against Staphylococci and Streptococci compare to other 3rd generation of cephalosporins), Ceftibuten, Ceftizoxime, Moxalactam, Ceftriaxone, Cephalosporins (Fourth generation), Cefepime, Cephalosporins (Fifth generation), Ceftaroline fosamilCeftobiprole, Glycopeptides, Teicoplanin, Vancomycin, Telavancin, Dalbavancin, Oritavancin, Lincosamides(Bs), Clindamycin, Lincomycin, Lipopeptide, Daptomycin, urine Stabilur tablet, Macrolides(Bs), AzithromycinClarithromycinErythromycin, RoxithromycinTelithromycin, Spiramycin, Fidaxomicin, Monobactams, Aztreonam, Nitrofurans, Furazolidone, Nitrofurantoin(Bs), Oxazolidinones(Bs), Linezolid, Posizolid, Radezolid, Torezolid, Penicillins, Amoxicillin, Ampicillin, Azlocillin, Dicloxacillin, Flucloxacillin, Mezlocillin, Methicillin, Nafcillin, Oxacillin, Penicillin G, Penicillin V, Piperacillin, Penicillin G, Temocillin, Ticarcillin, Penicillin combinations, Amoxicillin/clavulanate, Ampicillin/sulbactam, Piperacillin/tazobactam, Ticarcillin/clavulanate, Polypeptides, Bacitracin, Colistin, Polymyxin B, Quinolones/Fluoroquinolones, Ciprofloxacin, Enoxacin, Gatifloxacin, Gemifloxacin, Levofloxacin, Lomefloxacin, Moxifloxacin, Nadifloxacin, Nalidixic acid, Norfloxacin, Ofloxacin, Trovafloxacin, Grepafloxacin, Sparfloxacin, Temafloxacin, Sulfonamides(Bs), MafenideSulfacetamide, Sulfadiazine, Silver sulfadiazine, Sulfadimethoxine, Sulfamethizole, Sulfamethoxazole, Sulfanilimide (archaic), Sulfasalazine, Sulfisoxazole, Trimethoprim-Sulfamethoxazole (Co-trimoxazole) (TMP-SMX), Sulfonamidochrysoidine (archaic), Tetracyclines(Bs), Demeclocycline, Doxycycline, Metacycline, Minocycline, Oxytetracycline, Tetracycline, Clofazimine, Dapsone, Capreomycin, Cycloserine, Ethambutol(Bs), Ethionamide, Isoniazid, Pyrazinamide, Rifampicin (Rifampin in US), Rifabutin, Rifapentine, Streptomycin, Others, Arsphenamine, Chloramphenicol (Bs), Fosfomycin, Fusidic acid, Metronidazole, Mupirocin, Platensimycin, Quinupristin/Dalfopristin, Thiamphenicol, Tigecycline(Bs), Tinidazole, and Trimethoprim(Bs).

In another aspect, the preservation mixture may include siderophores selected from the group consisting of Achromobactina, Acinetobactin, Acinetoferrin, Aerobactin, Aeruginic acid, Agrobactin, Agrobactin A, Albomycin, Alcaligin, Alterobactin A, Alterobactin A, Aminochelin, Amonabactin P693, Amonabactin P750, Amonabactin T732, Amonabactin T789, Amphibactin B, Amphibactin C, Amphibactin D, Amphibactin E, Amphibactin F, Amphibactin G, Amphibactin H, Amphibactin I, Amphibactin S, Amphibactin T, Amphi-enterobactin, Amphi-enterobactin C12-OH, Amycolachrome, Anachelin 1, Anachelin 2, Anguibactin, Aquachelin A, Aquachelin B, Aquachelin C, Aquachelin D, Aquachelin I, Aquachelin J, Arthrobactin, Asperchrome A, Asperchrome B1, Asperchrome B2, Asperchrome B3, Asperchrome C, Asperchrome D1, Asperchrome D2, Asperchrome D3, Asperchrome E, Asperchrome F1, Asperchrome F2, Asperchrome F3, Aspergillic acid, Avenic acid, Azotobactin, Azotobactin 87, Azotobactin D, Azotochelin, Azoverdin, Bacillibactin, Basidiochrome, Bisucaberin, Carboxymycobactin, Carboxymycobactin 1, Carboxymycobactin 2, Carboxymycobactin 3, Carboxymycobactin 4, Cepabactin, Chrysobactin, Citrate, Coelichelin, Coprogen, Coprogen B, Corynebactin, Deoxydistichonic acid, 2'-Deoxymugineic acud, Deoxyschizokinen, Des(diserylglycyl)-ferrirhodin, Desacetylcoprogen, Deferoxamine Mesylate, Desferrioxamine A1A, Desferrioxamine A1B, Desferrioxamine A2, Desferrioxamine B, Desferrioxamine D1, Desferrioxamine D2, Desferrioxamine E, Desferrioxamine Et1, Desferrioxamine Et2, Desferrioxamine Et3, Desferrioxamine G1, Desferrioxamine G2A, Desferrioxamine G2B, Desferrioxamine G2C, Desferrioxamine H, Desferrioxamine N, Desferrioxamine P1, Desferrioxamine T1, Desferrioxamine T2, Desferrioxamine T3, Desferrioxamine T7, Desferrioxamine T8, Desferrioxamine Te1, Desferrioxamine Te2, Desferrioxamine Te3, Desferrioxamine X1, Desferrioxamine X2, Desferrioxamine X3, Desferrioxamine X4, Desferrithiocin, 2,3-Dihydroxybenzoylserine, Dimerum acid, Dimethylcoprogen, Dimethylneocoprogen I, Dimethyltriornicin, Distichonic acid, E,E-putrebactene, Enantio Rhizoferrin, Enantio-Pyochelin, Enterobactin, Enterochelin, E-putrebactene, Exochelin MN, Exochelin MS, Ferrichrome, Ferrichrome A, Ferrichrome C, Ferrichrysin, Ferricrocin, Ferrimycin A, Ferrirhodin, Ferrirubin, Ferrocin A, Fimsbactin A, Fimsbactin B, Fimsbactin C, Fimsbactin D, Fimsbactin E, Fimsbactin F, Fluvibactin, Formobactin, Fusarinine, Fusarinine A, Fusarinine B, Fusarinine C, Heterobactin A, Heterobactin B, Hydroxycopropen, Hydroxyisoneocoprogen I, 3-Hydroxymugineic acid, Hydroxy-neocoprogen I, Isoneocoprogen I, Isopyoverdin 10.7, Isopyoverdin 6.7, Isopyoverdin 7.13, Isopyoverdin 90-33, Isopyoverdin 90-44, Isopyoverdin BTP1, Isotriornicin, Itoic acid, Loihichelin A, Loihichelin B, Loihichelin C, Loihichelin D, Loihichelin E, Loihichelin F, Maduraferrin, Malonichrome, Marinobactin, Marinobactin, Marinobactin, Marinobactin, Marinobactin, Marinobactin, Micacocidin, Moanachelins, Moanachelins, Moanachelins, Moanachelins, Moanachelins, Monoglucosylated, Mugineic, Mycobactin A, Mycobactin Av, Mycobactin F, Mycobactin H, Mycobactin J, Mycobactin M, Mycobactin N, Mycobactin NA, Mycobactin P, Mycobactin R, Mycobactin S, Mycobactin T, Myxochelin, Nannochelin A, Nannochelin B, Nannochelin C, Neocoprogen I, Neocoprogen II, Neurosporin, Nocobactin, Ochrobactin A, Ochrobactin B, Ochrobactin C, Ornibactin-C4, Ornibactin-C6, Ornibactin-C8, Ornicorrugatin, Palmitoylcoprogen, Parabactin, Parabactin A, Petrobactin, Petrobactin disulphonate, Petrobactin sulphonate, Pistillarin, Protochelin, Pseudoalterobactin A, Pseudoalterobactin B, Pseudobactin, Pseudobactin 589A, Putrebactin, Pyochelin, Pyoverdin 1, Pyoverdin 10.1, Pyoverdin 10.10, Pyoverdin 10.2, Pyoverdin 10.3, Pyoverdin 10.4, Pyoverdin 10.5, Pyoverdin 10.6, Pyoverdin 10.8, Pyoverdin 10.9, Pyoverdin 11.1, Pyoverdin 11.2, Pyoverdin 11370, Pyoverdin 12, Pyoverdin 12.1, Pyoverdin 12.2, Pyoverdin 13525, Pyoverdin 1547, Pyoverdin 17400, Pyoverdin 18-1, Pyoverdin 19310, Pyoverdin 2192, Pyoverdin 2392, Pyoverdin 2461, Pyoverdin 2798, Pyoverdin 51 W, Pyoverdin 6.1, Pyoverdin 6.2, Pyoverdin 6.3, Pyoverdin 6.4, Pyoverdin 6.5, Pyoverdin 6.6, Pyoverdin 6.8, Pyoverdin 7.1, Pyoverdin 7.10, Pyoverdin 7.11, Pyoverdin 7.12, Pyoverdin 7.14, Pyoverdin 7.15, Pyoverdin 7.16, Pyoverdin 7.17, Pyoverdin 7.18, Pyoverdin 7.19, Pyoverdin 7.2, Pyoverdin 7.3, Pyoverdin 7.4, Pyoverdin 7.5, Pyoverdin 7.6, Pyoverdin 7.7, Pyoverdin 7.8, Pyoverdin 7.9, Pyoverdin 8.1, Pyoverdin 8.2, Pyoverdin 8.3, Pyoverdin 8.4, Pyoverdin 8.5, Pyoverdin 8.6, Pyoverdin 8.7, Pyoverdin 8.8, Pyoverdin 8.9, Pyoverdin 9.1, Pyoverdin 9.10, Pyoverdin 9.11, Pyoverdin 9.12, Pyoverdin 9.2, Pyoverdin 9.3, Pyoverdin 9.4, Pyoverdin 9.5, Pyoverdin 9.6, Pyoverdin 9.7, Pyoverdin 9.8, Pyoverdin 9.9, Pyoverdin 90-51, Pyoverdin 95-275, Pyoverdin 96-312, Pyoverdin 96-318, Pyoverdin 9AW, Pyoverdin A214, Pyoverdin BTP2, Pyoverdin C, Pyoverdin CHAO, Pyoverdin D-TR133, Pyoverdin E, Pyoverdin G, Pyoverdin GM, Pyoverdin I-III, Pyoverdin P19, Pyoverdin Pau, Pyoverdin PL8, Pyoverdin PVD, Pyoverdin R', Pyoverdin Thai, Pyoverdin TII, Pyridoxatin, Quinolobactin, Rhizobactin, Rhizobactin 1021, Rhizoferrin, Rhizoferrin analogues, Rhodotrulic acid, Sake Colorant A, Salmochelin S1, Salmochelin S2, Salmochelin S4, Salmochelin SX, Salmycin A, Schizokinen, Serratiochelin, Siderochelin A, Snychobactin A, Snychobactin B, Snychobactin C, Staphyloferrin A, Staphyloferrin B, Taiwachelin, Tetraglycine ferrichrome, Thiazostatin, Triacetylfusarine, Triomicin, Vibriobactin, Vibrioferrin, Vicibactin, Vulnibactin, and Yersiniabactin.

One aspect described herein is a preservation mixture comprising an iron chelator, wherein the preservation mixture is configured to preserve nucleic acid molecules in a urine sample and prevent growth of microbes in the sample.

The iron chelator may be configured to preserve nucleic acid molecules in a urine sample and prevent growth of microbes in the sample. The iron chelator may be selected from the group consisting of enterobactin and Deferoxamine Mesylate. The preservation mixture may further comprise EDTA. The preservation mixture may further comprise poly-L-lysine hydrobromide. The preservation mixture may further comprise D-alpha-tocopherol polyethylene glycol 1000 succinate. The preservation mixture may further comprise an antimicrobial selected from the group consisting of penicillin, streptomycin, Amphotericin B, and urine Stabilur tablet. The preservation mixture may further comprise penicillin, streptomycin, and Amphotericin B, and urine Stabilur tablet.

The preservation mixture may comprise a first chelator and one or more member(s) selected from the group consisting of: a pH buffer, a second chelator that is different from said first chelator, a cell membrane stabilizer, a nucleic acid compactor, and an antimicrobial agent. The preservation mixture may comprise said first chelator and said second chelator.

The pH buffer may maintain the preservation mixture at a pH that is between 7 and 9. The first chelator may have a first binding affinity for a first metal and the second chelator may have a second binding affinity for the first metal, the first binding affinity being greater than said second binding affinity. The first metal may comprise one or more member(s) selected from the group consisting of: vanadium (V), chromium (Cr), manganese (Mn), iron (Fe), cobalt (Co), copper (Cu), zinc (Zn), and molybdenum (Mo).

The first chelator may have a third binding affinity for a second metal and the second chelator may have a fourth binding affinity for the second metal, the second metal being different from the first metal, and the third binding affinity being less than the fourth binding affinity. The first chelator may comprise one or more member(s) selected from the group consisting of: a siderophore, a nucleoside monophosphate, a nucleoside diphosphate, a nucleoside triphosphate, and a functional variant thereof. The siderophore may comprise one or more member(s) selected from the group consisting of: Achromobactina, Acinetobactin, Acinetoferrin, Aerobactin, Aeruginic acid, Agrobactin, Agrobactin A, Albomycin, Alcaligin, Alterobactin A, Alterobactin A, Aminochelin, Amonabactin P693, Amonabactin P750, Amonabactin T732, Amonabactin T789, Amphibactin B, Amphibactin C, Amphibactin D, Amphibactin E, Amphibactin F, Amphibactin G, Amphibactin H, Amphibactin I, Amphibactin S, Amphibactin T, Amphi-enterobactin, Amphi-enterobactin C12-OH, Amycolachrome, Anachelin 1, Anachelin 2, Anguibactin, Aquachelin A, Aquachelin B, Aquachelin C, Aquachelin D, Aquachelin I, Aquachelin J, Arthrobactin, Asperchrome A, Asperchrome B1, Asperchrome B2, Asperchrome B3, Asperchrome C, Asperchrome D1, Asperchrome D2, Asperchrome D3, Asperchrome E, Asperchrome F1, Asperchrome F2, Asperchrome F3, Aspergillic acid, Avenic acid, Azotobactin, Azotobactin 87, Azotobactin D, Azotochelin, Azoverdin, Bacillibactin, Basidiochrome, Bisucaberin, Carboxymycobactin, Carboxymycobactin 1, Carboxymycobactin 2, Carboxymycobactin 3, Carboxymycobactin 4, Cepabactin, Chrysobactin, Citrate, Coelichelin, Coprogen, Coprogen B, Corynebactin, Deoxydistichonic acid, 2'-Deoxymugineic acud, Deoxyschizokinen, Des(diserylglycyl)-ferrirhodin, Desacetylcoprogen, Deferoxamine Mesylate, Desferrioxamine A1A, Desferrioxamine A1B, Desferrioxamine A2, Desferrioxamine B, Desferrioxamine D1, Desferrioxamine D2, Desferrioxamine E, Desferrioxamine Et1, Desferrioxamine Et2, Desferrioxamine Et3, Desferrioxamine G1, Desferrioxamine G2A, Desferrioxamine G2B, Desferrioxamine G2C, Desferrioxamine H, Desferrioxamine N, Desferrioxamine P1, Desferrioxamine T1, Desferrioxamine T2, Desferrioxamine T3, Desferrioxamine T7, Desferrioxamine T8, Desferrioxamine Te1, Desferrioxamine Te2, Desferrioxamine Te3, Desferrioxamine X1, Desferrioxamine X2, Desferrioxamine X3, Desferrioxamine X4, Desferrithiocin, 2,3-Dihydroxybenzoylserine, Dimerum acid, Dimethylcoprogen, Dimethylneocoprogen I, Dimethyltriornicin, Distichonic acid, E,E-putrebactene, Enantio Rhizoferrin, Enantio-Pyochelin, Enterobactin, Enterochelin, E-putrebactene, Exochelin MN, Exochelin MS, Ferrichrome, Ferrichrome A, Ferrichrome C, Ferrichrysin, Ferricrocin, Ferrimycin A, Ferrirhodin, Ferrirubin, Ferrocin A, Fimsbactin A, Fimsbactin B, Fimsbactin C, Fimsbactin D, Fimsbactin E, Fimsbactin F, Fluvibactin, Formobactin, Fusarinine, Fusarinine A, Fusarinine B, Fusarinine C, Heterobactin A, Heterobactin B, Hydroxycopropen, Hydroxyisoneocoprogen I, 3-Hydroxymugineic acid, Hydroxy-neocoprogen I, Isoneocoprogen I, Isopyoverdin 10.7, Isopyoverdin 6.7, Isopyoverdin 7.13, Isopyoverdin 90-33, Isopyoverdin 90-44, Isopyoverdin BTP1, Isotriornicin, Itoic acid, Loihichelin A, Loihichelin B, Loihichelin C, Loihichelin D, Loihichelin E, Loihichelin F, Maduraferrin, Malonichrome, Marinobactin, Marinobactin, Marinobactin, Marinobactin, Marinobactin, Marinobactin, Micacocidin, Moanachelins, Moanachelins, Moanachelins, Moanachelins, Moanachelins, Monoglucosylated, Mugineic, Mycobactin A, Mycobactin Av, Mycobactin F, Mycobactin H, Mycobactin J, Mycobactin M, Mycobactin N, Mycobactin NA, Mycobactin P, Mycobactin R, Mycobactin S, Mycobactin T, Myxochelin, Nannochelin A, Nannochelin B, Nannochelin C, Neocoprogen I, Neocoprogen II, Neurosporin, Nocobactin, Ochrobactin A, Ochrobactin B, Ochrobactin C, Ornibactin-C4, Ornibactin-C6, Ornibactin-C8, Ornicorrugatin, Palmitoylcoprogen, Parabactin, Parabactin A, Petrobactin, Petrobactin disulphonate, Petrobactin sulphonate, Pistillarin, Protochelin, Pseudoalterobactin A, Pseudoalterobactin B, Pseudobactin, Pseudobactin 589A, Putrebactin, Pyochelin, Pyoverdin 1, Pyoverdin 10.1, Pyoverdin 10.10, Pyoverdin 10.2, Pyoverdin 10.3, Pyoverdin 10.4, Pyoverdin 10.5, Pyoverdin 10.6, Pyoverdin 10.8, Pyoverdin 10.9, Pyoverdin 11.1, Pyoverdin 11.2, Pyoverdin 11370, Pyoverdin 12, Pyoverdin 12.1, Pyoverdin 12.2, Pyoverdin 13525, Pyoverdin 1547, Pyoverdin 17400, Pyoverdin 18-1, Pyoverdin 19310, Pyoverdin 2192, Pyoverdin 2392, Pyoverdin 2461, Pyoverdin 2798, Pyoverdin 51 W, Pyoverdin 6.1, Pyoverdin 6.2, Pyoverdin 6.3, Pyoverdin 6.4, Pyoverdin 6.5, Pyoverdin 6.6, Pyoverdin 6.8, Pyoverdin 7.1, Pyoverdin 7.10, Pyoverdin 7.11, Pyoverdin 7.12, Pyoverdin 7.14, Pyoverdin 7.15, Pyoverdin 7.16, Pyoverdin 7.17, Pyoverdin 7.18, Pyoverdin 7.19, Pyoverdin 7.2, Pyoverdin 7.3, Pyoverdin 7.4, Pyoverdin 7.5, Pyoverdin 7.6, Pyoverdin 7.7, Pyoverdin 7.8, Pyoverdin 7.9, Pyoverdin 8.1, Pyoverdin 8.2, Pyoverdin 8.3, Pyoverdin 8.4, Pyoverdin 8.5, Pyoverdin 8.6, Pyoverdin 8.7, Pyoverdin 8.8, Pyoverdin 8.9, Pyoverdin 9.1, Pyoverdin 9.10, Pyoverdin 9.11, Pyoverdin 9.12, Pyoverdin 9.2, Pyoverdin 9.3, Pyoverdin 9.4, Pyoverdin 9.5, Pyoverdin 9.6, Pyoverdin 9.7, Pyoverdin 9.8, Pyoverdin 9.9, Pyoverdin 90-51, Pyoverdin 95-275, Pyoverdin 96-312, Pyoverdin 96-318, Pyoverdin 9AW, Pyoverdin A214, Pyoverdin BTP2, Pyoverdin C, Pyoverdin CHAO, Pyoverdin D-TR133, Pyoverdin E, Pyoverdin G, Pyoverdin GM, Pyoverdin I-III, Pyoverdin P19, Pyoverdin Pau, Pyoverdin PL8, Pyoverdin PVD, Pyoverdin R', Pyoverdin Thai, Pyoverdin TII, Pyridoxatin, Quinolobactin, Rhizobactin, Rhizobactin 1021, Rhizoferrin, Rhizoferrin analogues, Rhodotrulic acid, Sake Colorant A, Salmochelin S1, Salmochelin S2, Salmochelin S4, Salmochelin SX, Salmycin A, Schizokinen, Serratiochelin, Siderochelin A, Snychobactin A, Snychobactin B, Snychobactin C, Staphyloferrin A, Staphyloferrin B, Taiwachelin, Tetraglycine ferrichrome, Thiazostatin, Triacetylfusarine, Triornicin, Vibriobactin, Vibrioferrin, Vicibactin, Vulnibactin, and Yersiniabactin.

The second chelator may comprise one or more member(s) selected from the group consisting of: ethylenediamintetraacetic acid (EDTA), nitrilotriacetic acid (NTA), trans-1,2-cyclohexanediaminetetraacetic acid (CyDTA), diethylenetriaminepentaacetic acid (DTPA), glycoletherdiaminetetraacetic acid (GEDTA), triethylenetetramine-N,N,N',N'',N''',N''''-hexaacetic acid (TTHA), dihydroxyethylglycine (DHEG), iminodiacetic acid (IDA), nitrilotrimethylphosphonic acid (NTP), N-(2-hydroxyethyl) iminodiacetic acid (HIDA), ethylenediamine-N,N'-dipropionic acid (EDDP), ethylenediaminetetra(methylenephosphonic) acid (EDTPO), nitrilotrimethylphosphonic acid (NTP) and 1,2-bis(o-aminophenoxy)ethane-N,N,N',N'-tetraacetic acid (BAPTA).

The cell membrane stabilizer may comprise one or more member(s) selected from the group consisting of: a vitamin E conjugate, poly-L-lysine, diazolidinyl urea, imidazolidinyl urea, dimethoylol-5,5dimethylhydantoin, dimethylol urea, 2-bromo-2-nitropropane-1,3-diol, oxazolidines, sodium hydroxymethyl glycinate, 5-hydroxymethoxymethyl-1-1-aza-3,7-dioxabicyclo [3,3.0]octane, 5-hydroxymethyl-1-1-aza-3,7-dioxabicyclo[3,3.0]octane, 5-hydroxypoly[methyleneoxy]methyl-1-1-aza-3, 7-dioxabicyclo[3, 3.0]octane, and quaternary adamantine.

The nucleic acid compactor may comprise one or more member(s) selected from the group consisting of: a cationic polymer, a polyamine, poly-L-lysine, spermine, and spermidine. The antimicrobial agent comprises one or more member(s) selected from the group consisting of: penicillin, streptomycin, and amphotericin B. In the presence of the preservation mixture for a time period of at least 3 days, the nucleic acid molecules may have an average length greater than about 30 nucleic acid bases. In the presence of the preservation mixture at a temperature that is within a range from about −40 degrees Celsius (° C.) to about 20° C., the nucleic acid molecules may have an average length greater than about 30 nucleic acid bases. In the presence of the preservation mixture at a temperature that is within a range from about 20° C. to about 40° C., the nucleic acid molecules may have an average length greater than about 30 nucleic acid bases. In the presence of the preservation mixture for a period of at least about 3 days at a temperature that is within a range from about 40° C. to about 80° C., the nucleic acid molecules may have an average length greater than about 30 nucleic acid bases.

Subsequent to storage of the preservation mixture for at least 6 months, when in presence of the preservation mixture, the nucleic acid molecules may have an average length greater than about 30 nucleic acid bases.

One aspect described herein is a method for processing a urine sample, comprising: receiving a solution comprising nucleic acid molecules in a urine of a subject, which solution comprises a preservation mixture; and sequencing a plurality of nucleic acid molecules derived from said nucleic acid molecules to generate a plurality of sequencing reads, wherein said preservation mixture provides for sequencing said plurality of nucleic acid molecules to generate said plurality of sequencing reads at a greater molecular complexity or with lower DNA damage as compared to other nucleic acid molecules in samples without preservation mixtures.

In another aspect, the present disclosure provides a system for identifying a urinary tract disorder. The system may comprise a database configured to contain a data set comprising a set of microbes in a urinary tract of the subject and one or more computer processors operatively coupled to the database. The one or more computer processors may be individually or collectively programmed to implement the method of FIG. 3. The one or more computer processors may be individually or collectively programmed to use a machine learning classifier to process the set of microbes to generate a classification of the urine sample as being positive or negative for the urinary tract disorder at an accuracy at least 90%. The one or more computer processors may be individually or collectively programmed to output a report identifying the classification.

Figure 4:
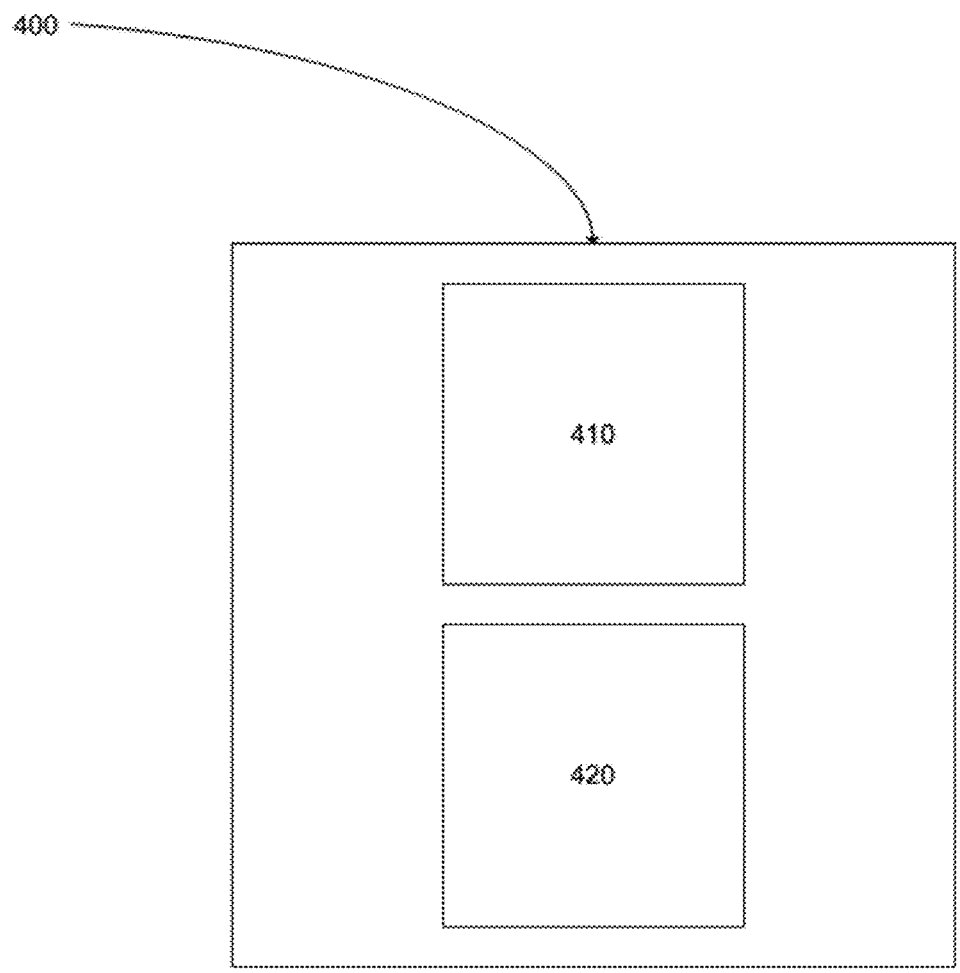
FIG. 4 shows a system for implementing any of the methods described herein.

FIG. 4 shows system 400 for implementing any of the methods described herein. The system may comprise a database 410. The system may further comprise one or more computer processors 420 operatively coupled to the database. The one or more processors may be individually or collectively programmed to implement one or more of methods 100, 200, 300, or 4200, or any operations thereof, as described herein.

For instance, the system may be configured to supplement a microbiome in a urinary tract of a subject. The one or more processors may be individually programmed to: (i) identify a relative abundance of a first set of microbes in the urinary tract of the subject, (ii) identify a second set of microbes for the urinary tract of the subject, which second set of microbes is different than the first set of microbes, wherein the second set of microbes is configured to supplement the microbiome in the urinary tract of the subject, and (iii) store the second set of microbes in the database. Operations (i) or (ii) may comprise any or all operations described herein with respect to methods 100 or 200.

Alternatively or in combination, the system may be configured to identify a urinary tract disorder. The database may be configured to contain a data set comprising a set of microbes in the urinary tract of the subject. The one or more processors may be individually or collectively programmed to: (i) use a machine learning classifier to process the set of microbes to generate a classification of the urine sample as being positive or negative for the urinary tract disorder, and (ii) output a report identifying the classification. The classification may have an accuracy of at least 90%, or any accuracy described herein. The classification may have any sensitivity or specificity described herein. Operations (i) or (ii) may comprise any or all operations described herein with respect to method 300. The system may further comprise a communications interface operatively coupled to the one or more computer processors. The communications interface may be configured to transmit the report to the subject or to a healthcare provider of the subject.

Figure 5:
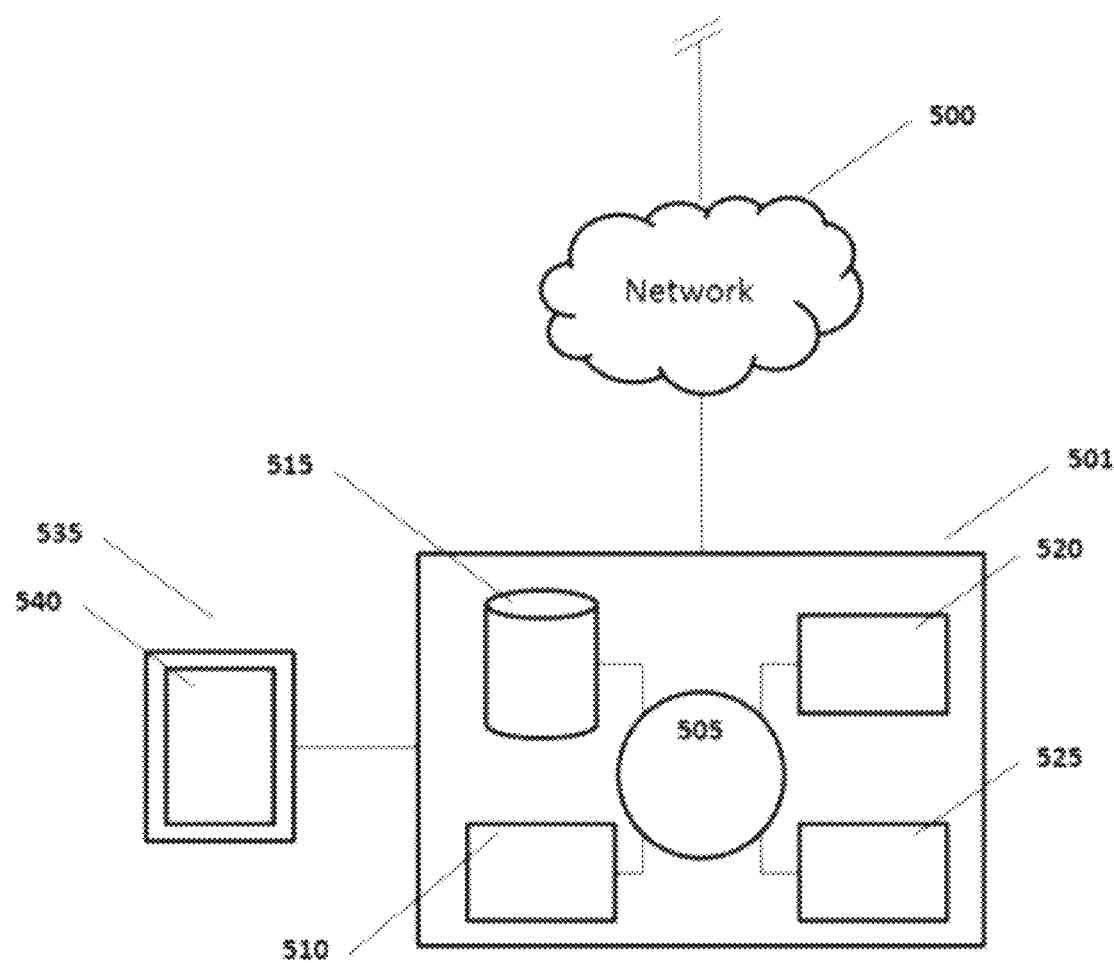
FIG. 5 shows a computer system that is programmed or otherwise configured to operate any of the methods or systems described herein.

FIG. 5 shows a computer system 501 that is programmed or otherwise configured to operate any method or system described herein (such as any method or system for supplementing a microbiome in a urinary tract of a subject described herein, or any method or system for identifying a urinary tract disorder described herein). The computer system 501 can regulate various aspects of the present disclosure. The computer system 501 can be an electronic device of a user or a computer system that is remotely located with respect to the electronic device. The electronic device can be a mobile electronic device.

The computer system 501 includes a central processing unit (CPU, also "processor" and "computer processor" herein) 505, which can be a single core or multi core processor, or a plurality of processors for parallel processing. The computer system 501 also includes memory or memory location 510 (e.g., random-access memory, read-only memory, flash memory), electronic storage unit 515 (e.g., hard disk), communication interface 520 (e.g., network adapter) for communicating with one or more other systems, and peripheral devices 525, such as cache, other memory, data storage and/or electronic display adapters. The memory 510, storage unit 515, interface 520 and peripheral devices 525 are in communication with the CPU 505 through a communication bus (solid lines), such as a motherboard. The storage unit 515 can be a data storage unit (or data repository) for storing data. The computer system 501 can be operatively coupled to a computer network ("network") 530 with the aid of the communication interface 520. The network 530 can be the Internet, an internet and/or extranet, or an intranet and/or extranet that is in communication with the Internet. The network 530 in some cases is a telecommunication and/or data network. The network 530 can include one or more computer servers, which can enable distributed computing, such as cloud computing. The network 530, in some cases with the aid of the computer system 501, can implement a peer-to-peer network, which may enable devices coupled to the computer system 501 to behave as a client or a server.

The CPU 505 can execute a sequence of machine-readable instructions, which can be embodied in a program or software. The instructions may be stored in a memory location, such as the memory 510. The instructions can be directed to the CPU 505, which can subsequently program or otherwise configure the CPU 505 to implement methods of the present disclosure. Examples of operations performed by the CPU 505 can include fetch, decode, execute, and writeback.

The CPU 505 can be part of a circuit, such as an integrated circuit. One or more other components of the system 501 can be included in the circuit. In some cases, the circuit is an application specific integrated circuit (ASIC).

The storage unit 515 can store files, such as drivers, libraries and saved programs. The storage unit 515 can store user data, e.g., user preferences and user programs. The computer system 501 in some cases can include one or more additional data storage units that are external to the computer system 501, such as located on a remote server that is in communication with the computer system 501 through an intranet or the Internet.

The computer system 501 can communicate with one or more remote computer systems through the network 530. For instance, the computer system 501 can communicate with a remote computer system of a user. Examples of remote computer systems include personal computers (e.g., portable PC), slate or tablet PC's (e.g., Apple® iPad, Samsung® Galaxy Tab), telephones, Smart phones (e.g., Apple® iPhone, Android-enabled device, Blackberry®), or personal digital assistants. The user can access the computer system 501 via the network 530.

Methods as described herein can be implemented by way of machine (e.g., computer processor) executable code stored on an electronic storage location of the computer system 501, such as, for example, on the memory 510 or electronic storage unit 515. The machine executable or machine readable code can be provided in the form of software. During use, the code can be executed by the processor 505. In some cases, the code can be retrieved from the storage unit 515 and stored on the memory 510 for ready access by the processor 505. In some situations, the electronic storage unit 515 can be precluded, and machine-executable instructions are stored on memory 510.

The code can be pre-compiled and configured for use with a machine having a processor adapted to execute the code, or can be compiled during runtime. The code can be supplied in a programming language that can be selected to enable the code to execute in a pre-compiled or as-compiled fashion.

Aspects of the systems and methods provided herein, such as the computer system 501, can be embodied in programming. Various aspects of the technology may be thought of as "products" or "articles of manufacture" typically in the form of machine (or processor) executable code and/or associated data that is carried on or embodied in a type of machine readable medium. Machine-executable code can be stored on an electronic storage unit, such as memory (e.g., read-only memory, random-access memory, flash memory) or a hard disk. "Storage" type media can include any or all of the tangible memory of the computers, processors or the like, or associated modules thereof, such as various semiconductor memories, tape drives, disk drives and the like, which may provide non-transitory storage at any time for the software programming. All or portions of the software may at times be communicated through the Internet or various other telecommunication networks. Such communications, for example, may enable loading of the software from one computer or processor into another, for example, from a management server or host computer into the computer platform of an application server. Thus, another type of media that may bear the software elements includes optical, electrical and electromagnetic waves, such as used across physical interfaces between local devices, through wired and optical landline networks and over various air-links. The physical elements that carry such waves, such as wired or wireless links, optical links or the like, also may be considered as media bearing the software. As used herein, unless restricted to non-transitory, tangible "storage" media, terms such as computer or machine "readable medium" refer to any medium that participates in providing instructions to a processor for execution.

Hence, a machine readable medium, such as computer-executable code, may take many forms, including but not limited to, a tangible storage medium, a carrier wave medium or physical transmission medium. Non-volatile storage media include, for example, optical or magnetic disks, such as any of the storage devices in any computer(s) or the like, such as may be used to implement the databases, etc. shown in the drawings. Volatile storage media include dynamic memory, such as main memory of such a computer platform. Tangible transmission media include coaxial cables; copper wire and fiber optics, including the wires that comprise a bus within a computer system. Carrier-wave transmission media may take the form of electric or electromagnetic signals, or acoustic or light waves such as those generated during radio frequency (RF) and infrared (IR) data communications. Common forms of computer-readable media therefore include for example: a floppy disk, a flexible disk, hard disk, magnetic tape, any other magnetic medium, a CD-ROM, DVD or DVD-ROM, any other optical medium, punch cards paper tape, any other physical storage medium with patterns of holes, a RAM, a ROM, a PROM and EPROM, a FLASH-EPROM, any other memory chip or cartridge, a carrier wave transporting data or instructions, cables or links transporting such a carrier wave, or any other medium from which a computer may read programming code and/or data. Many of these forms of computer readable media may be involved in carrying one or more sequences of one or more instructions to a processor for execution.

The computer system 501 can include or be in communication with an electronic display 535 that comprises a user interface (UI) 540. Examples of UI's include, without limitation, a graphical user interface (GUI) and web-based user interface.

Methods and systems of the present disclosure can be implemented by way of one or more algorithms. An algorithm can be implemented by way of software upon execution by the central processing unit 505. The algorithm can, for example, supplement a urinary microbiome or identify a urinary tract disorder using the systems and methods described herein.

The present disclosure provides kits for preserving a urine sample described herein in a preservation mixture described herein. The kit may comprise a preservation mixture and instructions for using the preservation mixture to preserve the urine sample.

EXAMPLES

Example 1

Measurement of Quantities

Assignment of sequencing reads to a microbial genome may be performed as follows. We utilize either the Centrifuge or the KrakenUniq algorithm to assign taxonomic identifications to short DNA sequences. The Centrifuge algorithm is described by, for example, [Kim, Daehwan, et al. "Centrifuge: rapid and sensitive classification of metagenomic sequences." *Genome research* 26.12 (2016): 1721-1729], which is incorporated herein by reference in its entirety. The KrakenUniq algorithm is described by, for example, [KrakenUniq: confident and fast metagenomics classification using unique k-mer counts. Breitwieser F P, Baker D N, Salzberg S L. Genome Biology, December 2018], which is incorporated herein by reference in its entirety. The KrakenUniq algorithm may be used to determine the coverage of unique k-mers found in each species in a dataset to ensure there are distinct locations in the microbial genome the sequencing read maps to. When performing analyses of the present disclosure, we may consider a read to match a microbial genome if there are at least 100 k-mers, with k=30 base pairs, supporting the match. We may denote reads matching a microbe given index "i", in an individual sample, given index "j", by $r_{i,j}$. If a read maps to a microbial genome with at least 100 k-mers, with k=30 base pairs, we may consider the read to "map with confidence" to the specific microbial genome.

Microbial expression per sample. The microbial signature of an individual microbe, given index "i", in an individual sample, given index "j", is given by the ratio of reads that map with confidence to a specific microbial genome, denoted $r_{i,j}$, to the total number of sequencing reads for an individual, denoted $R_j$ used to characterize the genome of the sample, e.g., the total number of sequenced reads for the sample. The expression of a single microbe in a sample can then be given by: $e_{i,j}=r_{i,j}/R_j$. Letting M denote the total number of microbes with positive expression in sample "j", then the total microbial expression in a sample, denoted $e_j$, is given by a sum over all individual microbial expressions as: $e_j = \Sigma_{i=1}^{M} e_{i,j}$.

Normalized (Mean) Expression—referred to as "normalized expression" in the figures. Throughout the analysis described herein of microbial enrichment across cohorts with and without bladder cancer, we deploy the concept of Normalized Expression. Here, we provide an example method of measuring this quantity. For a given level of taxonomic classification of a microbe, the sample level expression of the microbe is given above by $e_{i,j}$. Letting "N" denote the number of patients in cohort "C", we take the average value of a microbe's expression across a cohort of patients, and denote the mean as $C_i$, then $$C_i = \frac{1}{N} \sum_{j=1}^{N} e_{i,j}.$$

We require that for any microbe to be considered positive at the cohort level we require N≥2.

Among figures and descriptions provided herein, we compute $C_i$ across two cohorts: one consisting of individuals known to have bladder cancer when their urine specimen was collected, and the other consisting of individuals with no known bladder cancer when at the time of sample collection. We denote the cohort mean expression for the positive and negative cohorts as $P_i$ and $N_i$, respectively. Lastly, we normalize each $P_i$ and $N_i$ such that $P_i+N_i=100$.

Normalized (Median) Expression—referred to as "normalized (median) expression" in the figures. Throughout the analysis described herein of microbial enrichment across cohorts with and without lower urinary tract symptoms (LUTS), we deploy the concept of Normalized Median Expression. Here, we provide an example method of measuring this quantity. For a given level of taxonomic classification of a microbe, the sample level expression of the microbe is given as above by $e_{i,j}$.

Letting "N" denote the number of patients in cohort "C", we take the median value of a microbe's expression across a cohort of patients, and denote the median as $C_i$, then $C_i$=Median($e_{i,j}$). Here the median value is computed across the j-index. As we have done in the definition of Normalized Mean Expression, here we again require that for any microbe to be considered positive at the cohort level, we require the presence of the microbe's expression in N≥2 samples. We denote the cohort median expression for the positive and negative cohorts as $P_i$ and $N_i$, respectively. Lastly, we normalize each $P_i$ and $N_i$ such that $P_i+N_i=100$.

The pooled (over sample) enrichment score is defined as the sum of $e_{i,j}$ in Equation (1) of Example 1 over the sample or "j" index, the resulting summand for each microbe $$\left(e_i = \sum_{j=1}^{N} e_{i,j}\right)$$

is expressed as stacked bar plots for each microbe.

Example 2

Differential Expression of Microbes in Cancerous and Non-Cancerous Individuals

FIGS. 6-22 show differential expression of microbes in the urinary microbiomes of individuals who have been diagnosed with bladder cancer (cancerous individuals) and individuals who have not been diagnosed with bladder cancer (non-cancerous individuals), at every level of taxonomic organization.

TABLE 1 shows examples of microbes detected in urine by methods and systems described herein, and their utility in cancer diagnosis. Microbes listed are either enriched in individuals with bladder cancer (denoted[ec]) or individuals without bladder cancer (denoted[en]), or are observed only in normal individuals (denoted[n]) or are observed only in individuals with bladder cancer (denoted[c]) or are shared between normal and individuals (denoted[s]). "Enriched" is defined as microbes with greater than greater than 60% normalized expression (see definitions) in a cohort. "Shared" in this context is defined as 40%-60% normalized expression across both cohorts. "Observed only in" is defined as 0% prevalence in the cohort.

TABLE 1

| Usage of Microbe | Microbes Used |
|---|---|
| Cancer Diagnosis: Kingdom Level | Bacteria[en], Viruses[s] |

TABLE 1-continued

| Usage of Microbe | Microbes Used |
|---|---|
| Cancer Diagnosis: Phylum Level | Proteobacteria$^{en}$, Firmicutes$^{en}$, Actinobacteria$^{en}$, and Bacteriodetes$^{ec}$, Aquificae$^{n}$, Deinococcus-Thermus$^{n}$, Fusobacteria$^{n}$, Tenericutes$^{n}$ |
| Cancer Diagnosis: Class Level | Gammaproteobacteria$^{en}$, Betaproteobacteria$^{en}$, Clostridia$^{en}$, Alphaproteobacteria$^{en}$, Bacilli$^{en}$, Actinobacteria$^{en}$, Tissierellia$^{en}$, Bacteroidia$^{ec}$, Aquificiae$^{n}$, Deinococci$^{n}$, Epsilonproteobacteria$^{n}$, Flavobacteria$^{n}$, Fusobacteria$^{n}$, Mollicutes$^{n}$, Negativicutes$^{n}$, Erysipelotrichia$^{c}$ |
| Cancer Diagnosis: Order Level | Pseudomonadales$^{en}$, Enterobacterales$^{en}$, Caudovirales$^{en}$, Actinomycetales$^{en}$, Corynebacteriales$^{en}$, Burkholderiales$^{en}$, Clostridiales$^{en}$, Rhizobiales$^{en}$, Streptomycetales$^{en}$, Sphingomonadales$^{en}$, Lactobacillus$^{en}$, Tissierellales$^{en}$, Bifidobacteriales$^{en}$, Pseudonocardiales$^{s}$, Bacteroidales$^{ec}$, Xanthomonadales$^{ec}$, Bacillales$^{ec}$, Acidaminococcales$^{n}$, Campylobacterales$^{n}$, Desulfurobacteriales$^{n}$, Flavobacteriales$^{n}$, Fusobacteriales$^{n}$, Herpesvirales$^{n}$, Micrococcales$^{n}$, Mycoplasmatales$^{n}$, Neisseriales$^{n}$, Pasteurellales$^{n}$, Picornavirales$^{n}$, Propionibacteriales$^{n}$, Thermales$^{n}$, Veillonellales$^{n}$, Vibrionales$^{n}$, Erysipelotrichales$^{n}$ |
| Cancer Diagnosis: Family Level | Myoviridae$^{en}$, Porphyromonadaceae$^{en}$, Pseudomonoadaceae$^{en}$, Enterobacteriaceae$^{en}$, Actinomycetaceae$^{en}$, Prevotellaceae$^{en}$, Burkholderiaceae$^{en}$, Siphoviridae$^{en}$, Hyphoicrobiaceae$^{en}$, Streptomycetaceae$^{en}$, Sphingomonadaceae$^{en}$, Peptoniphilaceae$^{en}$, Bifidobacteriaceae$^{en}$, Streptococcaceae$^{s}$, Peptostreptococcaceae$^{ec}$, Polyomaviridae$^{ec}$, Xanthomonadaceae$^{ec}$, Enterococcaceae$^{ec}$, Staphylococcaceae$^{ec}$, Bacteroidaceae$^{ec}$, Acidaminococcaceae$^{n}$, Aerococcaceae$^{n}$, Bradyrhizobiaceae$^{n}$, Campylobacteraceae$^{n}$, Comamonadaceae$^{n}$, Corynebacteriaceae$^{n}$, Desulfurobacteriaceae$^{n}$, Erwiniaceae$^{n}$, Flavobacteriaceae$^{n}$, Hafniaceae$^{n}$, Helicobacteraceae$^{n}$, Herpesviridae$^{n}$, Lachnospiraceae$^{n}$, Lactobacilluseae$^{n}$, Leptotrichiaceae$^{n}$, Microbacteriaceae$^{n}$, Micrococcaceae$^{n}$, Morganellaceae$^{n}$, Mycoplasmataceae$^{n}$, Neisseriaceae$^{n}$, Oxalobacteraceae$^{n}$, Paenibacillaceae$^{n}$, Pasteurellaceae$^{n}$, Peptococcaceae$^{n}$, Picornaviridae$^{n}$, Podoviridae$^{n}$, Propionibacteriaceae$^{n}$, Rhizobiaceae$^{n}$, Ruminococcaceae$^{n}$, Thermaceae$^{n}$, Veillonellaceae$^{n}$, Vibrionaceae$^{n}$, Yersiniaceae$^{n}$, Erysipelotrichaceae$^{c}$, Nocardiaceae$^{c}$, Rikenellaceae$^{c}$ |
| Cancer Diagnosis: Genus Level | Klebsiella$^{en}$, Lambdavirus$^{en}$, Shigella$^{en}$, Pseudomonas$^{en}$, Citrobacter$^{en}$, Salmonella$^{en}$, Escherichia$^{en}$, Prevoltella$^{en}$, Barnesiella$^{en}$, Devosia$^{en}$, Streptomyces$^{en}$, Bifidobacterium$^{en}$, Sphingomonas$^{en}$, Helcococcus$^{en}$, Parabacteroides$^{en}$, Mobilunus$^{en}$, Gardnerella$^{en}$, Finegoldia$^{s}$, Streptococcus$^{s}$, Betapolyomavirus$^{ec}$, Stenotrophomonas$^{ec}$, Enterococcus$^{ec}$, Ralstonia$^{ec}$, Staphylococcus$^{ec}$, Bacteroides$^{ec}$, Acidaminococcus$^{n}$, Actinomyces$^{n}$, Actinotignum$^{n}$, Aerococcus$^{n}$, Aggregatibacter$^{n}$, Anaerococcus$^{n}$, Blautia$^{n}$, Bradyrhizobium$^{n}$, Burkholderia$^{n}$, Campylobacter$^{n}$, Cornyebacterium$^{n}$, Cutibacterium$^{n}$, Desulfitobacterium$^{n}$, Enterobacter$^{n}$, Epsilon15virus$^{n}$, Ezakiella$^{n}$, F116virus$^{n}$, Faecalibacterium$^{n}$, Filifactor$^{n}$, Fusobacterium$^{n}$, Haemophilus$^{n}$, Hafnia$^{n}$, Helicobacter$^{n}$, Histophilus$^{n}$, Janthinobacterium$^{n}$, Kluyvera$^{n}$, Lacnoclostridium$^{n}$, Lactobacillus$^{n}$, Lawsonella$^{n}$, Limnohabitans$^{n}$, Lymphocryptovirus$^{n}$, Mageeibacillus$^{n}$, Microbacterium$^{n}$, Micrococcus$^{n}$, Morganella$^{n}$, Neisseria$^{n}$, Ornithobacterium$^{n}$, P22virus$^{n}$, P2virus$^{n}$, Paenibacillus$^{n}$, Pantoea$^{n}$, Parvimonas$^{n}$, Peptoniphilus$^{n}$, Porphyromonas$^{n}$, Propionibacterium$^{n}$, Propionmicrobium$^{n}$, Proteus$^{n}$, Pseudarthrobacter$^{n}$, Raoultella$^{n}$, Rhizobium$^{n}$, Rhodopseudomonas$^{n}$, Roseolovirus$^{n}$, Rothia$^{n}$, Ruminiclostridium$^{n}$, Ruminococcus$^{n}$, Salivirus$^{n}$, Serratia$^{n}$, Sneathia$^{n}$, Sphingobium$^{n}$, Thermovibrio$^{n}$, Thermus$^{n}$, Ureaplasma$^{n}$, Varibaculum$^{n}$, Veillonella$^{n}$, Vibrio$^{n}$, Xenorhabdus$^{n}$, Yersinia$^{n}$, Alistipes$^{c}$, Clostridioides$^{c}$, Erysipelothrix$^{c}$, Rhodococcus$^{c}$, Triavirus$^{c}$ |
| Cancer Diagnosis: Species Level | Klebsiella pneumoniae$^{en}$, Shigella sonnei$^{en}$, Klebsiella variicola$^{en}$, Prevotella sp. oral taxon 299$^{en}$, Shigella dysenteriae$^{en}$, Shigella$^{en}$, Pseudomonas aeruginosa$^{en}$, Pseudomonas aeruginosa group$^{en}$, Salmonella enterica$^{en}$, Escherichia coli$^{en}$, Shigella boydii$^{en}$, Shigella sp. PAMC 28760$^{en}$, Shigella flexneri$^{en}$, Betapolyomavirus Human polyomavirus 2$^{en}$, Escherichia fergusonii$^{en}$, Prevotella scopos$^{en}$, Prevotella melaninogenica$^{en}$, Escherichia albertii$^{en}$, Klebsiella [Enterobacter] aerogenes$^{en}$, Barnesiella viscericola$^{en}$, Bacteroides$^{en}$, Devosias sp. H5989$^{en}$, Streptococcus pneumoniae$^{en}$, Citrobacter freundii$^{en}$, Prevotella enoeca$^{en}$, Bacteroides thetaiotaomicron$^{en}$, Escherichia uncultured Escherichia sp.$^{en}$, Helcococcus kunzii$^{en}$, Parabacteroides distasonis$^{en}$, Pseudomonas oleovorans/pseudoalcaligenes group$^{en}$, Pseudomonas pseudoalcaligenes$^{en}$, Mobiluncus curtisii$^{en}$, Streptococcus dysgalactiae$^{en}$, Streptococcus dysgalactiae group$^{en}$, Streptococcus pyogenes$^{en}$, Gardnerella vaginalis$^{en}$, Finegoldia magna$^{s}$, Bacteroides dorei$^{s}$, Bacteroides vulgatus$^{ec}$, Pseudomonas sp. 1217$^{ec}$, Enterococcus sp. 7L76$^{ec}$, Staphylococcus$^{ec}$, Bacteroides sp. 148$^{ec}$, Stenotrophomonas maltophilia$^{ec}$, Ralstonia insidiosa$^{ec}$, Streptococcus pasteurianus$^{ec}$, Bifidobacterium longum$^{ec}$, Bacteroides ovatus$^{ec}$, Enterococcus faecalis$^{ec}$, Staphylococcus epidermidis$^{ec}$, Staphylococcus aureus$^{ec}$, Bacteroides fragilis$^{ec}$, Betapolyomavirus Human polyomavirus$^{ec}$, Alistipes shahii$^{c}$, Bacteroides salanitronis$^{c}$, Clostridioides difficile$^{c}$, Erysipelothrix rhusiopathiae$^{c}$, Lambdavirus uncultured virus$^{c}$, Pseudomonas frederiksbergensis$^{c}$, Ralstonia mannitolilytica$^{c}$, Rhodococcus erythropolis$^{c}$, Rhodoccus species 008$^{c}$, Sphingomonas echinoides$^{c}$, Staphylococcus agnetis$^{c}$, Staphylococcus lugdunensis$^{c}$, Staphyloccus saprophyticus$^{c}$, Streptococcus gallolyticus$^{c}$, Streptococcus infantarius$^{c}$, Streptococcus lutetiensis$^{c}$, Streptococcus macedonicus$^{c}$, Streptomyces uncultured bacteria 37b14$^{c}$, Streptomyces uncultured bacterium 39k17$^{c}$, Triavirus staphylococcus phage 3A$^{c}$, Triavirus staphylococcus phage tp310-2$^{c}$, and Triavirus staphylococcus phage StB20$^{c}$ |

Figure 6:
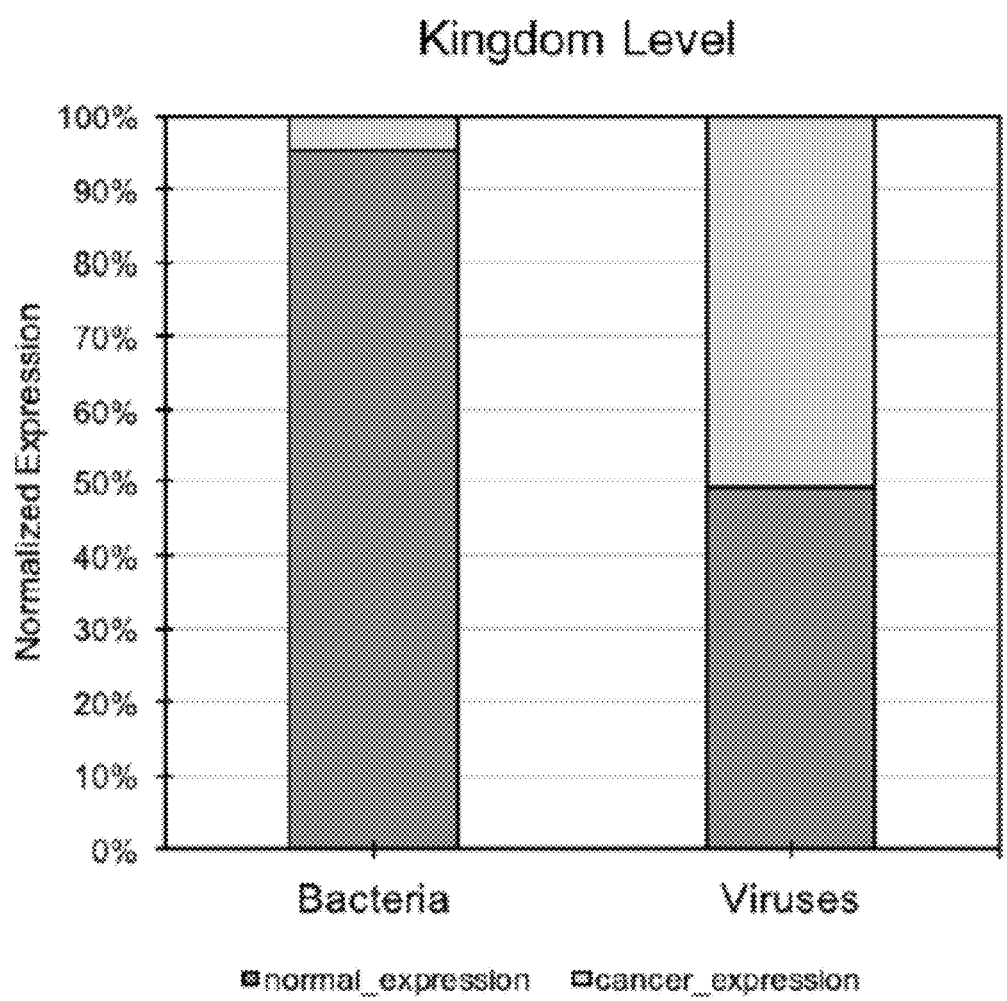
FIG. 6 shows differential expression of microbes in the urinary microbiomes of cancerous and non-cancerous individuals at the kingdom level.

FIG. 6 shows normalized expression (see Example 1) of microbes in the urinary microbiomes of cancerous and non-cancerous individuals at the kingdom level. As shown in FIG. 6, microbes belonging to the kingdoms Bacteria and Viruses are differentially expressed in cancerous vs. non-cancerous individuals. As shown in FIG. 6, the expression of Bacteria are enriched at greater than 60% prevalence in individuals without cancer. Additionally, the relative proportion of these microbes can be used to define the microbial constituency of the healthy, normal, or cancer-free bladder. Similarly, a combination of microbes enriched in individuals with cancer and rarely found in patients without cancer may define the microbial constituency of the cancerous urinary microbiome.

Figure 7:
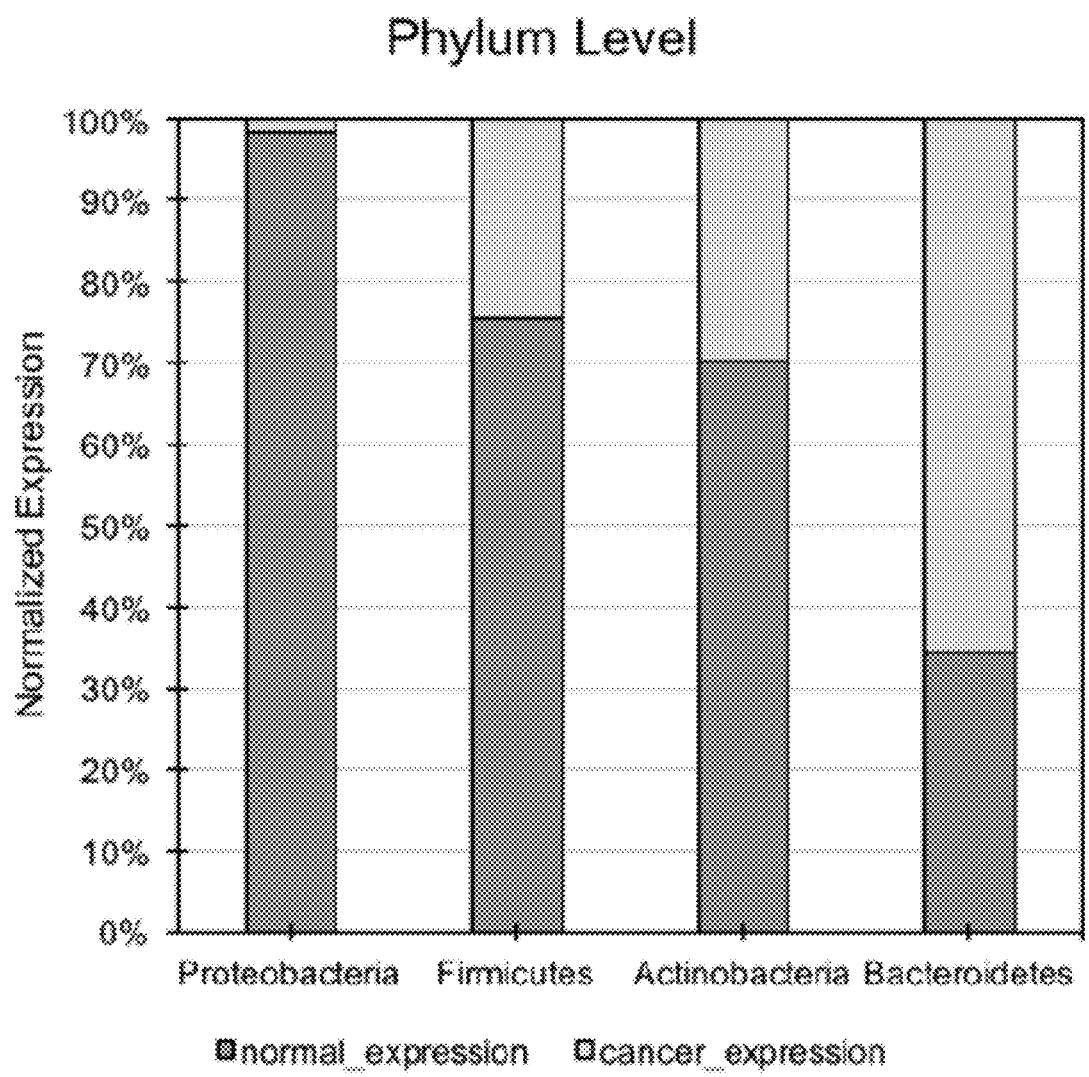
FIG. 7 shows differential expression of microbes in the urinary microbiomes of cancerous and non-cancerous individuals at the phylum level.

FIG. 7 shows normalized expression (see Example 1) of microbes in the urinary microbiomes of cancerous and non-cancerous individuals at the phylum level. As shown in FIG. 7, the microbes Proteobacteria, Firmicutes, Actinobacteria, and Bacteriodetes are differentially expressed in cancerous vs. non-cancerous individuals. As shown in FIG. 7, the expression of Proteobacteria, Firmicutes, and Actinobacteria are enriched at greater than greater than 60% prevalence in individuals without cancer, whereas the expression of Bacteriodetes are enriched at greater than greater than 60% prevalence in individuals with cancer. Thus, a combination of microbes enriched in normal individuals and rarely found in disease-positive patients may define the microbial constituency of the healthy, normal, or cancer-free bladder. Similarly, a combination of microbes enriched in individuals with cancer and rarely found in patients without cancer may define the microbial constituency of the cancerous urinary microbiome. Further, the relative abundance of Proteobacteria, Firmicutes, Actinobacteria, and Bacteriodetes in a sample corresponding to an individual may provide an indication of whether the individual possesses a disease, e.g., cancer, or not, based on the relative abundance of microbes associated with normal bladders and those associated with diseased bladders. Further, if a sample corresponding to an individual is found to possess deficient levels of microbes typically found to be enriched in healthy individuals—the deficient microbes identified can form the basis of a treatment in which deficient microbe(s) are augmented by administration of that microbe(s), so as to bring the microbial constituency of the bladder back to the expected state for normal individuals.

Figure 8:
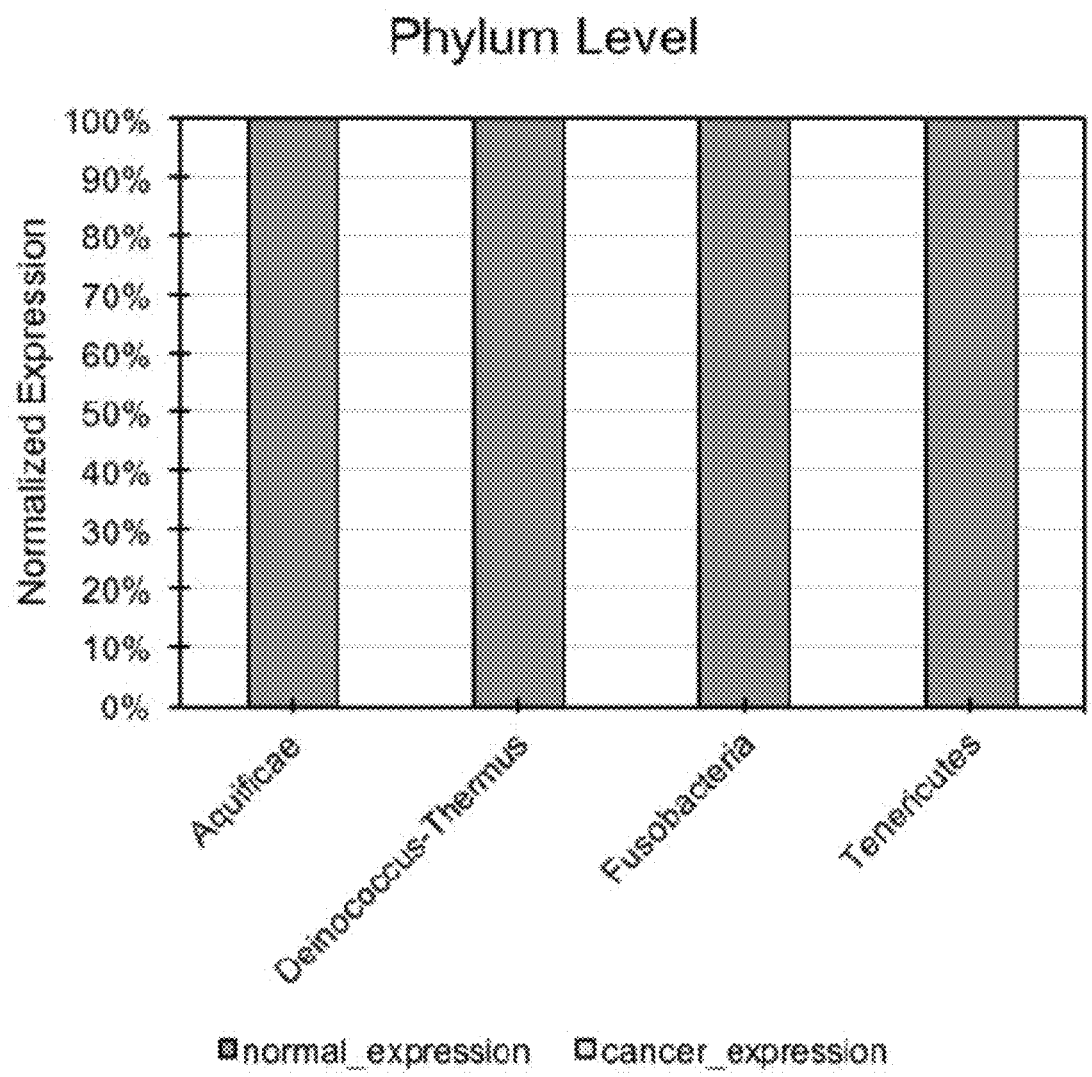
FIG. 8 shows expression of microbes only in the urinary microbiomes of non-cancerous individuals at the phylum level.

FIG. 8 shows normalized expression (see Example 1) of microbes found only in the urinary microbiomes of non-cancerous individuals at the phylum level and not in individuals with cancer. As shown in FIG. 8, microbes belonging to the phyla Aquificae, Deinococcus-Thermus, Fusobacteria, and Tenericutes are only expressed in non-cancerous individuals. Thus, the presence of microbes belonging to any one or more of the phyla Aquificae, Deinococcus-Thermus, Fusobacteria, and Tenericutes in a sample corresponding to an individual (e.g., relative abundance as compared to reference samples obtained from cancerous or non-cancerous individuals) may provide an indication that the individual is non-cancerous. Additionally, the relative proportion of these microbes can be used to define the microbial constituency of the healthy, normal, or cancer-free bladder. Similarly, a combination of microbes enriched in individuals with cancer and rarely found in patients without cancer may define the microbial constituency of the cancerous urinary microbiome. Further, the relative abundance of these microbes can be used to guide both the amount and types of these microbes needed to treat an individual so as to bring the microbial constituency of the bladder back to the expected state. A person displaying low levels of various combinations of microbes associated with healthy bladders (e.g., various combinations of phyla Aquificae, Deinococcus-Thermus, Fusobacteria, and Tenericutes) can then have their bladder microbiome reconstituted by reintroducing the amount and type of one or more of phyla Aquificae, Deinococcus-Thermus, Fusobacteria, and Tenericutes to bring their profile to the expected state for individuals without cancer. For example, about $10^3$, $10^4$, $10^5$, $10^6$, $10^7$, $10^8$, $10^9$, $10^{10}$, $10^{11}$, $10^{12}$, $10^{13}$, $10^{14}$, $10^{15}$, or more than $10^{15}$ colony forming units of microbes of one or more such phyla may be administered to an individual to reconstitute their bladder microbiome.

Figure 9:
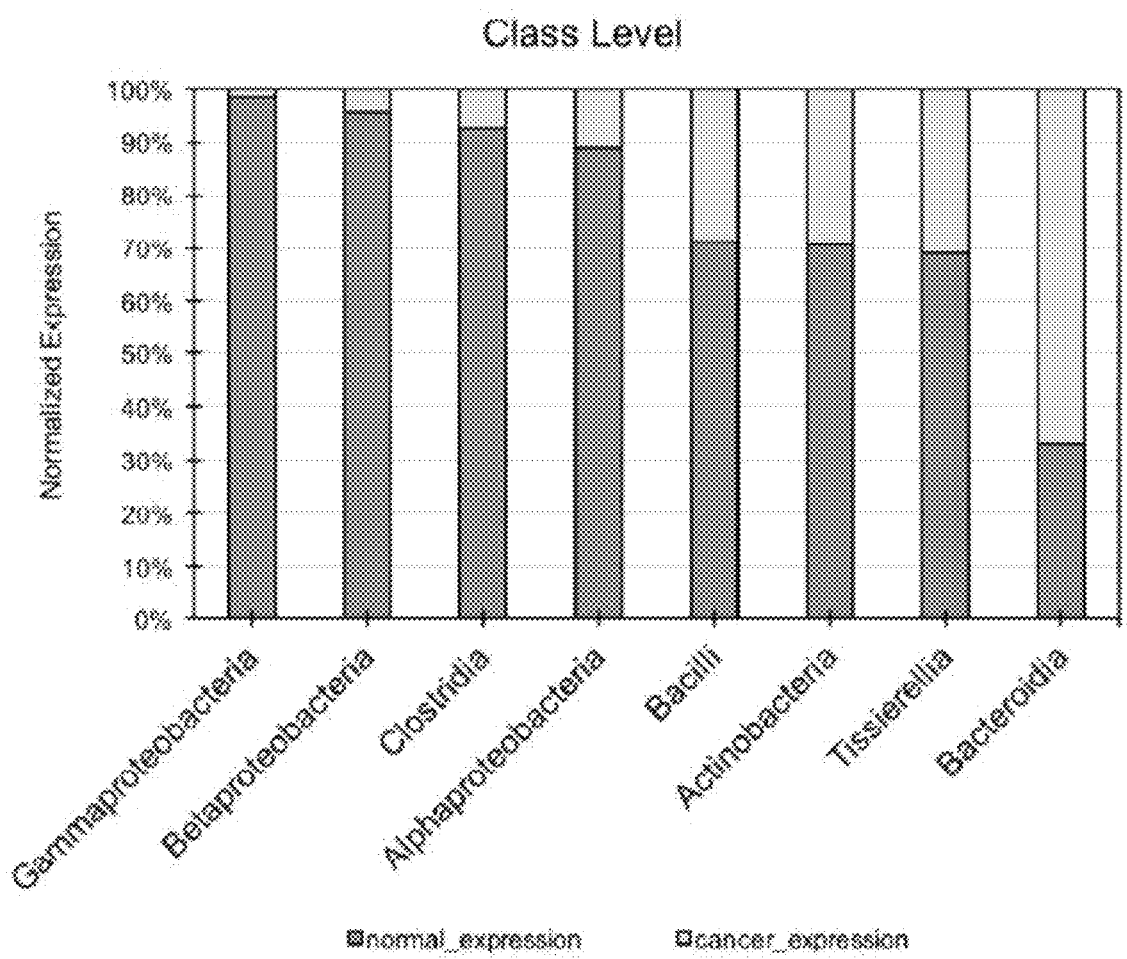
FIG. 9 shows differential expression of microbes in the urinary microbiomes of cancerous and non-cancerous individuals at the class level.

FIG. 9 shows normalized expression (see Example 1) of microbes in the urinary microbiomes of cancerous and non-cancerous individuals at the class level. As shown in FIG. 9, microbes of classes Gammaproteobacteria, Betaproteobacteria, Clostridia, Alphaproteobacteria, Bacilli, Actinobacteria, Tissierellia, and Bacteroidia are differentially expressed in cancerous vs. non-cancerous individuals. As shown in FIG. 9, the expression of Gammaproteobacteria, Betaproteobacteria, Clostridia, Alphaproteobacteria, Bacilli, Actinobacteria, and Tissierellia are enriched at greater than greater than 60% prevalence in individuals without cancer, whereas the expression of Bacteroidia are enriched at greater than 60% prevalence in individuals with cancer. Thus, a combination of one or more populations of microbes enriched in normal individuals and rarely found in disease-positive patients may define the microbial constituency of the healthy, normal, or cancer-free bladder. Similarly, a combination of one or more populations of microbes enriched in individuals with cancer and rarely found in patients without cancer may define the microbial constituency of the cancerous urinary microbiome. Further, the relative abundance of any one or more of Gammaproteobacteria, Betaproteobacteria, Clostridia, Alphaproteobacteria, Bacilli, Actinobacteria, Tissierellia, and Bacteroidia in a sample corresponding to an individual may provide an indication of whether the individual possesses a disease, e.g., cancer, or not based on the relative abundance of microbes associated with normal bladders and those associated with diseased bladders. Further, if a sample corresponding to an individual is found to possess deficient levels of microbes typically found to be enriched in healthy individuals, the deficient microbes identified may form the basis of a treatment in which deficient microbe(s) are augmented by administration of that microbe(s) so as to bring the microbial constituency of the bladder back to the expected state for normal individuals. For example, about $10^3$, $10^4$, $10^5$, $10^6$, $10^7$, $10^8$, $10^9$, $10^{10}$, $10^{11}$, $10^{12}$, $10^{13}$, $10^{14}$, $10^{15}$, or more than $10^{15}$ microbes of one or more such classes may be administered to an individual to reconstitute their bladder microbiome.

Figure 10:
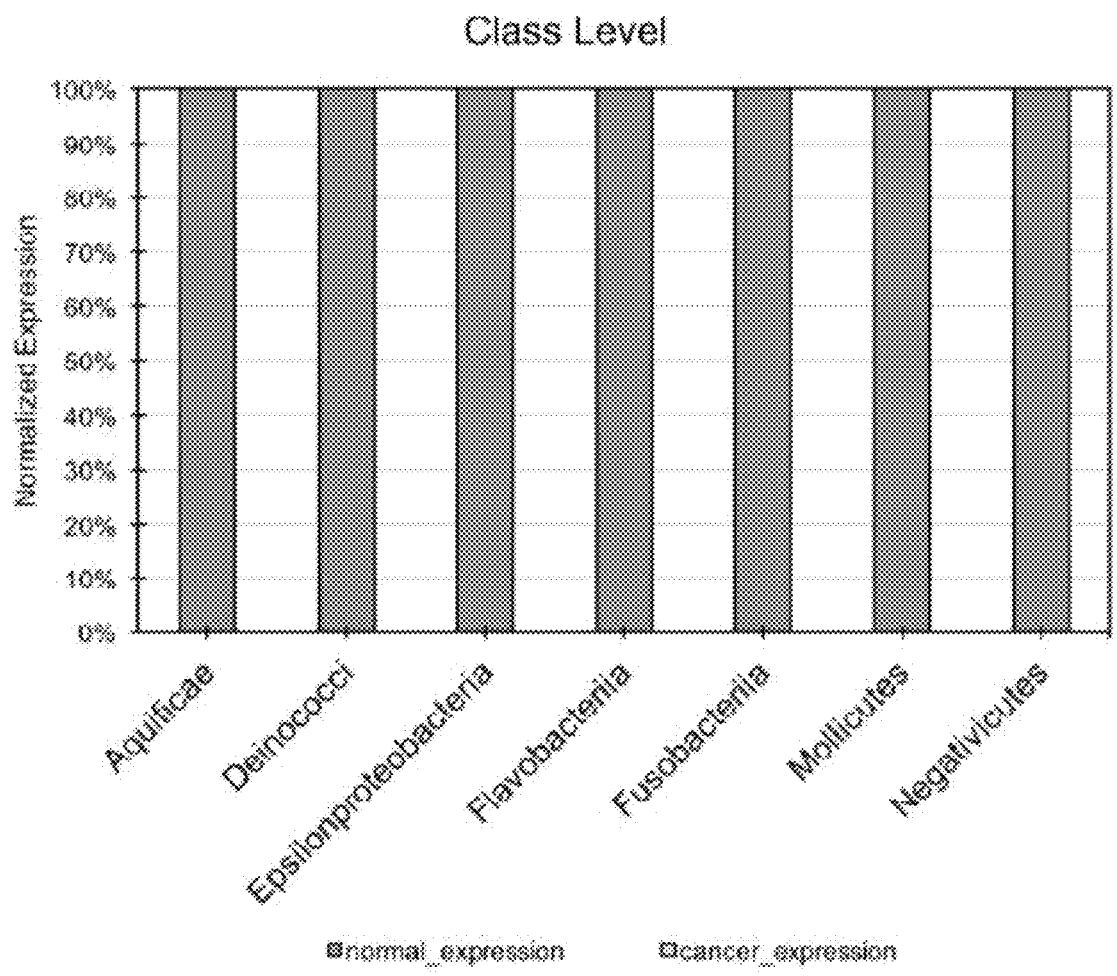
FIG. 10 shows expression of microbes only in the urinary microbiomes of non-cancerous individuals at the class level.

FIG. 10 shows normalized expression (see Example 1) of microbes found only in the urinary microbiomes of non-cancerous individuals at the phylum level and not in individuals with cancer. As shown in FIG. 10, microbes belonging to the classes Aquificiae, Deinococci, Epsilonproteobacteria, Flavobacteria, Fusobacteria, Mollicutes, Negativicutes are only expressed in non-cancerous individuals. Thus, the presence of microbes belonging to any one or more of the classes Aquificiae, Deinococci, Epsilonproteobacteria, Flavobacteria, Fusobacteria, Mollicutes, Negativicutes in a sample corresponding to an individual (e.g., relative abundance as compared to reference samples obtained from cancerous or non-cancerous individuals) may provide an indication that the individual is non-cancerous.

Additionally, the relative proportion of these microbes can be used to define the microbial constituency of the healthy, normal, or cancer-free bladder. Similarly, a combination of one or more populations of microbes enriched in individuals with cancer and rarely found in patients without cancer may define the microbial constituency of the cancerous urinary microbiome. Further, the relative abundance of these microbes can be used to guide both the amount and types of these microbes needed to treat an individual so as to bring the microbial constituency of the bladder back to the expected state. A person displaying low levels of various combinations of microbes associated with healthy bladders (various combinations of classes), such as Aquificiae, Deinococci, Epsilonproteobacteria, Flavobacteria, Fusobacteria, Mollicutes, and Negativicutes, can then have their bladder microbiome reconstituted by reintroducing the amount and type of any one or more of classes Aquificiae, Deinococci, Epsilonproteobacteria, Flavobacteria, Fusobacteria, Mollicutes, and Negativicutes to bring their profile to the expected state for individuals without cancer. For example, about $10^3$, $10^4$, $10^5$, $10^6$, $10^7$, $10^8$, $10^9$, $10^{10}$, $10^{11}$, $10^{12}$, $10^{13}$, $10^{14}$, $10^{15}$, or more than $10^{15}$ microbes of one or more such classes may be administered to an individual to reconstitute their bladder microbiome.

Figure 11:
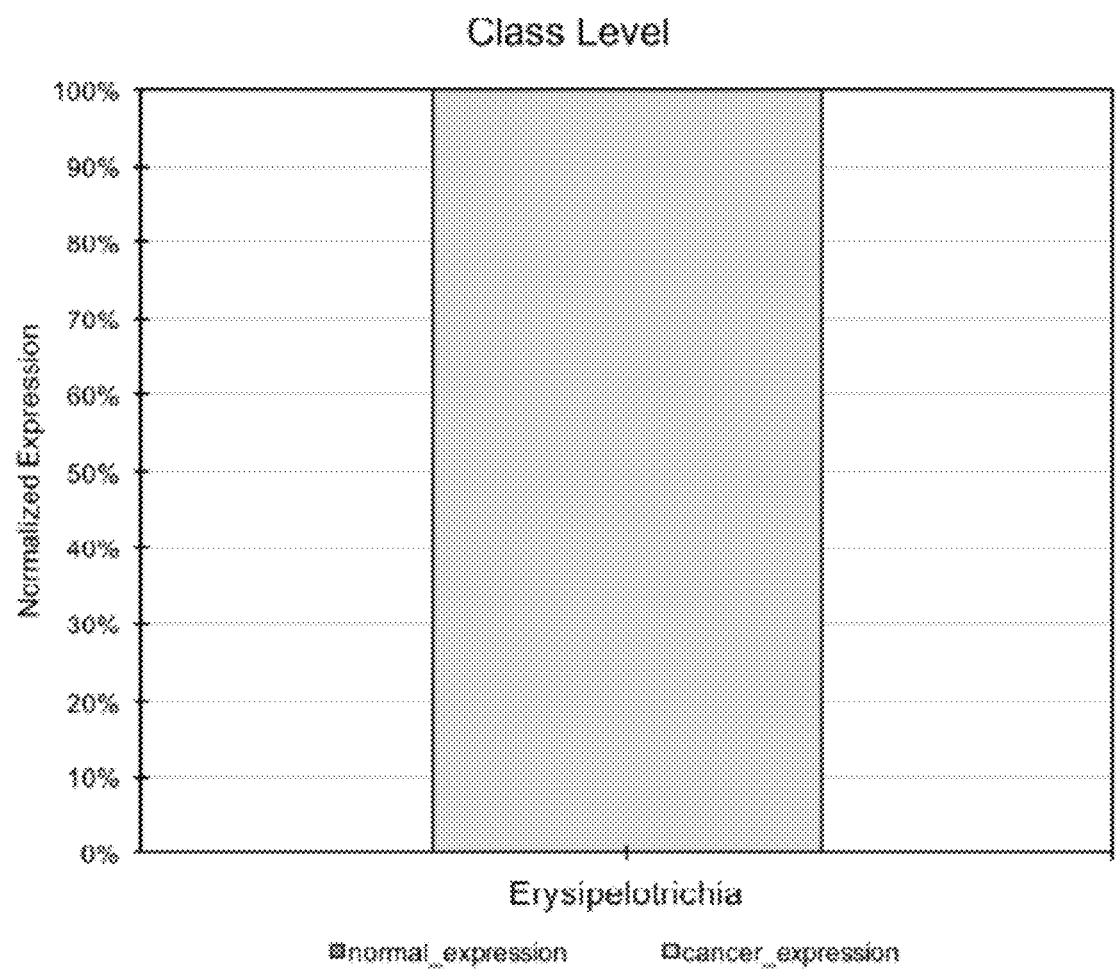
FIG. 11 shows expression of microbes only in the urinary microbiomes of cancerous individuals at the class level.

FIG. 11 shows expression of microbes only in the urinary microbiomes of cancerous individuals at the class level. As shown in FIG. 11, microbes belonging to the class Erysipelotrichia are only expressed in cancerous individuals. Thus, the presence of microbes belong to the class Erysipelotrichia in a sample corresponding to an individual (e.g., relative abundance as compared to reference samples obtained from cancerous or non-cancerous individuals) may provide an indication that the individual is cancerous.

Figure 12:
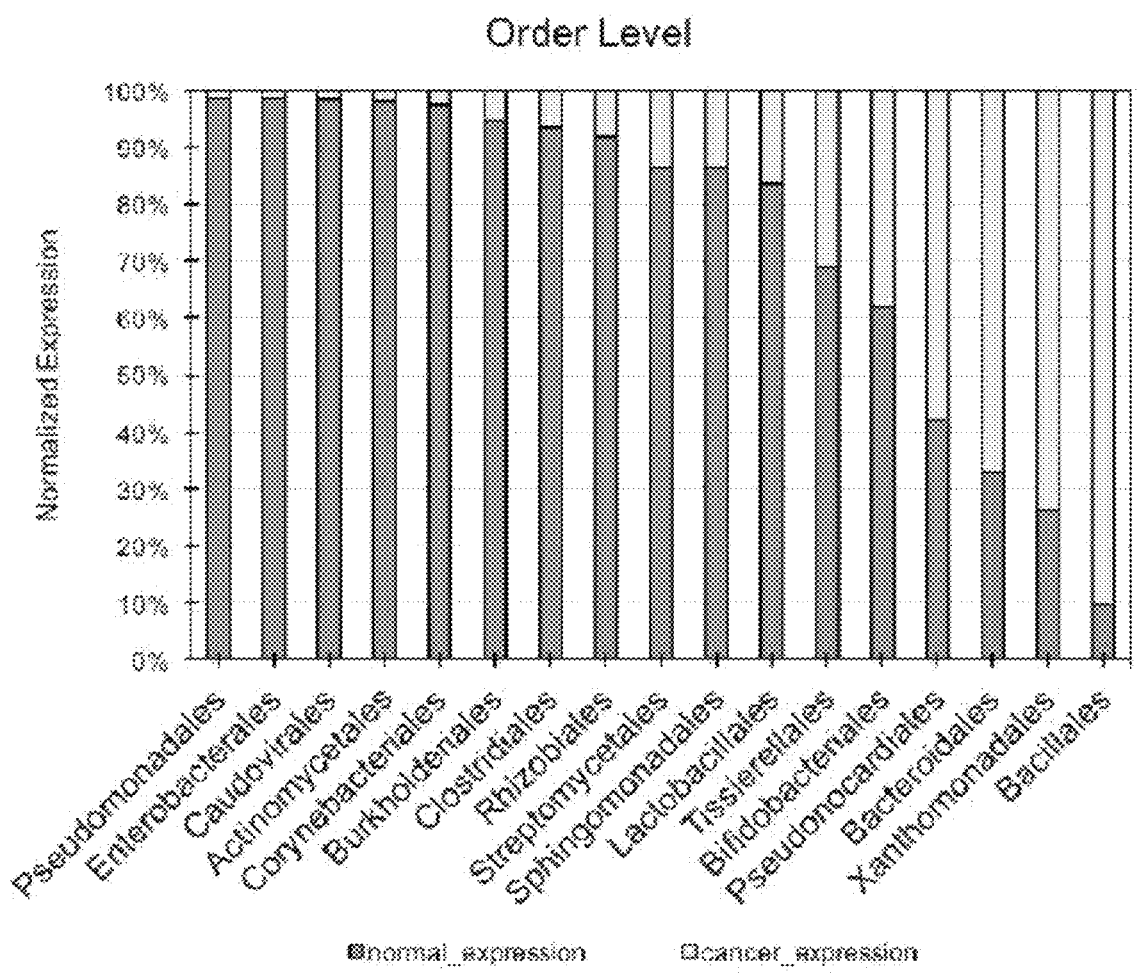
FIG. 12 shows differential expression of microbes in the urinary microbiomes of cancerous and non-cancerous individuals at the order level.

FIG. 12 shows normalized expression (see Example 1) of microbes in the urinary microbiomes of cancerous and non-cancerous individuals at the order level. As shown in FIG. 12, microbes of orders Pseudomonadales, Enterobacterales, Caudovirales, Actinomycetales, Corynebacteriales, Burkholderiales, Clostridiales, Rhizobiales, Streptomycetales, Sphingomonadales, Lactobacillales, Tissierellales, Bifidobacteriales, Pseudonocardiales, Bacteroidales, Xanthomonadales, and Bacillales are differentially expressed in cancerous vs. non-cancerous individuals. As shown in FIG. 12, the expression of Pseudomonadales, Enterobacterales, Caudovirales, Actinomycetales, Corynebacteriales, Burkholderiales, Clostridiales, Rhizobiales, Streptomycetales, Sphingomonadales, Lactobacillales, Tissierellales, and Bifidobacteriales are enriched at greater than 60% prevalence in individuals without cancer, whereas the expression of Pseudonocardiales, Bacteroidales, Xanthomonadales, and Bacillales are enriched at greater than greater than 60% prevalence in individuals with cancer. Thus, a combination of one or more populations of microbes enriched in normal individuals and rarely found in disease-positive patients may define the microbial constituency of the healthy, normal, or cancer-free bladder. Similarly, a combination of one or more populations of microbes enriched in individuals with cancer and rarely found in patients without cancer may define the microbial constituency of the cancerous urinary microbiome. Further, the relative abundance of any one or more of Pseudomonadales, Enterobacterales, Caudovirales, Actinomycetales, Corynebacteriales, Burkholderiales, Clostridiales, Rhizobiales, Streptomycetales, Sphingomonadales, Lactobacillales, Tissierellales, Bifidobacteriales, Pseudonocardiales, Bacteroidales, Xanthomonadales, and Bacillales in a sample corresponding to an individual may provide an indication of whether the individual possesses a disease, e.g., cancer, or not based on the relative abundance of microbes associated with normal bladders and those associated with diseased bladders. Further, if a sample corresponding to an individual is found to possess deficient levels of microbes typically found to be enriched in healthy individuals, the deficient microbes identified may form the basis of a treatment in which deficient microbe(s) are augmented by administration of that microbe(s) so as to bring the microbial constituency of the bladder back to the expected state for normal individuals. For example, about $10^3$, $10^4$, $10^5$, $10^6$, $10^7$, $10^8$, $10^9$, $10^{10}$, $10^{11}$, $10^{12}$, $10^{13}$, $10^{14}$, $10^{15}$, or more than $10^{15}$ microbes of one or more such orders may be administered to an individual to reconstitute their bladder microbiome.

Figure 13:
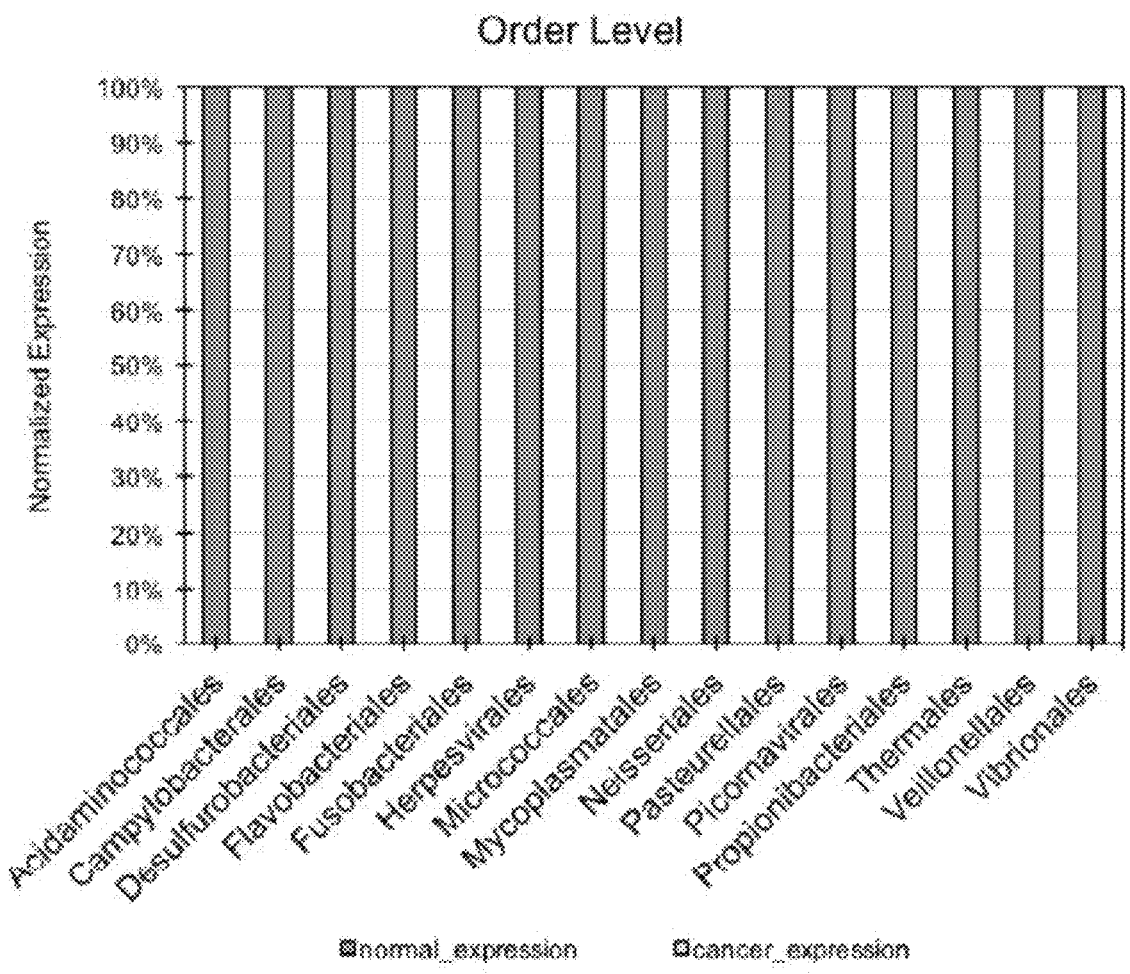
FIG. 13 shows expression of microbes only in the urinary microbiomes of non-cancerous individuals at the order level.

FIG. 13 shows normalized expression (see Example 1) of microbes found only in the urinary microbiomes of non-cancerous individuals at the phylum level and not in individuals with cancer. As shown in FIG. 13, microbes belonging to the orders Acidaminococcales, Campylobacterales, Desulfurobacteriales, Fusobacteriales, Herpesvirales, Micrococcales, Mycoplasmatales, Neisseriales, Pasteurellales, Picornavirales, Propionibacteriales, Thermales, Veillonellales, and Vibrionales are only expressed in non-cancerous individuals. Thus, the presence of microbes belonging to any one or more of the orders Acidaminococcales, Campylobacterales, Desulfurobacteriales, Fusobacteriales, Herpesvirales, Micrococcales, Mycoplasmatales, Neisseriales, Pasteurellales, Picornavirales, Propionibacteriales, Thermales, Veillonellales, and Vibrionales in a sample corresponding to an individual (e.g., relative abundance as compared to reference samples obtained from cancerous or non-cancerous individuals) may provide an indication that the individual is non-cancerous. Additionally, the relative proportion of these microbes can be used to define the microbial constituency of the healthy, normal, or cancer-free bladder. Similarly, a combination of one or more populations of microbes enriched in individuals with cancer and rarely found in patients without cancer may define the microbial constituency of the cancerous urinary microbiome. Further, the relative abundance of these microbes can be used to guide both the amount and types of these microbes needed to treat an individual so as to bring the microbial constituency of the bladder back to the expected state. A person displaying low levels of various combinations of microbes associated with healthy bladders (various combinations of orders), such as Acidaminococcales, Campylobacterales, Desulfurobacteriales, Fusobacteriales, Herpesvirales, Micrococcales, Mycoplasmatales, Neisseriales, Pasteurellales, Picornavirales, Propionibacteriales, Thermales, Veillonellales, and Vibrionales, may then have their bladder microbiome reconstituted by reintroducing the amount and type of any one or more of orders Acidaminococcales, Campylobacterales, Desulfurobacteriales, Fusobacteriales, Herpesvirales, Micrococcales, Mycoplasmatales, Neisseriales, Pasteurellales, Picornavirales, Propionibacteriales, Thermales, Veillonellales, and Vibrionales to bring their profile to the expected state for individuals without cancer. For example, about $10^3$, $10^4$, $10^5$, $10^6$, $10^7$, $10^8$, $10^9$, $10^{10}$, $10^{11}$, $10^{12}$, $10^{13}$, $10^{14}$, $10^{15}$, or more than $10^{15}$ microbes of one or more such orders may be administered to an individual to reconstitute their bladder microbiome.

Figure 14:
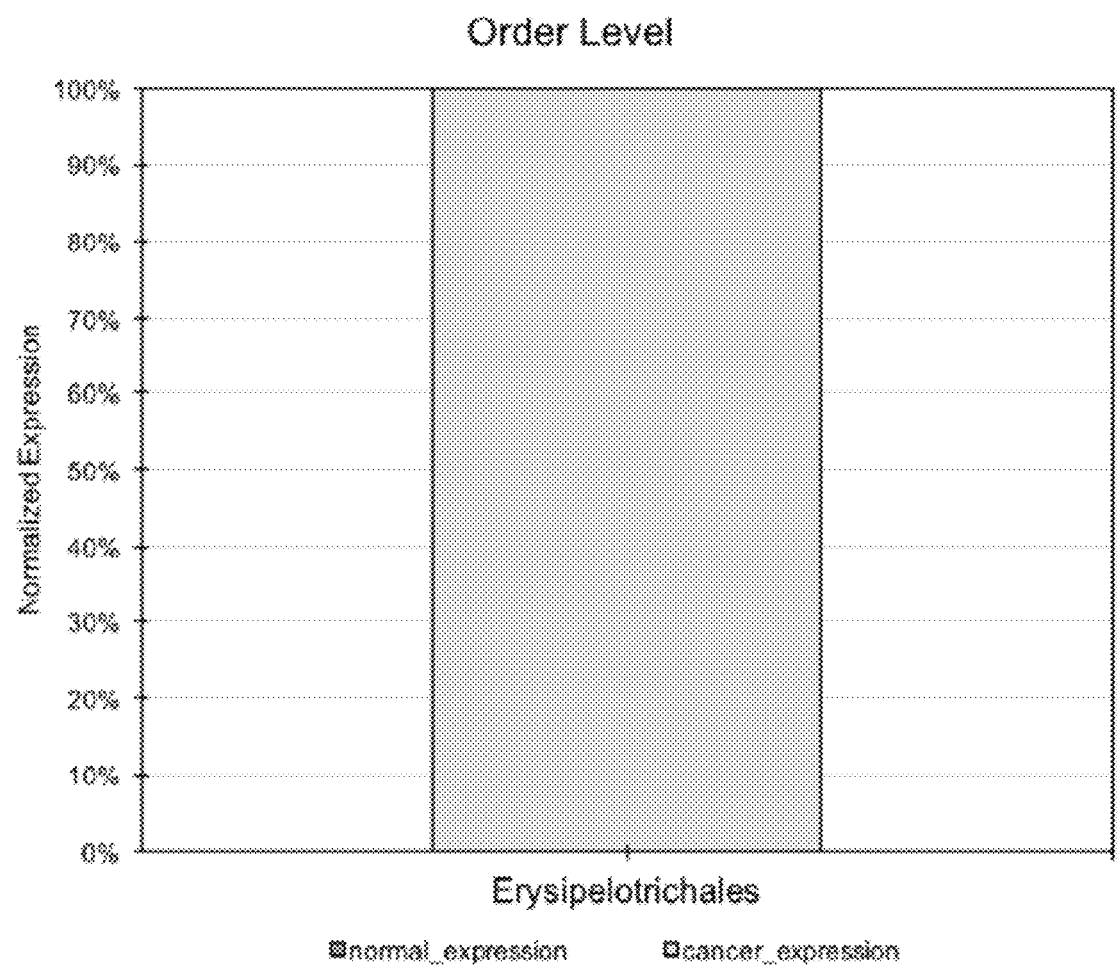
FIG. 14 shows expression of microbes only in the urinary microbiomes of cancerous individuals at the order level.

FIG. 14 shows expression of microbes only in the urinary microbiomes of cancerous individuals at the order level. As shown in FIG. 14, microbes belonging to the order Erysipelotrichales are only expressed in cancerous individuals. Thus, the presence of microbes belonging to the order Erysipelotrichales in a sample corresponding to an individual (e.g., relative abundance as compared to reference samples obtained from cancerous or non-cancerous individuals) may provide an indication that the individual is cancerous.

Figure 15:
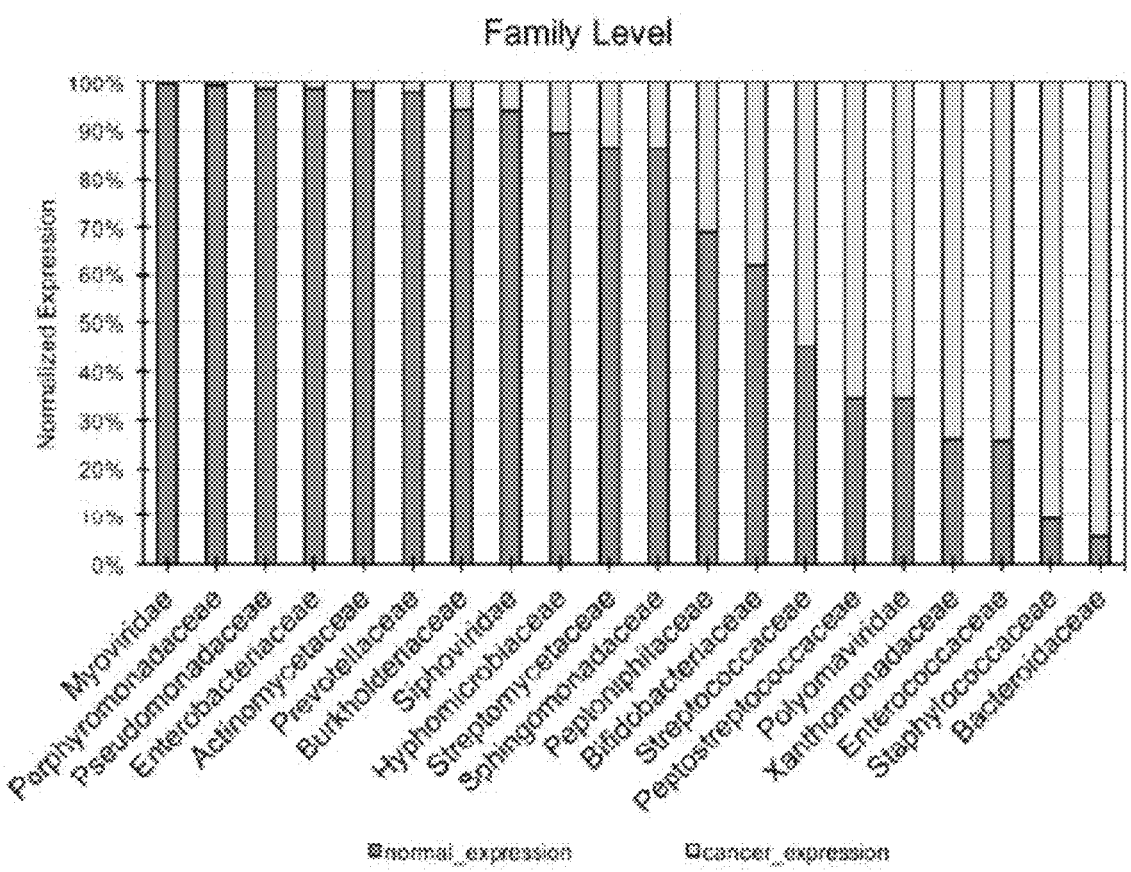
FIG. 15 shows differential expression of microbes in the urinary microbiomes of cancerous and non-cancerous individuals at the family level.

FIG. 15 shows normalized expression (see Example 1) of microbes in the urinary microbiomes of cancerous and non-cancerous individuals at the family level. As shown in FIG. 15, microbes of families Myoviridae, Porphyromonadaceae, Pseudomonoadaceae, Enterobacteriaceae, Actinomycetaceae, Prevotellaceae, Burkholderiaceae, Siphoviridae, Hyphoicrobiaceae, Streptomycetaceae, Sphingomonadaceae, Peptoniphilaceae, Bifidobacteriaceae, Peptostreptococcaceae, Polyomaviridae, Xanthomonadaceae, Staphylococcaceae, and Bacteroidaceae are differentially expressed in cancerous vs. non-cancerous individuals. As shown in FIG. 15, the expression of Myoviridae, Porphyromonadaceae, Pseudomonoadaceae, Enterobacteriaceae, Actinomycetaceae, Prevotellaceae, Burkholderiaceae, Siphoviridae, and Hyphoicrobiaceae are enriched at greater than greater than 60% prevalence in individuals without cancer, whereas the expression of Streptomycetaceae, Sphingomonadaceae, Peptoniphilaceae, Bifidobacteriaceae, Peptostreptococcaceae, Polyomaviridae, Xanthomonadaceae, Staphylococcaceae, and Bacteroidaceae are enriched at greater than greater than 60% prevalence in individuals with cancer. Thus, a combination of microbes enriched in normal individuals and rarely found in disease-positive patients may define the microbial constituency of the healthy, normal, or cancer-free bladder. Similarly, a combination of one or more populations of microbes enriched in individuals with cancer and rarely found in patients without cancer may define the microbial constituency of the cancerous urinary microbiome. Further, the relative abundance of any one or more of Myoviridae, Porphyromonadaceae, Pseudomonoadaceae, Enterobacteriaceae, Actinomycetaceae, Prevotellaceae, Burkholderiaceae, Siphoviridae, Hyphoicrobiaceae, Streptomycetaceae, Sphingomonadaceae, Peptoniphilaceae, Bifidobacteriaceae, Peptostreptococcaceae, Polyomaviridae, Xanthomonadaceae, Staphylococcaceae, and Bacteroidaceae in a sample corresponding to an individual may provide an indication of whether the individual possesses a disease, e.g., cancer, or not based on the relative abundance of microbes associated with normal bladders and those associated with diseased bladders. Further, if a sample corresponding to an individual is found to possess deficient levels of microbes typically found to be enriched in healthy individuals, the deficient microbes identified may form the basis of a treatment in which deficient microbe(s) are augmented by administration of that microbe(s) so as to bring the microbial constituency of the bladder back to the expected state for normal individuals. For example, about $10^3$, $10^4$, $10^5$, $10^6$, $10^7$, $10^8$, $10^9$, $10^{10}$, $10^{11}$, $10^{12}$, $10^{13}$, $10^{14}$, $10^{15}$, or more than $10^{15}$ microbes of one or more such families may be administered to an individual to reconstitute their bladder microbiome.

Figure 16:
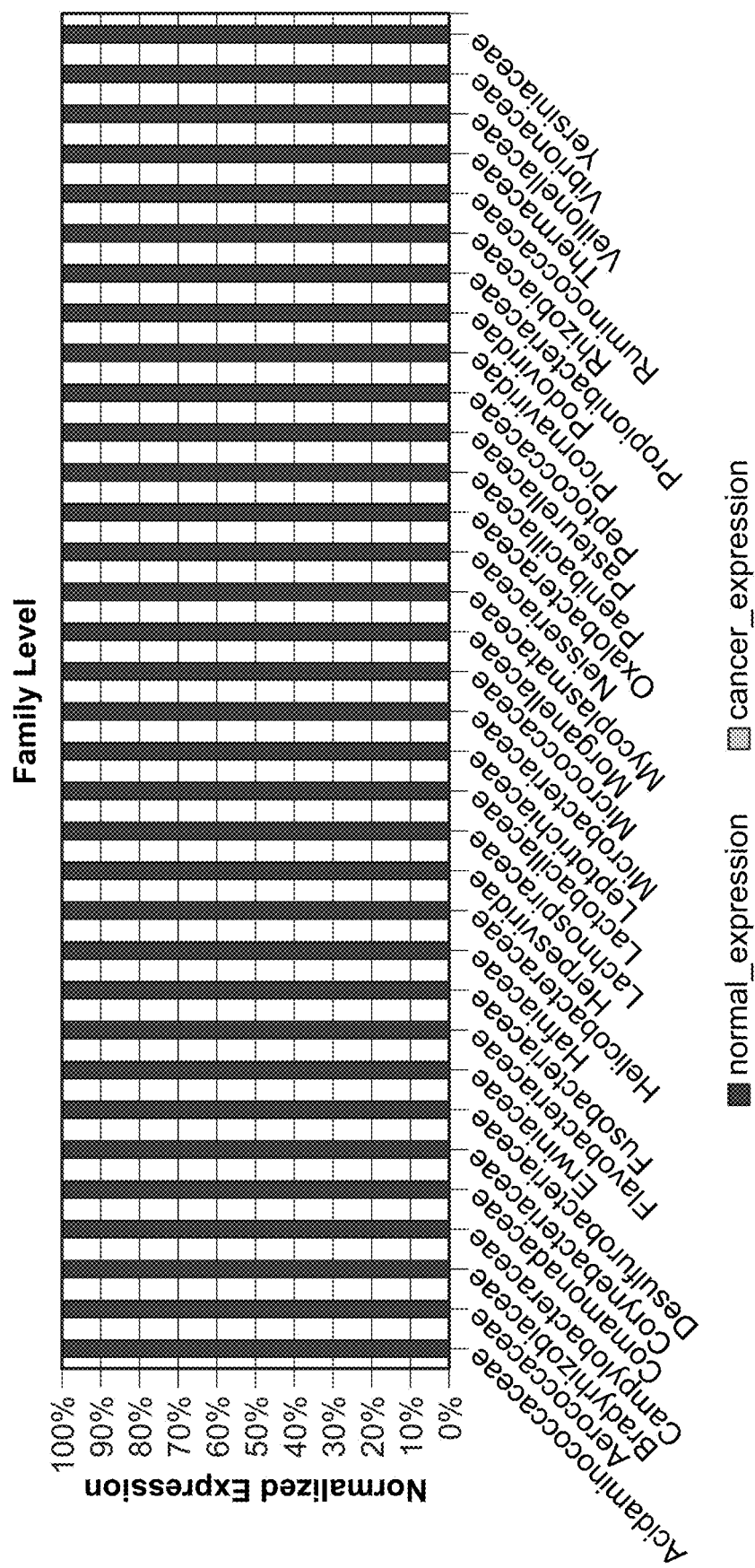
FIG. 16 shows expression of microbes only in the urinary microbiomes of non-cancerous individuals at the family level.

FIG. 16 shows normalized expression (see Example 1) of microbes found only in the urinary microbiomes of non-cancerous individuals at the phylum level and not in individuals with cancer. As shown in FIG. 16, microbes of the families Acidaminococcaceae, Aerococcaceae, Bradyrhizobiaceae, Campylobacteraceae, Comamonadaceae, Corynebacteriaceae, Desulfurobacteriaceae, Erwiniaceae, Flavobacteriaceae, Hafniaceae, Helicobacteraceae, Herpesviridae, Lachnospiraceae, Lactobacillaceae, Leptotrichiaceae, Microbacteriaceae, Micrococcaceae, Morganellaceae, Mycoplasmataceae, Neisseriaceae, Oxalobacteraceae, Paenibacillaceae, Pasteurellaceae, Peptococcaceae, Picornaviridae, Podoviridae, Propionibacteriaceae, Rhizobiaceae, Ruminococcaceae, Thermaceae, Veillonellaceae, Vibrionaceae, and Yersiniaceae are only expressed in non-cancerous individuals. Thus, the presence of microbes belonging to any one or more of the families Acidaminococcaceae, Aerococcaceae, Bradyrhizobiaceae, Campylobacteraceae, Comamonadaceae, Corynebacteriaceae, Desulfurobacteriaceae, Erwiniaceae, Flavobacteriaceae, Hafniaceae, Helicobacteraceae, Herpesviridae, Lachnospiraceae, Lactobacillaceae, Leptotrichiaceae, Microbacteriaceae, Micrococcaceae, Morganellaceae, Mycoplasmataceae, Neisseriaceae, Oxalobacteraceae, Paenibacillaceae, Pasteurellaceae, Peptococcaceae, Picornaviridae, Podoviridae, Propionibacteriaceae, Rhizobiaceae, Ruminococcaceae, Thermaceae, Veillonellaceae, Vibrionaceae, and Yersiniaceae in a sample corresponding to an individual (e.g., relative abundance as compared to reference samples obtained from cancerous or non-cancerous individuals) may provide an indication that the individual is non-cancerous. Additionally, the relative proportion of these microbes can be used to define the microbial constituency of the healthy, normal, or cancer-free bladder. Similarly, a combination of one or more populations of microbes enriched in individuals with cancer and rarely found in patients without cancer may define the microbial constituency of the cancerous urinary microbiome. Further, the relative abundance of one or more populations of these microbes can be used to guide both the amount and types of these microbes needed to treat an individual so as to bring the microbial constituency of the bladder back to the expected state. A person displaying low levels of various combinations of microbes associated with healthy bladders (various combinations of families), such as Acidaminococcaceae, Aerococcaceae, Bradyrhizobiaceae, Campylobacteraceae, Comamonadaceae, Corynebacteriaceae, Desulfurobacteriaceae, Erwiniaceae, Flavobacteriaceae, Hafniaceae, Helicobacteraceae, Herpesviridae, Lachnospiraceae, Lactobacillaceae, Leptotrichiaceae, Microbacteriaceae, Micrococcaceae, Morganellaceae, Mycoplasmataceae, Neisseriaceae, Oxalobacteraceae, Paenibacillaceae, Pasteurellaceae, Peptococcaceae, Picornaviridae, Podoviridae, Propionibacteriaceae, Rhizobiaceae, Ruminococcaceae, Thermaceae, Veillonellaceae, Vibrionaceae, and Yersiniaceae, may then have their bladder microbiome reconstituted by reintroducing the amount and type of any one or more of families Acidaminococcaceae, Aerococcaceae, Bradyrhizobiaceae, Campylobacteraceae, Comamonadaceae, Corynebacteriaceae, Desulfurobacteriaceae, Erwiniaceae, Flavobacteriaceae, Hafniaceae, Helicobacteraceae, Herpesviridae, Lachnospiraceae, Lactobacillaceae, Leptotrichiaceae, Microbacteriaceae, Micrococcaceae, Morganellaceae, Mycoplasmataceae, Neisseriaceae, Oxalobacteraceae, Paenibacillaceae, Pasteurellaceae, Peptococcaceae, Picornaviridae, Podoviridae, Propionibacteriaceae, Rhizobiaceae, Ruminococcaceae, Thermaceae, Veillonellaceae, Vibrionaceae, and Yersiniaceae to bring their profile to the expected state for individuals without cancer. For example, about $10^3$, $10^4$, $10^5$, $10^6$, $10^7$, $10^8$, $10^9$, $10^{10}$, $10^{11}$, $10^{12}$, $10^{13}$, $10^{14}$, $10^{15}$, or more than $10^{15}$ microbes of one or more such families may be administered to an individual to reconstitute their bladder microbiome.

Figure 17:
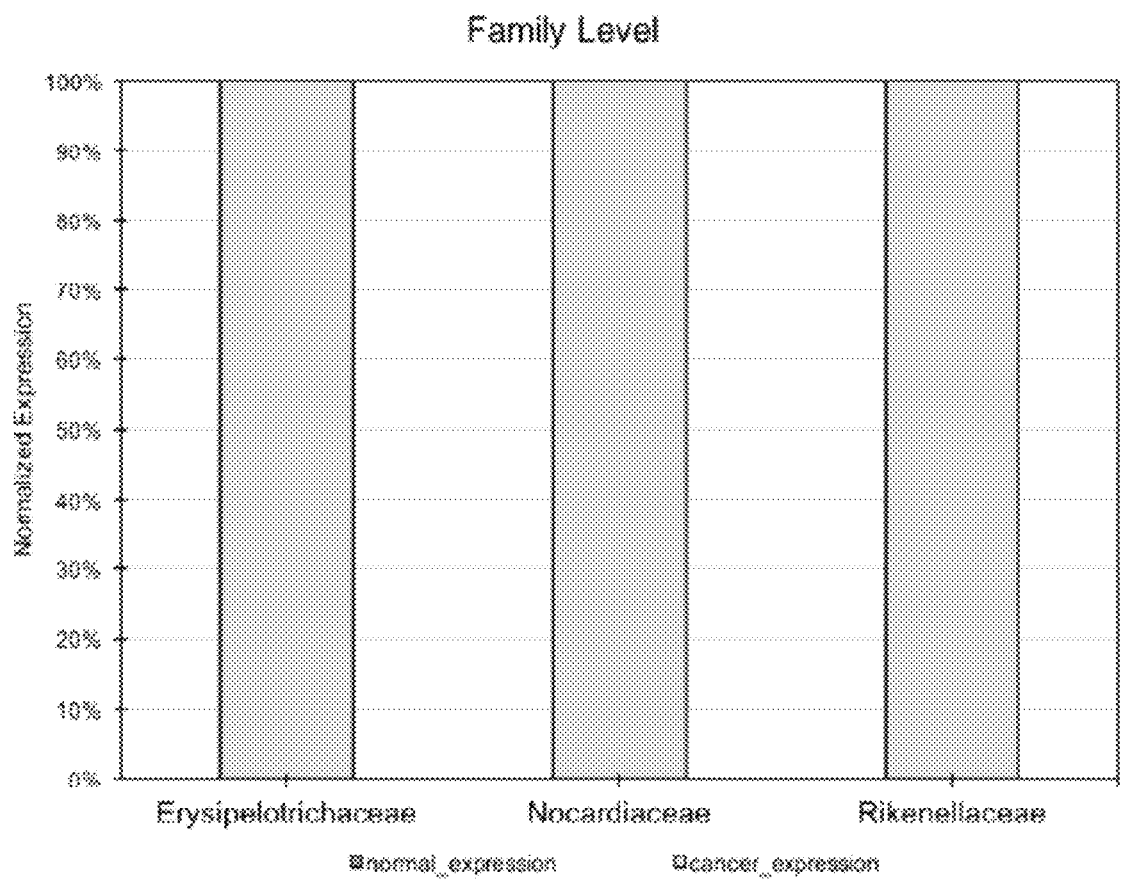
FIG. 17 shows expression of microbes only in the urinary microbiomes of cancerous individuals at the family level.

FIG. 17 shows expression of microbes only in the urinary microbiomes of cancerous individuals at the family level. As shown in FIG. 17, microbes belonging to the families Erysipelotrichaceae, Nocardiaceae, and Rikenellaceae are only expressed in cancerous individuals. Thus, the 100% normalized expression of microbes belonging to any one or more of the families Erysipelotrichaceae, Nocardiaceae, and Rikenellaceae in a sample corresponding to an individual (e.g., relative abundance as compared to reference samples obtained from cancerous or non-cancerous individuals) may provide an indication that the individual is cancerous.

Figure 18:
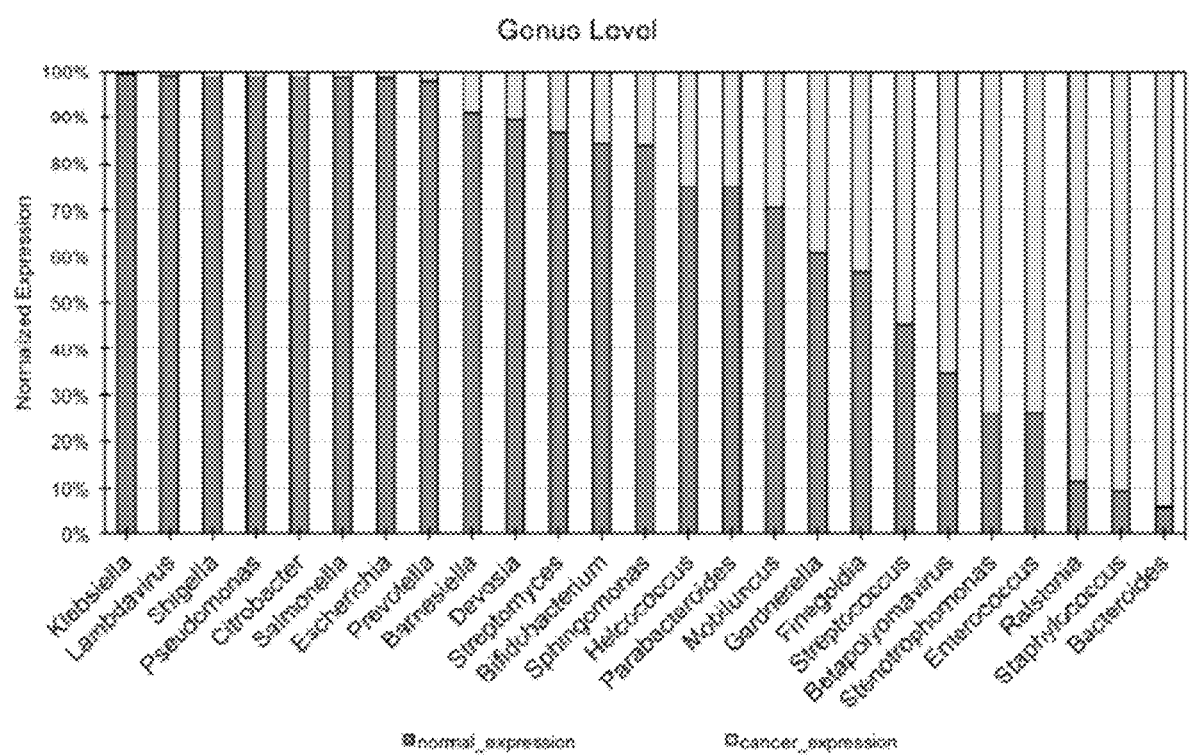
FIG. 18 shows differential expression of microbes in the urinary microbiomes of cancerous and non-cancerous individuals at the genus level.

FIG. 18 shows normalized expression (see Example 1) of microbes in the urinary microbiomes of cancerous and non-cancerous individuals at the genus level. As shown in FIG. 18, microbes of genera *Klebsiella, Lambdavirus, Shigella, Pseudomonas, Citrobacter, Salmonella, Escherichia, Prevoltella, Barnesiella, Devosia, Streptomyces, Bifidobacterium, Sphingomonas, Helcococcus, Parabacteroides, Mobilunus, Gardnerella, Finegoldia, Streptococcus*, Betapolyomavirus, *Stenotrophomonas, Enterococcus, Ralstonia, Staphylococcus*, and *Bacteroides* are differentially expressed in cancerous vs. non-cancerous individuals. As shown in FIG. 18, the expression of *Klebsiella, Lambdavirus, Shigella, Pseudomonas, Citrobacter, Salmonella, Escherichia, Prevoltella, Bamesiella, Devosia, Streptomyces, Bifidobacterium, Sphingomonas, Helcococcus, Parabacteroides, Mobilunus, Gardnerella*, and *Finegoldia* are enriched at greater than 60% prevalence in individuals without cancer, whereas the expression of *Streptococcus*, Betapolyomavirus, *Stenotrophomonas, Enterococcus, Ralstonia, Staphylococcus*, and *Bacteroides* are enriched at greater than 60% prevalence in individuals with cancer. Thus, a combination of one or more populations of microbes enriched in normal individuals and rarely found in disease-positive patients may define the microbial constituency of the healthy, normal, or cancer-free bladder. Similarly, a combination of one or more populations of microbes enriched in individuals with cancer and rarely found in patients without cancer may define the microbial constituency of the cancerous urinary microbiome. Further the relative abundance of any one or more of *Klebsiella, Lambdavirus, Shigella, Pseudomonas, Citrobacter, Salmonella, Escherichia, Prevoltella, Bamesiella, Devosia, Streptomyces, Bifidobacterium, Sphingomonas, Helcococcus, Parabacteroides, Mobilunus, Gardnerella, Finegoldia, Streptococcus*, Betapolyomavirus, *Stenotrophomonas, Enterococcus, Ralstonia, Staphylococcus*, and *Bacteroides* in a sample corresponding to an individual may provide an indication of whether the individual possesses a disease, e.g., cancer, or not based on the relative abundance of microbes associated with normal bladders and those associated with diseased bladders. Further, if a sample corresponding to an individual is found to possess deficient levels of microbes typically found to be enriched in healthy individuals, the deficient microbes identified may form the basis of a treatment in which deficient microbe(s) are augmented by administration of that microbe(s) so as to bring the microbial constituency of the bladder back to the expected state for normal individuals. For example, about $10^3, 10^4, 10^5, 10^6, 10^7, 10^8, 10^9, 10^{10}, 10^{11}, 10^{12}, 10^{13}, 10^{14}, 10^{15}$, or more than $10^{15}$ microbes of one or more such genera may be administered to an individual to reconstitute their bladder microbiome.

Figure 19:
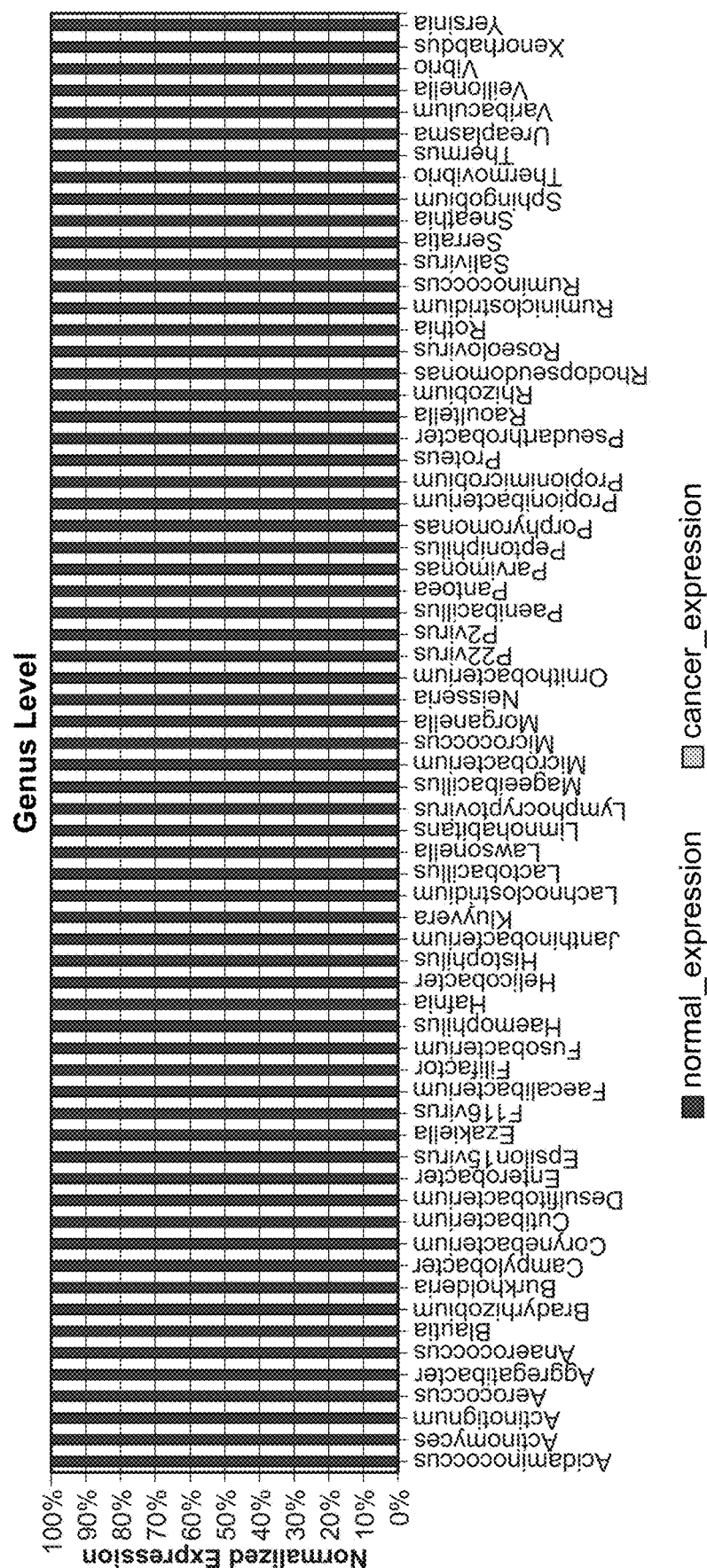
FIG. 19 shows expression of microbes only in the urinary microbiomes of non-cancerous individuals at the genus level.

FIG. 19 shows normalized expression (see Example 1) of microbes found only in the urinary microbiomes of non-cancerous individuals at the phylum level and not in individuals with cancer. As shown in FIG. 19, microbes belonging to the genera *Acidaminococcus, Actinomyces, Actinotignum, Aerococcus, Aggregatibacter, Anaerococcus, Blautia, Bradyrhizobium, Burkholderia, Campylobacter, Cornyebacterium, Cutibacterium, Desulfitobacterium, Enterobacter*, Epsilon15virus, *Ezakiella*, F16virus, *Faecalibacterium, Filifactor, Fusobacterium, Haemophilus, Hafnia, Helicobacter, Histophilus, Janthinobacterium, Kluyvera, Lacnoclostridium, Lactobacillus, Lawsonella, Limnohabitans, Lymphocryptovirus, Mageeibacillus, Microbacterium, Micrococcus, Morganella, Neisseria, Ornithobacterium*, P22virus, P2virus, *Paenibacillus, Pantoea, Parvimonas, Peptoniphilus, Porphyromonas, Propionibacterium, Propionmicrobium, Proteus, Pseudarthrobacter, Raoultella, Rhizobium, Rhodopseudomonas, Roseolovirus, Rothia, Ruminiclostridium, Ruminococcus, Salivirus, Serratia, Sneathia, Sphingobium, Thermovibrio, Thermus, Ureaplasma, Varibaculum, Veillonella, Vibrio, Xenorhabdus*, and *Yersinia* are only expressed in non-cancerous individuals. Thus, the presence of microbes belonging to any one or more of the genera *Acidaminococcus, Actinomyces, Actinotignum, Aerococcus, Aggregatibacter, Anaerococcus, Blautia, Bradyrhizobium, Burkholderia, Campylobacter, Cornyebacterium, Cutibacterium, Desulfitobacterium, Enterobacter*, Epsilon15virus, *Ezakiella*, F116virus, *Faecalibacterium, Filifactor, Fusobacterium, Haemophilus, Hafnia, Helicobacter, Histophilus, Janthinobacterium, Kluyvera, Lacnoclostridium, Lactobacillus, Lawsonella, Limnohabitans, Lymphocryptovirus, Mageeibacillus, Microbacterium, Micrococcus, Morganella, Neisseria, Ornithobacterium*, P22virus, P2virus, *Paenibacillus, Pantoea, Parvimonas, Peptoniphilus, Porphyromonas, Propionibacterium, Propionmicrobium, Proteus, Pseudarthrobacter, Raoultella, Rhizobium, Rhodopseudomonas, Roseolovirus, Rothia, Ruminiclostridium, Ruminococcus, Salivirus, Serratia, Sneathia, Sphingobium, Thermovibrio, Thermus, Ureaplasma, Varibaculum, Veillonella, Vibrio, Xenorhabdus*, and *Yersinia* in a sample corresponding to an individual (e.g., relative abundance as compared to reference samples obtained from cancerous or non-cancerous individuals) may provide an indication that the individual is non-cancerous. Additionally, the relative proportion of one or more populations of these microbes can be used to define the microbial constituency of the healthy, normal, or cancer-free bladder. Similarly, a combination of one or more populations of microbes enriched in individuals with cancer and rarely found in patients without cancer may define the microbial constituency of the cancerous urinary microbiome. Further, the relative abundance of these microbes can be used to guide both the amount and types of these microbes needed to treat an individual so as to bring the microbial constituency of the bladder back to the expected state. A person displaying low levels of various combinations of microbes associated with healthy bladders (various combinations of genera), such as *Acidaminococcus, Actinomyces, Actinotignum, Aerococcus, Aggregatibacter, Anaerococcus, Blautia, Bradyrhizobium, Burkholderia, Campylobacter, Cornyebacterium, Cutibacterium, Desulfitobacterium, Enterobacter*, Epsilon15virus, *Ezakiella*, F16virus, *Faecalibacterium, Filifactor, Fusobacterium, Haemophilus, Hafnia, Helicobacter, Histophilus, Janthinobacterium, Kluyvera, Lacnoclostridium, Lactobacillus, Lawsonella, Limnohabitans, Lymphocryptovirus, Mageeibacillus, Microbacterium, Micrococcus, Morganella, Neisseria, Ornithobacterium*, P22virus, P2virus, *Paenibacillus, Pantoea, Parvimonas, Peptoniphilus, Porphyromonas, Propionibacterium, Propionmicrobium, Proteus, Pseudarthrobacter, Raoultella, Rhizobium, Rhodopseudomonas, Roseolovirus, Rothia, Ruminiclostridium, Ruminococcus, Salivirus, Serratia, Sneathia, Sphingobium, Thermovibrio, Thermus, Ureaplasma, Varibaculum, Veillonella, Vibrio, Xenorhabdus*, and *Yersinia*, may then have their bladder microbiome reconstituted by reintroducing the amount and type of one or more of genera *Acidaminococcus, Actinomyces, Actinotignum, Aerococcus, Aggregatibacter,*

*Anaerococcus, Blautia, Bradyrhizobium, Burkholderia, Campylobacter, Cornyebacterium, Cutibacterium, Desulfitobacterium, Enterobacter,* Epsilon15virus, *Ezakiella,* F16virus, *Faecalibacterium, Filifactor, Fusobacterium, Haemophilus, Hafnia, Helicobacter, Histophilus, Janthinobacterium, Kluyvera, Lacnoclostridium, Lactobacillus, Lawsonella, Limnohabitans, Lymphocryptovirus, Mageeibacillus, Microbacterium, Micrococcus, Morganella, Neisseria, Ornithobacterium,* P22virus, P2virus, *Paenibacillus, Pantoea, Parvimonas, Peptoniphilus, Porphyromonas, Propionibacterium, Propionmicrobium, Proteus, Pseudarthrobacter, Raoultella, Rhizobium, Rhodopseudomonas, Roseolovirus, Rothia, Ruminiclostridium, Ruminococcus, Salivirus, Serratia, Sneathia, Sphingobium, Thermovibrio, Thermus, Ureaplasma, Varibaculum, Veillonella, Vibrio, Xenorhabdus,* and *Yersinia* to bring their profile to the expected state for individuals without cancer. For example, about $10^3$, $10^4$, $10^5$, $10^6$, $10^7$, $10^8$, $10^9$, $10^{10}$, $10^{11}$, $10^{12}$, $10^{13}$, $10^{14}$, $10^{15}$, or more than $10^{15}$ microbes of one or more such genera may be administered to an individual to reconstitute their bladder microbiome.

Figure 20:
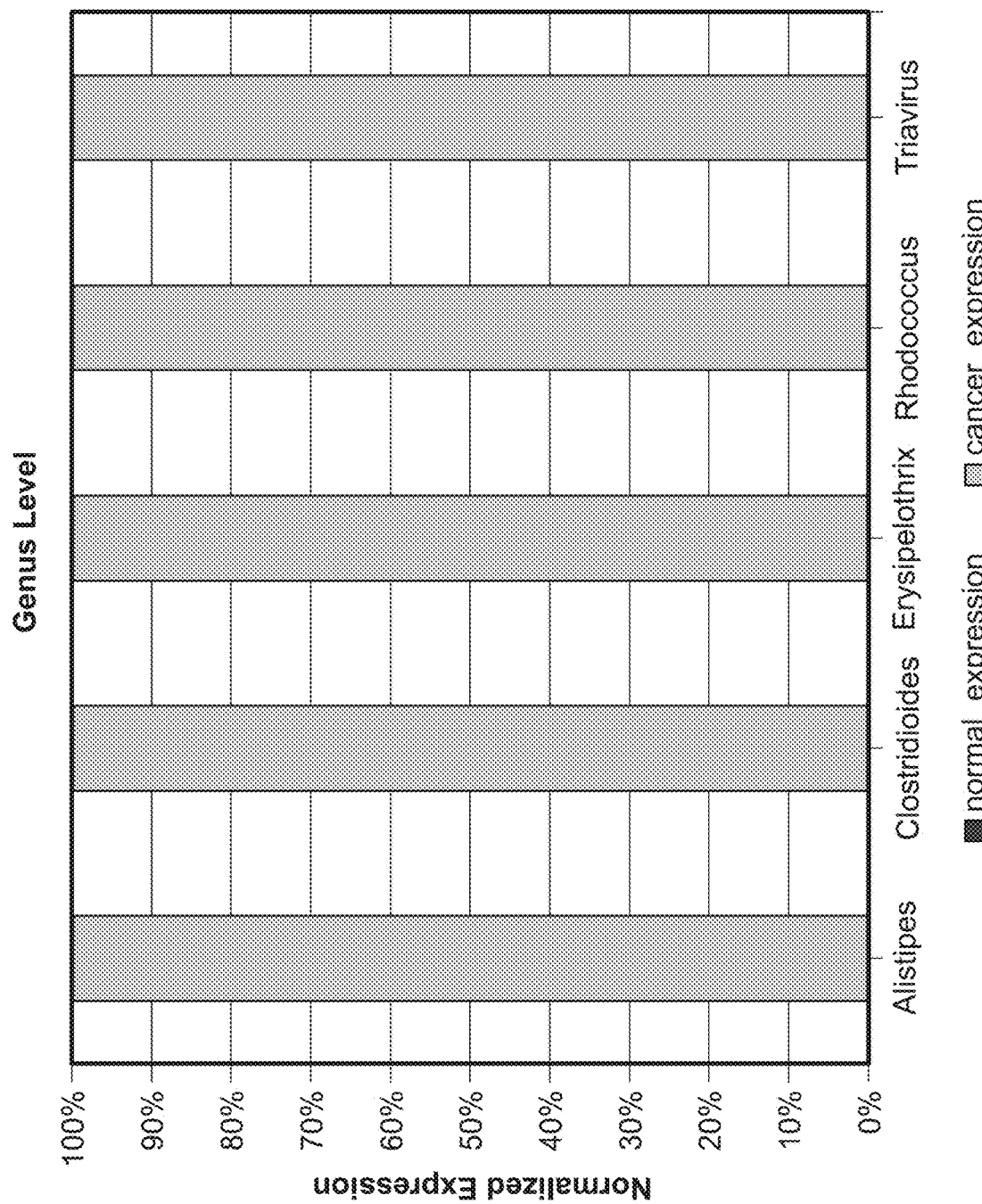
FIG. 20 shows expression of microbes only in the urinary microbiomes of cancerous individuals at the genus level.

FIG. 20 shows expression of microbes only in the urinary microbiomes of cancerous individuals at the genus level. As shown in FIG. 20, microbes belonging to the genera *Alistipes, Clostridioides, Erysipelothrix, Rhodococcus,* and *Triavirus* are only expressed in cancerous individuals. Thus, the presence of microbes belonging to any one or more of the genera *Alistipes, Clostridioides, Erysipelothrix, Rhodococcus,* and *Triavirus* in a sample corresponding to an individual (e.g., relative abundance as compared to reference samples obtained from cancerous or non-cancerous individuals) may provide an indication that the individual is non-cancerous.

Figure 21:
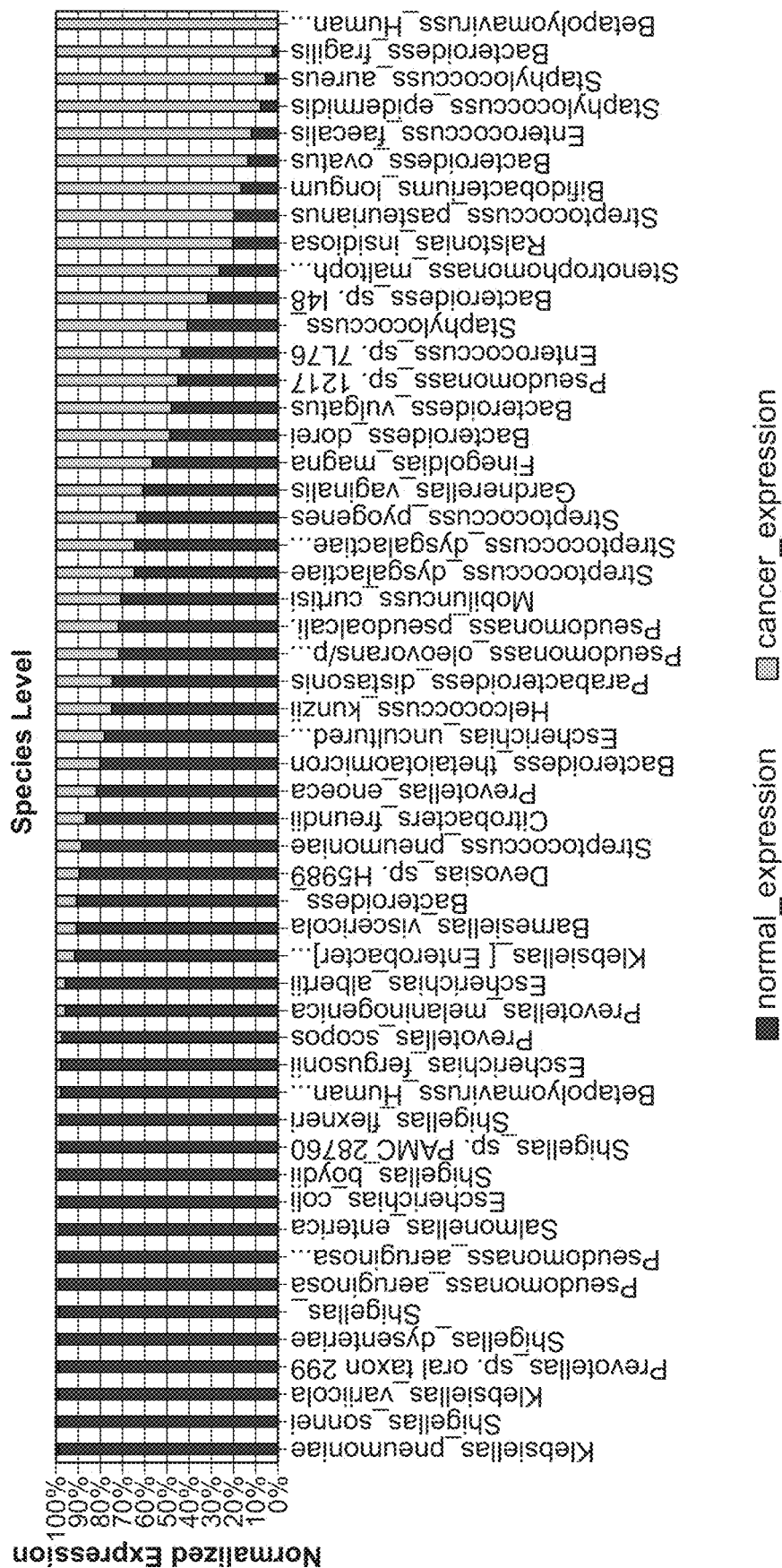
FIG. 21 shows differential expression of microbes in the urinary microbiomes of cancerous and non-cancerous individuals at the species level.

FIG. 21 shows normalized expression (see Example 1) of microbes in the urinary microbiomes of cancerous and non-cancerous individuals at the species level. As shown in FIG. 21, microbes of species *Klebsiellas pneumoniae, Shigellas sonnei, Klebsiellas varicola, Prevotellas* species oral taxon 299, *Shigellas dysenteriae, Pseudomonas aeruginosa, Salmonellas enterica, Escherichias coli, Shigellas boydii, Shigellas* species PAMC 28760, *Shigellas flexneri,* Betapolyomavirus human, *Excherichias fergusonii, Prevotellas scopos, Prevotellas melaninogenica, Escherichias albertii barnesiellas viscericola, Devosias* species H5989, *Streptococcus pneumoniae, Citrobacters freundii, Prevotellas enoeca, Bacteroides thetaiotaomicron, Helcococcus kunzii, Parabacteroidess distasonis, Pseudomonas oleovorans, Mobiluncus curtisii, Bacteroides vulgatus, Pseudomonas* species 1217, *Enterococcus* species 7L76, *Bacteroides* species L48, *Ralstonias insidiosa, Streptococcus pasteurianus, Bifidobacterium longum, Bacteroides ovatus, Enterococcus faecalis, Staphylococcus epidermis, Staphylococcus aureus, Bacteroides fragilis,* and Betapolyomavirus human are differentially expressed in cancerous vs. non-cancerous individuals. As shown in FIG. 21, the expression of *Klebsiellas pneumoniae, Shigellas sonnei, Klebsiellas varicola, Prevotellas* species oral taxon 299, *Shigellas dysenteriae, Pseudomonas aeruginosa, Salmonellas enterica, Escherichias coli, Shigellas boydii, Shigellas* species PAMC 28760, *Shigellas flexneri,* Betapolyomavirus human, *Excherichias fergusonii, Prevotellas scopos, Prevotellas melaninogenica, Escherichias albertii barnesiellas viscericola, Devosias* species H5989, *Streptococcus pneumoniae, Citrobacters freundii, Prevotellas enoeca, Bacteroides thetaiotaomicron, Helcococcus kunzii, Parabacteroidess distasonis, Pseudomonas oleovorans,* and *Mobiluncus curtisii* are enriched at greater than greater than 60% prevalence in individuals without cancer, whereas the expression of *Bacteroides vulgatus, Pseudomonas* species 1217, *Enterococcus* species 7L76, *Bacteroides* species L48, *Ralstonias insidiosa, Streptococcus pasteurianus, Bifidobacterium longum, Bacteroides ovatus, Enterococcus faecalis, Staphylococcus epidermis, Staphylococcus aureus, Bacteroides fragilis,* Betapolyomavirus human are enriched at greater than greater than 60% prevalence in individuals with cancer. Thus, a combination of one or more populations of microbes enriched in normal individuals and rarely found in disease-positive patients may define the microbial constituency of the healthy, normal, or cancer-free bladder. Similarly, a combination of one or more populations of microbes enriched in individuals with cancer and rarely found in patients without cancer may define the microbial constituency of the cancerous urinary microbiome. Further, the relative abundance of any one or more of *Klebsiellas pneumoniae, Shigellas sonnei, Klebsiellas varicola, Prevotellas* species oral taxon 299, *Shigellas dysenteriae, Pseudomonas aeruginosa, Salmonellas enterica, Escherichias coli, Shigellas boydii, Shigellas* species PAMC 28760, *Shigellas flexneri,* Betapolyomavirus human, *Excherichias fergusonii, Prevotellas scopos, Prevotellas melaninogenica, Escherichias albertii barnesiellas viscericola, Devosias* species H5989, *Streptococcus pneumoniae, Citrobacters freundii, Prevotellas enoeca, Bacteroides thetaiotaomicron, Helcococcus kunzii, Parabacteroidess distasonis, Pseudomonas oleovorans, Mobiluncus curtisii, Bacteroides vulgatus, Pseudomonas* species 1217, *Enterococcus* species 7L76, *Bacteroides* species L48, *Ralstonias insidiosa, Streptococcus pasteurianus, Bifidobacterium longum, Bacteroides ovatus, Enterococcus faecalis, Staphylococcus epidermis, Staphylococcus aureus, Bacteroides fragilis,* and Betapolyomavirus human in a sample corresponding to an individual (e.g., relative abundance as compared to reference samples obtained from cancerous or non-cancerous individuals) may provide an indication of whether the individual possesses a disease, e.g., cancer, or not based on the relative abundance of microbes associated with normal bladders and those associated with diseased bladders. Further, if a sample corresponding to an individual is found to possess deficient levels of microbes typically found to be enriched in healthy individuals, the deficient microbes identified may form the basis of a treatment in which deficient microbe(s) are augmented by administration of that microbe(s) so as to bring the microbial constituency of the bladder back to the expected state for normal individuals. For example, about $10^3$, $10^4$, $10^5$, $10^6$, $10^7$, $10^8$, $10^9$, $10^{10}$, $10^{11}$, $10^{12}$, $10^{13}$, $10^{14}$, $10^{15}$, or more than $10^{15}$ microbes of one or more such species may be administered to an individual to reconstitute their bladder microbiome.

Figure 22:
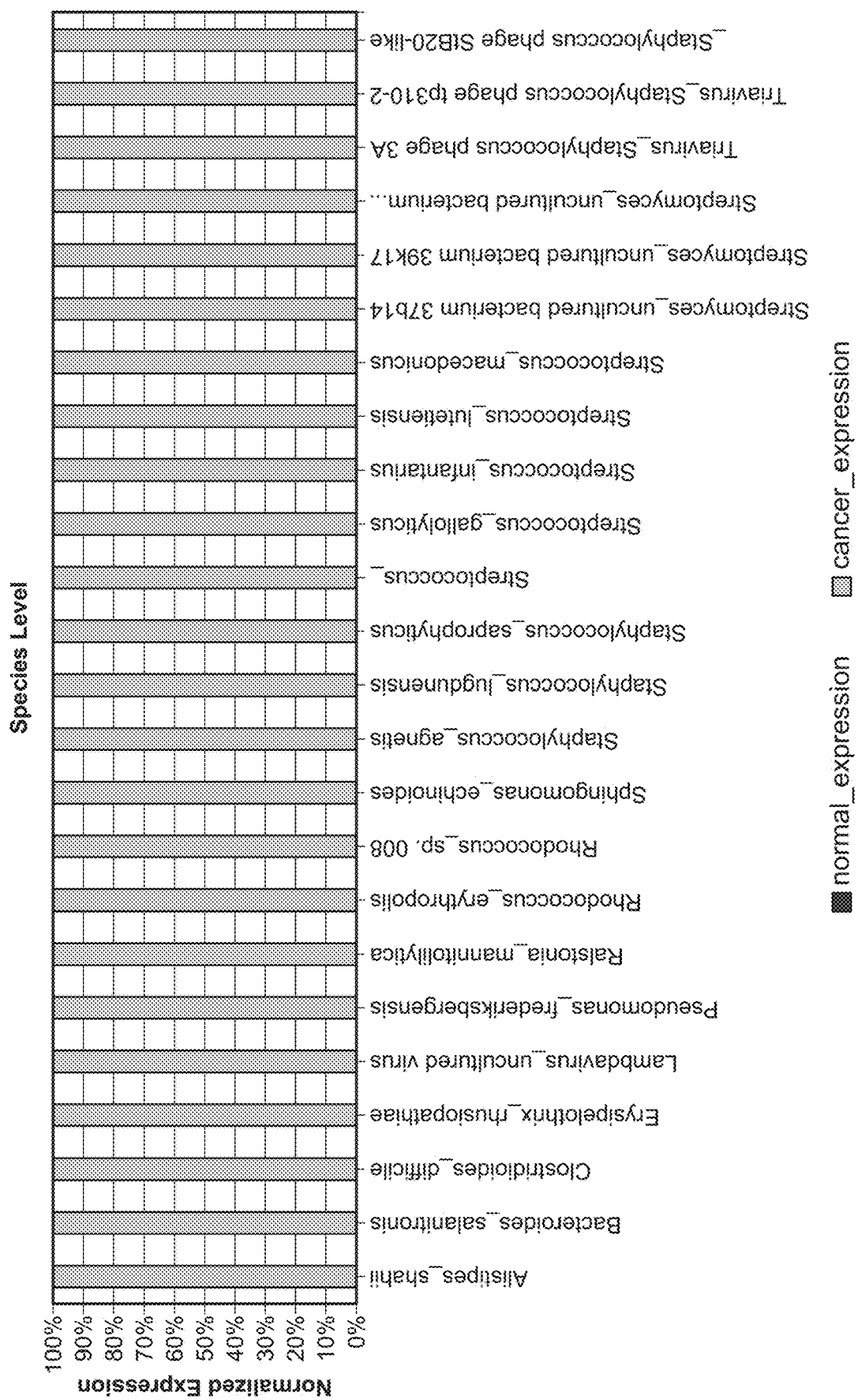
FIG. 22 shows expression of microbes only in the urinary microbiomes of cancerous individuals at the species level.

FIG. 22 shows expression of microbes only in the urinary microbiomes of cancerous individuals at the species level. As shown in FIG. 22, microbes belonging to the species *Alistipes shahii, Bacteroides salanitronis, Clostridioides difficile, Erysipelothrix rhusiopathiae,* Lambdavirus uncultured virus, *Pseudomonas frederiksbergensis, Ralstonia mannitolilytica, Rhodococcus erythropolis, Rhodoccus* species 008, *Sphingomonas echinoides, Staphylococcus agnetis, Staphylococcus lugdunensis, Staphyloccus saprophyticus, Streptococcus gallolyticus, Streptococcus infantarius, Streptococcus lutetiensis, Streptococcus macedonicus, Streptomyces* uncultured bacteria 37b14, *Streptomyces* uncultured bacterium 39k17, *Triavirus staphylococcus* phage 3A, *Triavirus staphylococcus* phage tp310-2, and *Triavirus staphylococcus* phage StB20 are only expressed in cancerous individuals. Thus, the presence of microbes belonging to any one or more of the species *Alistipes shahii,*

*Bacteroides salanitronis, Clostridioides difficile, Erysipelothrix rhusiopathiae,* Lambdavirus uncultured virus, *Pseudomonas frederiksbergensis, Ralstonia mannitolilytica, Rhodococcus erythropolis, Rhodoccus* species 008, *Sphingomonas echinoides, Staphylococcus agnetis, Staphylococcus lugdunensis, Staphyloccus saprophyticus, Streptococcus gallolyticus, Streptococcus infantarius, Streptococcus lutetiensis, Streptococcus macedonicus, Streptomyces* uncultured bacteria 37b14, *Streptomyces* uncultured bacterium 39k17, *Triavirus staphylococcus* phage 3A, *Triavirus staphylococcus* phage tp310-2, and *Triavirus staphylococcus* phage StB20 in a sample corresponding to an individual (e.g., relative abundance as compared to reference samples obtained from cancerous or non-cancerous individuals) may provide an indication that the individual is cancerous.

Though not depicted in the figures, microbes belonging to any one or more of the species Human herpesvirus 6, Human gammaherpesvirus 4, *Bordetella hinzii, Methylibium petroleiphilum, Shigella* species LN126, Podoviridae, *Lactobacillus jensenii, Burkholderia pseudomallei* group, *Pseudomonas* phage phi297, *Klebsiella michiganensis, Lactobacillus* species B164, *Streptococcus* species I-G2, *Kosakonia sacchari, Ruminococcus bicirculans, Prevotella jejuni, Bradyrhizobium* species 11w), *Agrobacterium tumefaciens* complex, *Pseudomonas* phage YMC/0/01/P52_PAE_BP, *Aerococcus sanguinicola, Prevotella* species S4-10, *Corynebacterium frankenforstense, Prevotella* species Sc00026, *Streptococcus* phage EJ-1, *Comamonas* bacterium 36B, *Micrococcus luteus, Pseudomonas sihuiensis, Staphylococcus haemolyticus, Streptococcus* phage phiD12, *Staphylococcus hominis, Pseudomonas* species ATCC 13867, *Streptococcus oralis, Streptococcus salivarius, Streptococcus suis, Acinetobacter chlamydia*-associated clinical sample 198-T, *Sphingobium* species TKS, *Streptococcus parasanguinis, Tessaracoccus aquimaris, Pluralibacter lignolyticus, Streptococcus intermedius, Ureaplasma parvum, Pseudomonas fluorescens* group, *Pseudomonas putida* group, *Sphingobium yanoikuyae, Aerococcus urinae, Burkholderia* species BDU6, *Sphingomonas* species LK11, *Bacillus cereus, Paenibacillus polymyxa, Streptococcus* species VT 162, *Comamonadaceae* bacterium B1, *Klebsiella quasipneumoniae, Corynebacterium simulans, Lactobacillus iners, Corynebacterium* species ATCC 6931, *Klebsiella* species NCTC 8172, *Lawsonella clevelandensis, Lactobacillus* species wkB8, *Sphingomonas taxi, Bradyrhizobium* species lamp2, *Streptococcus* phage SpSL1, *Enterobacteria* phage P88, *Corynebacterium riegelii, Corynebacterium imitans, Lactobacillus acidophilus, Lactobacillus buchneri, Lactobacillus delbrueckii, Lactobacillus helveticus, Cedecea neteri, Enterobacter hormaechei, Lactobacillus plantarum, Lactobacillus gassed, Lactobacillus acetotolerans, Lactobacillus amylophilus, Lactobacillus amylovorus, Tessaracoccus flavus, Lactobacillus farciminis, Corynebacterium singulare, Erwinia gerundensis, Hoeflea* species IMCC20628, *Lactobacillus ruminis, Pseudomonas lini, Propionibacterium* phage PHL030, *Propionibacterium* phage PHLD64, *Propionibacterium* phage PHL082, *Yersinia pseudotuberculosis* complex, *Actinomyces naeslundii, Acidovorax* species NA2, *Acidovorax* species P3, *Acidovorax* species P4, *Bifidobacterium adolescentis, Bifidobacterium breve, Corynebacterium aurimucosum, Negativicoccus massiliensis, Massilia* species WG5, *Turicibacter* species H121, *Corynebacterium diphtheriae, Corynebacterium glutamicum, Rothia aeria, Propionibacterium freudenreichii, Cutibacterium acnes, Pseudomonas* phage phi1, *Streptococcus* species A12, *Pseudomonas* species bs2935, *Pseudomonas* phage JBD44, *Pseudomonas* phage YMC11/07/P54_PAE_BP, *Gemella* species oral taxon 928, *Sinorhizobium* species RAC02, *Hydrogenophaga* species RAC07, *Acidovorax* species T1, Lambdavirus, *Sneathia amnii, Ndongobacter massiliensis, Acidaminococcus intestini, Varibaculum* species, *Streptococcus* species NPS 308, *Tessaracoccus* species 72.5-30, *Corynebacterium sphenisci, Corynebacterium atypicum, Streptococcus* phage IPPS, *Delftia* species HK171, *Klebsiella* species M5a1, *Staphylococcus* phage St 134, *Propionibacterium* virus Lauchelly, *Propionibacterium* virus PHLD82M03, *Propionibacterium* virus PHLJ17M01, *Propionibacterium* virus Stormborn, *Microbacterium paraoxydans, Thauera* species K11, *Escherichia* phage Ayreon, *Dickeya zeae, Pseudomonas* species HLS-6, *Mobiluncus curtisii, Paracoccus* species CBA4604, *Citrobacter freundii* complex species CFNIH2, *Citrobacter freundii* complex species CFNIH3, *Alkaliphilus metalliredigens, Lachnoclostridium bolteae, Ureaplasma urealyticum, Yersinia* virus L413C, *Pseudomonas* species M18, *Lachnoclostridium butyrate*-producing bacterium SM4/1, *Lachnoclostridium butyrate*-producing bacterium SS3/4, Plasmid ColV-K30, *Bacteroides cellulosilyticus,* Plasmid R1-19, *Haemophilus pittmaniae, Bradyrhizobium canariense, Streptococcus pseudopneumoniae, Corynebacterium resistens, Lactobacillus kefiranofaciens, Sphaerochaeta coccoides, Thermus thermophilus, Bifidobacterium animalis, Streptococcus mitis, Acinetobacter lwoffli, Porphyromonas asaccharolytica, Prevotella denticola, Prevotella disiens, Ornithobacterium rhinotracheale, Enterobacteria* phage CP-1639, *Burkholderia cepacia, Brevundimonas diminuta, Staphylococcus capitis, Pseudomonas fluorescens, Pseudomonas tolaasii, Veillonella parvula, Shigella* species AR-21793, *Turneriella parva, Roseburia hominis, Pseudomonas putida,* Human betaherpesvirus 6B, *Cutibacterium avidum, Cutibacterium granulosum, Parvimonas micra, Anaerococcus prevotii, Sphingobium indicum, Sphingobium japonicum, Variovorax paradoxus, Pseudomonas* phage PA11, *Enterobacter cloacae* complex, *Citrobacter amalonaticus, Agrobacterium tumefaciens, Verminephrobacter eiseniae, Bacteroides xylanisolvens, Corynebacterium* species L2-79-05, *Enterobacteria* phage 933 W sensu lato, *Lactobacillus backii, Thermus scotoductus, Sinorhizobium fredii, Rhizobium leguminosarum, Prevotella timonensis, Mesorhizobium ciceri, Veillonella atypica, Tessaracoccus flavescens, Enterobacter* species 638, *Streptococcus merionis, Micrococcus* species A1, *Blautia obeum, Polyangium brachysporum, Azoarcus olearius, Thiomonas arsenitoxydans, Ralstonia* species Is-C065, *Variovorax boronicumulans, Rothia mucilaginosa, Enterococcus cecorum, Bradyrhizobium oligotrophicum, Phycicoccus dokdonensis, Enterobacteria* phage VT1-Sakai, *Lactobacillus crispatus, Pseudomonas azotoformans, Pseudomonas fulva, Neisseria gonorrhoeae, Neisseria lactamica, Neisseria meningitidis, Burkholderia contaminans, Neisseria sicca, Prevotella dentalis, Lactobacillus gallinarum, Ochrobactrum anthropi, Peptoniphilus harei, Raoultella ornithinolytica, Enterobacter cloacae, Pantoea cypripedii, Acidovorax* species NA3, *Thiomonas* species CB2, *Enterobacteria* phage YYZ-2008, *Thermus brockianus, Afipia* genospecies 3, *Citrobacter braakii, Lactobacillus* phage Lv-1, *Burkholderia thailandensis, Proteus mirabilis, Klebsiella* species 2N3, *Prevotella fusca, Actinotignum schaalii, Serratia liquefaciens, Serratia marcescens, Kluyvera intermedia, Yersinia pestis, Yersinia pseudotuberculosis, Edwardsiella tarda, Aeromonas salmonicida, Anaerostipes hadrus, Prevotella* species oral taxon 299, *Myxococcus* mixed culture bacterium AM_gF3SD01_05, *Desulfitobacterium* mixed culture bacterium AX_gF3SD01_48, *Coma-* monas mixed culture bacterium PE_gF1DD01_04, *Streptococcus anginosus* group, *Rhodoplanes* species Z2-YC6860, *Citrobacter rodentium*, *Citrobacter gillenii*, *Altererythrobacter dongtanensis*, *Corynebacterium* species NML98-0116, *Actinomyces* species oral taxon 414, *Streptococcus* species oral taxon 064, *Streptococcus* species oral taxon 431, *Kocuria palustris*, *Haemophilus influenzae*, *Haemophilus parainfluenzae*, *Aggregatibacter aphrophilus*, *Collinsella aerofaciens*, *Campylobacter hominis*, *Streptococcus constellatus*, *Myxococcus* mixed culture bacterium AM_gF3SD01_05, *Desulfitobacterium* mixed culture bacterium AX_gF3SD01_48, *Comamonas* mixed culture bacterium PE_gF1DD01_04, *Streptococcus anginosus* group, *Rhodoplanes* species Z2-YC6860, *Citrobacter rodentium*, *Citrobacter gillenii*, *Altererythrobacter dongtanensis*, *Corynebacterium* species NML98-0116, *Actinomyces* species oral taxon 414, *Streptococcus* species oral taxon 064, *Streptococcus* species oral taxon 431, *Kocuria palustris*, *Haemophilus influenzae*, *Haemophilus parainfluenzae*, *Aggregatibacter aphrophilus*, *Collinsella aerofaciens*, *Campylobacter hominis*, *Streptococcus constellatus*, *Hydrogenophaga* species PBC, *Delftia acidovorans*, *Campylobacter ureolyticus*, *Leclercia adecarboxylata*, *Lactobacillus amylolyticus*, *Porphyromonas gingivalis*, *Lachnoclostridium saccharolyticum*, *Eggerthella lenta*, *Fusobacterium nucleatum*, *Faecalibacterium prausnitzii*, *Streptococcus* phage phi-SsUD.1, *Bacillus cereus* group, *Aerococcus christensenii*, *Burkholderia cepacia* complex, *Corynebacterium flavum*, *Micrococcus* species MG-2010-D12, *Hydrogenophaga* species PBC, and *Delftia acidovorans* are only expressed in non-cancerous individuals. Thus, the presence of microbes belonging to any one or more of the species Human herpesvirus 6, Human gammaherpesvirus 4, *Bordetella hinzii*, *Methylibium petroleiphilum*, *Shigella* species LN126, *Podoviridae*, *Lactobacillus jensenii*, *Burkholderia pseudomallei* group, *Pseudomonas* phage phi297, *Klebsiella michiganensis*, *Lactobacillus* species B164, *Streptococcus* species I-G2, *Kosakonia sacchari*, *Ruminococcus bicirculans*, *Prevotella jejuni*, *Bradyrhizobium* species llw1, *Agrobacterium tumefaciens* complex, *Pseudomonas* phage YMC/01/01/P52_PAE_BP, *Aerococcus sanguinicola*, *Prevotella* species S4-10, *Corynebacterium frankenforstense*, *Prevotella* species Sc00026, *Streptococcus* phage EJ-1, *Comamonas* bacterium 36B, *Micrococcus luteus*, *Pseudomonas sihuiensis*, *Staphylococcus haemolyticus*, *Streptococcus* phage phiD12, *Staphylococcus hominis*, *Pseudomonas* species ATCC 13867, *Streptococcus oralis*, *Streptococcus salivarius*, *Streptococcus suis*, *Acinetobacter chlamydia*-associated clinical sample 198-T, *Sphingobium* species TKS, *Streptococcus parasanguinis*, *Tessaracoccus aquimaris*, *Pluralibacter lignolyticus*, *Streptococcus intermedius*, *Ureaplasma parvum*, *Pseudomonas fluorescens* group, *Pseudomonas putida* group, *Sphingobium yanoikuyae*, *Aerococcus urinae*, *Burkholderia* species BDU6, *Sphingomonas* species LK11, *Bacillus cereus*, *Paenibacillus polymyxa*, *Streptococcus* species VT 162, *Comamonadaceae* bacterium B1, *Klebsiella quasipneumoniae*, *Corynebacterium simulans*, *Lactobacillus iners*, *Corynebacterium* species ATCC 6931, *Klebsiella* species NCTC 8172, *Lawsonella clevelandensis*, *Lactobacillus* species wkB8, *Sphingomonas taxi*, *Bradyrhizobium* species lamp2, *Streptococcus* phage SpSL1, *Enterobacteria* phage P88, *Corynebacterium riegelii*, *Corynebacterium imitans*, *Lactobacillus acidophilus*, *Lactobacillus buchneri*, *Lactobacillus delbrueckii*, *Lactobacillus helveticus*, *Cedecea neteri*, *Enterobacter hormaechei*, *Lactobacillus plantarum*, *Lactobacillus gasseri*, *Lactobacillus acetotolerans*, *Lactobacillus amylophilus*, *Lactobacillus amylovorus*, *Tessaracoccus flavus*, *Lactobacillus farciminis*, *Corynebacterium singulare*, *Erwinia gerundensis*, *Hoeflea* species IMCC20628, *Lactobacillus ruminis*, *Pseudomonas lini*, *Propionibacterium* phage PHLD30, *Propionibacterium* phage PHLD64, *Propionibacterium* phage PHL082, *Yersinia pseudotuberculosis* complex, *Actinomyces naeslundii*, *Acidovorax* species NA2, *Acidovorax* species P3, *Acidovorax* species P4, *Bifidobacterium adolescentis*, *Bifidobacterium breve*, *Corynebacterium aurimucosum*, *Negativicoccus massiliensis*, *Massilia* species WG5, *Turicibacter* species H121, *Corynebacterium diphtheriae*, *Corynebacterium glutamicum*, *Rothia aeria*, *Propionibacterium freudenreichii*, *Cutibacterium acnes*, *Pseudomonas* phage phi1, *Streptococcus* species A12, *Pseudomonas* species bs2935, *Pseudomonas* phage JBD44, *Pseudomonas* phage YMC11/07/P54_PAE_BP, *Gemella* species oral taxon 928, *Sinorhizobium* species RAC02, *Hydrogenophaga* species RAC07, *Acidovorax* species T1, Lambdavirus, *Sneathia amnii*, *Ndongobacter massiliensis*, *Acidaminococcus intestini*, *Varibaculum* species, *Streptococcus* species NPS 308, *Tessaracoccus* species 72.5-30, *Corynebacterium sphenisci*, *Corynebacterium atypicum*, *Streptococcus* phage IPPS, *Delftia* species HK171, *Klebsiella* species M5a1, *Staphylococcus* phage St 134, *Propionibacterium* virus Lauchelly, *Propionibacterium* virus PHL82M03, *Propionibacterium* virus PHLJ17M01, *Propionibacterium* virus Stormborn, *Microbacterium paraoxydans*, *Thauera* species K11, *Escherichia* phage Ayreon, *Dickeya zeae*, *Pseudomonas* species HLS-6, *Mobiluncus curtisii*, *Paracoccus* species CBA4604, *Citrobacter freundii* complex species CFNIH2, *Citrobacter freundii* complex species CFNIH3, *Alkaliphilus metalliredigens*, *Lachnoclostridium bolteae*, *Ureaplasma urealyticum*, *Yersinia* virus L413C, *Pseudomonas* species M18, *Lachnoclostridium* butyrate-producing bacterium SM4/1, *Lachnoclostridium* butyrate-producing bacterium SS3/4, Plasmid ColV-K30, *Bacteroides cellulosilyticus*, Plasmid R1-19, *Haemophilus pittmaniae*, *Bradyrhizobium canariense*, *Streptococcus pseudopneumoniae*, *Corynebacterium resistens*, *Lactobacillus kefiranofaciens*, *Sphaerochaeta coccoides*, *Thermus thermophilus*, *Bifidobacterium animalis*, *Streptococcus mitis*, *Acinetobacter lwoffii*, *Porphyromonas asaccharolytica*, *Prevotella denticola*, *Prevotella disiens*, *Ornithobacterium rhinotracheale*, *Enterobacteria* phage CP-1639, *Burkholderia cepacia*, *Brevundimonas diminuta*, *Staphylococcus capitis*, *Pseudomonas fluorescens*, *Pseudomonas tolaasii*, *Veillonella parvula*, *Shigella* species AR-21793, *Turneriella parva*, *Roseburia hominis*, *Pseudomonas putida*, Human betaherpesvirus 6B, *Cutibacterium avidum*, *Cutibacterium granulosum*, *Parvimonas micra*, *Anaerococcus prevotii*, *Sphingobium indicum*, *Sphingobium japonicum*, *Variovorax paradoxus*, *Pseudomonas* phage PA11, *Enterobacter cloacae* complex, *Citrobacter amalonaticus*, *Agrobacterium tumefaciens*, *Verminephrobacter eiseniae*, *Bacteroides xylanisolvens*, *Corynebacterium* species L2-79-05, *Enterobacteria* phage 933 W sensu lato, *Lactobacillus backii*, *Thermus scotoductus*, *Sinorhizobium fredii*, *Rhizobium leguminosarum*, *Prevotella timonensis*, *Mesorhizobium ciceri*, *Veillonella atypica*, *Tessaracoccus fiavescens*, *Enterobacter* species 638, *Streptococcus merionis*, *Micrococcus* species A1, *Blautia obeum*, *Polyangium brachysporum*, *Azoarcus olearius*, *Thiomonas arsenitoxydans*, *Ralstonia* species Is-C065, *Variovorax boronicumulans*, *Rothia mucilaginosa*, *Enterococcus cecorum*, *Bradyrhizobium oligotrophicum*, *Phycicoccus dokdonensis*, *Enterobacteria* phage VT1-Sakai, *Lactobacillus crispatus*, *Pseudomonas azotoformans*, *Pseudomonas fulva*, *Neisseria* gonorrhoeae, Neisseria lactamica, Neisseria meningitidis, Burkholderia contaminans, Neisseria sicca, Prevotella dentalis, Lactobacillus gallinarum, Ochrobactrum anthropi, Peptoniphilus harei, Raoultella ornithinolytica, Enterobacter cloacae, Pantoea cypripedii, Acidovorax species NA3, Thiomonas species CB2, Enterobacteria phage YYZ-2008, Thermus brockianus, Afipia genospecies 3, Citrobacter braakii, Lactobacillus phage Lv-1, Burkholderia thailandensis, Proteus mirabilis, Klebsiella species 2N3, Prevotella fusca, Actinotignum schaalii, Serratia liquefaciens, Serratia marcescens, Kluyvera intermedia, Yersinia pestis, Yersinia pseudotuberculosis, Edwardsiella tarda, Aeromonas salmonicida, Anaerostipes hadrus, Prevotella species oral taxon 299, Myxococcus mixed culture bacterium AM_gF3SD01_05, Desulfitobacterium mixed culture bacterium AX_gF3SD01_48, Comamonas mixed culture bacterium PE_gF1DD01_04, Streptococcus anginosus group, Rhodoplanes species Z2-YC6860, Citrobacter rodentium, Citrobacter gillenii, Altererythrobacter dongtanensis, Corynebacterium species NML98-0116, Actinomyces species oral taxon 414, Streptococcus species oral taxon 064, Streptococcus species oral taxon 431, Kocuria palustris, Haemophilus influenzae, Haemophilus parainfluenzae, Aggregatibacter aphrophilus, Collinsella aerofaciens, Campylobacter hominis, Streptococcus constellatus, Myxococcus mixed culture bacterium AM_gF3SD01_05, Desulfitobacterium mixed culture bacterium AX_gF3SD01_48, Comamonas mixed culture bacterium PE_gF1DD01_04, Streptococcus anginosus group, Rhodoplanes species 72-YC6860, Citrobacter rodentium, Citrobacter gillenii, Altererythrobacter dongtanensis, Corynebacterium species NML98-0116, Actinomyces species oral taxon 414, Streptococcus species oral taxon 064, Streptococcus species oral taxon 431, Kocuria palustris, Haemophilus influenzae, Haemophilus parainfluenzae, Aggregatibacter aphrophilus, Collinsella aerofaciens, Campylobacter hominis, Streptococcus constellatus, Hydrogenophaga species PBC, Delftia acidovorans, Campylobacter ureolyticus, Leclercia adecarboxylata, Lactobacillus amylolyticus, Porphyromonas gingivalis, Lachnoclostridium saccharolyticum, Eggerthella lenta, Fusobacterium nucleatum, Faecalibacterium prausnitzii, Streptococcus phage phi-SsUD.1, Bacillus cereus group, Aerococcus christensenii, Burkholderia cepacia complex, Corynebacterium flavum, Micrococcus species MG-2010-D12, Hydrogenophaga species PBC, and Delftia acidovorans in a sample corresponding to an individual (e.g., relative abundance as compared to reference samples obtained from cancerous or non-cancerous individuals) may provide an indication that the individual is non-cancerous.

Though FIGS. 6-22 refer to determination of whether an individual has bladder cancer, similar methods may be applied to determine whether an individual has any other cancer or urologic condition described herein.

TABLE 1 shows examples of microbes having utility in cancer diagnosis, at each level of taxonomic classification of microbes measured in the urine. The first column of the table lists taxonomic level, while the second column presents microbes characterized at that taxonomic level and having utility in diagnosis or detection of cancer as a microbe being evident in either cancer-positive individuals only or cancer-negative individuals only, or more prevalent in normal individuals (e.g., greater than 60% normalized expression) or more prevalent in individuals with cancer (e.g., greater than 60% normalized expression) or shared (e,g, 40-60% normalized expression) between normal individuals and individuals with cancer.

TABLE 2 shows examples of microbes and their use in cancer recurrence monitoring. Individuals were initially treated for bladder cancer via TURBT, followed by BCG instillation. Urine samples were collected from these individuals 3-12 months following their treatment. We then quantified the microbial constituency of the DNA present in the urine sample. Microbes listed are either enriched in individuals without bladder cancer recurrence (recurrence negative) or individuals with bladder cancer recurrence (recurrence positive). "Enriched" is defined as microbes with greater than greater than 60% normalized expression (see definitions) in a cohort. "Shared" in this context is defined as 40%-60% normalized expression across both cohorts. "Observed only in" is defined as 0% prevalence in the other cohort.

TABLE 2

| Usage of Microbe | Microbes Used |
|---|---|
| Cancer Recurrence Negative: Species Level | Corynebacterium jeikeium, Kocuria palustris, Lactobacillus crispatus, Amycolatopsis lurida, Finegoldia magna, Streptococcus thermophilus, Human polyomavirus 2, Shigella boydii, Spirometra erinaceieuropaei, Streptococcus pneumoniae, Schistosoma curassoni, Desulfitobacterium hafniense, Klebsiella pneumoniae, Shigella sonnei |
| Cancer Recurrence Positive: Species Level | Corynebacterium sp. NML98-0116, Corynebacterium resistens, Aerococcus urinae, Anaerococcus prevotii, Bacteroides fragilis, Clostridioides difficile, Erysipelothrix rhusiopathiae, Fusobacterium nucleatum, Helcococcus kunzii, Lawsonella clevelandensis, Ruminiclostridium sp. KB18, Ruminococcus bromii, Streptococcus agalactiae, Streptococcus anginosus, Streptococcus anginosus group, Streptococcus gallolyticus, Streptococcus infantarius, Streptococcus lutetiensis, Streptococcus macedonicus, Streptococcus mitis, Streptococcus parasanguinis, Streptococcus pasteurianus, Streptococcus pseudopneumoniae, Streptococcus pyogenes, Streptococcus sp. VT 162, Streptococcus sp. oral taxon 064, Streptococcus sp. oral taxon 431, Eubacterium rectale |

TABLE 3 shows examples of microbes at species-level taxonomic classification and their utility in the pathologic staging and grading of cancer. Microbes listed are enriched in individuals with specific stage and grade of their bladder cancer tumors. "Enriched" is defined as microbes with greater than 60% normalized expression (see Example 1) in a cohort.

TABLE 3

| Microbe Usage | Microbe Used |
| --- | --- |
| Classification of Bladder Cancer Tumors as stage Ta | *Streptococcus gallolyticus*, *Streptococcus pasteurianus*, *Pseudomonas* sp. 1217, Enterobacter aerogenes, Erysipelothrix rhusiopathiae, Bifidobacterium longum, Stenotrophomonas maltophilia, *Staphylococcus saprophyticus*, Ruminococcus bromii, Sneathia amnii, *Bradyrhizobium* sp., *Streptococcus salivarius*, Clostridioides difficile, Ralstonia insidiosa, Pseudomonas aeruginosa group, *Staphylococcus epidermidis*, *Streptococcus agalactiae*, *Streptococcus pyogenes*, Pseudomonas aeruginosa, Burkholderia cepacia, Faecalibacterium prausnitzii, *Streptococcus lutetiensis*, Anaerococcus prevotii, Barnesiella viscericola, Protopolystoma xenopodis, Eubacterium rectale, Firmicutes bacterium, Prevotella enoeca |
| Classification of Bladder Cancer Tumors as Stage T1 | Human Polyomavirus 1 |
| Classification of Bladder Cancer Tumors as Stage T2 | Morganella morganii, *Staphylococcus aureus*, Pseudomonas oleovorans, Pseudomonas pseudoalcaligenes, *Enterococcus* sp. 7L76 |
| Classification of Bladder Cancer Tumors as Stage T3 | Bacteroides fragilis, uncultured *Escherichia* sp., Bacteroides ovatus, Alistipes shahii, Gardnerella vaginalis, *Escherichia coli*, *Escherichia albertii*, *Salmonella enterica*, Rhodopseudomonas palustris, Shigella flexneri, *Bacteroides* sp. 148, Brugia timori, Bacteroides dorei, *Escherichia fergusonii*, Shigella dysenteriae, Parabacteroides distasonis, Bacteroides thetaiotaomicron, Shigella boydii |
| Classification of Bladder Cancer Tumors as Low Grade in pathology from microbes. | *Streptococcus gallolyticus*, *Streptococcus pasteurianus*, Pseudomonas aeruginosa group, Bifidobacterium longum, Pseudomonas aeruginosa, *Streptococcus salivarius*, Clostridioides difficile, Ruminococcus bromii, *Streptococcus lutetiensis* |
| Classification of Bladder Cancer Tumors as High Grade in pathology from microbes. | Bacteroides fragilis, Human polyomavirus 1, *Staphylococcus aureus*, Gardnerella vaginalis, Alistipes shahii, Bacteroides ovatus, *Staphylococcus epidermidis*, Brugia timori, Bacteroides dorei, *Bacteroides* sp. 148, Ralstonia insidiosa, Enterococcus faecalis, Stenotrophomonas maltophilia, Morganella morganii |

Example 3

Differential Enrichment of Microbial Diversity in Cancerous and Non-Cancerous Individuals FIGS. 23A-D show differential enrichment of microbial diversity, at the order level of taxonomic classification, in the urinary microbiomes of individuals who have been diagnosed with bladder cancer (cancerous individuals) and individuals who have not been diagnosed with bladder cancer (non-cancerous, or normal, individuals).

FIG. 23A shows shared microbial signatures at the order level between cancer and normal samples. Expression is quantified for microbes shared between the urinary microbiomes of cancerous and normal individuals. These include Bacialles, cyclophyllidea, clostridiales, micrococcales, rhizobiales, enterobacterales, corynebacteriales, lactobacillales, bifidobacetiales, and bacteriodales. The absolute expression of any one or more of Bacialles, cyclophyllidea, clostridiales, micrococcales, rhizobiales, enterobacterales, corynebacteriales, lactobacillales, bifidobacetiales, and bacteriodales may be used to detect a diseased state or to identify microbes that may be reintroduced into the bladder for curative treatment. For example, a curative treatment may comprise administering to an individual about $10^3$, $10^4$, $10^5$, $10^6$, $10^7$, $10^8$, $10^9$, $10^{10}$, $10^{11}$, $10^{12}$, $10^{13}$, $10^{14}$, $10^{15}$, or more than $10^{15}$ microbes of one or more such microbe populations.

FIG. 23B shows pooled enrichment scores for microbes enriched in the urinary microbiomes of normal individuals. This figure indicates there are microbes found significantly enriched in healthy individuals (Caudovirales, Veillonellales, Tissierellales, thermals, flavobacteriales, actinomycetlaes, mycoplasmatales, pasteurellales, and campylobacterales) and expressed at reduced levels in individuals with cancer. Any one or more of the microbes Caudovirales, Veillonellales, Tissierellales, thermals, flavobacteriales, actinomycetlaes, mycoplasmatales, pasteurellales, and campylobacterales may be used to detect a diseased state or to identify microbes that may be reintroduced into the bladder for curative treatment. For example, a curative treatment may comprise administering to an individual about $10^3$, $10^4$, $10^5$, $10^6$, $10^7$, $10^8$, $10^9$, $10^{10}$, $10^{11}$, $10^{12}$, $10^{13}$, $10^{14}$, $10^{15}$, or more than $10^{15}$ microbes of one or more such microbe populations.

FIG. 23C shows pooled enrichment scores for microbes enriched in the urinary microbiomes of cancerous individuals. These microbes (Saccharomycetales, xanthomonadales, pseudomondales, burholderiales, fusobacteriales, rhabditida) and are found significantly enriched in individuals with cancer and are expressed at reduced levels in healthy individuals. Thus, any one or more of the microbes Saccharomycetales, xanthomonadales, pseudomondales, burholderiales, fusobacteriales, and rhabditida may be used to detect a diseased state or to identify microbes that may be targeted by antimicrobial agents for curative treatment. For example, a curative treatment may comprise administering to an individual about $10^3$, $10^4$, $10^5$, $10^6$, $10^7$, $10^8$, $10^9$, $10^{10}$, $10^{11}$, $10^{12}$, $10^{13}$, $10^{14}$, $10^{15}$, or more than $10^{15}$ microbes of one or more such microbe populations.

FIG. 23D shows alpha-diversity scores for the urinary microbiomes of cancerous and non-cancerous individuals.

As shown in FIG. 23D, alpha-diversity scores are decreased in cancerous urinary microbiomes.

Example 4

Figure 24:
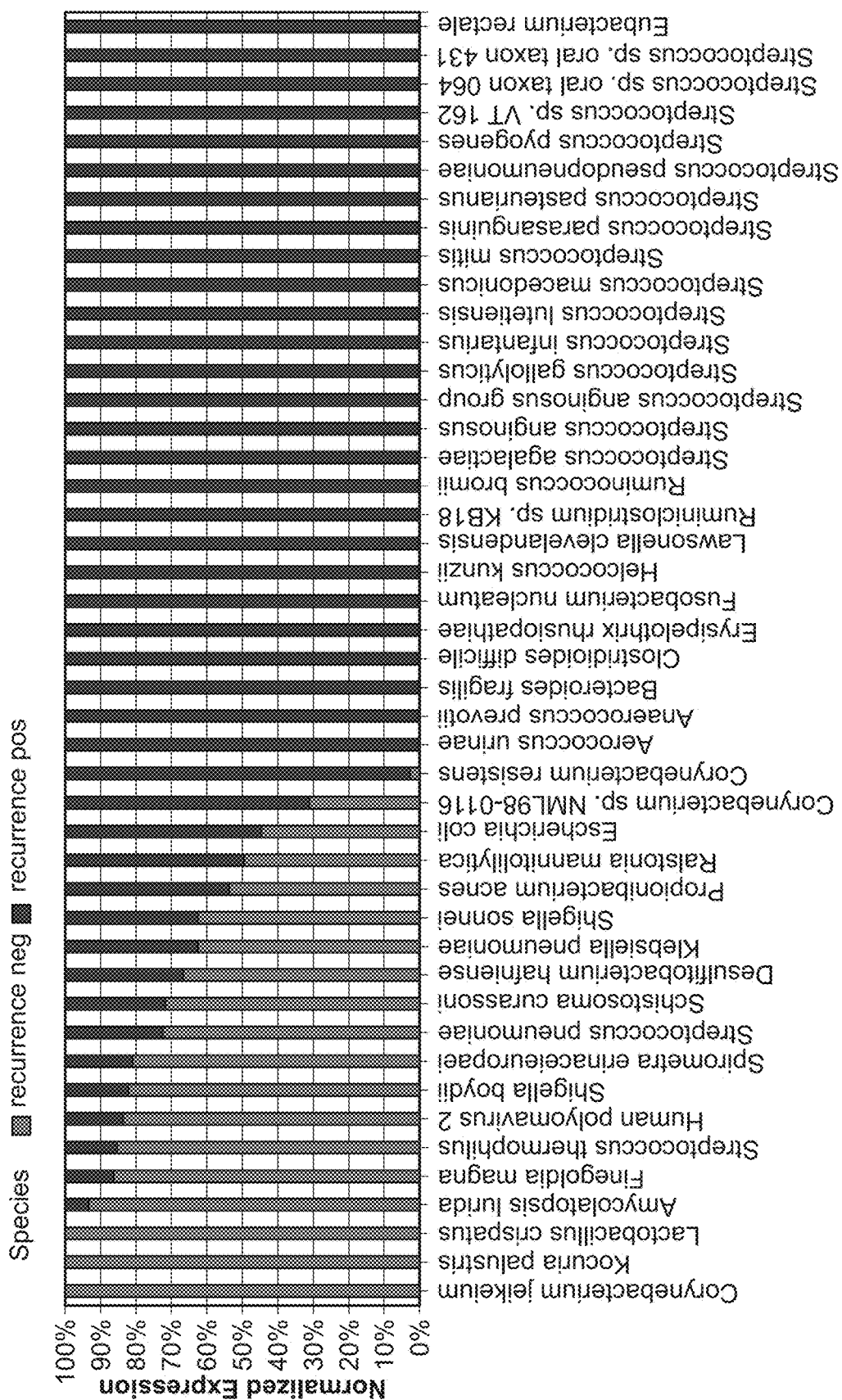
FIG. 24 shows differential enrichment of microbes in the urinary microbiomes of individuals who have been treated for bladder cancer but have had recurrence of the cancer and individuals who have been diagnosed with bladder cancer but have not had recurrence of the cancer.

Differential Expression of Microbes in Recurrent and Non-Recurrent Cancerous Individuals FIG. 24 shows differential enrichment of microbes in the urinary microbiomes (species-level chacarcterization) of individuals who have been treated for bladder cancer but have had recurrence of the cancer (recurrence+individuals) and individuals who have been diagnosed with bladder cancer but have not had recurrence of the cancer (recurrence-individuals) following treatment. This finding demonstrates the presence of any one or more populations of microbes that correspond to recurrent bladder cancer (Corynebacterium resistens, Aerococcus urinae, Anaerococcus prevotii, Bacteroides fragilis, Clostridioides difficile, Erysipelothrix rhusiopathiae, Fusobacterium nucleatum, Helcococcus kunzii, Lawsonella clevelandensis, Ruminiclostridium sp. KB18, Ruminococcus bromii, Streptococcus agalactiae, Streptococcus anginosus, Streptococcus anginosus group, Streptococcus gallolyticus, Streptococcus infantarius, Streptococcus lutetiensis, Streptococcus macedonicus, Streptococcus mitis, Streptococcus parasanguinis, Streptococcus pasteurianus, Streptococcus pseudopneumoniae, Streptococcus pyogenes, Streptococcus sp. VT 162, Streptococcus sp. oral taxon 064, Streptococcus sp. oral taxon 431, and [Eubacterium] rectale) (e.g., relative abundance as compared to reference samples obtained from individuals with recurrent bladder cancer or individuals without recurrent bladder cancer) may provide a basis of detection of bladder recurrence. Further, the presence of any one or more populations of microbes enriched in the bladders of individuals with a recurrence negative status (Corynebacterium jeikeium, Kocuria palustris, Lactobacillus crispatus, Amycolatopsis lurida, Echinostoma caproni, Parastrongyloides trichosuri, Toxocara canis, Finegoldia magna, Streptococcus thermophilus, Human polyomavirus 2, Shigella boydii, Spirometra erinaceieuropaei, Streptococcus pneumoniae, Schistosoma curassoni, Desulfitobacterium hafniense, Onchocerca flexuosa, Strongyloides papillosus, Klebsiella pneumoniae, and Shigella sonnei) (e.g., relative abundance as compared to reference samples obtained from individuals with recurrent bladder cancer or individuals without recurrent bladder cancer) may be used to identify successful treatment in bladder cancer patients. Further, these microbes may be used as putative treatment agents to drive the bladder to a balanced microbial state.

Example 5

Longitudinal Monitoring of a Cancerous Patient's Bladder Microbiome

Figure 25:
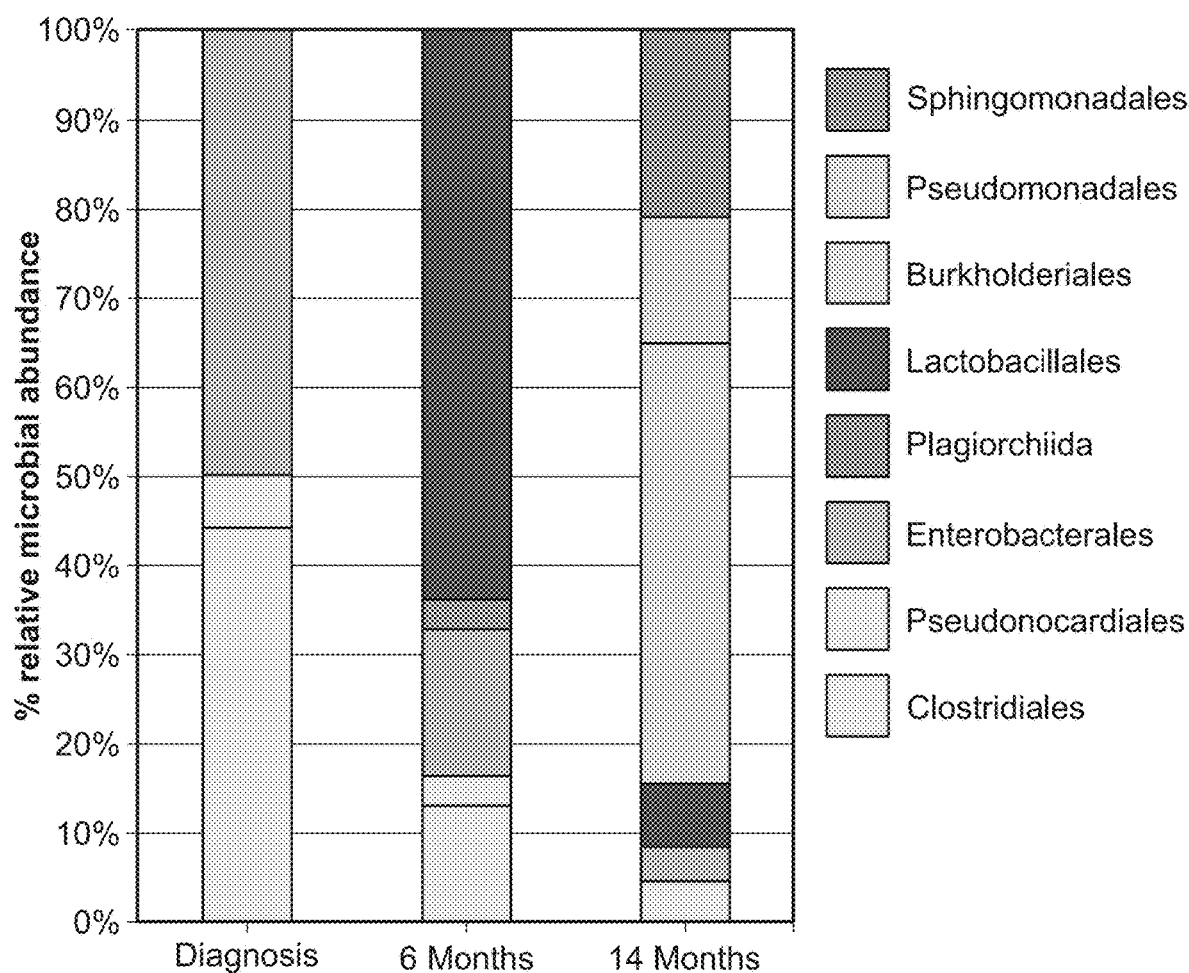
FIG. 25 shows microbial dynamics in an individual who has been diagnosed with recurrent bladder cancer.

FIG. 25 shows microbial dynamics (at the order level) in an individual who has been diagnosed with recurrent bladder cancer. The individual was initially diagnosed with a high grade Ta bladder cancer. Transurethral resection of the bladder tumor (TURBT) was performed to remove the tumor. An endoscopic evaluation 6 months after TURBT showed no recurrence. An endoscopic evaluation 11 months after TURBT showed suspicious results. The endoscopic evaluation was followed with a subsequent TURBT, and recurrence of a Tis grade bladder cancer was noted. Bacillus Calmette-Guérin (BCG) immunotherapy was initiated 13 months after the initial TURBT. Microbial expression levels were recorded 14 months after the initial TURBT. In an orthogonal analysis of host mutational load, multiple mutations were observed at both the 6-month and 14-month timepoints, suggesting residual disease and tumor evolution, as evidenced by the detection of diverse new mutations between 6 and 14 months. In tandem, we observe an expansion of microbes typically associated with immunosuppression/opportunistic pathogens seen over time and found to be associated with the cancerous state, including the orders Sphingomonadales, Pseudomonadales, and Burkholderiales. The orders sphingomonas and burkholderiales were previously characterized as associated with bladders harboring tumors—here we observe the dynamic evolution of the microbiome to a dysbiotic state: enrichment of the microbiome constituency with microbes with known associations to cancer.

TABLE 2 summarizes the microbes identified in the urine of individuals with recurrence-positive bladder cancer and recurrence-negative bladder cancers.

Example 6

Staging and Grading of Cancerous Patients Based on their Bladder Microbiome

Figure 26A:
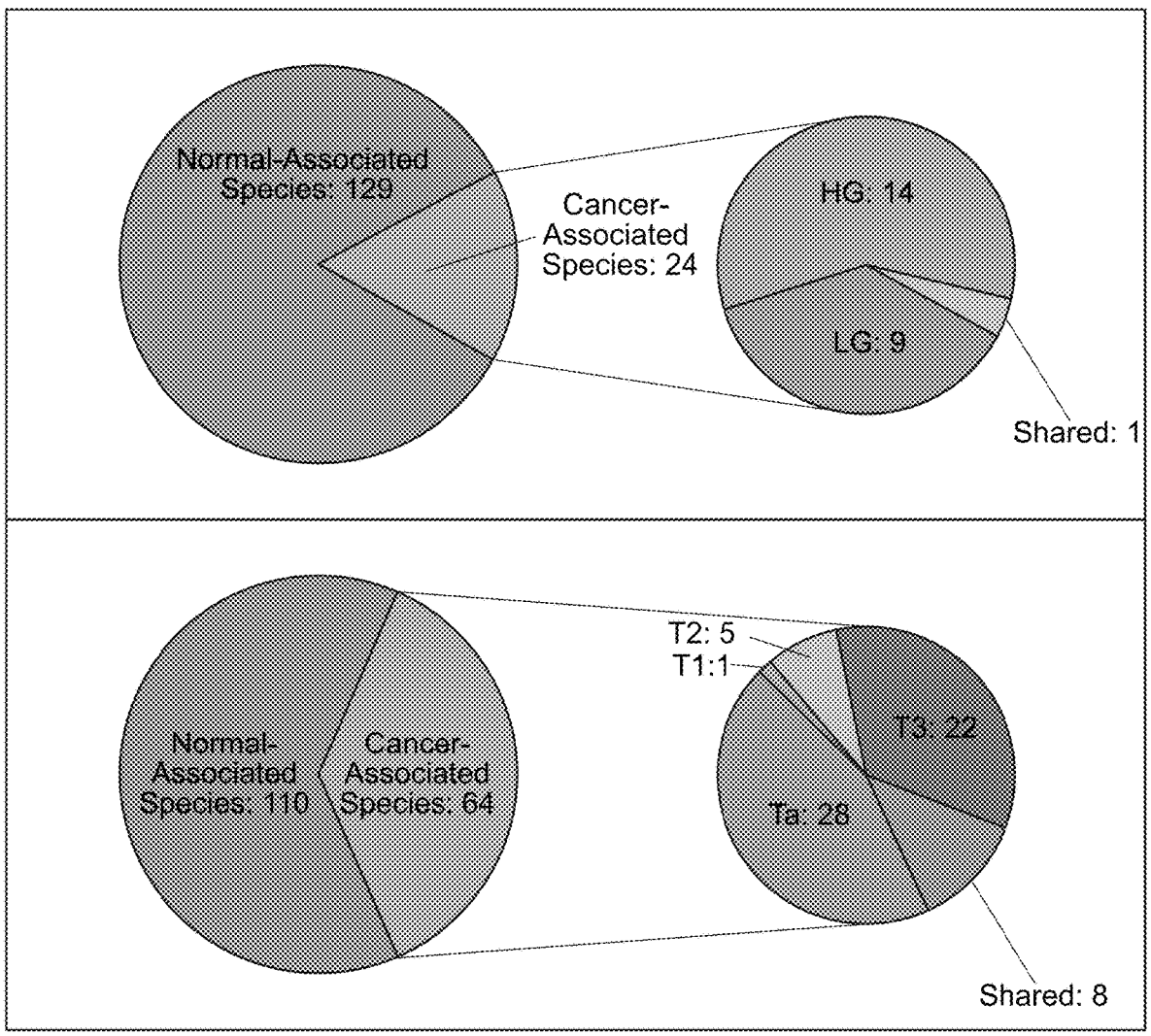
FIG. 26A shows staging and grading of individuals who have been diagnosed with bladder cancer.

In FIG. 26A, we characterized those microbial species (with normalized expression (see Example 1) in the 60-100% enrichment range for individuals with cancer) identified in urine that are enriched in particular grading or staging of the subsequent tumor resected via TURBT present in the bladder at the time of sample collection. Pathologic staging and grading were conducted in accordance with American Medical Association best practices. Among cancer-positive patients for which tumor grade data was available; we observed that at the species level, there were 24 total species with enriched expression in cancer patients. Of these species, 9 were enriched in low-grade tumors, 14 were enriched in high-grade tumors, and 1 species was shared between the grades. Similarly, among patients for whom staging information was available, we observed 64 cancer-specific species. Of these, 28 were enriched for Ta disease, 1 was enriched for T1 disease, 5 was enriched in T2 disease, and 22 were enriched in T3 disease, with 8 species shared across staging. These data suggest that microbial content of urine may be specific to the stage and grade of a tumor residing in the bladder. Further, these microbes may be used to understand the risk profile of the tumor by providing insight into stage and grade from a microbial measurement.

Figure 26B:
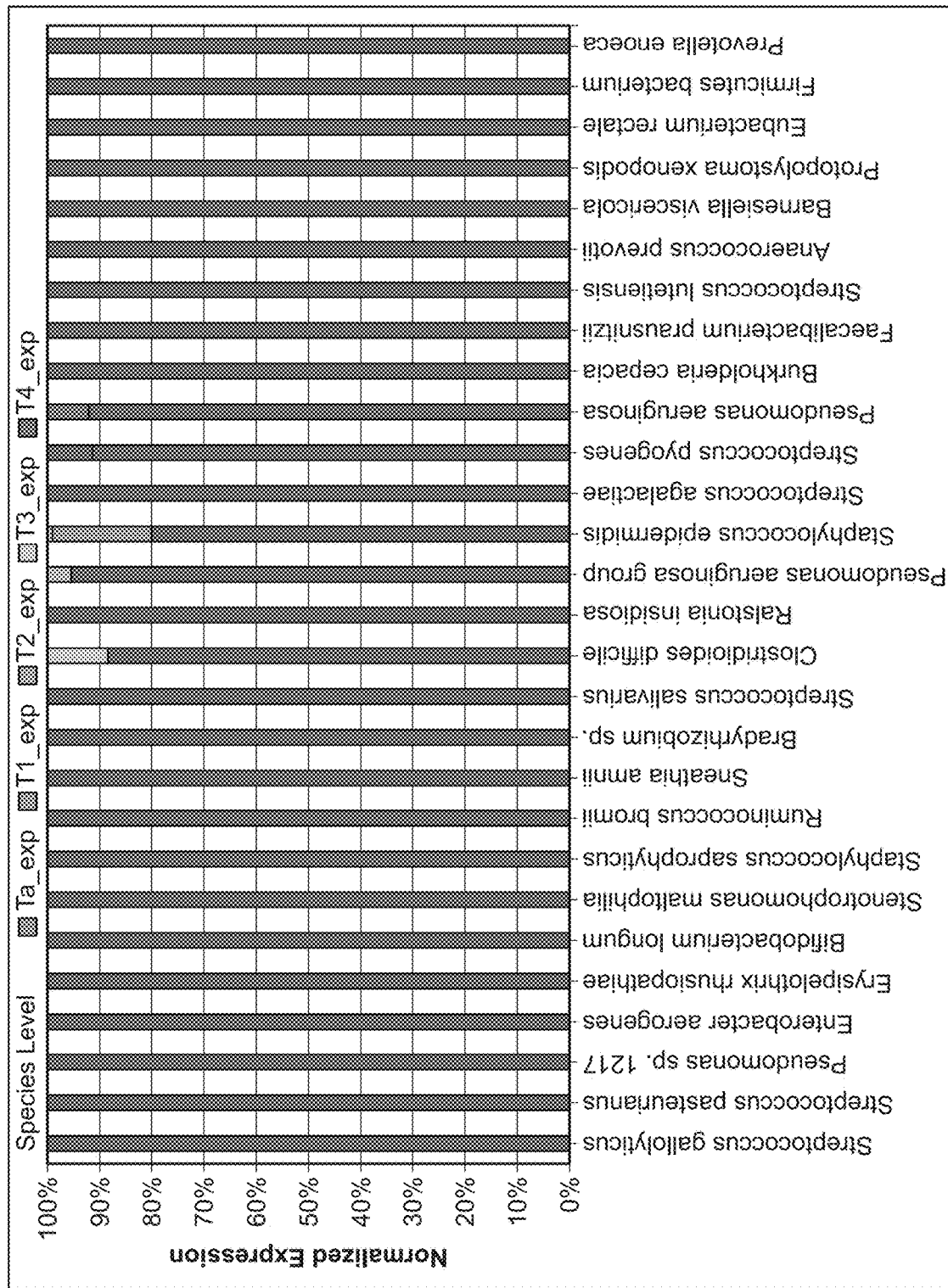
FIG. 26B shows differential enrichment of microbes at the species level in the urinary microbiomes of individuals who have confirmed stage Ta bladder cancer.

FIG. 26B shows normalized expression (see Example 1) of microbes in the urinary microbiomes of individuals with bladder cancer. Urine samples were collected while the bladder tumor was still present in the bladder. Subsequent to TURBT, the tumors underwent pathologic staging and grading by a pathologist. FIG. 26B shows the normalized expression of species Streptococcus gallolyticus, Streptococcus pasteurianus, Pseudomonas sp. 1217, Enterobacter aerogenes, Erysipelothrix rhusiopathiae, Bifidobacterium longum, Stenotrophomonas maltophilia, Staphylococcus saprophyticus, Ruminococcus bromii, Sneathia amnii, Bradyrhizobium sp., Streptococcus salivarius, Clostridioides difficile, Ralstonia insidiosa, Pseudomonas aeruginosa group, Staphylococcus epidermidis, Streptococcus agalactiae, Streptococcus pyogenes, Pseudomonas aeruginosa, Burkholderia cepacia, Faecalibacterium prausnitzii, Streptococcus lutetiensis, Anaerococcus prevotii, Barnesiella viscericola, Protopolystoma xenopodis, Eubacterium rectale, Firmicutes bacterium, and *Prevotella enoeca* enriched at greater than 60% prevalence in individuals with stage Ta bladder cancer. Thus, a combination of microbes enriched in individuals with stage Ta disease but rarely found in urine from individuals with stage T1, T2, T3, T4 or Tis tumors or rarely found in healthy individuals may define the microbial constituency associated with stage Ta bladder cancer. The relative abundance of any one or more of species *Streptococcus gallolyticus, Streptococcus pasteurianus, Pseudomonas* sp. 1217, *Enterobacter aerogenes, Erysipelothrix rhusiopathiae, Bifidobacterium longum, Stenotrophomonas maltophilia, Staphylococcus saprophyticus, Ruminococcus bromii, Sneathia amnii, Bradyrhizobium* sp., *Streptococcus salivarius, Clostridioides difficile, Ralstonia insidiosa, Pseudomonas aeruginosa* group, *Staphylococcus epidermidis, Streptococcus agalactiae, Streptococcus pyogenes, Pseudomonas aeruginosa, Burkholderia cepacia, Faecalibacterium prausnitzii, Streptococcus lutetiensis, Anaerococcus prevotii, Barnesiella viscericola, Protopolystoma xenopodis, Eubacterium rectale, Firmicutes bacterium,* and *Prevotella enoeca* in a sample corresponding to an individual (e.g., relative abundance as compared to reference samples obtained from individuals with recurrent bladder cancer or individuals without recurrent bladder cancer) may provide an indication of whether the individual possesses a stage Ta disease or not based on the relative abundance of microbes associated with normal bladders and those associated with diseased bladders. Further, if a sample corresponding to an individual is found to possess deficient levels of microbes typically found to be enriched in healthy individuals—the deficient microbes identified may form the basis of a treatment in which deficient microbe(s) are augmented by administration of that microbe(s) so as to bring the microbial constituency of the bladder back to the expected state for normal individuals. For example, about $10^3$, $10^4$, $10^5$, $10^6$, $10^7$, $10^8$, $10^9$, $10^{10}$, $10^{11}$, $10^{12}$, $10^{13}$, $10^{14}$, $10^{15}$, or more than $10^{15}$ microbes of one or more such species may be administered to an individual to reconstitute their bladder microbiome.

Figure 26C:
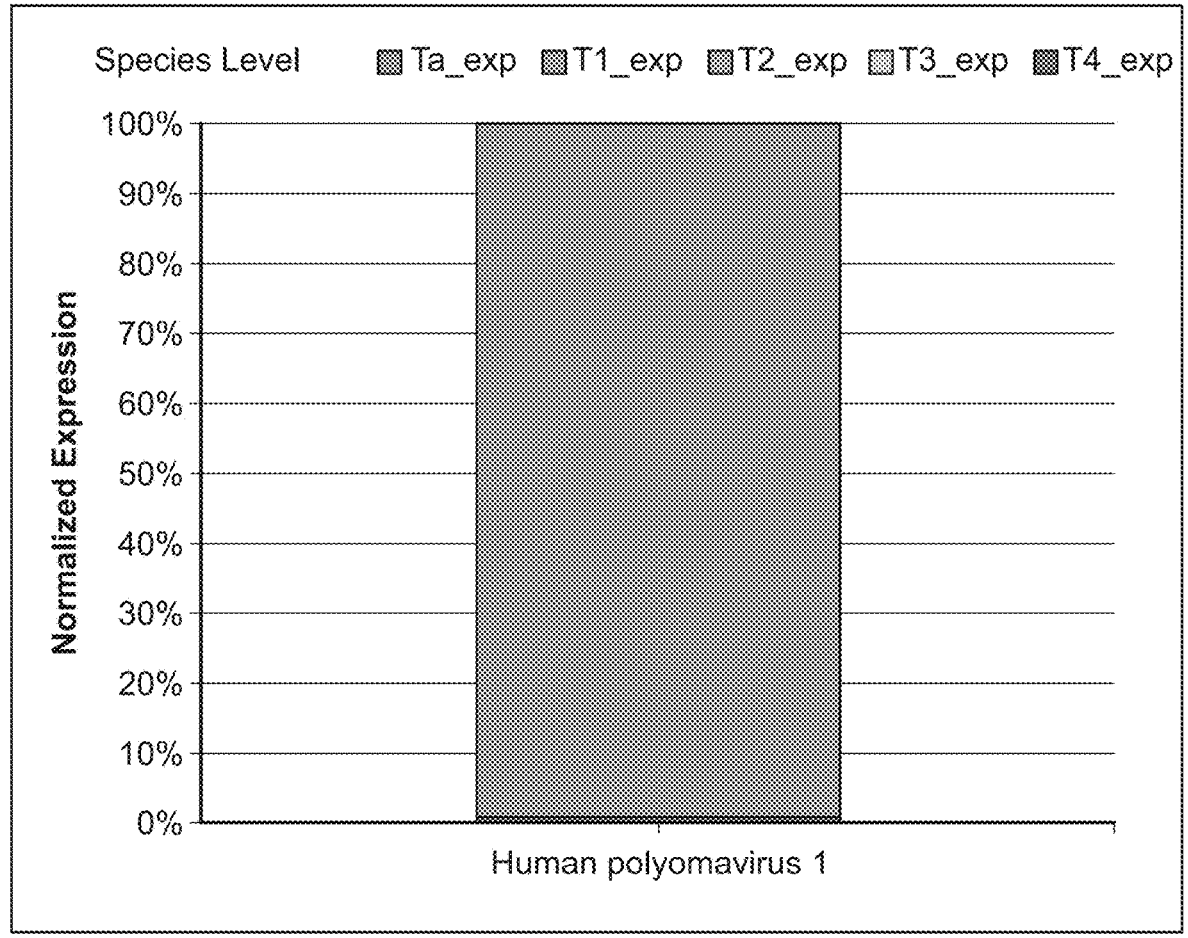
FIG. 26C shows differential enrichment of microbes at the species level in the urinary microbiomes of individuals who have confirmed stage T1 bladder cancer.

FIG. 26C shows normalized expression (see Example) of microbes in the urinary microbiomes of individuals with bladder cancer. Urine samples were collected while the bladder tumor was still present in the bladder. Subsequent to TURBT, the tumors underwent pathologic staging and grading by a pathologist. FIG. 26C shows the normalized expression of species Human Polyomavirus 1 enriched at greater than 60% prevalence in individuals with stage Ta disease. Thus, a combination of microbes enriched in individuals with stage T1 disease but rarely found in urine from individuals with stage Ta, T2, T3, T4 or Tis tumors or rarely found in healthy individuals may define the microbial constituency associated with stage T1 bladder cancer. The relative abundance of Human Polyomavirus 1 in a sample corresponding to an individual (e.g., relative abundance as compared to reference samples obtained from individuals with recurrent bladder cancer or individuals without recurrent bladder cancer) may provide an indication of whether the individual possesses a stage T1 disease or not based on the relative abundance of microbes associated with normal bladders and those associated with diseased bladders. Further, if a sample corresponding to an individual is found to possess deficient levels of microbes typically found to be enriched in healthy individuals—the deficient microbes identified may form the basis of a treatment in which deficient microbe(s) are augmented by administration of that microbe(s) so as to bring the microbial constituency of the bladder back to the expected state for normal individuals. For example, about $10^3$, $10^4$, $10^5$, $10^6$, $10^7$, $10^8$, $10^9$, $10^{10}$, $10^{11}$, $10^{12}$, $10^{13}$, $10^{14}$, $10^{15}$, or more than $10^{15}$ microbes of one or more such species may be administered to an individual to reconstitute their bladder microbiome.

Figure 26D:
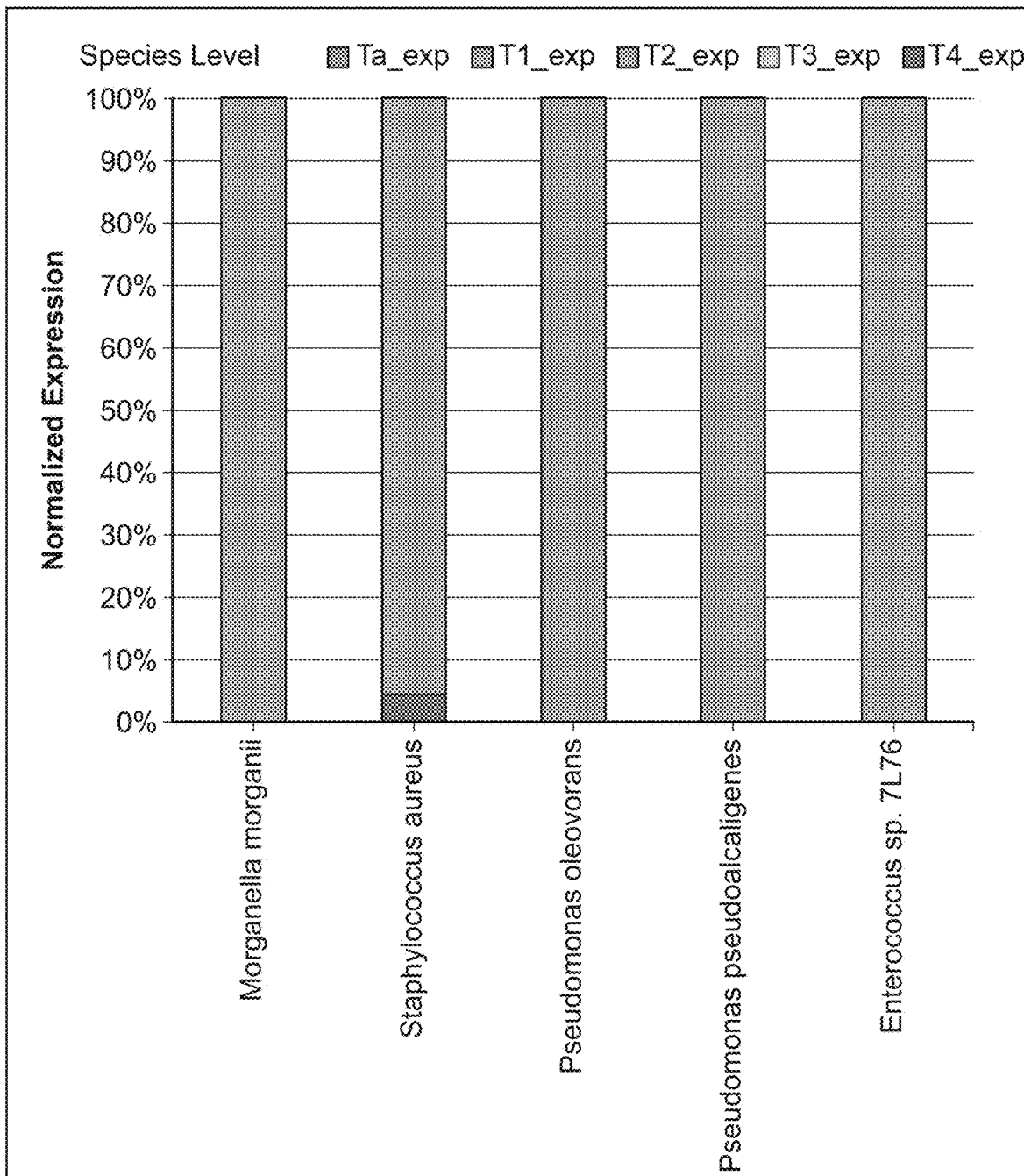
FIG. 26D shows differential enrichment of microbes at the species level in the urinary microbiomes of individuals who have confirmed stage T2 bladder cancer.

FIG. 26D shows normalized expression (see Example 1) of microbes in the urinary microbiomes of individuals with bladder cancer. Urine samples were collected while the bladder tumor was still present in the bladder. Subsequent to TURBT, the tumors underwent pathologic staging and grading by a pathologist. FIG. 26D shows the normalized expression of species *Morganella Morganii, Staphylococcus aureas, Pseudomonas oleovorans, Pseudomonas pseudoalcaligenes, Enterococcus* sp. 7L76 enriched at greater than 60% prevalence in individuals with stage T2 disease. Thus, a combination of microbes enriched in individuals with stage T2 disease but rarely found in urine from individuals with stage Ta, T1, T3, T4 or Tis tumors or rarely found in healthy individuals may define the microbial constituency associated with stage T2 bladder cancer. The relative abundance of any one or more of *Morganella Morganii, Staphylococcus aureas, Pseudomonas oleovorans, Pseudomonas pseudoalcaligenes,* and *Enterococcus* sp. 7L76 in a sample corresponding to an individual (e.g., relative abundance as compared to reference samples obtained from individuals with recurrent bladder cancer or individuals without recurrent bladder cancer) may provide an indication of whether the individual possesses a stage T2 disease or not based on the relative abundance of microbes associated with normal bladders and those associated with diseased bladders. Further, if a sample corresponding to an individual is found to possess deficient levels of microbes typically found to be enriched in healthy individuals—the deficient microbes identified can form the basis of a treatment in which deficient microbe(s) are augmented by administration of that microbe(s) so as to bring the microbial constituency of the bladder back to the expected state for normal individuals. For example, about $10^3$, $10^4$, $10^5$, $10^6$, $10^7$, $10^8$, $10^9$, $10^{10}$, $10^{11}$, $10^{12}$, $10^{13}$, $10^{14}$, $10^{15}$, or more than $10^{15}$ microbes of one or more such species may be administered to an individual to reconstitute their bladder microbiome.

Figure 26E:
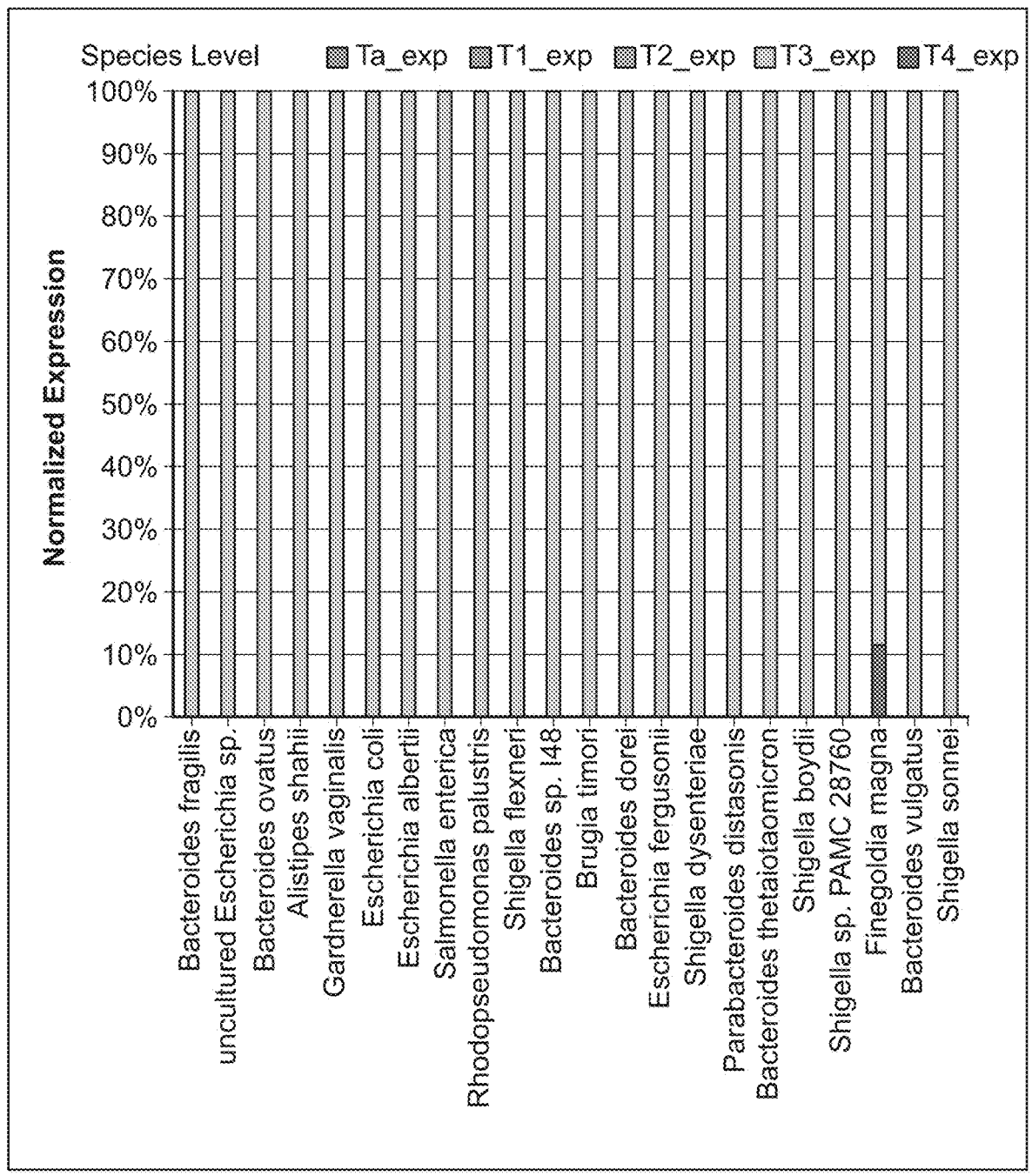
FIG. 26E shows differential enrichment of microbes at the species level in the urinary microbiomes of individuals who have confirmed stage T3 bladder cancer.

FIG. 26E shows normalized expression (see Example 1) of microbes in the urinary microbiomes of individuals with bladder cancer. Urine samples were collected while the bladder tumor was still present in the bladder. Subsequent to TURBT, the tumors underwent pathologic staging and grading by a pathologist. FIG. 26E shows the normalized expression of species *Bacteroides fragilis,* uncultured *Escherichia* sp., *Bacteroides ovatus, Alistipes shahii, Gardnerella vaginalis, Escherichia coli, Escherichia albertii, Salmonella enterica, Rhodopseudomonas palustris, Shigella flexneri, Bacteroides* sp. 148, *Brugia timori, Bacteroides dorei, Escherichia fergusonii, Shigella dysenteriae, Parabacteroides distasonis, Bacteroides thetaiotaomicron, Shigella boydii, Shigella* sp. PAMC 28760, *Finegoldia magna, Bacteroides vulgatus,* and *Shigella sonnei* enriched at greater than 60% prevalence in individuals with stage T3 disease. Thus, a combination of microbes enriched in individuals with stage T3 disease but rarely found in urine from individuals with stage Ta, T1, T2, T4 or Tis tumors or rarely found in healthy individuals may define the microbial constituency associated with stage T3 bladder cancer. The relative abundance of any one or more of *Bacteroides fragilis,* uncultured *Escherichia* sp., *Bacteroides ovatus, Alistipes shahii, Gardnerella vaginalis, Escherichia coli, Escherichia albertii, Salmonella enterica, Rhodopseudomonas palustris, Shigella flexneri, Bacteroides* sp. 148, *Brugia timori, Bacteroides dorei, Escherichia fergusonii, Shigella dysenteriae, Para-

*bacteroides distasonis*, *Bacteroides thetaiotaomicron*, *Shigella boydii*, *Shigella* sp. PAMC 28760, *Finegoldia magna*, *Bacteroides vulgatus*, and *Shigella sonnei* in a sample corresponding to an individual (e.g., relative abundance as compared to reference samples obtained from individuals with recurrent bladder cancer or individuals without recurrent bladder cancer) may provide an indication of whether the individual possesses a stage T3 disease or not based on the relative abundance of microbes associated with normal bladders and those associated with diseased bladders. Further, if a sample corresponding to an individual is found to possess deficient levels of microbes typically found to be enriched in healthy individuals—the deficient microbes identified may form the basis of a treatment in which deficient microbe(s) are augmented by administration of that microbe(s) so as to bring the microbial constituency of the bladder back to the expected state for normal individuals. For example, about $10^3$, $10^4$, $10^5$, $10^6$, $10^7$, $10^8$, $10^9$, $10^{10}$, $10^{11}$, $10^{12}$, $10^{13}$, $10^{14}$, $10^{15}$, or more than $10^{15}$ microbes of one or more such species may be administered to an individual to reconstitute their bladder microbiome.

Figure 26F:
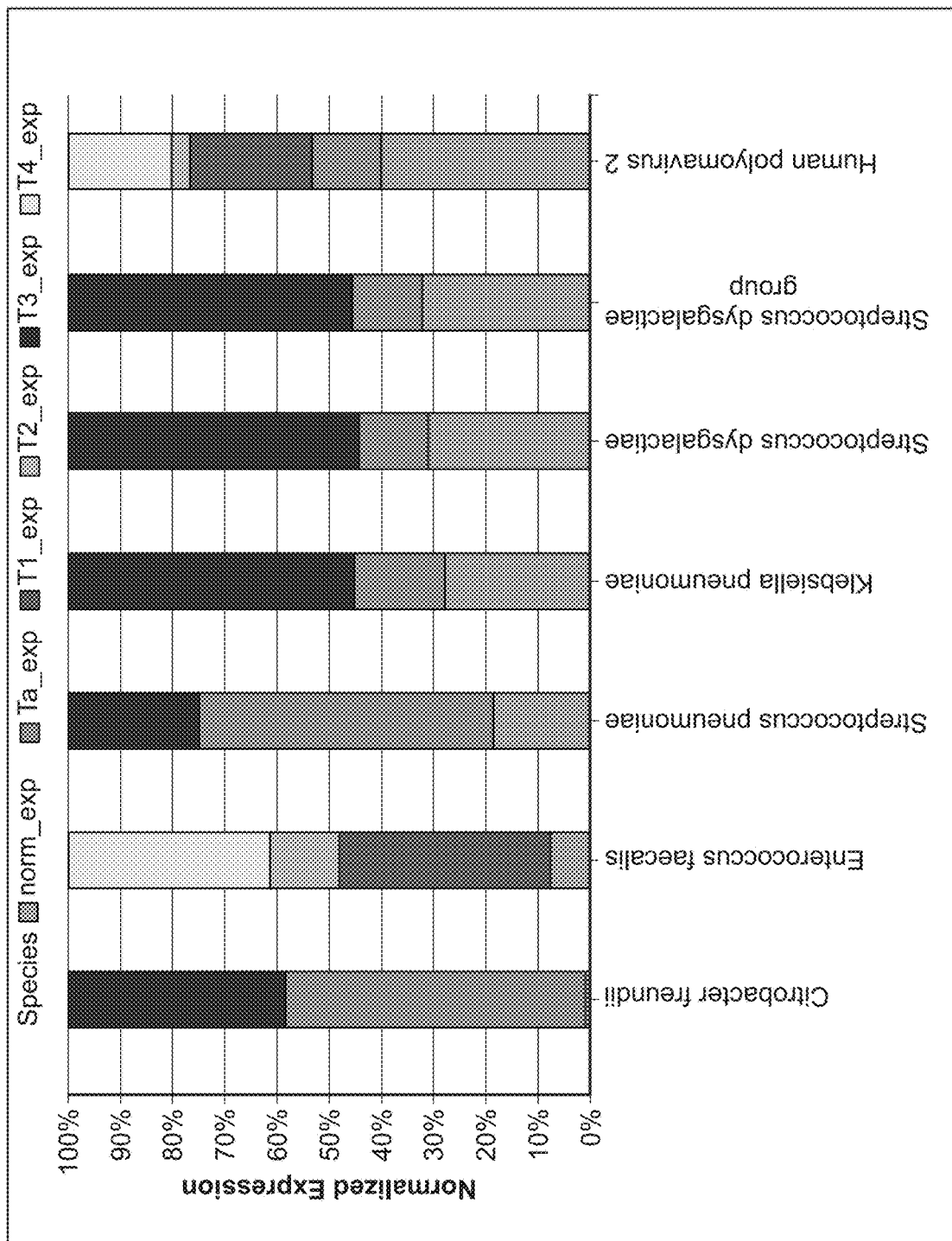
FIG. 26F shows differential enrichment of microbes at the species level in the urinary microbiomes of individuals who have confirmed staging of their bladder cancer.

FIG. 26F shows normalized expression (see Example 1) of microbes in the urinary microbiomes of individuals with bladder cancer. Urine samples were collected while the bladder tumor was still present in the bladder. Subsequent to TURBT, the tumors underwent pathologic staging and grading by a pathologist. FIG. 26F shows the normalized expression of species *Citrobacter freundii*, *Enterococcus faecalis*, *Streptococcus pneumoniae*, *Klebsiella pneumoniae*, *Streptococcus dysgalactiae*, *Streptococcus dysgalactiae* group, and Human Polyomavirus 2 enriched at greater than 60% prevalence in individuals with bladder cancer of various stages. Thus, a combination of microbes enriched in individuals with bladder cancer but rarely found in urine from healthy individuals may define the microbial constituency associated with bladder cancer. The relative abundance of *Citrobacter freundii*, *Enterococcus faecalis*, *Streptococcus pneumoniae*, *Klebsiella pneumoniae*, *Streptococcus dysgalactiae*, *Streptococcus dysgalactiae* group, Human Polyomavirus 2 in a sample corresponding to an individual (e.g., relative abundance as compared to reference samples obtained from individuals with recurrent bladder cancer or individuals without recurrent bladder cancer) may provide an indication of whether the individual possesses bladder cancer or not based on the relative abundance of microbes associated with normal bladders and those associated with diseased bladders. Further, if a sample corresponding to an individual is found to possess deficient levels of microbes typically found to be enriched in healthy individuals—the deficient microbes identified can form the basis of a treatment in which deficient microbe(s) are augmented by administration of that microbe(s) so as to bring the microbial constituency of the bladder back to the expected state for normal individuals. For example, about $10^3$, $10^4$, $10^5$, $10^6$, $10^7$, $10^8$, $10^9$, $10^{10}$, $10^{11}$, $10^{12}$, $10^{13}$, $10^{14}$, $10^{15}$, or more than $10^{15}$ microbes of one or more such species may be administered to an individual to reconstitute their bladder microbiome.

Figure 26G:
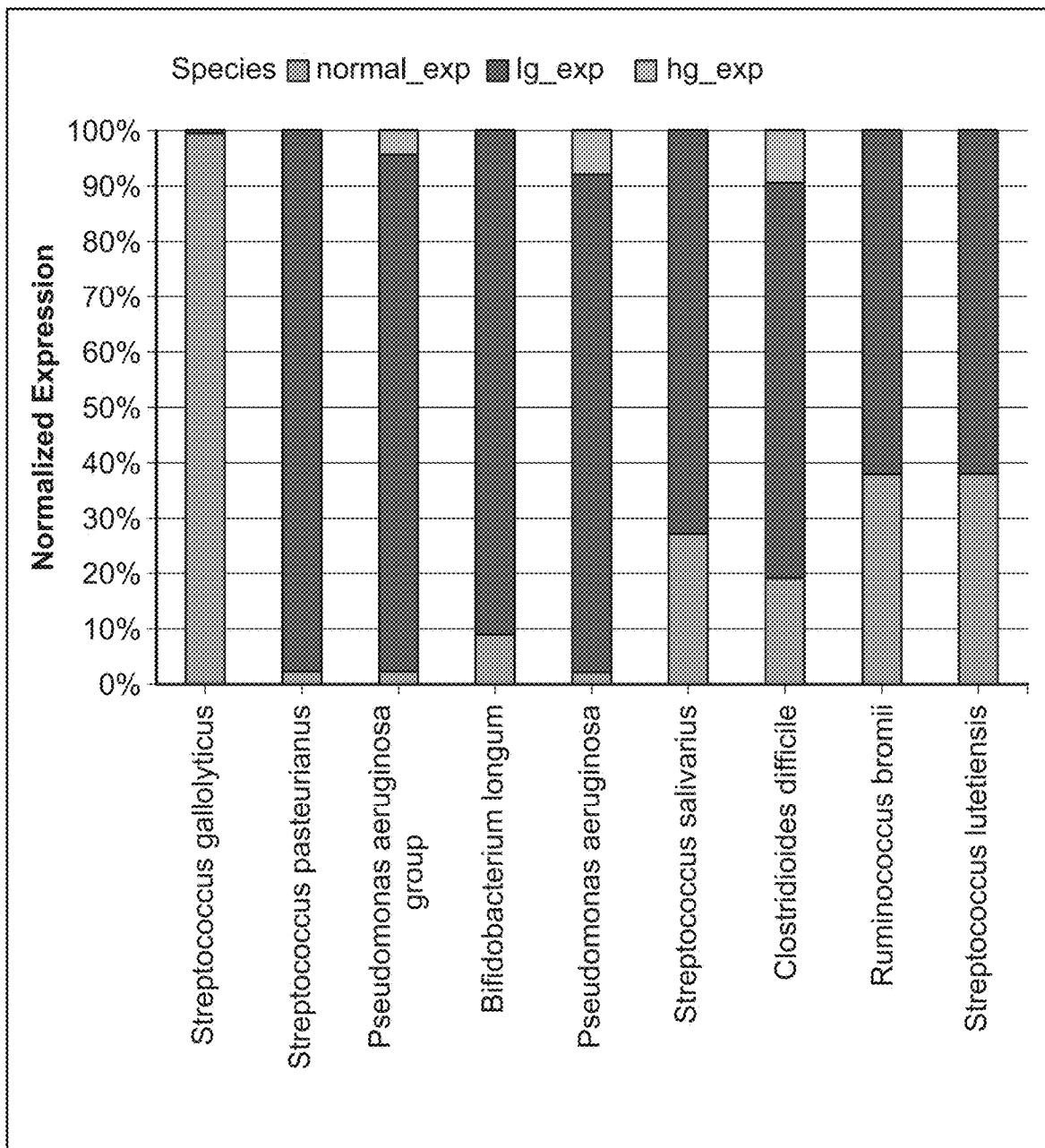
FIG. 26G shows differential enrichment of microbes at the species level in the urinary microbiomes of individuals who have confirmed low grade (LG) bladder cancer.

FIG. 26G shows normalized expression (see Example 1) of microbes in the urinary microbiomes of individuals with bladder cancer. Urine samples were collected while the bladder tumor was still present in the bladder. Subsequent to TURBT, the tumors underwent pathologic staging and grading by a pathologist. FIG. 26G shows the normalized expression of species *Streptococcus gallolyticus*, *Streptococcus pasteurianus*, *Pseudomonas aeruginosa* group, *Bifidobacterium longum*, *Pseudomonas aeruginosa*, *Streptococcus salivarius*, *Clostridioides difficile*, *Ruminococcus bromii*, and *Streptococcus lutetiensis* enriched at greater than greater than 60% prevalence in individuals with low-grade (lg) disease. Thus, a combination of microbes enriched in individuals with low-grade disease but rarely found in urine from individuals with high-grade tumors or rarely found in healthy individuals may define the microbial constituency associated with low grade bladder cancer. The relative abundance of any one or more of *Streptococcus gallolyticus*, *Streptococcus pasteurianus*, *Pseudomonas aeruginosa* group, *Bifidobacterium longum*, *Pseudomonas aeruginosa*, *Streptococcus salivarius*, *Clostridioides difficile*, *Ruminococcus bromii*, and *Streptococcus lutetiensis* in a sample corresponding to an individual (e.g., relative abundance as compared to reference samples obtained from individuals with recurrent bladder cancer or individuals without recurrent bladder cancer) may provide an indication of whether the individual possesses low-grade disease or not based on the relative abundance of microbes associated with normal bladders and those associated with diseased bladders. Further, if a sample corresponding to an individual is found to possess deficient levels of microbes typically found to be enriched in healthy individuals—the deficient microbes identified may form the basis of a treatment in which deficient microbe(s) are augmented by administration of that microbe(s) so as to bring the microbial constituency of the bladder back to the expected state for normal individuals. For example, about $10^3$, $10^4$, $10^5$, $10^6$, $10^7$, $10^8$, $10^9$, $10^{10}$, $10^{11}$, $10^{12}$, $10^{13}$, $10^{14}$, $10^{15}$, or more than $10^{15}$ microbes of one or more such species may be administered to an individual to reconstitute their bladder microbiome.

Figure 26H:
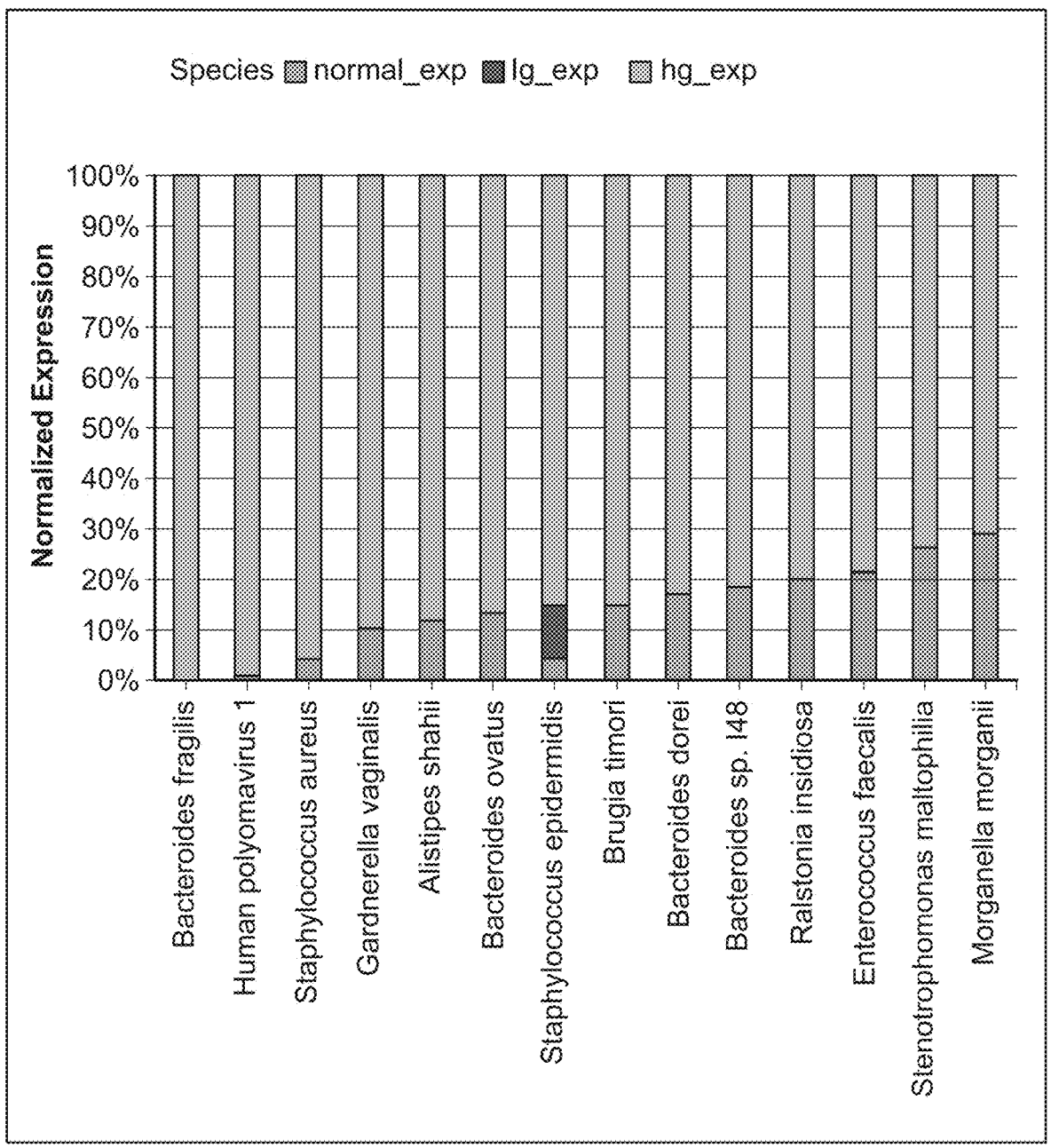
FIG. 26H shows differential enrichment of microbes at the species level in the urinary microbiomes of individuals who have confirmed high grade (HG) bladder cancer.

FIG. 26H shows normalized expression (see Example 1) of microbes in the urinary microbiomes of individuals with bladder cancer. Urine samples were collected while the bladder tumor was still present in the bladder. Subsequent to TURBT, the tumors underwent pathologic staging and grading by a pathologist. FIG. 26H shows the normalized expression of species *Bacteroides fragilis*, Human polyomavirus 1, *Staphylococcus aureus*, *Gardnerella vaginalis*, *Alistipes shahii*, *Bacteroides ovatus*, *Staphylococcus epidermidis*, *Brugia timori*, *Bacteroides dorei*, *Bacteroides* sp. 148, *Ralstonia insidiosa*, *Enterococcus faecalis*, *Stenotrophomonas maltophilia*, and *Morganella morganii* enriched at greater than 60% prevalence in individuals with high-grade (hg) disease. Thus, a combination of microbes enriched in individuals with high-grade disease but rarely found in urine from individuals with low-grade tumors or rarely found in healthy individuals may define the microbial constituency associated with high-grade bladder cancer. The relative abundance of *Bacteroides fragilis*, Human polyomavirus 1, *Staphylococcus aureus*, *Gardnerella vaginalis*, *Alistipes shahii*, *Bacteroides ovatus*, *Staphylococcus epidermidis*, *Brugia timori*, *Bacteroides dorei*, *Bacteroides* sp. 148, *Ralstonia insidiosa*, *Enterococcus faecalis*, *Stenotrophomonas maltophilia*, and *Morganella morganii* in a sample corresponding to an individual (e.g., relative abundance as compared to reference samples obtained from individuals with recurrent bladder cancer or individuals without recurrent bladder cancer) may provide an indication of whether the individual possesses high-grade disease or not based on the relative abundance of microbes associated with normal bladders and those associated with diseased bladders. Further, if a sample corresponding to an individual is found to possess deficient levels of microbes typically found to be enriched in healthy individuals—the deficient microbes identified may form the basis of a treatment in which deficient microbe(s) are augmented by administration of that microbe(s) so as to bring the microbial constituency of the bladder back to the expected state for normal individuals. For example, about $10^3$, $10^4$, $10^5$, $10^6$, $10^7$, $10^8$, $10^9$, $10^{10}$, $10^{11}$, $10^{12}$, $10^{13}$, $10^{14}$, $10^{15}$, or more than $10^{15}$ microbes of one or more such species may be administered to an individual to reconstitute their bladder microbiome.

TABLE 3 summarizes microbes at species level and their association with the pathologic staging and grading of cancer. Microbes listed are enriched in individuals with specific stage or grade of their bladder cancer tumors. "Enriched" may be defined as microbes with greater than 60% normalized expression (see Example 1) in a cohort.

Example 7

Machine Learning Classification of Bladder Cancers from Urinary Microbiomes

Figure 27:
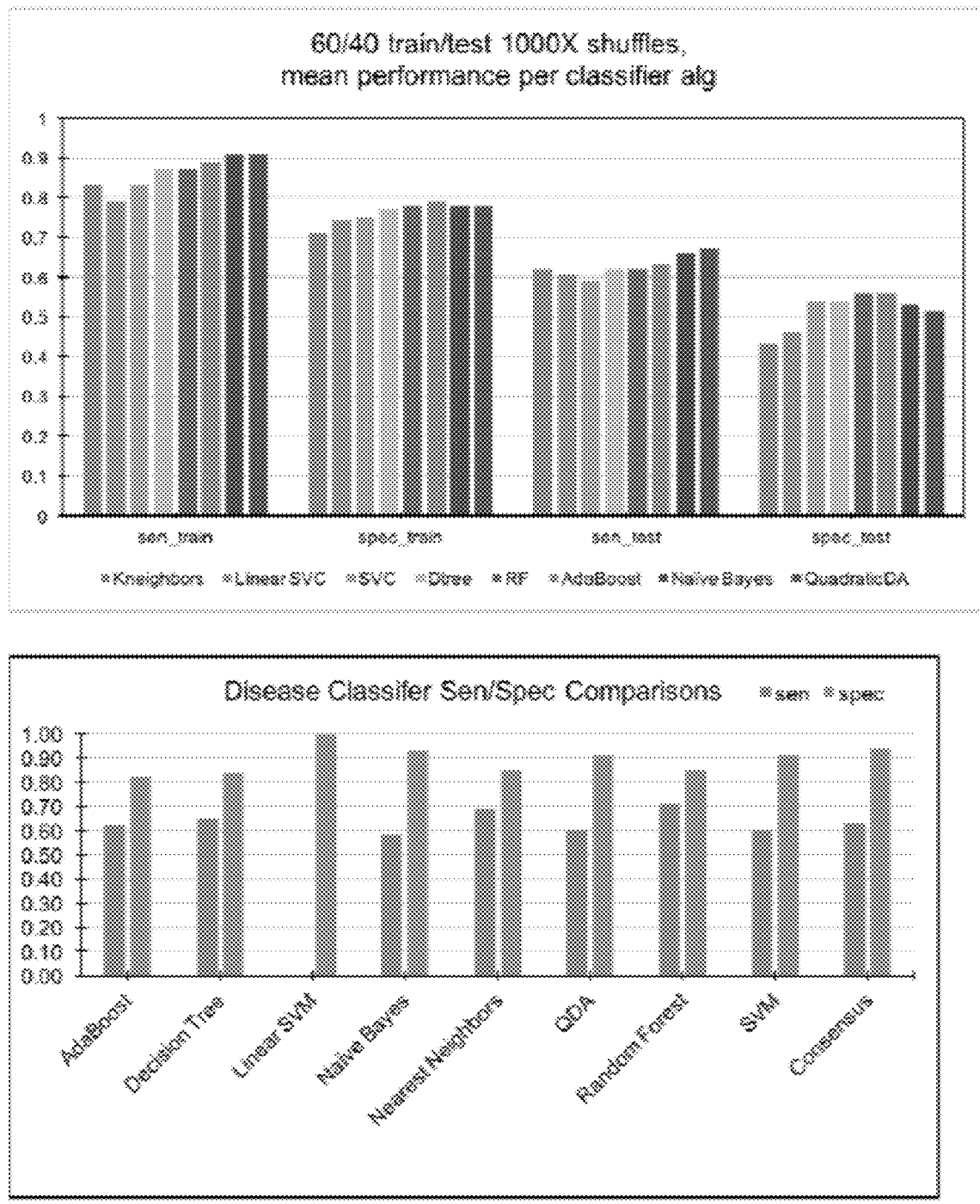
FIG. 27 shows the performance of a variety of machine learning techniques in the classification of bladder cancer from urinary microbiomes.
Figure 28A:
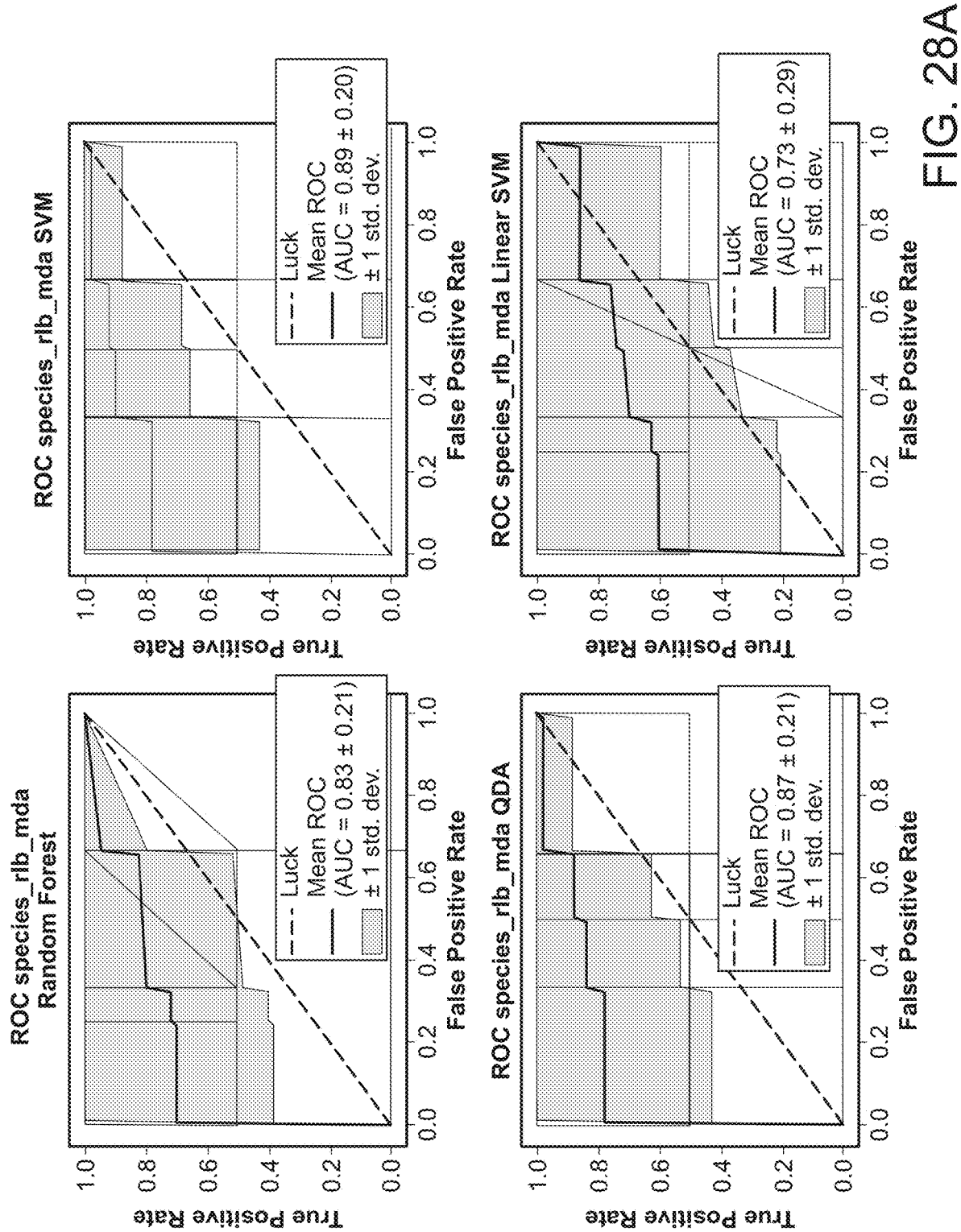
FIG. 28A shows a first set of receiver operator characteristic (ROC) curves for machine learning techniques used to classify bladder cancer from urinary microbiomes.
Figure 28B:
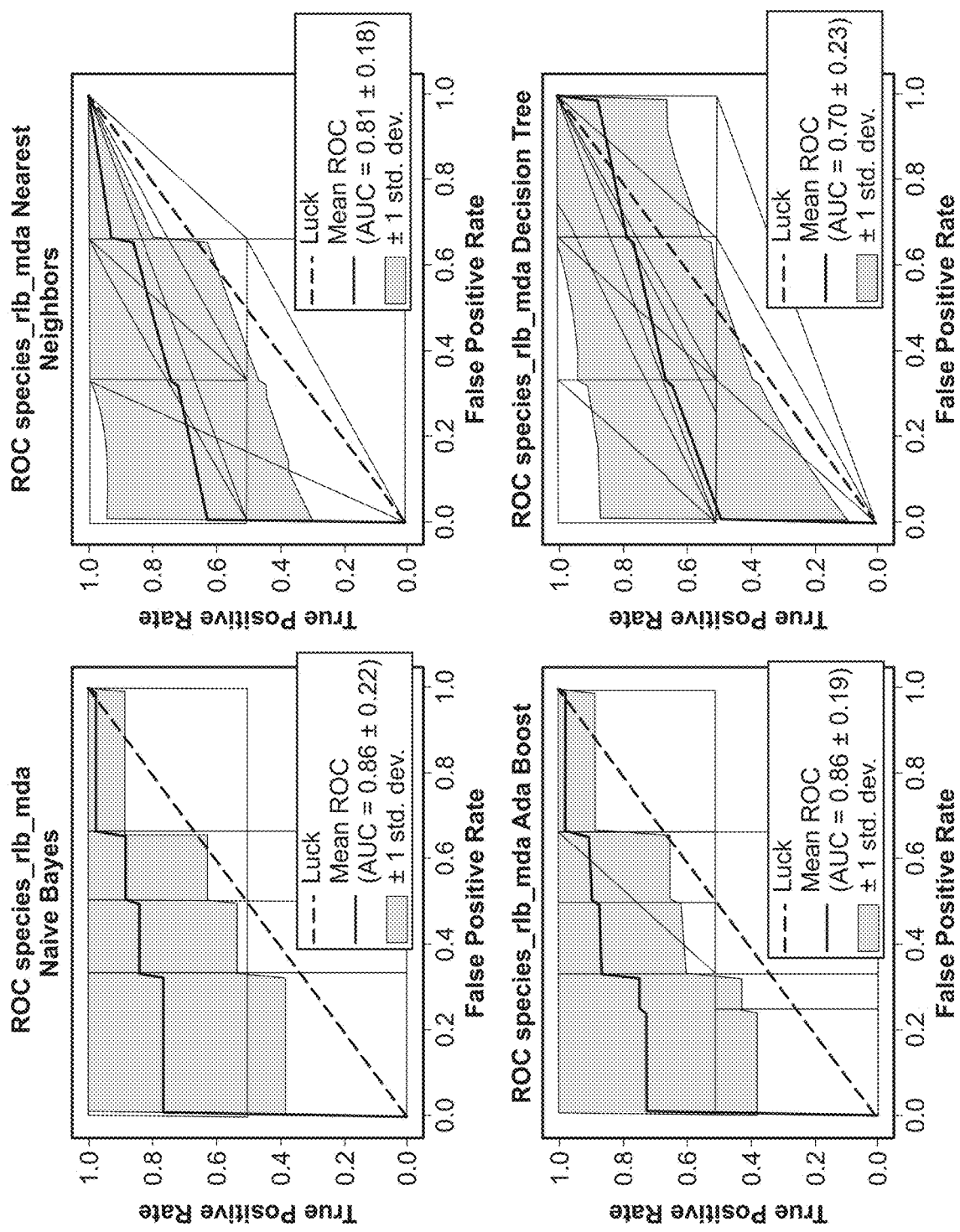
FIG. 28B shows a second set of receiver operator characteristic (ROC) curves for machine learning techniques used to classify bladder cancer from urinary microbiomes.

FIG. 27 shows the performance of a variety of machine learning techniques (K-nearest neighbors, linear SVC, Decision tree, random forest, Ada boost, Naïve Bayes, and Quadratic Discriminant Analysis) in the classification of bladder cancer from urinary microbiomes. Microbial measures conducted on sequenced urine-derived DNA served as the underlying data for the disease classification techniques. To assess the performance of each classifier, a 60/40 train/test cross validation was performed using 1000× randomized shuffles. K-fold cross validation was performed with k=25. For each classifier, we examined the receiver operator characteristic curve (ROC) to infer the maximal sensitivity and specificity of the algorithms, as shown in FIGS. 28A-28B. We then obtained the consensus of the algorithms' performance (FIG. 27, lower panel) and found that the consensus of the classifiers predicted the presence of cancer from microbial measurements along with a preliminary sensitivity of 63% and a preliminary specificity of 92%.

Figure 40A:
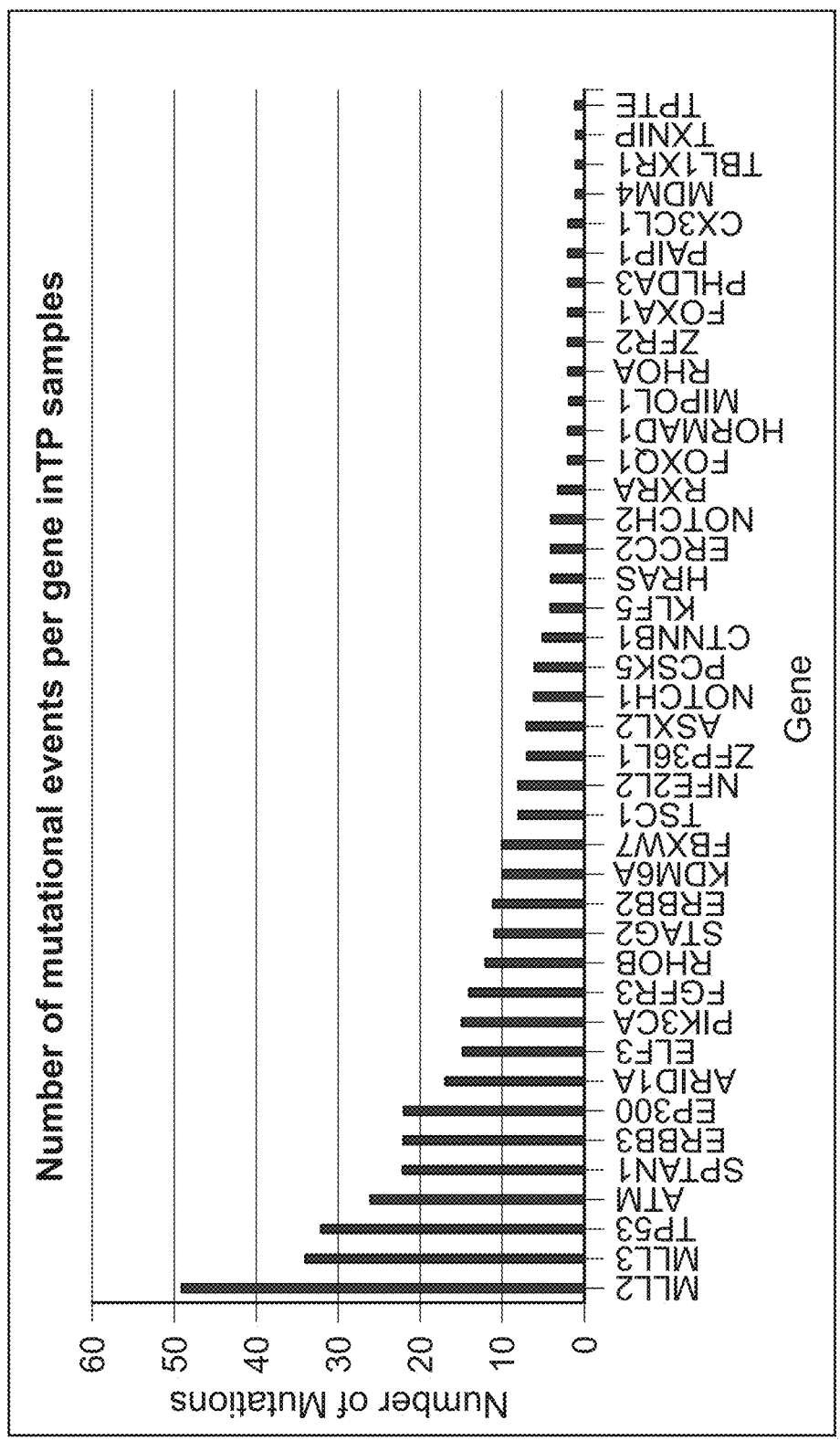
FIG. 40A shows genetic mutations associated with bladder cancer that were detected in a subject's urine.
Figure 40B:
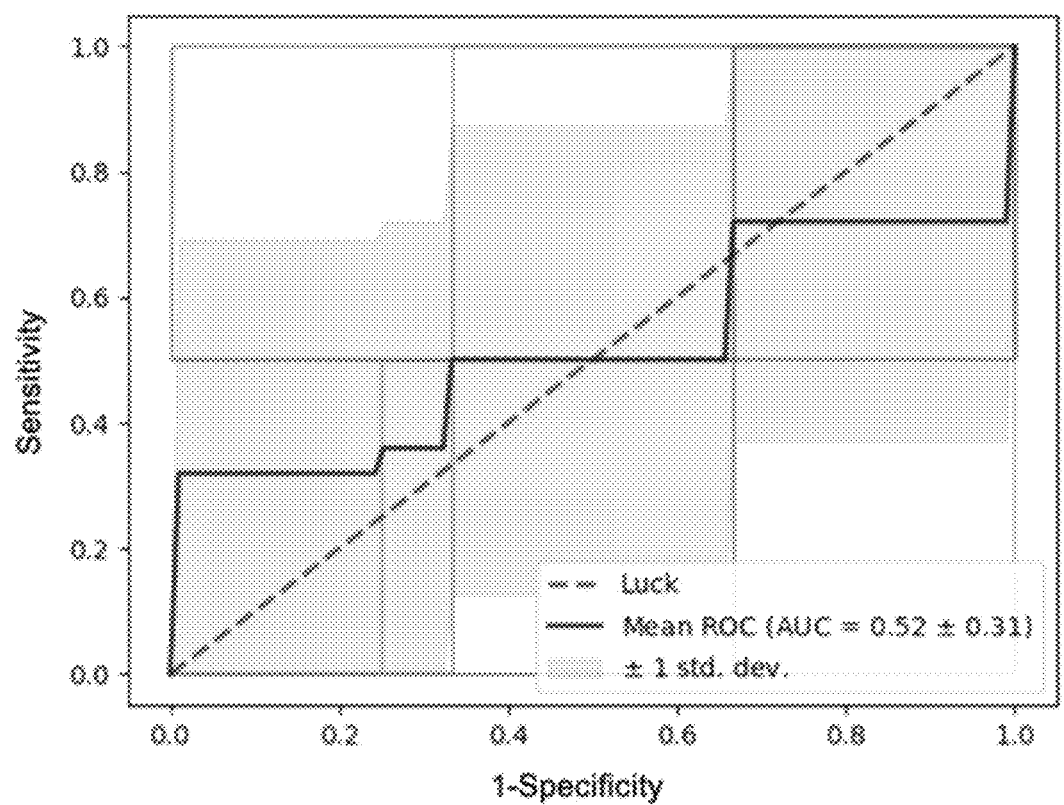
FIG. 40B shows results from a linear SVM trained on microbial normalized (mean) expression data for each patient and microbe $e_{i,j}$ using 25-fold cross validation, where sensitivity and specificity are no better than a coin flip.
Figure 40C:
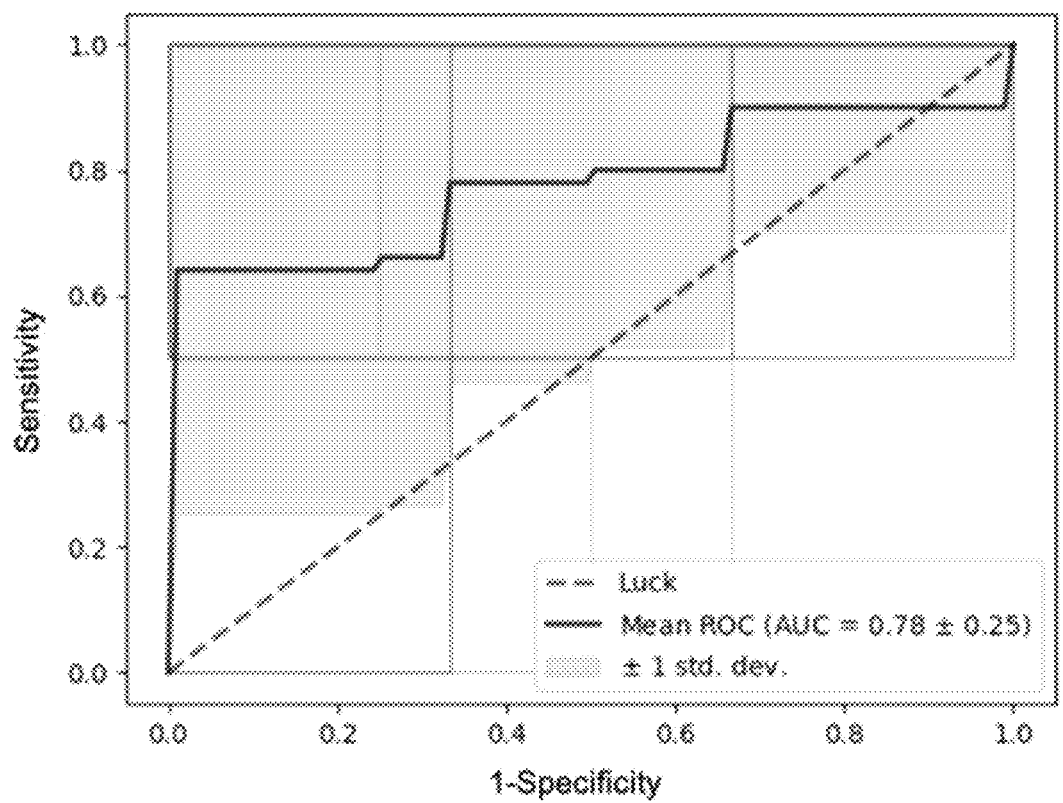
FIG. 40C shows results from a linear SVM trained on non-linear dimensionality reduced normalized (mean) expression data using the "RLB" distance metric listed in Table 1 of Koleff; et. al using 25-fold cross validation, where sensitivity and specificity vastly improved to AUC=0.78±0.25.
Figure 40D:
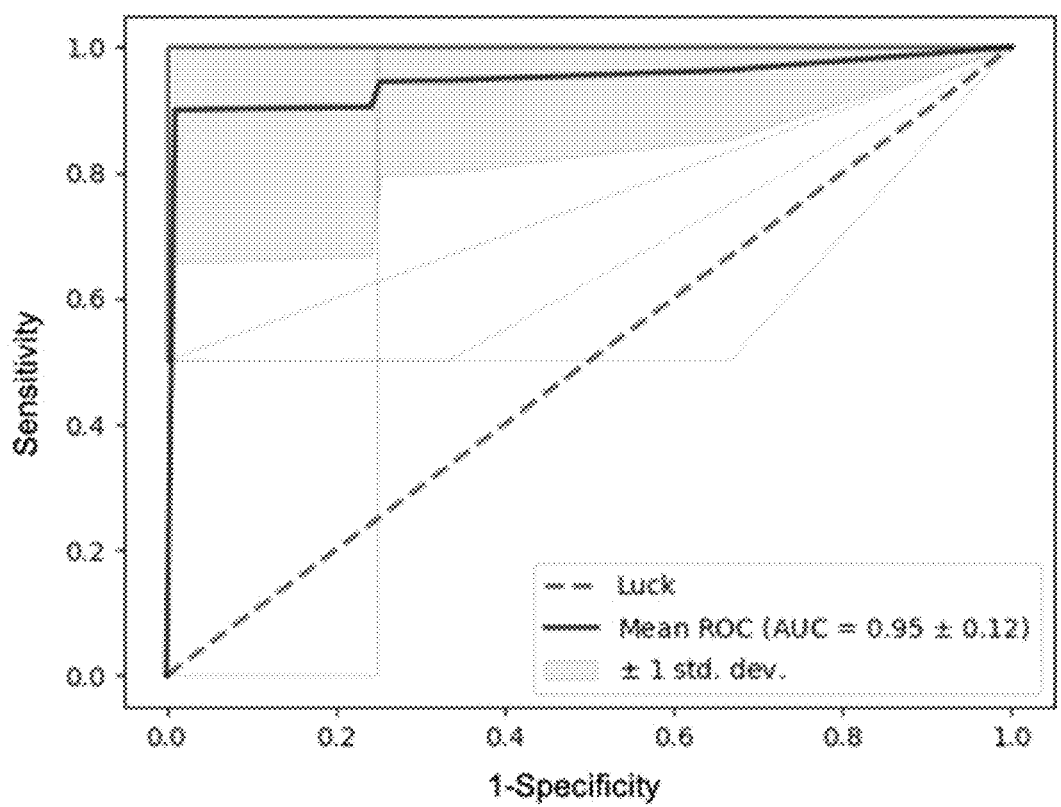
FIG. 40D shows results from a linear SVM trained on genomic mutational data alone, where sensitivity and specificity vastly improved with AUC=0.95±0.12.

In FIG. 40D, a combined classifier based on the microbiome and additional mutational information about the individual from whom the urine sample was taken yielded a preliminary sensitivity of 98% and a preliminary specificity of 91%.

FIG. 28A shows a first set of receiver operator characteristic (ROC) curves for machine learning techniques used to classify bladder cancer from urinary microbiomes. The top left curve corresponds to a random forest classifier. The top right curve corresponds to a support vector method (SVM) classifier. The bottom left curve corresponds to a quadratic discriminant analysis (QDA) classifier. The bottom right curve corresponds to a linear SVM classifier. The maximal sensitivity/specificity were ascertained from the graphs and used to form a consensus classification of the test cohort.

FIG. 28B shows a second set of receiver operator characteristic (ROC) curves for machine learning techniques used to classify bladder cancer from urinary microbiomes. The top left curve corresponds to a Naïve Bayes classifier. The top right curve corresponds to a nearest neighbors classifier. The bottom left curve corresponds to an AdaBoost classifier. The bottom right curve corresponds to a decision tree classifier. The maximal sensitivity/specificity were ascertained from the graphs and used to form a consensus classification of the test cohort.

Example 8

Differential Expression of Microbes in Individuals with and without Lower Urinary Tract Symptoms (LUTS)

FIGS. 29-39 show normalized median expression (see Example 1) of microbes in the urinary microbiomes of individuals who have been diagnosed with lower urinary tract symptoms (LUTS-positive individuals) and individuals who have not been diagnosed with lower urinary tract symptoms (LUTS-negative individuals), at a variety of levels of taxonomic organization.

Figure 29:
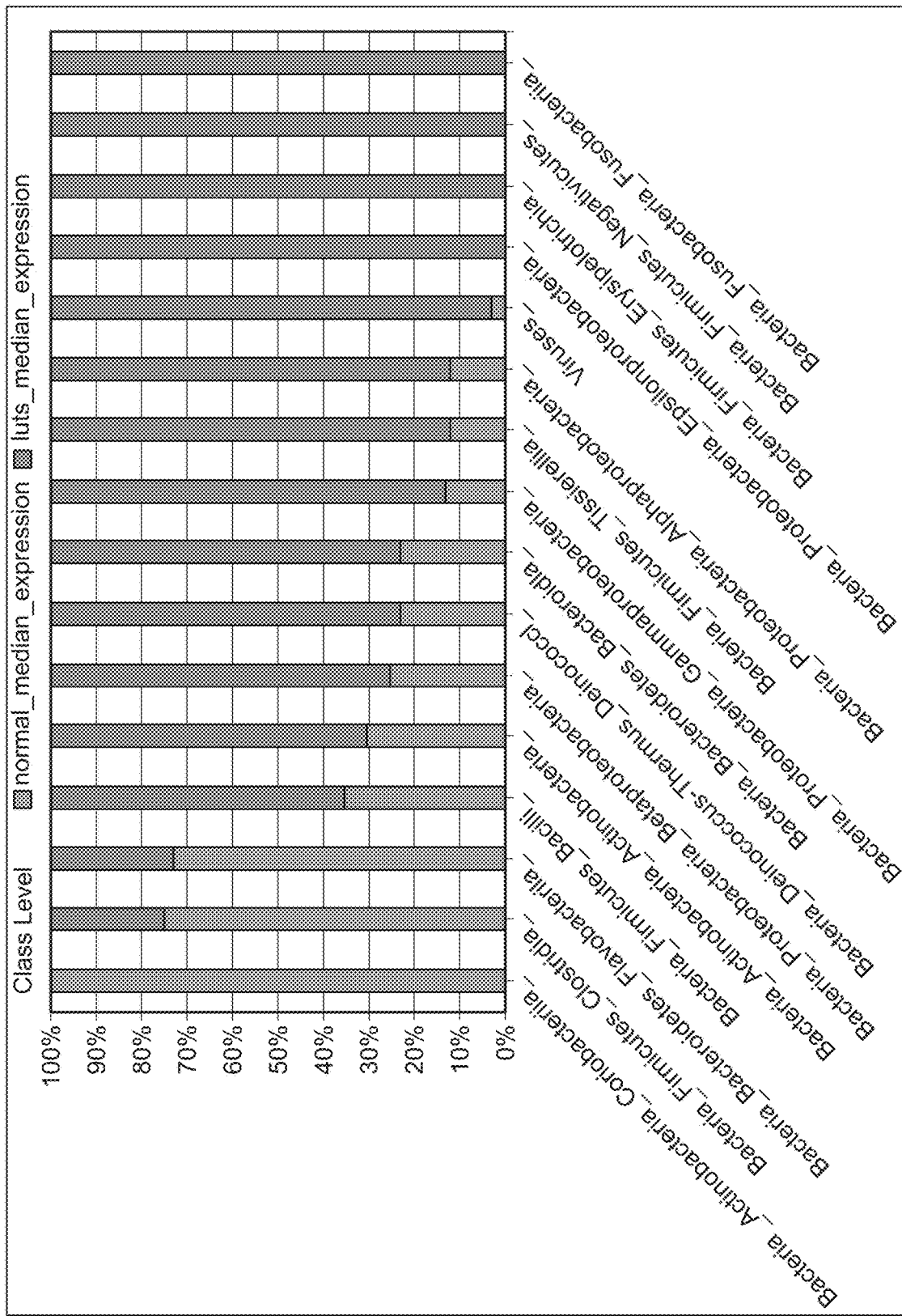
FIG. 29 shows differential expression of microbes in the urinary microbiomes of lower urinary tract syndrome-positive (LUTS-positive) and lower urinary tract syndrome-negative (LUTS-negative) individuals at the class level.

FIG. 29 shows normalized median expression (see Example 1) of microbes in the urinary microbiomes of LUTS-positive and LUTS-negative individuals at the class level. As shown in FIG. 29, microbes belonging to the classes Coriobacteria, Clostridia, Flavobacteria, Bacilli, Actinobacteria, Betaproteobacteria, Deinococci, Bacteroidia, Gammaproteobacteria, Tissierellia, Aphaproteobacteria, Epsilonproteobacteria, Erysipelotrichia, Negativicutes, and Fusobacteria are differentially expressed in LUTS-positive vs. LUTS-negative individuals. As shown in FIG. 29, the expression of the classes Coriobacteria, Clostridia, and Flavobacteria are enriched at greater than 60% prevalence in individuals without LUTS, whereas the expression of Bacilli, Actinobacteria, Betaproteobacteria, Deinococci, Bacteroidia, Gammaproteobacteria, Tissierellia, Aphaproteobacteria, Epsilonproteobacteria, Erysipelotrichia, Negativicutes, and Fusobacteria are enriched at greater than 60% prevalence in individuals with LUTS. Thus, a combination of microbes enriched in normal individuals and rarely found in disease-positive patients may define the microbial constituency of the healthy, normal, or LUTS-free bladder. Similarly, a combination of microbes enriched in individuals with LUTS and rarely found in patients without LUTS may define the microbial constituency of the LUTS urinary microbiome. Further, the relative abundance of any one or more of Coriobacteria, Clostridia, Flavobacteria, Bacilli, Actinobacteria, Betaproteobacteria, Deinococci, Bacteroidia, Gammaproteobacteria, Tissierellia, Aphaproteobacteria, Epsilonproteobacteria, Erysipelotrichia, Negativicutes, and Fusobacteria in a sample corresponding to an individual (e.g., relative abundance as compared to reference samples obtained from individuals with recurrent bladder cancer or individuals without recurrent bladder cancer) may provide an indication of whether the individual possesses a disease, e.g., LUTS, or not based on the relative abundance of microbes associated with normal bladders and those associated with diseased bladders. Further, if a sample corresponding to an individual is found to possess deficient levels of microbes typically found to be enriched in healthy individuals—the deficient microbes identified may form the basis of a treatment in which deficient microbe(s) are augmented by administration of that microbe(s) so as to bring the microbial constituency of the bladder back to the expected state for normal individuals. For example, a curative treatment for may comprise administering to a LUTS-positive individual about $10^3$, $10^4$, $10^5$, $10^6$, $10^7$, $10^8$, $10^9$, $10^{10}$, $10^{11}$, $10^{12}$, $10^{13}$, $10^{14}$, $10^{15}$, or more than $10^{15}$ microbes of one or more such classes.

Figure 30:
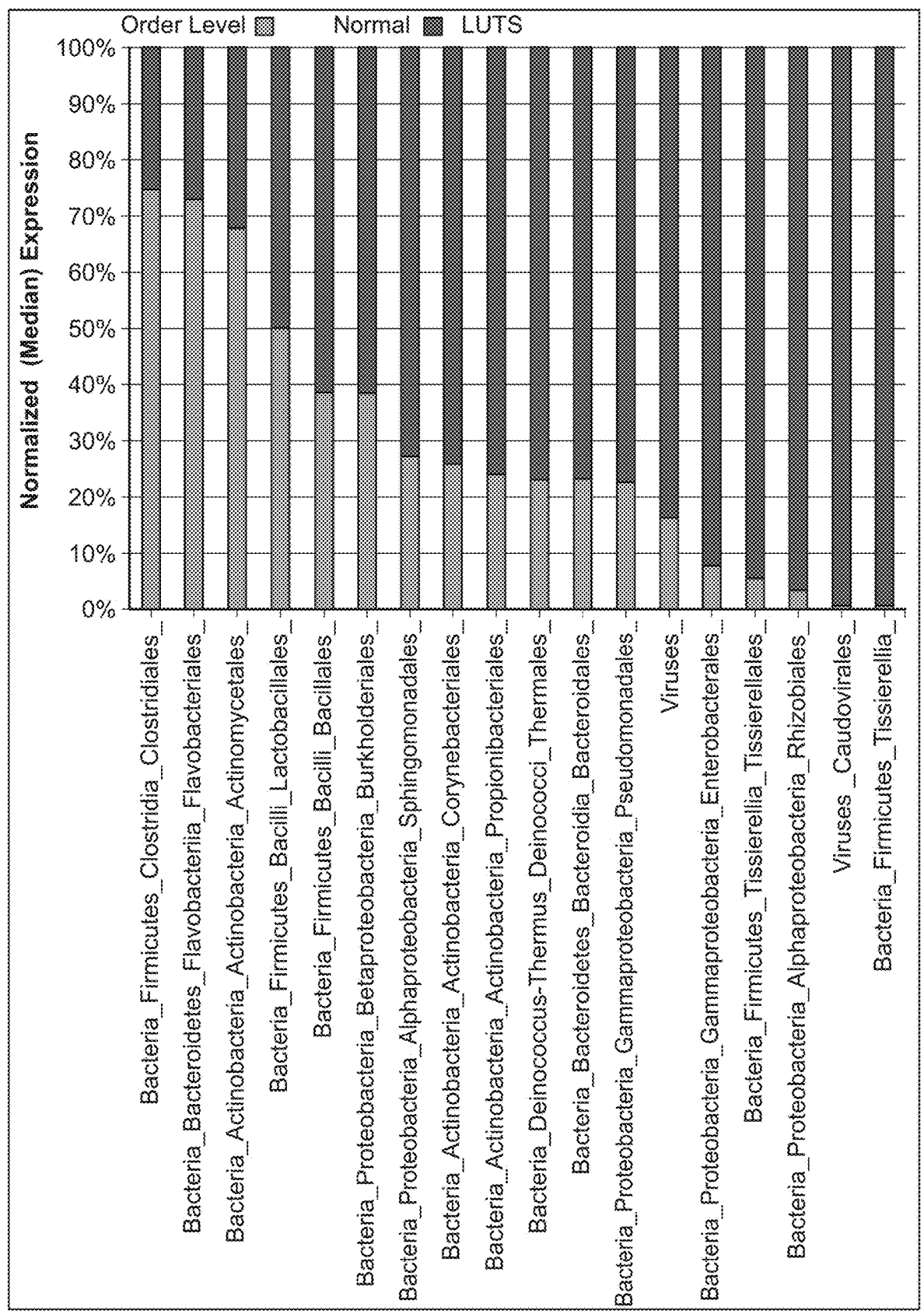
FIG. 30 shows differential expression of microbes in the urinary microbiomes of LUTS-positive and LUTS-negative individuals at the order level.

FIG. 30 shows normalized median expression of microbes in the urinary microbiomes of LUTS-positive and LUTS-negative individuals at the order level. As shown in FIG. 30, microbes belonging to the orders Clostridiales, Flavobacteriales, Actinomycetales, Lactobacillales, Bacillales, Burkholderiales, Sphingomonadales, Corynebacteriales, Propionibacteriales, Thermales, Bacteroidales, Pseudomonadales, Enterobacterales, Tissierellales, Rhizobiales, and Caudovirales are differentially expressed in LUTS-positive vs. LUTS-negative individuals. As shown in FIG. 30, the expression of Clostridiales, Flavobacteriales, and Actinomycetales are enriched at greater than 60% prevalence in individuals without LUTS, whereas the expression of Lactobacillales, Bacillales, Burkholderiales, Sphingomonadales, Corynebacteriales, Propionibacteriales, Thermales, Bacteroidales, Pseudomonadales, Enterobacterales, Tissierellales, Rhizobiales, and Caudovirales are enriched at greater than 60% prevalence in individuals with LUTS. Thus, a combination of microbes enriched in normal individuals and rarely found in disease-positive patients may define the microbial constituency of the healthy, normal, or LUTS-free bladder. Similarly, a combination of microbes enriched in individuals with LUTS and rarely found in patients without LUTS may define the microbial constituency of the cancerous urinary microbiome. Further, the relative abundance of any one or more of Clostridiales, Flavobacteriales, Actinomycetales, Lactobacillales, Bacillales, Burkholderiales, Sphingomonadales, Corynebacteriales, Propionibacteriales, Thermales, Bacteroidales, Pseudomonadales, Enterobacterales, Tissierellales, Rhizobiales, and Caudovirales in a sample corresponding to an individual may provide an indication of whether the individual possesses a disease, e.g., LUTS, or not based on the relative abundance of microbes associated with normal bladders and those associated with diseased bladders. Further, if a sample corresponding to an individual is found to possess deficient levels of microbes typically found to be enriched in healthy individuals—the deficient microbes identified may form the basis of a treatment in which deficient microbe(s) are augmented by administration of that microbe(s) so as to bring the microbial constituency of the bladder back to the expected state for normal individuals. For example, a curative treatment for may comprise administering to a LUTS-positive individual about $10^3$, $10^4$, $10^5$, $10^6$, $10^7$, $10^8$, $10^9$, $10^{10}$, $10^{11}$, $10^{12}$, $10^{13}$, $10^{14}$, $10^{15}$, or more than $10^{15}$ microbes of one or more such orders.

Figure 31:
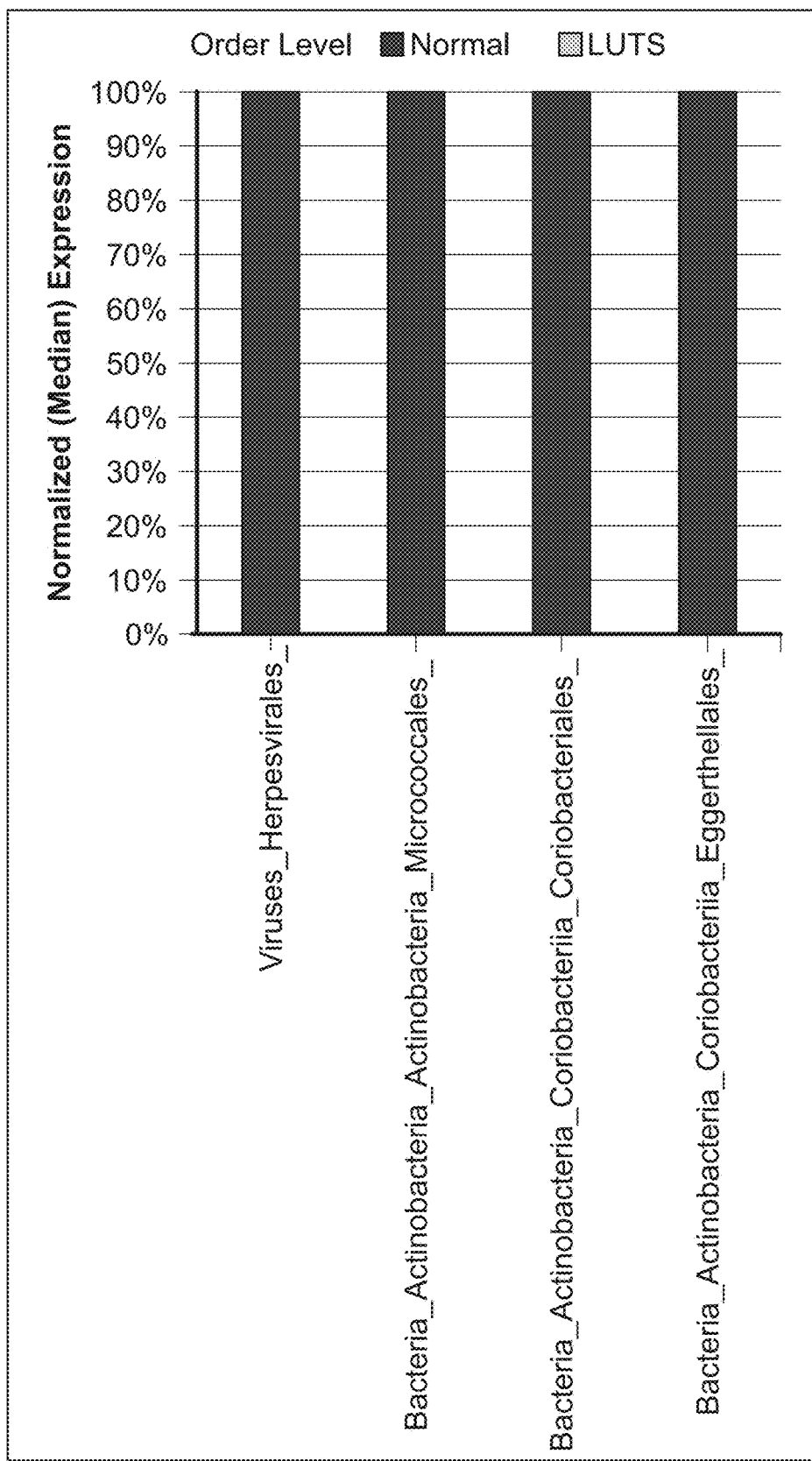
FIG. 31 shows expression of microbes only in the urinary microbiomes of LUTS-negative individuals at the order level.

FIG. 31 shows expression of microbes only in the urinary microbiomes of LUTS-negative individuals at the order level. As shown in FIG. 31, microbes belonging to the orders Herpesvirales, Micrococcales, Coriobacteriales, and Eggerthellales are expressed only in LUTS-negative individuals. Thus, the presence of microbes belonging to any one or more of the orders Herpesvirales, Micrococcales, Coriobacteriales, and Eggerthellales in a sample corresponding to an individual (e.g., relative abundance as compared to reference samples obtained from LUTS-positive individuals or LUTS-negative individuals) may provide an indication that the individual is LUTS-negative. These microbes may also be therapeutic candidates that if found deficient in individuals with LUTS and combinations of them may be reintroduced back into the bladder to return the microbial constituency of the bladder the expected state for normal individuals. For example, a curative treatment for may comprise administering to a LUTS-positive individual about $10^3$, $10^4$, $10^5$, $10^6$, $10^7$, $10^8$, $10^9$, $10^{10}$, $10^{11}$, $10^{12}$, $10^{13}$, $10^{14}$, $10^{15}$, or more than $10^{15}$ microbes of one or more such orders.

Figure 32:
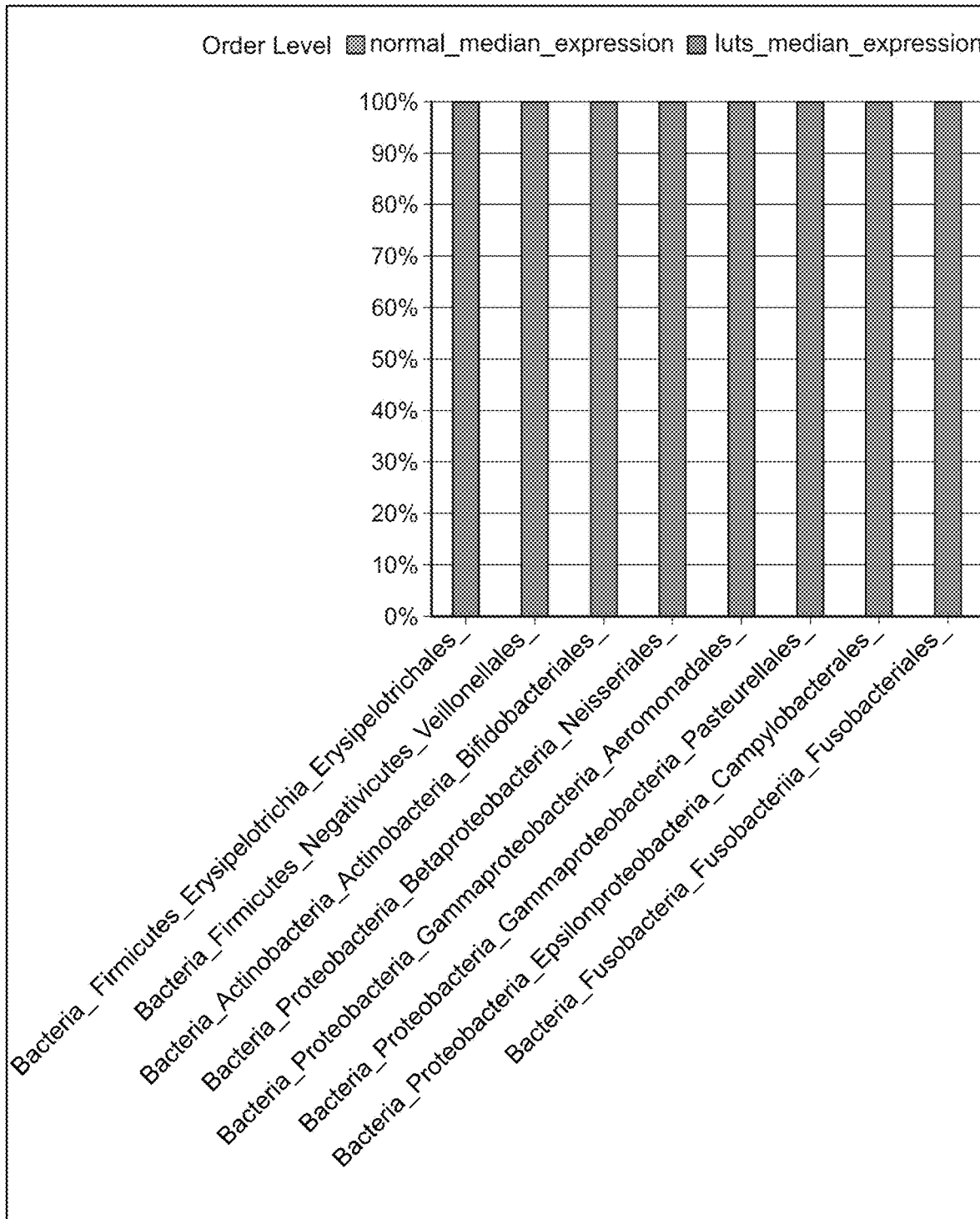
FIG. 32 shows expression of microbes only in the urinary microbiomes of LUTS-positive individuals at the order level.

FIG. 32 shows expression of microbes only in the urinary microbiomes of LUTS-positive individuals at the order level. As shown in FIG. 32, microbes belonging to the orders Erysipelotrichales, Veillonellales, Bifidobacteriales, Neisseriales, Aeromonadales, Pasteurellales, Campylobacterales, and Fusobacteriales are expressed only in LUTS-positive individuals. Thus, the presence of microbes belonging to any one or more of the orders Erysipelotrichales, Veillonellales, Bifidobacteriales, Neisseriales, Aeromonadales, Pasteurellales, Campylobacterales, and Fusobacteriales in a sample corresponding to an individual may provide an indication that the individual is LUTS-positive. Further, these microbes may serve as therapeutic targets in LUTS as their disruption would bring the microbial constituency of the bladder back to the expected state for normal individuals. For example, a treatment may comprise administering to a LUTS-positive individual about $10^3$, $10^4$, $10^5$, $10^6$, $10^7$, $10^8$, $10^9$, $10^{10}$, $10^{11}$, $10^{12}$, $10^{13}$, $10^{14}$, $10^{15}$, or more than $10^{15}$ microbes of one or more such orders.

Figure 33:
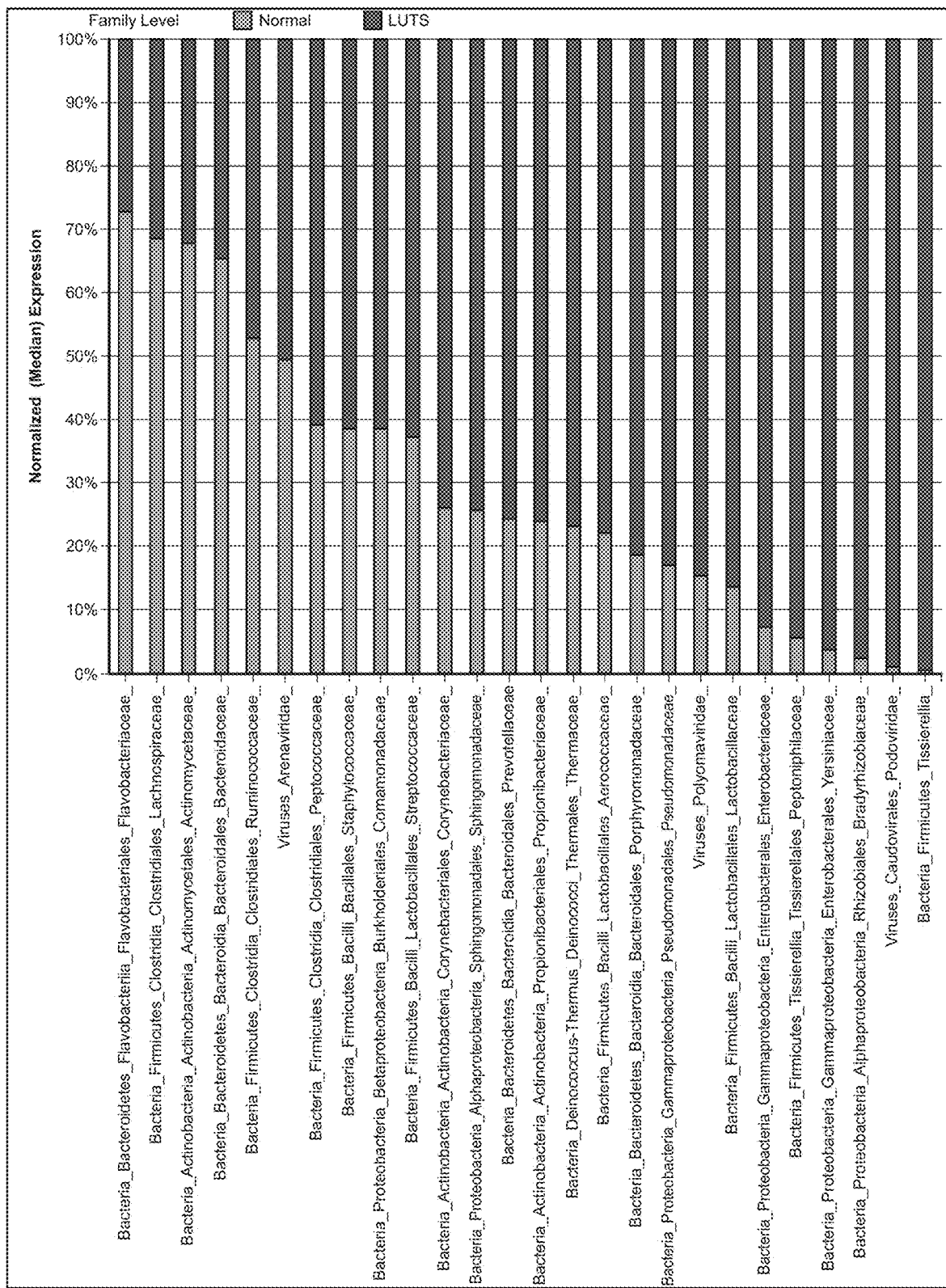
FIG. 33 shows differential expression of microbes in the urinary microbiomes of LUTS-positive and LUTS-negative individuals at the family level.

FIG. 33 shows differential expression of microbes in the urinary microbiomes of LUTS-positive and LUTS-negative individuals at the family level. As shown in FIG. 33, microbes belonging to the families Flavobacteriaceae, Lachnospiraceae, Actinomycetaceae, Bacteroidaceae, Ruminococcaceae, Arenaviridae, Peptococcaceae, Staphylococcaceae, Comamonadaceae, Streptococcaceae, Corynebacteriaceae, Sphingomonadaceae, Prevotellaceae, Propionibacteriaceae, Thermaceae, Aerococcaceae, Porphyromonadaceae, Polyomaviridae, Lactobacillaceae, Enterobacteriaceae, Peptoniphilaceae, Yersiniaceae, Bradyrhizobiaceae, Podoviridae, and Tissierellacea are differentially expressed in LUTS-positive vs. LUTS-negative individuals. As shown in FIG. 33, the expression of Flavobacteriaceae, Lachnospiraceae, Actinomycetaceae, and Bacteroidaceae are enriched at greater than 60% prevalence in individuals without LUTS, whereas the expression of Bacteroidaceae, Ruminococcaceae, Arenaviridae, Peptococcaceae, Staphylococcaceae, Comamonadaceae, Streptococcaceae, Corynebacteriaceae, Sphingomonadaceae, Prevotellaceae, Propionibacteriaceae, Thermaceae, Aerococcaceae, Porphyromonadaceae, Polyomaviridae, Lactobacillaceae, Enterobacteriaceae, Peptoniphilaceae, Yersiniaceae, Bradyrhizobiaceae, Podoviridae, and Tissierellacea are enriched at greater than greater than 60% prevalence in individuals with LUTS. Thus, a combination of microbes enriched in normal individuals and rarely found in disease-positive patients may define the microbial constituency of the healthy, normal, or LUTS-free bladder. Similarly, a combination of microbes enriched in individuals with LUTS and rarely found in patients without LUTS may define the microbial constituency of the LUTS urinary microbiome. Further, the relative abundance of any one or more of Flavobacteriaceae, Lachnospiraceae, Actinomycetaceae, Bacteroidaceae, Ruminococcaceae, Arenaviridae, Peptococcaceae, Staphylococcaceae, Comamonadaceae, Streptococcaceae, Corynebacteriaceae, Sphingomonadaceae, Prevotellaceae, Propionibacteriaceae, Thermaceae, Aerococcaceae, Porphyromonadaceae, Polyomaviridae, Lactobacillaceae, Enterobacteriaceae, Peptoniphilaceae, Yersiniaceae, Bradyrhizobiaceae, Podoviridae, and Tissierellacea in a sample corresponding to an individual (e.g., relative abundance as compared to reference samples obtained from LUTS-positive individuals or LUTS-negative individuals) may provide an indication of whether the individual possesses a disease, e.g., LUTS, or not based on the relative abundance of microbes associated with normal bladders and those associated with diseased bladders. Further, if a sample corresponding to an individual is found to possess deficient levels of microbes typically found to be enriched in healthy individuals—the deficient microbes identified can be reintroduced to the bladder so as to bring the microbial constituency of the bladder back to the expected state for normal individuals. For example, a treatment may comprise administering to a LUTS-positive individual about $10^3$, $10^4$, $10^5$, $10^6$, $10^7$, $10^8$, $10^9$, $10^{10}$, $10^{11}$, $10^{12}$, $10^{13}$, $10^{14}$, $10^{15}$, or more than $10^{15}$ microbes of one or more such families.

Figure 34:
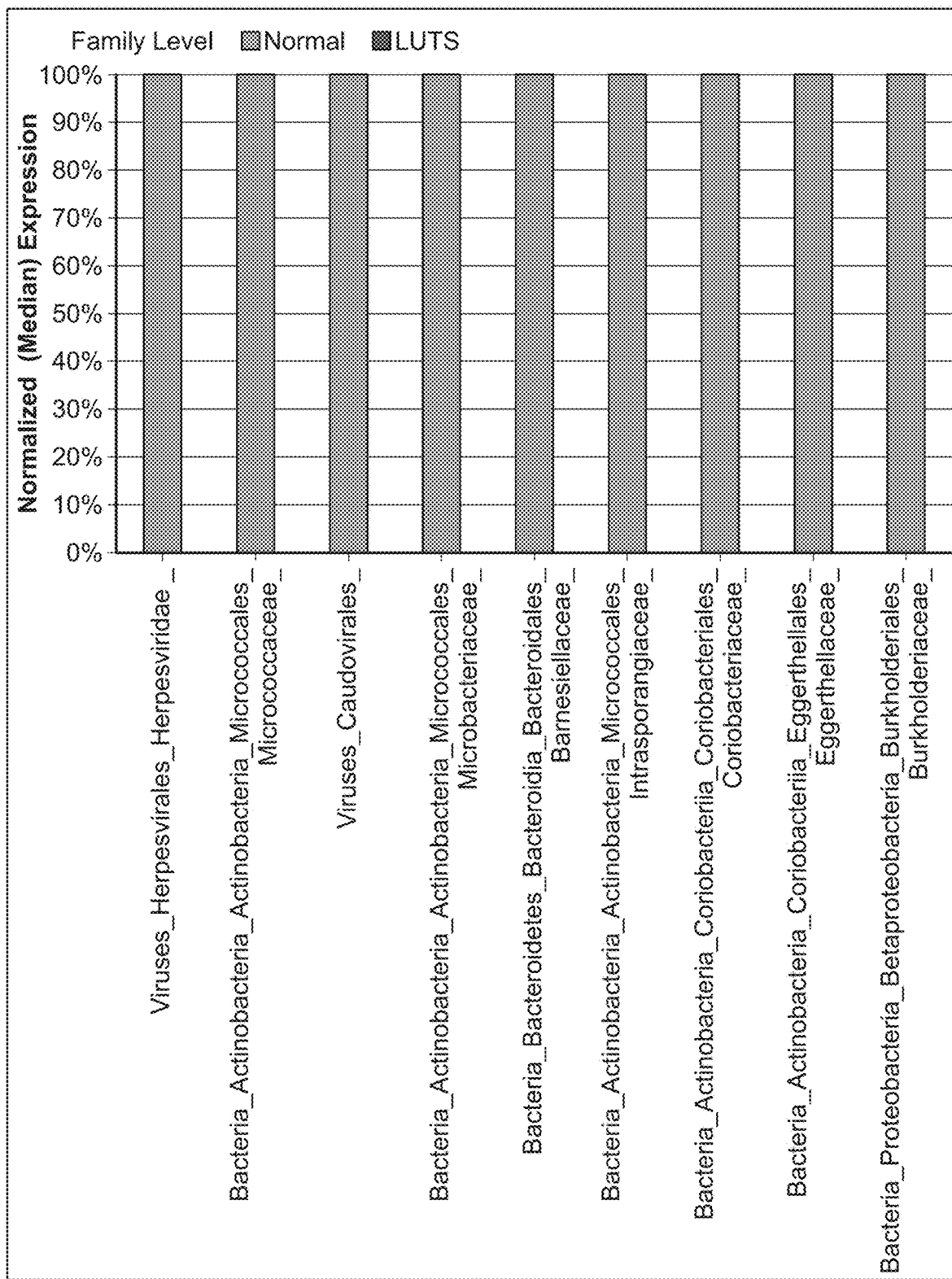
FIG. 34 shows expression of microbes only in the urinary microbiomes of LUTS-negative individuals at the family level.

FIG. 34 shows normalized median expression of microbes only in the urinary microbiomes of LUTS-negative individuals at the family level. As shown in FIG. 34, microbes belonging to the families Herpesviridae, Micrococcaceae, Microbacteriaceae, Barnesiellaceae, Intrasporangiaceae, Coriobacteriaceae, Eggerthellaceae, and Burkholderiaceae are expressed only in LUTS-negative individuals. Thus, the presence of microbes belonging to any one or more of the families Herpesviridae, Micrococcaceae, Microbacteriaceae, Barnesiellaceae, Intrasporangiaceae, Coriobacteriaceae, Eggerthellaceae, and Burkholderiaceae in a sample corresponding to an individual (e.g., relative abundance as compared to reference samples obtained from LUTS-positive individuals or LUTS-negative individuals) may provide an indication that the individual is LUTS-negative. These microbes may also be therapeutic candidates that if found deficient in individuals with LUTS as they may be reintroduced to the bladder so as to bring the microbial constituency of the bladder back to the expected state for normal individuals. For example, a treatment may comprise administering to a LUTS-positive individual about $10^3$, $10^4$, $10^5$, $10^6$, $10^7$, $10^8$, $10^9$, $10^{10}$, $10^{11}$, $10^{12}$, $10^{13}$, $10^{14}$, $10^{15}$, or more than $10^{15}$ microbes of one or more such families.

Figure 35:
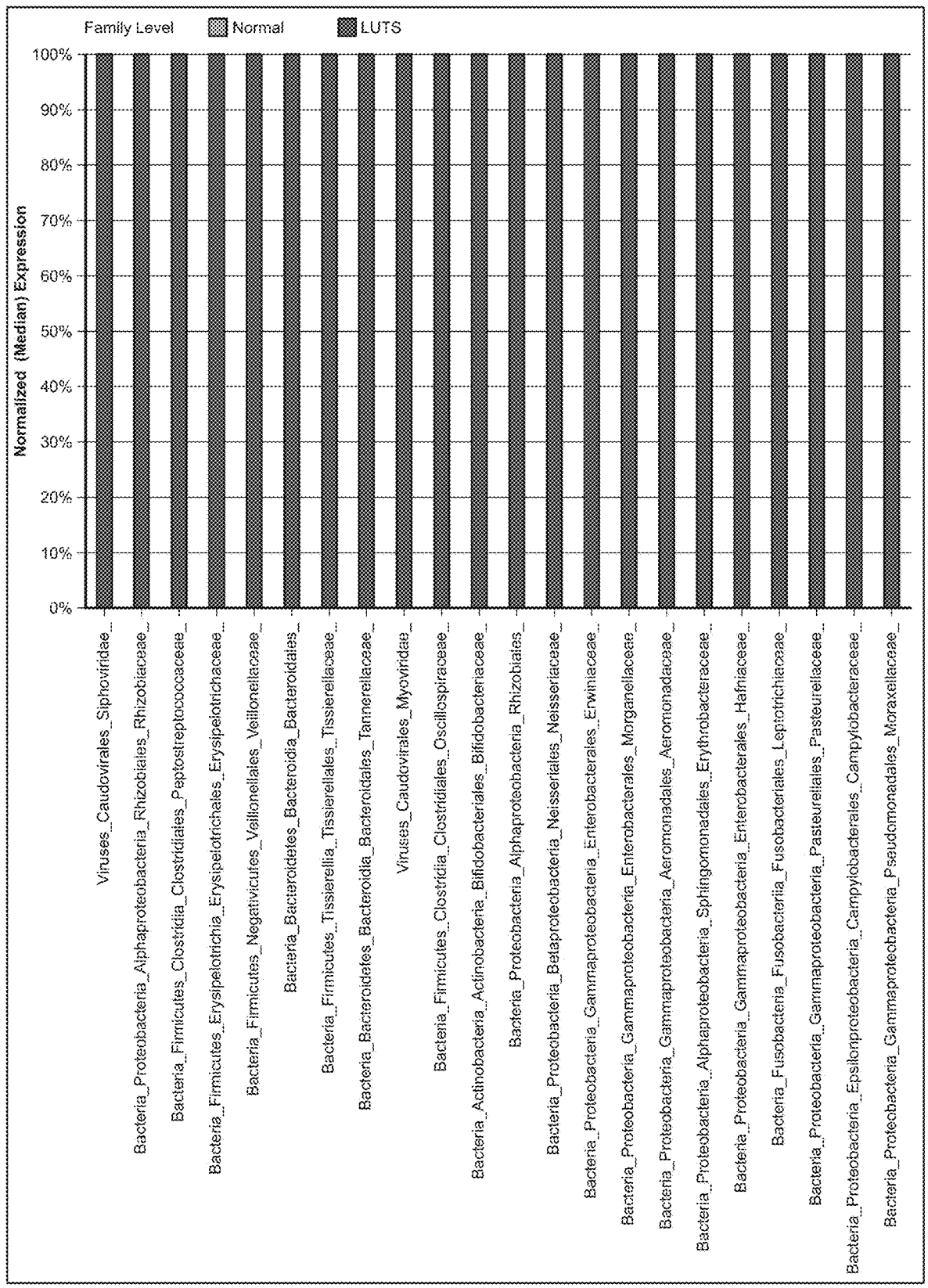
FIG. 35 shows expression of microbes only in the urinary microbiomes of LUTS-positive individuals at the family level.

FIG. 35 shows expression of microbes only in the urinary microbiomes of LUTS-positive individuals at the family level. As shown in FIG. 35, microbes belonging to the families Siphoviridae, Rhizobiaceae, Peptostreptococcaceae, Erysipelotrichaceae, Veillonellaceae, Tissierellaceae, Tannerellaceae, Myoviridae, Oscillospiraceae, Bifidobacteriaceae, Neisseriaceae, Erwiniaceae, Morganellaceae, Aeromonadaceae, Erythrobacteraceae, Hafniaceae, Leptotrichiaceae, Pasteurellaceae, Campylobacteraceae, and Moraxellaceae are expressed only in LUTS-positive individuals. Thus, the presence of microbes belonging to any one or more of the families Siphoviridae, Rhizobiaceae, Peptostreptococcaceae, Erysipelotrichaceae, Veillonellaceae, Tissierellaceae, Tannerellaceae, Myoviridae, Oscillospiraceae, Bifidobacteriaceae, Neisseriaceae, Erwiniaceae, Morganellaceae, Aeromonadaceae, Erythrobacteraceae, Hafniaceae, Leptotrichiaceae, Pasteurellaceae, Campylobacteraceae, and Moraxellaceae in a sample corresponding to an individual (e.g., relative abundance as compared to reference samples obtained from LUTS-positive individuals or LUTS-negative individuals) may provide an indication that the individual is LUTS-positive. Further, these microbes may serve as therapeutic targets in LUTS as their disruption may bring the microbial constituency of the bladder back to the expected state for normal individuals. For example, a treatment may comprise administering to a LUTS-positive individual about $10^3$, $10^4$, $10^5$, $10^6$, $10^7$, $10^8$, $10^9$, $10^{10}$, $10^{11}$, $10^{12}$, $10^{13}$, $10^{14}$, $10^{15}$, or more than $10^{15}$ microbes of one or more such families.

Figure 36:
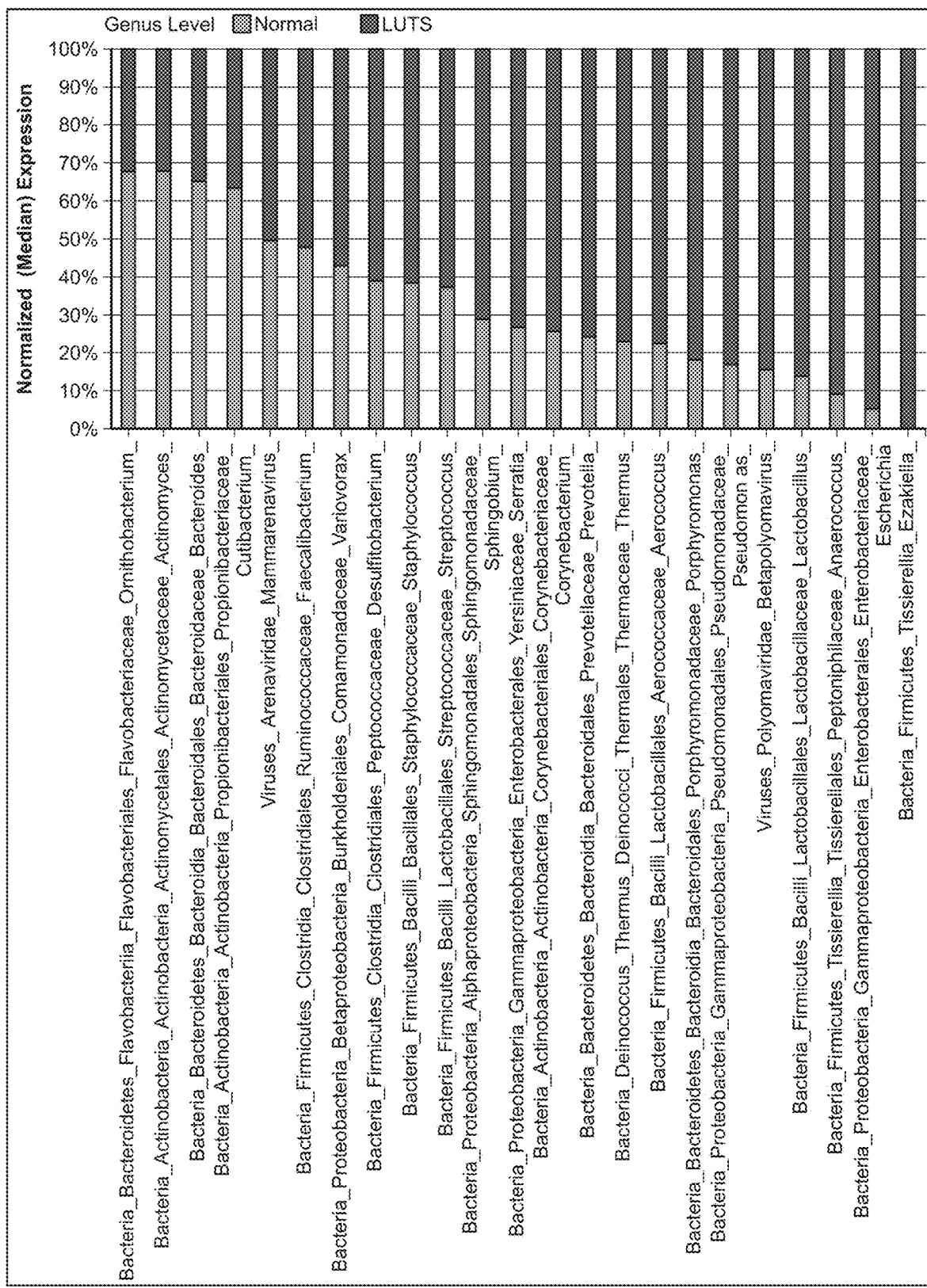
FIG. 36 shows differential expression of microbes in the urinary microbiomes of LUTS-positive and LUTS-negative individuals at the genus level.

FIG. 36 shows normalized median expression of microbes in the urinary microbiomes of LUTS-positive and LUTS-negative individuals at the genus level. As shown in FIG. 36, microbes belonging to the genera *Ornithobacterium*, *Actinomyces*, *Bacteroides*, *Cutibacterium*, Mammarenavirus, *Faecalibacterium*, *Variovorax*, *Desulfitobacterium*, *Staphylococcus*, *Streptococcus*, *Sphingobium*, *Serratia*, *Corynebacterium*, *Prevotella*, *Thermus*, *Aerococcus*, *Porphyromonas*, *Pseudomonas*, Betapolyomavirus, *Lactobacillus*, *Anaerococcus*, *Escherichia*, and *Ezakiella* are differentially expressed in LUTS-positive vs. LUTS-negative individuals. As shown in FIG. 36, the expression of *Ornithobacterium*, *Actinomyces*, *Bacteroides*, *Cutibacterium* are enriched at greater than 60% prevalence in individuals without LUTS, whereas the expression of *Desulfitobacterium*, *Staphylococcus*, *Streptococcus*, *Sphingobium*, *Serratia*, *Corynebacterium*, *Prevotella*, *Thermus*, *Aerococcus*, *Porphyromonas*, *Pseudomonas*, Betapolyomavirus, *Lactobacillus*, *Anaerococcus*, *Escherichia*, and *Ezakiella* are enriched at greater than 60% prevalence in individuals with LUTS. Thus, a combination of microbes enriched in normal individuals and rarely found in disease-positive patients may define the microbial constituency of the healthy, normal, or LUTS-free bladder. Similarly, a combination of microbes enriched in individuals with LUTS and rarely found in patients without LUTS may define the microbial constituency of the LUTS urinary microbiome. Further, the presence of any one or more of *Ornithobacterium*, *Actinomyces*, *Bacteroides*, *Cutibacterium*, Mammarenavirus, *Faecalibacterium*, *Variovorax*, *Desulfitobacterium*, *Staphylococcus*, *Streptococcus*, *Sphingobium*, *Serratia*, *Corynebacterium*, *Prevotella*, *Thermus*, *Aerococcus*, *Porphyromonas*, *Pseudomonas*, Betapolyomavirus, *Lactobacillus*, *Anaerococcus*, *Escherichia*, and *Ezakiella* in a sample corresponding to an individual (e.g., relative abundance as compared to reference samples obtained from LUTS-positive individuals or LUTS-negative individuals) may provide an indication of whether the individual possesses a disease, e.g., LUTS, or not based on the relative abundance of microbes associated with normal bladders and those associated with diseased bladders. Further, if a sample corresponding to an individual is found to possess deficient levels of microbes typically found to be enriched in healthy individuals—the deficient microbes identified may be reintroduced to the bladder so as to bring the microbial constituency of the bladder back to the expected state for normal individuals. For example, a treatment may comprise administering to a LUTS-positive individual about $10^3$, $10^4$, $10^5$, $10^6$, $10^7$, $10^8$, $10^9$, $10^{10}$, $10^{11}$, $10^{12}$, $10^{13}$, $10^{14}$, $10^{15}$, or more than $10^{15}$ microbes of one or more such genera.

Figure 37:
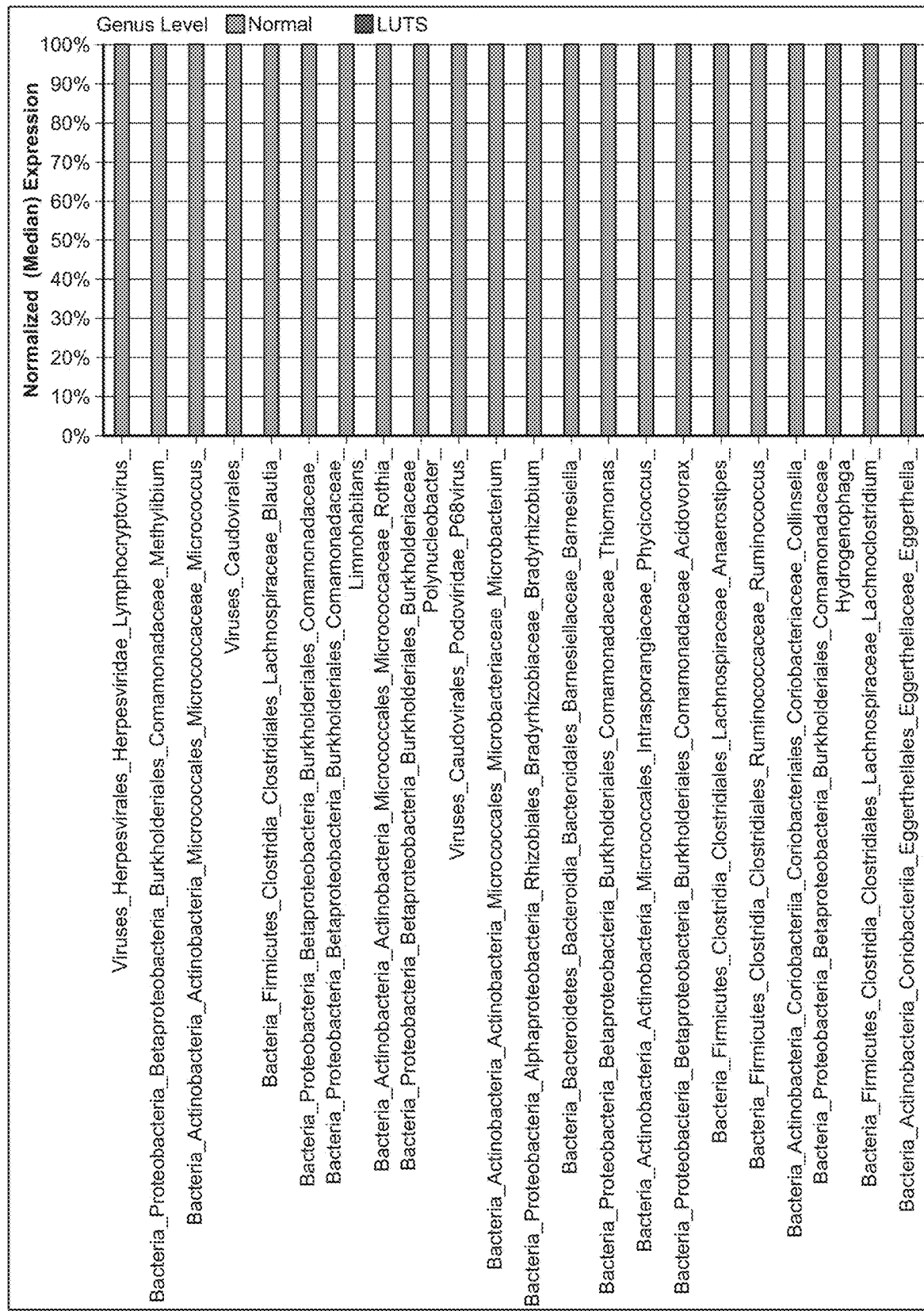
FIG. 37 shows expression of microbes only in the urinary microbiomes of LUTS-negative individuals at the genus level.

FIG. 37 shows expression of microbes only in the urinary microbiomes of LUTS-negative individuals at the genus level. As shown in FIG. 37, microbes belonging to the genera Lymphocryptovirus, *Methylibium*, Caudovirales, *Blautia*, *Limnohabitans*, *Rothia*, *Polynucleobacter*, P68virus, *Microbacterium*, *Bradyrhizobium*, *Barnesiella*, *Thiomonas*, *Phycicoccus*, *Acidovorax*, *Anaerostipes*, *Ruminococcus*, *Collinsella*, *Hydrogenophaga*, *Lachnoclostridium*, and *Eggerthella* are expressed only in LUTS-negative individuals. Thus, the presence of microbes belonging to any one or more of the genera Lymphocryptovirus, *Methylibium*, Caudovirales, *Blautia*, *Limnohabitans*, *Rothia*, *Polynucleobacter*, P68virus, *Microbacterium*, *Bradyrhizobium*, *Barnesiella*, *Thiomonas*, *Phycicoccus*, *Acidovorax*, *Anaerostipes*, *Ruminococcus*, *Collinsella*, *Hydrogenophaga*, *Lachnoclostridium*, and *Eggerthella* in a sample corresponding to an individual (e.g., relative abundance as compared to reference samples obtained from LUTS-positive individuals or LUTS-negative individuals) may provide an indication that the individual is LUTS-negative. These microbes may also be therapeutic candidates that, if found deficient in individuals with LUTS, may be reintroduced to the bladder so as to bring the microbial constituency of the bladder back to the expected state for normal individuals. For example, a treatment may comprise administering to a LUTS-positive individual about $10^3$, $10^4$, $10^5$, $10^6$, $10^7$, $10^8$, $10^9$, $10^{10}$, $10^{11}$, $10^{12}$, $10^{13}$, $10^{14}$, $10^{15}$, or more than $10^{15}$ microbes of one or more such genera.

Figure 38:
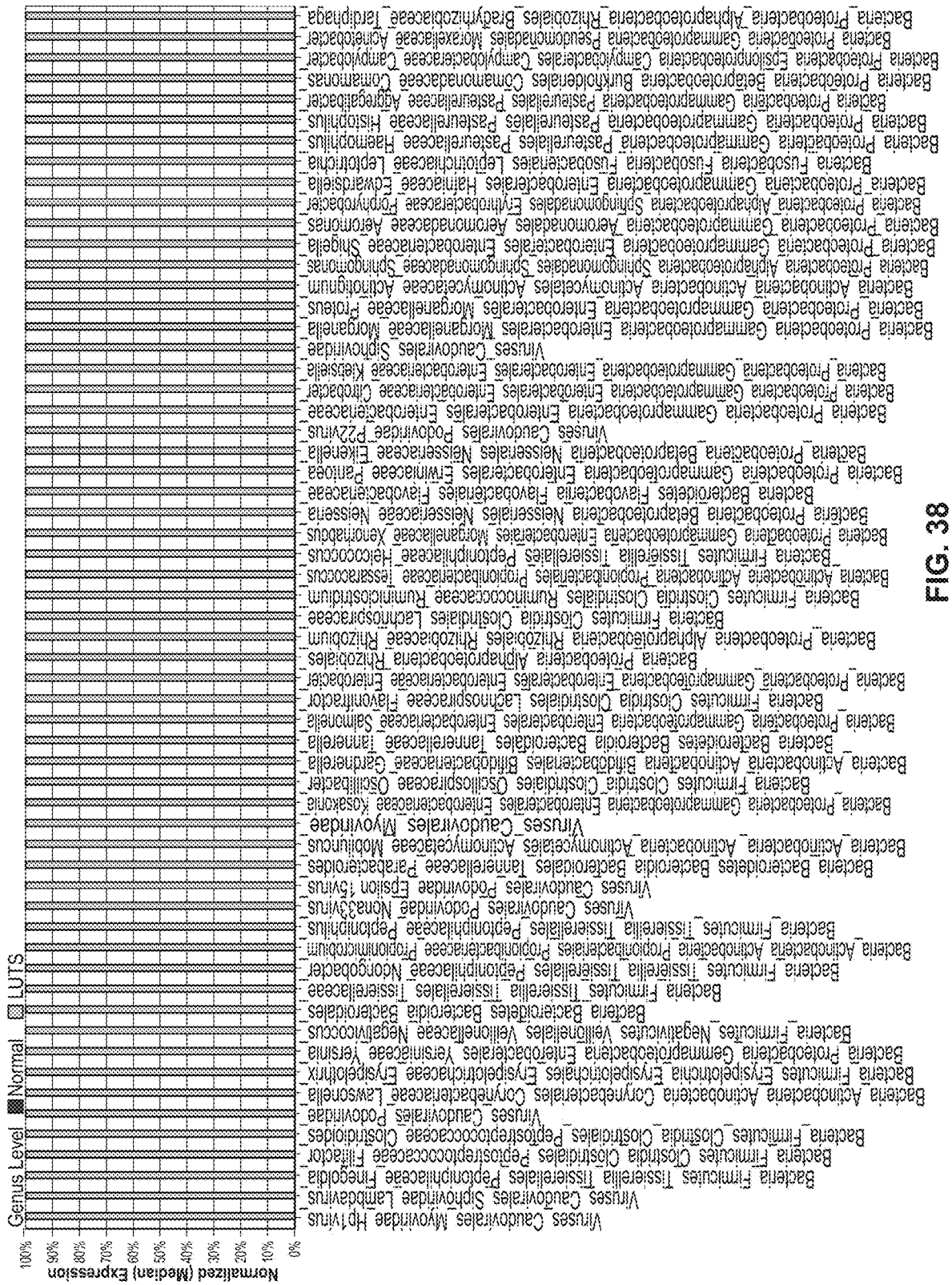
FIG. 38 shows expression of microbes only in the urinary microbiomes of LUTS-positive individuals at the genus level.

FIG. 38 shows expression of microbes only in the urinary microbiomes of LUTS-positive individuals at the genus level. As shown in FIG. 38, microbes belonging to the genera Lambdavirus, *Finegoldia*, *Filifactor*, *Clostridioides*, *Lawsonella*, *Erysipelothrix*, *Yersinia*, *Negativicoccus*, *Ndongobacter*, *Propionimicrobium*, *Peptoniphilus*, Epsilon15virus, *Parabacteroides*, *Mobiluncus*, *Kosakonia*, *Oscillibacter*, *Gardnerella*, *Tannerella*, *Salmonella*, *Flavonifractor*, *Enterobacter*, *Rhizobium*, *Ruminiclostridium*, *Tessaracoccus*, *Helcococcus*, *Xenorhabdus*, *Neisseria*, *Pan-* toea, Eikenella, P22virus, Citrobacter, Klebsiella, Morganella, Proteus, Actinotignum, Sphingomonas, Shigella, Aeromonas, Porphyrobacter, Edwardsiella, Leptotrichia, Haemophilus, Histophilus, Aggregatibacter, Comamonas, Campylobacter, Acinetobacter, and Tardiphaga are expressed only in LUTS-positive individuals. Thus, the presence of microbes belonging to any one or more of the genera Lambdavirus, Finegoldia, Filifactor, Clostridioides, Lawsonella, Erysipelothrix, Yersinia, Negativicoccus, Ndongobacter, Propionimicrobium, Peptoniphilus, Epsilon15virus, Parabacteroides, Mobiluncus, Kosakonia, Oscillibacter, Gardnerella, Tannerella, Salmonella, Flavonifractor, Enterobacter, Rhizobium, Ruminiclostridium, Tessaracoccus, Helcococcus, Xenorhabdus, Neisseria, Pantoea, Eikenella, P22virus, Citrobacter, Klebsiella, Morganella, Proteus, Actinotignum, Sphingomonas, Shigella, Aeromonas, Porphyrobacter, Edwardsiella, Leptotrichia, Haemophilus, Histophilus, Aggregatibacter, Comamonas, Campylobacter, Acinetobacter, and Tardiphaga in a sample corresponding to an individual (e.g., relative abundance as compared to reference samples obtained from LUTS-positive individuals or LUTS-negative individuals) may provide an indication that the individual is LUTS-positive. Further, these microbes may serve as therapeutic targets in LUTS as their disruption may bring the microbial constituency of the bladder back to the expected state of normal individuals. For example, a treatment may comprise administering to a LUTS-positive individual about $10^3$, $10^4$, $10^5$, $10^6$, $10^7$, $10^8$, $10^9$, $10^{10}$, $10^{11}$, $10^{12}$, $10^{13}$, $10^{14}$, $10^{15}$, or more than $10^{15}$ microbes of one or more such genera.

Figure 39:
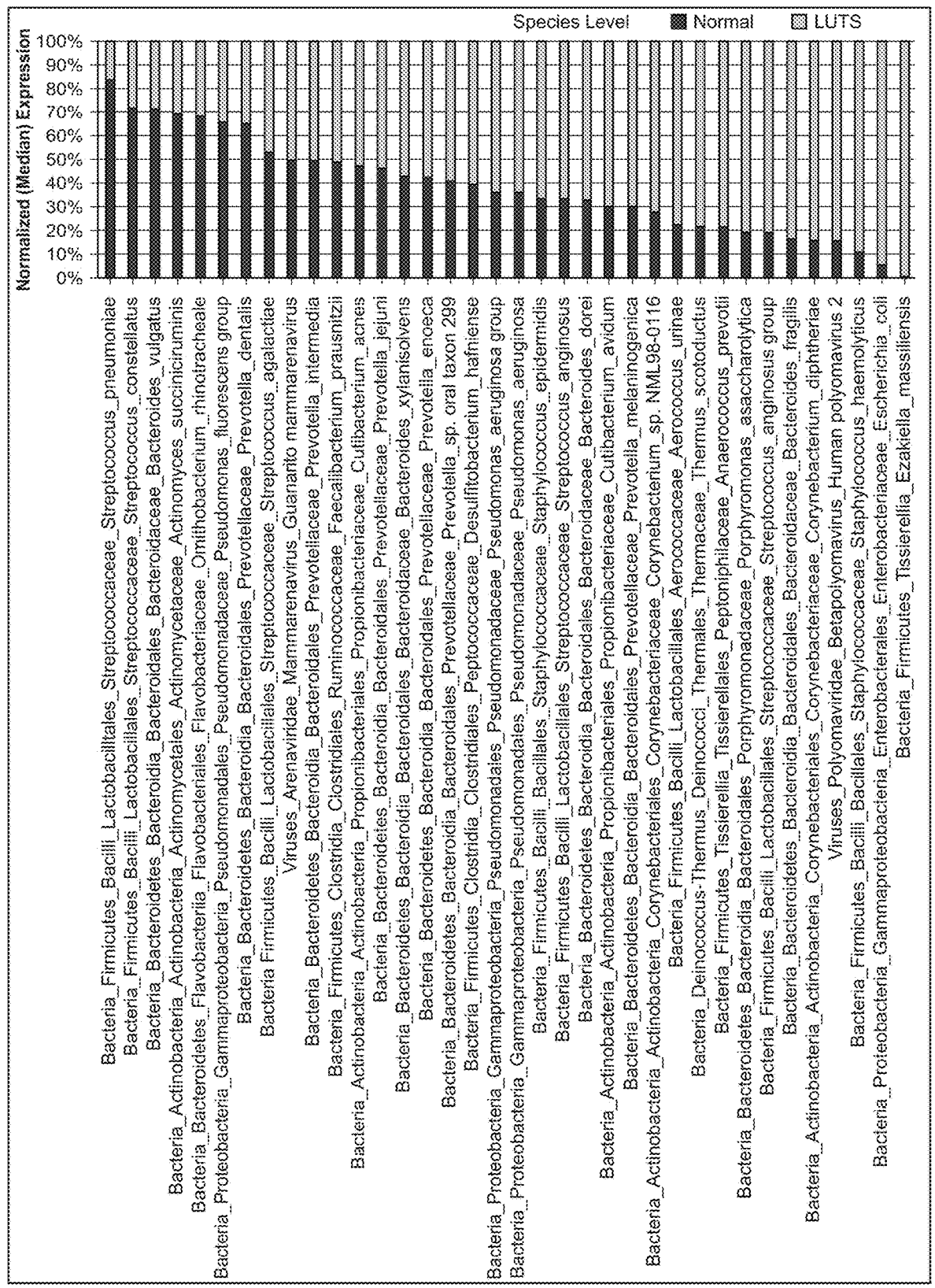
FIG. 39 shows differential expression of microbes in the urinary microbiomes of LUTS-positive and LUTS-negative individuals at the species level.

FIG. 39 shows differential expression of microbes in the urinary microbiomes of LUTS-positive and LUTS-negative individuals at the species level. As shown in FIG. 39, microbes belonging to the species Streptococcus pneumoniae, Streptococcus constellatus, Bacteroides vulgatus, Actinomyces succiniciruminis, Ornithobacterium rhinotracheale, Pseudomonas fluorescens group, Prevotella dentalis, Streptococcus agalactiae, Guanarito mammarenavirus, Prevotella intermedia, Faecalibacterium prausnitzii, Cutibacterium acnes, Prevotella jejuni, Bacteroides xylanisolvens, Prevotella enoeca, Prevotella species oral taxon 299, Desulfitobacterium hafniense, Pseudomonas eruginosa group, Pseudomonas aeruginosa, Staphylococcus epidermidis, Streptococcus anginosus, Bacteroides dorei, Cutibacterium avidum, Prevotella melaninogenica, Corynebacterium species ML98-0116, Aerococcus urinae, Thermus scotoductus, Anaerococcus prevotii, Porphyromonas saccharolytica, Streptococcus anginosus group, Bacteroides fragilis, Corynebacterium diphtheriae, Human polyomavirus 2, Staphylococcus haemolyticus, Escherichia coli, and Ezakiella massiliensis are differentially expressed in LUTS-positive vs. LUTS-negative individuals. As shown in FIG. 39, the expression of Streptococcus pneumoniae, Streptococcus constellatus, Bacteroides vulgatus, Actinomyces succiniciruminis, Ornithobacterium rhinotracheale, Pseudomonas fluorescens group, Prevotella dentalis are enriched at greater than 60% prevalence in individuals without LUTS, whereas the expression of Desulfitobacterium hafniense, Pseudomonas eruginosa group, Pseudomonas aeruginosa, Staphylococcus epidermidis, Streptococcus anginosus, Bacteroides dorei, Cutibacterium avidum, Prevotella melaninogenica, Corynebacterium species ML98-0116, Aerococcus urinae, Thermus scotoductus, Anaerococcus prevotii, Porphyromonas saccharolytica, Streptococcus anginosus group, Bacteroides fragilis, Corynebacterium diphtheriae, Human polyomavirus 2, Staphylococcus haemolyticus, Escherichia coli, and Ezakiella massiliensis are enriched at greater than 60% prevalence in individuals with LUTS. Thus, a combination of microbes enriched in normal individuals and rarely found in disease-positive patients may define the microbial constituency of the healthy, normal, or LUTS-free bladder. Similarly, a combination of microbes enriched in individuals with LUTS and rarely found in patients without LUTS may define the microbial constituency of the cancerous urinary microbiome. Further, the presence of any one or more of Streptococcus pneumoniae, Streptococcus constellatus, Bacteroides vulgatus, Actinomyces succiniciruminis, Ornithobacterium rhinotracheale, Pseudomonas fluorescens group, Prevotella dentalis, Streptococcus agalactiae, Guanarito mammarenavirus, Prevotella intermedia, Faecalibacterium prausnitzii, Cutibacterium acnes, Prevotella jejuni, Bacteroides xylanisolvens, Prevotella enoeca, Prevotella species oral taxon 299, Desulfitobacterium hafniense, Pseudomonas eruginosa group, Pseudomonas aeruginosa, Staphylococcus epidermidis, Streptococcus anginosus, Bacteroides dorei, Cutibacterium avidum, Prevotella melaninogenica, Corynebacterium species ML98-0116, Aerococcus urinae, Thermus scotoductus, Anaerococcus prevotii, Porphyromonas saccharolytica, Streptococcus anginosus group, Bacteroides fragilis, Corynebacterium diphtheriae, Human polyomavirus 2, Staphylococcus haemolyticus, Escherichia coli, and Ezakiella massiliensis in a sample corresponding to an individual (e.g., relative abundance as compared to reference samples obtained from LUTS-positive individuals or LUTS-negative individuals) may provide an indication of whether the individual possesses a disease, e.g., LUTS, or not based on the relative abundance of microbes associated with normal bladders and those associated with diseased bladders. Further, if a sample corresponding to an individual is found to possess deficient levels of microbes typically found to be enriched in healthy individuals—the deficient microbes identified may be reintroduced to the bladder so as to bring the microbial constituency of the bladder back to the expected state for normal individuals. For example, a treatment may comprise administering to a LUTS-positive individual about $10^3$, $10^4$, $10^5$, $10^6$, $10^7$, $10^8$, $10^9$, $10^{10}$, $10^{11}$, $10^{12}$, $10^{13}$, $10^{14}$, $10^{15}$, or more than $10^{15}$ microbes of one or more such species.

TABLE 4 shows examples of microbes and their role in lower urinary tract symptoms (LUTS)diagnosis. Microbes listed are enriched in individuals with LUTS. "Enriched" is defined as microbes with greater than greater than 60% normalized expression (see Example 1) in a cohort.

TABLE 4

| Microbe Usage | Microbe Used |
| --- | --- |
| LUTS Diagnosis: Species Level | Bacteria_Firmicutes_Clostridia_Clostridiales_Peptococcaceae_Desulfitobacterium_hafniense, Bacteria_Proteobacteria_Gammaproteobacteria_Pseudomonadales_Pseudomonadaceae_Pseudomonas aeruginosa group, Bacteria_Proteobacteria_Gammaproteobacteria_Pseudomonadales_Pseudomonadaceae_Pseudomonas_aeruginosa, Bacteria_Firmicutes_Bacilli_Bacillales_Staphylococcaceae_Staphylococcus_epidermidis, |

TABLE 4-continued

| Microbe Usage | Microbe Used |
|---|---|
| | Bacteria_Firmicutes_Bacilli_Lactobacillococcaceae_*Streptococcus_anginosus*,<br>Bacteria_Bacteroidetes_Bacteroidia_Bacteroidales_Bacteroidaceae_Bacteroides_dorei,<br>Bacteria_Actinobacteria_Actinobacteria_Propionibacteriales_Propionibacteriaceae_Cutibacterium_avidum,<br>Bacteria_Bacteroidetes_Bacteroidia_Bacteroidales_Prevotellaceae_Prevotella_melaninogenica,<br>Bacteria_Actinobacteria_Actinobacteria_Corynebacteriales_Corynebacteriaceae_*Corynebacterium*_sp. NML98-0116,<br>Bacteria_Firmicutes_Bacilli_Lactobacillococcaceae_Aerococcus_urinae,<br>Bacteria_Firmicutes_Tissierellia_Tissierellales_Peptoniphilaceae_Anaerococcus_prevotii,<br>Bacteria_Bacteroidetes_Bacteroidia_Bacteroidales_Porphyromonadaceae_Porphyromonas_asaccharolytica,<br>Bacteria_Firmicutes_Bacilli_Lactobacillococcaceae_*Streptococcus_anginosus* group,<br>Bacteria_Bacteroidetes_Bacteroidia_Bacteroidales_Bacteroidaceae_Bacteroides_fragilis,<br>Bacteria_Actinobacteria_Actinobacteria_Corynebacteriales_Corynebacteriaceae_Corynebacterium_diphtheriae,<br>Viruses_Polyomaviridae_Betapolyomavirus_Human polyomavirus 2,<br>Bacteria_Firmicutes_Bacilli_Bacillales_Staphylococcaceae_*Staphylococcus_haemolyticus*,<br>Bacteria_Proteobacteria_Gammaproteobacteria_Enterobacterales_Enterobacteriaceae_*Escherichia_coli*,<br>Bacteria_Firmicutes_Tissierellia_Ezakiella_massiliensis<br>Viruses_Caudovirales_Myoviridae_Hp1virus_Haemophilus virus HP1,<br>Viruses_Caudovirales_Siphoviridae___, Viruses_Caudovirales_Siphoviridae_Lambdavirus_Phage 21,<br>Viruses_Caudovirales_Siphoviridae_Lambdavirus_Enterobacteria phage mEp043 c-1,<br>Bacteria_Firmicutes_Bacilli_Lactobacillococcaceae_*Streptococcus_dysgalactiae* group,<br>Viruses_Caudovirales_Siphoviridae_Lambdavirus_Stx2-converting phage Stx2a_F451,<br>Bacteria_Firmicutes_Tissierellia_Tissierellales_Peptoniphilaceae_Finegoldia_magna,<br>Bacteria_Proteobacteria_Betaproteobacteria_Burkholderiales_Comamonadaceae_Comamonas_bacterium 36B,<br>Bacteria_Firmicutes_Bacilli_Lactobacilloptococcaceae_*Streptococcus_suis*,<br>Bacteria_Actinobacteria_Actinobacteria_Actinomycetales_Actinomycetaceae_Actinomyces_radingae,<br>Bacteria_Firmicutes_Bacilli_Lactobacillococcaceae_*Streptococcus_pyogenes*,<br>Bacteria_Firmicutes_Bacilli_Lactobacillococcaceae_*Streptococcus_dysgalactiae*,<br>Bacteria_Firmicutes_Bacilli_Lactobacillococcaceae_*Streptococcus_intermedius*,<br>Bacteria_Proteobacteria_Gammaproteobacteria_Enterobacterales_Enterobacteriaceae_Citrobacter_freundii complex,<br>Bacteria_Proteobacteria_Gammaproteobacteria_Pseudomonadales_Pseudomonadaceae_Pseudomonas_<br>putida group, Viruses_Caudovirales_Podoviridae_P22virus_*Escherichia* phage MSU52-L1,<br>Bacteria_Proteobacteria_Alphaproteobacteria_Sphingomonadales_Erythrobacteraceae_Porphyrobacter_uncultured<br>bacterium Contig1644,<br>Bacteria_Firmicutes_Clostridia_Clostridiales_Peptostreptococcaceae_Filifactor_alocis,<br>Bacteria_Firmicutes_Tissierellia_Ezakiella_peruensis,<br>Bacteria_Actinobacteria_Actinobacteria_Corynebacteriales_Corynebacteriaceae_Corynebacterium_sp. ATCC 6931,<br>Bacteria_Firmicutes_Clostridia_Clostridiales_Peptostreptococcaceae_Clostridioides_difficile,<br>Bacteria_Proteobacteria_Gammaproteobacteria_Enterobacterales_Enterobacteriaceae_*Escherichia_marmotae*,<br>Viruses_Caudovirales_Podoviridae_*Escherichia coli* O157 typing phage 10,<br>Viruses_Caudovirales_Podoviridae_*Escherichia coli* O157 typing phage 9,<br>Viruses_Caudovirales_Podoviridae_Enterobacteria phage Sf101,<br>Bacteria_Actinobacteria_Actinobacteria_Corynebacteriales_Corynebacteriaceae_Lawsonella_clevelandensis,<br>Bacteria_Proteobacteria_Alphaproteobacteria_Sphingomonadales_Sphingomonadaceae_Sphingomonas_panacis,<br>Viruses_Caudovirales_Myoviridae_Enterobacteria phage P88,<br>Bacteria_Actinobacteria_Actinobacteria_Corynebacteriales_Corynebacteriaceae_Corynebacterium_imitans,<br>Bacteria_Proteobacteria_Gammaproteobacteria_Enterobacterales_Enterobacteriaceae_Enterobacter_hormaechei,<br>Bacteria_Firmicutes_Bacilli_Lactobacillobacillaceae_Lactobacillus_gasseri,<br>Bacteria_Actinobacteria_Actinobacteria_Propionibacteriales_Propionibacteriaceae_Tessaracoccus_flavus,<br>Bacteria_Firmicutes_Erysipelotrichia_Erysipelotrichales_Erysipelotrichaceae_Erysipelothrix_rhusiopathiae,<br>Bacteria_Proteobacteria_Gammaproteobacteria_Enterobacterales_Yersiniaceae_Yersinia_pseudotuberculosis complex,<br>Bacteria_Actinobacteria_Actinobacteria_Corynebacteriales_Corynebacteriaceae_Corynebacterium_aurimucosum,<br>Bacteria_Firmicutes_Negativicutes_Veillonellales_Veillonellaceae_Negativicoccus_massiliensis,<br>Bacteria_Bacteroidetes_Bacteroidia_Bacteroidales,<br>Bacteria_Firmicutes_Clostridia_Clostridiales_Peptostreptococcaceae_Clostridioides_uncultured<br>Clostridiales bacterium,<br>Bacteria_Proteobacteria_Gammaproteobacteria_Pseudomonadales_Pseudomonadaceae_Pseudomonas_versuta,<br>Bacteria_Bacteroidetes_Bacteroidia_Bacteroidales_Bacteroidaceae_Bacteroides_caecimuris,<br>Bacteria_Proteobacteria_Gammaproteobacteria_Enterobacterales_Enterobacteriaceae_*Shigella*_sp. PAMC 28760,<br>Bacteria_Firmicutes_Tissierellia_Tissierellales_Tissierellaceae___uncultured Tissierellaceae bacterium,<br>Bacteria_Firmicutes_Tissierellia_Tissierellales_Peptoniphilaceae_Anaerococcus_mediterraneensis,<br>Bacteria_Firmicutes_Tissierellia_Tissierellales_Peptoniphilaceae_Ndongobacter_massiliensis,<br>Bacteria_Actinobacteria_Actinobacteria_Propionibacteriales_Propionibacteriaceae_*Propionimicrobium*_sp. Marseille-P3275,<br>Bacteria_Firmicutes_Tissierellia_Tissierellales_Peptoniphilaceae_*Peptoniphilus*_sp. ING2-D1G,<br>Bacteria_Firmicutes_Bacilli_Lactobacillus_Streptococcaceae_*Streptococcus_pasteurianus*,<br>Viruses_Caudovirales_Podoviridae_Nona33virus,<br>Viruses_Caudovirales_Podoviridae_Nona33virus_*Escherichia* virus Min27,<br>Viruses_Caudovirales_Podoviridae_Epsilon15virus_*Escherichia* virus phiV10,<br>Bacteria_Bacteroidetes_Bacteroidia_Bacteroidales_Tannerellaceae_*Parabacteroides*_sp. CT06,<br>Viruses_Caudovirales_Myoviridae___*Escherichia* phage APC_JM3.2,<br>Bacteria_Actinobacteria_Actinobacteria_Actinomycetales_Actinomycetaceae_Mobiluncus_curtisii,<br>Viruses_Caudovirales_Myoviridae___*Escherichia* phage YDC107_2,<br>Bacteria_Proteobacteria_Gammaproteobacteria_Enterobacterales_Enterobacteriaceae_Kosakonia_cowanii,<br>Bacteria_Proteobacteria_Gammaproteobacteria_Enterobacterales_Enterobacteriaceae_*Escherichia_albertii*,<br>Bacteria_Proteobacteria_Gammaproteobacteria_Enterobacterales_Enterobacteriaceae_*Escherichia*_uncultured<br>*Escherichia* sp.,<br>Bacteria_Firmicutes_Clostridia_Clostridiales_Oscillospiraceae_Oscillibacter_uncultured Clostridia bacterium,<br>Bacteria_Bacteroidetes_Bacteroidia_Bacteroidales_Bacteroidaceae_Bacteroides_cellulosilyticus,<br>Bacteria_Proteobacteria_Gammaproteobacteria_Pasteurellales_Pasteurellaceae_Haemophilus_pittmaniae, |

TABLE 4-continued

| Microbe Usage | Microbe Used |
|---|---|
| | Bacteria_Actinobacteria_Actinobacteria_Bifidobacteriales_Bifidobacteriaceae_Gardnerella_vaginalis,<br>Bacteria_Firmicutes_Bacilli_Bacillales_Staphylococcaceae_*Staphylococcus_lugdunensis*,<br>Bacteria_Bacteroidetes_Bacteroidia_Bacteroidales_Tannerellaceae_Tannerella_forsythia,<br>Bacteria_Bacteroidetes_Bacteroidia_Bacteroidales_Prevotellaceae_Prevotella_buccalis,<br>Bacteria_Bacteroidetes_Bacteroidia_Bacteroidales_Prevotellaceae_Prevotella_denticola,<br>Bacteria_Proteobacteria_Gammaproteobacteria_Pseudomonadales_Pseudomonadaceae_Pseudomonas_,<br>Bacteria_Proteobacteria_Gammaproteobacteria_Enterobacterales_Enterobacteriaceae_*Salmonella_enterica*,<br>Viruses_Caudovirales_Siphoviridae_Lambdavirus_Enterobacteria phage CP-1639,<br>Bacteria_Firmicutes_Clostridia_Clostridiales_Lachnospiraceae_Flavonifractor_plautii,<br>Bacteria_Proteobacteria_Gammaproteobacteria_Pseudomonadales_Pseudomonadaceae_Pseudomonas_putida,<br>Bacteria_Actinobacteria_Actinobacteria_Propionibacteriales_Propionibacteriaceae_Propionimicrobium_lymphophilum,<br>Bacteria_Firmicutes_Bacilli_Lactobacillies_Lactobacillus_Lactobacillus_johnsonii,<br>Bacteria_Actinobacteria_Actinobacteria_Corynebacteriales_Corynebacteriaceae_Corynebacterium_marinum,<br>Bacteria_Firmicutes_Clostridia_Clostridiales_Oscillospiraceae_Oscillibacter_valericigenes,<br>Bacteria_Proteobacteria_Gammaproteobacteria_Enterobacterales_Enterobacteriaceae_Enterobacter_cloacae complex,<br>Bacteria_Proteobacteria_Alphaproteobacteria_Rhizobiales,<br>Bacteria_Proteobacteria_Gammaproteobacteria_Enterobacterales_Enterobacteriaceae_Citrobacter_amalonaticus,<br>Bacteria_Proteobacteria_Alphaproteobacteria_Rhizobiales_Rhizobiaceae_Rhizobium,<br>Bacteria_Actinobacteria_Actinobacteria_Corynebacteriales_Corynebacteriaceae_Corynebacterium_jeikeium,<br>Bacteria_Bacteroidetes_Bacteroidia_Bacteroidales_Prevotellaceae_Prevotella_timonensis,<br>Bacteria_Firmicutes_Clostridia_Clostridiales_Lachnospiraceae_Eubacterium rectale,<br>Bacteria_Firmicutes_Clostridia_Clostridiales_Ruminococcaceae_Ruminiclostridium_[Eubacterium] siraeum,<br>Bacteria_Firmicutes_Tissierellia_Tissierellales_Peptoniphilaceae_Helcococcus_kunzii,<br>Bacteria_Actinobacteria_Actinobacteria_Corynebacteriales_Corynebacteriaceae_Corynebacterium_ureicelerivorans,<br>Bacteria_Proteobacteria_Gammaproteobacteria_Enterobacterales_Morganellaceae_Xenorhabdus_bovienii,<br>Bacteria_Proteobacteria_Alphaproteobacteria_Sphingomonadales_Sphingomonadaceae_*Sphingobium*_sp. MI1205,<br>Viruses_Caudovirales_Siphoviridae_Lambdavirus_Enterobacteria phage HK106,<br>Bacteria_Proteobacteria_Betaproteobacteria_Burkholderiales_Comamonadaceae_Variovorax_boronicumulans,<br>Bacteria_Actinobacteria_Actinobacteria_Corynebacteriales_Corynebacteriaceae_Corynebacterium_striatum,<br>Bacteria_Proteobacteria_Alphaproteobacteria_Sphingomonadales_Sphingomonadaceae_Sphingobium_chlorophenolicum,<br>Bacteria_Proteobacteria_Gammaproteobacteria_Pseudomonadales_Moraxellaceae_Acinetobacter_baumannii,<br>Bacteria_Proteobacteria_Gammaproteobacteria_Pseudomonadales_Pseudomonadaceae_Pseudomonas_azotoformans,<br>Bacteria_Proteobacteria_Alphaproteobacteria_Sphingomonadales_Sphingomonadaceae_*Sphingobium*_sp. YBL2,<br>Bacteria_Proteobacteria_Betaproteobacteria_Neisseriales_Neisseriaceae_Neisseria_gonorrhoeae,<br>Bacteria_Proteobacteria_Betaproteobacteria_Neisseriales_Neisseriaceae_Neisseria_meningitidis,<br>Bacteria_Proteobacteria_Betaproteobacteria_Neisseriales_Neisseriaceae_Neisseria_sicca,<br>Bacteria_Proteobacteria_Betaproteobacteria_Neisseriales_Neisseriaceae_Neisseria_elongata,<br>Bacteria_Bacteroidetes_Flavobacteriia_Flavobacteriales_Flavobacteriaceae,<br>Bacteria_Bacteroidetes_Bacteroidia_Bacteroidales_Porphyromonadaceae_Porphyromonas_bennonis,<br>Bacteria_Proteobacteria_Gammaproteobacteria_Pasteurellales_Pasteurellaceae_*Haemophilus*_sp. 1595,<br>Bacteria_Proteobacteria_Gammaproteobacteria_Enterobacterales_Erwiniaceae_Pantoea_,<br>Bacteria_Proteobacteria_Betaproteobacteria_Neisseriales_Neisseriaceae_Eikenella_corrodens,<br>Viruses_Caudovirales_Podoviridae_P22virus_Enterobacteria phage CUS-3,<br>Viruses_Caudovirales_Podoviridae_Epsilon15virus,<br>Bacteria_Proteobacteria_Gammaproteobacteria_Enterobacterales_Enterobacteriaceae,<br>Bacteria_Proteobacteria_Gammaproteobacteria_Enterobacterales_Enterobacteriaceae_Citrobacter_koseri,<br>Bacteria_Proteobacteria_Gammaproteobacteria_Enterobacterales_Enterobacteriaceae_Citrobacter_freundii,<br>Bacteria_Proteobacteria_Gammaproteobacteria_Enterobacterales_Enterobacteriaceae_Klebsiella_aerogenes,<br>Bacteria_Proteobacteria_Gammaproteobacteria_Enterobacterales_Enterobacteriaceae_Enterobacter_cloacae,<br>Bacteria_Proteobacteria_Gammaproteobacteria_Pasteurellales_Pasteurellaceae_*Haemophilus*_sp. CCUG 30218,<br>Bacteria_Proteobacteria_Gammaproteobacteria_Enterobacterales_Enterobacteriaceae_*Escherichia*,<br>Bacteria_Proteobacteria_Gammaproteobacteria_Enterobacterales_Enterobacteriaceae_*Escherichia_fergusonii*,<br>Bacteria_Proteobacteria_Gammaproteobacteria_Enterobacterales_Enterobacteriaceae_Klebsiella,<br>Bacteria_Proteobacteria_Gammaproteobacteria_Enterobacterales_Enterobacteriaceae_Klebsiella_pneumoniae,<br>Bacteria_Proteobacteria_Gammaproteobacteria_Enterobacterales_Enterobacteriaceae_*Klebsiella*_sp.,<br>Bacteria_Proteobacteria_Gammaproteobacteria_Enterobacterales_Morganellaceae_Morganella_morganii,<br>Bacteria_Proteobacteria_Gammaproteobacteria_Enterobacterales_Morganellaceae_Proteus_mirabilis,<br>Bacteria_Proteobacteria_Gammaproteobacteria_Enterobacterales_Enterobacteriaceae_*Klebsiella*_sp. 2N3,<br>Bacteria_Bacteroidetes_Bacteroidia_Bacteroidales_Prevotellaceae_Prevotella_fusca,<br>Bacteria_Bacteroidetes_Bacteroidia_Bacteroidales_Prevotellaceae_Prevotella_scopos,<br>Bacteria_Actinobacteria_Actinobacteria_Actinomycetales_Actinomycetaceae_Actinotignum_schaalii,<br>Bacteria_Proteobacteria_Gammaproteobacteria_Enterobacterales_Yersiniaceae_Serratia,<br>Bacteria_Proteobacteria_Gammaproteobacteria_Enterobacterales_Enterobacteriaceae_Shigella,<br>Bacteria_Proteobacteria_Gammaproteobacteria_Enterobacterales_Enterobacteriaceae_Shigella_boydii,<br>Bacteria_Proteobacteria_Gammaproteobacteria_Enterobacterales_Enterobacteriaceae_Shigella_dysenteriae,<br>Bacteria_Proteobacteria_Gammaproteobacteria_Enterobacterales_Enterobacteriaceae_Shigella_flexneri,<br>Bacteria_Proteobacteria_Gammaproteobacteria_Enterobacterales_Enterobacteriaceae_Shigella_sonnei,<br>Bacteria_Proteobacteria_Gammaproteobacteria_Enterobacterales_Yersiniaceae_Yersinia,<br>Bacteria_Proteobacteria_Gammaproteobacteria_Enterobacterales_Yersiniaceae_Yersinia_enterocolitica,<br>Bacteria_Proteobacteria_Gammaproteobacteria_Enterobacterales_Yersiniaceae_Yersinia_pestis,<br>Bacteria_Proteobacteria_Gammaproteobacteria_Enterobacterales_Yersiniaceae_Yersinia_pseudotuberculosis,<br>Bacteria_Proteobacteria_Gammaproteobacteria_Aeromonadales_Aeromonadaceae_Aeromonas_veronii,<br>Bacteria_Proteobacteria_Betaproteobacteria_Neisseriales_Neisseriaceae_*Neisseria*_sp. KEM232,<br>Bacteria_Proteobacteria_Alphaproteobacteria_Sphingomonadales_Erythrobacteraceae_Porphyrobacter_mixed culture bacterium CY_gF1DD01_14,<br>Bacteria_Proteobacteria_Gammaproteobacteria_Enterobacterales_Hafniaceae_Edwardsiella_ictaluri,<br>Bacteria_Proteobacteria_Gammaproteobacteria_Enterobacterales_Enterobacteriaceae_Citrobacter_rodentium, |

TABLE 4-continued

| Microbe Usage | Microbe Used |
|---|---|
| | Bacteria_Proteobacteria_Gammaproteobacteria_Enterobacterales_Enterobacteriaceae_Citrobacter_werkmanii, |
| | Viruses___Caudovirales_Siphoviridae_Lambdavirus_Enterobacteria phage H-19B, |
| | Bacteria_Proteobacteria_Gammaproteobacteria_Pseudomonadales_Pseudomonadaceae_Pseudomonas_plecoglossicida, |
| | Bacteria_Fusobacteria_Fusobacteriia_Fusobacteriales_Leptotrichiaceae_*Leptotrichia*_sp. oral taxon 212, |
| | Bacteria_Proteobacteria_Gammaproteobacteria_Pasteurellales_Pasteurellaceae_Aggregatibacter_actinomycetemcomitans, |
| | Bacteria_Proteobacteria_Gammaproteobacteria_Pasteurellales_Pasteurellaceae_Haemophilus_haemolyticus, |
| | Bacteria_Proteobacteria_Gammaproteobacteria_Pasteurellales_Pasteurellaceae_Haemophilus_influenzae, |
| | Bacteria_Proteobacteria_Gammaproteobacteria_Pasteurellales_Pasteurellaceae_Haemophilus_parainfluenzae, |
| | Bacteria_Proteobacteria_Gammaproteobacteria_Pasteurellales_Pasteurellaceae_Histophilus_somni, |
| | Bacteria_Proteobacteria_Gammaproteobacteria_Pasteurellales_Pasteurellaceae_Aggregatibacter_aphrophilus, |
| | Bacteria_Proteobacteria_Epsilonproteobacteria_Campylobacterales_Campylobacteraceae_Campylobacter_hominis, |
| | Bacteria_Proteobacteria_Gammaproteobacteria_Pseudomonadales_Pseudomonadaceae_Pseudomonas_monteilii, |
| | Bacteria_Proteobacteria_Betaproteobacteria_Burkholderiales_Comamonadaceae_Comamonas_uncultured bacterium, |
| | Bacteria_Proteobacteria_Epsilonproteobacteria_Campylobacterales_Campylobacteraceae_Campylobacter_ureolyticus, |
| | Bacteria_Bacteroidetes_Bacteroidia_Bacteroidales_Porphyromonadaceae_Porphyromonas_gingivalis, |
| | Bacteria_Proteobacteria_Gammaproteobacteria_Pseudomonadales_Moraxellaceae_Acinetobacter_calcoaceticus/baumannii complex, |
| | Bacteria_Proteobacteria_Alphaproteobacteria_Rhizobiales_Bradyrhizobiaceae_Tardiphaga_robiniae |
| LUTS Diagnosis: Genus Level | Bacteria_Firmicutes_Clostridia_Clostridiales_Peptococcaceae_Desulfitobacterium, |
| | Bacteria_Firmicutes_Bacilli_Bacillales_Staphylococcaceae_*Staphylococcus*, |
| | Bacteria_Firmicutes_Bacilli_Lactobacillies_Streptococcaceae_*Streptococcus*, |
| | Bacteria_Proteobacteria_Alphaproteobacteria_Sphingomonadales_Sphingomonadaceae_Sphingobium, |
| | Bacteria_Proteobacteria_Gammaproteobacteria_Enterobacterales_Yersiniaceae_Serratia, |
| | Bacteria_Actinobacteria_Actinobacteria_Corynebacteriales_Corynebacteriaceae_Corynebacterium, |
| | Bacteria_Bacteroidetes_Bacteroidia_Bacteroidales_Prevotellaceae_Prevotella, |
| | Bacteria_Firmicutes_Bacilli_Lactobacillies_Aerococcaceae_Aerococcus, |
| | Bacteria_Bacteroidetes_Bacteroidia_Bacteroidales_Porphyromonadaceae_Porphyromonas, |
| | Bacteria_Proteobacteria_Gammaproteobacteria_Pseudomonadales_Pseudomonadaceae_Pseudomonas, |
| | Viruses_Polyomaviridae_Betapolyomavirus, |
| | Bacteria_Firmicutes_Bacilli_Lactobacillies_Lactobacilluseae_Lactobacillus, |
| | Bacteria_Firmicutes_Tissierellia_Tissierellales_Peptoniphilaceae_Anaerococcus, |
| | Bacteria_Proteobacteria_Gammaproteobacteria_Enterobacterales_Enterobacteriaceae_*Escherichia*, |
| | Bacteria_Firmicutes_Tissierellia_Ezakiella, Viruses_Caudovirales_Myoviridae_Hp 1 virus, |
| | Bacteria_Firmicutes_Tissierellia_Tissierellales_Peptoniphilaceae_Finegoldia, |
| | Bacteria_Firmicutes_Clostridia_Clostridiales_Peptostreptococcaceae_Filifactor, |
| | Bacteria_Firmicutes_Clostridia_Clostridiales_Peptostreptococcaceae_Clostridioides, |
| | Viruses_Caudovirales_Podoviridae, |
| | Bacteria_Actinobacteria_Actinobacteria_Corynebacteriales_Corynebacteriaceae_Lawsonella, |
| | Bacteria_Firmicutes_Erysipelotrichia_Erysipelotrichales_Erysipelotrichaceae_Erysipelothrix, |
| | Bacteria_Proteobacteria_Gammaproteobacteria_Enterobacterales_Yersiniaceae_Yersinia, |
| | Bacteria_Firmicutes_Negativicutes_Veillonellales_Veillonellaceae_Negativicoccus, |
| | Bacteria_Bacteroidetes_Bacteroidia_Bacteroidales, |
| | Bacteria_Firmicutes_Tissierellia_Tissierellales_Tissierellaceae, |
| | Bacteria_Firmicutes_Tissierellia_Tissierellales_Peptoniphilaceae_Ndongobacter, |
| | Bacteria_Actinobacteria_Actinobacteria_Propionibacteriales_Propionibacteriaceae_Propionimicrobium, |
| | Bacteria_Firmicutes_Tissierellia_Tissierellales_Peptoniphilaceae_Peptoniphilus, |
| | Viruses_Caudovirales_Podoviridae_Nona33virus, Viruses_Caudovirales_Podoviridae_Epsilon15virus, |
| | Bacteria_Bacteroidetes_Bacteroidia_Bacteroidales_Tannerellaceae_Parabacteroides, |
| | Bacteria_Actinobacteria_Actinobacteria_Actinomycetales_Actinomycetaceae_Mobiluncus, |
| | Viruses_Caudovirales_Myoviridae, |
| | Bacteria_Proteobacteria_Gammaproteobacteria_Enterobacterales_Enterobacteriaceae_Kosakonia, |
| | Bacteria_Firmicutes_Clostridia_Clostridiales_Oscillospiraceae_Oscillibacter, |
| | Bacteria_Actinobacteria_Actinobacteria_Bifidobacteriales_Bifidobacteriaceae_Gardnerella, |
| | Bacteria_Bacteroidetes_Bacteroidia_Bacteroidales_Tannerellaceae_Tannerella, |
| | Bacteria_Proteobacteria_Gammaproteobacteria_Enterobacterales_Enterobacteriaceae_*Salmonella*, |
| | Bacteria_Firmicutes_Clostridia_Clostridiales_Lachnospiraceae_Flavonifractor, |
| | Bacteria_Proteobacteria_Gammaproteobacteria_Enterobacterales_Enterobacteriaceae_Enterobacter, |
| | Bacteria_Proteobacteria_Alphaproteobacteria_Rhizobiales, |
| | Bacteria_Proteobacteria_Alphaproteobacteria_Rhizobiales_Rhizobiaceae_Rhizobium, |
| | Bacteria_Firmicutes_Clostridia_Clostridiales_Lachnospiraceae, |
| | Bacteria_Firmicutes_Clostridia_Clostridiales_Ruminococcaceae_Ruminiclostridium, |
| | Bacteria_Actinobacteria_Actinobacteria_Propionibacteriales_Propionibacteriaceae_Tessaracoccus, |
| | Bacteria_Firmicutes_Tissierellia_Tissierellales_Peptoniphilaceae_Helcococcus, |
| | Bacteria_Proteobacteria_Gammaproteobacteria_Enterobacterales_Morganellaceae_Xenorhabdus, |
| | Bacteria_Proteobacteria_Betaproteobacteria_Neisseriales_Neisseriaceae_Neisseria, |
| | Bacteria_Bacteroidetes_Flavobacteriia_Flavobacteriales_Flavobacteriaceae, |
| | Bacteria_Proteobacteria_Gammaproteobacteria_Enterobacterales_Erwiniaceae_Pantoea, |
| | Bacteria_Proteobacteria_Betaproteobacteria_Neisseriales_Neisseriaceae_Eikenella, |
| | Viruses_Caudovirales_Podoviridae_P22virus, |
| | Bacteria_Proteobacteria_Gammaproteobacteria_Enterobacterales_Enterobacteriaceae, |
| | Bacteria_Proteobacteria_Gammaproteobacteria_Enterobacterales_Enterobacteriaceae_Citrobacter, |
| | Bacteria_Proteobacteria_Gammaproteobacteria_Enterobacterales_Enterobacteriaceae_Klebsiella, |
| | Viruses_Caudovirales_Siphoviridae, |
| | Bacteria_Proteobacteria_Gammaproteobacteria_Enterobacterales_Morganellaceae_Morganella, |
| | Bacteria_Proteobacteria_Gammaproteobacteria_Enterobacterales_Morganellaceae_Proteus, |
| | Bacteria_Actinobacteria_Actinobacteria_Actinomycetales_Actinomycetaceae_Actinotignum, |
| | Bacteria_Proteobacteria_Alphaproteobacteria_Sphingomonadales_Sphingomonadaceae_Sphingomonas, |

TABLE 4-continued

| Microbe Usage | Microbe Used |
|---|---|
| | Bacteria_Proteobacteria_Gammaproteobacteria_Enterobacterales_Enterobacteriaceae_Shigella, |
| | Bacteria_Proteobacteria_Gammaproteobacteria_Aeromonadales_Aeromonadaceae_Aeromonas, |
| | Bacteria_Proteobacteria_Alphaproteobacteria_Sphingomonadales_Erythrobacteraceae_Porphyrobacter, |
| | Bacteria_Proteobacteria_Gammaproteobacteria_Enterobacterales_Hafniaceae_Edwardsiella, |
| | Bacteria_Fusobacteria_Fusobacteriia_Fusobacteriales_Leptotrichiaceae_Leptotrichia, |
| | Bacteria_Proteobacteria_Gammaproteobacteria_Pasteurellales_Pasteurellaceae_Haemophilus, |
| | Bacteria_Proteobacteria_Gammaproteobacteria_Pasteurellales_Pasteurellaceae_Histophilus, |
| | Bacteria_Proteobacteria_Gammaproteobacteria_Pasteurellales_Pasteurellaceae_Aggregatibacter, |
| | Bacteria_Proteobacteria_Betaproteobacteria_Burkholderiales_Comamonadaceae_Comamonas, |
| | Bacteria_Proteobacteria_Epsilonproteobacteria_Campylobacterales_Campylobacteraceae_Campylobacter, |
| | Bacteria_Proteobacteria_Gammaproteobacteria_Pseudomonadales_Moraxellaceae_Acinetobacter, |
| | Bacteria_Proteobacteria_Alphaproteobacteria_Rhizobiales_Bradyrhizobiaceae_Tardiphaga |
| LUTS Diagnosis: Family Level | Bacteria_Firmicutes_Clostridia_Clostridiales_Peptococcaceae, |
| | Bacteria_Firmicutes_Bacilli_Bacillales_Staphylococcaceae, |
| | Bacteria_Proteobacteria_Betaproteobacteria_Burkholderiales_Comamonadaceae, |
| | Bacteria_Firmicutes_Bacilli_Lactobacillies_Streptococcaceae, |
| | Bacteria_Actinobacteria_Actinobacteria_Corynebacteriales_Corynebacteriaceae, |
| | Bacteria_Proteobacteria_Alphaproteobacteria_Sphingomonadales_Sphingomonadaceae, |
| | Bacteria_Bacteroidetes_Bacteroidia_Bacteroidales_Prevotellaceae, |
| | Bacteria_Actinobacteria_Actinobacteria_Propionibacteriales_Propionibacteriaceae, |
| | Bacteria_Deinococcus-Thermus_Deinococci_Thermales_Thermaceae, |
| | Bacteria_Firmicutes_Bacilli_Lactobacillococcaceae, |
| | Bacteria_Bacteroidetes_Bacteroidia_Bacteroidales_Porphyromonadaceae, |
| | Bacteria_Proteobacteria_Gammaproteobacteria_Pseudomonadales_Pseudomonadaceae, |
| | Viruses_Polyomaviridae, Bacteria_Firmicutes_Bacilli_Lactobacillustobacillaceae, |
| | Bacteria_Proteobacteria_Gammaproteobacteria_Enterobacterales_Enterobacteriaceae, |
| | Bacteria_Firmicutes_Tissierellia_Tissierellales_Peptoniphilaceae, |
| | Bacteria_Proteobacteria_Gammaproteobacteria_Enterobacterales_Yersiniaceae, |
| | Bacteria_Proteobacteria_Alphaproteobacteria_Rhizobiales_Bradyrhizobiaceae, |
| | Viruses_Caudovirales_Podoviridae, Bacteria_Firmicutes_Tissierellia, |
| | Viruses_Caudovirales_Siphoviridae, |
| | Bacteria_Proteobacteria_Alphaproteobacteria_Rhizobiales_Rhizobiaceae, |
| | Bacteria_Firmicutes_Clostridia_Clostridiales_Peptostreptococcaceae, |
| | Bacteria_Firmicutes_Erysipelotrichia_Erysipelotrichales_Erysipelotrichaceae, |
| | Bacteria_Firmicutes_Negativicutes_Veillonellales_Veillonellaceae, |
| | Bacteria_Bacteroidetes_Bacteroidia_Bacteroidales, |
| | Bacteria_Firmicutes_Tissierellia_Tissierellales_Tissierellaceae, |
| | Bacteria_Bacteroidetes_Bacteroidia_Bacteroidales_Tannerellaceae, Viruses_Caudovirales_Myoviridae, |
| | Bacteria_Firmicutes_Clostridia_Clostridiales_Oscillospiraceae, |
| | Bacteria_Actinobacteria_Actinobacteria_Bifidobacteriales_Bifidobacteriaceae, |
| | Bacteria_Proteobacteria_Alphaproteobacteria_Rhizobiales, |
| | Bacteria_Proteobacteria_Betaproteobacteria_Neisseriales_Neisseriaceae, |
| | Bacteria_Proteobacteria_Gammaproteobacteria_Enterobacterales_Erwiniaceae, |
| | Bacteria_Proteobacteria_Gammaproteobacteria_Enterobacterales_Morganellaceae, |
| | Bacteria_Proteobacteria_Gammaproteobacteria_Aeromonadales_Aeromonadaceae, |
| | Bacteria_Proteobacteria_Alphaproteobacteria_Sphingomonadales_Erythrobacteraceae, |
| | Bacteria_Proteobacteria_Gammaproteobacteria_Enterobacterales_Hafniaceae, |
| | Bacteria_Fusobacteria_Fusobacteriia_Fusobacteriales_Leptotrichiaceae, |
| | Bacteria_Proteobacteria_Gammaproteobacteria_Pasteurellales_Pasteurellaceae, |
| | Bacteria_Proteobacteria_Epsilonproteobacteria_Campylobacterales_Campylobacteraceae, |
| | Bacteria_Proteobacteria_Gammaproteobacteria_Pseudomonadales_Moraxellaceae |
| LUTS Diagnosis: Order Level | Bacteria_Firmicutes_Bacilli_Bacillales, Bacteria_Proteobacteria_Betaproteobacteria_Burkholderiales, |
| | Bacteria_Proteobacteria_Alphaproteobacteria_Sphingomonadales, |
| | Bacteria_Actinobacteria_Actinobacteria_Corynebacteriales, |
| | Bacteria_Actinobacteria_Actinobacteria_Propionibacteriales, |
| | Bacteria_Bacteroidetes_Bacteroidia_Bacteroidales, |
| | Bacteria_Proteobacteria_Gammaproteobacteria_Pseudomonadales, |
| | Bacteria_Proteobacteria_Gammaproteobacteria_Enterobacterales, |
| | Bacteria_Firmicutes_Tissierellia_Tissierellales, |
| | Bacteria_Proteobacteria_Alphaproteobacteria_Rhizobiales, Bacteria_Firmicutes_Tissierellia, |
| | Bacteria_Firmicutes_Erysipelotrichia_Erysipelotrichales, |
| | Bacteria_Firmicutes_Negativicutes_ Veillonellales, |
| | Bacteria_Actinobacteria_Actinobacteria_Bifidobacteriales, |
| | Bacteria_Proteobacteria_Betaproteobacteria_Neisseriales, |
| | Bacteria_Proteobacteria_Gammaproteobacteria_Aeromonadales, |
| | Bacteria_Proteobacteria_Gammaproteobacteria_Pasteurellales, |
| | Bacteria_Proteobacteria_Epsilonproteobacteria_Campylobacterales, |
| | Bacteria_Fusobacteria_Fusobacteriia_Fusobacteriales, |
| | Bacteria_Firmicutes_Erysipelotrichia_Erysipelotrichales, |
| | Bacteria_Firmicutes_Negativicutes_ Veillonellales, |
| | Bacteria_Actinobacteria_Actinobacteria_Bifidobacteriales, |
| | Bacteria_Proteobacteria_Betaproteobacteria_Neisseriales, |
| | Bacteria_Proteobacteria_Gammaproteobacteria_Aeromonadales, |
| | Bacteria_Proteobacteria_Gammaproteobacteria_Pasteurellales, |
| | Bacteria_Proteobacteria_Epsilonproteobacteria_Campylobacterales, |
| | Bacteria_Fusobacteria_Fusobacteriia_Fusobacteriales |

TABLE 4-continued

| Microbe Usage | Microbe Used |
|---|---|
| LUTS Diagnosis: Class Level | Bacteria_Firmicutes_Bacilli, Bacteria_Actinobacteria_Actinobacteria, Bacteria_Proteobacteria_Betaproteobacteria, Bacteria_Deinococcus-Thermus_Deinococci, Bacteria_Bacteroidetes_Bacteroidia, Bacteria_Proteobacteria_Gammaproteobacteria, Bacteria_Firmicutes_Tissierellia, Bacteria_Proteobacteria_Alphaproteobacteria, Bacteria_Proteobacteria_Epsilonproteobacteria, Bacteria_Firmicutes_Erysipelotrichia, Bacteria_Firmicutes_Negativicutes, Bacteria_Fusobacteria_Fusobacteriia |

Example 9

Identification of Beneficial Species to Treat Bladder Cancer, or Lower Urinary Tract Symptoms Though not depicted in the figures, species can be classified as beneficial by identifying disease-free patients harboring both disease-associated (defined as >60% normalized expression in disease positive cohorts) and disease-independent microbes (defined as >60% normalized expression in disease negative cohorts). Beneficial species are defined as the collection of disease-independent microbes in individuals harboring disease-associated microbes. Statistical testing of expression across disease-free and disease-positive cohorts enables a determination of statistically significant ($p<0.05$, Kruskal-Wallis test) enrichment (defined as normalized expression in disease-negative greater than normalized expression in disease positive-individuals) of beneficial species.

TABLE 5 presents microbes, classified at all levels of taxonomic classification, their associated statistical p-value statistically significant ($p<0.05$) prevalence among non-diseased individuals, and the population-level prevalence (percentage of individuals in the normal cohort) with the beneficial microbe. Any one or more of these microbes may be administered to individuals with bladder cancer to bring the microbial constituency of the bladder to a state expected in normal individuals.

TABLE 5 shows examples of beneficial species in the bladder cancer setting. Species are classified as beneficial by identifying cancer-free patients harboring both cancer-associated (defined as >60% normalized expression in cancer-positive cohorts) and disease-independent microbes (defined as >60% normalized expression in disease-negative cohorts). Beneficial species are defined as the collection of disease-independent microbes (not expressed in individuals with disease, e.g., cancer) in individuals harboring disease-associated microbes. Statistical testing of expression across disease-free and disease positive cohorts enables a determination of statistically significant ($p<0.05$, Kruskal-Wallis test) enrichment (defined as normalized expression in disease negative greater than normalized expression in disease positive individuals) of beneficial species.

TABLE 5

| Microbe | P-Value | % Prevalence Among Normals |
|---|---|---|
| Bacteria_Bacteroidetes_Bacteroidia_Bacteroidales_Prevotellaceae_Prevotella_jejuni | 5.38E−05 | 15.6 |
| Bacteria_Firmicutes_Bacilli_Lactobacillales_Lactobacillaceae_Lactobacillus_gasseri | 5.38E−05 | 15.6 |
| Bacteria_Actinobacteria_Actinobacteria_Corynebacteriales_Corynebacteriaceae_Corynebacterium_(sp. NML98-0116) | 5.38E−05 | 15.6 |
| Bacteria_Actinobacteria_Actinobacteria_Propionibacteriales_Propionibacteriaceae_Cutibacterium_acnes | 1.33E−04 | 14.1 |
| Bacteria_Firmicutes_Bacilli_Lactobacillales_Lactobacillaceae_Lactobacillus_amylovorus | 3.31E−04 | 12.5 |
| Bacteria_Firmicutes_Bacilli_Lactobacillales_Lactobacillaceae_Lactobacillus_johnsonii | 3.31E−04 | 12.5 |
| Bacteria_Firmicutes_Bacilli_Lactobacillales_Lactobacillaceae_Lactobacillus_jensenii | 8.29E−04 | 10.9 |
| Bacteria_Proteobacteria_Gammaproteobacteria_Pseudomonadales_Pseudomonadaceae_Pseudomonas_fluorescens group | 8.29E−04 | 10.9 |
| Bacteria_Deinococcus-Thermus_Deinococci_Thermales_Thermacease_Thermus_scotoductus | 8.29E−04 | 10.9 |
| Bacteria_Firmicutes_Bacilli_Lactobacillales_Streptococcaceae_Streptococcus_anginosus group | 8.29E−04 | 10.9 |
| Bacteria_Firmicutes_Bacilli_Lactobacillales_Stroptococcaceae_Streptococcus_anginosus | 2.09E−03 | 9.4 |
| Bacteria_Firmicutes_Bacilli_Lactobacillales_Streptococcaceae_Streptococcus_mitis | 2.09E−03 | 9.4 |
| Bacteria_Bacteroidetes_Bacteroidia_Bacterodales_Porphyromonadaceae_Porphyromonas_asaccharolytica | 2.09E−03 | 9.4 |
| Bacteria_Firmicutes_Bacilli_Lactobacillales_Lactobacillaceae_Lactobacillus_crispatus | 2.09E−03 | 9.4 |
| Bacteria_Actinobacteria_Actinobacteria_Micrococcales_Micrococcaceaea_Micrococcus_luteus | 5.35E−03 | 7.8 |
| Bacteria_Firmicutes_Bacilli_Lactobacillales_Lactobacillaceae_Lactobacillus_helveticus | 5.35E−03 | 7.8 |
| Bacteria_Proteobacteria_Gammaproteobacteria_Pseudomonadales_Pseudomonadaceae_Pseudomonas_tolaasii | 5.35E−03 | 7.8 |
| Bacteria_Bacteroidetes_Bacteroidia_Bacteroidales_Prevotellaceae_Prevotella_fusca | 5.35E−03 | 7.8 |
| Bacteria_Firmicutes_Bacilli_Lactobacillales_Aerococcaceae_Aerococcus_christensenii | 5.35E−03 | 7.8 |
| Bacteria_Firmicutes_Bacilli_Lactobacillales_Streptococcaceae_Streptococcus_parasanguinis | 1.39E−02 | 6.2 |

TABLE 5-continued

| Microbe | P-Value | % Prevalence Among Normals |
|---|---|---|
| Bacteria_Actinobacteria_Actinobacteria_Corynebacteriales_Corynebacteriaceao_Lawsonella_clevelandensis | 1.39E−02 | 6.2 |
| Bacteria_Firmicutes_Bacilli_Lactobacillales_Lactobacillaceae_Lactobacillus_delbrueckii | 1.39E−02 | 6.2 |
| Bacteria_Firmicutes_Bacilli_Lactobacillales_Streptococcaceae_Streptococcus_pseudopneumoniae | 1.39E−02 | 6.2 |
| Bacteria_Deinococcus-Thermus_Deinococci_Thermales_Thermaceae_Thermus_thermophilus | 1.39E−02 | 6.2 |
| Bacteria_Firmicutes_Tissierellia_Tissierellales_Peptoniphilaceae_Anaerococcus_prevotii | 1.39E−02 | 6.2 |
| Bacteria_Bacteroidetes_Bacteroidia_Bacteroidales_Prevotellaceae_Prevotella_sp. oraltaxon 299 | 1.39E−02 | 6.2 |
| Bacteria_Proteobacteria_Gammaproteobacteria_Pasteurellales_Pasteurellaceae_Haemophilus_influenzae | 1.39E−02 | 6.2 |
| Bacteria_Proteobacteria_Epsilonproteobacteria_Campylobacterales_Campylobacteraceae_Campylobacter_ureolyticus | 1.39E−02 | 6.2 |
| Bacteria_Bacteroidetes_Bacteroidia_Bacteroidales_Porphyromonadaceae_Porphyromonas_gingivalis | 1.39E−02 | 6.2 |
| Bacteria_Firmicutes_Bacilli_Lactobacillales_Streptococcaceae_Streptococcus_oralis | 3.69E−02 | 4.7 |
| Bacteria_Firmicutes_Bacilli_Lactobacillales_Lactobacillaceae_Lactobacillis | 3.69E−02 | 4.7 |
| Bacteria_Firmicutes_Bacilli_Lactobacillales_Lactobacillaceae_Lactobacillus_acidophilus | 3.69E−02 | 4.7 |
| Bacteria_Actinobacteria_Actinobacteria_Bifidobacteriales_Bifidobacteriaceae_Bifidobacterium_breve | 3.69E−02 | 4.7 |
| Bacteria_Actinobacteria_Actinobacteria_Corynebacteriales_Corynebacteriaceae_Corynebacterium_aurimucosum | 3.69E−02 | 4.7 |
| Bacteria_Actinobacteria_Actinobacteria_Actinomycetales_Actinomycetaceae_Mobiluncus_curtisii | 3.69E−02 | 4.7 |
| Bacteria_Firmicutes_Bacilli_Lactobacillales_Lactobacillaceae_Lactobacillus_kefiranofaciens | 3.69E−02 | 4.7 |
| Bacteria_Bacteroidetes_Flavobacteriia_Flavobacteriales_Flavobacteriaceae_Ornithobacterium_rhinotracheale | 3.69E−02 | 4.7 |
| Bacteria_Actinobacteria_Actinobacteria_Propionibacteriales_Propionibacteriaceae_Cutibacterium_avidum | 3.69E−02 | 4.7 |
| Bacteria_Firmicutes_Negativicutes_Veillonellales_Veillonellaceae_Veillonella_atypica | 3.69E−02 | 4.7 |
| Bacteria_Firmicutes_Bacilli_Lactobacillales_Lactobacillaceae_Lactobacillus_gallinarum | 3.69E−02 | 4.7 |
| Bacteria_Proteobacteria_Gammaproteobacteria_Pasteurellales_Pasteurellaceae_Aggregatibacter_aphrophilus | 3.69E−02 | 4.7 |
| Bacteria_Firmicutes_Clostridia_Clostridiales_Ruminococcaceae_Faecalibacterium_prausnitzii | 3.69E−02 | 4.7 |
| Bacteria_Bacteroidetes_Flavobacteriia_Flavobacteriales_Flavobacteriaceae_Ornithobacterium_rhinotracheale | 3.69E−02 | 4.7 |
| Bacteria_Actinobacteria_Actinobacteria_Propionibacteriales_Propionibacteriaceae_Cutibacterium_avidum | 3.69E−02 | 4.7 |
| Bacteria_Firmicutes_Negativicutes_Veillonellales_Veillonellaceae_Veillonella_atypica | 3.69E−02 | 4.7 |

TABLE 6 presents microbes, classified at all levels of taxonomic classification, their associated statistical p-value statistically significant (p<0.05) prevalence among non-diseased individuals, and the population-level prevalence (percentage of individuals in the normal cohort) with the probiotic microbe. Any one or more of these microbes may be administered to individuals with bladder cancer to bring the microbial constituency of the bladder to a state expected in normal individuals.

TABLE 6 shows examples of beneficial species in the LUTS setting. Species can be classified as beneficial by identifying disease-free patients harboring both disease-associated (defined as >60% normalized expression in LUTS-positive cohorts) and disease-independent microbes (defined as >60% normalized expression in LUTS-negative cohorts). Probiotic or beneficial species are defined as the collection of disease-independent microbes (not expressed in individuals with disease, e.g., LUTS) in individuals harboring disease-associated microbes. Statistical testing of expression across disease-free and disease-positive cohorts enables a determination of statistically significant (p<0.05, Kruskal-Wallis test) enrichment (defined as normalized expression in disease-negative greater than normalized expression in disease-positive individuals) of probiotic species.

TABLE 6

| Microbe | P-Value | % Prevalence Among Normals | % Prevalence Among LUTS Patients |
|---|---|---|---|
| Bacteria_Firmicutes_Bacilli_Lactobacillales_Lactobacillaceae_Lactobacillus_amylovorus | 3.31E−04 | 12.5 | 0 |
| Bacteria_Firmicutes_Bacilli_Lactobacillales_Lactobacillus_Lactobacillus_jensenii | 8.29E−04 | 10.9 | 0 |

TABLE 6-continued

| Microbe | P-Value | % Prevalence Among Normals | % Prevalence Among LUTS Patients |
|---|---|---|---|
| Bacteria_Proteobacteria_Alphaproteobacteria_Rhizobiales_Bradyrhizobiaceae_*Bradyrhizobium_diazoefficiens* | 2.09E−03 | 9.4 | 0 |
| Bacteria_Firmicutes_Bacilli_Lactobacillales_Streptococcaceae_*Streptococcus_mitis* | 2.09E−03 | 9.4 | 0 |
| Bacteria_Firmicutes_Bacilli_Lactobacillales_Lactobacillaceae_*Lactobacillus_crispatus* | 2.09E−03 | 9.4 | 0 |
| Bacteria_Actinobacteria_Actinobacteria_Micrococcales_Micrococcaceae_*Micrococcus_luteus* | 5.35E−03 | 7.8 | 0 |
| Bacteria_Firmicutes_Bacilli_Lactobacillales_Lactobacillaceae_*Lactobacillus_helveticus* | 5.35E−03 | 7.8 | 0 |
| Bacteria_Proteobacteria_Gammaproteobacteria_Pseudomonadales_Pseudomonadaceae_*Pseudomonas_tolaasii* | 5.35E−03 | 7.8 | 0 |
| Bacteria_Firmicutes_Bacilli_Lactobacillales_Aerococcaceae_*Aerococcus_christensenii* | 5.35E−03 | 7.8 | 0 |
| Bacteria_Proteobacteria_Alphaproteobacteria_Rhizobiales_Bradyrhizobiaceae_*Rhodopseudomonas_palustris* | 1.39E−02 | 6.2 | 0 |
| Bacteria_Firmicutes_Bacilli_Lactobacillales_Streptococcaceae_*Streptococcus_parasanguinis* | 1.39E−02 | 6.2 | 0 |
| Bacteria_Firmicutes_Bacilli_Lactobacillales_Lactobacillaceae_*Lactobacillus_delbrueckii* | 1.39E−02 | 6.2 | 0 |
| Bacteria_Proteobacteria_Alphaproteobacteria_Rhizobiales_Hyphomicrobiaceae_*Devosia*_sp. H5989 | 1.39E−02 | 6.2 | 0 |
| Bacteria_Proteobacteria_Alphaproteobacteria_Rhizobiales_Bradyrhizobiaceae_*Bradyrhizobium*_sp. SK17 | 1.39E−02 | 6.2 | 0 |
| Bacteria_Firmicutes_Bacilli_Lactobacillales_Streptococcaceae_*Streptococcus_pseudopneumoniae* | 1.39E−02 | 6.2 | 0 |
| Bacteria_Deinococcus-Thermus_Deinococci_Thermales_Thermaceae_*Thermus_thermophilus* | 1.39E−02 | 6.2 | 0 |
| Bacteria_Proteobacteria_Alphaproteobacteria_Rhizobiales_Bradyrhizobiaceae_*Bradyrhizobium*_sp. | 1.39E−02 | 6.2 | 0 |
| Bacteria_Firmicutes_Bacilli_Lactobacillales_Streptococcaceae_*Streptococcus_oralis* | 3.69E−02 | 4.7 | 0 |
| Bacteria_Firmicutes_Bacilli_Lactobacillales_Lactobacillaceae_*Lactobacillus* | 3.69E−02 | 4.7 | 0 |
| Bacteria_Firmicutes_Bacilli_Lactobacillales_Lactobacillaceae_*Lactobacillus_acidophilus* | 3.69E−02 | 4.7 | 0 |
| Bacteria_Actinobacteria_Actinobacteria_Bifidobacteriales_Bifidobacteriaceae_*Bifidobacterium_breve* | 3.69E−02 | 4.7 | 0 |
| Viruses_Polyomaviridae_Betapolyomavirus_Human polyomavirus 1 | 3.69E−02 | 4.7 | 0 |
| Bacteria_Proteobacteria_Gammaproteobacteria_Pseudomonadales_Pseudomonadaceae_*Pseudomonas*_sp. AK6U | 3.69E−02 | 4.7 | 0 |
| Bacteria_Actinobacteria_Actinobacteria_Bifidobacteriales_Bifidobacteriaceae_*Bifidobacterium_longum* | 3.69E−02 | 4.7 | 0 |
| Bacteria_Firmicutes_Bacilli_Lactobacillales_Lactobacillaceae_*Lactobacillus_kefiranofaciens* | 3.69E−02 | 4.7 | 0 |
| Bacteria_Proteobacteria_Alphaproteobacteria_Rhizobiales_Bradyrhizobiaceae_*Bradyrhizobium*_sp. S23321 | 3.69E−02 | 4.7 | 0 |
| Bacteria_Firmicutes_Negativicutes_Veillonellales_Veillonellaceae_*Veillonella_atypica* | 3.69E−02 | 4.7 | 0 |
| Bacteria_Firmicutes_Bacilli_Lactobacillales_Lactobacillaceae_*Lactobacillus_gallinarum* | 3.69E−02 | 4.7 | 0 |
| Bacteria_Bacteroidetes_Bacteroidia_Bacteroidales_Bacteroidaceae_*Bacteroides_thetaiotaomicron* | 3.69E−02 | 4.7 | 0 |
| Bacteria_Firmicutes_Clostridia_Clostridiales_Ruminococcaceae_*Mageeibacillus_indolicus* | 3.69E−02 | 4.7 | 0 |

Example 10

Figure 40E:
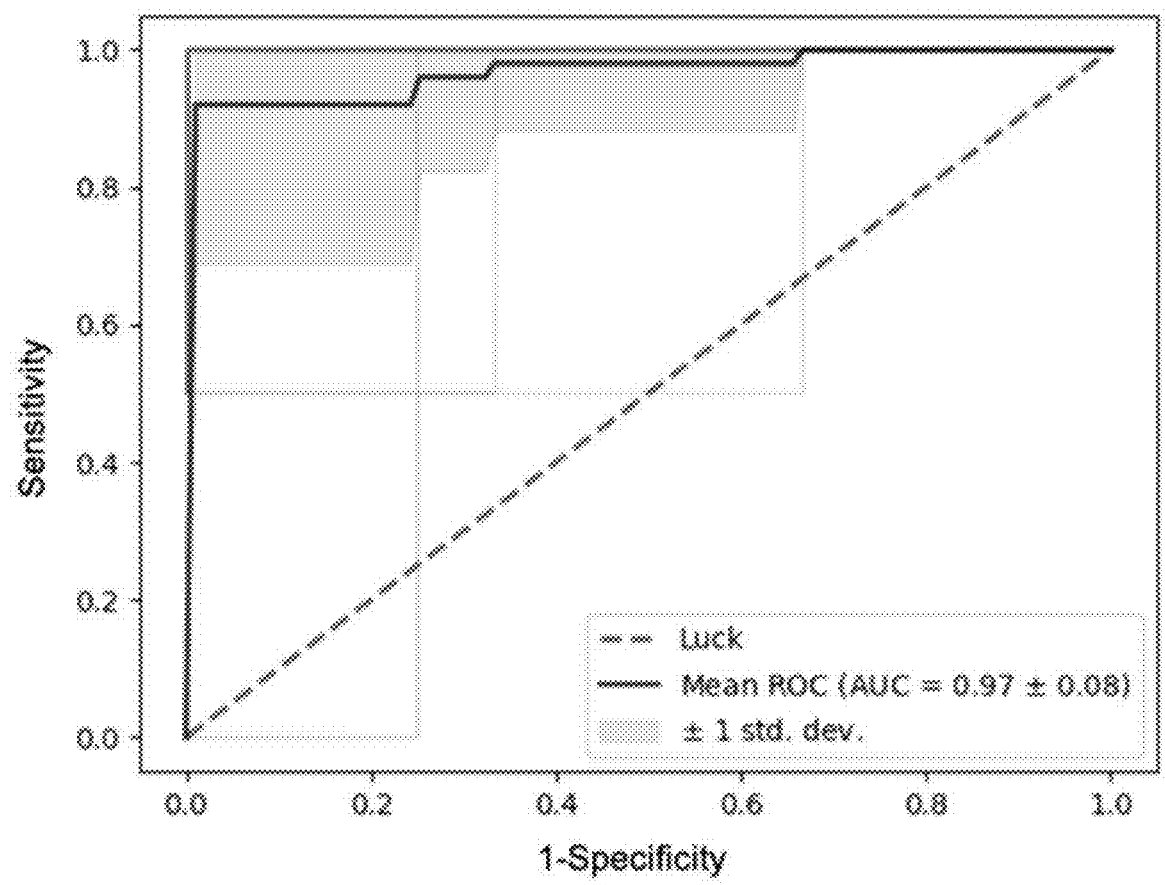
FIG. 40E shows results from a linear SVM trained on non-linear dimensionality reduced normalized (mean) expression data using "RLB" the distance metric listed in Table 1 of Koleff; et. al in combination with genomic mutational data using 25-fold cross validation, where sensitivity and specificity vastly improved with AUC=0.97±0.08.

Genetic Mutations Associated with Bladder Cancer Detected in a Subject's Urine and Integrated with Microbiomics to Enhance Disease Classification FIG. 40A shows genetic mutations associated with bladder cancer that were detected in plurality of nucleic acid purified from the urine in a cohort of cancer positive individuals. Such genetic mutations are associated with the subject(s)' tumors and not with the microbiome of the subject's urinary tract. The population-level prevalence of the genetic mutations are displayed and the genetic mutations are ranked from left to right in terms of their utility for bladder cancer classification. As shown in FIG. 40A, the genetic mutations most correlated with bladder cancer are, in descending order, MLL2, MLL3, TP53, ATM, SPTAN1, ERBB3, EP300, ARID1A, ELF3, PIK3CA, FGFR3, RHOB, STAG2, ERBB2, KDM6A, FBXW7, TSC1, NFE2L2, ZFP36L1, ASXL2, NOTCH1, PCSK5, CTNNB1, KLF5, HRAS, ERCC2, NOTCH2, RXRA, FOXQ1, HORMAD1, MIPOL1, RHOA, ZFR2, FOXA1, PHLDA3, PAIP1, CX3CL1, MDM4, TBL1XR1, TXNIP, and TPTE. Thus, the presence of any one of more of the genetic mutations MLL3, TP53, ATM, SPTAN1, ERBB3, EP300, ARID1A, ELF3, PIK3CA, FGFR3, RHOB, STAG2, ERBB2, KDM6A, FBXW7, TSC1, NFE2L2, ZFP36L1, ASXL2, NOTCH1, PCSK5, CTNNB1, KLF5, HRAS, ERCC2, NOTCH2, RXRA, FOXQ1, HORMAD1, MIPOL1, RHOA, ZFR2, FOXA1, PHLDA3, PAIP1, CX3CL1, MDM4, TBL1XR1, TXNIP, and TPTE in a sample corresponding to an individual may provide an indication that the individual has bladder cancer. As such, information about these mutations may be combined with the microbiomics information described herein to further enhance the accuracy, sensitivity, or specificity of classifying a subject as having or not having any urinary tract disorder described herein. As shown in FIG. 40B, the linear SVM classifier trained on microbial normalized (mean) expression data for each patient and microbe $e_{i,j}$ using 25-fold cross validation results in a poor sensitivity and specificity no better than a coin flip. However, after applying non-linear dimensionality reduction to the normalized (mean) microbiome expression data using the "RLB" distance metric listed in Table 1 of Koleff; et. al, the trained classifier results in a vastly improved sensitivity >60% and specificity >90% with an AUC=0.78±0.25. As shown in FIG. 40C, we investigate a linear SVM classifier on genetic mutations alone, and a sensitivity >80% and specificity >90% with an AUC=0.95±0.12 is obtained. As shown in FIG. 40E, we demonstrate the utility of combining mutational and microbiomics data by training a linear SVM classifier on non-linear dimensionality reduced normalized (mean) expression data using the "RLB" distance metric listed in Table 1 of Koleff; et. al in combination with genomic mutational data using 25-fold cross validation. The resulting sensitivity is 0.91 and specificity is 0.98 with AUC=0.97±0.08.

Example 11

Preservation of Urine Samples in a Preservation Solution

FIGS. 41A-G show the performance of a preservation solution described herein. The preservation solution was composed of 100 mM Tris-HCl buffer, 50 mM EDTA, 110 µg poly-L-lysine hydrobormide at a mixed molecular weight of 1,000 Da to 5,000 Da, 1 mg D-alpha-tocopherol polyethylene glycol 1000 succinate (water-soluble vitamin E conjugate), 5 µM Enterobactin, 100 units of penicillin, 100 units of streptomycin, and 0.25 µg/mL Amphotericin B.

FIG. 41A shows the total DNA yield from urine samples containing no preservation solution (no buffer) and urine samples containing the preservation solution (preservation buffer) described herein. As shown in FIG. 41A, the total DNA extracted from urine increases substantially in the no buffer condition after 5 days, while the total DNA extracted from urine does not increase appreciably in the preservation buffer condition after 5 days. Bars represent the average of 5 independent samples and error bars represent the standard error.

FIG. 41B shows the total DNA post Kappa amplification from urine samples containing no preservation solution (no buffer) and urine samples containing the preservation solution (preservation buffer) described herein. As shown in FIG. 41B, the DNA is significantly degraded in the no buffer condition after 5 days, while the DNA is not significantly degraded in the preservation buffer condition after 5 days. Bars represent the average of 5 independent samples and error bars represent the standard error.

FIG. 41C shows the total number of nucleic acid sequencing reads from urine samples containing no preservation solution (no buffer) and urine samples containing the preservation solution (preservation buffer) described herein. As shown in FIG. 41C, the number of sequencing reads decreases substantially in the no buffer condition after 5 days, while the number of sequencing reads does not decrease appreciably in the preservation buffer condition after 5 days. Bars represent the average of 5 independent samples and error bars represent the standard error.

FIG. 41D shows the hybrid capture efficiency from urine samples containing no preservation solution (no buffer) and urine samples containing the preservation solution (preservation buffer) described herein. As shown in FIG. 41D, the hybrid capture efficiency does not decrease substantially in the no buffer condition after 5 days, or in the preservation buffer condition after 5 days. Bars represent the average of 5 independent samples and error bars represent the standard error.

Figure 41E:
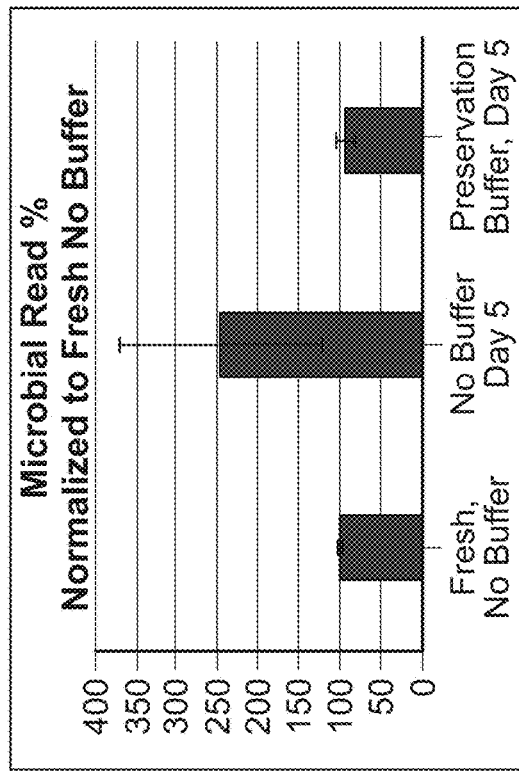
FIG. 41E shows the nucleic acid sequencing efficiency for detection of rare mutant molecules from urine samples containing no preservation solution (no buffer) and urine samples containing the preservation solution (preservation buffer) described herein.

FIG. 41E shows the nucleic acid sequencing efficiency for detection of rare mutant molecules from urine samples containing no preservation solution (no buffer) and urine samples containing the preservation solution (preservation buffer) described herein. As shown in FIG. 41E, the sequencing efficiency decreases substantially in the no buffer condition after 5 days, while the sequencing efficiency increases substantially in the preservation buffer condition after 5 days. Bars represent the average of 5 independent samples and error bars represent the standard error.

Figure 41F:
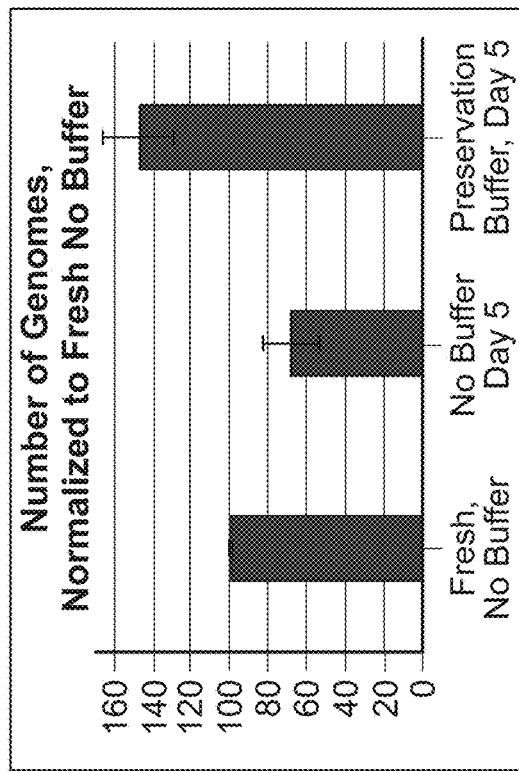
FIG. 41F shows the microbial composition from urine samples containing no preservation solution (no buffer) and urine samples containing the preservation solution (preservation buffer) described herein.

FIG. 41F shows the microbial composition from urine samples containing no preservation solution (no buffer) and urine samples containing the preservation solution (preservation buffer) described herein. As shown in FIG. 41F, the percentage of nucleic acid sequencing reads associated with microbes significantly increases in the no buffer condition after 5 days, while the percentage of nucleic acid sequencing reads associated with microbes does not increase appreciably in the preservation buffer condition after 5 days. Bars represent the average of 5 independent samples and error bars represent the standard error.

Figure 41G:
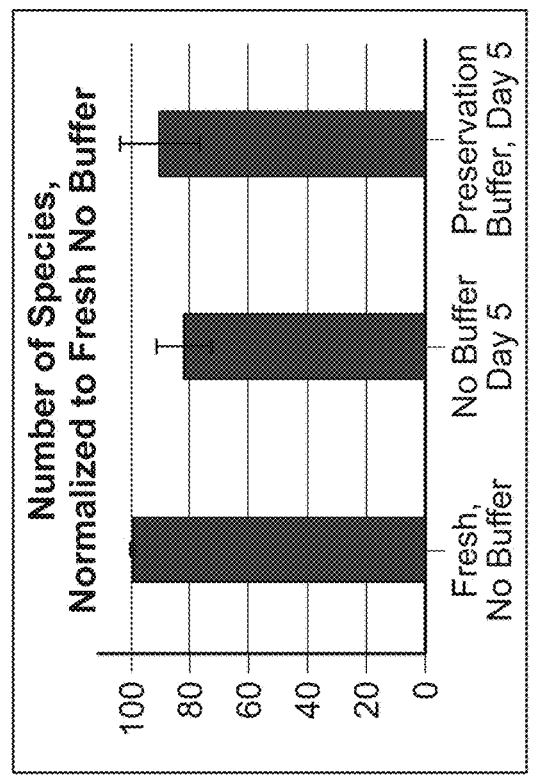
FIG. 41G shows the bacterial diversity of urine samples containing no preservation solution (no buffer) and urine samples containing the preservation solution (preservation buffer) described herein.

FIG. 41G shows the bacterial diversity of urine samples containing no preservation solution (no buffer) and urine samples containing the preservation solution (preservation buffer) described herein. As shown in FIG. 41G, the number of bacterial species decreases substantially in the no buffer condition after 5 days, while the number of bacterial species does not decrease substantially in the preservation buffer condition after 5 days. Bars represent the average of 5 independent samples and error bars represent the standard error.

Example 12

Increased Nucleic Acid Sequencing Reads Using a Preservation Solution

A urine sample preserved in a reference composition failed to produce satisfactory sequencing read depths (e.g., read depths less than 12,000,000) in a majority of quality control tests performed. In comparison, a urine sample preserved in the preservation solution described herein produced satisfactory sequencing reads depths in all quality control tests performed. In addition, preserving the urine sample in the preservation solution described herein increased the sequencing read depth in all quality control tests performed.

Example 13

Case Study—Identification of Previously Unidentifiable Urinary Disorder

A subject complained of recurring urinary tract infections (UTIs). Over the course of at least 20 years, the subject had been treated for at least 20 UTIs. The subject experienced waves of pain and urgency approximately once every 2-3 weeks for the period of at least 20 years. The subject had been treated by both primary care physicians and urological specialists. Numerous attempts had been made to identify the cause of the UTIs using urine chemistry and urine cultures. However, such samples had failed to reveal any culturable bacteria. Immediately before testing of the subject's urinary microbiome, the subject had been receiving treatment for a period of three months using three different antimicrobials with no resolution of symptoms.

A urine sample from the subject was analyzed using the urinary microbiomics systems and methods described herein. The urine sample was characterized by a low to moderate bacterial load with a very diverse bacterial community of 65 distinct species. The top four most abundant bacterial species groups were all opportunistic pathogens and had been implicated in urinary tract infections. In order of most abundant to least abundant, the bacteria including *Burkholderia cepacia* complex (17,063 sequencing reads, 948 sequencing reads/milliliter (mL) of urine, 68 cells/mL of urine), *pseudomallei* group (1,858 sequencing reads, 103 sequencing reads/mL, 7 cells/mL), *Stenotrophomonas maltophilia* group (1,781 sequencing reads, 99 sequencing reads/mL, 7 cells/mL), *Pseudomonas aeruginoisa* group (432 sequencing reads, 24 sequencing reads/mL, 2 cells/mL), and *Pseudomonas fluorescens* group (240 sequencing reads, 13 sequencing reads/mL, 1 cell/mL). *Burkholderia*, *Stenotrophomonas maltophilia*, and *Pseudomonas aeruginosa* are rare atypical causes of UTI, previously identifiable only using specialized non-standard cell culture techniques.

Example 14

A Urine Buffering System

TABLE 7 shows examples of components of a urine buffering system. Here, A, B, C, and D represent the amount of each component in the formulation. For example, A can range from about 1 pM to 10 mM, B can range from about 1 pM to 10 mM, C can range from about 1 pM to 10 mM, and D can range from about 1 pM to 10 mM.

TABLE 7

| Formulation Name | Formula |
| --- | --- |
| Formulation 1 | A*[Enterobactin] + B*[penicillin] + C*[poly-L-lysine] + D*[Vitamin E conjugate] |
| Formulation 2 | A*[Enterobactin] + B*[streptomycin] + C*[poly-L-lysine] + D*[Vitamin E conjugate] |
| Formulation 3 | A*[Enterobactin] + B*[amphotericin B] + C*[poly-L-lysine] + D*[Vitamin E conjugate] |
| Formulation 4 | A*[EDTA] + B*[penicillin] + C*[poly-L-lysine] + D*[Vitamin E conjugate] |
| Formulation 5 | A*[EDTA] + B*[streptomycin] + C*[poly-L-lysine] + D*[Vitamin E conjugate] |
| Formulation 6 | A*[EDTA] + B*[amphotericin B] + C*[poly-L-lysine] + D*[Vitamin E conjugate] |
| Formulation 7 | A*[CyDTA] + B*[penicillin] + C*[poly-L-lysine] + D*[Vitamin E conjugate] |
| Formulation 8 | A*[CyDTA] + B*[streptomycin] + C*[poly-L-lysine] + D*[Vitamin E conjugate] |
| Formulation 9 | A*[CyDTA] + B*[amphotericin B] + C*[poly-L-lysine] + D*[Vitamin E conjugate] |
| Formulation 10 | A*[GEDTA] + B*[penicillin] + C*[poly-L-lysine] + D*[Vitamin E conjugate] |
| Formulation 11 | A*[GEDTA] + B*[streptomycin] + C*[poly-L-lysine] + D*[Vitamin E conjugate] |
| Formulation 12 | A*[GEDTA] + B*[amphotericin B] + C*[poly-L-lysine] + D*[Vitamin E conjugate] |
| Formulation 13 | A*[NTA] + B*[penicillin] + C*[poly-L-lysine] + D*[Vitamin E conjugate] |
| Formulation 14 | A*[NTA] + B*[streptomycin] + C*[poly-L-lysine] + D*[Vitamin E conjugate] |
| Formulation 15 | A*[NTA] + B*[amphotericin B] + C*[poly-L-lysine] + D*[Vitamin E conjugate] |
| Formulation 16 | A*[TTHA] + B*[penicillin] + C*[poly-L-lysine] + D*[Vitamin E conjugate] |
| Formulation 17 | A*[TTHA] + B*[streptomycin] + C*[poly-L-lysine] + D*[Vitamin E conjugate] |
| Formulation 18 | A*[TTHA] + B*[amphotericin B] + C*[poly-L-lysine] + D*[Vitamin E conjugate] |
| Formulation 19 | A*[DHEG] + B*[penicillin] + C*[poly-L-lysine] + D*[Vitamin E conjugate] |
| Formulation 20 | A*[DHEG] + B*[streptomycin] + C*[poly-L-lysine] + D*[Vitamin E conjugate] |
| Formulation 21 | A*[DHEG] + B*[amphotericin B] + C*[poly-L-lysine] + D*[Vitamin E conjugate] |
| Formulation 22 | A*[IDA] + B*[penicillin] + C*[poly-L-lysine] + D*[Vitamin E conjugate] |
| Formulation 23 | A*[IDA] + B*[streptomycin] + C*[poly-L-lysine] + D*[Vitamin E conjugate] |
| Formulation 24 | A*[IDA] + B*[amphotericin B] + C*[poly-L-lysine] + D*[Vitamin E conjugate] |
| Formulation 25 | A*[NTP] + B*[penicillin] + C*[poly-L-lysine] + D*[Vitamin E conjugate] |
| Formulation 26 | A*[NTP] + B*[streptomycin] + C*[poly-L-lysine] + D*[Vitamin E conjugate] |
| Formulation 27 | A*[NTP] + B*[amphotericin B] + C*[poly-L-lysine] + D*[Vitamin E conjugate] |
| Formulation 28 | A*[HIDA] + B*[penicillin] + C*[poly-L-lysine] + D*[Vitamin E conjugate] |
| Formulation 29 | A*[HIDA] + B*[streptomycin] + C*[poly-L-lysine] + D*[Vitamin E conjugate] |
| Formulation 30 | A*[HIDA] + B*[amphotericin B] + C*[poly-L-lysine] + D*[Vitamin E conjugate] |
| Formulation 31 | A*[EDDP] + B*[penicillin] + C*[poly-L-lysine] + D*[Vitamin E conjugate] |
| Formulation 32 | A*[EDDP] + B*[streptomycin] + C*[poly-L-lysine] + D*[Vitamin E conjugate] |
| Formulation 33 | A*[EDDP] + B*[amphotericin B] + C*[poly-L-lysine] + D*[Vitamin E conjugate] |
| Formulation 34 | A*[EDTPO] + B*[penicillin] + C*[poly-L-lysine] + D*[Vitamin E conjugate] |
| Formulation 35 | A*[EDTPO] + B*[streptomycin] + C*[poly-L-lysine] + D*[Vitamin E conjugate] |
| Formulation 36 | A*[EDTPO] + B*[amphotericin B] + C*[poly-L-lysine] + D*[Vitamin E conjugate] |
| Formulation 37 | A*[BAPTA] + B*[penicillin] + C*[poly-L-lysine] + D*[Vitamin E conjugate] |
| Formulation 38 | A*[BAPTA] + B*[streptomycin] + C*[poly-L-lysine] + D*[Vitamin E conjugate] |
| Formulation 39 | A*[BAPTA] + B*[amphotericin B] + C*[poly-L-lysine] + D*[Vitamin E conjugate] |
| Formulation 40 | A*[Achromobactina] + B*[penicillin] + C*[poly-L-lysine] + D*[Vitamin E conjugate] |
| Formulation 41 | A*[Achromobactina] + B*[streptomycin] + C*[poly-L-lysine] + D*[Vitamin E conjugate] |
| Formulation 42 | A*[Achromobactina] + B*[amphotericin B] + C*[poly-L-lysine] + D*[Vitamin E conjugate] |
| Formulation 43 | A*[Achromobactina] + B*[penicillin] + C*[poly-L-lysine] + D*[Vitamin E conjugate] |
| Formulation 44 | A*[Achromobactina] + B*[streptomycin] + C*[poly-L-lysine] + D*[Vitamin E conjugate] |
| Formulation 45 | A*[Achromobactina] + B*[amphotericin B] + C*[poly-L-lysine] + D*[Vitamin E conjugate] |
| Formulation 46 | A*[Acinetobactin] + B*[penicillin] + C*[poly-L-lysine] + D*[Vitamin E conjugate] |
| Formulation 47 | A*[Acinetobactin] + B*[streptomycin] + C*[poly-L-lysine] + D*[Vitamin E conjugate] |
| Formulation 48 | A*[Acinetobactin] + B*[amphotericin B] + C*[poly-L-lysine] + D*[Vitamin E conjugate] |
| Formulation 49 | A*[Acinetoferrin] + B*[penicillin] + C*[poly-L-lysine] + D*[Vitamin E conjugate] |
| Formulation 50 | A*[Acinetoferrin] + B*[streptomycin] + C*[poly-L-lysine] + D*[Vitamin E conjugate] |

TABLE 7-continued

| Formulation Name | Formula |
|---|---|
| Formulation 51 | A*[Acinetoferrin] + B*[amphotericin B] + C*[poly-L-lysine] + D*[Vitamin E conjugate] |
| Formulation 52 | A*[Aerobactin] + B*[penicillin] + C*[poly-L-lysine] + D*[Vitamin E conjugate] |
| Formulation 53 | A*[Aerobactin] + B*[streptomycin] + C*[poly-L-lysine] + D*[Vitamin E conjugate] |
| Formulation 54 | A*[Aerobactin] + B*[amphotericin B] + C*[poly-L-lysine] + D*[Vitamin E conjugate] |
| Formulation 55 | A*[Aeruginic acid] + B*[penicillin] + C*[poly-L-lysine] + D*[Vitamin E conjugate] |
| Formulation 56 | A*[Aeruginic acid] + B*[streptomycin] + C*[poly-L-lysine] + D*[Vitamin E conjugate] |
| Formulation 57 | A*[Aeruginic acid] + B*[amphotericin B] + C*[poly-L-lysine] + D*[Vitamin E conjugate] |
| Formulation 58 | A*[Agrobactin] + B*[penicillin] + C*[poly-L-lysine] + D*[Vitamin E conjugate] |
| Formulation 59 | A*[Agrobactin] + B*[streptomycin] + C*[poly-L-lysine] + D*[Vitamin E conjugate] |
| Formulation 60 | A*[Agrobactin] + B*[amphotericin B] + C*[poly-L-lysine] + D*[Vitamin E conjugate] |
| Formulation 61 | A*[Agrobactin A] + B*[penicillin] + C*[poly-L-lysine] + D*[Vitamin E conjugate] |
| Formulation 62 | A*[Agrobactin A] + B*[streptomycin] + C*[poly-L-lysine] + D*[Vitamin E conjugate] |
| Formulation 63 | A*[Agrobactin A] + B*[amphotericin B] + C*[poly-L-lysine] + D*[Vitamin E conjugate] |
| Formulation 64 | A*[Albomycin] + B*[penicillin] + C*[poly-L-lysine] + D*[Vitamin E conjugate] |
| Formulation 65 | A*[Albomycin] + B*[streptomycin] + C*[poly-L-lysine] + D*[Vitamin E conjugate] |
| Formulation 66 | A*[Albomycin] + B*[amphotericin B] + C*[poly-L-lysine] + D*[Vitamin E conjugate] |
| Formulation 67 | A*[Alcaligin] + B*[penicillin] + C*[poly-L-lysine] + D*[Vitamin E conjugate] |
| Formulation 68 | A*[Alcaligin] + B*[streptomycin] + C*[poly-L-lysine] + D*[Vitamin E conjugate] |
| Formulation 69 | A*[Alcaligin] + B*[amphotericin B] + C*[poly-L-lysine] + D*[Vitamin E conjugate] |
| Formulation 70 | A*[Alterobactin A] + B*[penicillin] + C*[poly-L-lysine] + D*[Vitamin E conjugate] |
| Formulation 71 | A*[Alterobactin A] + B*[streptomycin] + C*[poly-L-lysine] + D*[Vitamin E conjugate] |
| Formulation 72 | A*[Alterobactin A] + B*[amphotericin B] + C*[poly-L-lysine] + D*[Vitamin E conjugate] |
| Formulation 73 | A*[Alterobactin A] + B*[penicillin] + C*[poly-L-lysine] + D*[Vitamin E conjugate] |
| Formulation 74 | A*[Alterobactin A] + B*[streptomycin] + C*[poly-L-lysine] + D*[Vitamin E conjugate] |
| Formulation 75 | A*[Alterobactin A] + B*[amphotericin B] + C*[poly-L-lysine] + D*[Vitamin E conjugate] |
| Formulation 76 | A*[Aminochelin] + B*[penicillin] + C*[poly-L-lysine] + D*[Vitamin E conjugate] |
| Formulation 77 | A*[Aminochelin] + B*[streptomycin] + C*[poly-L-lysine] + D*[Vitamin E conjugate] |
| Formulation 78 | A*[Aminochelin] + B*[amphotericin B] + C*[poly-L-lysine] + D*[Vitamin E conjugate] |
| Formulation 79 | A*[Amonabactin P693] + B*[penicillin] + C*[poly-L-lysine] + D*[Vitamin E conjugate] |
| Formulation 80 | A*[Amonabactin P693] + B*[streptomycin] + C*[poly-L-lysine] + D*[Vitamin E conjugate] |
| Formulation 81 | A*[Amonabactin P693] + B*[amphotericin B] + C*[poly-L-lysine] + D*[Vitamin E conjugate] |
| Formulation 82 | A*[Amonabactin P750] + B*[penicillin] + C*[poly-L-lysine] + D*[Vitamin E conjugate] |
| Formulation 83 | A*[Amonabactin P750] + B*[streptomycin] + C*[poly-L-lysine] + D*[Vitamin E conjugate] |
| Formulation 84 | A*[Amonabactin P750] + B*[amphotericin B] + C*[poly-L-lysine] + D*[Vitamin E conjugate] |
| Formulation 85 | A*[Amonabactin T732] + B*[penicillin] + C*[poly-L-lysine] + D*[Vitamin E conjugate] |
| Formulation 86 | A*[Amonabactin T732] + B*[streptomycin] + C*[poly-L-lysine] + D*[Vitamin E conjugate] |
| Formulation 87 | A*[Amonabactin T732] + B*[amphotericin B] + C*[poly-L-lysine] + D*[Vitamin E conjugate] |
| Formulation 88 | A*[Amonabactin T789] + B*[penicillin] + C*[poly-L-lysine] + D*[Vitamin E conjugate] |
| Formulation 89 | A*[Amonabactin T789] + B*[streptomycin] + C*[poly-L-lysine] + D*[Vitamin E conjugate] |
| Formulation 90 | A*[Amonabactin T789] + B*[amphotericin B] + C*[poly-L-lysine] + D*[Vitamin E conjugate] |
| Formulation 91 | A*[Amphibactin B] + B*[penicillin] + C*[poly-L-lysine] + D*[Vitamin E conjugate] |
| Formulation 92 | A*[Amphibactin B] + B*[streptomycin] + C*[poly-L-lysine] + D*[Vitamin E conjugate] |
| Formulation 93 | A*[Amphibactin B] + B*[amphotericin B] + C*[poly-L-lysine] + D*[Vitamin E conjugate] |
| Formulation 94 | A*[Amphibactin C] + B*[penicillin] + C*[poly-L-lysine] + D*[Vitamin E conjugate] |
| Formulation 95 | A*[Amphibactin C] + B*[streptomycin] + C*[poly-L-lysine] + D*[Vitamin E conjugate] |
| Formulation 96 | A*[Amphibactin C] + B*[amphotericin B] + C*[poly-L-lysine] + D*[Vitamin E conjugate] |
| Formulation 97 | A*[Amphibactin D] + B*[penicillin] + C*[poly-L-lysine] + D*[Vitamin E conjugate] |
| Formulation 98 | A*[Amphibactin D] + B*[streptomycin] + C*[poly-L-lysine] + D*[Vitamin E conjugate] |
| Formulation 99 | A*[Amphibactin D] + B*[amphotericin B] + C*[poly-L-lysine] + D*[Vitamin E conjugate] |
| Formulation 100 | A*[Amphibactin E] + B*[penicillin] + C*[poly-L-lysine] + D*[Vitamin E conjugate] |
| Formulation 101 | A*[Amphibactin E] + B*[streptomycin] + C*[poly-L-lysine] + D*[Vitamin E conjugate] |
| Formulation 102 | A*[Amphibactin E] + B*[amphotericin B] + C*[poly-L-lysine] + D*[Vitamin E conjugate] |
| Formulation 103 | A*[Amphibactin F] + B*[penicillin] + C*[poly-L-lysine] + D*[Vitamin E conjugate] |
| Formulation 104 | A*[Amphibactin F] + B*[streptomycin] + C*[poly-L-lysine] + D*[Vitamin E conjugate] |
| Formulation 105 | A*[Amphibactin F] + B*[amphotericin B] + C*[poly-L-lysine] + D*[Vitamin E conjugate] |
| Formulation 106 | A*[Amphibactin G] + B*[penicillin] + C*[poly-L-lysine] + D*[Vitamin E conjugate] |
| Formulation 107 | A*[Amphibactin G] + B*[streptomycin] + C*[poly-L-lysine] + D*[Vitamin E conjugate] |
| Formulation 108 | A*[Amphibactin G] + B*[amphotericin B] + C*[poly-L-lysine] + D*[Vitamin E conjugate] |
| Formulation 109 | A*[Amphibactin H] + B*[penicillin] + C*[poly-L-lysine] + D*[Vitamin E conjugate] |
| Formulation 110 | A*[Amphibactin H] + B*[streptomycin] + C*[poly-L-lysine] + D*[Vitamin E conjugate] |
| Formulation 111 | A*[Amphibactin H] + B*[amphotericin B] + C*[poly-L-lysine] + D*[Vitamin E conjugate] |
| Formulation 112 | A*[Amphibactin I] + B*[penicillin] + C*[poly-L-lysine] + D*[Vitamin E conjugate] |
| Formulation 113 | A*[Amphibactin I] + B*[streptomycin] + C*[poly-L-lysine] + D*[Vitamin E conjugate] |
| Formulation 114 | A*[Amphibactin I] + B*[amphotericin B] + C*[poly-L-lysine] + D*[Vitamin E conjugate] |
| Formulation 115 | A*[Amphibactin S] + B*[penicillin] + C*[poly-L-lysine] + D*[Vitamin E conjugate] |
| Formulation 116 | A*[Amphibactin S] + B*[streptomycin] + C*[poly-L-lysine] + D*[Vitamin E conjugate] |
| Formulation 117 | A*[Amphibactin S] + B*[amphotericin B] + C*[poly-L-lysine] + D*[Vitamin E conjugate] |
| Formulation 118 | A*[Amphibactin T] + B*[penicillin] + C*[poly-L-lysine] + D*[Vitamin E conjugate] |
| Formulation 119 | A*[Amphibactin T] + B*[streptomycin] + C*[poly-L-lysine] + D*[Vitamin E conjugate] |
| Formulation 120 | A*[Amphibactin T] + B*[amphotericin B] + C*[poly-L-lysine] + D*[Vitamin E conjugate] |
| Formulation 121 | A*[Amphi-enterobactin] + B*[penicillin] + C*[poly-L-lysine] + D*[Vitamin E conjugate] |
| Formulation 122 | A*[Amphi-enterobactin] + B*[streptomycin] + C*[poly-L-lysine] + D*[Vitamin E conjugate] |
| Formulation 123 | A*[Amphi-enterobactin] + B*[amphotericin B] + C*[poly-L-lysine] + D*[Vitamin E conjugate] |
| Formulation 124 | A*[Amphi-enterobactin C12-OH] + B*[penicillin] + C*[poly-L-lysine] + D*[Vitamin E conjugate] |
| Formulation 125 | A*[Amphi-enterobactin C12-OH] + B*[streptomycin] + C*[poly-L-lysine] + D*[Vitamin E conjugate] |
| Formulation 126 | A*[Amphi-enterobactin C12-OH] + B*[amphotericin B] + C*[poly-L-lysine] + D*[Vitamin E conjugate] |
| Formulation 127 | A*[Amycolachrome] + B*[penicillin] + C*[poly-L-lysine] + D*[Vitamin E conjugate] |

TABLE 7-continued

| Formulation Name | Formula |
|---|---|
| Formulation 128 | A*[Amycolachrome] + B*[streptomycin] + C*[poly-L-lysine] + D*[Vitamin E conjugate] |
| Formulation 129 | A*[Amycolachrome] + B*[amphotericin B] + C*[poly-L-lysine] + D*[Vitamin E conjugate] |
| Formulation 130 | A*[Anachelin 1] + B*[penicillin] + C*[poly-L-lysine] + D*[Vitamin E conjugate] |
| Formulation 131 | A*[Anachelin 1] + B*[streptomycin] + C*[poly-L-lysine] + D*[Vitamin E conjugate] |
| Formulation 132 | A*[Anachelin 1] + B*[amphotericin B] + C*[poly-L-lysine] + D*[Vitamin E conjugate] |
| Formulation 133 | A*[Anachelin 2] + B*[penicillin] + C*[poly-L-lysine] + D*[Vitamin E conjugate] |
| Formulation 134 | A*[Anachelin 2] + B*[streptomycin] + C*[poly-L-lysine] + D*[Vitamin E conjugate] |
| Formulation 135 | A*[Anachelin 2] + B*[amphotericin B] + C*[poly-L-lysine] + D*[Vitamin E conjugate] |
| Formulation 136 | A*[Anguibactin] + B*[penicillin] + C*[poly-L-lysine] + D*[Vitamin E conjugate] |
| Formulation 137 | A*[Anguibactin] + B*[streptomycin] + C*[poly-L-lysine] + D*[Vitamin E conjugate] |
| Formulation 138 | A*[Anguibactin] + B*[amphotericin B] + C*[poly-L-lysine] + D*[Vitamin E conjugate] |
| Formulation 139 | A*[Aquachelin A] + B*[penicillin] + C*[poly-L-lysine] + D*[Vitamin E conjugate] |
| Formulation 140 | A*[Aquachelin A] + B*[streptomycin] + C*[poly-L-lysine] + D*[Vitamin E conjugate] |
| Formulation 141 | A*[Aquachelin A] + B*[amphotericin B] + C*[poly-L-lysine] + D*[Vitamin E conjugate] |
| Formulation 142 | A*[Aquachelin B] + B*[penicillin] + C*[poly-L-lysine] + D*[Vitamin E conjugate] |
| Formulation 143 | A*[Aquachelin B] + B*[streptomycin] + C*[poly-L-lysine] + D*[Vitamin E conjugate] |
| Formulation 144 | A*[Aquachelin B] + B*[amphotericin B] + C*[poly-L-lysine] + D*[Vitamin E conjugate] |
| Formulation 145 | A*[Aquachelin C] + B*[penicillin] + C*[poly-L-lysine] + D*[Vitamin E conjugate] |
| Formulation 146 | A*[Aquachelin C] + B*[streptomycin] + C*[poly-L-lysine] + D*[Vitamin E conjugate] |
| Formulation 147 | A*[Aquachelin C] + B*[amphotericin B] + C*[poly-L-lysine] + D*[Vitamin E conjugate] |
| Formulation 148 | A*[Aquachelin D] + B*[penicillin] + C*[poly-L-lysine] + D*[Vitamin E conjugate] |
| Formulation 149 | A*[Aquachelin D] + B*[streptomycin] + C*[poly-L-lysine] + D*[Vitamin E conjugate] |
| Formulation 150 | A*[Aquachelin D] + B*[amphotericin B] + C*[poly-L-lysine] + D*[Vitamin E conjugate] |
| Formulation 151 | A*[Aquachelin I] + B*[penicillin] + C*[poly-L-lysine] + D*[Vitamin E conjugate] |
| Formulation 152 | A*[Aquachelin I] + B*[streptomycin] + C*[poly-L-lysine] + D*[Vitamin E conjugate] |
| Formulation 153 | A*[Aquachelin I] + B*[amphotericin B] + C*[poly-L-lysine] + D*[Vitamin E conjugate] |
| Formulation 154 | A*[Aquachelin J] + B*[penicillin] + C*[poly-L-lysine] + D*[Vitamin E conjugate] |
| Formulation 155 | A*[Aquachelin J] + B*[streptomycin] + C*[poly-L-lysine] + D*[Vitamin E conjugate] |
| Formulation 156 | A*[Aquachelin J] + B*[amphotericin B] + C*[poly-L-lysine] + D*[Vitamin E conjugate] |
| Formulation 157 | A*[Arthrobactin] + B*[penicillin] + C*[poly-L-lysine] + D*[Vitamin E conjugate] |
| Formulation 158 | A*[Arthrobactin] + B*[streptomycin] + C*[poly-L-lysine] + D*[Vitamin E conjugate] |
| Formulation 159 | A*[Arthrobactin] + B*[amphotericin B] + C*[poly-L-lysine] + D*[Vitamin E conjugate] |
| Formulation 160 | A*[Asperchrome A] + B*[penicillin] + C*[poly-L-lysine] + D*[Vitamin E conjugate] |
| Formulation 161 | A*[Asperchrome A] + B*[streptomycin] + C*[poly-L-lysine] + D*[Vitamin E conjugate] |
| Formulation 162 | A*[Asperchrome A] + B*[amphotericin B] + C*[poly-L-lysine] + D*[Vitamin E conjugate] |
| Formulation 163 | A*[Asperchrome B1] + B*[penicillin] + C*[poly-L-lysine] + D*[Vitamin E conjugate] |
| Formulation 164 | A*[Asperchrome B1] + B*[streptomycin] + C*[poly-L-lysine] + D*[Vitamin E conjugate] |
| Formulation 165 | A*[Asperchrome B1] + B*[amphotericin B] + C*[poly-L-lysine] + D*[Vitamin E conjugate] |
| Formulation 166 | A*[Asperchrome B2] + B*[penicillin] + C*[poly-L-lysine] + D*[Vitamin E conjugate] |
| Formulation 167 | A*[Asperchrome B2] + B*[streptomycin] + C*[poly-L-lysine] + D*[Vitamin E conjugate] |
| Formulation 168 | A*[Asperchrome B2] + B*[amphotericin B] + C*[poly-L-lysine] + D*[Vitamin E conjugate] |
| Formulation 169 | A*[Asperchrome B3] + B*[penicillin] + C*[poly-L-lysine] + D*[Vitamin E conjugate] |
| Formulation 170 | A*[Asperchrome B3] + B*[streptomycin] + C*[poly-L-lysine] + D*[Vitamin E conjugate] |
| Formulation 171 | A*[Asperchrome B3] + B*[amphotericin B] + C*[poly-L-lysine] + D*[Vitamin E conjugate] |
| Formulation 172 | A*[Asperchrome C] + B*[penicillin] + C*[poly-L-lysine] + D*[Vitamin E conjugate] |
| Formulation 173 | A*[Asperchrome C] + B*[streptomycin] + C*[poly-L-lysine] + D*[Vitamin E conjugate] |
| Formulation 174 | A*[Asperchrome C] + B*[amphotericin B] + C*[poly-L-lysine] + D*[Vitamin E conjugate] |
| Formulation 175 | A*[Asperchrome D1] + B*[penicillin] + C*[poly-L-lysine] + D*[Vitamin E conjugate] |
| Formulation 176 | A*[Asperchrome D1] + B*[streptomycin] + C*[poly-L-lysine] + D*[Vitamin E conjugate] |
| Formulation 177 | A*[Asperchrome D1] + B*[amphotericin B] + C*[poly-L-lysine] + D*[Vitamin E conjugate] |
| Formulation 178 | A*[Asperchrome D2] + B*[penicillin] + C*[poly-L-lysine] + D*[Vitamin E conjugate] |
| Formulation 179 | A*[Asperchrome D2] + B*[streptomycin] + C*[poly-L-lysine] + D*[Vitamin E conjugate] |
| Formulation 180 | A*[Asperchrome D2] + B*[amphotericin B] + C*[poly-L-lysine] + D*[Vitamin E conjugate] |
| Formulation 181 | A*[Asperchrome D3] + B*[penicillin] + C*[poly-L-lysine] + D*[Vitamin E conjugate] |
| Formulation 182 | A*[Asperchrome D3] + B*[streptomycin] + C*[poly-L-lysine] + D*[Vitamin E conjugate] |
| Formulation 183 | A*[Asperchrome D3] + B*[amphotericin B] + C*[poly-L-lysine] + D*[Vitamin E conjugate] |
| Formulation 184 | A*[Asperchrome E] + B*[penicillin] + C*[poly-L-lysine] + D*[Vitamin E conjugate] |
| Formulation 185 | A*[Asperchrome E] + B*[streptomycin] + C*[poly-L-lysine] + D*[Vitamin E conjugate] |
| Formulation 186 | A*[Asperchrome E] + B*[amphotericin B] + C*[poly-L-lysine] + D*[Vitamin E conjugate] |
| Formulation 187 | A*[Asperchrome F1] + B*[penicillin] + C*[poly-L-lysine] + D*[Vitamin E conjugate] |
| Formulation 188 | A*[Asperchrome F1] + B*[streptomycin] + C*[poly-L-lysine] + D*[Vitamin E conjugate] |
| Formulation 189 | A*[Asperchrome F1] + B*[amphotericin B] + C*[poly-L-lysine] + D*[Vitamin E conjugate] |
| Formulation 190 | A*[Asperchrome F2] + B*[penicillin] + C*[poly-L-lysine] + D*[Vitamin E conjugate] |
| Formulation 191 | A*[Asperchrome F2] + B*[streptomycin] + C*[poly-L-lysine] + D*[Vitamin E conjugate] |
| Formulation 192 | A*[Asperchrome F2] + B*[amphotericin B] + C*[poly-L-lysine] + D*[Vitamin E conjugate] |
| Formulation 193 | A*[Asperchrome F3] + B*[penicillin] + C*[poly-L-lysine] + D*[Vitamin E conjugate] |
| Formulation 194 | A*[Asperchrome F3] + B*[streptomycin] + C*[poly-L-lysine] + D*[Vitamin E conjugate] |
| Formulation 195 | A*[Asperchrome F3] + B*[amphotericin B] + C*[poly-L-lysine] + D*[Vitamin E conjugate] |
| Formulation 196 | A*[Aspergillic acid] + B*[penicillin] + C*[poly-L-lysine] + D*[Vitamin E conjugate] |
| Formulation 197 | A*[Aspergillic acid] + B*[streptomycin] + C*[poly-L-lysine] + D*[Vitamin E conjugate] |
| Formulation 198 | A*[Aspergillic acid] + B*[amphotericin B] + C*[poly-L-lysine] + D*[Vitamin E conjugate] |
| Formulation 199 | A*[Avenic acid] + B*[penicillin] + C*[poly-L-lysine] + D*[Vitamin E conjugate] |
| Formulation 200 | A*[Avenic acid] + B*[streptomycin] + C*[poly-L-lysine] + D*[Vitamin E conjugate] |
| Formulation 201 | A*[Avenic acid] + B*[amphotericin B] + C*[poly-L-lysine] + D*[Vitamin E conjugate] |
| Formulation 202 | A*[Azotobactin] + B*[penicillin] + C*[poly-L-lysine] + D*[Vitamin E conjugate] |
| Formulation 203 | A*[Azotobactin] + B*[streptomycin] + C*[poly-L-lysine] + D*[Vitamin E conjugate] |
| Formulation 204 | A*[Azotobactin] + B*[amphotericin B] + C*[poly-L-lysine] + D*[Vitamin E conjugate] |

TABLE 7-continued

| Formulation Name | Formula |
|---|---|
| Formulation 205 | A*[Azotobactin 87] + B*[penicillin] + C*[poly-L-lysine] + D*[Vitamin E conjugate] |
| Formulation 206 | A*[Azotobactin 87] + B*[streptomycin] + C*[poly-L-lysine] + D*[Vitamin E conjugate] |
| Formulation 207 | A*[Azotobactin 87] + B*[amphotericin B] + C*[poly-L-lysine] + D*[Vitamin E conjugate] |
| Formulation 208 | A*[Azotobactin D] + B*[penicillin] + C*[poly-L-lysine] + D*[Vitamin E conjugate] |
| Formulation 209 | A*[Azotobactin D] + B*[streptomycin] + C*[poly-L-lysine] + D*[Vitamin E conjugate] |
| Formulation 210 | A*[Azotobactin D] + B*[amphotericin B] + C*[poly-L-lysine] + D*[Vitamin E conjugate] |
| Formulation 211 | A*[Azotochelin] + B*[penicillin] + C*[poly-L-lysine] + D*[Vitamin E conjugate] |
| Formulation 212 | A*[Azotochelin] + B*[streptomycin] + C*[poly-L-lysine] + D*[Vitamin E conjugate] |
| Formulation 213 | A*[Azotochelin] + B*[amphotericin B] + C*[poly-L-lysine] + D*[Vitamin E conjugate] |
| Formulation 214 | A*[Azoverdin] + B*[penicillin] + C*[poly-L-lysine] + D*[Vitamin E conjugate] |
| Formulation 215 | A*[Azoverdin] + B*[streptomycin] + C*[poly-L-lysine] + D*[Vitamin E conjugate] |
| Formulation 216 | A*[Azoverdin] + B*[amphotericin B] + C*[poly-L-lysine] + D*[Vitamin E conjugate] |
| Formulation 217 | A*[Bacillibactin] + B*[penicillin] + C*[poly-L-lysine] + D*[Vitamin E conjugate] |
| Formulation 218 | A*[Bacillibactin] + B*[streptomycin] + C*[poly-L-lysine] + D*[Vitamin E conjugate] |
| Formulation 219 | A*[Bacillibactin] + B*[amphotericin B] + C*[poly-L-lysine] + D*[Vitamin E conjugate] |
| Formulation 220 | A*[Basidiochrome] + B*[penicillin] + C*[poly-L-lysine] + D*[Vitamin E conjugate] |
| Formulation 221 | A*[Basidiochrome] + B*[streptomycin] + C*[poly-L-lysine] + D*[Vitamin E conjugate] |
| Formulation 222 | A*[Basidiochrome] + B*[amphotericin B] + C*[poly-L-lysine] + D*[Vitamin E conjugate] |
| Formulation 223 | A*[Bisucaberin] + B*[penicillin] + C*[poly-L-lysine] + D*[Vitamin E conjugate] |
| Formulation 224 | A*[Bisucaberin] + B*[streptomycin] + C*[poly-L-lysine] + D*[Vitamin E conjugate] |
| Formulation 225 | A*[Bisucaberin] + B*[amphotericin B] + C*[poly-L-lysine] + D*[Vitamin E conjugate] |
| Formulation 226 | A*[Carboxymycobactin] + B*[penicillin] + C*[poly-L-lysine] + D*[Vitamin E conjugate] |
| Formulation 227 | A*[Carboxymycobactin] + B*[streptomycin] + C*[poly-L-lysine] + D*[Vitamin E conjugate] |
| Formulation 228 | A*[Carboxymycobactin] + B*[amphotericin B] + C*[poly-L-lysine] + D*[Vitamin E conjugate] |
| Formulation 229 | A*[Carboxymycobactin 1] + B*[penicillin] + C*[poly-L-lysine] + D*[Vitamin E conjugate] |
| Formulation 230 | A*[Carboxymycobactin 1] + B*[streptomycin] + C*[poly-L-lysine] + D*[Vitamin E conjugate] |
| Formulation 231 | A*[Carboxymycobactin 1] + B*[amphotericin B] + C*[poly-L-lysine] + D*[Vitamin E conjugate] |
| Formulation 232 | A*[Carboxymycobactin 2] + B*[penicillin] + C*[poly-L-lysine] + D*[Vitamin E conjugate] |
| Formulation 233 | A*[Carboxymycobactin 2] + B*[streptomycin] + C*[poly-L-lysine] + D*[Vitamin E conjugate] |
| Formulation 234 | A*[Carboxymycobactin 2] + B*[amphotericin B] + C*[poly-L-lysine] + D*[Vitamin E conjugate] |
| Formulation 235 | A*[Carboxymycobactin 3] + B*[penicillin] + C*[poly-L-lysine] + D*[Vitamin E conjugate] |
| Formulation 236 | A*[Carboxymycobactin 3] + B*[streptomycin] + C*[poly-L-lysine] + D*[Vitamin E conjugate] |
| Formulation 237 | A*[Carboxymycobactin 3] + B*[amphotericin B] + C*[poly-L-lysine] + D*[Vitamin E conjugate] |
| Formulation 238 | A*[Carboxymycobactin 4] + B*[penicillin] + C*[poly-L-lysine] + D*[Vitamin E conjugate] |
| Formulation 239 | A*[Carboxymycobactin 4] + B*[streptomycin] + C*[poly-L-lysine] + D*[Vitamin E conjugate] |
| Formulation 240 | A*[Carboxymycobactin 4] + B*[amphotericin B] + C*[poly-L-lysine] + D*[Vitamin E conjugate] |
| Formulation 241 | A*[Cepabactin] + B*[penicillin] + C*[poly-L-lysine] + D*[Vitamin E conjugate] |
| Formulation 242 | A*[Cepabactin] + B*[streptomycin] + C*[poly-L-lysine] + D*[Vitamin E conjugate] |
| Formulation 243 | A*[Cepabactin] + B*[amphotericin B] + C*[poly-L-lysine] + D*[Vitamin E conjugate] |
| Formulation 244 | A*[Chrysobactin] + B*[penicillin] + C*[poly-L-lysine] + D*[Vitamin E conjugate] |
| Formulation 245 | A*[Chrysobactin] + B*[streptomycin] + C*[poly-L-lysine] + D*[Vitamin E conjugate] |
| Formulation 246 | A*[Chrysobactin] + B*[amphotericin B] + C*[poly-L-lysine] + D*[Vitamin E conjugate] |
| Formulation 247 | A*[Citrate] + B*[penicillin] + C*[poly-L-lysine] + D*[Vitamin E conjugate] |
| Formulation 248 | A*[Citrate] + B*[streptomycin] + C*[poly-L-lysine] + D*[Vitamin E conjugate] |
| Formulation 249 | A*[Citrate] + B*[amphotericin B] + C*[poly-L-lysine] + D*[Vitamin E conjugate] |
| Formulation 250 | A*[Coelichelin] + B*[penicillin] + C*[poly-L-lysine] + D*[Vitamin E conjugate] |
| Formulation 251 | A*[Coelichelin] + B*[streptomycin] + C*[poly-L-lysine] + D*[Vitamin E conjugate] |
| Formulation 252 | A*[Coelichelin] + B*[amphotericin B] + C*[poly-L-lysine] + D*[Vitamin E conjugate] |
| Formulation 253 | A*[Coprogen] + B*[penicillin] + C*[poly-L-lysine] + D*[Vitamin E conjugate] |
| Formulation 254 | A*[Coprogen] + B*[streptomycin] + C*[poly-L-lysine] + D*[Vitamin E conjugate] |
| Formulation 255 | A*[Coprogen] + B*[amphotericin B] + C*[poly-L-lysine] + D*[Vitamin E conjugate] |
| Formulation 256 | A*[Coprogen B] + B*[penicillin] + C*[poly-L-lysine] + D*[Vitamin E conjugate] |
| Formulation 257 | A*[Coprogen B] + B*[streptomycin] + C*[poly-L-lysine] + D*[Vitamin E conjugate] |
| Formulation 258 | A*[Coprogen B] + B*[amphotericin B] + C*[poly-L-lysine] + D*[Vitamin E conjugate] |
| Formulation 259 | A*[Corynebactin] + B*[penicillin] + C*[poly-L-lysine] + D*[Vitamin E conjugate] |
| Formulation 260 | A*[Corynebactin] + B*[streptomycin] + C*[poly-L-lysine] + D*[Vitamin E conjugate] |
| Formulation 261 | A*[Corynebactin] + B*[amphotericin B] + C*[poly-L-lysine] + D*[Vitamin E conjugate] |
| Formulation 262 | A*[Deoxydistichonic acid] + B*[penicillin] + C*[poly-L-lysine] + D*[Vitamin E conjugate] |
| Formulation 263 | A*[Deoxydistichonic acid] + B*[streptomycin] + C*[poly-L-lysine] + D*[Vitamin E conjugate] |
| Formulation 264 | A*[Deoxydistichonic acid] + B*[amphotericin B] + C*[poly-L-lysine] + D*[Vitamin E conjugate] |
| Formulation 265 | A*[2-Deoxymugineic acud] + B*[penicillin] + C*[poly-L-lysine] + D*[Vitamin E conjugate] |
| Formulation 266 | A*[2-Deoxymugineic acud] + B*[streptomycin] + C*[poly-L-lysine] + D*[Vitamin E conjugate] |
| Formulation 267 | A*[2-Deoxymugineic acud] + B*[amphotericin B] + C*[poly-L-lysine] + D*[Vitamin E conjugate] |
| Formulation 268 | A*[Deoxyschizokinen] + B*[penicillin] + C*[poly-L-lysine] + D*[Vitamin E conjugate] |
| Formulation 269 | A*[Deoxyschizokinen] + B*[streptomycin] + C*[poly-L-lysine] + D*[Vitamin E conjugate] |
| Formulation 270 | A*[Deoxyschizokinen] + B*[amphotericin B] + C*[poly-L-lysine] + D*[Vitamin E conjugate] |
| Formulation 271 | A*[Des(diserylglycyl)-ferrirhodin] + B*[penicillin] + C*[poly-L-lysine] + D*[Vitamin E conjugate] |
| Formulation 272 | A*[Des(diserylglycyl)-ferrirhodin] + B*[streptomycin] + C*[poly-L-lysine] + D*[Vitamin E conjugate] |
| Formulation 273 | A*[Des(diserylglycyl)-ferrirhodin] + B*[amphotericin B] + C*[poly-L-lysine] + D*[Vitamin E conjugate] |
| Formulation 274 | A*[Desacetylcoprogen] + B*[penicillin] + C*[poly-L-lysine] + D*[Vitamin E conjugate] |
| Formulation 275 | A*[Desacetylcoprogen] + B*[streptomycin] + C*[poly-L-lysine] + D*[Vitamin E conjugate] |
| Formulation 276 | A*[Desacetylcoprogen] + B*[amphotericin B] + C*[poly-L-lysine] + D*[Vitamin E conjugate] |
| Formulation 277 | A*[Desferrioxamine A1A] + B*[penicillin] + C*[poly-L-lysine] + D*[Vitamin E conjugate] |
| Formulation 278 | A*[Desferrioxamine A1A] + B*[streptomycin] + C*[poly-L-lysine] + D*[Vitamin E conjugate] |
| Formulation 279 | A*[Desferrioxamine A1A] + B*[amphotericin B] + C*[poly-L-lysine] + D*[Vitamin E conjugate] |
| Formulation 280 | A*[Desferrioxamine A1B] + B*[penicillin] + C*[poly-L-lysine] + D*[Vitamin E conjugate] |
| Formulation 281 | A*[Desferrioxamine A1B] + B*[streptomycin] + C*[poly-L-lysine] + D*[Vitamin E conjugate] |

TABLE 7-continued

| Formulation Name | Formula |
|---|---|
| Formulation 282 | A*[Desferrioxamine A1B] + B*[amphotericin B] + C*[poly-L-lysine] + D*[Vitamin E conjugate] |
| Formulation 283 | A*[Desferrioxamine A2] + B*[penicillin] + C*[poly-L-lysine] + D*[Vitamin E conjugate] |
| Formulation 284 | A*[Desferrioxamine A2] + B*[streptomycin] + C*[poly-L-lysine] + D*[Vitamin E conjugate] |
| Formulation 285 | A*[Desferrioxamine A2] + B*[amphotericin B] + C*[poly-L-lysine] + D*[Vitamin E conjugate] |
| Formulation 286 | A*[Desferrioxamine B] + B*[penicillin] + C*[poly-L-lysine] + D*[Vitamin E conjugate] |
| Formulation 287 | A*[Desferrioxamine B] + B*[streptomycin] + C*[poly-L-lysine] + D*[Vitamin E conjugate] |
| Formulation 288 | A*[Desferrioxamine B] + B*[amphotericin B] + C*[poly-L-lysine] + D*[Vitamin E conjugate] |
| Formulation 289 | A*[Desferrioxamine D1] + B*[penicillin] + C*[poly-L-lysine] + D*[Vitamin E conjugate] |
| Formulation 290 | A*[Desferrioxamine D1] + B*[streptomycin] + C*[poly-L-lysine] + D*[Vitamin E conjugate] |
| Formulation 291 | A*[Desferrioxamine D1] + B*[amphotericin B] + C*[poly-L-lysine] + D*[Vitamin E conjugate] |
| Formulation 292 | A*[Desferrioxamine D2] + B*[penicillin] + C*[poly-L-lysine] + D*[Vitamin E conjugate] |
| Formulation 293 | A*[Desferrioxamine D2] + B*[streptomycin] + C*[poly-L-lysine] + D*[Vitamin E conjugate] |
| Formulation 294 | A*[Desferrioxamine D2] + B*[amphotericin B] + C*[poly-L-lysine] + D*[Vitamin E conjugate] |
| Formulation 295 | A*[Desferrioxamine E] + B*[penicillin] + C*[poly-L-lysine] + D*[Vitamin E conjugate] |
| Formulation 296 | A*[Desferrioxamine E] + B*[streptomycin] + C*[poly-L-lysine] + D*[Vitamin E conjugate] |
| Formulation 297 | A*[Desferrioxamine E] + B*[amphotericin B] + C*[poly-L-lysine] + D*[Vitamin E conjugate] |
| Formulation 298 | A*[Desferrioxamine Et1] + B*[penicillin] + C*[poly-L-lysine] + D*[Vitamin E conjugate] |
| Formulation 299 | A*[Desferrioxamine Et1] + B*[streptomycin] + C*[poly-L-lysine] + D*[Vitamin E conjugate] |
| Formulation 300 | A*[Desferrioxamine Et1] + B*[amphotericin B] + C*[poly-L-lysine] + D*[Vitamin E conjugate] |
| Formulation 301 | A*[Desferrioxamine Et2] + B*[penicillin] + C*[poly-L-lysine] + D*[Vitamin E conjugate] |
| Formulation 302 | A*[Desferrioxamine Et2] + B*[streptomycin] + C*[poly-L-lysine] + D*[Vitamin E conjugate] |
| Formulation 303 | A*[Desferrioxamine Et2] + B*[amphotericin B] + C*[poly-L-lysine] + D*[Vitamin E conjugate] |
| Formulation 304 | A*[Desferrioxamine Et3] + B*[penicillin] + C*[poly-L-lysine] + D*[Vitamin E conjugate] |
| Formulation 305 | A*[Desferrioxamine Et3] + B*[streptomycin] + C*[poly-L-lysine] + D*[Vitamin E conjugate] |
| Formulation 306 | A*[Desferrioxamine Et3] + B*[amphotericin B] + C*[poly-L-lysine] + D*[Vitamin E conjugate] |
| Formulation 307 | A*[Desferrioxamine G1] + B*[penicillin] + C*[poly-L-lysine] + D*[Vitamin E conjugate] |
| Formulation 308 | A*[Desferrioxamine G1] + B*[streptomycin] + C*[poly-L-lysine] + D*[Vitamin E conjugate] |
| Formulation 309 | A*[Desferrioxamine G1] + B*[amphotericin B] + C*[poly-L-lysine] + D*[Vitamin E conjugate] |
| Formulation 310 | A*[Desferrioxamine G2A] + B*[penicillin] + C*[poly-L-lysine] + D*[Vitamin E conjugate] |
| Formulation 311 | A*[Desferrioxamine G2A] + B*[streptomycin] + C*[poly-L-lysine] + D*[Vitamin E conjugate] |
| Formulation 312 | A*[Desferrioxamine G2A] + B*[amphotericin B] + C*[poly-L-lysine] + D*[Vitamin E conjugate] |
| Formulation 313 | A*[Desferrioxamine G2B] + B*[penicillin] + C*[poly-L-lysine] + D*[Vitamin E conjugate] |
| Formulation 314 | A*[Desferrioxamine G2B] + B*[streptomycin] + C*[poly-L-lysine] + D*[Vitamin E conjugate] |
| Formulation 315 | A*[Desferrioxamine G2B] + B*[amphotericin B] + C*[poly-L-lysine] + D*[Vitamin E conjugate] |
| Formulation 316 | A*[Desferrioxamine G2C] + B*[penicillin] + C*[poly-L-lysine] + D*[Vitamin E conjugate] |
| Formulation 317 | A*[Desferrioxamine G2C] + B*[streptomycin] + C*[poly-L-lysine] + D*[Vitamin E conjugate] |
| Formulation 318 | A*[Desferrioxamine G2C] + B*[amphotericin B] + C*[poly-L-lysine] + D*[Vitamin E conjugate] |
| Formulation 319 | A*[Desferrioxamine H] + B*[penicillin] + C*[poly-L-lysine] + D*[Vitamin E conjugate] |
| Formulation 320 | A*[Desferrioxamine H] + B*[streptomycin] + C*[poly-L-lysine] + D*[Vitamin E conjugate] |
| Formulation 321 | A*[Desferrioxamine H] + B*[amphotericin B] + C*[poly-L-lysine] + D*[Vitamin E conjugate] |
| Formulation 322 | A*[Desferrioxamine N] + B*[penicillin] + C*[poly-L-lysine] + D*[Vitamin E conjugate] |
| Formulation 323 | A*[Desferrioxamine N] + B*[streptomycin] + C*[poly-L-lysine] + D*[Vitamin E conjugate] |
| Formulation 324 | A*[Desferrioxamine N] + B*[amphotericin B] + C*[poly-L-lysine] + D*[Vitamin E conjugate] |
| Formulation 325 | A*[Desferrioxamine P1] + B*[penicillin] + C*[poly-L-lysine] + D*[Vitamin E conjugate] |
| Formulation 326 | A*[Desferrioxamine P1] + B*[streptomycin] + C*[poly-L-lysine] + D*[Vitamin E conjugate] |
| Formulation 327 | A*[Desferrioxamine P1] + B*[amphotericin B] + C*[poly-L-lysine] + D*[Vitamin E conjugate] |
| Formulation 328 | A*[Desferrioxamine T1] + B*[penicillin] + C*[poly-L-lysine] + D*[Vitamin E conjugate] |
| Formulation 329 | A*[Desferrioxamine T1] + B*[streptomycin] + C*[poly-L-lysine] + D*[Vitamin E conjugate] |
| Formulation 330 | A*[Desferrioxamine T1] + B*[amphotericin B] + C*[poly-L-lysine] + D*[Vitamin E conjugate] |
| Formulation 331 | A*[Desferrioxamine T2] + B*[penicillin] + C*[poly-L-lysine] + D*[Vitamin E conjugate] |
| Formulation 332 | A*[Desferrioxamine T2] + B*[streptomycin] + C*[poly-L-lysine] + D*[Vitamin E conjugate] |
| Formulation 333 | A*[Desferrioxamine T2] + B*[amphotericin B] + C*[poly-L-lysine] + D*[Vitamin E conjugate] |
| Formulation 334 | A*[Desferrioxamine T3] + B*[penicillin] + C*[poly-L-lysine] + D*[Vitamin E conjugate] |
| Formulation 335 | A*[Desferrioxamine T3] + B*[streptomycin] + C*[poly-L-lysine] + D*[Vitamin E conjugate] |
| Formulation 336 | A*[Desferrioxamine T3] + B*[amphotericin B] + C*[poly-L-lysine] + D*[Vitamin E conjugate] |
| Formulation 337 | A*[Desferrioxamine T7] + B*[penicillin] + C*[poly-L-lysine] + D*[Vitamin E conjugate] |
| Formulation 338 | A*[Desferrioxamine T7] + B*[streptomycin] + C*[poly-L-lysine] + D*[Vitamin E conjugate] |
| Formulation 339 | A*[Desferrioxamine T7] + B*[amphotericin B] + C*[poly-L-lysine] + D*[Vitamin E conjugate] |
| Formulation 340 | A*[Desferrioxamine T8] + B*[penicillin] + C*[poly-L-lysine] + D*[Vitamin E conjugate] |
| Formulation 341 | A*[Desferrioxamine T8] + B*[streptomycin] + C*[poly-L-lysine] + D*[Vitamin E conjugate] |
| Formulation 342 | A*[Desferrioxamine T8] + B*[amphotericin B] + C*[poly-L-lysine] + D*[Vitamin E conjugate] |
| Formulation 343 | A*[Desferrioxamine Te1] + B*[penicillin] + C*[poly-L-lysine] + D*[Vitamin E conjugate] |
| Formulation 344 | A*[Desferrioxamine Te1] + B*[streptomycin] + C*[poly-L-lysine] + D*[Vitamin E conjugate] |
| Formulation 345 | A*[Desferrioxamine Te1] + B*[amphotericin B] + C*[poly-L-lysine] + D*[Vitamin E conjugate] |
| Formulation 346 | A*[Desferrioxamine Te2] + B*[penicillin] + C*[poly-L-lysine] + D*[Vitamin E conjugate] |
| Formulation 347 | A*[Desferrioxamine Te2] + B*[streptomycin] + C*[poly-L-lysine] + D*[Vitamin E conjugate] |
| Formulation 348 | A*[Desferrioxamine Te2] + B*[amphotericin B] + C*[poly-L-lysine] + D*[Vitamin E conjugate] |
| Formulation 349 | A*[Desferrioxamine Te3] + B*[penicillin] + C*[poly-L-lysine] + D*[Vitamin E conjugate] |
| Formulation 350 | A*[Desferrioxamine Te3] + B*[streptomycin] + C*[poly-L-lysine] + D*[Vitamin E conjugate] |
| Formulation 351 | A*[Desferrioxamine Te3] + B*[amphotericin B] + C*[poly-L-lysine] + D*[Vitamin E conjugate] |
| Formulation 352 | A*[Desferrioxamine X1] + B*[penicillin] + C*[poly-L-lysine] + D*[ Vitamin E conjugate] |
| Formulation 353 | A*[Desferrioxamine X1] + B*[streptomycin] + C*[poly-L-lysine] + D*[Vitamin E conjugate] |
| Formulation 354 | A*[Desferrioxamine X1] + B*[amphotericin B] + C*[poly-L-lysine] + D*[Vitamin E conjugate] |
| Formulation 355 | A*[Desferrioxamine X2] + B*[penicillin] + C*[poly-L-lysine] + D*[Vitamin E conjugate] |
| Formulation 356 | A*[Desferrioxamine X2] + B*[streptomycin] + C*[poly-L-lysine] + D*[Vitamin E conjugate] |
| Formulation 357 | A*[Desferrioxamine X2] + B*[amphotericin B] + C*[poly-L-lysine] + D*[Vitamin E conjugate] |
| Formulation 358 | A*[Desferrioxamine X3] + B*[penicillin] + C*[poly-L-lysine] + D*[Vitamin E conjugate] |

TABLE 7-continued

| Formulation Name | Formula |
|---|---|
| Formulation 359 | A*[Desferrioxamine X3] + B*[streptomycin] + C*[poly-L-lysine] + D*[Vitamin E conjugate] |
| Formulation 360 | A*[Desferrioxamine X3] + B*[amphotericin B] + C*[poly-L-lysine] + D*[Vitamin E conjugate] |
| Formulation 361 | A*[Desferrioxamine X4] + B*[penicillin] + C*[poly-L-lysine] + D*[Vitamin E conjugate] |
| Formulation 362 | A*[Desferrioxamine X4] + B*[streptomycin] + C*[poly-L-lysine] + D*[Vitamin E conjugate] |
| Formulation 363 | A*[Desferrioxamine X4] + B*[amphotericin B] + C*[poly-L-lysine] + D*[Vitamin E conjugate] |
| Formulation 364 | A*[Desferrithiocin] + B*[penicillin] + C*[poly-L-lysine] + D*[Vitamin E conjugate] |
| Formulation 365 | A*[Desferrithiocin] + B*[streptomycin] + C*[poly-L-lysine] + D*[Vitamin E conjugate] |
| Formulation 366 | A*[Desferrithiocin] + B*[amphotericin B] + C*[poly-L-lysine] + D*[Vitamin E conjugate] |
| Formulation 367 | A*[2,3-Dihydroxybenzoylserine] + B*[penicillin] + C*[poly-L-lysine] + D*[Vitamin E conjugate] |
| Formulation 368 | A*[2,3-Dihydroxybenzoylserine] + B*[streptomycin] + C*[poly-L-lysine] + D*[Vitamin E conjugate] |
| Formulation 369 | A*[2,3-Dihydroxybenzoylserine] + B*[amphotericin B] + C*[poly-L-lysine] + D*[Vitamin E conjugate] |
| Formulation 370 | A*[Dimerum acid] + B*[penicillin] + C*[poly-L-lysine] + D*[Vitamin E conjugate] |
| Formulation 371 | A*[Dimerum acid] + B*[streptomycin] + C*[poly-L-lysine] + D*[Vitamin E conjugate] |
| Formulation 372 | A*[Dimerum acid] + B*[amphotericin B] + C*[poly-L-lysine] + D*[Vitamin E conjugate] |
| Formulation 373 | A*[Dimethylcoprogen] + B*[penicillin] + C*[poly-L-lysine] + D*[Vitamin E conjugate] |
| Formulation 374 | A*[Dimethylcoprogen] + B*[streptomycin] + C*[poly-L-lysine] + D*[Vitamin E conjugate] |
| Formulation 375 | A*[Dimethylcoprogen] + B*[amphotericin B] + C*[poly-L-lysine] + D*[Vitamin E conjugate] |
| Formulation 376 | A*[Dimethylneocoprogen I] + B*[penicillin] + C*[poly-L-lysine] + D*[Vitamin E conjugate] |
| Formulation 377 | A*[Dimethylneocoprogen I] + B*[streptomycin] + C*[poly-L-lysine] + D*[Vitamin E conjugate] |
| Formulation 378 | A*[Dimethylneocoprogen I] + B*[amphotericin B] + C*[poly-L-lysine] + D*[Vitamin E conjugate] |
| Formulation 379 | A*[Dimethyltriornicin] + B*[penicillin] + C*[poly-L-lysine] + D*[Vitamin E conjugate] |
| Formulation 380 | A*[Dimethyltriornicin] + B*[streptomycin] + C*[poly-L-lysine] + D*[Vitamin E conjugate] |
| Formulation 381 | A*[Dimethyltriornicin] + B*[amphotericin B] + C*[poly-L-lysine] + D*[Vitamin E conjugate] |
| Formulation 382 | A*[Distichonic acid] + B*[penicillin] + C*[poly-L-lysine] + D*[Vitamin E conjugate] |
| Formulation 383 | A*[Distichonic acid] + B*[streptomycin] + C*[poly-L-lysine] + D*[Vitamin E conjugate] |
| Formulation 384 | A*[Distichonic acid] + B*[amphotericin B] + C*[poly-L-lysine] + D*[Vitamin E conjugate] |
| Formulation 385 | A*[E,E-putrebactene] + B*[penicillin] + C*[poly-L-lysine] + D*[Vitamin E conjugate] |
| Formulation 386 | A*[E,E-putrebactene] + B*[streptomycin] + C*[poly-L-lysine] + D*[Vitamin E conjugate] |
| Formulation 387 | A*[E,E-putrebactene] + B*[amphotericin B] + C*[poly-L-lysine] + D*[Vitamin E conjugate] |
| Formulation 388 | A*[Enantio Rhizoferrin] + B*[penicillin] + C*[poly-L-lysine] + D*[Vitamin E conjugate] |
| Formulation 389 | A*[Enantio Rhizoferrin] + B*[streptomycin] + C*[poly-L-lysine] + D*[Vitamin E conjugate] |
| Formulation 390 | A*[Enantio Rhizoferrin] + B*[amphotericin B] + C*[poly-L-lysine] + D*[Vitamin E conjugate] |
| Formulation 391 | A*[Enantio-Pyochelin] + B*[penicillin] + C*[poly-L-lysine] + D*[Vitamin E conjugate] |
| Formulation 392 | A*[Enantio-Pyochelin] + B*[streptomycin] + C*[poly-L-lysine] + D*[Vitamin E conjugate] |
| Formulation 393 | A*[Enantio-Pyochelin] + B*[amphotericin B] + C*[poly-L-lysine] + D*[Vitamin E conjugate] |
| Formulation 394 | A*[Enterobactin] + B*[penicillin] + C*[poly-L-lysine] + D*[Vitamin E conjugate] |
| Formulation 395 | A*[Enterobactin] + B*[streptomycin] + C*[poly-L-lysine] + D*[Vitamin E conjugate] |
| Formulation 396 | A*[Enterobactin] + B*[amphotericin B] + C*[poly-L-lysine] + D*[Vitamin E conjugate] |
| Formulation 397 | A*[Enterochelin] + B*[penicillin] + C*[poly-L-lysine] + D*[Vitamin E conjugate] |
| Formulation 398 | A*[Enterochelin] + B*[streptomycin] + C*[poly-L-lysine] + D*[Vitamin E conjugate] |
| Formulation 399 | A*[Enterochelin] + B*[amphotericin B] + C*[poly-L-lysine] + D*[Vitamin E conjugate] |
| Formulation 400 | A*[E-putrebactene] + B*[penicillin] + C*[poly-L-lysine] + D*[Vitamin E conjugate] |
| Formulation 401 | A*[E-putrebactene] + B*[streptomycin] + C*[poly-L-lysine] + D*[Vitamin E conjugate] |
| Formulation 402 | A*[E-putrebactene] + B*[amphotericin B] + C*[poly-L-lysine] + D*[Vitamin E conjugate] |
| Formulation 403 | A*[Exochelin MN] + B*[penicillin] + C*[poly-L-lysine] + D*[Vitamin E conjugate] |
| Formulation 404 | A*[Exochelin MN] + B*[streptomycin] + C*[poly-L-lysine] + D*[Vitamin E conjugate] |
| Formulation 405 | A*[Exochelin MN] + B*[amphotericin B] + C*[poly-L-lysine] + D*[Vitamin E conjugate] |
| Formulation 406 | A*[Exochelin MS] + B*[penicillin] + C*[poly-L-lysine] + D*[Vitamin E conjugate] |
| Formulation 407 | A*[Exochelin MS] + B*[streptomycin] + C*[poly-L-lysine] + D*[Vitamin E conjugate] |
| Formulation 408 | A*[Exochelin MS] + B*[amphotericin B] + C*[poly-L-lysine] + D*[Vitamin E conjugate] |
| Formulation 409 | A*[Ferrichrome] + B*[penicillin] + C*[poly-L-lysine] + D*[Vitamin E conjugate] |
| Formulation 410 | A*[Ferrichrome] + B*[streptomycin] + C*[poly-L-lysine] + D*[Vitamin E conjugate] |
| Formulation 411 | A*[Ferrichrome] + B*[amphotericin B] + C*[poly-L-lysine] + D*[Vitamin E conjugate] |
| Formulation 412 | A*[Ferrichrome A] + B*[penicillin] + C*[poly-L-lysine] + D*[Vitamin E conjugate] |
| Formulation 413 | A*[Ferrichrome A] + B*[streptomycin] + C*[poly-L-lysine] + D*[Vitamin E conjugate] |
| Formulation 414 | A*[Ferrichrome A] + B*[amphotericin B] + C*[poly-L-lysine] + D*[Vitamin E conjugate] |
| Formulation 415 | A*[Ferrichrome C] + B*[penicillin] + C*[poly-L-lysine] + D*[Vitamin E conjugate] |
| Formulation 416 | A*[Ferrichrome C] + B*[streptomycin] + C*[poly-L-lysine] + D*[Vitamin E conjugate] |
| Formulation 417 | A*[Ferrichrome C] + B*[amphotericin B] + C*[poly-L-lysine] + D*[Vitamin E conjugate] |
| Formulation 418 | A*[Ferrichrysin] + B*[penicillin] + C*[poly-L-lysine] + D*[Vitamin E conjugate] |
| Formulation 419 | A*[Ferrichrysin] + B*[streptomycin] + C*[poly-L-lysine] + D*[Vitamin E conjugate] |
| Formulation 420 | A*[Ferrichrysin] + B*[amphotericin B] + C*[poly-L-lysine] + D*[Vitamin E conjugate] |
| Formulation 421 | A*[Ferricrocin] + B*[penicillin] + C*[poly-L-lysine] + D*[Vitamin E conjugate] |
| Formulation 422 | A*[Ferricrocin] + B*[streptomycin] + C*[poly-L-lysine] + D*[Vitamin E conjugate] |
| Formulation 423 | A*[Ferricrocin] + B*[amphotericin B] + C*[poly-L-lysine] + D*[Vitamin E conjugate] |
| Formulation 424 | A*[Ferrimycin A] + B*[penicillin] + C*[poly-L-lysine] + D*[Vitamin E conjugate] |
| Formulation 425 | A*[Ferrimycin A] + B*[streptomycin] + C*[poly-L-lysine] + D*[Vitamin E conjugate] |
| Formulation 426 | A*[Ferrimycin A] + B*[amphotericin B] + C*[poly-L-lysine] + D*[Vitamin E conjugate] |
| Formulation 427 | A*[Ferrirhodin] + B*[penicillin] + C*[poly-L-lysine] + D*[Vitamin E conjugate] |
| Formulation 428 | A*[Ferrirhodin] + B*[streptomycin] + C*[poly-L-lysine] + D*[Vitamin E conjugate] |
| Formulation 429 | A*[Ferrirhodin] + B*[amphotericin B] + C*[poly-L-lysine] + D*[Vitamin E conjugate] |
| Formulation 430 | A*[Ferrirubin] + B*[penicillin] + C*[poly-L-lysine] + D*[Vitamin E conjugate] |
| Formulation 431 | A*[Ferrirubin] + B*[streptomycin] + C*[poly-L-lysine] + D*[Vitamin E conjugate] |
| Formulation 432 | A*[Ferrirubin] + B*[amphotericin B] + C*[poly-L-lysine] + D*[Vitamin E conjugate] |
| Formulation 433 | A*[Ferrocin A] + B*[penicillin] + C*[poly-L-lysine] + D*[Vitamin E conjugate] |
| Formulation 434 | A*[Ferrocin A] + B*[streptomycin] + C*[poly-L-lysine] + D*[Vitamin E conjugate] |
| Formulation 435 | A*[Ferrocin A] + B*[amphotericin B] + C*[poly-L-lysine] + D*[Vitamin E conjugate] |

TABLE 7-continued

| Formulation Name | Formula |
|---|---|
| Formulation 436 | A*[Fimsbactin A] + B*[penicillin] + C*[poly-L-lysine] + D*[Vitamin E conjugate] |
| Formulation 437 | A*[Fimsbactin A] + B*[streptomycin] + C*[poly-L-lysine] + D*[Vitamin E conjugate] |
| Formulation 438 | A*[Fimsbactin A] + B*[amphotericin B] + C*[poly-L-lysine] + D*[Vitamin E conjugate] |
| Formulation 439 | A*[Fimsbactin B] + B*[penicillin] + C*[poly-L-lysine] + D*[Vitamin E conjugate] |
| Formulation 440 | A*[Fimsbactin B] + B*[streptomycin] + C*[poly-L-lysine] + D*[Vitamin E conjugate] |
| Formulation 441 | A*[Fimsbactin B] + B*[amphotericin B] + C*[poly-L-lysine] + D*[Vitamin E conjugate] |
| Formulation 442 | A*[Fimsbactin C] + B*[penicillin] + C*[poly-L-lysine] + D*[Vitamin E conjugate] |
| Formulation 443 | A*[Fimsbactin C] + B*[streptomycin] + C*[poly-L-lysine] + D*[Vitamin E conjugate] |
| Formulation 444 | A*[Fimsbactin C] + B*[amphotericin B] + C*[poly-L-lysine] + D*[Vitamin E conjugate] |
| Formulation 445 | A*[Fimsbactin D] + B*[penicillin] + C*[poly-L-lysine] + D*[Vitamin E conjugate] |
| Formulation 446 | A*[Fimsbactin D] + B*[streptomycin] + C*[poly-L-lysine] + D*[Vitamin E conjugate] |
| Formulation 447 | A*[Fimsbactin D] + B*[amphotericin B] + C*[poly-L-lysine] + D*[Vitamin E conjugate] |
| Formulation 448 | A*[Fimsbactin E] + B*[penicillin] + C*[poly-L-lysine] + D*[Vitamin E conjugate] |
| Formulation 449 | A*[Fimsbactin E] + B*[streptomycin] + C*[poly-L-lysine] + D*[Vitamin E conjugate] |
| Formulation 450 | A*[Fimsbactin E] + B*[amphotericin B] + C*[poly-L-lysine] + D*[Vitamin E conjugate] |
| Formulation 451 | A*[Fimsbactin F] + B*[penicillin] + C*[poly-L-lysine] + D*[Vitamin E conjugate] |
| Formulation 452 | A*[Fimsbactin F] + B*[streptomycin] + C*[poly-L-lysine] + D*[Vitamin E conjugate] |
| Formulation 453 | A*[Fimsbactin F] + B*[amphotericin B] + C*[poly-L-lysine] + D*[Vitamin E conjugate] |
| Formulation 454 | A*[Fluvibactin] + B*[penicillin] + C*[poly-L-lysine] + D*[Vitamin E conjugate] |
| Formulation 455 | A*[Fluvibactin] + B*[streptomycin] + C*[poly-L-lysine] + D*[Vitamin E conjugate] |
| Formulation 456 | A*[Fluvibactin] + B*[amphotericin B] + C*[poly-L-lysine] + D*[Vitamin E conjugate] |
| Formulation 457 | A*[Formobactin] + B*[penicillin] + C*[poly-L-lysine] + D*[Vitamin E conjugate] |
| Formulation 458 | A*[Formobactin] + B*[streptomycin] + C*[poly-L-lysine] + D*[Vitamin E conjugate] |
| Formulation 459 | A*[Formobactin] + B*[amphotericin B] + C*[poly-L-lysine] + D*[Vitamin E conjugate] |
| Formulation 460 | A*[Fusarinine] + B*[penicillin] + C*[poly-L-lysine] + D*[Vitamin E conjugate] |
| Formulation 461 | A*[Fusarinine] + B*[streptomycin] + C*[poly-L-lysine] + D*[Vitamin E conjugate] |
| Formulation 462 | A*[Fusarinine] + B*[amphotericin B] + C*[poly-L-lysine] + D*[Vitamin E conjugate] |
| Formulation 463 | A*[Fusarinine A] + B*[penicillin] + C*[poly-L-lysine] + D*[Vitamin E conjugate] |
| Formulation 464 | A*[Fusarinine A] + B*[streptomycin] + C*[poly-L-lysine] + D*[Vitamin E conjugate] |
| Formulation 465 | A*[Fusarinine A] + B*[amphotericin B] + C*[poly-L-lysine] + D*[Vitamin E conjugate] |
| Formulation 466 | A*[Fusarinine B] + B*[penicillin] + C*[poly-L-lysine] + D*[Vitamin E conjugate] |
| Formulation 467 | A*[Fusarinine B] + B*[streptomycin] + C*[poly-L-lysine] + D*[Vitamin E conjugate] |
| Formulation 468 | A*[Fusarinine B] + B*[amphotericin B] + C*[poly-L-lysine] + D*[Vitamin E conjugate] |
| Formulation 469 | A*[Fusarinine C] + B*[penicillin] + C*[poly-L-lysine] + D*[Vitamin E conjugate] |
| Formulation 470 | A*[Fusarinine C] + B*[streptomycin] + C*[poly-L-lysine] + D*[Vitamin E conjugate] |
| Formulation 471 | A*[Fusarinine C] + B*[amphotericin B] + C*[poly-L-lysine] + D*[Vitamin E conjugate] |
| Formulation 472 | A*[Heterobactin A] + B*[penicillin] + C*[poly-L-lysine] + D*[Vitamin E conjugate] |
| Formulation 473 | A*[Heterobactin A] + B*[streptomycin] + C*[poly-L-lysine] + D*[Vitamin E conjugate] |
| Formulation 474 | A*[Heterobactin A] + B*[amphotericin B] + C*[poly-L-lysine] + D*[Vitamin E conjugate] |
| Formulation 475 | A*[Heterobactin B] + B*[penicillin] + C*[poly-L-lysine] + D*[Vitamin E conjugate] |
| Formulation 476 | A*[Heterobactin B] + B*[streptomycin] + C*[poly-L-lysine] + D*[Vitamin E conjugate] |
| Formulation 477 | A*[Heterobactin B] + B*[amphotericin B] + C*[poly-L-lysine] + D*[Vitamin E conjugate] |
| Formulation 478 | A*[Hydroxycopropen] + B*[penicillin] + C*[poly-L-lysine] + D*[Vitamin E conjugate] |
| Formulation 479 | A*[Hydroxycopropen] + B*[streptomycin] + C*[poly-L-lysine] + D*[Vitamin E conjugate] |
| Formulation 480 | A*[Hydroxycopropen] + B*[amphotericin B] + C*[poly-L-lysine] + D*[Vitamin E conjugate] |
| Formulation 481 | A*[Hydroxyisoneocoprogen I] + B*[penicillin] + C*[poly-L-lysine] + D*[Vitamin E conjugate] |
| Formulation 482 | A*[Hydroxyisoneocoprogen I] + B*[streptomycin] + C*[poly-L-lysine] + D*[Vitamin E conjugate] |
| Formulation 483 | A*[Hydroxyisoneocoprogen I] + B*[amphotericin B] + C*[poly-L-lysine] + D*[Vitamin E conjugate] |
| Formulation 484 | A*[3-Hydroxymugineic acid] + B*[penicillin] + C*[poly-L-lysine] + D*[Vitamin E conjugate] |
| Formulation 485 | A*[3-Hydroxymugineic acid] + B*[streptomycin] + C*[poly-L-lysine] + D*[Vitamin E conjugate] |
| Formulation 486 | A*[3-Hydroxymugineic acid] + B*[amphotericin B] + C*[poly-L-lysine] + D*[Vitamin E conjugate] |
| Formulation 487 | A*[Hydroxy-neocoprogen I] + B*[penicillin] + C*[poly-L-lysine] + D*[Vitamin E conjugate] |
| Formulation 488 | A*[Hydroxy-neocoprogen I] + B*[streptomycin] + C*[poly-L-lysine] + D*[Vitamin E conjugate] |
| Formulation 489 | A*[Hydroxy-neocoprogen I] + B*[amphotericin B] + C*[poly-L-lysine] + D*[Vitamin E conjugate] |
| Formulation 490 | A*[Isoneocoprogen I] + B*[penicillin] + C*[poly-L-lysine] + D*[Vitamin E conjugate] |
| Formulation 491 | A*[Isoneocoprogen I] + B*[streptomycin] + C*[poly-L-lysine] + D*[Vitamin E conjugate] |
| Formulation 492 | A*[Isoneocoprogen I] + B*[amphotericin B] + C*[poly-L-lysine] + D*[Vitamin E conjugate] |
| Formulation 493 | A*[Isopyoverdin 10.7] + B*[penicillin] + C*[poly-L-lysine] + D*[Vitamin E conjugate] |
| Formulation 494 | A*[Isopyoverdin 10.7] + B*[streptomycin] + C*[poly-L-lysine] + D*[Vitamin E conjugate] |
| Formulation 495 | A*[Isopyoverdin 10.7] + B*[amphotericin B] + C*[poly-L-lysine] + D*[Vitamin E conjugate] |
| Formulation 496 | A*[Isopyoverdin 6.7] + B*[penicillin] + C*[poly-L-lysine] + D*[Vitamin E conjugate] |
| Formulation 497 | A*[Isopyoverdin 6.7] + B*[streptomycin] + C*[poly-L-lysine] + D*[Vitamin E conjugate] |
| Formulation 498 | A*[Isopyoverdin 6.7] + B*[amphotericin B] + C*[poly-L-lysine] + D*[Vitamin E conjugate] |
| Formulation 499 | A*[Isopyoverdin 7.13] + B*[penicillin] + C*[poly-L-lysine] + D*[Vitamin E conjugate] |
| Formulation 500 | A*[Isopyoverdin 7.13] + B*[streptomycin] + C*[poly-L-lysine] + D*[Vitamin E conjugate] |
| Formulation 501 | A*[Isopyoverdin 7.13] + B*[amphotericin B] + C*[poly-L-lysine] + D*[Vitamin E conjugate] |
| Formulation 502 | A*[Isopyoverdin 90-33] + B*[penicillin] + C*[poly-L-lysine] + D*[Vitamin E conjugate] |
| Formulation 503 | A*[Isopyoverdin 90-33] + B*[streptomycin] + C*[poly-L-lysine] + D*[Vitamin E conjugate] |
| Formulation 504 | A*[Isopyoverdin 90-33] + B*[amphotericin B] + C*[poly-L-lysine] + D*[Vitamin E conjugate] |
| Formulation 505 | A*[Isopyoverdin 90-44] + B*[penicillin] + C*[poly-L-lysine] + D*[Vitamin E conjugate] |
| Formulation 506 | A*[Isopyoverdin 90-44] + B*[streptomycin] + C*[poly-L-lysine] + D*[Vitamin E conjugate] |
| Formulation 507 | A*[Isopyoverdin 90-44] + B*[amphotericin B] + C*[poly-L-lysine] + D*[Vitamin E conjugate] |
| Formulation 508 | A*[Isopyoverdin BTP1] + B*[penicillin] + C*[poly-L-lysine] + D*[Vitamin E conjugate] |
| Formulation 509 | A*[Isopyoverdin BTP1] + B*[streptomycin] + C*[poly-L-lysine] + D*[Vitamin E conjugate] |
| Formulation 510 | A*[Isopyoverdin BTP1] + B*[amphotericin B] + C*[poly-L-lysine] + D*[Vitamin E conjugate] |
| Formulation 511 | A*[Isotriornicin] + B*[penicillin] + C*[poly-L-lysine] + D*[Vitamin E conjugate] |
| Formulation 512 | A*[Isotriornicin] + B*[streptomycin] + C*[poly-L-lysine] + D*[Vitamin E conjugate] |

TABLE 7-continued

| Formulation Name | Formula |
|---|---|
| Formulation 513 | A*[Isotriornicin] + B*[amphotericin B] + C*[poly-L-lysine] + D*[Vitamin E conjugate] |
| Formulation 514 | A*[Itoic acid] + B*[penicillin] + C*[poly-L-lysine] + D*[Vitamin E conjugate] |
| Formulation 515 | A*[Itoic acid] + B*[streptomycin] + C*[poly-L-lysine] + D*[Vitamin E conjugate] |
| Formulation 516 | A*[Itoic acid] + B*[amphotericin B] + C*[poly-L-lysine] + D*[Vitamin E conjugate] |
| Formulation 517 | A*[Loihichelin A] + B*[penicillin] + C*[poly-L-lysine] + D*[Vitamin E conjugate] |
| Formulation 518 | A*[Loihichelin A] + B*[streptomycin] + C*[poly-L-lysine] + D*[Vitamin E conjugate] |
| Formulation 519 | A*[Loihichelin A] + B*[amphotericin B] + C*[poly-L-lysine] + D*[Vitamin E conjugate] |
| Formulation 520 | A*[Loihichelin B] + B*[penicillin] + C*[poly-L-lysine] + D*[Vitamin E conjugate] |
| Formulation 521 | A*[Loihichelin B] + B*[streptomycin] + C*[poly-L-lysine] + D*[Vitamin E conjugate] |
| Formulation 522 | A*[Loihichelin B] + B*[amphotericin B] + C*[poly-L-lysine] + D*[Vitamin E conjugate] |
| Formulation 523 | A*[Loihichelin C] + B*[penicillin] + C*[poly-L-lysine] + D*[Vitamin E conjugate] |
| Formulation 524 | A*[Loihichelin C] + B*[streptomycin] + C*[poly-L-lysine] + D*[Vitamin E conjugate] |
| Formulation 525 | A*[Loihichelin C] + B*[amphotericin B] + C*[poly-L-lysine] + D*[Vitamin E conjugate] |
| Formulation 526 | A*[Loihichelin D] + B*[penicillin] + C*[poly-L-lysine] + D*[Vitamin E conjugate] |
| Formulation 527 | A*[Loihichelin D] + B*[streptomycin] + C*[poly-L-lysine] + D*[Vitamin E conjugate] |
| Formulation 528 | A*[Loihichelin D] + B*[amphotericin B] + C*[poly-L-lysine] + D*[Vitamin E conjugate] |
| Formulation 529 | A*[Loihichelin E] + B*[penicillin] + C*[poly-L-lysine] + D*[Vitamin E conjugate] |
| Formulation 530 | A*[Loihichelin E] + B*[streptomycin] + C*[poly-L-lysine] + D*[Vitamin E conjugate] |
| Formulation 531 | A*[Loihichelin E] + B*[amphotericin B] + C*[poly-L-lysine] + D*[Vitamin E conjugate] |
| Formulation 532 | A*[Loihichelin F] + B*[penicillin] + C*[poly-L-lysine] + D*[Vitamin E conjugate] |
| Formulation 533 | A*[Loihichelin F] + B*[streptomycin] + C*[poly-L-lysine] + D*[Vitamin E conjugate] |
| Formulation 534 | A*[Loihichelin F] + B*[amphotericin B] + C*[poly-L-lysine] + D*[Vitamin E conjugate] |
| Formulation 535 | A*[Maduraferrin] + B*[penicillin] + C*[poly-L-lysine] + D*[Vitamin E conjugate] |
| Formulation 536 | A*[Maduraferrin] + B*[streptomycin] + C*[poly-L-lysine] + D*[Vitamin E conjugate] |
| Formulation 537 | A*[Maduraferrin] + B*[amphotericin B] + C*[poly-L-lysine] + D*[Vitamin E conjugate] |
| Formulation 538 | A*[Malonichrome] + B*[penicillin] + C*[poly-L-lysine] + D*[Vitamin E conjugate] |
| Formulation 539 | A*[Malonichrome] + B*[streptomycin] + C*[poly-L-lysine] + D*[Vitamin E conjugate] |
| Formulation 540 | A*[Malonichrome] + B*[amphotericin B] + C*[poly-L-lysine] + D*[Vitamin E conjugate] |
| Formulation 541 | A*[Marinobactin] + B*[penicillin] + C*[poly-L-lysine] + D*[Vitamin E conjugate] |
| Formulation 542 | A*[Marinobactin] + B*[streptomycin] + C*[poly-L-lysine] + D*[Vitamin E conjugate] |
| Formulation 543 | A*[Marinobactin] + B*[amphotericin B] + C*[poly-L-lysine] + D*[Vitamin E conjugate] |
| Formulation 544 | A*[Marinobactin] + B*[penicillin] + C*[poly-L-lysine] + D*[Vitamin E conjugate] |
| Formulation 545 | A*[Marinobactin] + B*[streptomycin] + C*[poly-L-lysine] + D*[Vitamin E conjugate] |
| Formulation 546 | A*[Marinobactin] + B*[amphotericin B] + C*[poly-L-lysine] + D*[Vitamin E conjugate] |
| Formulation 547 | A*[Marinobactin] + B*[penicillin] + C*[poly-L-lysine] + D*[Vitamin E conjugate] |
| Formulation 548 | A*[Marinobactin] + B*[streptomycin] + C*[poly-L-lysine] + D*[Vitamin E conjugate] |
| Formulation 549 | A*[Marinobactin] + B*[amphotericin B] + C*[poly-L-lysine] + D*[Vitamin E conjugate] |
| Formulation 550 | A*[Marinobactin] + B*[penicillin] + C*[poly-L-lysine] + D*[Vitamin E conjugate] |
| Formulation 551 | A*[Marinobactin] + B*[streptomycin] + C*[poly-L-lysine] + D*[Vitamin E conjugate] |
| Formulation 552 | A*[Marinobactin] + B*[amphotericin B] + C*[poly-L-lysine] + D*[Vitamin E conjugate] |
| Formulation 553 | A*[Marinobactin] + B*[penicillin] + C*[poly-L-lysine] + D*[Vitamin E conjugate] |
| Formulation 554 | A*[Marinobactin] + B*[streptomycin] + C*[poly-L-lysine] + D*[Vitamin E conjugate] |
| Formulation 555 | A*[Marinobactin] + B*[amphotericin B] + C*[poly-L-lysine] + D*[Vitamin E conjugate] |
| Formulation 556 | A*[Marinobactin] + B*[penicillin] + C*[poly-L-lysine] + D*[Vitamin E conjugate] |
| Formulation 557 | A*[Marinobactin] + B*[streptomycin] + C*[poly-L-lysine] + D*[Vitamin E conjugate] |
| Formulation 558 | A*[Marinobactin] + B*[amphotericin B] + C*[poly-L-lysine] + D*[Vitamin E conjugate] |
| Formulation 559 | A*[Micacocidin] + B*[penicillin] + C*[poly-L-lysine] + D*[Vitamin E conjugate] |
| Formulation 560 | A*[Micacocidin] + B*[streptomycin] + C*[poly-L-lysine] + D*[Vitamin E conjugate] |
| Formulation 561 | A*[Micacocidin] + B*[amphotericin B] + C*[poly-L-lysine] + D*[Vitamin E conjugate] |
| Formulation 562 | A*[Moanachelins] + B*[penicillin] + C*[poly-L-lysine] + D*[Vitamin E conjugate] |
| Formulation 563 | A*[Moanachelins] + B*[streptomycin] + C*[poly-L-lysine] + D*[Vitamin E conjugate] |
| Formulation 564 | A*[Moanachelins] + B*[amphotericin B] + C*[poly-L-lysine] + D*[Vitamin E conjugate] |
| Formulation 565 | A*[Moanachelins] + B*[penicillin] + C*[poly-L-lysine] + D*[Vitamin E conjugate] |
| Formulation 566 | A*[Moanachelins] + B*[streptomycin] + C*[poly-L-lysine] + D*[Vitamin E conjugate] |
| Formulation 567 | A*[Moanachelins] + B*[amphotericin B] + C*[poly-L-lysine] + D*[Vitamin E conjugate] |
| Formulation 568 | A*[Moanachelins] + B*[penicillin] + C*[poly-L-lysine] + D*[Vitamin E conjugate] |
| Formulation 569 | A*[Moanachelins] + B*[streptomycin] + C*[poly-L-lysine] + D*[Vitamin E conjugate] |
| Formulation 570 | A*[Moanachelins] + B*[amphotericin B] + C*[poly-L-lysine] + D*[Vitamin E conjugate] |
| Formulation 571 | A*[Moanachelins] + B*[penicillin] + C*[poly-L-lysine] + D*[Vitamin E conjugate] |
| Formulation 572 | A*[Moanachelins] + B*[streptomycin] + C*[poly-L-lysine] + D*[Vitamin E conjugate] |
| Formulation 573 | A*[Moanachelins] + B*[amphotericin B] + C*[poly-L-lysine] + D*[Vitamin E conjugate] |
| Formulation 574 | A*[Moanachelins] + B*[penicillin] + C*[poly-L-lysine] + D*[Vitamin E conjugate] |
| Formulation 575 | A*[Moanachelins] + B*[streptomycin] + C*[poly-L-lysine] + D*[Vitamin E conjugate] |
| Formulation 576 | A*[Moanachelins] + B*[amphotericin B] + C*[poly-L-lysine] + D*[Vitamin E conjugate] |
| Formulation 577 | A*[Monoglucosylated] + B*[penicillin] + C*[poly-L-lysine] + D*[Vitamin E conjugate] |
| Formulation 578 | A*[Monoglucosylated] + B*[streptomycin] + C*[poly-L-lysine] + D*[Vitamin E conjugate] |
| Formulation 579 | A*[Monoglucosylated] + B*[amphotericin B] + C*[poly-L-lysine] + D*[Vitamin E conjugate] |
| Formulation 580 | A*[Mugineic] + B*[penicillin] + C*[poly-L-lysine] + D*[Vitamin E conjugate] |
| Formulation 581 | A*[Mugineic] + B*[streptomycin] + C*[poly-L-lysine] + D*[Vitamin E conjugate] |
| Formulation 582 | A*[Mugineic] + B*[amphotericin B] + C*[poly-L-lysine] + D*[Vitamin E conjugate] |
| Formulation 583 | A*[Mycobactin A] + B*[penicillin] + C*[poly-L-lysine] + D*[Vitamin E conjugate] |
| Formulation 584 | A*[Mycobactin A] + B*[streptomycin] + C*[poly-L-lysine] + D*[Vitamin E conjugate] |
| Formulation 585 | A*[Mycobactin A] + B*[amphotericin B] + C*[poly-L-lysine] + D*[Vitamin E conjugate] |
| Formulation 586 | A*[Mycobactin Av] + B*[penicillin] + C*[poly-L-lysine] + D*[Vitamin E conjugate] |
| Formulation 587 | A*[Mycobactin Av] + B*[streptomycin] + C*[poly-L-lysine] + D*[Vitamin E conjugate] |
| Formulation 588 | A*[Mycobactin Av] + B*[amphotericin B] + C*[poly-L-lysine] + D*[Vitamin E conjugate] |
| Formulation 589 | A*[Mycobactin F] + B*[penicillin] + C*[poly-L-lysine] + D*[Vitamin E conjugate] |

TABLE 7-continued

| Formulation Name | Formula |
| --- | --- |
| Formulation 590 | A*[Mycobactin F] + B*[streptomycin] + C*[poly-L-lysine] + D*[Vitamin E conjugate] |
| Formulation 591 | A*[Mycobactin F] + B*[amphotericin B] + C*[poly-L-lysine] + D*[Vitamin E conjugate] |
| Formulation 592 | A*[Mycobactin H] + B*[penicillin] + C*[poly-L-lysine] + D*[Vitamin E conjugate] |
| Formulation 593 | A*[Mycobactin H] + B*[streptomycin] + C*[poly-L-lysine] + D*[Vitamin E conjugate] |
| Formulation 594 | A*[Mycobactin H] + B*[amphotericin B] + C*[poly-L-lysine] + D*[Vitamin E conjugate] |
| Formulation 595 | A*[Mycobactin J] + B*[penicillin] + C*[poly-L-lysine] + D*[Vitamin E conjugate] |
| Formulation 596 | A*[Mycobactin J] + B*[streptomycin] + C*[poly-L-lysine] + D*[Vitamin E conjugate] |
| Formulation 597 | A*[Mycobactin J] + B*[amphotericin B] + C*[poly-L-lysine] + D*[Vitamin E conjugate] |
| Formulation 598 | A*[Mycobactin M] + B*[penicillin] + C*[poly-L-lysine] + D*[Vitamin E conjugate] |
| Formulation 599 | A*[Mycobactin M] + B*[streptomycin] + C*[poly-L-lysine] + D*[Vitamin E conjugate] |
| Formulation 600 | A*[Mycobactin M] + B*[amphotericin B] + C*[poly-L-lysine] + D*[Vitamin E conjugate] |
| Formulation 601 | A*[Mycobactin N] + B*[penicillin] + C*[poly-L-lysine] + D*[Vitamin E conjugate] |
| Formulation 602 | A*[Mycobactin N] + B*[streptomycin] + C*[poly-L-lysine] + D*[Vitamin E conjugate] |
| Formulation 603 | A*[Mycobactin N] + B*[amphotericin B] + C*[poly-L-lysine] + D*[Vitamin E conjugate] |
| Formulation 604 | A*[Mycobactin NA] + B*[penicillin] + C*[poly-L-lysine] + D*[Vitamin E conjugate] |
| Formulation 605 | A*[Mycobactin NA] + B*[streptomycin] + C*[poly-L-lysine] + D*[Vitamin E conjugate] |
| Formulation 606 | A*[Mycobactin NA] + B*[amphotericin B] + C*[poly-L-lysine] + D*[Vitamin E conjugate] |
| Formulation 607 | A*[Mycobactin P] + B*[penicillin] + C*[poly-L-lysine] + D*[Vitamin E conjugate] |
| Formulation 608 | A*[Mycobactin P] + B*[streptomycin] + C*[poly-L-lysine] + D*[Vitamin E conjugate] |
| Formulation 609 | A*[Mycobactin P] + B*[amphotericin B] + C*[poly-L-lysine] + D*[Vitamin E conjugate] |
| Formulation 610 | A*[Mycobactin R] + B*[penicillin] + C*[poly-L-lysine] + D*[Vitamin E conjugate] |
| Formulation 611 | A*[Mycobactin R] + B*[streptomycin] + C*[poly-L-lysine] + D*[Vitamin E conjugate] |
| Formulation 612 | A*[Mycobactin R] + B*[amphotericin B] + C*[poly-L-lysine] + D*[Vitamin E conjugate] |
| Formulation 613 | A*[Mycobactin S] + B*[penicillin] + C*[poly-L-lysine] + D*[Vitamin E conjugate] |
| Formulation 614 | A*[Mycobactin S] + B*[streptomycin] + C*[poly-L-lysine] + D*[Vitamin E conjugate] |
| Formulation 615 | A*[Mycobactin S] + B*[amphotericin B] + C*[poly-L-lysine] + D*[Vitamin E conjugate] |
| Formulation 616 | A*[Mycobactin T] + B*[penicillin] + C*[poly-L-lysine] + D*[Vitamin E conjugate] |
| Formulation 617 | A*[Mycobactin T] + B*[streptomycin] + C*[poly-L-lysine] + D*[Vitamin E conjugate] |
| Formulation 618 | A*[Mycobactin T] + B*[amphotericin B] + C*[poly-L-lysine] + D*[Vitamin E conjugate] |
| Formulation 619 | A*[Myxochelin] + B*[penicillin] + C*[poly-L-lysine] + D*[Vitamin E conjugate] |
| Formulation 620 | A*[Myxochelin] + B*[streptomycin] + C*[poly-L-lysine] + D*[Vitamin E conjugate] |
| Formulation 621 | A*[Myxochelin] + B*[amphotericin B] + C*[poly-L-lysine] + D*[Vitamin E conjugate] |
| Formulation 622 | A*[Nannochelin A] + B*[penicillin] + C*[poly-L-lysine] + D*[Vitamin E conjugate] |
| Formulation 623 | A*[Nannochelin A] + B*[streptomycin] + C*[poly-L-lysine] + D*[Vitamin E conjugate] |
| Formulation 624 | A*[Nannochelin A] + B*[amphotericin B] + C*[poly-L-lysine] + D*[Vitamin E conjugate] |
| Formulation 625 | A*[Nannochelin B] + B*[penicillin] + C*[poly-L-lysine] + D*[Vitamin E conjugate] |
| Formulation 626 | A*[Nannochelin B] + B*[streptomycin] + C*[poly-L-lysine] + D*[Vitamin E conjugate] |
| Formulation 627 | A*[Nannochelin B] + B*[amphotericin B] + C*[poly-L-lysine] + D*[Vitamin E conjugate] |
| Formulation 628 | A*[Nannochelin C] + B*[penicillin] + C*[poly-L-lysine] + D*[Vitamin E conjugate] |
| Formulation 629 | A*[Nannochelin C] + B*[streptomycin] + C*[poly-L-lysine] + D*[Vitamin E conjugate] |
| Formulation 630 | A*[Nannochelin C] + B*[amphotericin B] + C*[poly-L-lysine] + D*[Vitamin E conjugate] |
| Formulation 631 | A*[Neocoprogen I] + B*[penicillin] + C*[poly-L-lysine] + D*[Vitamin E conjugate] |
| Formulation 632 | A*[Neocoprogen I] + B*[streptomycin] + C*[poly-L-lysine] + D*[Vitamin E conjugate] |
| Formulation 633 | A*[Neocoprogen I] + B*[amphotericin B] + C*[poly-L-lysine] + D*[Vitamin E conjugate] |
| Formulation 634 | A*[Neocoprogen II] + B*[penicillin] + C*[poly-L-lysine] + D*[Vitamin E conjugate] |
| Formulation 635 | A*[Neocoprogen II] + B*[streptomycin] + C*[poly-L-lysine] + D*[Vitamin E conjugate] |
| Formulation 636 | A*[Neocoprogen II] + B*[amphotericin B] + C*[poly-L-lysine] + D*[Vitamin E conjugate] |
| Formulation 637 | A*[Neurosporin] + B*[penicillin] + C*[poly-L-lysine] + D*[Vitamin E conjugate] |
| Formulation 638 | A*[Neurosporin] + B*[streptomycin] + C*[poly-L-lysine] + D*[Vitamin E conjugate] |
| Formulation 639 | A*[Neurosporin] + B*[amphotericin B] + C*[poly-L-lysine] + D*[Vitamin E conjugate] |
| Formulation 640 | A*[Nocobactin] + B*[penicillin] + C*[poly-L-lysine] + D*[Vitamin E conjugate] |
| Formulation 641 | A*[Nocobactin] + B*[streptomycin] + C*[poly-L-lysine] + D*[Vitamin E conjugate] |
| Formulation 642 | A*[Nocobactin] + B*[amphotericin B] + C*[poly-L-lysine] + D*[Vitamin E conjugate] |
| Formulation 643 | A*[Ochrobactin A] + B*[penicillin] + C*[poly-L-lysine] + D*[Vitamin E conjugate] |
| Formulation 644 | A*[Ochrobactin A] + B*[streptomycin] + C*[poly-L-lysine] + D*[Vitamin E conjugate] |
| Formulation 645 | A*[Ochrobactin A] + B*[amphotericin B] + C*[poly-L-lysine] + D*[Vitamin E conjugate] |
| Formulation 646 | A*[Ochrobactin B] + B*[penicillin] + C*[poly-L-lysine] + D*[Vitamin E conjugate] |
| Formulation 647 | A*[Ochrobactin B] + B*[streptomycin] + C*[poly-L-lysine] + D*[Vitamin E conjugate] |
| Formulation 648 | A*[Ochrobactin B] + B*[amphotericin B] + C*[poly-L-lysine] + D*[Vitamin E conjugate] |
| Formulation 649 | A*[Ochrobactin C] + B*[penicillin] + C*[poly-L-lysine] + D*[Vitamin E conjugate] |
| Formulation 650 | A*[Ochrobactin C] + B*[streptomycin] + C*[poly-L-lysine] + D*[Vitamin E conjugate] |
| Formulation 651 | A*[Ochrobactin C] + B*[amphotericin B] + C*[poly-L-lysine] + D*[Vitamin E conjugate] |
| Formulation 652 | A*[Ornibactin - C4] + B*[penicillin] + C*[poly-L-lysine] + D*[Vitamin E conjugate] |
| Formulation 653 | A*[Ornibactin - C4] + B*[streptomycin] + C*[poly-L-lysine] + D*[Vitamin E conjugate] |
| Formulation 654 | A*[Ornibactin - C4] + B*[amphotericin B] + C*[poly-L-lysine] + D*[Vitamin E conjugate] |
| Formulation 655 | A*[Ornibactin - C6] + B*[penicillin] + C*[poly-L-lysine] + D*[Vitamin E conjugate] |
| Formulation 656 | A*[Ornibactin - C6] + B*[streptomycin] + C*[poly-L-lysine] + D*[Vitamin E conjugate] |
| Formulation 657 | A*[Ornibactin - C6] + B*[amphotericin B] + C*[poly-L-lysine] + D*[Vitamin E conjugate] |
| Formulation 658 | A*[Ornibactin - C8] + B*[penicillin] + C*[poly-L-lysine] + D*[Vitamin E conjugate] |
| Formulation 659 | A*[Ornibactin - C8] + B*[streptomycin] + C*[poly-L-lysine] + D*[Vitamin E conjugate] |
| Formulation 660 | A*[Ornibactin - C8] + B*[amphotericin B] + C*[poly-L-lysine] + D*[Vitamin E conjugate] |
| Formulation 661 | A*[Ornicorrugatin] + B*[penicillin] + C*[poly-L-lysine] + D*[Vitamin E conjugate] |
| Formulation 662 | A*[Ornicorrugatin] + B*[streptomycin] + C*[poly-L-lysine] + D*[Vitamin E conjugate] |
| Formulation 663 | A*[Ornicorrugatin] + B*[amphotericin B] + C*[poly-L-lysine] + D*[Vitamin E conjugate] |
| Formulation 664 | A*[Palmitoylcoprogen] + B*[penicillin] + C*[poly-L-lysine] + D*[Vitamin E conjugate] |
| Formulation 665 | A*[Palmitoylcoprogen] + B*[streptomycin] + C*[poly-L-lysine] + D*[Vitamin E conjugate] |
| Formulation 666 | A*[Palmitoylcoprogen] + B*[amphotericin B] + C*[poly-L-lysine] + D*[Vitamin E conjugate] |

TABLE 7-continued

| Formulation Name | Formula |
|---|---|
| Formulation 667 | A*[Parabactin] + B*[penicillin] + C*[poly-L-lysine] + D*[Vitamin E conjugate] |
| Formulation 668 | A*[Parabactin] + B*[streptomycin] + C*[poly-L-lysine] + D*[Vitamin E conjugate] |
| Formulation 669 | A*[Parabactin] + B*[amphotericin B] + C*[poly-L-lysine] + D*[Vitamin E conjugate] |
| Formulation 670 | A*[Parabactin A] + B*[penicillin] + C*[poly-L-lysine] + D*[Vitamin E conjugate] |
| Formulation 671 | A*[Parabactin A] + B*[streptomycin] + C*[poly-L-lysine] + D*[Vitamin E conjugate] |
| Formulation 672 | A*[Parabactin A] + B*[amphotericin B] + C*[poly-L-lysine] + D*[Vitamin E conjugate] |
| Formulation 673 | A*[Petrobactin] + B*[penicillin] + C*[poly-L-lysine] + D*[Vitamin E conjugate] |
| Formulation 674 | A*[Petrobactin] + B*[streptomycin] + C*[poly-L-lysine] + D*[Vitamin E conjugate] |
| Formulation 675 | A*[Petrobactin] + B*[amphotericin B] + C*[poly-L-lysine] + D*[Vitamin E conjugate] |
| Formulation 676 | A*[Petrobactin disulphonate] + B*[penicillin] + C*[poly-L-lysine] + D*[Vitamin E conjugate] |
| Formulation 677 | A*[Petrobactin disulphonate] + B*[streptomycin] + C*[poly-L-lysine] + D*[Vitamin E conjugate] |
| Formulation 678 | A*[Petrobactin disulphonate] + B*[amphotericin B] + C*[poly-L-lysine] + D*[Vitamin E conjugate] |
| Formulation 679 | A*[Petrobactin sulphonate] + B*[penicillin] + C*[poly-L-lysine] + D*[Vitamin E conjugate] |
| Formulation 680 | A*[Petrobactin sulphonate] + B*[streptomycin] + C*[poly-L-lysine] + D*[Vitamin E conjugate] |
| Formulation 681 | A*[Petrobactin sulphonate] + B*[amphotericin B] + C*[poly-L-lysine] + D*[Vitamin E conjugate] |
| Formulation 682 | A*[Pistillarin] + B*[penicillin] + C*[poly-L-lysine] + D*[Vitamin E conjugate] |
| Formulation 683 | A*[Pistillarin] + B*[streptomycin] + C*[poly-L-lysine] + D*[Vitamin E conjugate] |
| Formulation 684 | A*[Pistillarin] + B*[amphotericin B] + C*[poly-L-lysine] + D*[Vitamin E conjugate] |
| Formulation 685 | A*[Protochelin] + B*[penicillin] + C*[poly-L-lysine] + D*[Vitamin E conjugate] |
| Formulation 686 | A*[Protochelin] + B*[streptomycin] + C*[poly-L-lysine] + D*[Vitamin E conjugate] |
| Formulation 687 | A*[Protochelin] + B*[amphotericin B] + C*[poly-L-lysine] + D*[Vitamin E conjugate] |
| Formulation 688 | A*[Pseudoalterobactin A] + B*[penicillin] + C*[poly-L-lysine] + D*[Vitamin E conjugate] |
| Formulation 689 | A*[Pseudoalterobactin A] + B*[streptomycin] + C*[poly-L-lysine] + D*[Vitamin E conjugate] |
| Formulation 690 | A*[Pseudoalterobactin A] + B*[amphotericin B] + C*[poly-L-lysine] + D*[Vitamin E conjugate] |
| Formulation 691 | A*[Pseudoalterobactin B] + B*[penicillin] + C*[poly-L-lysine] + D*[Vitamin E conjugate] |
| Formulation 692 | A*[Pseudoalterobactin B] + B*[streptomycin] + C*[poly-L-lysine] + D*[Vitamin E conjugate] |
| Formulation 693 | A*[Pseudoalterobactin B] + B*[amphotericin B] + C*[poly-L-lysine] + D*[Vitamin E conjugate] |
| Formulation 694 | A*[Pseudobactin] + B*[penicillin] + C*[poly-L-lysine] + D*[Vitamin E conjugate] |
| Formulation 695 | A*[Pseudobactin] + B*[streptomycin] + C*[poly-L-lysine] + D*[Vitamin E conjugate] |
| Formulation 696 | A*[Pseudobactin] + B*[amphotericin B] + C*[poly-L-lysine] + D*[Vitamin E conjugate] |
| Formulation 697 | A*[Pseudobactin 589A] + B*[penicillin] + C*[poly-L-lysine] + D*[Vitamin E conjugate] |
| Formulation 698 | A*[Pseudobactin 589A] + B*[streptomycin] + C*[poly-L-lysine] + D*[Vitamin E conjugate] |
| Formulation 699 | A*[Pseudobactin 589A] + B*[amphotericin B] + C*[poly-L-lysine] + D*[Vitamin E conjugate] |
| Formulation 700 | A*[Putrebactin] + B*[penicillin] + C*[poly-L-lysine] + D*[Vitamin E conjugate] |
| Formulation 701 | A*[Putrebactin] + B*[streptomycin] + C*[poly-L-lysine] + D*[Vitamin E conjugate] |
| Formulation 702 | A*[Putrebactin] + B*[amphotericin B] + C*[poly-L-lysine] + D*[Vitamin E conjugate] |
| Formulation 703 | A*[Pyochelin] + B*[penicillin] + C*[poly-L-lysine] + D*[Vitamin E conjugate] |
| Formulation 704 | A*[Pyochelin] + B*[streptomycin] + C*[poly-L-lysine] + D*[Vitamin E conjugate] |
| Formulation 705 | A*[Pyochelin] + B*[amphotericin B] + C*[poly-L-lysine] + D*[Vitamin E conjugate] |
| Formulation 706 | A*[Pyoverdin 1] + B*[penicillin] + C*[poly-L-lysine] + D*[Vitamin E conjugate] |
| Formulation 707 | A*[Pyoverdin 1] + B*[streptomycin] + C*[poly-L-lysine] + D*[Vitamin E conjugate] |
| Formulation 708 | A*[Pyoverdin 1] + B*[amphotericin B] + C*[poly-L-lysine] + D*[Vitamin E conjugate] |
| Formulation 709 | A*[Pyoverdin 10.1] + B*[penicillin] + C*[poly-L-lysine] + D*[Vitamin E conjugate] |
| Formulation 710 | A*[Pyoverdin 10.1] + B*[streptomycin] + C*[poly-L-lysine] + D*[Vitamin E conjugate] |
| Formulation 711 | A*[Pyoverdin 10.1] + B*[amphotericin B] + C*[poly-L-lysine] + D*[Vitamin E conjugate] |
| Formulation 712 | A*[Pyoverdin 10.10] + B*[penicillin] + C*[poly-L-lysine] + D*[Vitamin E conjugate] |
| Formulation 713 | A*[Pyoverdin 10.10] + B*[streptomycin] + C*[poly-L-lysine] + D*[Vitamin E conjugate] |
| Formulation 714 | A*[Pyoverdin 10.10] + B*[amphotericin B] + C*[poly-L-lysine] + D*[Vitamin E conjugate] |
| Formulation 715 | A*[Pyoverdin 10.2] + B*[penicillin] + C*[poly-L-lysine] + D*[Vitamin E conjugate] |
| Formulation 716 | A*[Pyoverdin 10.2] + B*[streptomycin] + C*[poly-L-lysine] + D*[Vitamin E conjugate] |
| Formulation 717 | A*[Pyoverdin 10.2] + B*[amphotericin B] + C*[poly-L-lysine] + D*[Vitamin E conjugate] |
| Formulation 718 | A*[Pyoverdin 10.3] + B*[penicillin] + C*[poly-L-lysine] + D*[Vitamin E conjugate] |
| Formulation 719 | A*[Pyoverdin 10.3] + B*[streptomycin] + C*[poly-L-lysine] + D*[Vitamin E conjugate] |
| Formulation 720 | A*[Pyoverdin 10.3] + B*[amphotericin B] + C*[poly-L-lysine] + D*[Vitamin E conjugate] |
| Formulation 721 | A*[Pyoverdin 10.4] + B*[penicillin] + C*[poly-L-lysine] + D*[Vitamin E conjugate] |
| Formulation 722 | A*[Pyoverdin 10.4] + B*[streptomycin] + C*[poly-L-lysine] + D*[Vitamin E conjugate] |
| Formulation 723 | A*[Pyoverdin 10.4] + B*[amphotericin B] + C*[poly-L-lysine] + D*[Vitamin E conjugate] |
| Formulation 724 | A*[Pyoverdin 10.5] + B*[penicillin] + C*[poly-L-lysine] + D*[Vitamin E conjugate] |
| Formulation 725 | A*[Pyoverdin 10.5] + B*[streptomycin] + C*[poly-L-lysine] + D*[Vitamin E conjugate] |
| Formulation 726 | A*[Pyoverdin 10.5] + B*[amphotericin B] + C*[poly-L-lysine] + D*[Vitamin E conjugate] |
| Formulation 727 | A*[Pyoverdin 10.6] + B*[penicillin] + C*[poly-L-lysine] + D*[Vitamin E conjugate] |
| Formulation 728 | A*[Pyoverdin 10.6] + B*[streptomycin] + C*[poly-L-lysine] + D*[Vitamin E conjugate] |
| Formulation 729 | A*[Pyoverdin 10.6] + B*[amphotericin B] + C*[poly-L-lysine] + D*[Vitamin E conjugate] |
| Formulation 730 | A*[Pyoverdin 10.8] + B*[penicillin] + C*[poly-L-lysine] + D*[Vitamin E conjugate] |
| Formulation 731 | A*[Pyoverdin 10.8] + B*[streptomycin] + C*[poly-L-lysine] + D*[Vitamin E conjugate] |
| Formulation 732 | A*[Pyoverdin 10.8] + B*[amphotericin B] + C*[poly-L-lysine] + D*[Vitamin E conjugate] |
| Formulation 733 | A*[Pyoverdin 10.9] + B*[penicillin] + C*[poly-L-lysine] + D*[Vitamin E conjugate] |
| Formulation 734 | A*[Pyoverdin 10.9] + B*[streptomycin] + C*[poly-L-lysine] + D*[Vitamin E conjugate] |
| Formulation 735 | A*[Pyoverdin 10.9] + B*[amphotericin B] + C*[poly-L-lysine] + D*[Vitamin E conjugate] |
| Formulation 736 | A*[Pyoverdin 11.1] + B*[penicillin] + C*[poly-L-lysine] + D*[Vitamin E conjugate] |
| Formulation 737 | A*[Pyoverdin 11.1] + B*[streptomycin] + C*[poly-L-lysine] + D*[Vitamin E conjugate] |
| Formulation 738 | A*[Pyoverdin 11.1] + B*[amphotericin B] + C*[poly-L-lysine] + D*[Vitamin E conjugate] |
| Formulation 739 | A*[Pyoverdin 11.2] + B*[penicillin] + C*[poly-L-lysine] + D*[Vitamin E conjugate] |
| Formulation 740 | A*[Pyoverdin 11.2] + B*[streptomycin] + C*[poly-L-lysine] + D*[Vitamin E conjugate] |
| Formulation 741 | A*[Pyoverdin 11.2] + B*[amphotericin B] + C*[poly-L-lysine] + D*[Vitamin E conjugate] |
| Formulation 742 | A*[Pyoverdin 11370] + B*[penicillin] + C*[poly-L-lysine] + D*[Vitamin E conjugate] |
| Formulation 743 | A*[Pyoverdin 11370] + B*[streptomycin] + C*[poly-L-lysine] + D*[Vitamin E conjugate] |

TABLE 7-continued

| Formulation Name | Formula |
|---|---|
| Formulation 744 | A*[Pyoverdin 11370] + B*[amphotericin B] + C*[poly-L-lysine] + D*[Vitamin E conjugate] |
| Formulation 745 | A*[Pyoverdin 12] + B*[penicillin] + C*[poly-L-lysine] + D*[Vitamin E conjugate] |
| Formulation 746 | A*[Pyoverdin 12] + B*[streptomycin] + C*[poly-L-lysine] + D*[Vitamin E conjugate] |
| Formulation 747 | A*[Pyoverdin 12] + B*[amphotericin B] + C*[poly-L-lysine] + D*[Vitamin E conjugate] |
| Formulation 748 | A*[Pyoverdin 12.1] + B*[penicillin] + C*[poly-L-lysine] + D*[Vitamin E conjugate] |
| Formulation 749 | A*[Pyoverdin 12.1] + B*[streptomycin] + C*[poly-L-lysine] + D*[Vitamin E conjugate] |
| Formulation 750 | A*[Pyoverdin 12.1] + B*[amphotericin B] + C*[poly-L-lysine] + D*[Vitamin E conjugate] |
| Formulation 751 | A*[Pyoverdin 12.2] + B*[penicillin] + C*[poly-L-lysine] + D*[Vitamin E conjugate] |
| Formulation 752 | A*[Pyoverdin 12.2] + B*[streptomycin] + C*[poly-L-lysine] + D*[Vitamin E conjugate] |
| Formulation 753 | A*[Pyoverdin 12.2] + B*[amphotericin B] + C*[poly-L-lysine] + D*[Vitamin E conjugate] |
| Formulation 754 | A*[Pyoverdin 13525] + B*[penicillin] + C*[poly-L-lysine] + D*[Vitamin E conjugate] |
| Formulation 755 | A*[Pyoverdin 13525] + B*[streptomycin] + C*[poly-L-lysine] + D*[Vitamin E conjugate] |
| Formulation 756 | A*[Pyoverdin 13525] + B*[amphotericin B] + C*[poly-L-lysine] + D*[Vitamin E conjugate] |
| Formulation 757 | A*[Pyoverdin 1547] + B*[penicillin] + C*[poly-L-lysine] + D*[Vitamin E conjugate] |
| Formulation 758 | A*[Pyoverdin 1547] + B*[streptomycin] + C*[poly-L-lysine] + D*[Vitamin E conjugate] |
| Formulation 759 | A*[Pyoverdin 1547] + B*[amphotericin B] + C*[poly-L-lysine] + D*[Vitamin E conjugate] |
| Formulation 760 | A*[Pyoverdin 17400] + B*[penicillin] + C*[poly-L-lysine] + D*[Vitamin E conjugate] |
| Formulation 761 | A*[Pyoverdin 17400] + B*[streptomycin] + C*[poly-L-lysine] + D*[Vitamin E conjugate] |
| Formulation 762 | A*[Pyoverdin 17400] + B*[amphotericin B] + C*[poly-L-lysine] + D*[Vitamin E conjugate] |
| Formulation 763 | A*[Pyoverdin 18-1] + B*[penicillin] + C*[poly-L-lysine] + D*[Vitamin E conjugate] |
| Formulation 764 | A*[Pyoverdin 18-1] + B*[streptomycin] + C*[poly-L-lysine] + D*[Vitamin E conjugate] |
| Formulation 765 | A*[Pyoverdin 18-1] + B*[amphotericin B] + C*[poly-L-lysine] + D*[Vitamin E conjugate] |
| Formulation 766 | A*[Pyoverdin 19310] + B*[penicillin] + C*[poly-L-lysine] + D*[Vitamin E conjugate] |
| Formulation 767 | A*[Pyoverdin 19310] + B*[streptomycin] + C*[poly-L-lysine] + D*[Vitamin E conjugate] |
| Formulation 768 | A*[Pyoverdin 19310] + B*[amphotericin B] + C*[poly-L-lysine] + D*[Vitamin E conjugate] |
| Formulation 769 | A*[Pyoverdin 2192] + B*[penicillin] + C*[poly-L-lysine] + D*[Vitamin E conjugate] |
| Formulation 770 | A*[Pyoverdin 2192] + B*[streptomycin] + C*[poly-L-lysine] + D*[Vitamin E conjugate] |
| Formulation 771 | A*[Pyoverdin 2192] + B*[amphotericin B] + C*[poly-L-lysine] + D*[Vitamin E conjugate] |
| Formulation 772 | A*[Pyoverdin 2392] + B*[penicillin] + C*[poly-L-lysine] + D*[Vitamin E conjugate] |
| Formulation 773 | A*[Pyoverdin 2392] + B*[streptomycin] + C*[poly-L-lysine] + D*[Vitamin E conjugate] |
| Formulation 774 | A*[Pyoverdin 2392] + B*[amphotericin B] + C*[poly-L-lysine] + D*[Vitamin E conjugate] |
| Formulation 775 | A*[Pyoverdin 2461] + B*[penicillin] + C*[poly-L-lysine] + D*[Vitamin E conjugate] |
| Formulation 776 | A*[Pyoverdin 2461] + B*[streptomycin] + C*[poly-L-lysine] + D*[Vitamin E conjugate] |
| Formulation 777 | A*[Pyoverdin 2461] + B*[amphotericin B] + C*[poly-L-lysine] + D*[Vitamin E conjugate] |
| Formulation 778 | A*[Pyoverdin 2798] + B*[penicillin] + C*[poly-L-lysine] + D*[Vitamin E conjugate] |
| Formulation 779 | A*[Pyoverdin 2798] + B*[streptomycin] + C*[poly-L-lysine] + D*[Vitamin E conjugate] |
| Formulation 780 | A*[Pyoverdin 2798] + B*[amphotericin B] + C*[poly-L-lysine] + D*[Vitamin E conjugate] |
| Formulation 781 | A*[Pyoverdin 51W] + B*[penicillin] + C*[poly-L-lysine] + D*[Vitamin E conjugate] |
| Formulation 782 | A*[Pyoverdin 51W] + B*[streptomycin] + C*[poly-L-lysine] + D*[Vitamin E conjugate] |
| Formulation 783 | A*[Pyoverdin 51W] + B*[amphotericin B] + C*[poly-L-lysine] + D*[Vitamin E conjugate] |
| Formulation 784 | A*[Pyoverdin 6.1] + B*[penicillin] + C*[poly-L-lysine] + D*[Vitamin E conjugate] |
| Formulation 785 | A*[Pyoverdin 6.1] + B*[streptomycin] + C*[poly-L-lysine] + D*[Vitamin E conjugate] |
| Formulation 786 | A*[Pyoverdin 6.1] + B*[amphotericin B] + C*[poly-L-lysine] + D*[Vitamin E conjugate] |
| Formulation 787 | A*[Pyoverdin 6.2] + B*[penicillin] + C*[poly-L-lysine] + D*[Vitamin E conjugate] |
| Formulation 788 | A*[Pyoverdin 6.2] + B*[streptomycin] + C*[poly-L-lysine] + D*[Vitamin E conjugate] |
| Formulation 789 | A*[Pyoverdin 6.2] + B*[amphotericin B] + C*[poly-L-lysine] + D*[Vitamin E conjugate] |
| Formulation 790 | A*[Pyoverdin 6.3] + B*[penicillin] + C*[poly-L-lysine] + D*[Vitamin E conjugate] |
| Formulation 791 | A*[Pyoverdin 6.3] + B*[streptomycin] + C*[poly-L-lysine] + D*[Vitamin E conjugate] |
| Formulation 792 | A*[Pyoverdin 6.3] + B*[amphotericin B] + C*[poly-L-lysine] + D*[Vitamin E conjugate] |
| Formulation 793 | A*[Pyoverdin 6.4] + B*[penicillin] + C*[poly-L-lysine] + D*[Vitamin E conjugate] |
| Formulation 794 | A*[Pyoverdin 6.4] + B*[streptomycin] + C*[poly-L-lysine] + D*[Vitamin E conjugate] |
| Formulation 795 | A*[Pyoverdin 6.4] + B*[amphotericin B] + C*[poly-L-lysine] + D*[Vitamin E conjugate] |
| Formulation 796 | A*[Pyoverdin 6.5] + B*[penicillin] + C*[poly-L-lysine] + D*[Vitamin E conjugate] |
| Formulation 797 | A*[Pyoverdin 6.5] + B*[streptomycin] + C*[poly-L-lysine] + D*[Vitamin E conjugate] |
| Formulation 798 | A*[Pyoverdin 6.5] + B*[amphotericin B] + C*[poly-L-lysine] + D*[Vitamin E conjugate] |
| Formulation 799 | A*[Pyoverdin 6.6] + B*[penicillin] + C*[poly-L-lysine] + D*[Vitamin E conjugate] |
| Formulation 800 | A*[Pyoverdin 6.6] + B*[streptomycin] + C*[poly-L-lysine] + D*[Vitamin E conjugate] |
| Formulation 801 | A*[Pyoverdin 6.6] + B*[amphotericin B] + C*[poly-L-lysine] + D*[Vitamin E conjugate] |
| Formulation 802 | A*[Pyoverdin 6.8] + B*[penicillin] + C*[poly-L-lysine] + D*[Vitamin E conjugate] |
| Formulation 803 | A*[Pyoverdin 6.8] + B*[streptomycin] + C*[poly-L-lysine] + D*[Vitamin E conjugate] |
| Formulation 804 | A*[Pyoverdin 6.8] + B*[amphotericin B] + C*[poly-L-lysine] + D*[Vitamin E conjugate] |
| Formulation 805 | A*[Pyoverdin 7.1] + B*[penicillin] + C*[poly-L-lysine] + D*[Vitamin E conjugate] |
| Formulation 806 | A*[Pyoverdin 7.1] + B*[streptomycin] + C*[poly-L-lysine] + D*[Vitamin E conjugate] |
| Formulation 807 | A*[Pyoverdin 7.1] + B*[amphotericin B] + C*[poly-L-lysine] + D*[Vitamin E conjugate] |
| Formulation 808 | A*[Pyoverdin 7.10] + B*[penicillin] + C*[poly-L-lysine] + D*[Vitamin E conjugate] |
| Formulation 809 | A*[Pyoverdin 7.10] + B*[streptomycin] + C*[poly-L-lysine] + D*[Vitamin E conjugate] |
| Formulation 810 | A*[Pyoverdin 7.10] + B*[amphotericin B] + C*[poly-L-lysine] + D*[Vitamin E conjugate] |
| Formulation 811 | A*[Pyoverdin 7.11] + B*[penicillin] + C*[poly-L-lysine] + D*[Vitamin E conjugate] |
| Formulation 812 | A*[Pyoverdin 7.11] + B*[streptomycin] + C*[poly-L-lysine] + D*[Vitamin E conjugate] |
| Formulation 813 | A*[Pyoverdin 7.11] + B*[amphotericin B] + C*[poly-L-lysine] + D*[Vitamin E conjugate] |
| Formulation 814 | A*[Pyoverdin 7.12] + B*[penicillin] + C*[poly-L-lysine] + D*[Vitamin E conjugate] |
| Formulation 815 | A*[Pyoverdin 7.12] + B*[streptomycin] + C*[poly-L-lysine] + D*[Vitamin E conjugate] |
| Formulation 816 | A*[Pyoverdin 7.12] + B*[amphotericin B] + C*[poly-L-lysine] + D*[Vitamin E conjugate] |
| Formulation 817 | A*[Pyoverdin 7.14] + B*[penicillin] + C*[poly-L-lysine] + D*[Vitamin E conjugate] |
| Formulation 818 | A*[Pyoverdin 7.14] + B*[streptomycin] + C*[poly-L-lysine] + D*[Vitamin E conjugate] |
| Formulation 819 | A*[Pyoverdin 7.14] + B*[amphotericin B] + C*[poly-L-lysine] + D*[Vitamin E conjugate] |
| Formulation 820 | A*[Pyoverdin 7.15] + B*[penicillin] + C*[poly-L-lysine] + D*[Vitamin E conjugate] |

TABLE 7-continued

| Formulation Name | Formula |
|---|---|
| Formulation 821 | A*[Pyoverdin 7.15] + B*[streptomycin] + C*[poly-L-lysine] + D*[Vitamin E conjugate] |
| Formulation 822 | A*[Pyoverdin 7.15] + B*[amphotericin B] + C*[poly-L-lysine] + D*[Vitamin E conjugate] |
| Formulation 823 | A*[Pyoverdin 7.16] + B*[penicillin] + C*[poly-L-lysine] + D*[Vitamin E conjugate] |
| Formulation 824 | A*[Pyoverdin 7.16] + B*[streptomycin] + C*[poly-L-lysine] + D*[Vitamin E conjugate] |
| Formulation 825 | A*[Pyoverdin 7.16] + B*[amphotericin B] + C*[poly-L-lysine] + D*[Vitamin E conjugate] |
| Formulation 826 | A*[Pyoverdin 7.17] + B*[penicillin] + C*[poly-L-lysine] + D*[Vitamin E conjugate] |
| Formulation 827 | A*[Pyoverdin 7.17] + B*[streptomycin] + C*[poly-L-lysine] + D*[Vitamin E conjugate] |
| Formulation 828 | A*[Pyoverdin 7.17] + B*[amphotericin B] + C*[poly-L-lysine] + D*[Vitamin E conjugate] |
| Formulation 829 | A*[Pyoverdin 7.18] + B*[penicillin] + C*[poly-L-lysine] + D*[Vitamin E conjugate] |
| Formulation 830 | A*[Pyoverdin 7.18] + B*[streptomycin] + C*[poly-L-lysine] + D*[Vitamin E conjugate] |
| Formulation 831 | A*[Pyoverdin 7.18] + B*[amphotericin B] + C*[poly-L-lysine] + D*[Vitamin E conjugate] |
| Formulation 832 | A*[Pyoverdin 7.19] + B*[penicillin] + C*[poly-L-lysine] + D*[Vitamin E conjugate] |
| Formulation 833 | A*[Pyoverdin 7.19] + B*[streptomycin] + C*[poly-L-lysine] + D*[Vitamin E conjugate] |
| Formulation 834 | A*[Pyoverdin 7.19] + B*[amphotericin B] + C*[poly-L-lysine] + D*[Vitamin E conjugate] |
| Formulation 835 | A*[Pyoverdin 7.2] + B*[penicillin] + C*[poly-L-lysine] + D*[Vitamin E conjugate] |
| Formulation 836 | A*[Pyoverdin 7.2] + B*[streptomycin] + C*[poly-L-lysine] + D*[Vitamin E conjugate] |
| Formulation 837 | A*[Pyoverdin 7.2] + B*[amphotericin B] + C*[poly-L-lysine] + D*[Vitamin E conjugate] |
| Formulation 838 | A*[Pyoverdin 7.3] + B*[penicillin] + C*[poly-L-lysine] + D*[Vitamin E conjugate] |
| Formulation 839 | A*[Pyoverdin 7.3] + B*[streptomycin] + C*[poly-L-lysine] + D*[Vitamin E conjugate] |
| Formulation 840 | A*[Pyoverdin 7.3] + B*[amphotericin B] + C*[poly-L-lysine] + D*[Vitamin E conjugate] |
| Formulation 841 | A*[Pyoverdin 7.4] + B*[penicillin] + C*[poly-L-lysine] + D*[Vitamin E conjugate] |
| Formulation 842 | A*[Pyoverdin 7.4] + B*[streptomycin] + C*[poly-L-lysine] + D*[Vitamin E conjugate] |
| Formulation 843 | A*[Pyoverdin 7.4] + B*[amphotericin B] + C*[poly-L-lysine] + D*[Vitamin E conjugate] |
| Formulation 844 | A*[Pyoverdin 7.5] + B*[penicillin] + C*[poly-L-lysine] + D*[Vitamin E conjugate] |
| Formulation 845 | A*[Pyoverdin 7.5] + B*[streptomycin] + C*[poly-L-lysine] + D*[Vitamin E conjugate] |
| Formulation 846 | A*[Pyoverdin 7.5] + B*[amphotericin B] + C*[poly-L-lysine] + D*[Vitamin E conjugate] |
| Formulation 847 | A*[Pyoverdin 7.6] + B*[penicillin] + C*[poly-L-lysine] + D*[Vitamin E conjugate] |
| Formulation 848 | A*[Pyoverdin 7.6] + B*[streptomycin] + C*[poly-L-lysine] + D*[Vitamin E conjugate] |
| Formulation 849 | A*[Pyoverdin 7.6] + B*[amphotericin B] + C*[poly-L-lysine] + D*[Vitamin E conjugate] |
| Formulation 850 | A*[Pyoverdin 7.7] + B*[penicillin] + C*[poly-L-lysine] + D*[Vitamin E conjugate] |
| Formulation 851 | A*[Pyoverdin 7.7] + B*[streptomycin] + C*[poly-L-lysine] + D*[Vitamin E conjugate] |
| Formulation 852 | A*[Pyoverdin 7.7] + B*[amphotericin B] + C*[poly-L-lysine] + D*[Vitamin E conjugate] |
| Formulation 853 | A*[Pyoverdin 7.8] + B*[penicillin] + C*[poly-L-lysine] + D*[Vitamin E conjugate] |
| Formulation 854 | A*[Pyoverdin 7.8] + B*[streptomycin] + C*[poly-L-lysine] + D*[Vitamin E conjugate] |
| Formulation 855 | A*[Pyoverdin 7.8] + B*[amphotericin B] + C*[poly-L-lysine] + D*[Vitamin E conjugate] |
| Formulation 856 | A*[Pyoverdin 7.9] + B*[penicillin] + C*[poly-L-lysine] + D*[Vitamin E conjugate] |
| Formulation 857 | A*[Pyoverdin 7.9] + B*[streptomycin] + C*[poly-L-lysine] + D*[Vitamin E conjugate] |
| Formulation 858 | A*[Pyoverdin 7.9] + B*[amphotericin B] + C*[poly-L-lysine] + D*[Vitamin E conjugate] |
| Formulation 859 | A*[Pyoverdin 8.1] + B*[penicillin] + C*[poly-L-lysine] + D*[Vitamin E conjugate] |
| Formulation 860 | A*[Pyoverdin 8.1] + B*[streptomycin] + C*[poly-L-lysine] + D*[Vitamin E conjugate] |
| Formulation 861 | A*[Pyoverdin 8.1] + B*[amphotericin B] + C*[poly-L-lysine] + D*[Vitamin E conjugate] |
| Formulation 862 | A*[Pyoverdin 8.2] + B*[penicillin] + C*[poly-L-lysine] + D*[Vitamin E conjugate] |
| Formulation 863 | A*[Pyoverdin 8.2] + B*[streptomycin] + C*[poly-L-lysine] + D*[Vitamin E conjugate] |
| Formulation 864 | A*[Pyoverdin 8.2] + B*[amphotericin B] + C*[poly-L-lysine] + D*[Vitamin E conjugate] |
| Formulation 865 | A*[Pyoverdin 8.3] + B*[penicillin] + C*[poly-L-lysine] + D*[Vitamin E conjugate] |
| Formulation 866 | A*[Pyoverdin 8.3] + B*[streptomycin] + C*[poly-L-lysine] + D*[Vitamin E conjugate] |
| Formulation 867 | A*[Pyoverdin 8.3] + B*[amphotericin B] + C*[poly-L-lysine] + D*[Vitamin E conjugate] |
| Formulation 868 | A*[Pyoverdin 8.4] + B*[penicillin] + C*[poly-L-lysine] + D*[Vitamin E conjugate] |
| Formulation 869 | A*[Pyoverdin 8.4] + B*[streptomycin] + C*[poly-L-lysine] + D*[Vitamin E conjugate] |
| Formulation 870 | A*[Pyoverdin 8.4] + B*[amphotericin B] + C*[poly-L-lysine] + D*[Vitamin E conjugate] |
| Formulation 871 | A*[Pyoverdin 8.5] + B*[penicillin] + C*[poly-L-lysine] + D*[Vitamin E conjugate] |
| Formulation 872 | A*[Pyoverdin 8.5] + B*[streptomycin] + C*[poly-L-lysine] + D*[Vitamin E conjugate] |
| Formulation 873 | A*[Pyoverdin 8.5] + B*[amphotericin B] + C*[poly-L-lysine] + D*[Vitamin E conjugate] |
| Formulation 874 | A*[Pyoverdin 8.6] + B*[penicillin] + C*[poly-L-lysine] + D*[Vitamin E conjugate] |
| Formulation 875 | A*[Pyoverdin 8.6] + B*[streptomycin] + C*[poly-L-lysine] + D*[Vitamin E conjugate] |
| Formulation 876 | A*[Pyoverdin 8.6] + B*[amphotericin B] + C*[poly-L-lysine] + D*[Vitamin E conjugate] |
| Formulation 877 | A*[Pyoverdin 8.7] + B*[penicillin] + C*[poly-L-lysine] + D*[Vitamin E conjugate] |
| Formulation 878 | A*[Pyoverdin 8.7] + B*[streptomycin] + C*[poly-L-lysine] + D*[Vitamin E conjugate] |
| Formulation 879 | A*[Pyoverdin 8.7] + B*[amphotericin B] + C*[poly-L-lysine] + D*[Vitamin E conjugate] |
| Formulation 880 | A*[Pyoverdin 8.8] + B*[penicillin] + C*[poly-L-lysine] + D*[Vitamin E conjugate] |
| Formulation 881 | A*[Pyoverdin 8.8] + B*[streptomycin] + C*[poly-L-lysine] + D*[Vitamin E conjugate] |
| Formulation 882 | A*[Pyoverdin 8.8] + B*[amphotericin B] + C*[poly-L-lysine] + D*[Vitamin E conjugate] |
| Formulation 883 | A*[Pyoverdin 8.9] + B*[penicillin] + C*[poly-L-lysine] + D*[Vitamin E conjugate] |
| Formulation 884 | A*[Pyoverdin 8.9] + B*[streptomycin] + C*[poly-L-lysine] + D*[Vitamin E conjugate] |
| Formulation 885 | A*[Pyoverdin 8.9] + B*[amphotericin B] + C*[poly-L-lysine] + D*[Vitamin E conjugate] |
| Formulation 886 | A*[Pyoverdin 9.1] + B*[penicillin] + C*[poly-L-lysine] + D*[Vitamin E conjugate] |
| Formulation 887 | A*[Pyoverdin 9.1] + B*[streptomycin] + C*[poly-L-lysine] + D*[Vitamin E conjugate] |
| Formulation 888 | A*[Pyoverdin 9.1] + B*[amphotericin B] + C*[poly-L-lysine] + D*[Vitamin E conjugate] |
| Formulation 889 | A*[Pyoverdin 9.10] + B*[penicillin] + C*[poly-L-lysine] + D*[Vitamin E conjugate] |
| Formulation 890 | A*[Pyoverdin 9.10] + B*[streptomycin] + C*[poly-L-lysine] + D*[Vitamin E conjugate] |
| Formulation 891 | A*[Pyoverdin 9.10] + B*[amphotericin B] + C*[poly-L-lysine] + D*[Vitamin E conjugate] |
| Formulation 892 | A*[Pyoverdin 9.11] + B*[penicillin] + C*[poly-L-lysine] + D*[Vitamin E conjugate] |
| Formulation 893 | A*[Pyoverdin 9.11] + B*[streptomycin] + C*[poly-L-lysine] + D*[Vitamin E conjugate] |
| Formulation 894 | A*[Pyoverdin 9.11] + B*[amphotericin B] + C*[poly-L-lysine] + D*[Vitamin E conjugate] |
| Formulation 895 | A*[Pyoverdin 9.12] + B*[penicillin] + C*[poly-L-lysine] + D*[Vitamin E conjugate] |
| Formulation 896 | A*[Pyoverdin 9.12] + B*[streptomycin] + C*[poly-L-lysine] + D*[Vitamin E conjugate] |
| Formulation 897 | A*[Pyoverdin 9.12] + B*[amphotericin B] + C*[poly-L-lysine] + D*[Vitamin E conjugate] |

TABLE 7-continued

| Formulation Name | Formula |
|---|---|
| Formulation 898 | A*[Pyoverdin 9.2] + B*[penicillin] + C*[poly-L-lysine] + D*[Vitamin E conjugate] |
| Formulation 899 | A*[Pyoverdin 9.2] + B*[streptomycin] + C*[poly-L-lysine] + D*[Vitamin E conjugate] |
| Formulation 900 | A*[Pyoverdin 9.2] + B*[amphotericin B] + C*[poly-L-lysine] + D*[Vitamin E conjugate] |
| Formulation 901 | A*[Pyoverdin 9.3] + B*[penicillin] + C*[poly-L-lysine] + D*[Vitamin E conjugate] |
| Formulation 902 | A*[Pyoverdin 9.3] + B*[streptomycin] + C*[poly-L-lysine] + D*[Vitamin E conjugate] |
| Formulation 903 | A*[Pyoverdin 9.3] + B*[amphotericin B] + C*[poly-L-lysine] + D*[Vitamin E conjugate] |
| Formulation 904 | A*[Pyoverdin 9.4] + B*[penicillin] + C*[poly-L-lysine] + D*[Vitamin E conjugate] |
| Formulation 905 | A*[Pyoverdin 9.4] + B*[streptomycin] + C*[poly-L-lysine] + D*[Vitamin E conjugate] |
| Formulation 906 | A*[Pyoverdin 9.4] + B*[amphotericin B] + C*[poly-L-lysine] + D*[Vitamin E conjugate] |
| Formulation 907 | A*[Pyoverdin 9.5] + B*[penicillin] + C*[poly-L-lysine] + D*[Vitamin E conjugate] |
| Formulation 908 | A*[Pyoverdin 9.5] + B*[streptomycin] + C*[poly-L-lysine] + D*[Vitamin E conjugate] |
| Formulation 909 | A*[Pyoverdin 9.5] + B*[amphotericin B] + C*[poly-L-lysine] + D*[Vitamin E conjugate] |
| Formulation 910 | A*[Pyoverdin 9.6] + B*[penicillin] + C*[poly-L-lysine] + D*[Vitamin E conjugate] |
| Formulation 911 | A*[Pyoverdin 9.6] + B*[streptomycin] + C*[poly-L-lysine] + D*[Vitamin E conjugate] |
| Formulation 912 | A*[Pyoverdin 9.6] + B*[amphotericin B] + C*[poly-L-lysine] + D*[Vitamin E conjugate] |
| Formulation 913 | A*[Pyoverdin 9.7] + B*[penicillin] + C*[poly-L-lysine] + D*[Vitamin E conjugate] |
| Formulation 914 | A*[Pyoverdin 9.7] + B*[streptomycin] + C*[poly-L-lysine] + D*[Vitamin E conjugate] |
| Formulation 915 | A*[Pyoverdin 9.7] + B*[amphotericin B] + C*[poly-L-lysine] + D*[Vitamin E conjugate] |
| Formulation 916 | A*[Pyoverdin 9.8] + B*[penicillin] + C*[poly-L-lysine] + D*[Vitamin E conjugate] |
| Formulation 917 | A*[Pyoverdin 9.8] + B*[streptomycin] + C*[poly-L-lysine] + D*[Vitamin E conjugate] |
| Formulation 918 | A*[Pyoverdin 9.8] + B*[amphotericin B] + C*[poly-L-lysine] + D*[Vitamin E conjugate] |
| Formulation 919 | A*[Pyoverdin 9.9] + B*[penicillin] + C*[poly-L-lysine] + D*[Vitamin E conjugate] |
| Formulation 920 | A*[Pyoverdin 9.9] + B*[streptomycin] + C*[poly-L-lysine] + D*[Vitamin E conjugate] |
| Formulation 921 | A*[Pyoverdin 9.9] + B*[amphotericin B] + C*[poly-L-lysine] + D*[Vitamin E conjugate] |
| Formulation 922 | A*[Pyoverdin 90-51] + B*[penicillin] + C*[poly-L-lysine] + D*[Vitamin E conjugate] |
| Formulation 923 | A*[Pyoverdin 90-51] + B*[streptomycin] + C*[poly-L-lysine] + D*[Vitamin E conjugate] |
| Formulation 924 | A*[Pyoverdin 90-51] + B*[amphotericin B] + C*[poly-L-lysine] + D*[Vitamin E conjugate] |
| Formulation 925 | A*[Pyoverdin 95-275] + B*[penicillin] + C*[poly-L-lysine] + D*[Vitamin E conjugate] |
| Formulation 926 | A*[Pyoverdin 95-275] + B*[streptomycin] + C*[poly-L-lysine] + D*[Vitamin E conjugate] |
| Formulation 927 | A*[Pyoverdin 95-275] + B*[amphotericin B] + C*[poly-L-lysine] + D*[Vitamin E conjugate] |
| Formulation 928 | A*[Pyoverdin 96-312] + B*[penicillin] + C*[poly-L-lysine] + D*[Vitamin E conjugate] |
| Formulation 929 | A*[Pyoverdin 96-312] + B*[streptomycin] + C*[poly-L-lysine] + D*[Vitamin E conjugate] |
| Formulation 930 | A*[Pyoverdin 96-312] + B*[amphotericin B] + C*[poly-L-lysine] + D*[Vitamin E conjugate] |
| Formulation 931 | A*[Pyoverdin 96-318] + B*[penicillin] + C*[poly-L-lysine] + D*[Vitamin E conjugate] |
| Formulation 932 | A*[Pyoverdin 96-318] + B*[streptomycin] + C*[poly-L-lysine] + D*[Vitamin E conjugate] |
| Formulation 933 | A*[Pyoverdin 96-318] + B*[amphotericin B] + C*[poly-L-lysine] + D*[Vitamin E conjugate] |
| Formulation 934 | A*[Pyoverdin 9AW] + B*[penicillin] + C*[poly-L-lysine] + D*[Vitamin E conjugate] |
| Formulation 935 | A*[Pyoverdin 9AW] + B*[streptomycin] + C*[poly-L-lysine] + D*[Vitamin E conjugate] |
| Formulation 936 | A*[Pyoverdin 9AW] + B*[amphotericin B] + C*[poly-L-lysine] + D*[Vitamin E conjugate] |
| Formulation 937 | A*[Pyoverdin A214] + B*[penicillin] + C*[poly-L-lysine] + D*[Vitamin E conjugate] |
| Formulation 938 | A*[Pyoverdin A214] + B*[streptomycin] + C*[poly-L-lysine] + D*[Vitamin E conjugate] |
| Formulation 939 | A*[Pyoverdin A214] + B*[amphotericin B] + C*[poly-L-lysine] + D*[Vitamin E conjugate] |
| Formulation 940 | A*[Pyoverdin BTP2] + B*[penicillin] + C*[poly-L-lysine] + D*[Vitamin E conjugate] |
| Formulation 941 | A*[Pyoverdin BTP2] + B*[streptomycin] + C*[poly-L-lysine] + D*[Vitamin E conjugate] |
| Formulation 942 | A*[Pyoverdin BTP2] + B*[amphotericin B] + C*[poly-L-lysine] + D*[Vitamin E conjugate] |
| Formulation 943 | A*[Pyoverdin C] + B*[penicillin] + C*[poly-L-lysine] + D*[Vitamin E conjugate] |
| Formulation 944 | A*[Pyoverdin C] + B*[streptomycin] + C*[poly-L-lysine] + D*[Vitamin E conjugate] |
| Formulation 945 | A*[Pyoverdin C] + B*[amphotericin B] + C*[poly-L-lysine] + D*[Vitamin E conjugate] |
| Formulation 946 | A*[Pyoverdin CHAO] + B*[penicillin] + C*[poly-L-lysine] + D*[Vitamin E conjugate] |
| Formulation 947 | A*[Pyoverdin CHAO] + B*[streptomycin] + C*[poly-L-lysine] + D*[Vitamin E conjugate] |
| Formulation 948 | A*[Pyoverdin CHAO] + B*[amphotericin B] + C*[poly-L-lysine] + D*[Vitamin E conjugate] |
| Formulation 949 | A*[Pyoverdin D-TR133] + B*[penicillin] + C*[poly-L-lysine] + D*[Vitamin E conjugate] |
| Formulation 950 | A*[Pyoverdin D-TR133] + B*[streptomycin] + C*[poly-L-lysine] + D*[Vitamin E conjugate] |
| Formulation 951 | A*[Pyoverdin D-TR133] + B*[amphotericin B] + C*[poly-L-lysine] + D*[Vitamin E conjugate] |
| Formulation 952 | A*[Pyoverdin E] + B*[penicillin] + C*[poly-L-lysine] + D*[Vitamin E conjugate] |
| Formulation 953 | A*[Pyoverdin E] + B*[streptomycin] + C*[poly-L-lysine] + D*[Vitamin E conjugate] |
| Formulation 954 | A*[Pyoverdin E] + B*[amphotericin B] + C*[poly-L-lysine] + D*[Vitamin E conjugate] |
| Formulation 955 | A*[Pyoverdin G] + B*[penicillin] + C*[poly-L-lysine] + D*[Vitamin E conjugate] |
| Formulation 956 | A*[Pyoverdin G] + B*[streptomycin] + C*[poly-L-lysine] + D*[Vitamin E conjugate] |
| Formulation 957 | A*[Pyoverdin G] + B*[amphotericin B] + C*[poly-L-lysine] + D*[Vitamin E conjugate] |
| Formulation 958 | A*[Pyoverdin GM] + B*[penicillin] + C*[poly-L-lysine] + D*[Vitamin E conjugate] |
| Formulation 959 | A*[Pyoverdin GM] + B*[streptomycin] + C*[poly-L-lysine] + D*[Vitamin E conjugate] |
| Formulation 960 | A*[Pyoverdin GM] + B*[amphotericin B] + C*[poly-L-lysine] + D*[Vitamin E conjugate] |
| Formulation 961 | A*[Pyoverdin I-III] + B*[penicillin] + C*[poly-L-lysine] + D*[Vitamin E conjugate] |
| Formulation 962 | A*[Pyoverdin I-III] + B*[streptomycin] + C*[poly-L-lysine] + D*[Vitamin E conjugate] |
| Formulation 963 | A*[Pyoverdin I-III] + B*[amphotericin B] + C*[poly-L-lysine] + D*[Vitamin E conjugate] |
| Formulation 964 | A*[Pyoverdin P19] + B*[penicillin] + C*[poly-L-lysine] + D*[Vitamin E conjugate] |
| Formulation 965 | A*[Pyoverdin P19] + B*[streptomycin] + C*[poly-L-lysine] + D*[Vitamin E conjugate] |
| Formulation 966 | A*[Pyoverdin P19] + B*[amphotericin B] + C*[poly-L-lysine] + D*[Vitamin E conjugate] |
| Formulation 967 | A*[Pyoverdin Pau] + B*[penicillin] + C*[poly-L-lysine] + D*[Vitamin E conjugate] |
| Formulation 968 | A*[Pyoverdin Pau] + B*[streptomycin] + C*[poly-L-lysine] + D*[Vitamin E conjugate] |
| Formulation 969 | A*[Pyoverdin Pau] + B*[amphotericin B] + C*[poly-L-lysine] + D*[Vitamin E conjugate] |
| Formulation 970 | A*[Pyoverdin PL8] + B*[penicillin] + C*[poly-L-lysine] + D*[Vitamin E conjugate] |
| Formulation 971 | A*[Pyoverdin PL8] + B*[streptomycin] + C*[poly-L-lysine] + D*[Vitamin E conjugate] |
| Formulation 972 | A*[Pyoverdin PL8] + B*[amphotericin B] + C*[poly-L-lysine] + D*[Vitamin E conjugate] |
| Formulation 973 | A*[Pyoverdin PVD] + B*[penicillin] + C*[poly-L-lysine] + D*[Vitamin E conjugate] |
| Formulation 974 | A*[Pyoverdin PVD] + B*[streptomycin] + C*[poly-L-lysine] + D*[Vitamin E conjugate] |

TABLE 7-continued

| Formulation Name | Formula |
|---|---|
| Formulation 975 | A*[Pyoverdin PVD] + B*[amphotericin B] + C*[poly-L-lysine] + D*[Vitamin E conjugate] |
| Formulation 976 | A*[Pyoverdin R] + B*[penicillin] + C*[poly-L-lysine] + D*[Vitamin E conjugate] |
| Formulation 977 | A*[Pyoverdin R] + B*[streptomycin] + C*[poly-L-lysine] + D*[Vitamin E conjugate] |
| Formulation 978 | A*[Pyoverdin R] + B*[amphotericin B] + C*[poly-L-lysine] + D*[Vitamin E conjugate] |
| Formulation 979 | A*[Pyoverdin Thai] + B*[penicillin] + C*[poly-L-lysine] + D*[Vitamin E conjugate] |
| Formulation 980 | A*[Pyoverdin Thai] + B*[streptomycin] + C*[poly-L-lysine] + D*[Vitamin E conjugate] |
| Formulation 981 | A*[Pyoverdin Thai] + B*[amphotericin B] + C*[poly-L-lysine] + D*[Vitamin E conjugate] |
| Formulation 982 | A*[Pyoverdin TII] + B*[penicillin] + C*[poly-L-lysine] + D*[Vitamin E conjugate] |
| Formulation 983 | A*[Pyoverdin TII] + B*[streptomycin] + C*[poly-L-lysine] + D*[Vitamin E conjugate] |
| Formulation 984 | A*[Pyoverdin TII] + B*[amphotericin B] + C*[poly-L-lysine] + D*[Vitamin E conjugate] |
| Formulation 985 | A*[Pyridoxatin] + B*[penicillin] + C*[poly-L-lysine] + D*[Vitamin E conjugate] |
| Formulation 986 | A*[Pyridoxatin] + B*[streptomycin] + C*[poly-L-lysine] + D*[Vitamin E conjugate] |
| Formulation 987 | A*[Pyridoxatin] + B*[amphotericin B] + C*[poly-L-lysine] + D*[Vitamin E conjugate] |
| Formulation 988 | A*[Quinolobactin] + B*[penicillin] + C*[poly-L-lysine] + D*[Vitamin E conjugate] |
| Formulation 989 | A*[Quinolobactin] + B*[streptomycin] + C*[poly-L-lysine] + D*[Vitamin E conjugate] |
| Formulation 990 | A*[Quinolobactin] + B*[amphotericin B] + C*[poly-L-lysine] + D*[Vitamin E conjugate] |
| Formulation 991 | A*[Rhizobactin] + B*[penicillin] + C*[poly-L-lysine] + D*[Vitamin E conjugate] |
| Formulation 992 | A*[Rhizobactin] + B*[streptomycin] + C*[poly-L-lysine] + D*[Vitamin E conjugate] |
| Formulation 993 | A*[Rhizobactin] + B*[amphotericin B] + C*[poly-L-lysine] + D*[Vitamin E conjugate] |
| Formulation 994 | A*[Rhizobactin 1021] + B*[penicillin] + C*[poly-L-lysine] + D*[Vitamin E conjugate] |
| Formulation 995 | A*[Rhizobactin 1021] + B*[streptomycin] + C*[poly-L-lysine] + D*[Vitamin E conjugate] |
| Formulation 996 | A*[Rhizobactin 1021] + B*[amphotericin B] + C*[poly-L-lysine] + D*[Vitamin E conjugate] |
| Formulation 997 | A*[Rhizoferrin] + B*[penicillin] + C*[poly-L-lysine] + D*[Vitamin E conjugate] |
| Formulation 998 | A*[Rhizoferrin] + B*[streptomycin] + C*[poly-L-lysine] + D*[Vitamin E conjugate] |
| Formulation 999 | A*[Rhizoferrin] + B*[amphotericin B] + C*[poly-L-lysine] + D*[Vitamin E conjugate] |
| Formulation 1000 | A*[Rhizoferrin analogues] + B*[penicillin] + C*[poly-L-lysine] + D*[Vitamin E conjugate] |
| Formulation 1001 | A*[Rhizoferrin analogues] + B*[streptomycin] + C*[poly-L-lysine] + D*[Vitamin E conjugate] |
| Formulation 1002 | A*[Rhizoferrin analogues] + B*[amphotericin B] + C*[poly-L-lysine] + D*[Vitamin E conjugate] |
| Formulation 1003 | A*[Rhodotrulic acid] + B*[penicillin] + C*[poly-L-lysine] + D*[Vitamin E conjugate] |
| Formulation 1004 | A*[Rhodotrulic acid] + B*[streptomycin] + C*[poly-L-lysine] + D*[Vitamin E conjugate] |
| Formulation 1005 | A*[Rhodotrulic acid] + B*[amphotericin B] + C*[poly-L-lysine] + D*[Vitamin E conjugate] |
| Formulation 1006 | A*[Sake Colorant A] + B*[penicillin] + C*[poly-L-lysine] + D*[Vitamin E conjugate] |
| Formulation 1007 | A*[Sake Colorant A] + B*[streptomycin] + C*[poly-L-lysine] + D*[Vitamin E conjugate] |
| Formulation 1008 | A*[Sake Colorant A] + B*[amphotericin B] + C*[poly-L-lysine] + D*[Vitamin E conjugate] |
| Formulation 1009 | A*[Salmochelin S1] + B*[penicillin] + C*[poly-L-lysine] + D*[Vitamin E conjugate] |
| Formulation 1010 | A*[Salmochelin S1] + B*[streptomycin] + C*[poly-L-lysine] + D*[Vitamin E conjugate] |
| Formulation 1011 | A*[Salmochelin S1] + B*[amphotericin B] + C*[poly-L-lysine] + D*[Vitamin E conjugate] |
| Formulation 1012 | A*[Salmochelin S2] + B*[penicillin] + C*[poly-L-lysine] + D*[Vitamin E conjugate] |
| Formulation 1013 | A*[Salmochelin S2] + B*[streptomycin] + C*[poly-L-lysine] + D*[Vitamin E conjugate] |
| Formulation 1014 | A*[Salmochelin S2] + B*[amphotericin B] + C*[poly-L-lysine] + D*[Vitamin E conjugate] |
| Formulation 1015 | A*[Salmochelin S4] + B*[penicillin] + C*[poly-L-lysine] + D*[Vitamin E conjugate] |
| Formulation 1016 | A*[Salmochelin S4] + B*[streptomycin] + C*[poly-L-lysine] + D*[Vitamin E conjugate] |
| Formulation 1017 | A*[Salmochelin S4] + B*[amphotericin B] + C*[poly-L-lysine] + D*[Vitamin E conjugate] |
| Formulation 1018 | A*[Salmochelin SX] + B*[penicillin] + C*[poly-L-lysine] + D*[Vitamin E conjugate] |
| Formulation 1019 | A*[Salmochelin SX] + B*[streptomycin] + C*[poly-L-lysine] + D*[Vitamin E conjugate] |
| Formulation 1020 | A*[Salmochelin SX] + B*[amphotericin B] + C*[poly-L-lysine] + D*[Vitamin E conjugate] |
| Formulation 1021 | A*[Salmycin A] + B*[penicillin] + C*[poly-L-lysine] + D*[Vitamin E conjugate] |
| Formulation 1022 | A*[Salmycin A] + B*[streptomycin] + C*[poly-L-lysine] + D*[Vitamin E conjugate] |
| Formulation 1023 | A*[Salmycin A] + B*[amphotericin B] + C*[poly-L-lysine] + D*[Vitamin E conjugate] |
| Formulation 1024 | A*[Schizokinen] + B*[penicillin] + C*[poly-L-lysine] + D*[Vitamin E conjugate] |
| Formulation 1025 | A*[Schizokinen] + B*[streptomycin] + C*[poly-L-lysine] + D*[Vitamin E conjugate] |
| Formulation 1026 | A*[Schizokinen] + B*[amphotericin B] + C*[poly-L-lysine] + D*[Vitamin E conjugate] |
| Formulation 1027 | A*[Serratiochelin] + B*[penicillin] + C*[poly-L-lysine] + D*[Vitamin E conjugate] |
| Formulation 1028 | A*[Serratiochelin] + B*[streptomycin] + C*[poly-L-lysine] + D*[Vitamin E conjugate] |
| Formulation 1029 | A*[Serratiochelin] + B*[amphotericin B] + C*[poly-L-lysine] + D*[Vitamin E conjugate] |
| Formulation 1030 | A*[Siderochelin A] + B*[penicillin] + C*[poly-L-lysine] + D*[Vitamin E conjugate] |
| Formulation 1031 | A*[Siderochelin A] + B*[streptomycin] + C*[poly-L-lysine] + D*[Vitamin E conjugate] |
| Formulation 1032 | A*[Siderochelin A] + B*[amphotericin B] + C*[poly-L-lysine] + D*[Vitamin E conjugate] |
| Formulation 1033 | A*[Snychobactin A] + B*[penicillin] + C*[poly-L-lysine] + D*[Vitamin E conjugate] |
| Formulation 1034 | A*[Snychobactin A] + B*[streptomycin] + C*[poly-L-lysine] + D*[Vitamin E conjugate] |
| Formulation 1035 | A*[Snychobactin A] + B*[amphotericin B] + C*[poly-L-lysine] + D*[Vitamin E conjugate] |
| Formulation 1036 | A*[Snychobactin B] + B*[penicillin] + C*[poly-L-lysine] + D*[Vitamin E conjugate] |
| Formulation 1037 | A*[Snychobactin B] + B*[streptomycin] + C*[poly-L-lysine] + D*[Vitamin E conjugate] |
| Formulation 1038 | A*[Snychobactin B] + B*[amphotericin B] + C*[poly-L-lysine] + D*[Vitamin E conjugate] |
| Formulation 1039 | A*[Snychobactin C] + B*[penicillin] + C*[poly-L-lysine] + D*[Vitamin E conjugate] |
| Formulation 1040 | A*[Snychobactin C] + B*[streptomycin] + C*[poly-L-lysine] + D*[Vitamin E conjugate] |
| Formulation 1041 | A*[Snychobactin C] + B*[amphotericin B] + C*[poly-L-lysine] + D*[Vitamin E conjugate] |
| Formulation 1042 | A*[Staphyloferrin A] + B*[penicillin] + C*[poly-L-lysine] + D*[Vitamin E conjugate] |
| Formulation 1043 | A*[Staphyloferrin A] + B*[streptomycin] + C*[poly-L-lysine] + D*[Vitamin E conjugate] |
| Formulation 1044 | A*[Staphyloferrin A] + B*[amphotericin B] + C*[poly-L-lysine] + D*[Vitamin E conjugate] |
| Formulation 1045 | A*[Staphyloferrin B] + B*[penicillin] + C*[poly-L-lysine] + D*[Vitamin E conjugate] |
| Formulation 1046 | A*[Staphyloferrin B] + B*[streptomycin] + C*[poly-L-lysine] + D*[Vitamin E conjugate] |
| Formulation 1047 | A*[Staphyloferrin B] + B*[amphotericin B] + C*[poly-L-lysine] + D*[Vitamin E conjugate] |
| Formulation 1048 | A*[Taiwachelin] + B*[penicillin] + C*[poly-L-lysine] + D*[Vitamin E conjugate] |
| Formulation 1049 | A*[Taiwachelin] + B*[streptomycin] + C*[poly-L-lysine] + D*[Vitamin E conjugate] |
| Formulation 1050 | A*[Taiwachelin] + B*[amphotericin B] + C*[poly-L-lysine] + D*[Vitamin E conjugate] |
| Formulation 1051 | A*[Tetraglycine ferrichrome] + B*[penicillin] + C*[poly-L-lysine] + D*[Vitamin E conjugate] |

TABLE 7-continued

| Formulation Name | Formula |
|---|---|
| Formulation 1052 | A*[Tetraglycine ferrichrome] + B*[streptomycin] + C*[poly-L-lysine] + D*[Vitamin E conjugate] |
| Formulation 1053 | A*[Tetraglycine ferrichrome] + B*[amphotericin B] + C*[poly-L-lysine] + D*[Vitamin E conjugate] |
| Formulation 1054 | A*[Thiazostatin] + B*[penicillin] + C*[poly-L-lysine] + D*[Vitamin E conjugate] |
| Formulation 1055 | A*[Thiazostatin] + B*[streptomycin] + C*[poly-L-lysine] + D*[Vitamin E conjugate] |
| Formulation 1056 | A*[Thiazostatin] + B*[amphotericin B] + C*[poly-L-lysine] + D*[Vitamin E conjugate] |
| Formulation 1057 | A*[Triacetylfusarine] + B*[penicillin] + C*[poly-L-lysine] + D*[Vitamin E conjugate] |
| Formulation 1058 | A*[Triacetylfusarine] + B*[streptomycin] + C*[poly-L-lysine] + D*[Vitamin E conjugate] |
| Formulation 1059 | A*[Triacetylfusarine] + B*[amphotericin B] + C*[poly-L-lysine] + D*[Vitamin E conjugate] |
| Formulation 1060 | A*[Triornicin] + B*[penicillin] + C*[poly-L-lysine] + D*[Vitamin E conjugate] |
| Formulation 1061 | A*[Triornicin] + B*[streptomycin] + C*[poly-L-lysine] + D*[Vitamin E conjugate] |
| Formulation 1062 | A*[Triornicin] + B*[amphotericin B] + C*[poly-L-lysine] + D*[Vitamin E conjugate] |
| Formulation 1063 | A*[Vibriobactin] + B*[penicillin] + C*[poly-L-lysine] + D*[Vitamin E conjugate] |
| Formulation 1064 | A*[Vibriobactin] + B*[streptomycin] + C*[poly-L-lysine] + D*[Vitamin E conjugate] |
| Formulation 1065 | A*[Vibriobactin] + B*[amphotericin B] + C*[poly-L-lysine] + D*[Vitamin E conjugate] |
| Formulation 1066 | A*[Vibrioferrin] + B*[penicillin] + C*[poly-L-lysine] + D*[Vitamin E conjugate] |
| Formulation 1067 | A*[Vibrioferrin] + B*[streptomycin] + C*[poly-L-lysine] + D*[Vitamin E conjugate] |
| Formulation 1068 | A*[Vibrioferrin] + B*[amphotericin B] + C*[poly-L-lysine] + D*[Vitamin E conjugate] |
| Formulation 1069 | A*[Vicibactin] + B*[penicillin] + C*[poly-L-lysine] + D*[Vitamin E conjugate] |
| Formulation 1070 | A*[Vicibactin] + B*[streptomycin] + C*[poly-L-lysine] + D*[Vitamin E conjugate] |
| Formulation 1071 | A*[Vicibactin] + B*[amphotericin B] + C*[poly-L-lysine] + D*[Vitamin E conjugate] |
| Formulation 1072 | A*[Vulnibactin] + B*[penicillin] + C*[poly-L-lysine] + D*[Vitamin E conjugate] |
| Formulation 1073 | A*[Vulnibactin] + B*[streptomycin] + C*[poly-L-lysine] + D*[Vitamin E conjugate] |
| Formulation 1074 | A*[Vulnibactin] + B*[amphotericin B] + C*[poly-L-lysine] + D*[Vitamin E conjugate] |
| Formulation 1075 | A*[Yersiniabactin] + B*[penicillin] + C*[poly-L-lysine] + D*[Vitamin E conjugate] |
| Formulation 1076 | A*[Yersiniabactin] + B*[streptomycin] + C*[poly-L-lysine] + D*[Vitamin E conjugate] |
| Formulation 1077 | A*[Yersiniabactin] + B*[amphotericin B] + C*[poly-L-lysine] + D*[Vitamin E conjugate] |

While preferred embodiments of the present invention have been shown and described herein, it will be obvious to those skilled in the art that such embodiments are provided by way of example only. It is not intended that the invention be limited by the specific examples provided within the specification. While the invention has been described with reference to the aforementioned specification, the descriptions and illustrations of the embodiments herein are not meant to be construed in a limiting sense. Numerous variations, changes, and substitutions will now occur to those skilled in the art without departing from the invention. Furthermore, it shall be understood that all aspects of the invention are not limited to the specific depictions, configurations or relative proportions set forth herein which depend upon a variety of conditions and variables. It should be understood that various alternatives to the embodiments of the invention described herein may be employed in practicing the invention. It is therefore contemplated that the invention shall also cover any such alternatives, modifications, variations or equivalents. It is intended that the following claims define the scope of the invention and that methods and structures within the scope of these claims and their equivalents be covered thereby.

What is claimed is:

1. A nucleic acid preservation composition comprising:
(a) an iron chelator,
(b) poly-L-lysine hydrobromide at a mixed molecular weight of 1,000 Da to 5,000 Da, and
(c) one or more agents selected from: (i) a divalent cation chelator that is different from the iron chelator, (ii) D-alpha-tocopherol polyethylene glycol 1000 succinate and (iii) an antimicrobial agent.

2. The composition of claim 1, wherein the iron chelator is a siderophore.

3. The composition of claim 1, wherein the iron chelator is selected from the group consisting of Enterobactin and Deferoxamine Mesylate.

4. The composition of claim 3, wherein the iron chelator is Enterobactin.

5. The composition of claim 1, comprising:
(a) an iron chelator,
(b) poly-L-lysine hydrobromide at a mixed molecular weight of 1,000 Da to 5,000 Da, and
(c) a divalent cation chelator that is different from the iron chelator.

6. The composition of claim 5, wherein the divalent cation chelator is selected from ethylenediamintetraacetic acid (EDTA), nitrilotriacetic acid (NTA), trans-1,2-cyclohexanediaminetetraacetic acid (CyDTA), diethylenetriaminepentaacetic acid (DTPA), glycoletherdiaminetetraacetic acid (GEDTA), triethylenetetramine-N,N,N',N'',N''',N''''-hexaacetic acid (TTHA), dihydroxyethylglycine (DHEG), iminodiacetic acid (IDA), nitrilotrimethylphosphonic acid (NTP), N-(2-hydroxyethyl)iminodiacetic acid (HIDA), ethylenediamine-N,N'-dipropionic acid (EDDP), ethylenediaminetetra(methylenephosphonic) acid (EDTPO), nitrilotrimethylphosphonic acid (NTP) or 1,2-bis(o-aminophenoxy) ethane-N,N,N',N'-tetraacetic acid (BAPTA).

7. The composition of claim 5, wherein the divalent cation chelator is Ethylenediaminetetraacetic acid (EDTA).

8. The composition of claim 5, wherein:
the iron chelator has a stability constant of at least 25.2 for formation of a complex with iron; and
the divalent cation chelator has a stability constant that is less than 25.2 for formation of a complex with iron.

9. The composition of claim 1 comprising:
(a) an iron chelator,
(b) poly-L-lysine hydrobromide at a mixed molecular weight of 1,000 Da to 5,000 Da, and
(c) D-alpha-tocopherol polyethylene glycol 1000 succinate.

10. The composition of claim 9, further comprising a second chelator that is different from the iron chelator.

11. The composition of claim 10, wherein the second chelator is selected from ethylenediamintetraacetic acid (EDTA), nitrilotriacetic acid (NTA), trans-1,2-cyclohexanediaminetetraacetic acid (CyDTA), diethylenetriaminepentaacetic acid (DTPA), glycoletherdiaminetetraacetic acid (GEDTA), triethylenetetramine-N,N,N',N'',N''',N''''-hexaacetic acid (TTHA), dihydroxyethylglycine (DHEG), iminodiacetic acid (IDA), nitrilotrimethylphosphonic acid (NTP), N-(2-hydroxyethyl)iminodiacetic acid (HIDA), ethylenediamine-N,N'-dipropionic acid (EDDP), ethylenediaminetetra(methylenephosphonic) acid (EDTPO), nitrilotrimethylphosphonic acid (NTP) or 1,2-bis(o-aminophenoxy) ethane-N,N,N',N'-tetraacetic acid (BAPTA).

12. The composition of claim 10, wherein the second chelator is Ethylenediaminetetraacetic acid (EDTA).

13. The composition of claim 1 comprising:
  (a) an iron chelator,
  (b) poly-L-lysine hydrobromide at a mixed molecular weight of 1,000 Da to 5,000 Da, and
  (c) an antimicrobial agent.

14. The composition of claim 13, wherein the antimicrobial agent is selected from the group consisting of penicillin, streptomycin, Amphotericin B, and urine Stabilur tablet or a combination thereof.

15. The composition of claim 13, wherein the antimicrobial agent comprises (i) penicillin, (ii) streptomycin, (iii) Amphotericin B, and (iv) urine Stabilur tablet.

16. The composition of claim 9, further comprising a second chelator that is different from the iron chelator.

17. The composition of claim 16, wherein the second chelator is selected from ethylenediamintetraacetic acid (EDTA), nitrilotriacetic acid (NTA), trans-1,2-cyclohexanediaminetetraacetic acid (CyDTA), diethylenetriaminepentaacetic acid (DTPA), glycoletherdiaminetetraacetic acid (GEDTA), triethylenetetramine-N,N,N',N'',N''',N''''-hexaacetic acid (TTHA), dihydroxyethylglycine (DHEG), iminodiacetic acid (IDA), nitrilotrimethylphosphonic acid (NTP), N-(2-hydroxyethyl)iminodiacetic acid (HIDA), ethylenediamine-N,N'-dipropionic acid (EDDP), ethylenediaminetetra(methylenephosphonic) acid (EDTPO), nitrilotrimethylphosphonic acid (NTP) or 1,2-bis(o-aminophenoxy) ethane-N,N,N',N'-tetraacetic acid (BAPTA).

18. The composition of claim 10, wherein the second chelator is Ethylenediaminetetraacetic acid (EDTA).

19. A nucleic acid preservation composition comprising
  (a) an iron chelator,
  (b) EDTA,
  (c) poly-L-lysine hydrobromide at a mixed molecular weight of 1,000 Da to 5,000 Da, and
  (d) Enterobactin, penicillin, streptomycin, and Amphotericin B.

20. The composition of claim 19, wherein the iron chelator is a siderophore.

21. The composition of claim 19, wherein the iron chelator is selected from the group consisting of Enterobactin and Deferoxamine Mesylate.

22. The composition of claim 19, wherein the iron chelator is Enterobactin.

23. The composition of claim 19, further comprising a Tris-HCl buffer and D-alpha-tocopherol polyethylene glycol 1000 succinate.

24. A nucleic acid preservation composition comprising: 100 mM Tris-HCl buffer, 50 mM EDTA, 110 µg poly-L-lysine hydrobromide at a mixed molecular weight of 1,000 Da to 5,000 Da, 5 µM Enterobactin, 100 units of penicillin, 100 units of streptomycin, and 0.25 µg/mL Amphotericin B.

* * * * *